US011889754B2

(12) United States Patent
Shin et al.

(10) Patent No.: US 11,889,754 B2
(45) Date of Patent: Jan. 30, 2024

(54) ORGANIC COMPOUND, AND ORGANIC LIGHT EMITTING DIODE AND ORGANIC LIGHT EMITTING DISPLAY DEVICE INCLUDING THE SAME

(71) Applicants: LG Display Co., Ltd, Seoul (KR); P&H TECH, Yongin-si (KR)

(72) Inventors: Ji-Cheol Shin, Paju-si (KR); Seon-Keun Yoo, Paju-si (KR); Jeong-Dae Seo, Paju-si (KR); Sang-Beom Kim, Paju-si (KR); Hee-Jun Park, Paju-si (KR); Seo-Yong Hyun, Paju-si (KR); Seok-Keun Yoon, Paju-si (KR)

(73) Assignees: LG DISPLAY CO., LTD, Seoul (KR); P & HTECH, Yongin-si (KR)

( * ) Notice: Subject to any disclaimer, the term of this patent is extended or adjusted under 35 U.S.C. 154(b) by 637 days.

(21) Appl. No.: 16/985,079

(22) Filed: Aug. 4, 2020

(65) Prior Publication Data

US 2021/0050527 A1 Feb. 18, 2021

(30) Foreign Application Priority Data

Aug. 14, 2019 (KR) ........................ 10-2019-0099524

(51) Int. Cl.
*C07D 403/10* (2006.01)
*H10K 85/60* (2023.01)
(Continued)

(52) U.S. Cl.
CPC ......... *H10K 85/654* (2023.02); *C07D 403/10* (2013.01); *C07D 403/14* (2013.01);
(Continued)

(58) Field of Classification Search
CPC C07F 15/0033; C07F 15/002; C07F 15/0086; H01L 51/0085; H01L 51/5004;
(Continued)

(56) References Cited

U.S. PATENT DOCUMENTS 10,937,984 B2 3/2021 Shin et al.
2014/0367645 A1* 12/2014 Seo ...................... H10K 85/649 257/40
(Continued)

FOREIGN PATENT DOCUMENTS

CN 104835921 A 8/2015
CN 106946852 A 7/2017
(Continued)

*Primary Examiner* — Younes Boulghassoul
*Assistant Examiner* — Quinton A Brasfield
(74) *Attorney, Agent, or Firm* — Seed IP Law Group LLP

(57) ABSTRACT

The present disclosure provides an organic compound of the following formula and an organic light emitting diode and an OLED device including the same.

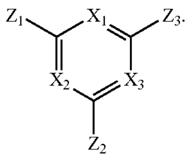

25 Claims, 5 Drawing Sheets

(51) Int. Cl.

| | |
|---|---|
| ***C07D 403/14*** | (2006.01) |
| ***C07D 519/00*** | (2006.01) |
| ***C07D 413/04*** | (2006.01) |
| ***C09K 11/06*** | (2006.01) |
| ***C07D 413/14*** | (2006.01) |
| *H10K 50/15* | (2023.01) |
| *H10K 50/17* | (2023.01) |
| *H10K 50/13* | (2023.01) |
| *H10K 59/12* | (2023.01) |
| *H10K 59/38* | (2023.01) |

(52) U.S. Cl.
CPC ......... *C07D 413/04* (2013.01); *C07D 413/14* (2013.01); *C07D 519/00* (2013.01); *C09K 11/06* (2013.01); *H10K 85/6572* (2023.02); *C09K 2211/1018* (2013.01); *H10K 50/131* (2023.02); *H10K 50/15* (2023.02); *H10K 50/17* (2023.02); *H10K 59/12* (2023.02); *H10K 59/38* (2023.02)

(58) Field of Classification Search
CPC ............. H01L 51/0088; H01L 51/5024; H01L 51/0087; H01L 2251/552; H01L 2251/308; H01L 51/5016; H10K 85/654; C07D 401/10; C07D 403/10; C07D 405/10
See application file for complete search history.

(56) References Cited

U.S. PATENT DOCUMENTS

| | | | | |
|---|---|---|---|---|
| 2018/0166647 | A1* | 6/2018 | Shin | H10K 59/32 |
| 2020/0194706 | A1* | 6/2020 | Han | H10K 85/6576 |
| 2021/0130336 | A1* | 5/2021 | Shirasaki | H10K 85/631 |
| 2022/0274952 | A1* | 9/2022 | Uchida | C07D 401/10 |

FOREIGN PATENT DOCUMENTS

| | | | | |
|---|---|---|---|---|
| CN | 107056783 | A | * | 8/2017 |
| CN | 107056783 | A | | 8/2017 |
| CN | 108218858 | A | | 6/2018 |
| CN | 109748909 | A | | 5/2019 |

* cited by examiner

ORGANIC COMPOUND, AND ORGANIC LIGHT EMITTING DIODE AND ORGANIC LIGHT EMITTING DISPLAY DEVICE INCLUDING THE SAME

CROSS-REFERENCE TO RELATED APPLICATIONS

The present application claims the benefit of Korean Patent Application No. 10-2019-0099524 filed in the Republic of Korea on Aug. 14, 2019, which is hereby incorporated by reference in its entirety.

BACKGROUND

Technical Field

The present disclosure relates to an organic compound, and more particularly, to an organic compound being capable of increasing an emitting efficiency and decreasing a driving voltage, and an organic light emitting diode and an organic light emitting display (OLED) device including the organic compound.

Description of the Related Art

Recently, requirement for flat panel display devices having small occupied area is increased. Among the flat panel display devices, a technology of an OLED device, which includes an organic light emitting diode and may be called to as an organic electroluminescent device, is rapidly developed.

The organic light emitting diode emits light by injecting electrons from a cathode as an electron injection electrode and holes from an anode as a hole injection electrode into an organic emitting layer, combining the electrons with the holes, generating an exciton, and transforming the exciton from an excited state to a ground state. A flexible transparent substrate, for example, a plastic substrate, can be used as a base substrate where elements are formed. In addition, the organic light emitting diode can be operated at a voltage lower than a voltage required to operate other display devices and has low power consumption. Moreover, the light from the organic light emitting diode has excellent color purity.

For example, the organic emitting layer may has a multi-layered structure having a hole injection layer (HIL), a hole transporting layer (HTL), an emitting material layer (EML), an electron transporting layer (ETL) and an electron injection layer (EIL).

However, in the related art organic light emitting diode, there is a limitation in a hole injection/transporting property into the EML. As a result, the organic light emitting diode and the OLED device have low emitting efficiency and high driving voltage.

SUMMARY

The present disclosure is directed to an organic compound, an organic light emitting diode and an OLED device that substantially obviate one or more of the problems associated with the limitations and disadvantages of the related conventional art.

Additional features and advantages of the present disclosure are set forth in the description which follows, and will be apparent from the description, or evident by practice of the present disclosure. The objectives and other advantages of the present disclosure are realized and attained by the features described herein as well as in the appended drawings.

To achieve these and other advantages in accordance with the purpose of the embodiments of the present disclosure, as described herein, an aspect of the present disclosure is an organic compound of Formula 1:

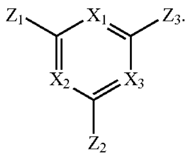

In Formula 1, each of $X_1$, $X_2$ and $X_3$ is independently selected from carbon (C) and nitrogen (N), provided that at least one of $X_1$ to $X_3$ is N; each of $Z_1$, $Z_2$ and $Z_3$ is independently selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, a substituted or unsubstituted C1 to C12 ether group, halogen, cyano (CN), and trimethylsilyl; or each of $Z_1$, $Z_2$ and $Z_3$ is represented by one of the following Formula 2, Formula 3 and Formula 4, provided that at least one of Z1 to Z3 is selected from one of the Formulas 2 to 4,

[Formula 2]

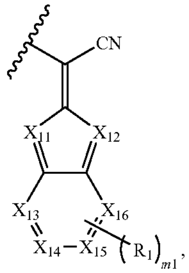

[Formula 3]

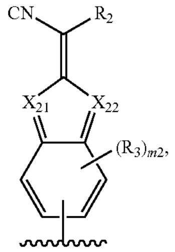

and

[Formula 4]

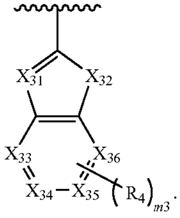

In Formula 2, each of $X_{11}$ and $X_{12}$ is independently selected from C and N, provided that at least one of $X_{11}$ and $X_{12}$ is N; each of $X_{13}$ to $X_{16}$ is independently selected from C and N; $R_1$ is selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, cyano, halogen and trifluoromethyl; and m1 is an integer of 0 to 4. In Formula 3, each of $X_2$ and $X_{22}$ is independently selected from C and N, provided that at least one of $X_{21}$ and $X_{22}$ is N; $R_2$ is selected from cyano and phenyl; $R_3$ is selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, cyano, halogen and trifluoromethyl; and m2 is an integer of 0 to 3. In Formula 4, each of $X_{31}$ and $X_{32}$ is independently selected from N and oxygen (O), provided that when one of $X_{31}$ and $X_{32}$ is N, then the other one of $X_{31}$ and $X_{32}$ is O; each of $X_{33}$ to $X_{36}$ is independently selected from C and N; $R_4$ is selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, cyano, halogen and trifluoromethyl; and m3 is an integer of 0 to 4.

Another aspect of the present disclosure is an organic light emitting diode including first and second electrodes facing each other; a first emitting material layer between the first and second electrodes; a first hole auxiliary layer between the first electrode and the first emitting material layer; and a first electron auxiliary layer between the first emitting material layer and the second electrode, wherein the first hole auxiliary layer include a first host and an organic compound of the present disclosure as a first dopant.

Another aspect of the present disclosure is an organic light emitting diode including first and second electrodes facing each other; a first charge generation layer positioned between the first and second electrodes and including a first N-type charge generation layer and a first P-type charge generation layer; a first emitting stack including a first emitting material layer between the first electrode and the first N-type charge generation layer, a first hole auxiliary layer between the first electrode and the first emitting material layer, and a first electron auxiliary layer between the first emitting material layer and the first N-type charge generation layer; and a second emitting stack including a second emitting material layer between the first P-type charge generation layer and the second electrode, a second hole auxiliary layer between the first P-type charge generation layer and the second emitting material layer, and a second electron auxiliary layer between the second emitting material layer and the second electrode, wherein the first P-type charge generation layer includes a first host and an organic compound of the present disclosure as a first dopant.

Another aspect of the present disclosure is an organic light emitting display device including a substrate; an organic light emitting diode disposed on or over the substrate; and a thin film transistor positioned between the substrate and the organic light emitting diode and connected to the organic light emitting diode.

It is to be understood that both the foregoing general description and the following detailed description are exemplary and explanatory and are intended to further explain the present disclosure as claimed.

BRIEF DESCRIPTION OF THE SEVERAL VIEWS OF THE DRAWINGS

The accompanying drawings, which are included to provide a further understanding of the present disclosure and are incorporated in and constitute a part of this specification, illustrate embodiments of the present disclosure and together with the description serve to explain the principles of the present disclosure.

DETAILED DESCRIPTION

Reference will now be made in detail to some of the examples and preferred embodiments, which are illustrated in the accompanying drawings.

Figure 1:
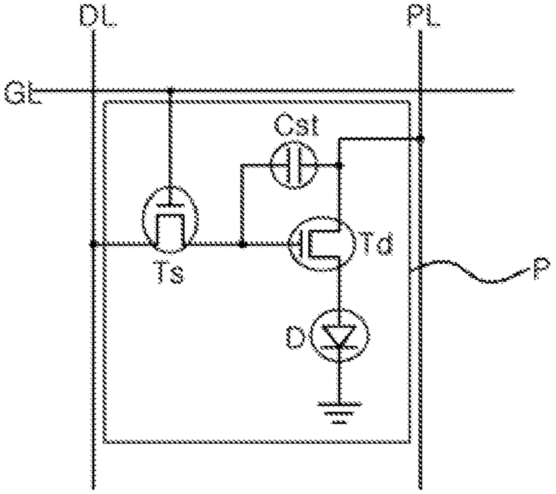
FIG. 1 is a schematic circuit diagram of an OLED device of the present disclosure.

FIG. 1 is a schematic circuit diagram of an OLED device of the present disclosure.

As shown in FIG. 1, an OLED device includes a gate line GL, a data line DL, a power line PL, a switching thin film transistor TFT Ts, a driving TFT Td, a storage capacitor Cst, and an organic light emitting diode D. The gate line GL and the data line DL cross each other to define a pixel region P.

The switching TFT Ts is connected to the gate line GL and the data line DL, and the driving TFT Td and the storage capacitor Cst are connected to the switching TFT Ts and the power line PL. The organic light emitting diode D is connected to the driving TFT Td.

In the OLED device, when the switching TFT Ts is turned on by a gate signal applied through the gate line GL, a data signal from the data line DL is applied to the gate electrode of the driving TFT Td and an electrode of the storage capacitor Cst.

When the driving TFT Td is turned on by the data signal, an electric current is supplied to the organic light emitting diode D from the power line PL. As a result, the organic light emitting diode D emits light. In this case, when the driving TFT Td is turned on, a level of an electric current applied from the power line PL to the organic light emitting diode D is determined such that the organic light emitting diode D can produce a gray scale.

The storage capacitor Cst serves to maintain the voltage of the gate electrode of the driving TFT Td when the switching TFT Ts is turned off. Accordingly, even if the switching TFT Ts is turned off, a level of an electric current applied from the power line PL to the organic light emitting diode D is maintained to next frame.

As a result, the OLED device displays a desired image.

Figure 2:
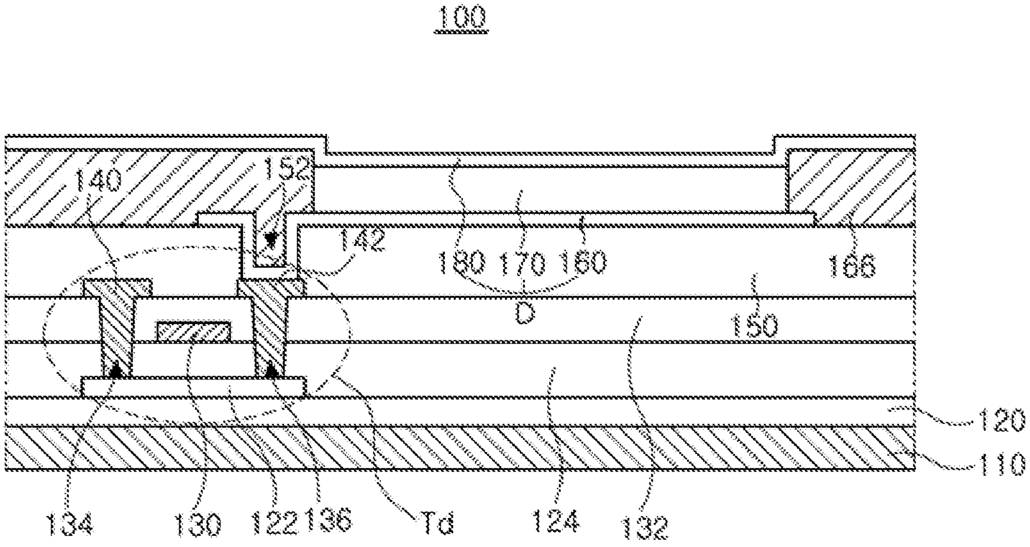
FIG. 2 is a schematic cross-sectional view of an OLED device according to a first embodiment of the present disclosure.

FIG. 2 is a schematic cross-sectional view of an OLED device according to a first embodiment of the present disclosure.

As shown in FIG. 2, the OLED device 100 according to the first embodiment of the present disclosure includes a substrate 110, a driving TFT Td and an organic light emitting diode D connected to the driving TFT Td.

The substrate 110 may be a glass substrate or a plastic substrate. For example, in some embodiments, the substrate 110 may be a polyimide substrate.

A buffer layer 120 is formed on the substrate, and the driving TFT Td is formed on the buffer layer 120. The buffer layer 120 may be omitted.

A semiconductor layer 122 is formed on the buffer layer 120. The semiconductor layer 122 may include an oxide semiconductor material or polycrystalline silicon.

When the semiconductor layer 122 includes the oxide semiconductor material, a light-shielding pattern (not shown) may be formed under the semiconductor layer 122. The light to the semiconductor layer 122 is shielded or blocked by the light-shielding pattern such that thermal degradation of the semiconductor layer 122 can be prevented. On the other hand, when the semiconductor layer 122 includes polycrystalline silicon, impurities may be doped into both sides of the semiconductor layer 122.

A gate insulating layer 124 is formed on the semiconductor layer 122. The gate insulating layer 124 may be formed of an inorganic insulating material such as silicon oxide or silicon nitride.

A gate electrode 130, which is formed of a conductive material, e.g., metal, is formed on the gate insulating layer 124 to correspond to a center of the semiconductor layer 122.

In FIG. 2, the gate insulating layer 124 is formed on an entire surface of the substrate 110. Alternatively, the gate insulating layer 124 may be patterned to have the same shape as the gate electrode 130.

An interlayer insulating layer 132, which is formed of an insulating material, is formed on the gate electrode 130. The interlayer insulating layer 132 may be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 122. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 is formed only through the interlayer insulating layer 132.

A source electrode 140 and a drain electrode 142, which are formed of a conductive material, e.g., metal, are formed on the interlayer insulating layer 132.

The source electrode 140 and the drain electrode 142 are spaced apart from each other with respect to the gate electrode 130 and respectively contact both sides of the semiconductor layer 122 through the first and second contact holes 134 and 136.

The semiconductor layer 122, the gate electrode 130, the source electrode 140 and the drain electrode 142 constitute the driving TFT Td.

In the driving TFT Td, the gate electrode 130, the source electrode 140, and the drain electrode 142 are positioned over the semiconductor layer 122. Namely, the driving TFT Td has a coplanar structure.

Alternatively, in the driving TFT Td, the gate electrode may be positioned under the semiconductor layer, and the source and drain electrodes may be positioned over the semiconductor layer such that the driving TFT Td may have an inverted staggered structure. In this instance, the semiconductor layer may include amorphous silicon.

Although not shown, the gate line and the data line cross each other to define the pixel region, and the switching TFT Ts (FIG. 1) is formed to be connected to the gate and data lines. The switching TFT Ts is connected to the driving TFT Td as the driving element.

In addition, the power line, which may be formed to be parallel to and spaced apart from one of the gate and data lines, and the storage capacitor for maintaining the voltage of the gate electrode of the driving TFT Td in one frame may be further formed.

A passivation layer 150, which includes a drain contact hole 152 exposing the drain electrode 142 of the driving TFT Td, is formed to cover the driving TFT Td.

A first electrode 160, which is connected to the drain electrode 142 of the driving TFT Td through the drain contact hole 152, is separately formed in each pixel region. The first electrode 160 may be an anode and may be formed of a conductive material having a relatively high work function. For example, in some embodiments, the first electrode 160 may be formed of a transparent conductive material such as indium-tin-oxide (ITO) or indium-zinc-oxide (IZO).

When the OLED device 100 is operated in a top-emission type, a reflection electrode or a reflection layer may be formed under the first electrode 160. For example, in some embodiments, the reflection electrode or the reflection layer may be formed of aluminum-palladium-copper (APC) alloy.

A bank layer 166 is formed on the passivation layer 150 to cover an edge of the first electrode 160. Namely, the bank layer 166 is positioned at a boundary of the pixel region and exposes a center of the first electrode 160 in the pixel region.

An organic emitting layer 170 is formed on the first electrode 160. The organic emitting layer 170 is formed in each pixel region P. For example, in some embodiments, the organic emitting layer 170 may include a red organic emitting layer, a green organic emitting layer and a blue organic emitting layer in red, green and blue pixel regions, respectively.

A second electrode 180 is formed over the substrate 110 where the organic emitting layer 170 is formed. The second electrode 180 covers an entire surface of the display area and may be formed of a conductive material having a relatively low work function to serve as a cathode. For example, in some embodiments, the second electrode 180 may be formed of aluminum (Al), magnesium (Mg) or Al—Mg alloy.

The first electrode 160, the organic emitting layer 170 and the second electrode 180 constitute the organic light emitting diode D.

Although not shown, an encapsulation film is formed on the second electrode 180 to prevent penetration of moisture into the organic light emitting diode D. The encapsulation film includes a first inorganic insulating layer, an organic insulating layer and a second inorganic insulating layer sequentially stacked, but it is not limited thereto.

A polarization plate (not shown) for reducing an ambient light reflection may be disposed over the top-emission type organic light emitting diode D. For example, in some embodiments, the polarization plate may be a circular polarization plate.

Figure 3:
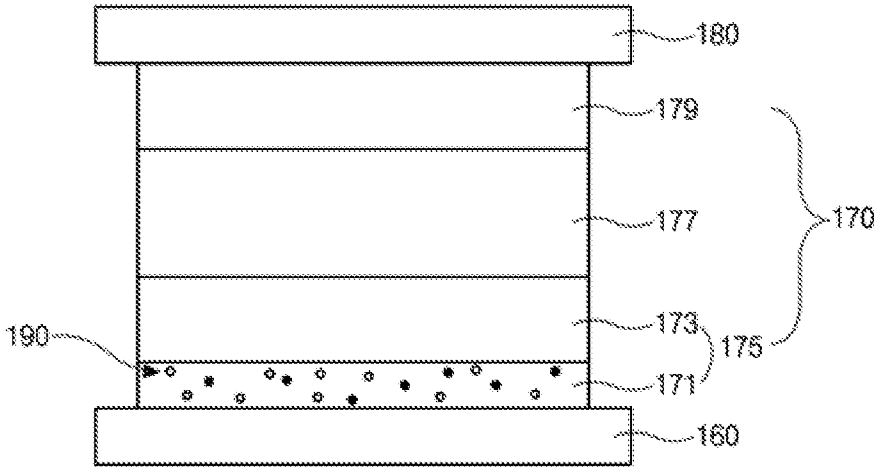
FIG. 3 is a schematic cross-sectional view of an organic light emitting diode included in the OLED device according to the first embodiment of the present disclosure.

FIG. 3 is a schematic cross-sectional view of an organic light emitting diode included in the OLED device according to the first embodiment of the present disclosure.

As shown in FIG. 3, the organic light emitting diode D includes the first and second electrodes 160 and 180, which face each other, and the organic emitting layer 170 therebetween. The organic emitting layer 170 includes an emitting material layer (EML) 177, a hole auxiliary layer 175 between the first electrode 160 and the EML 177, and an electron auxiliary layer 179 between the EML 177 and the second electrode 180.

The hole auxiliary layer 175 includes a host and a dopant of an organic compound of the present disclosure. For example, in some embodiments, the hole auxiliary layer 175 may include a hole injection layer (HIL) 171 and a hole transporting layer (HTL) 173 between the HIL 171 and the EML 177, and the organic compound of the present disclosure as the dopant 190 may be included in the HIL 171.

The organic compound of the present disclosure, which is used as a dopant in the hole auxiliary layer and/or a p-type charge generation layer, is represented by Formula 1.

[Formula 1]

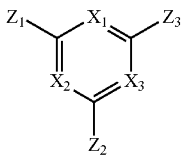

In Formula 1, each of $X_1$, $X_2$ and $X_3$ is independently selected from carbon (C) and nitrogen (N), and at least one of $X_1$ to $X_3$ is N. Each of $Z_1$, $Z_2$ and $Z_3$ is independently selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, a substituted or unsubstituted C1 to C12 ether group, halogen, cyano (CN) and trimethylsilyl; or each of $X_1$, $X_2$ and $X_3$ is independently selected from Formula 2, Formula 3 and Formula 4, and at least one of $Z_1$ to $Z_3$ is selected from Formulas 2 to 4. The alkyl group and/or the alkoxy group may be substituted by halogen. For example, in some embodiments, a substituted alkyl group may be trifluoromethyl, and a substituted alkoxy group may be trifluoromethoxy.

[Formula 2]

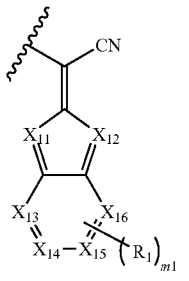

-continued

[Formula 3]

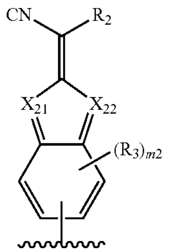

[Formula 4]

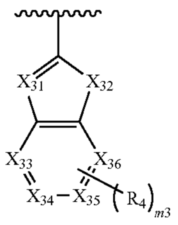

In Formula 2, each of $X_{11}$ and $X_{12}$ is independently selected from C and N, and at least one of $X_{11}$ and $X_{12}$ is N. Each of $X_{13}$ to $X_{16}$ is independently selected from C and N. $R_1$ is selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, cyano, halogen and trifluoromethyl, and m1 is an integer of 0 to 4.

For example, in some embodiments, at least one of $X_{13}$ to $X_{16}$ may be C, and $R_1$ may be selected from methyl, trifluoromethyl, trifluoromethoxy, cyano and fluorine (F).

In Formula 3, each of $X_{21}$ and $X_{22}$ is independently selected from C and N, and at least one of $X_{21}$ and $X_{22}$ is N. $R_2$ is selected from cyano and phenyl, and $R_3$ is selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, cyano, halogen and trifluoromethyl, and m2 is an integer of 0 to 3.

For example, in some embodiments, $R_2$ may be phenyl substituted by at least one of F and CN, and $R_3$ may be CN.

In Formula 4, one of $X_{31}$ and $X_{32}$ is N, and one of $X_{31}$ and $X_{32}$ is oxygen (O). Each of $X_{33}$ to $X_{36}$ is independently selected from C and N. $R_4$ is selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, cyano, halogen and trifluoromethyl, and m3 is an integer of 0 to 4.

For example, in some embodiments, at least one of $X_{33}$ to $X_{36}$ may be C, and $R_4$ may be selected from F, CN and trifluoromethyl.

For example, in some embodiments, the organic compound of the present disclosure may be one of compounds of Formula 5.

[Formula 5]
1
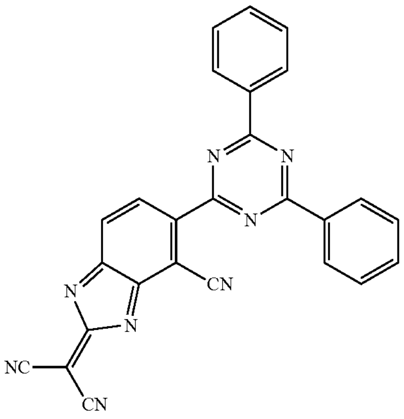
2
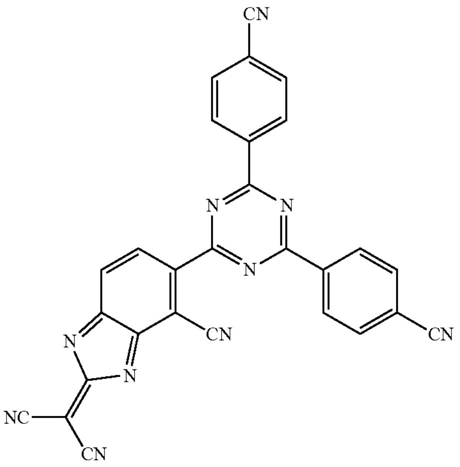
3
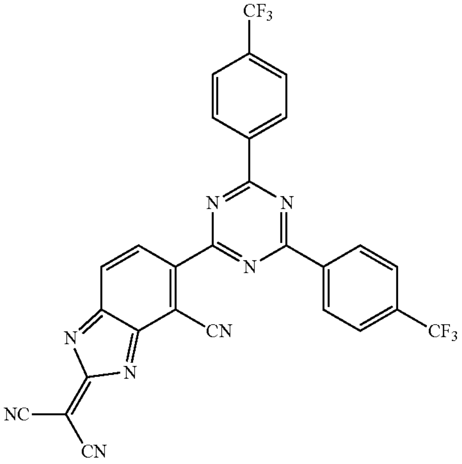
-continued
4
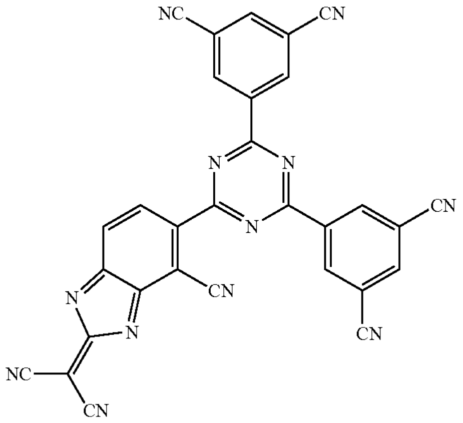
5
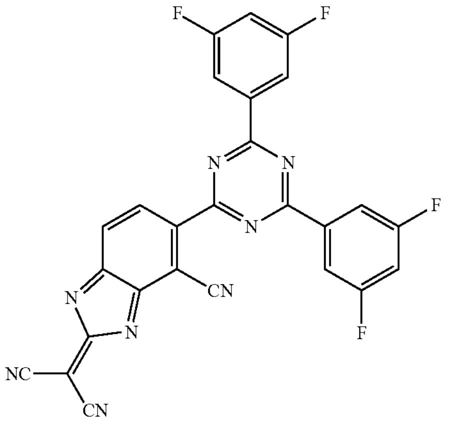
6
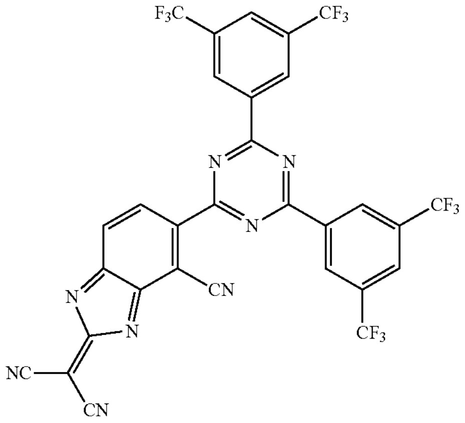

-continued
7
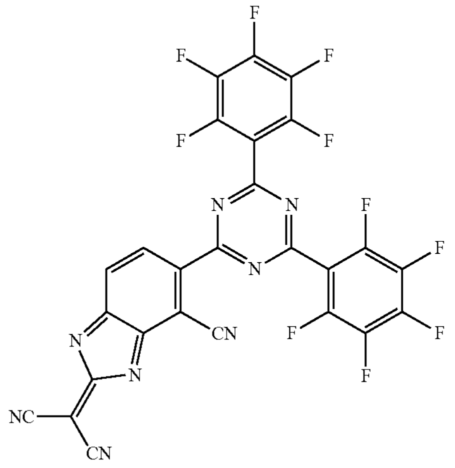
8
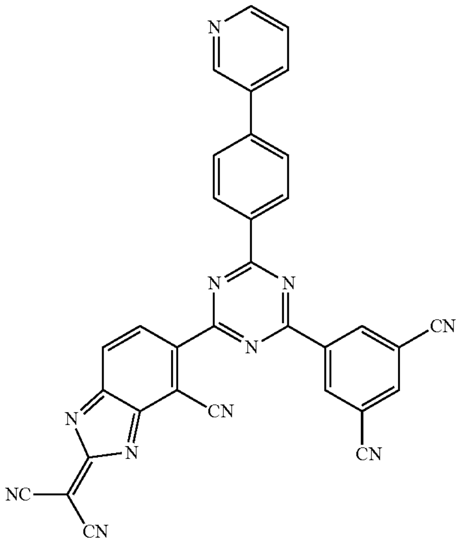
9
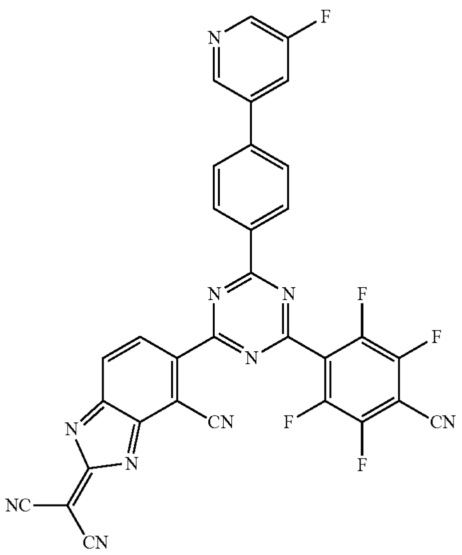
-continued
10
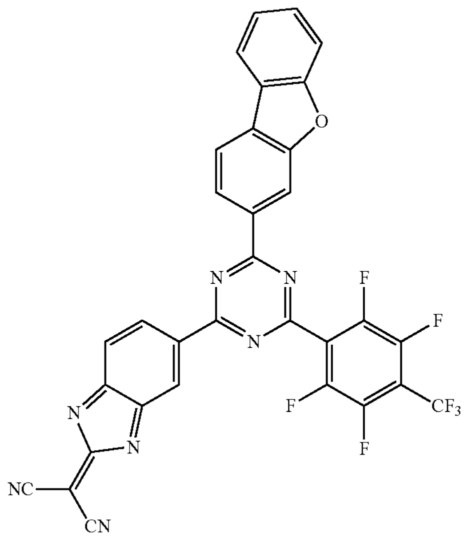
11
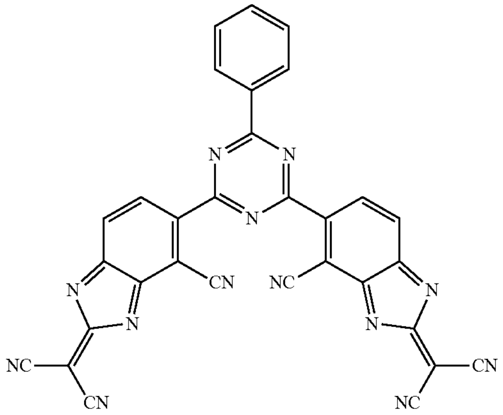
12
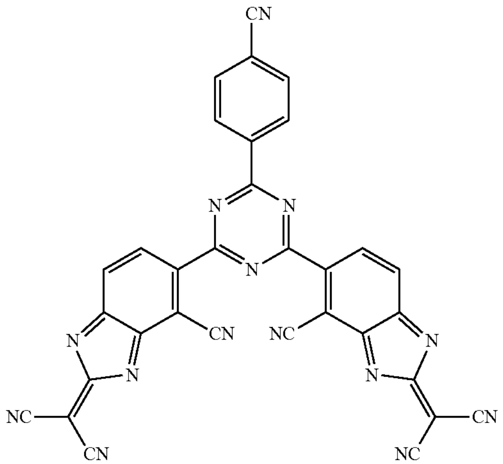

-continued
13
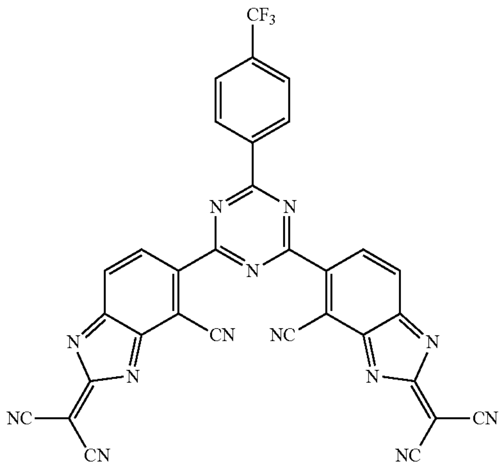
14
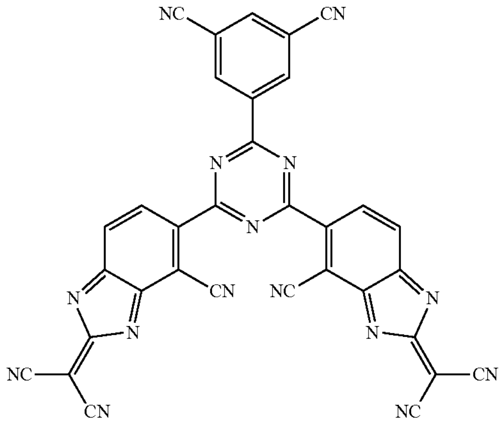
15
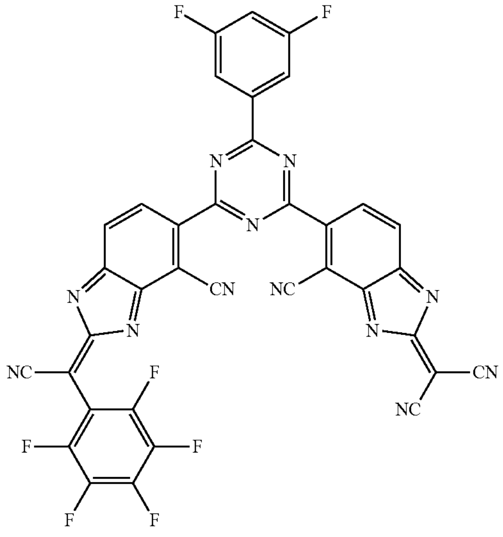
-continued
16
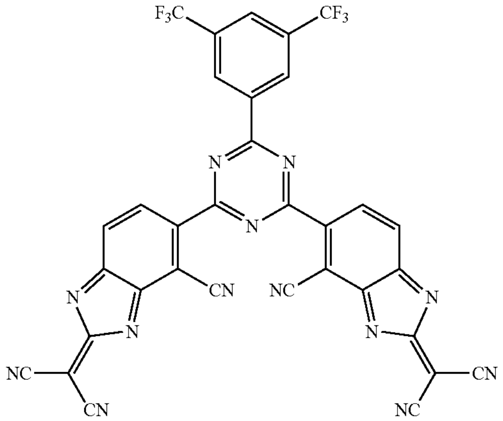
17
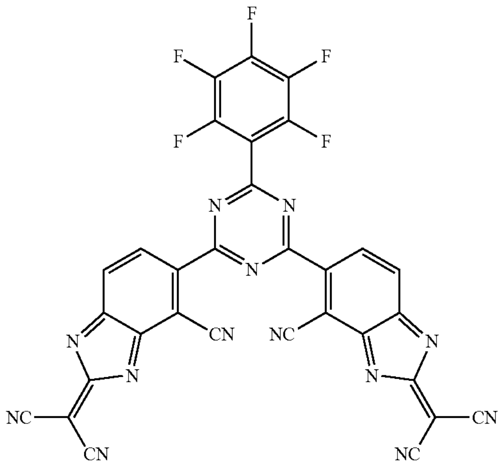
18
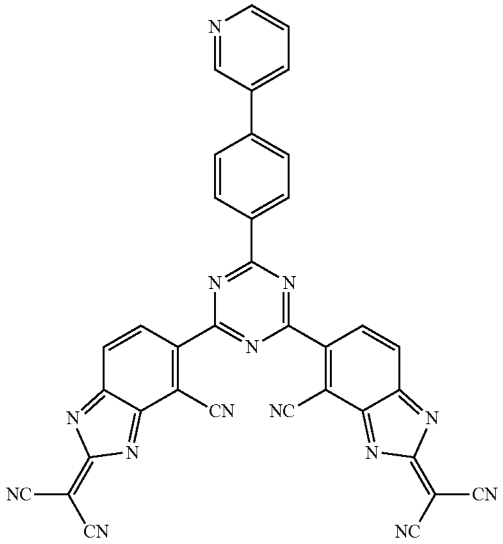

-continued
19
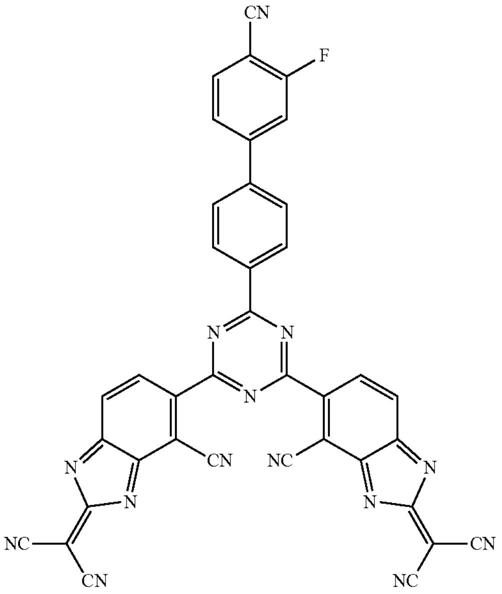
20
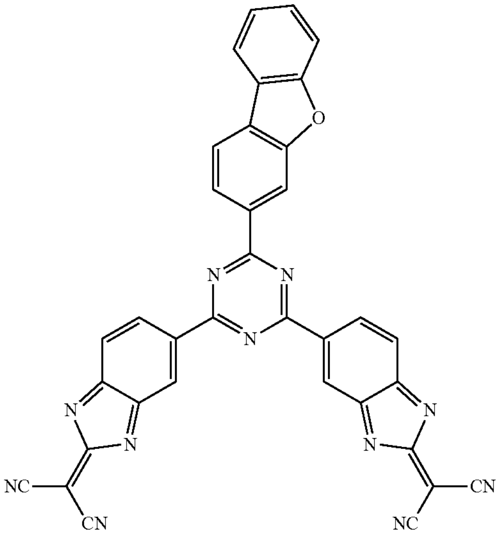
-continued
21
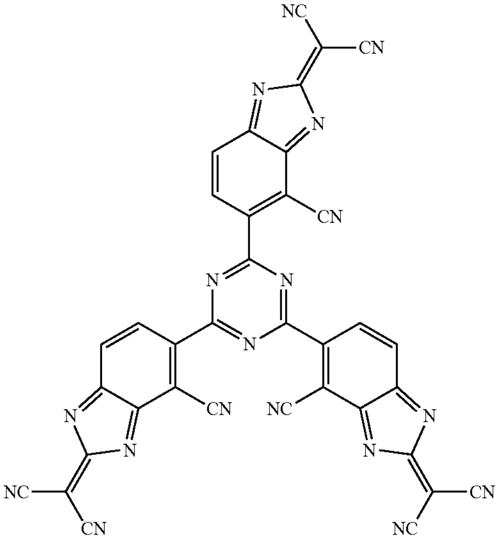
22
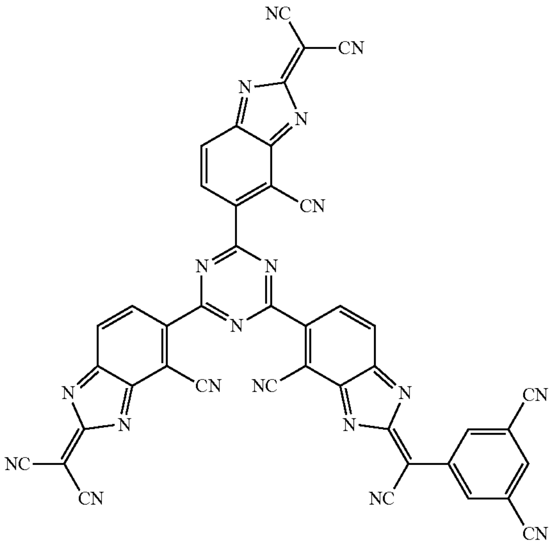
23
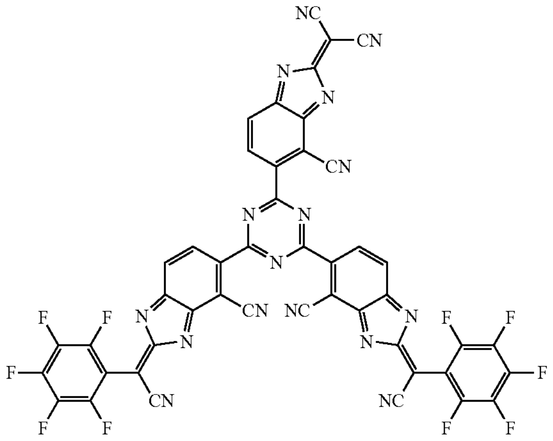

-continued
24
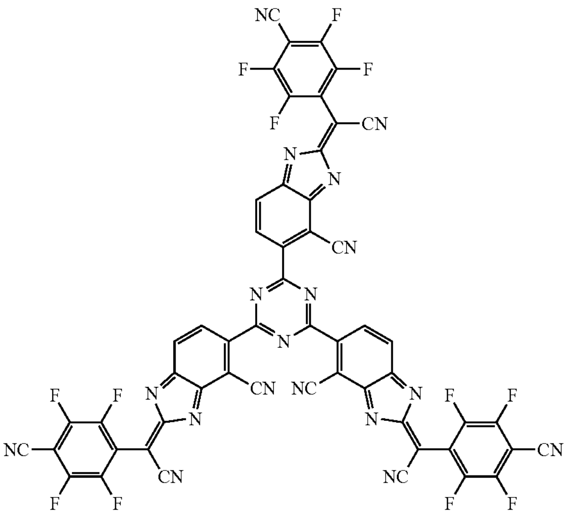
25
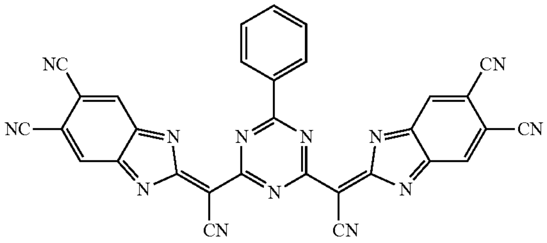
26
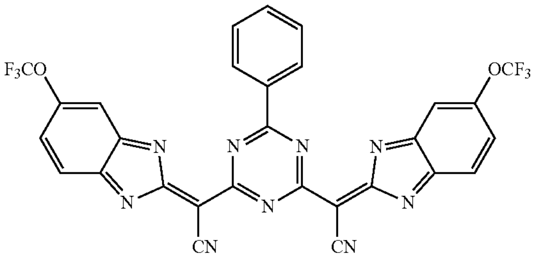
27
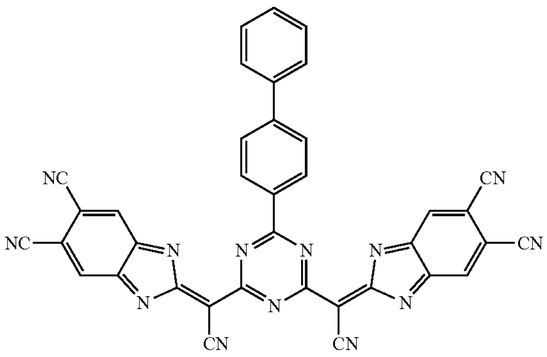
-continued
28
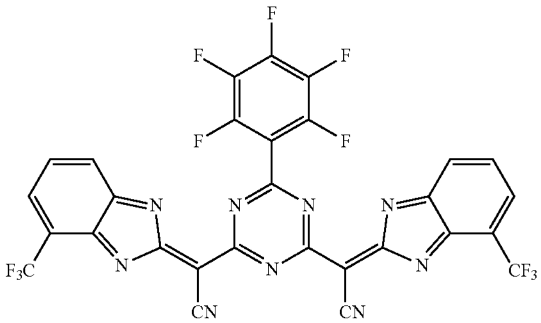
29
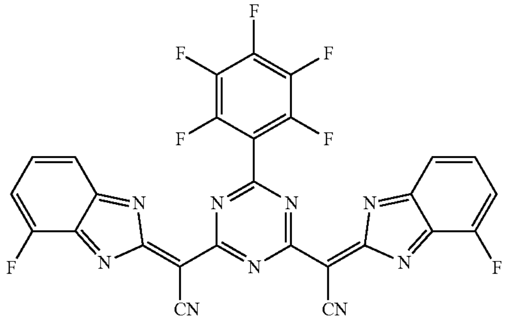
30
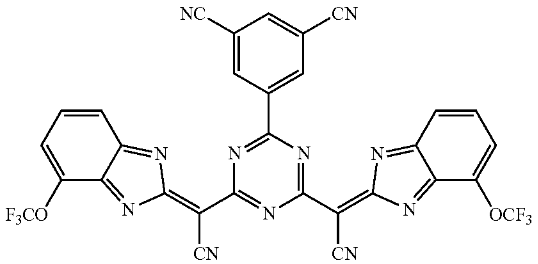
31
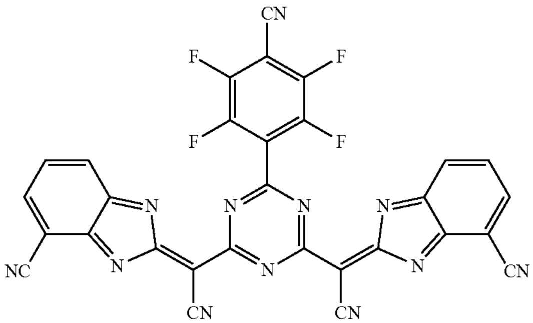
32
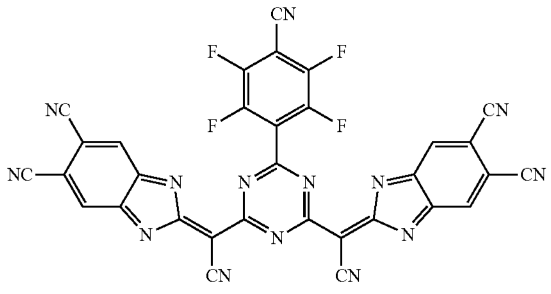

-continued
33
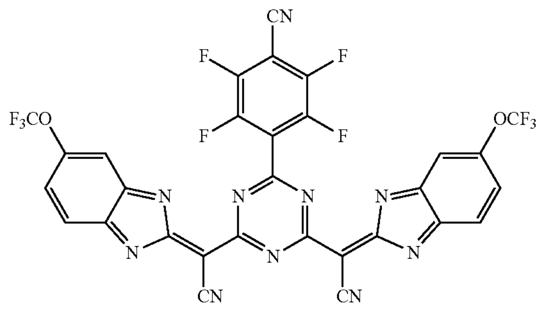
34
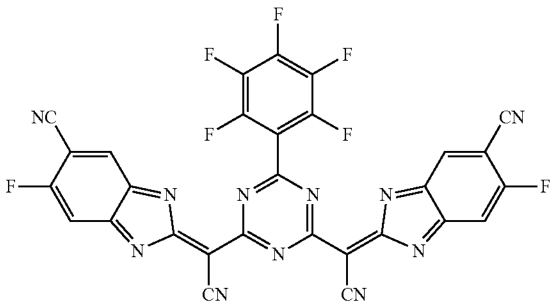
35
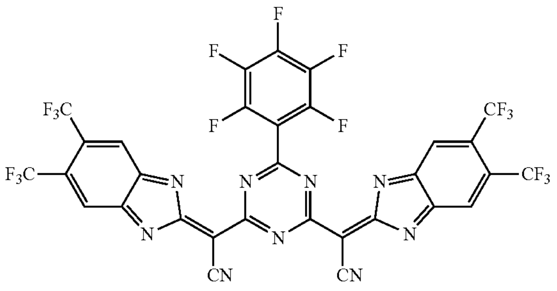
36
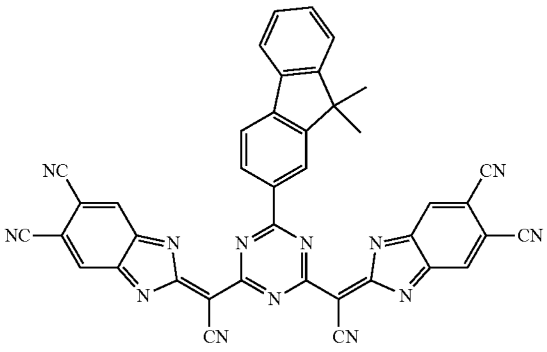
-continued
37
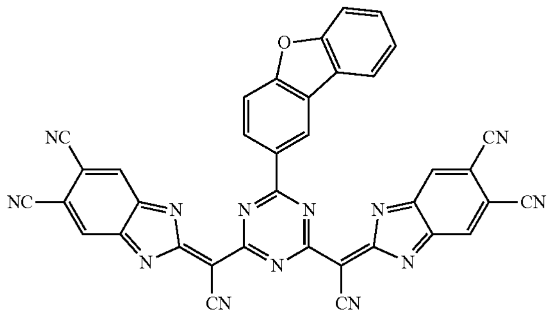
38
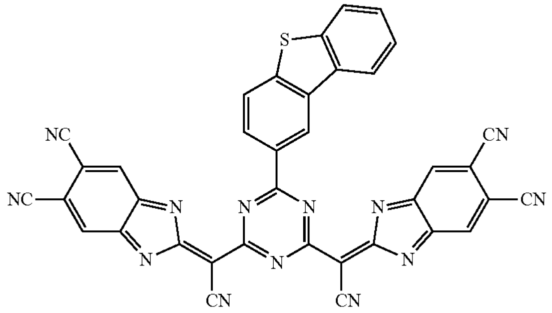
39
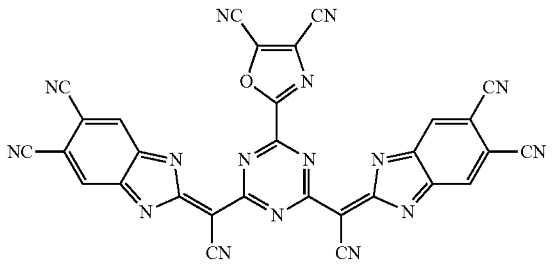
40
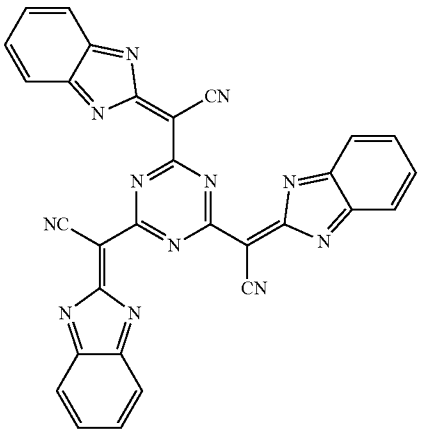

-continued
41
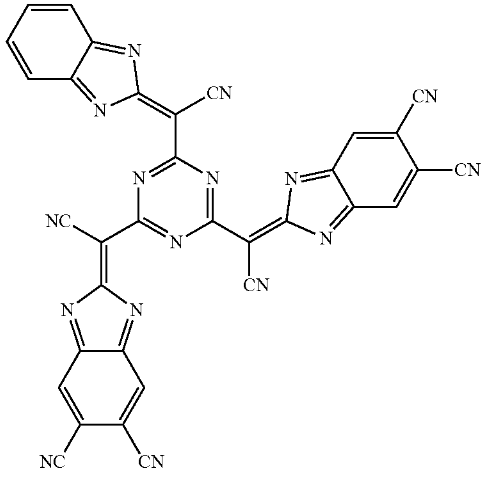
42
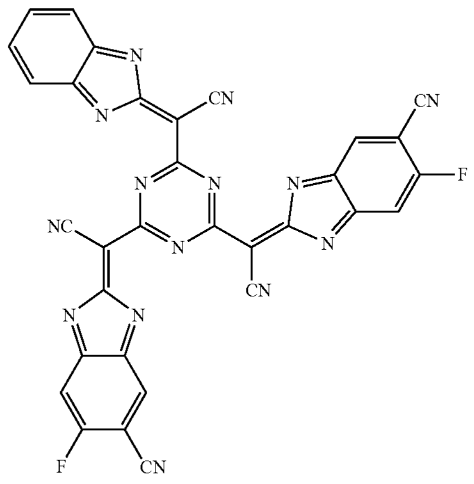
43
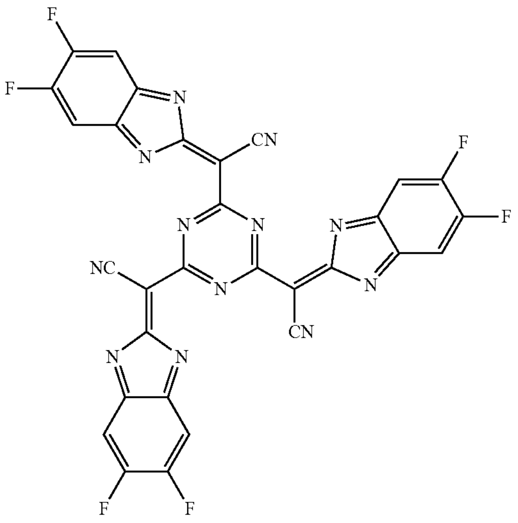
-continued
44
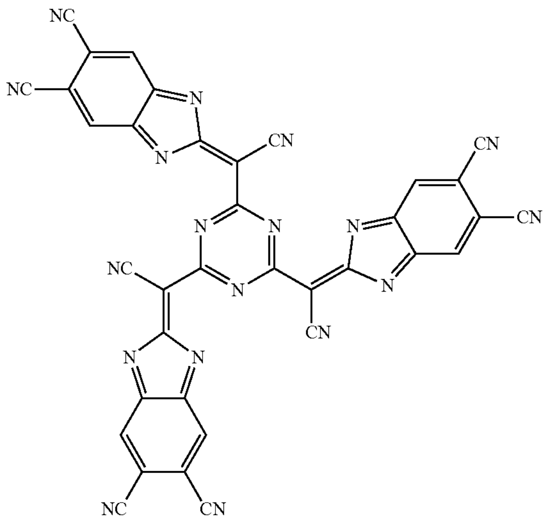
45
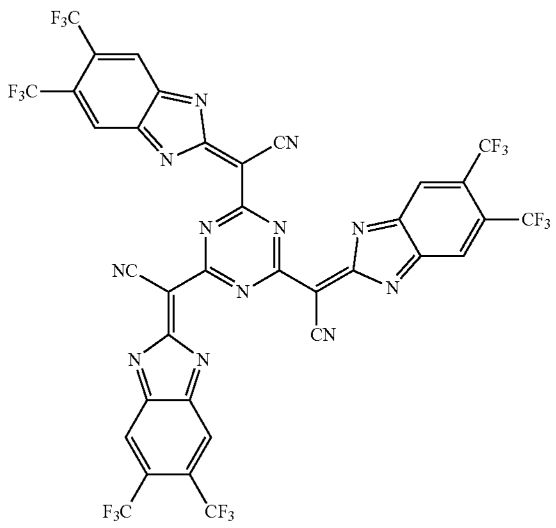
46
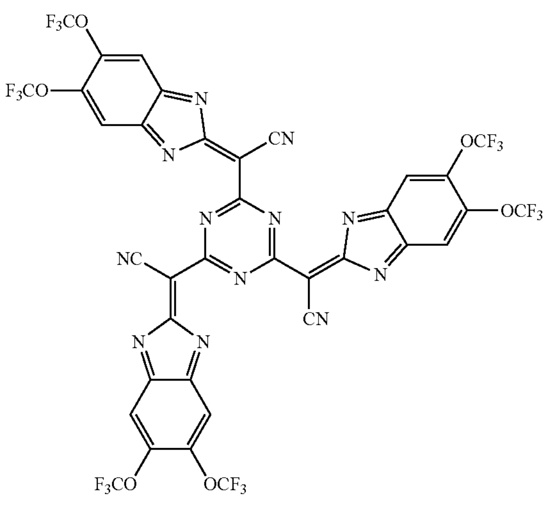

-continued
47
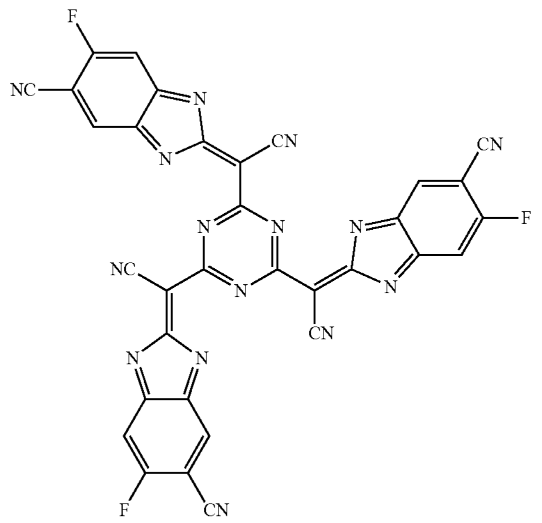
48
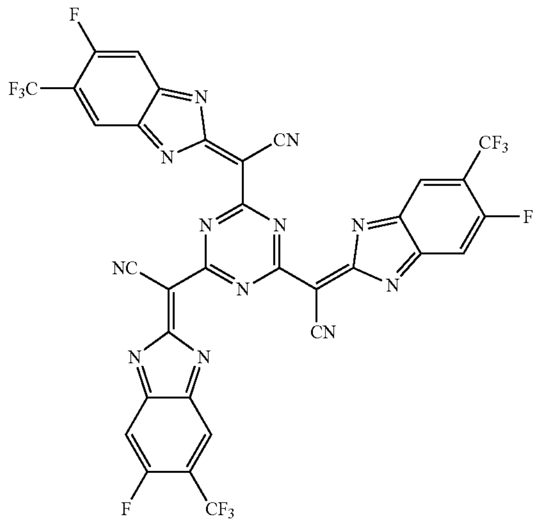
49
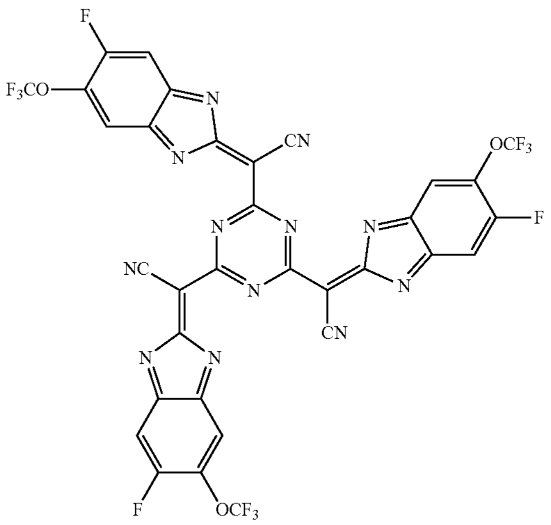
-continued
50
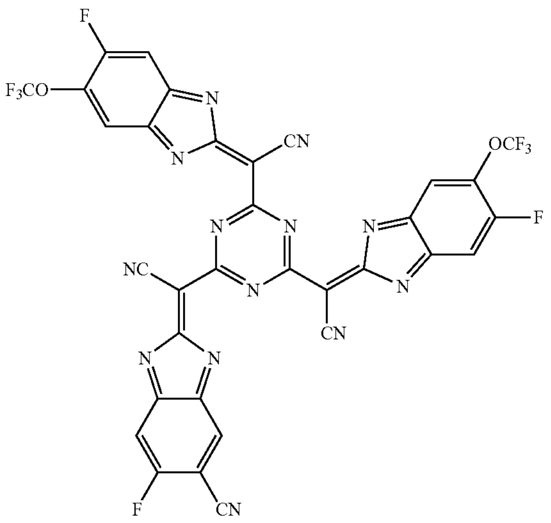
51
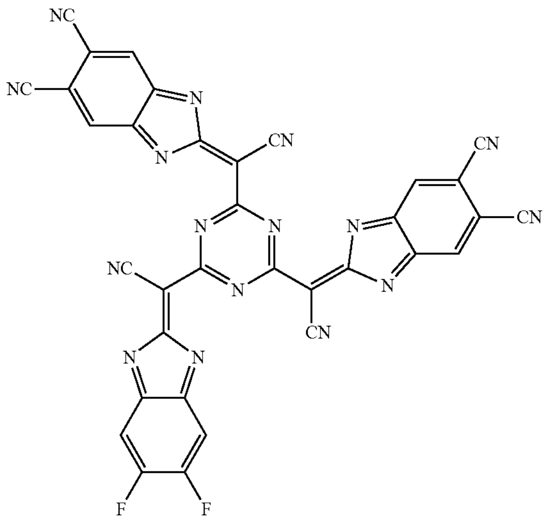
52
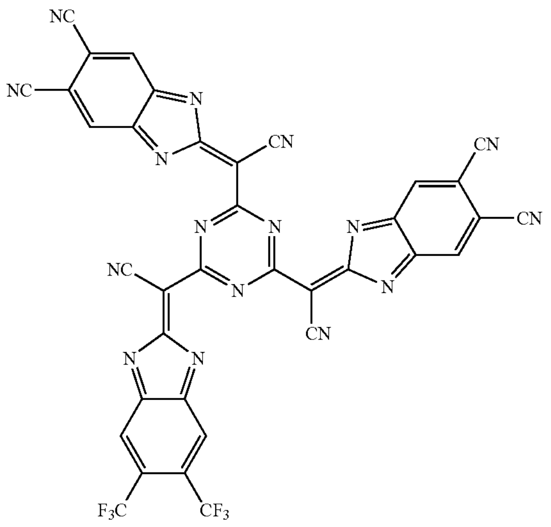

-continued
53
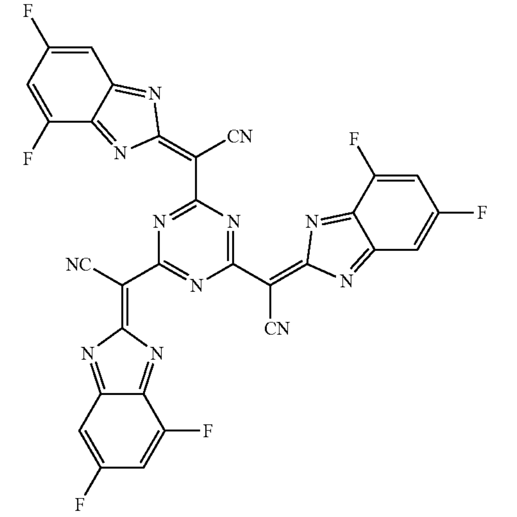
54
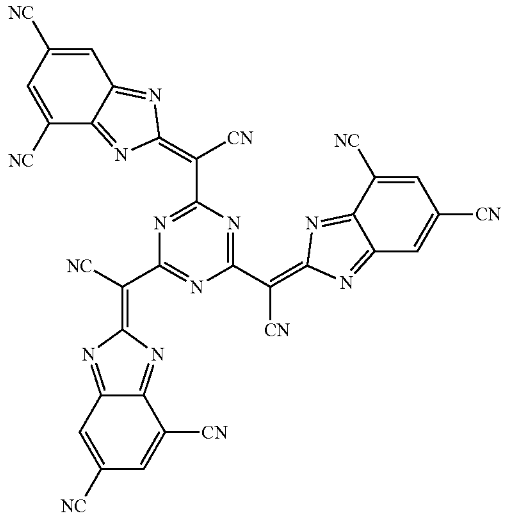
55
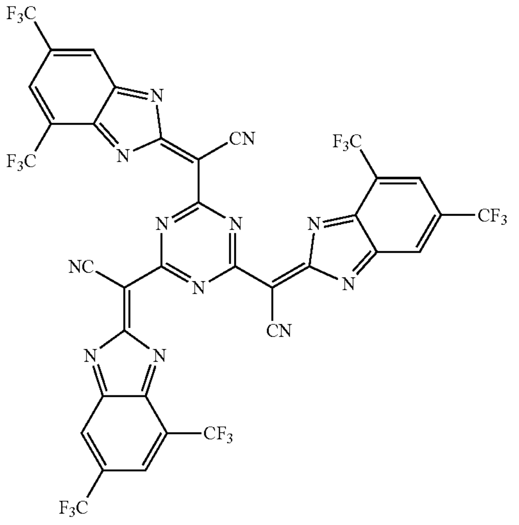
-continued
56
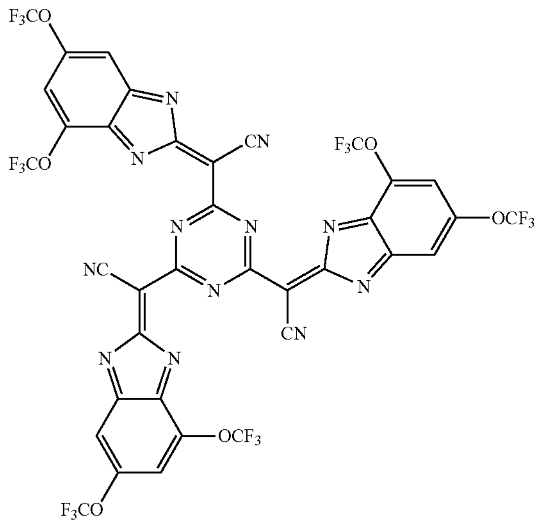
57
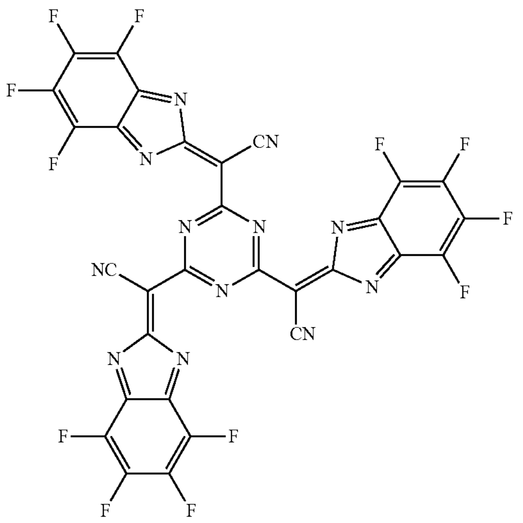
58
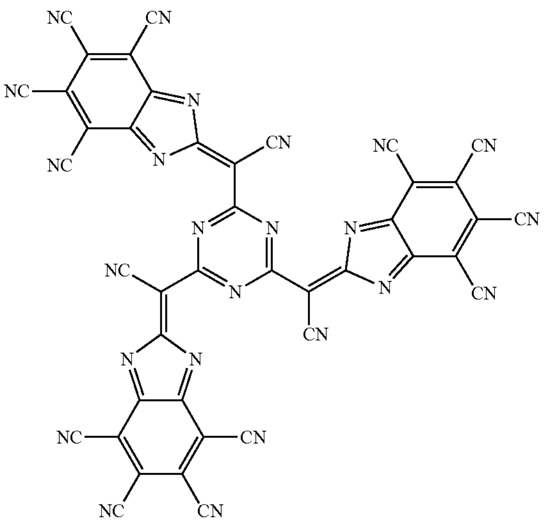

-continued
59
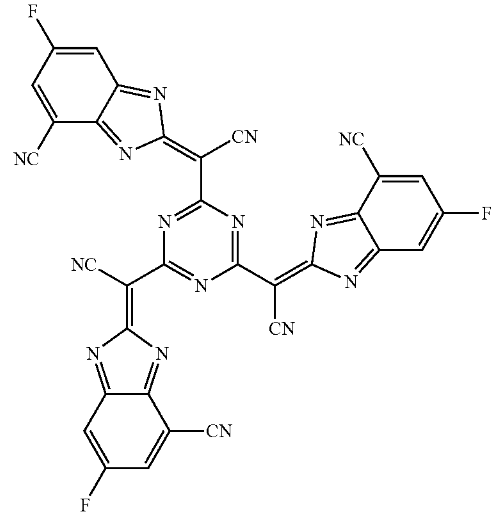
60
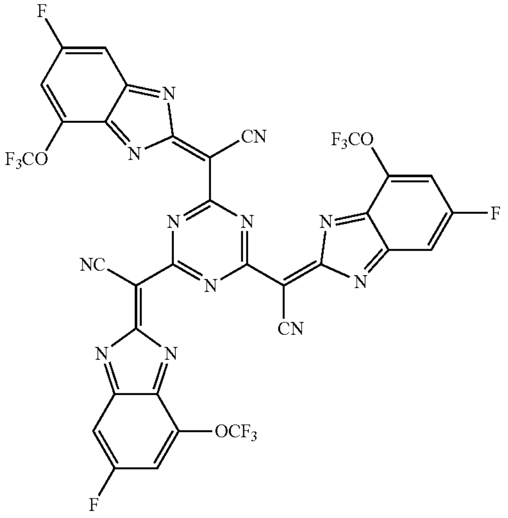
61
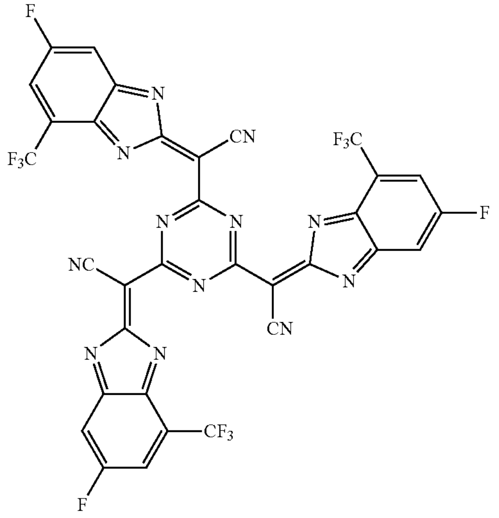
-continued
62
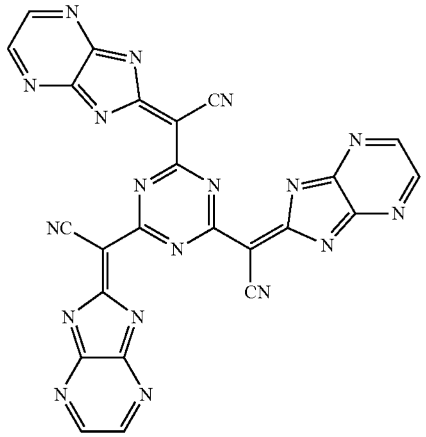
63
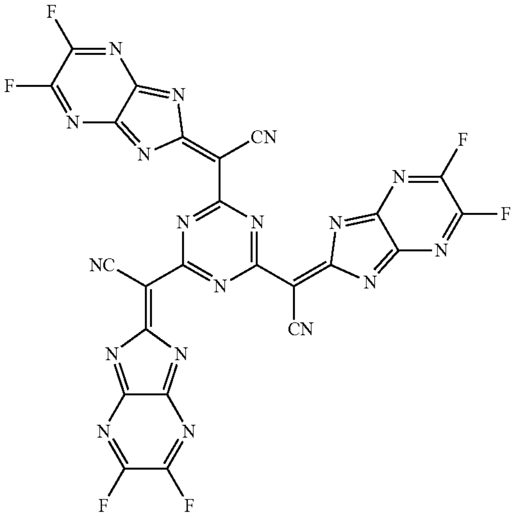
64
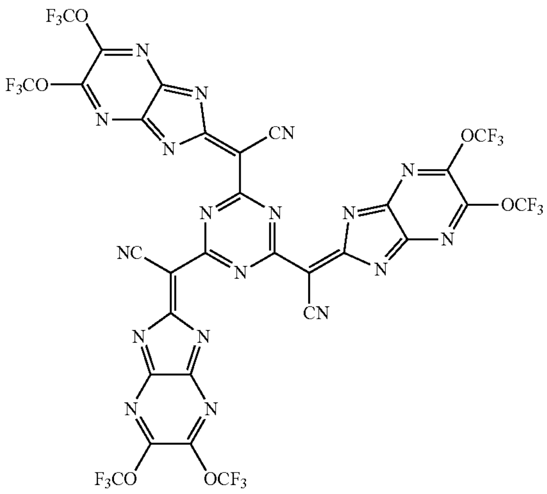

-continued
65
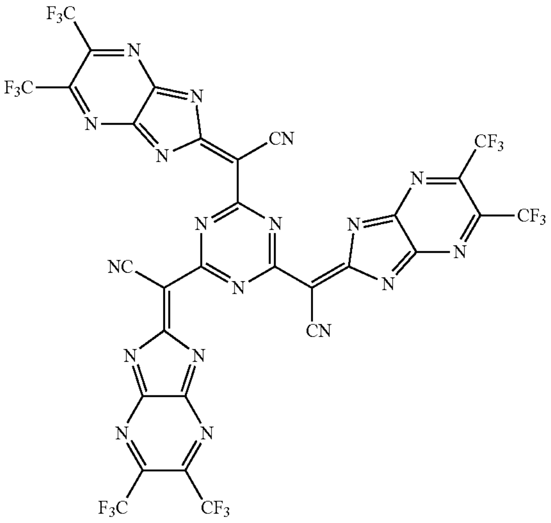
66
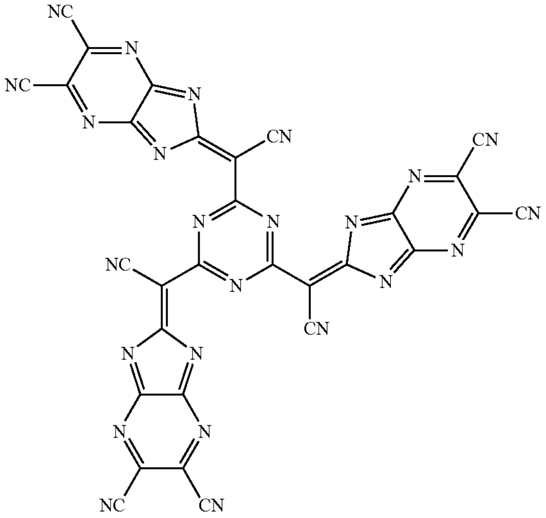
67
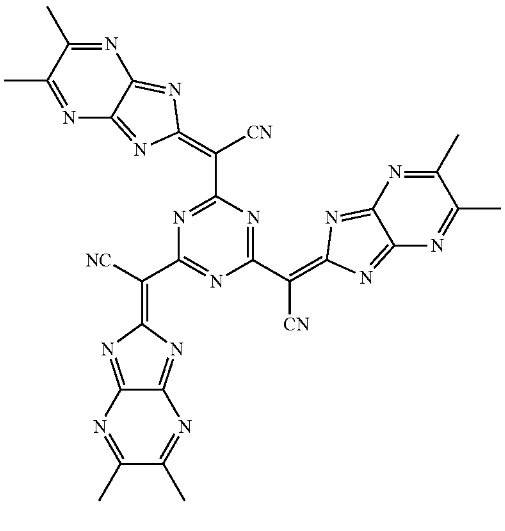
-continued
68
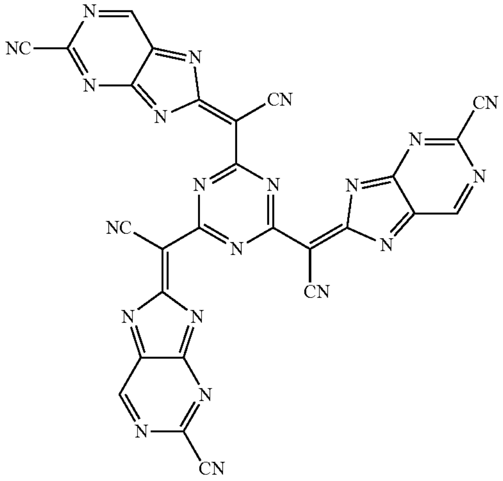
69
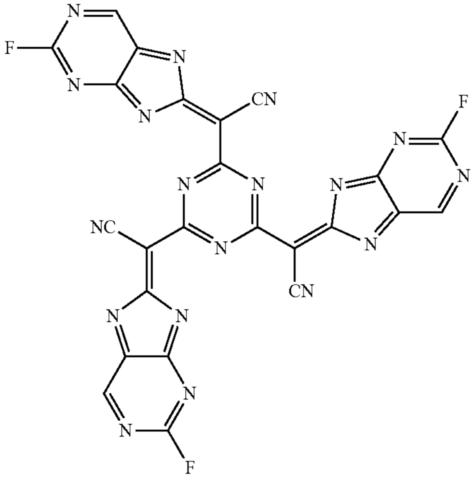
70
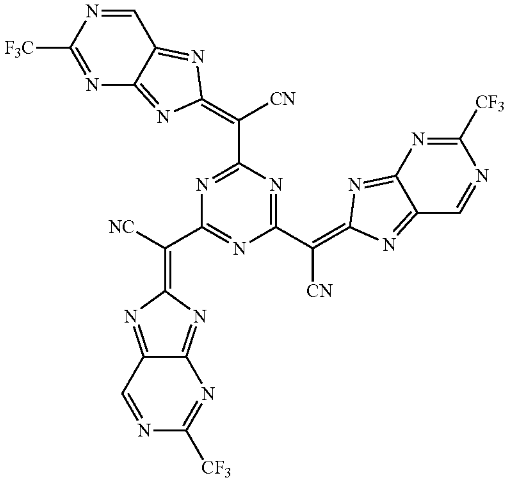

-continued
71
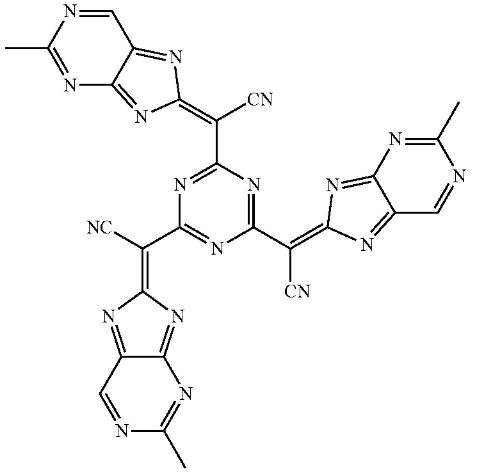
72
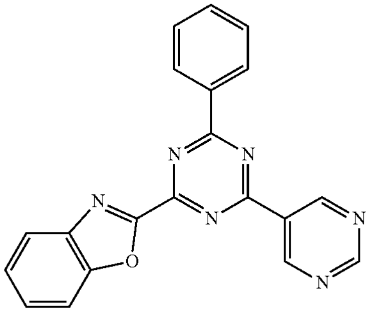
73
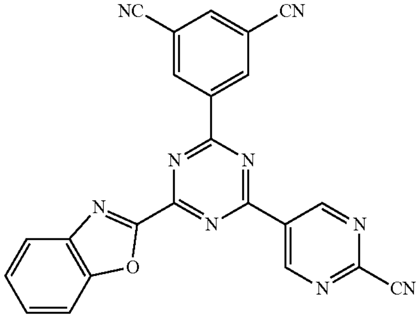
74
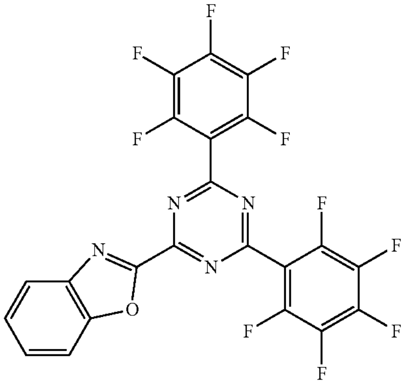
-continued
75
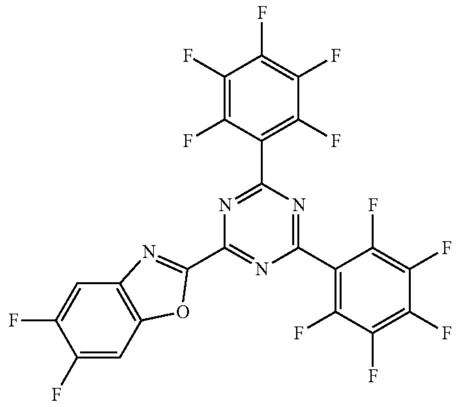
76
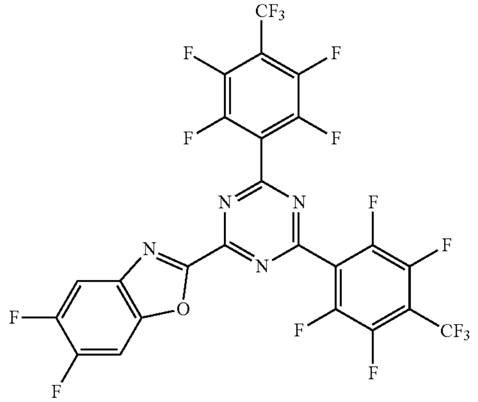
77
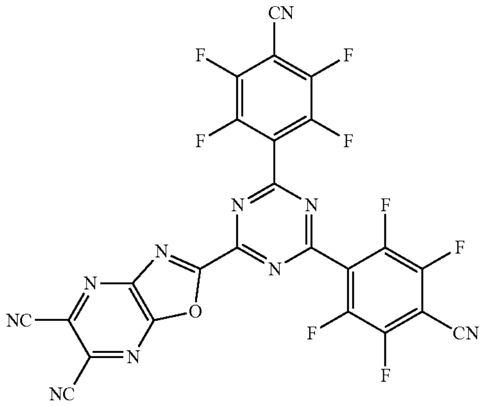
78
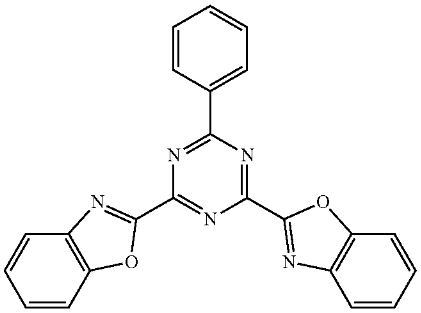

-continued
79
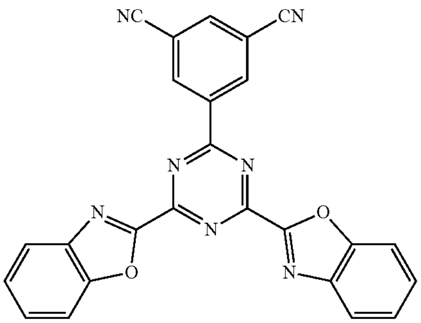
80
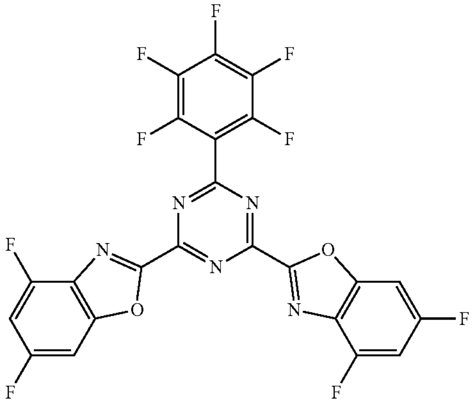
81
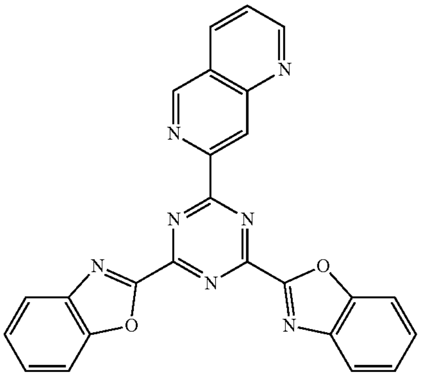
82
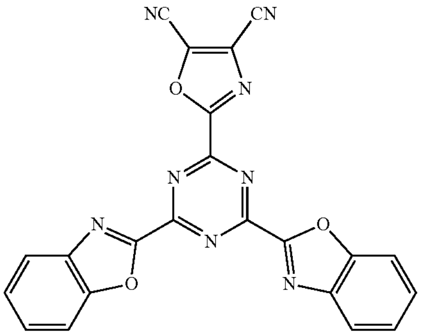
-continued
83
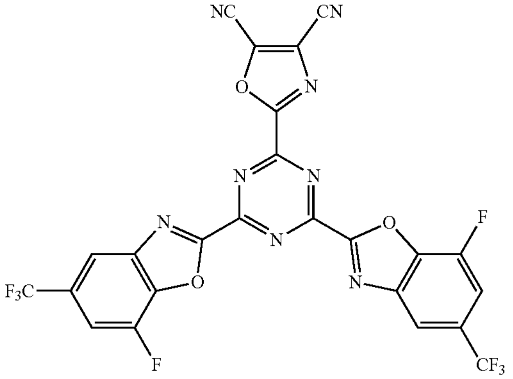
84
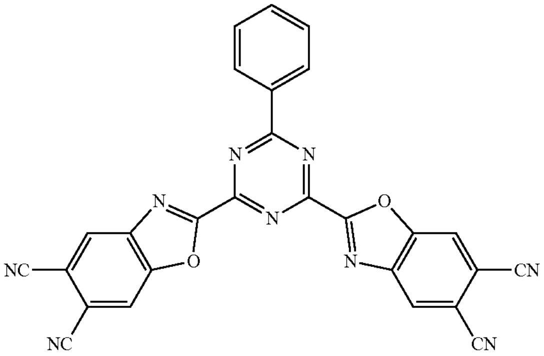
85
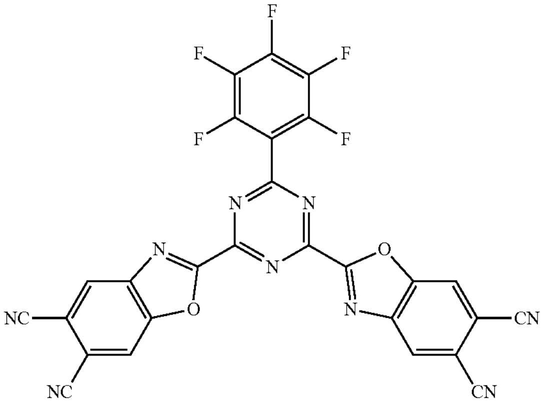
86
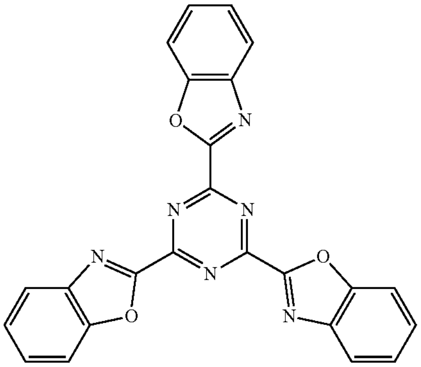

-continued
87
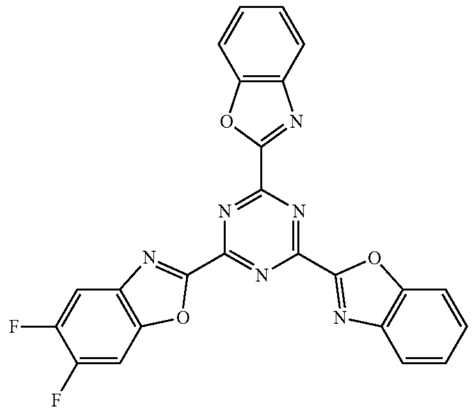
88
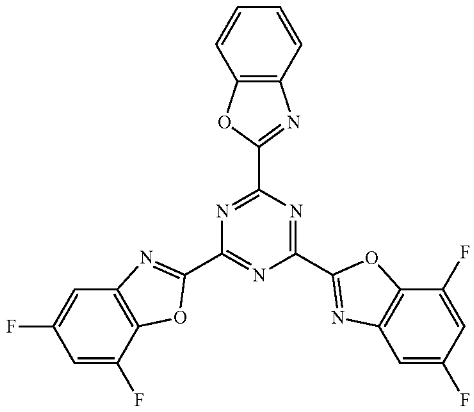
89
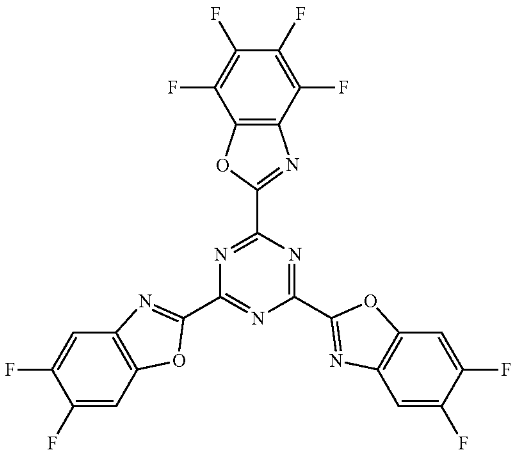
-continued
90
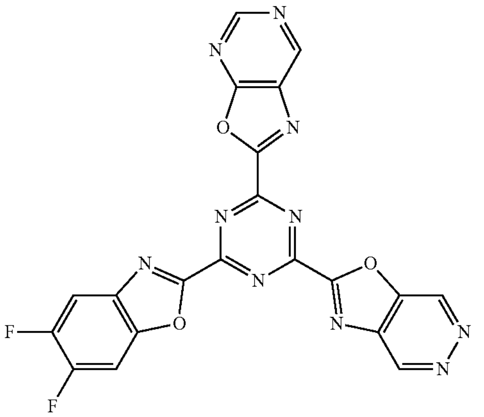
91
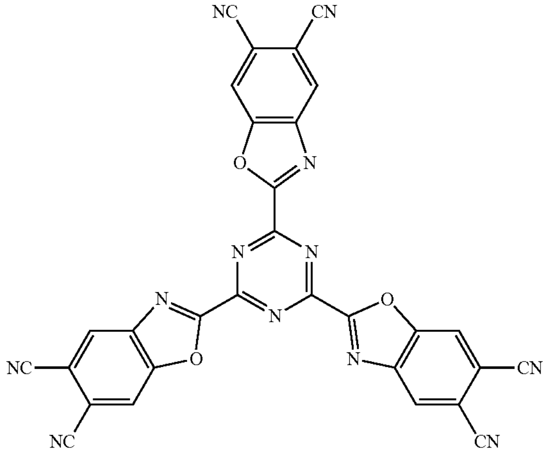
92
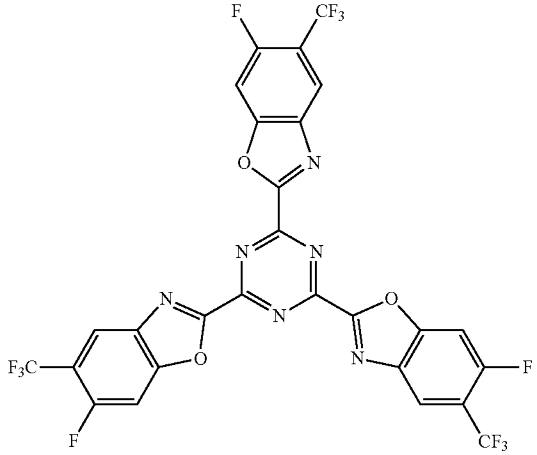

93
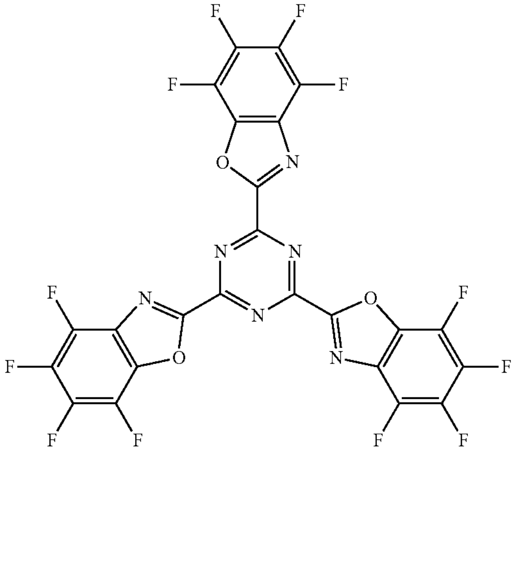
94
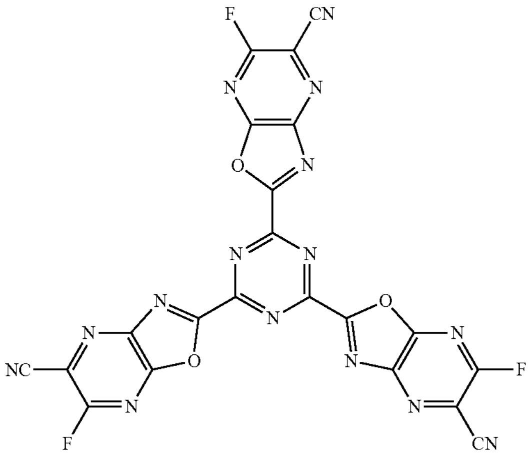
95
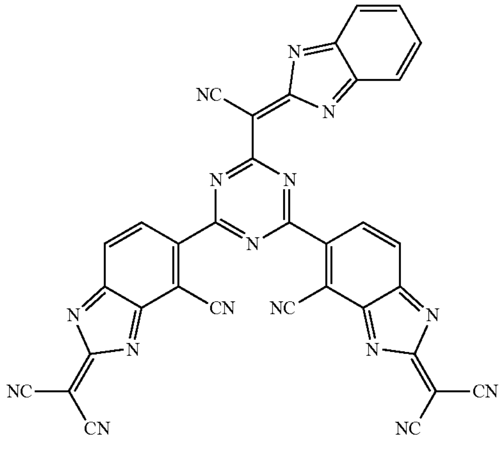
96
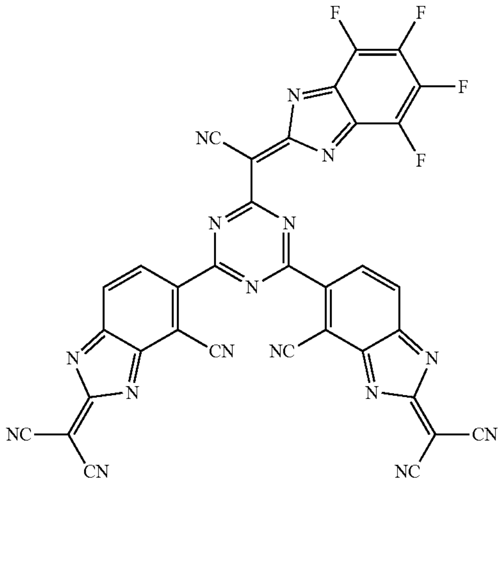
97
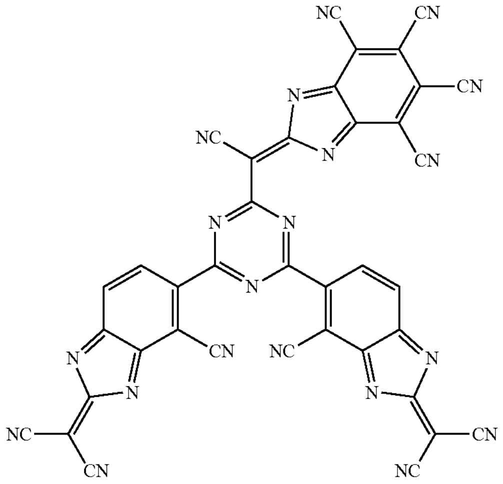
98
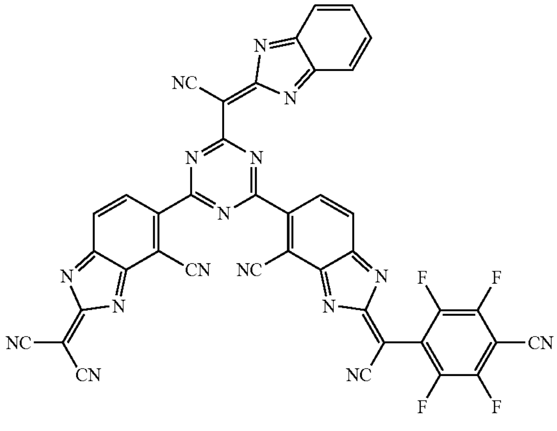

-continued
99
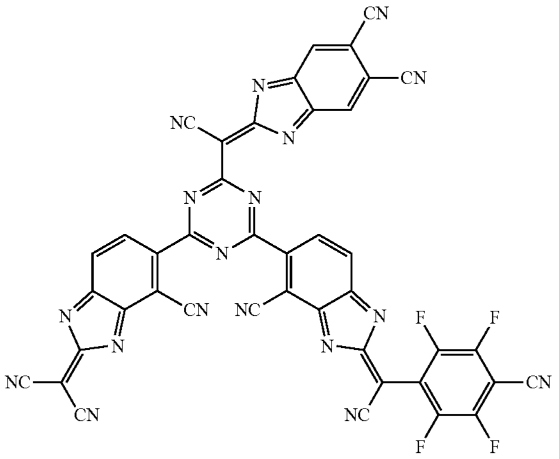
100
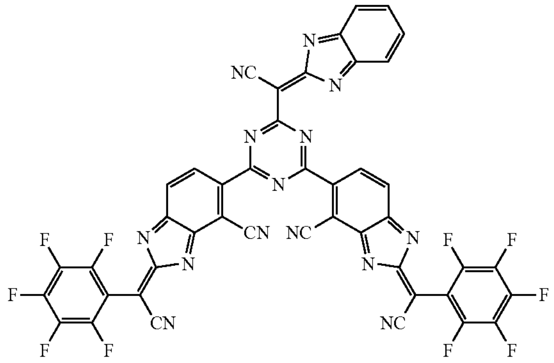
101
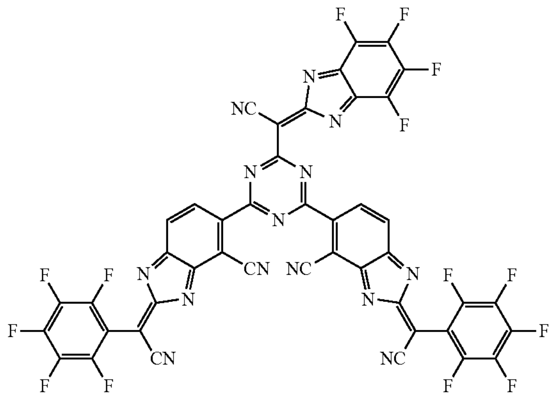
-continued
102
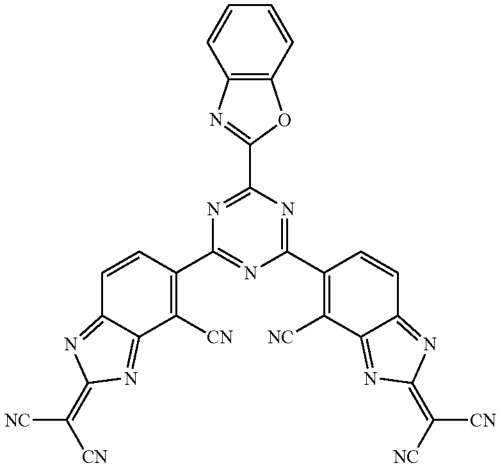
103
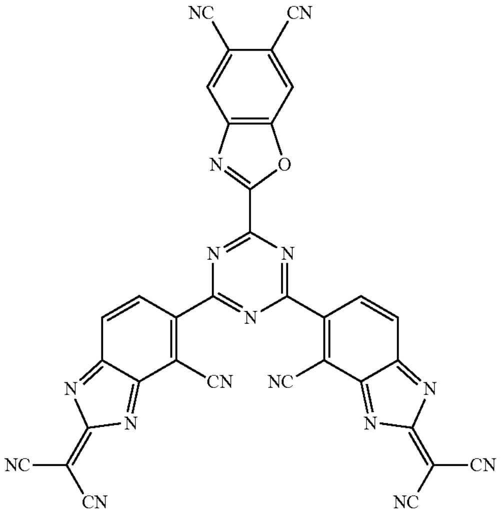
104
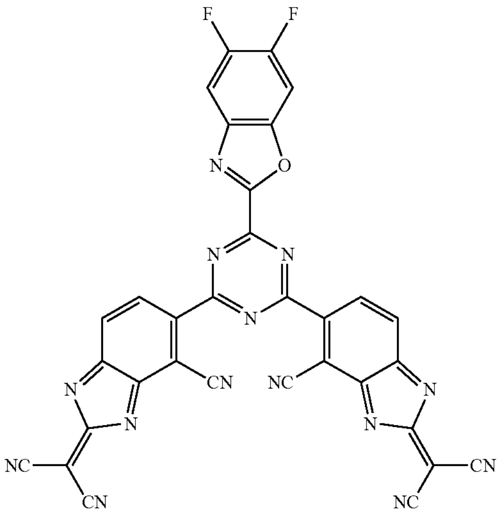

-continued
105
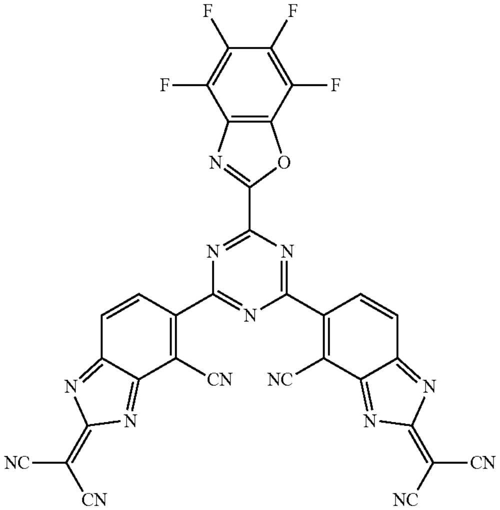
106
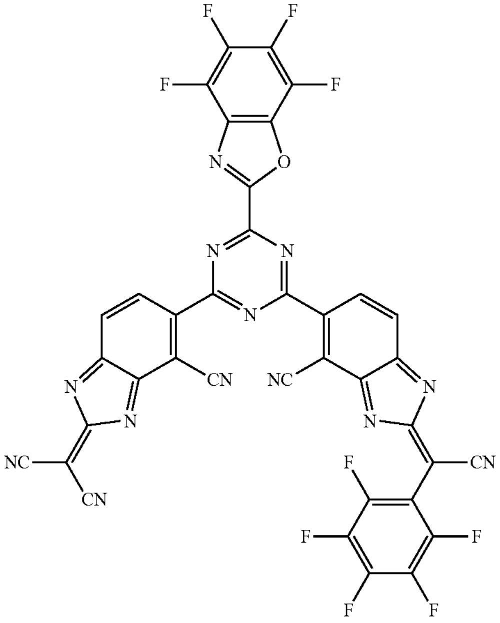
107
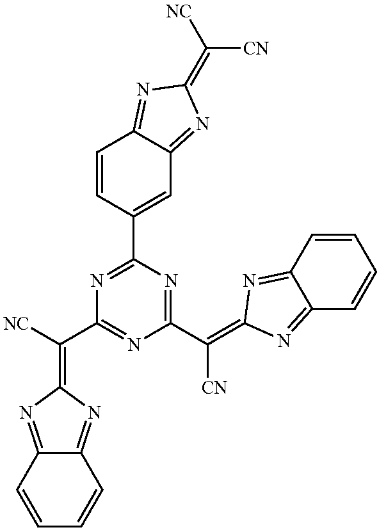
-continued
108
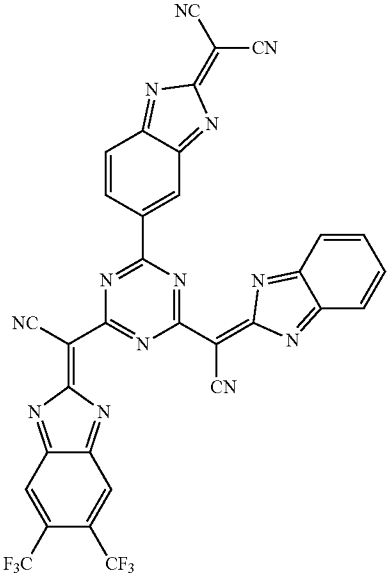
109
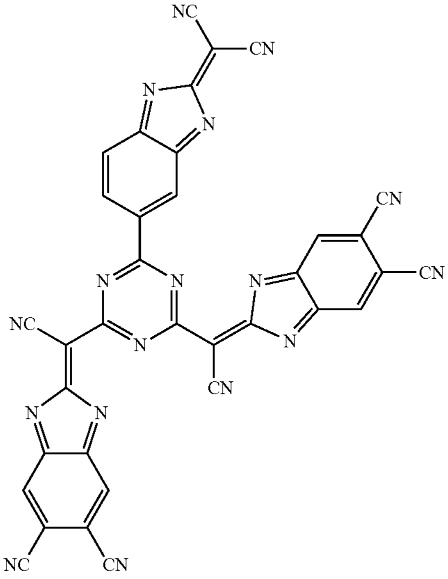

-continued
110
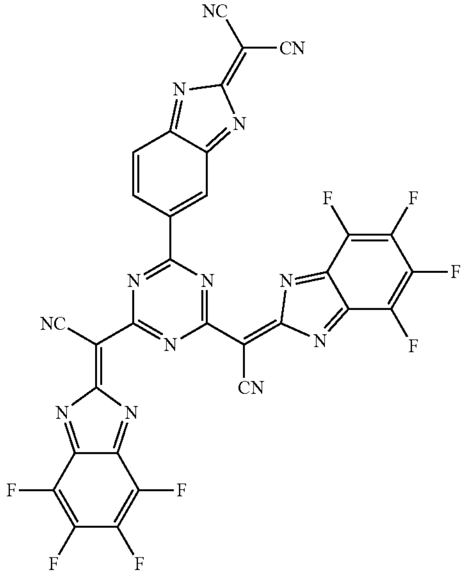
111
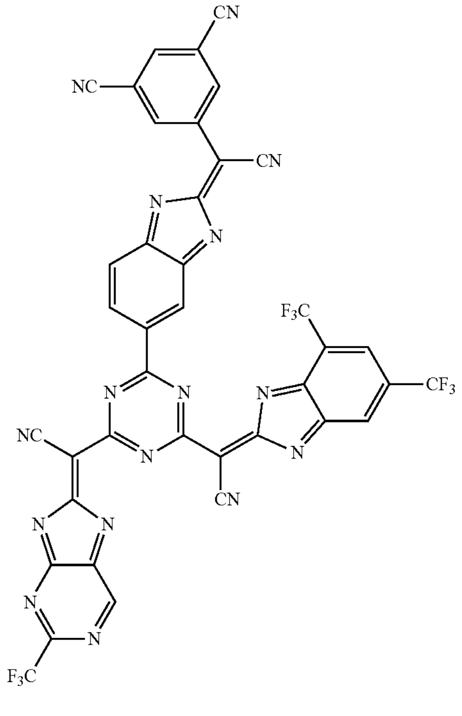
-continued
112
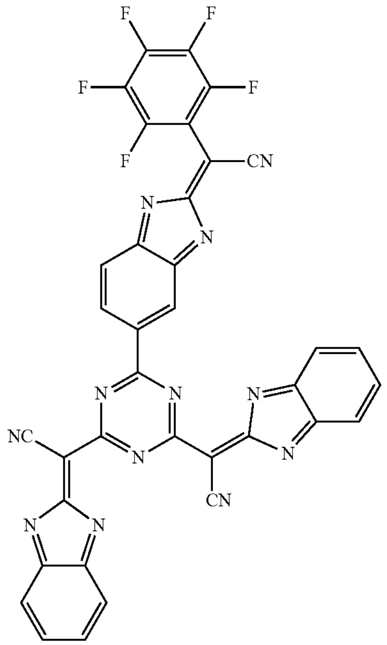
113
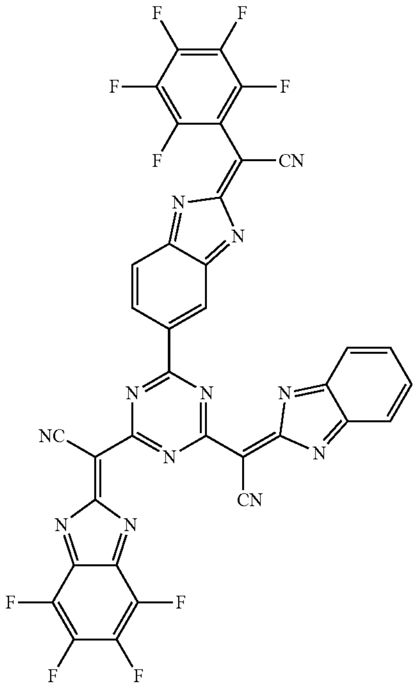

-continued
114
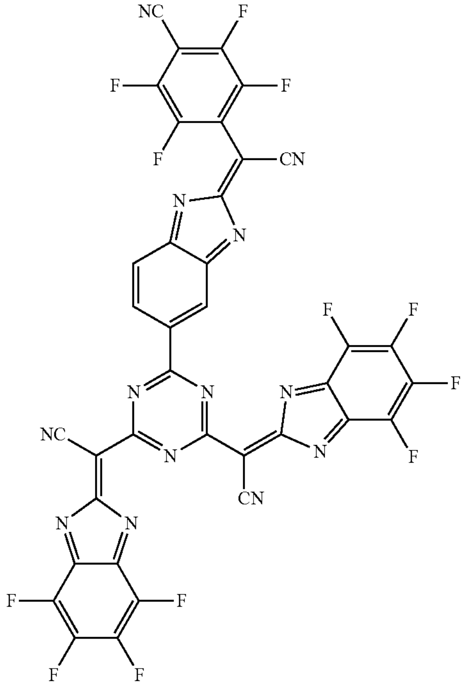
115
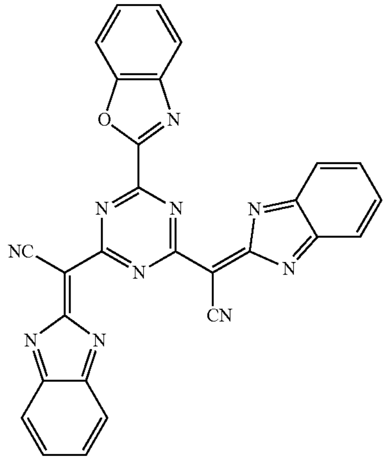
116
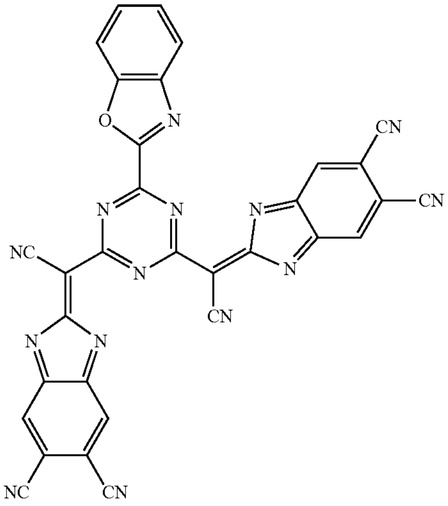
-continued
117
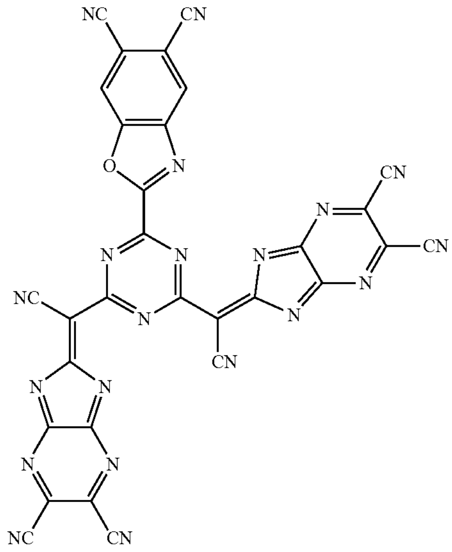
118
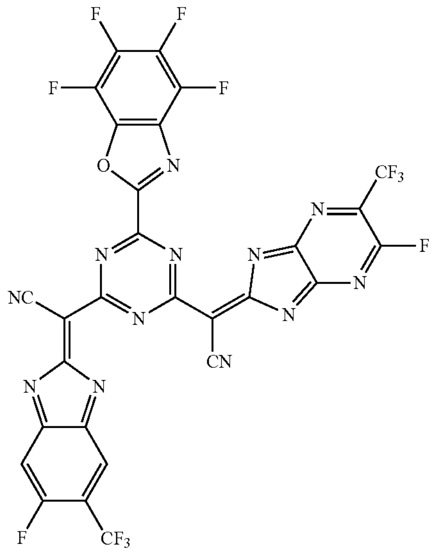
119
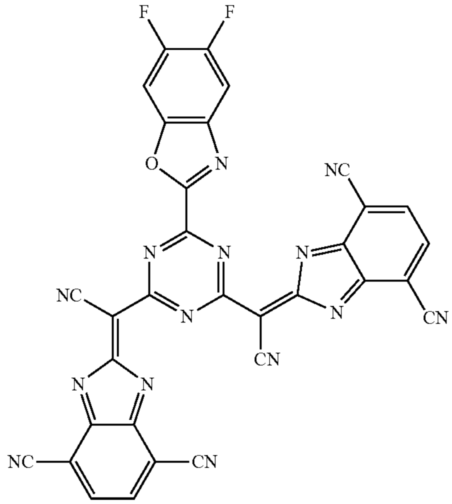

-continued
120
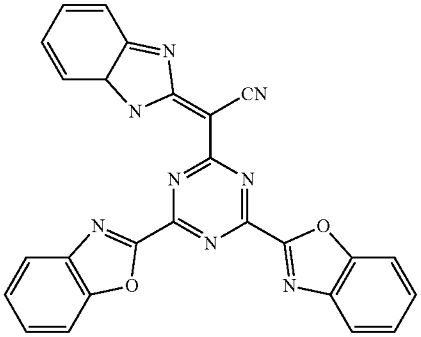
121
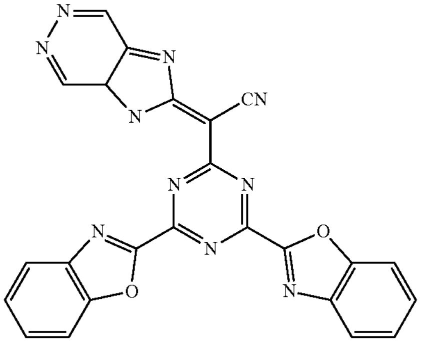
122
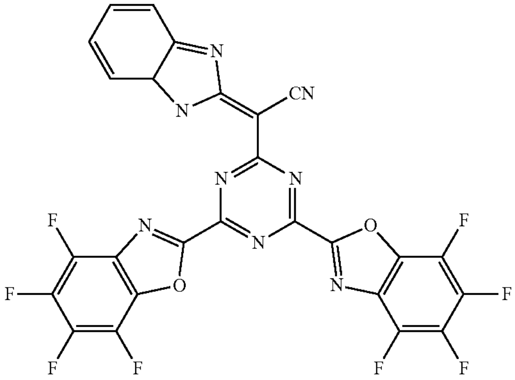
123
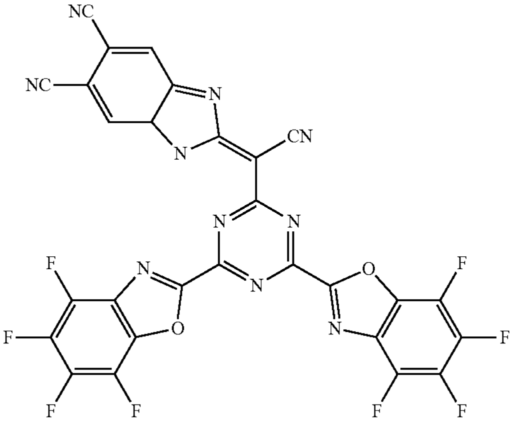
-continued
124
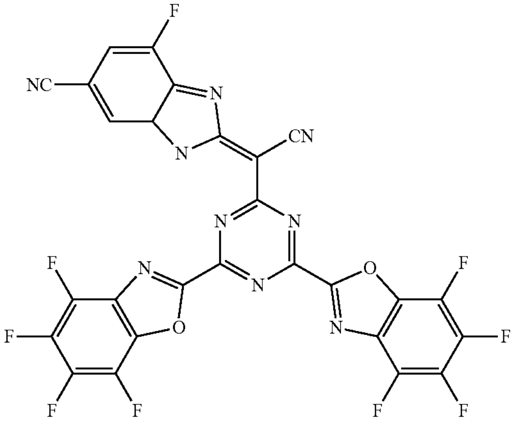
125
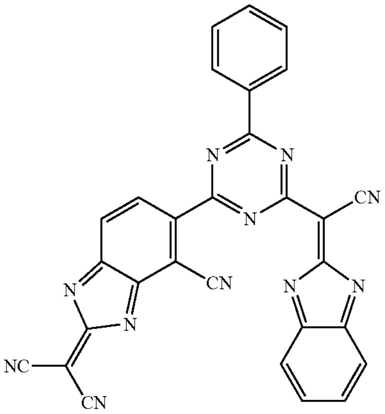
126
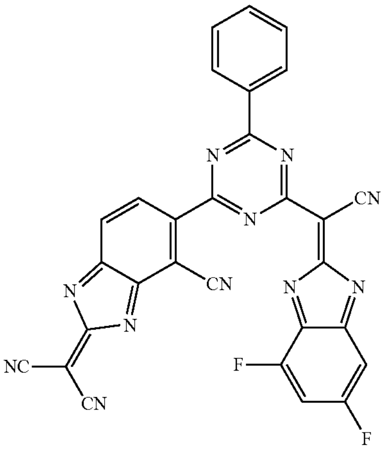

-continued
127
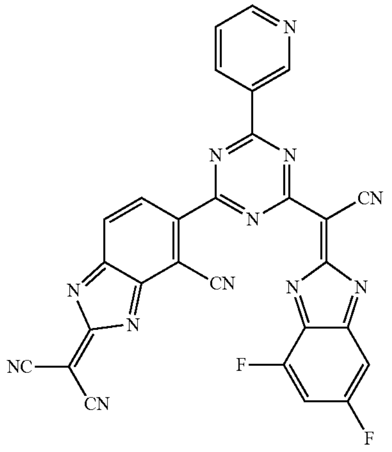
128
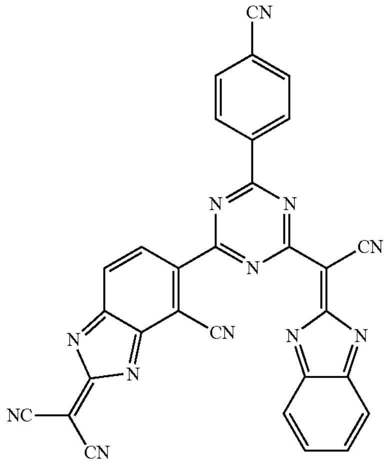
129
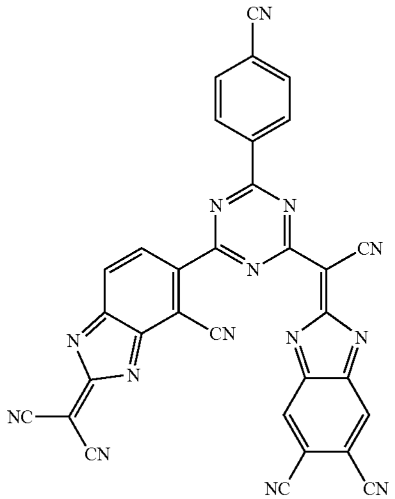
-continued
130
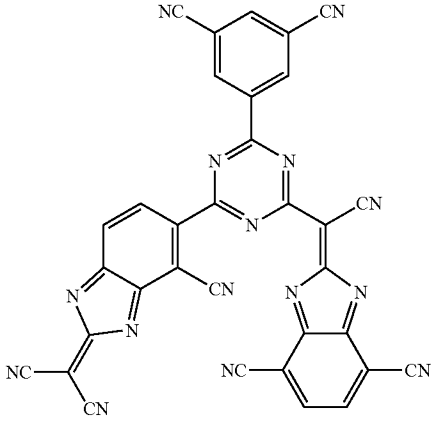
131
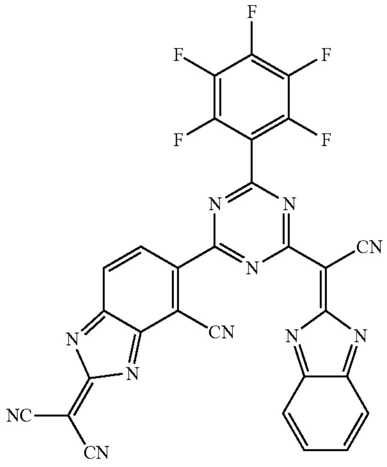
132
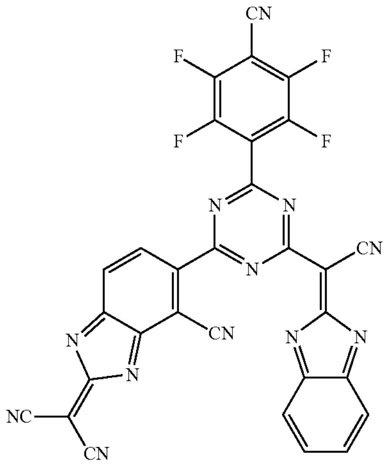

-continued
133
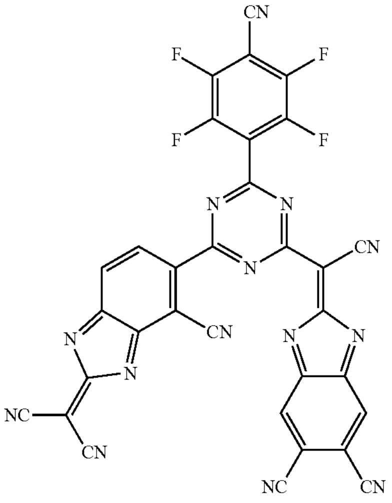
134
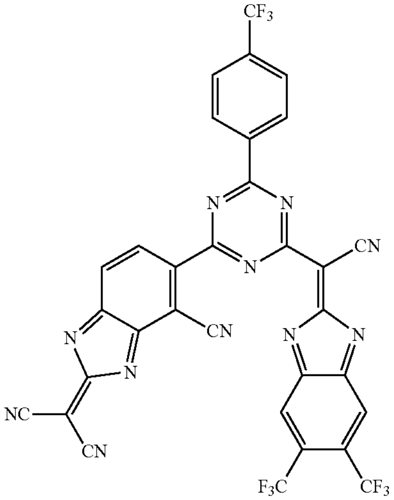
135
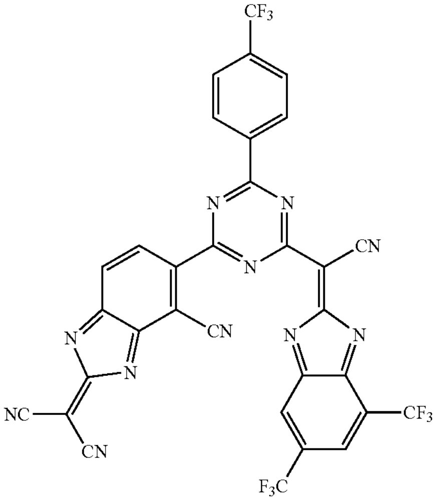
-continued
136
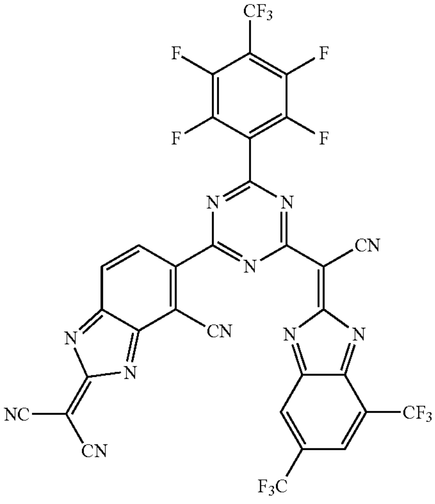
137
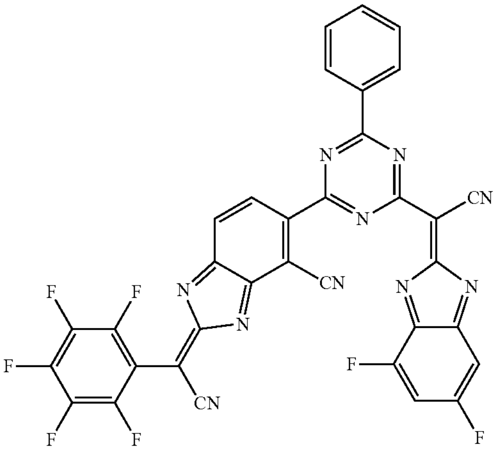
138
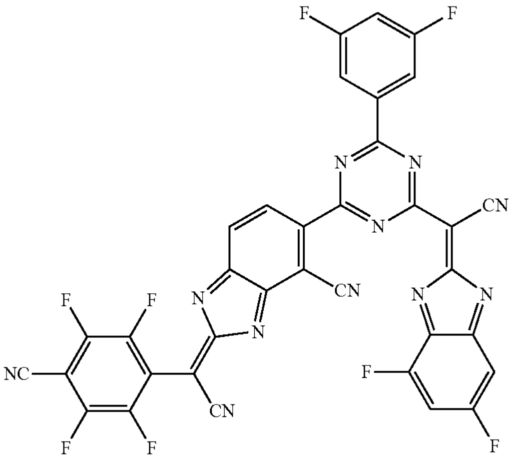

-continued
139
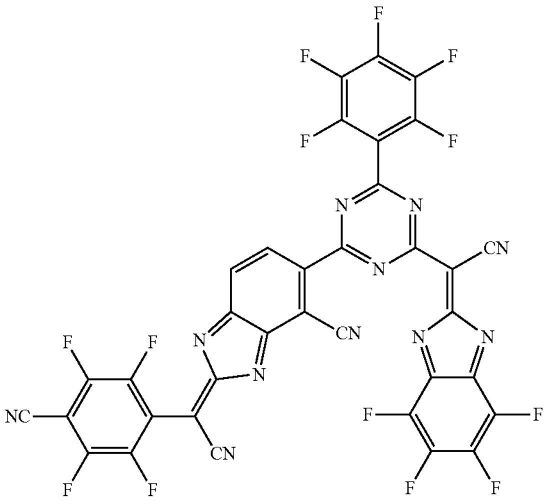
140
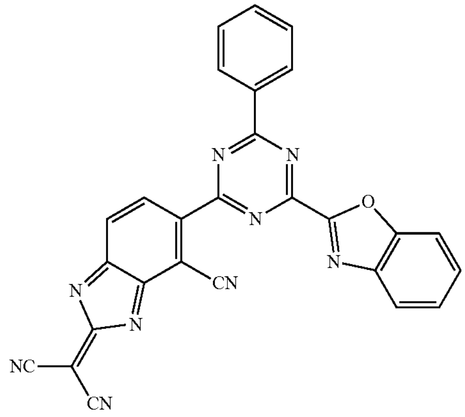
141
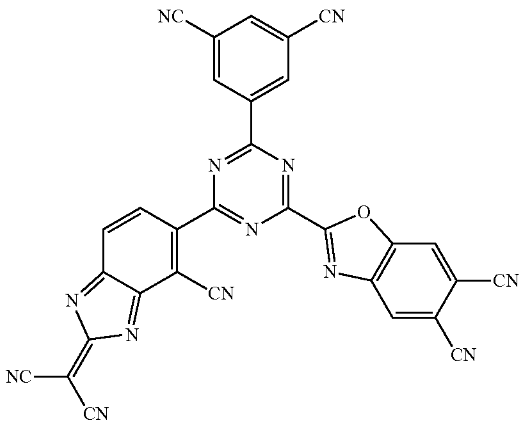
-continued
142
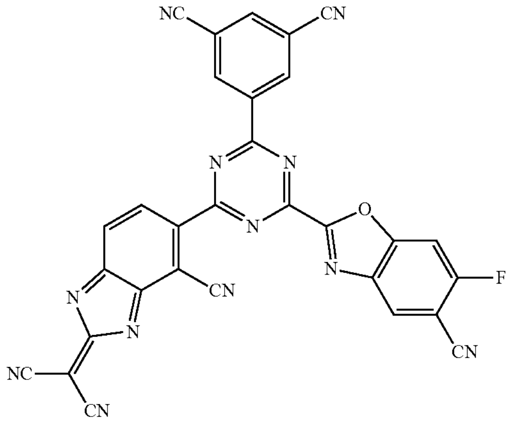
143
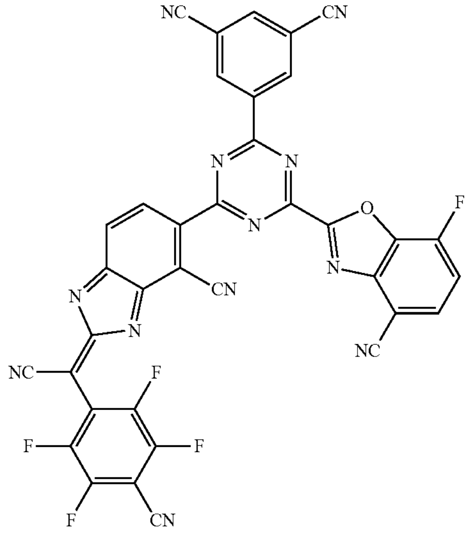
144
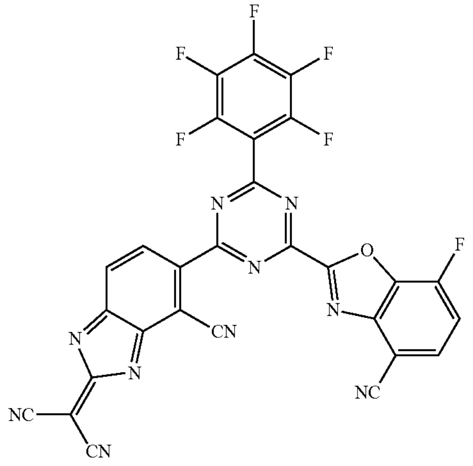

-continued
145
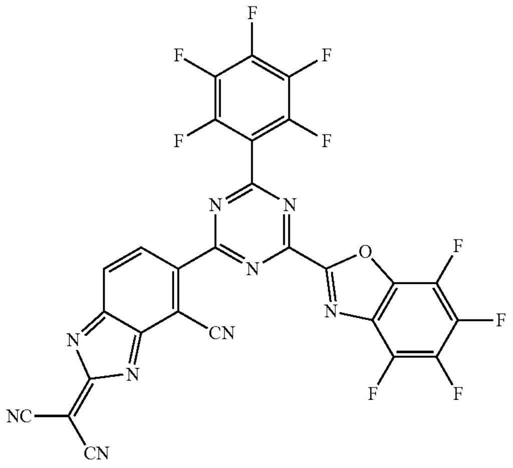
146
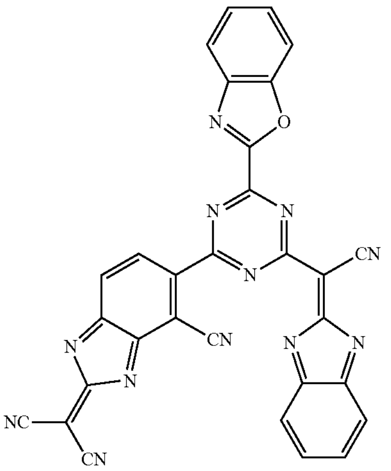
147
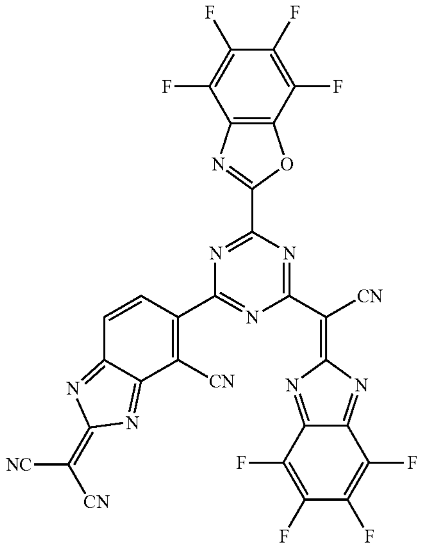
-continued
148
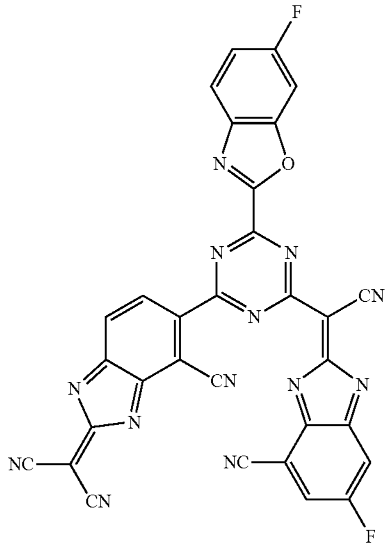
149
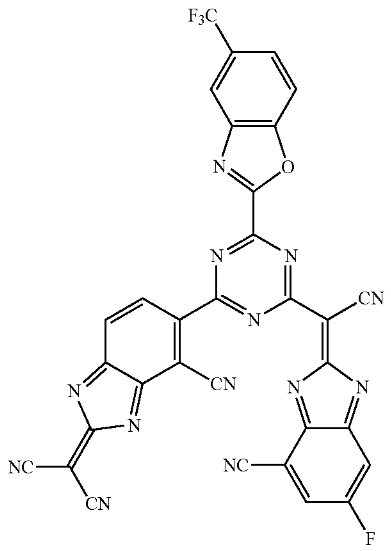
150
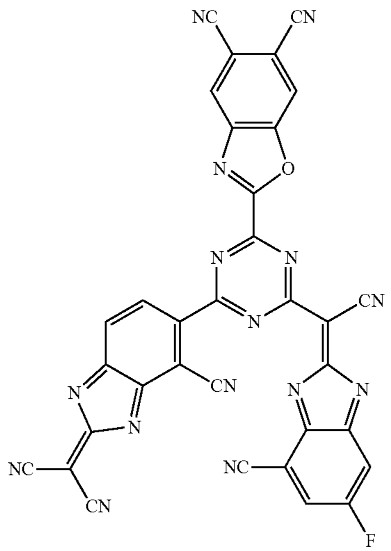

-continued
151
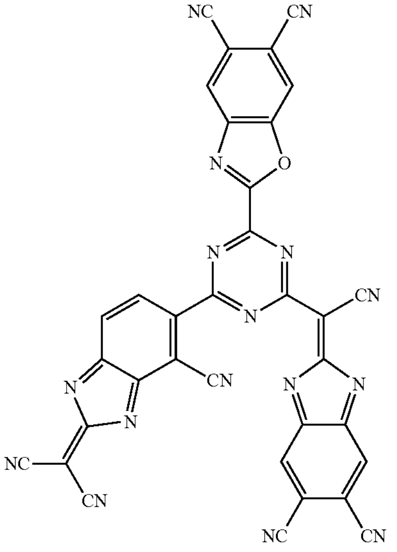
152
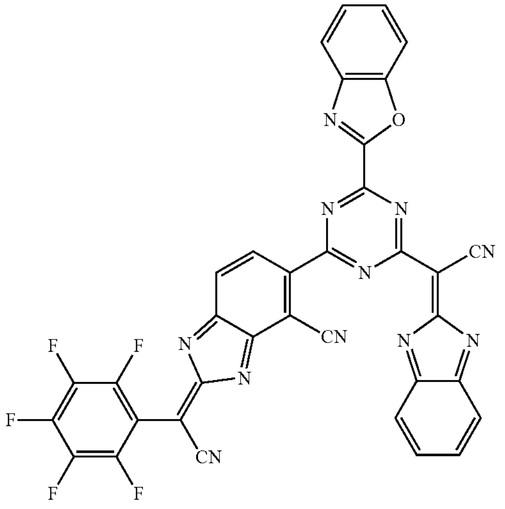
153
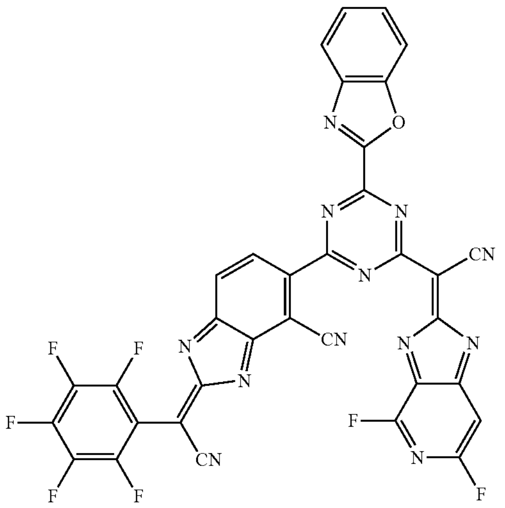
-continued
154
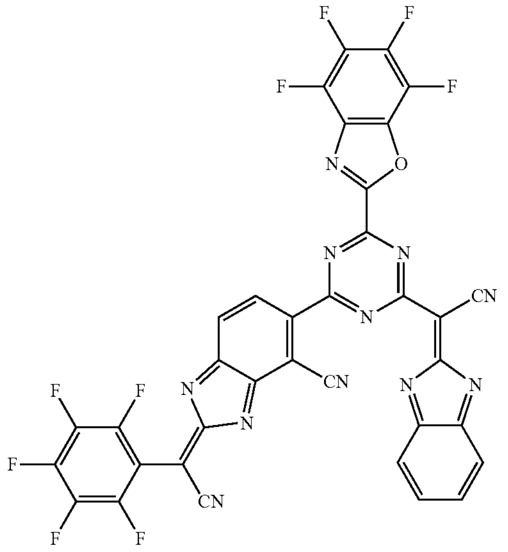
155
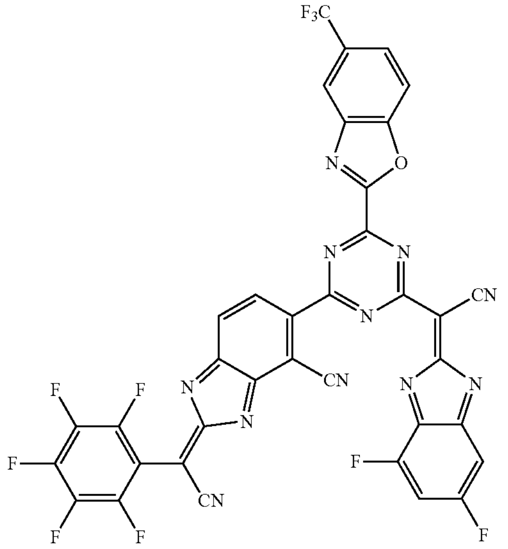
156
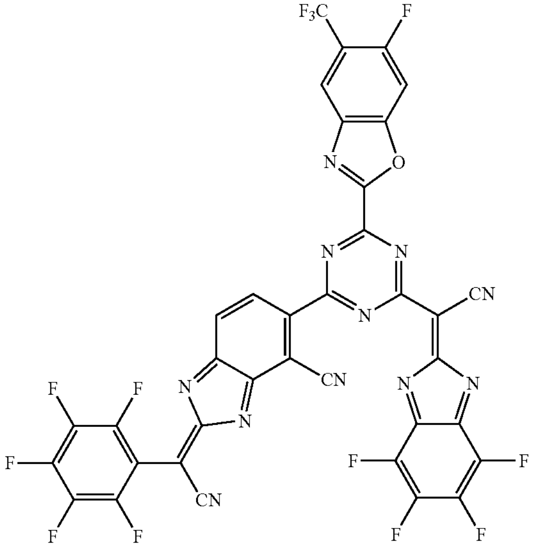

-continued
157
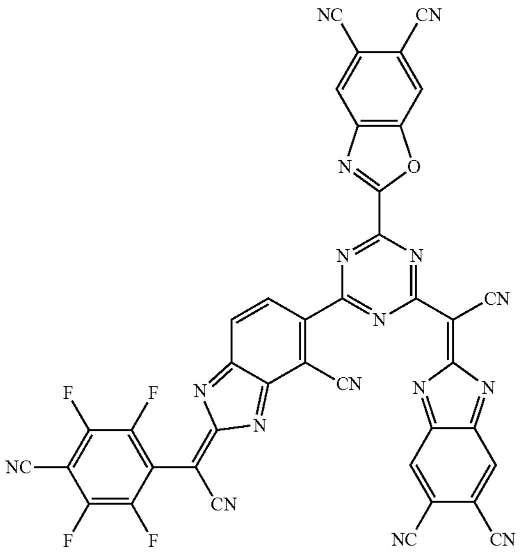
158
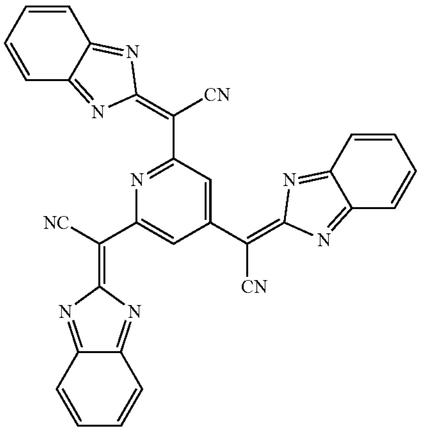
159
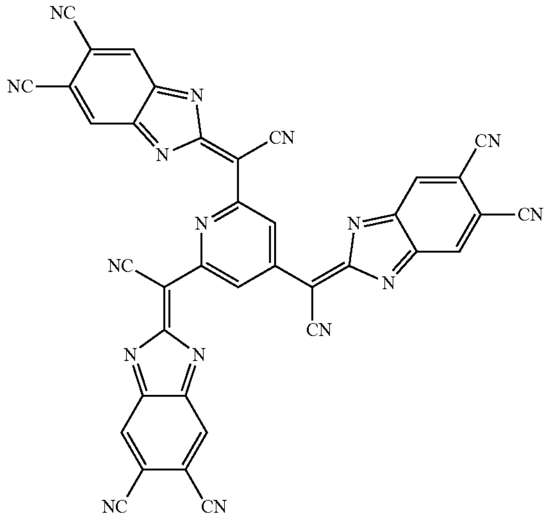
-continued
160
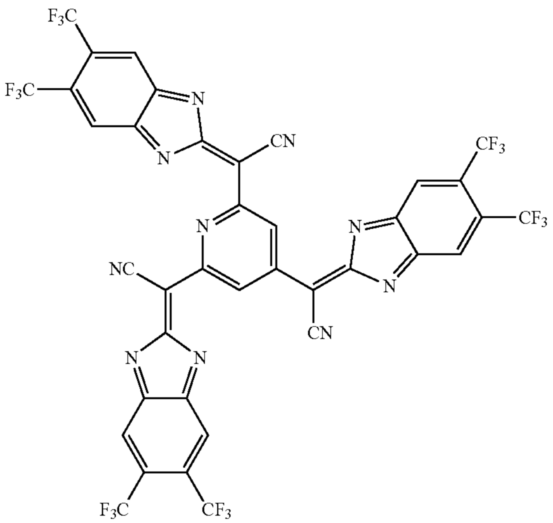
161
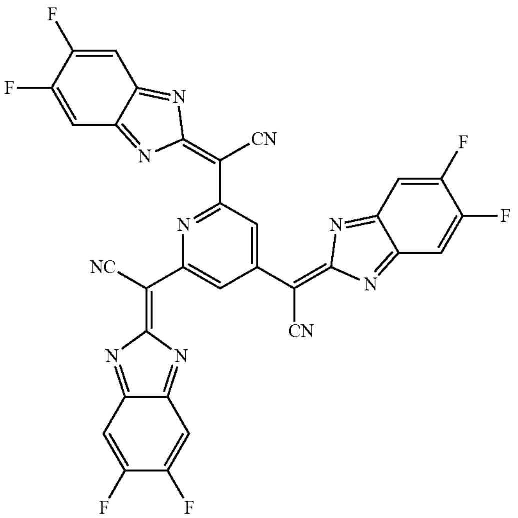
162
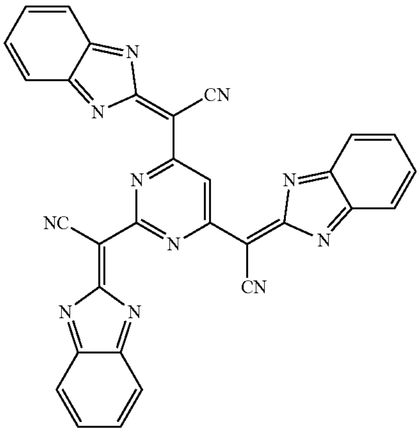

-continued
163
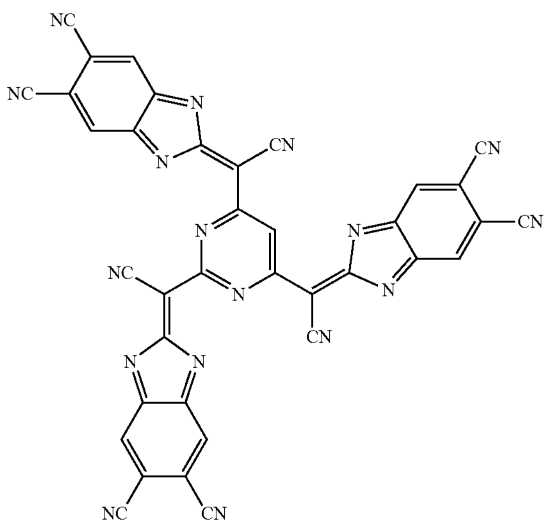
164
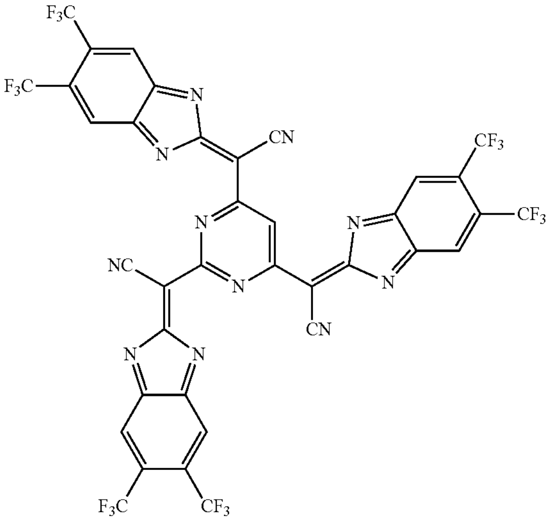
165
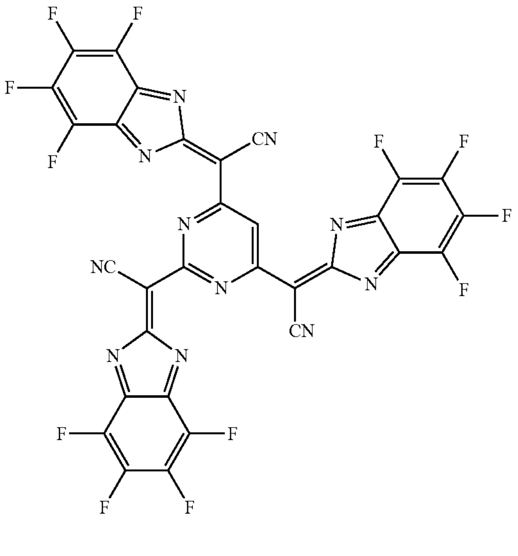
-continued
166
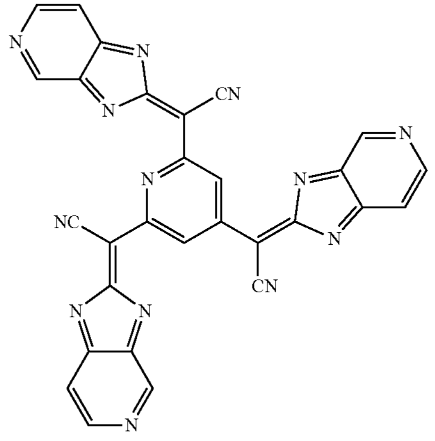
167
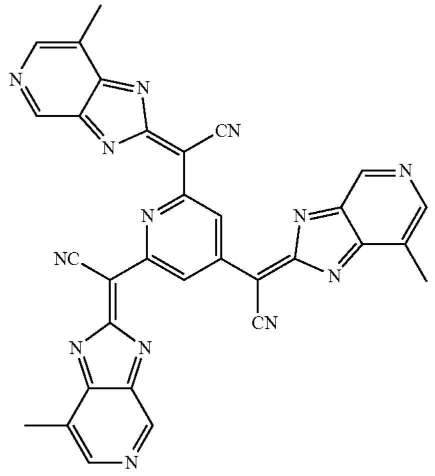
168
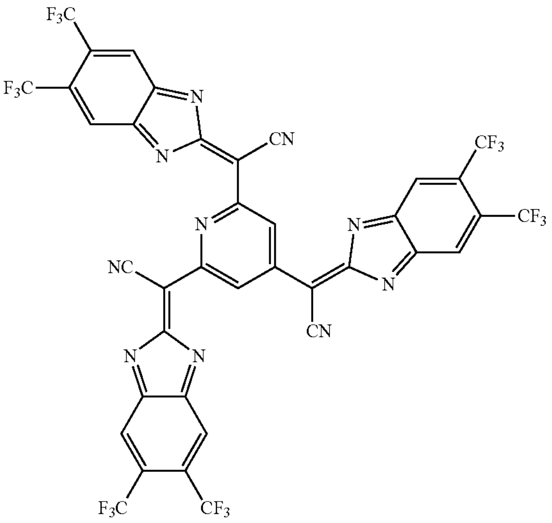

-continued
169
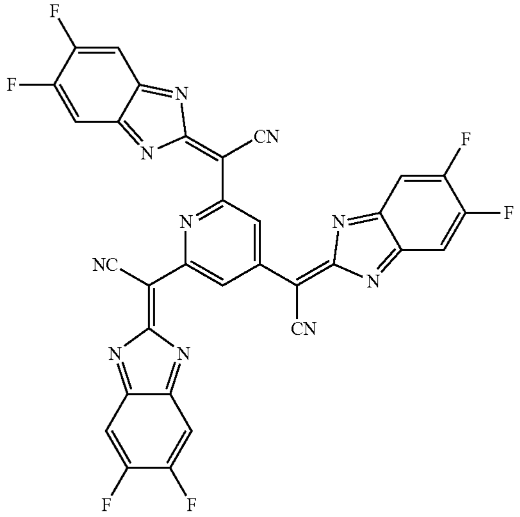
170
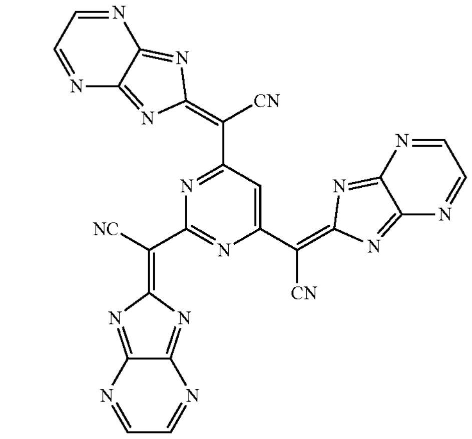
171
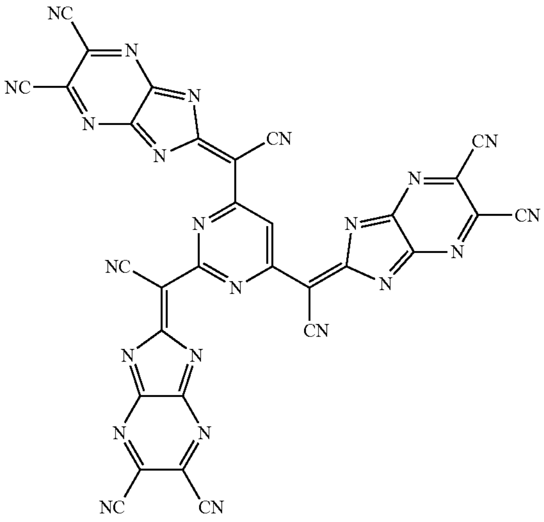
-continued
172
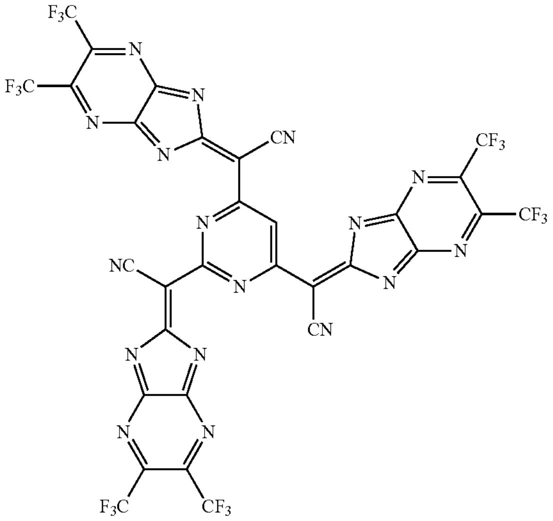
173
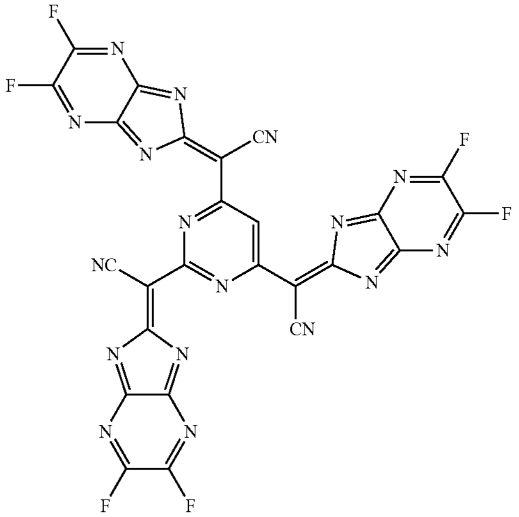
174
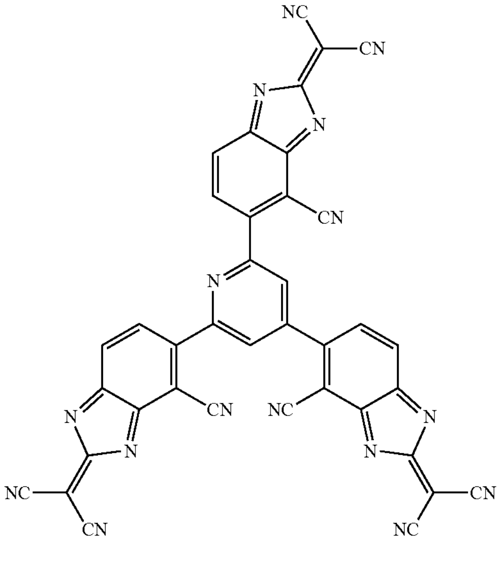

-continued
175
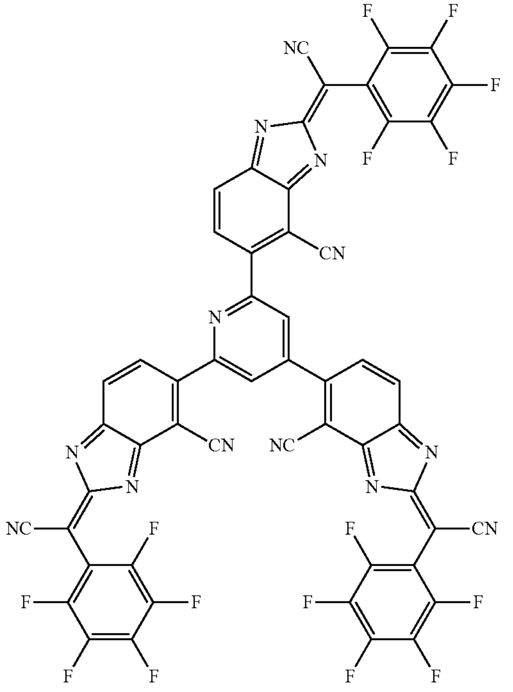
176
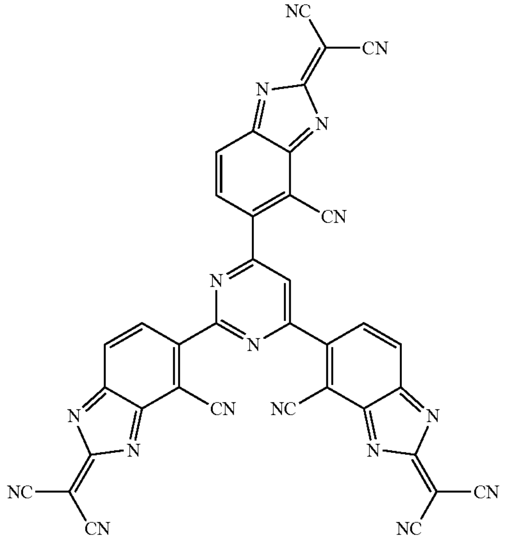
-continued
177
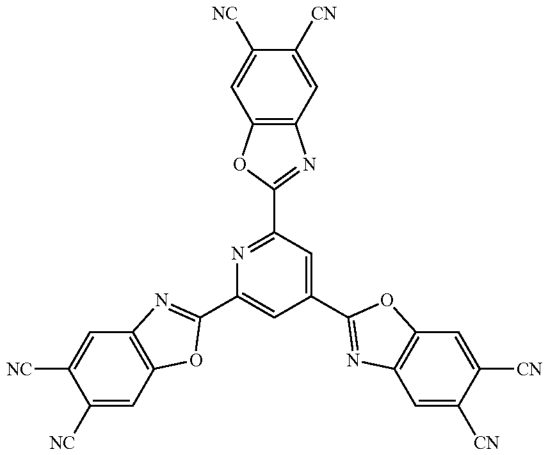
178
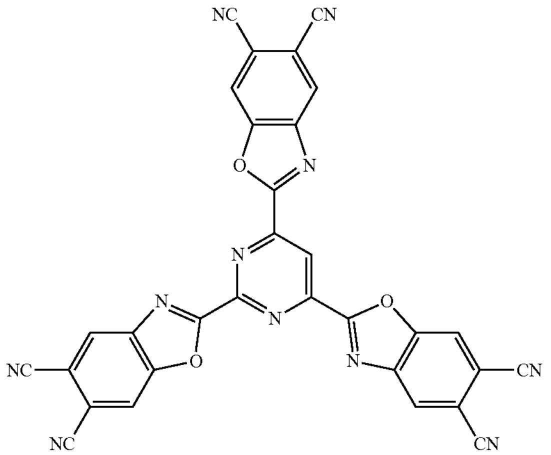
[Synthesis of Organic Compounds]
1. Synthesis of Compound 4
(1) Compound 4-1
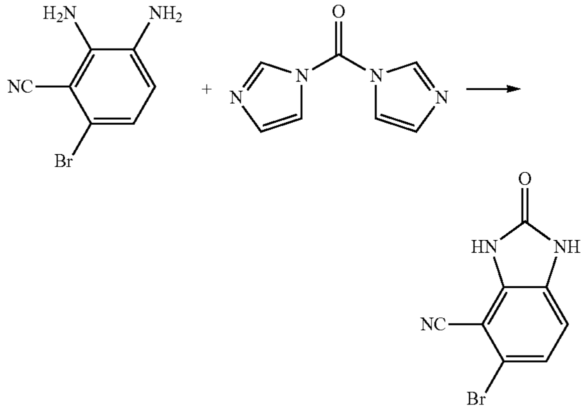
4-1
In a flask, 2,3-diamino-6-bromobenzonitrile (10 g, 0.047 mol), 1,1'-carbonyldiimidazole (9.29 g, 0.057 mol) and DMF (dimethylformamide, 200 ml) were stirred and reacted under the room temperature for 24 hrs. After completion of reaction, the resultant was extracted and re-crystalized to obtain the compound 4-1. (8.5 g, yield=75.7%)

(2) Compound 4-2

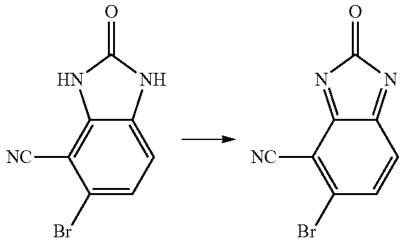

4-1 4-2

The compound 4-1 (10 g, 0.042 mol), potassium hydroxide (11.79 g, 0.210 mol), $H_2O$ (20 ml), and 1,4-dioxane (400 ml) were put into a flask. After $K_3Fe(CN)_6$ (41.49 g, 0.126 mol) and $H_2O$ (420 ml) was added, the mixture was stirred and reacted at 100° C. for 12 hrs. After completion of reaction, the resultant was extracted and column-refined to obtain the compound 4-2. (5 g, yield=33.7%)

(3) Compound 4-3

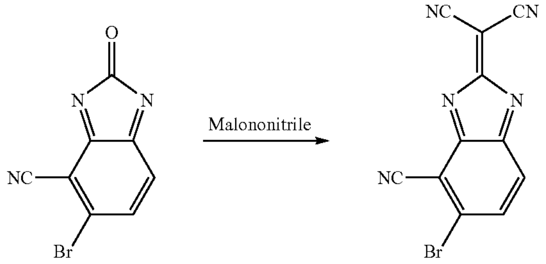

4-2 4-3

The compound 4-2 (10 g, 0.042 mol), malononitrile (4.2 g, 0.063 mol) and methylene chloride (300 ml) were put into a flask and cooled in an ice-bath. $TiCl_4$ (12.05 g, 0.063 mol) was slowly dropped, and pyridine (10.5 g, 0.127 mol) was very slowly added. After 1 hr, the ice-bath was removed. The mixture was stirred and reacted for 24 hrs. After completion of reaction, the resultant was extracted using hydrochloric acid aqueous solution and column-refined to obtain the compound 4-3. (7.6 g, yield=61.9%)

(4) Compound 4-4

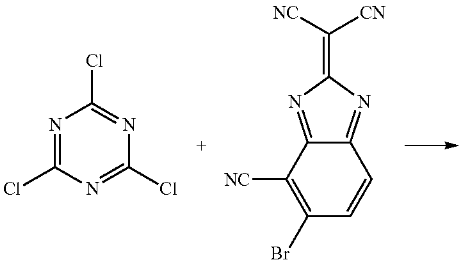

4-3

-continued

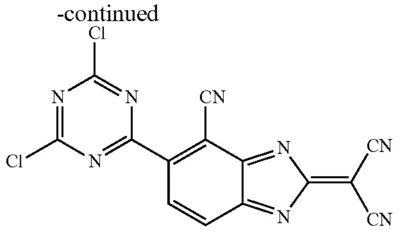

4-4

In a flask, magnesium (1.85 g, 0.076 mol), iodine ($I_2$) (0.83 g, 0.003 mol) and THE (tetrahydrofuran, 15 ml) were stirred, and the compound 4-3 (18.52 g, 0.065 mol) dissolved in THF (100 ml) was slowly added. The mixture was refluxed/stirred and reacted for 1 hr. After completion of reaction, the mixture was cooled into the room temperature to obtain the Grignard reagent. In another flask, 2,4,6-trichloro-1,3,5-triazine (10 g, 0.054 mol) and THF (100 ml) were added, and the mixture was cooled into 0° C. Grignard reagent was added into the mixture, and the mixture was stirred and reacted under the room temperature for 2 hrs. After completion of reaction, cool water was added at 0° C. to finish the reaction. The solid product was filtered and column-refined to obtain the compound 4-4. (9.8 g, yield=51.1%)

(5) Compound 4

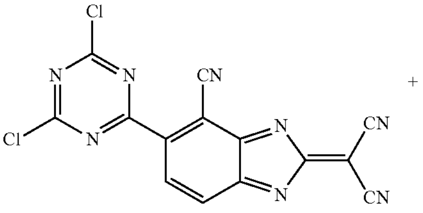

4-4

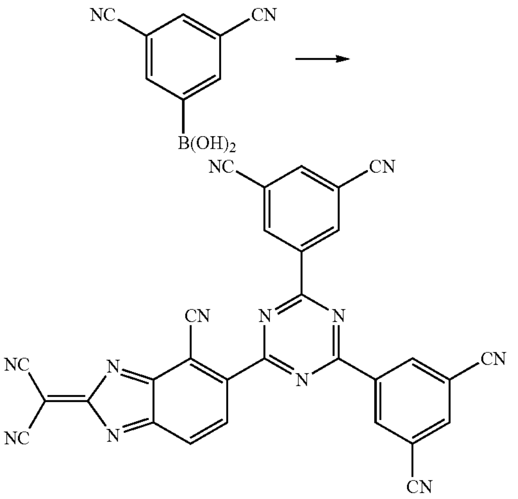

4

In a flask, the compound 4-4 (10 g, 0.028 mol), 3,5-dicyanophenylboronic acid (11.20 g, 0.065 mol), potassium carbonate (19.57 g, 0.141 mol), $Pd(PPh_3)_4$ (1.64 g, 0.0014 mol), toluene (200 ml), ethanol (40 ml) and $H_2O$ (20 ml) were refluxed/stirred and reacted for 8 hrs. After completion of reaction, the resultant was extracted and column-refined to obtain the compound 4. (10 g, yield=65.8%)

H-NMR (200 MHz, $CDCl_3$): δ ppm, 2H (8.79/s) 1H (7.99/d, 6.5/d) 2H (7.47/s) 4H (8.01/s), LC/MS: m/z=536 $[(M+1)^+]$ 2. Synthesis of Compound 17

(1) Compound 17-1

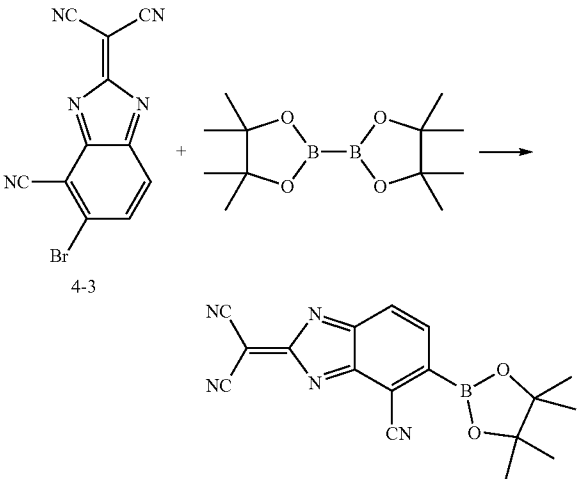

4-3

17-1

In a flask, the compound 4-3 (10 g, 0.035 mol), bis(pinacolato)diboron (11.62 g, 0.045 mol), potassium acetate (6.91 g, 0.070 mol), $PdCl_2(dppf)$ (0.77 g, 0.001 mol) and 1,4-dioxane (200 ml) were stirred and reacted at 95° C. for 12 hrs. After completion of reaction, the resultant was extracted and column-refined to obtain the compound 17-1. (8.6 g, yield=73.7%)

(2) Compound 17-2

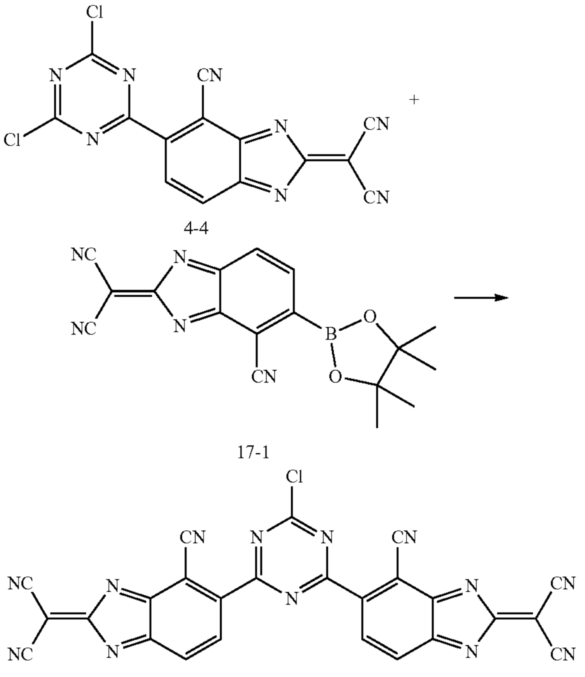

4-4

17-1

17-2

In a flask, the compound 4-4 (10 g, 0.028 mol), the compound 17-1 (10.32 g, 0.031 mol), potassium carbonate (11.74 g, 0.085 mol), $Pd(PPh_3)_4$ (1.64 g, 0.0014 mol), toluene (200 ml), ethanol (40 ml) and $H_2O$ (20 ml) were refluxed/stirred and reacted for 5 hrs. After completion of reaction, the resultant was extracted and column-refined to obtain the compound 17-2. (11.2 g, yield=74.4%)

(3) Compound 17

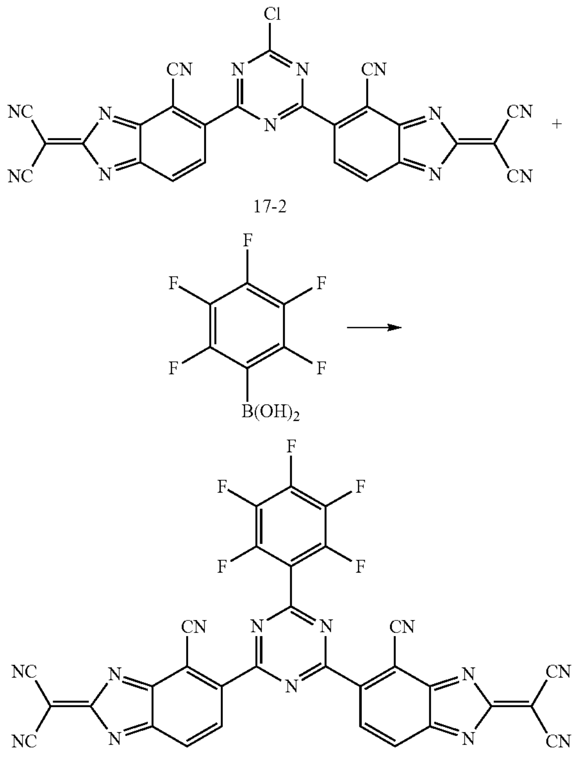

17-2

17

In a flask, the compound 17-2 (10 g, 0.019 mol), perfluorophenylboronic acid (4.47 g, 0.021 mol), potassium carbonate (7.95 g, 0.057 mol), $Pd(PPh_3)_4$ (1.11 g, 0.001 mol), toluene (200 ml), ethanol (40 ml), and $H_2O$ (20 ml) were refluxed/stirred and reacted for 7 hrs. After completion of reaction, the resultant was extracted and column-refined to obtain the compound 17. (8.0 g, yield=63.8%)

3. Synthesis of Compound 14

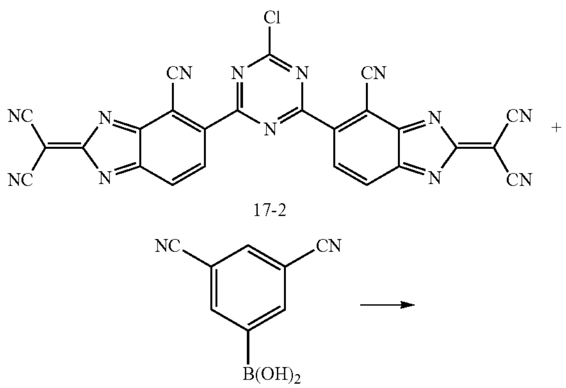

17-2

-continued

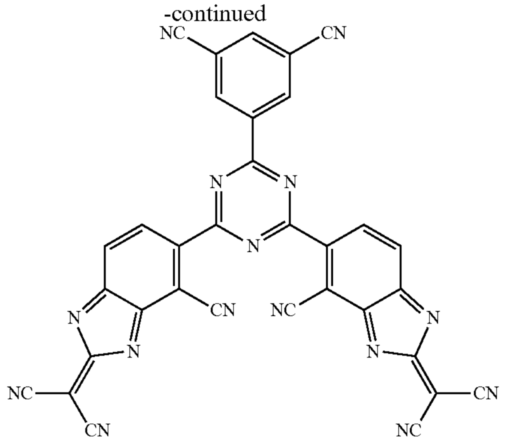

14

In a flask, the compound 17-2 (10 g, 0.019 mol), 3,5-dicyanophenylboronic acid (3.95 g, 0.021 mol, Mascot), potassium carbonate (7.95 g, 0.057 mol), $Pd(PPh_3)_4$ (1.11 g, 0.001 mol), toluene (200 ml), ethanol (40 ml) and $H_2O$ (20 ml) were refluxed/stirred and reacted for 7 hrs. After completion of reaction, the resultant was extracted and column-refined to obtain the compound 14. (8.4 g, yield=71.4%)

H-NMR (200 MHz, $CDCl_3$): δ ppm, 1H (7.47/s), 2H (7.99/d, 6.5/d, 8.01/s), LC/MS: m/z=613[$(M+1)^+$]

4. Synthesis of Compound 15

(1) Compound 15-1

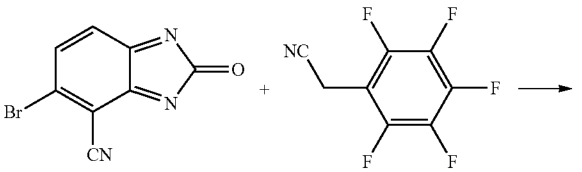

4-2

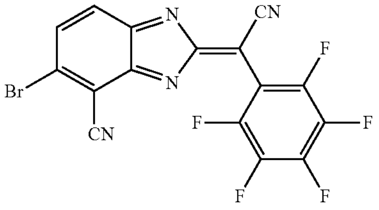

15-1

The compound 4-2 (10 g, 0.042 mol), (pentafluorophenyl) acetonitrile (12.3 g, 0.059 mol) and methylene chloride (400 ml) were put into a flask and cooled in an ice-bath. $TiCl_4$ (11.2 g, 0.059 mol) was slowly dropped, and pyridine (10.5 g, 0.127 mol) was very slowly added. After 1 hr, the ice-bath was removed. The mixture was stirred and reacted for 24 hrs. After completion of reaction, the resultant was extracted using hydrochloric acid aqueous solution and column-refined to obtain the compound 15-1. (10.9 g, yield=60.5%)

(2) Compound 15-2

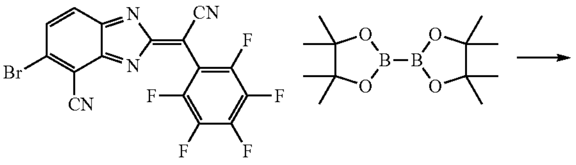

15-1

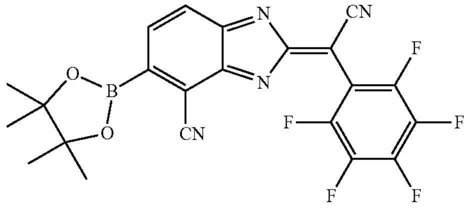

15-2

In a flask, the compound 15-1 (10 g, 0.023 mol), bis (pinacolato)diboron (7.8 g, 0.031 mol), potassium acetate (4.62 g, 0.047 mol), $PdCl_2$(dppf) (0.52 g, 0.0007 mol) and 1,4-dioxane (200 ml) were stirred and reacted at 95° C. for 12 hrs. After completion of reaction, the resultant was extracted and column-refined to obtain the compound 15-2. (8.3 g, yield=74.7%)

(3) Compound 15-3

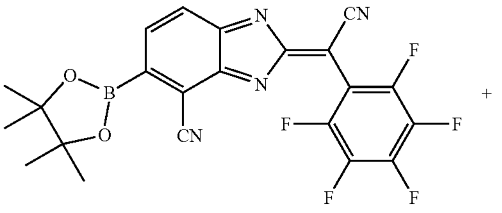

15-2

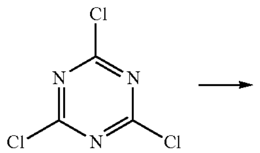

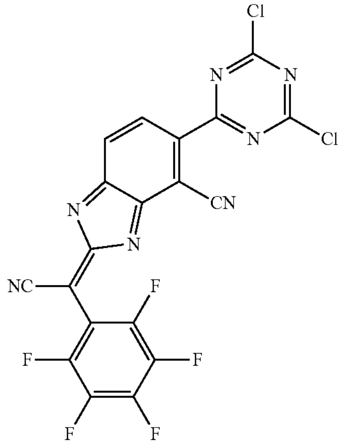

15-3

In a flask, the compound 15-2 (10 g, 0.021 mol), 2,4,6-trichloro-1,3,5-triazine (4.69 g, 0.025 mol), potassium carbonate (7.32 g, 0.053 mol), $Pd(PPh_3)_4$ (1.22 g, 0.001 mol), toluene (200 ml), ethanol (40 ml) and $H_2O$ (20 ml) were refluxed/stirred and reacted for 7 hrs. After completion of reaction, the resultant was extracted and column-refined to obtain the compound 15-3. (7.7 g, yield=73.6%)

(4) Compound 15-4

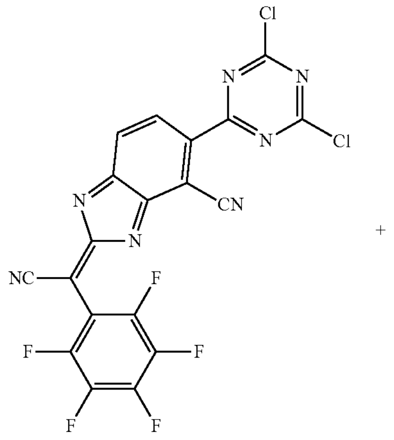

15-3

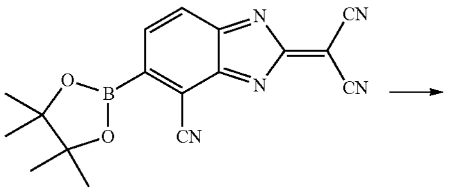

17-1

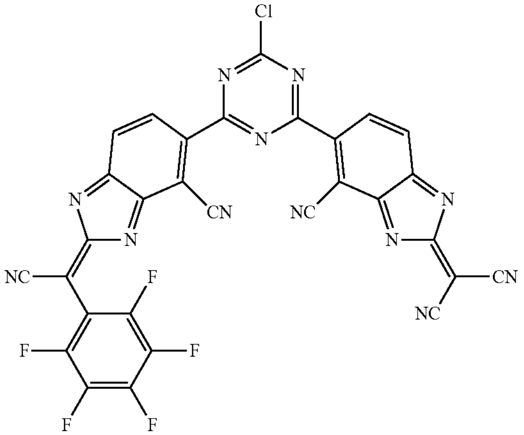

15-4

In a flask, the compound 15-3 (10 g, 0.020 mol), the compound 17-1 (8.04 g, 0.024 mol), potassium carbonate (6.99 g, 0.051 mol), $Pd(PPh_3)_4$ (1.17 g, 0.001 mol), toluene (200 ml), ethanol (40 ml) and $H_2O$ (20 ml) were refluxed/stirred and reacted for 7 hrs. After completion of reaction, the resultant was extracted and column-refined to obtain the compound 15-4. (10.3 g, yield=76.8%)

(5) Compound 15

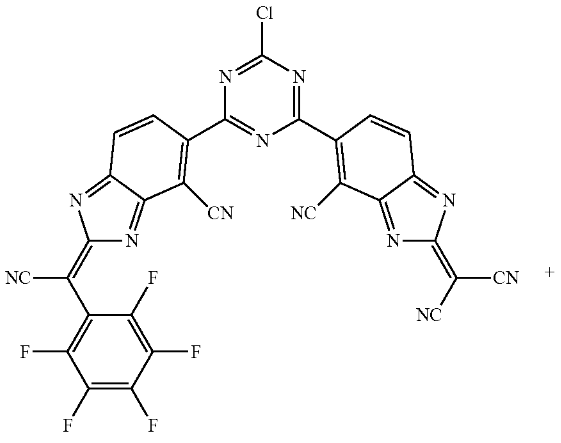

15-4

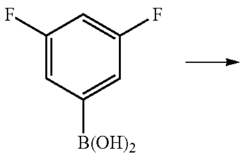

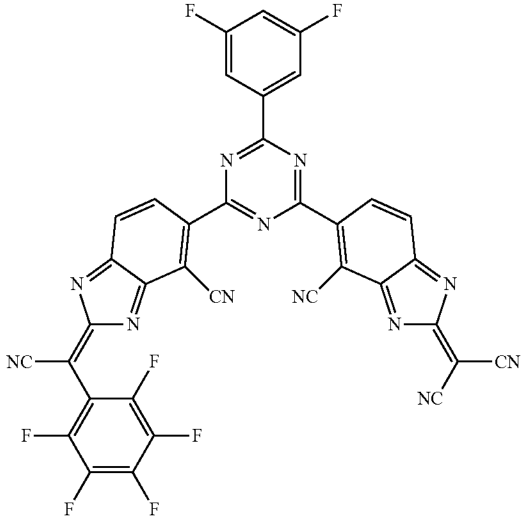

15

In a flask, the compound 15-4 (10 g, 0.015 mol), 3,5-difluorophenylboronic acid (2.86 g, 0.018 mol), potassium carbonate (5.21 g, 0.038 mol), $Pd(PPh_3)_4$ (0.87 g, 0.001 mol), toluene (200 ml), ethanol (40 ml) and $H_2O$ (20 ml) were refluxed/stirred and reacted for 7 hrs. After completion of reaction, the resultant was extracted and column-refined to obtain the compound 15. (7.4 g, yield=66.2%)

H-NMR (200 MHz, $CDCl_3$): δ ppm, 1H (6.64/s), 2H (7.99/s, 7.29/s, 6.5/d), LC/MS: m/z=740[$(M+1)^+$]

5. Synthesis of Compound 21

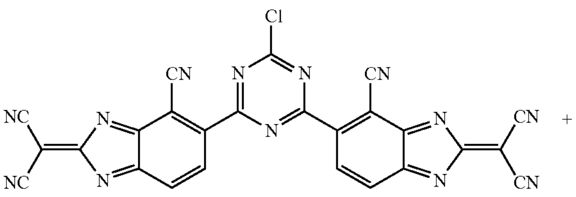

17-2

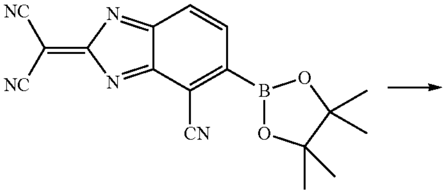

17-1

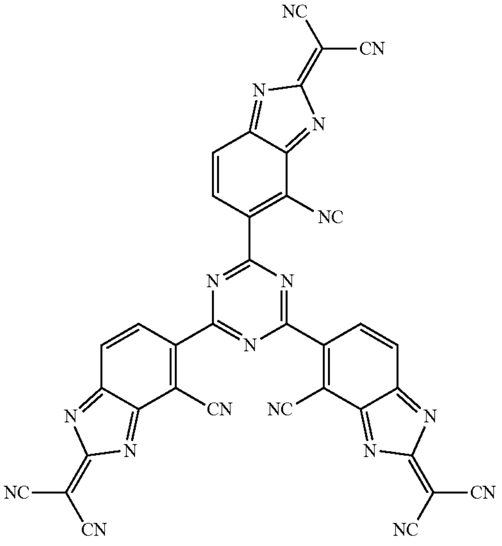

21

In a flask, the compound 17-2 (10 g, 0.019 mol), the compound 17-1 (7.29 g, 0.021 mol), potassium carbonate (7.95 g, 0.057 mol), $Pd(PPh_3)_4$ (1.11 g, 0.001 mol), toluene (200 ml), ethanol (40 ml) and $H_2O$ (20 ml) were refluxed/stirred and reacted for 7 hrs. After completion of reaction, the resultant was extracted and column-refined to obtain the compound 21. (9.7 g, yield=73.3%)

H-NMR (200 MHz, $CDCl_3$): δ ppm, 3H (7.99/d, 6.5/d), LC/MS: m/z=690[$(M+1)^+$]

6. Synthesis of Compound 22

(1) Compound 22-1

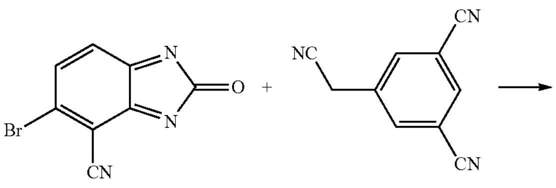

4-2

-continued

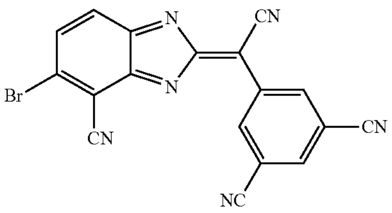

22-1

The compound 4-2 (10 g, 0.042 mol), 5-(cyanomethyl) isophthalonitrile (9.9 g, 0.059 mol) and methylene chloride (300 ml) were put into a flask and cooled in an ice-bath. $TiCl_4$ (11.2 g, 0.059 mol) was slowly dropped, and pyridine (10.5 g, 0.127 mol) was very slowly added. After 1 hr, the ice-bath was removed. The mixture was stirred and reacted for 24 hrs. After completion of reaction, the resultant was extracted using hydrochloric acid aqueous solution and column-refined to obtain the compound 22-1. (10.3 g, yield=63.1%)

(2) Compound 22-2

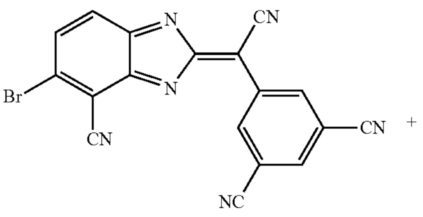

22-1

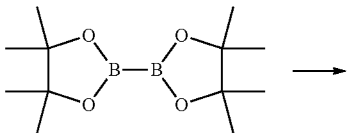

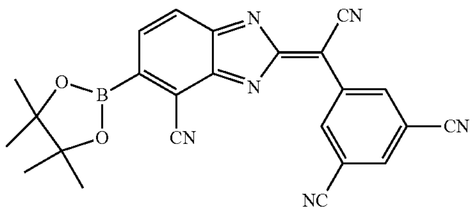

22-2

In a flask, the compound 22-1 (10 g, 0.026 mol), bis (pinacolato)diboron (8.57 g, 0.034 mol), potassium acetate (5.10 g, 0.052 mol), $PdCl_2(dppf)$ (0.57 g, 0.001 mol) and 1,4-dioxane (200 ml) were stirred and reacted at 95° C. for 12 hrs. After completion of reaction, the resultant was extracted and column-refined to obtain the compound 22-2. (8.5 g, yield=75.7%)

(3) Compound 22

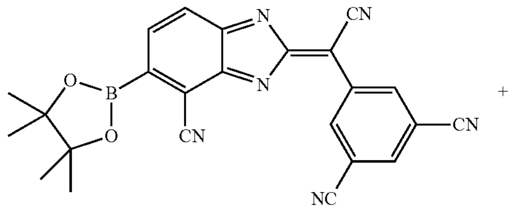

22-2

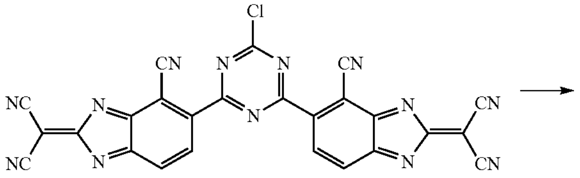

17-2

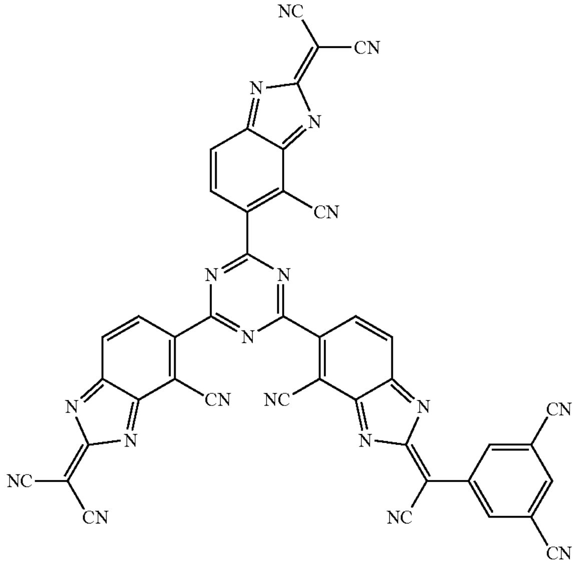

22

In a flask, the compound 22-2 (10 g, 0.023 mol), the compound 17-2 (14.5 g, 0.027 mol), potassium carbonate (7.99 g, 0.058 mol), $Pd(PPh_3)_4$ (1.34 g, 0.001 mol), toluene (200 ml), ethanol (40 ml) and $H_2O$ (20 ml) were refluxed/stirred and reacted for 7 hrs. After completion of reaction, the resultant was extracted and column-refined to obtain the compound 22. (13.3 g, yield=72.6%)

H-NMR (200 MHz, $CDCl_3$): δ ppm, 1H (7.39/s), 2H (8.11/s), 3H (7.99/d, 6.5/d), LC/MS: m/z=690[$(M+1)^+$]

7. Synthesis of Compound 29

(1) Compound 29-1

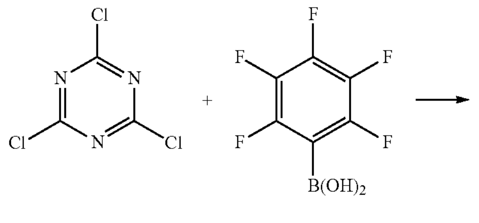

-continued

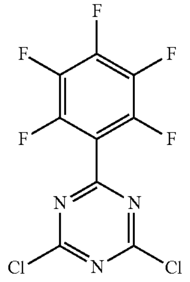

29-1

2,4,6-trichloro-1,3,5-triazine (10 g, 0.054 mol), pentafluorophenylboronic acid (13.8 g, 0.065 mol), potassium carbonate (18.74 g, 0.136 mol), $Pd(PPh_3)_4$ (3.13 g, 0.0027 mol), toluene (200 ml), ethanol (40 ml) and $H_2O$ (20 ml) were refluxed/stirred and reacted for 8 hrs. After completion of reaction, the resultant was extracted and column-refined to obtain the compound 29-1. (11.3 g, yield=65.9%)

(2) Compound 29-2

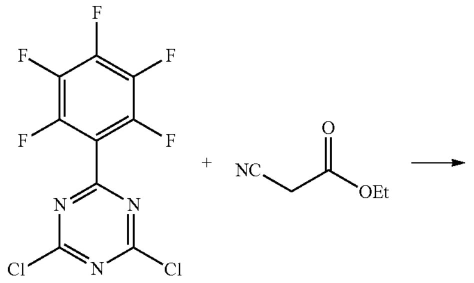

29-1

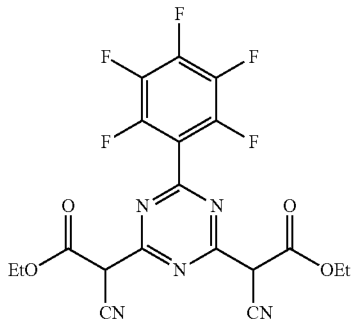

29-2

In a flask, ethyl-2-cyanoacetate (8.6 g, 0.076 mol) and THF (400 ml) were cooled at 0° C. After sodium hydride (2.11 g, 0.089 mol) was slowly added, the mixture was stirred for 1 hr. The compound 29-1 (10 g, 0.032 mol) dissolved in THE (60 ml) was added into the mixture, and the mixture was stirred and reacted under the room temperature for 12 hrs. After completion of reaction, the resultant was extracted and column-refined to obtain the compound 29-2. (11.7 g, yield=78.8%)

(3) Compound 29-3

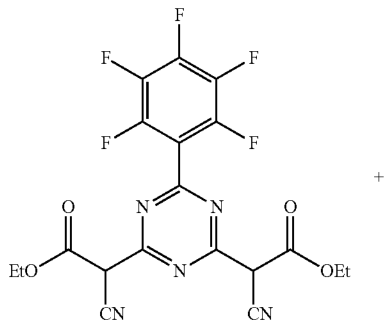

29-2

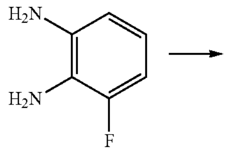

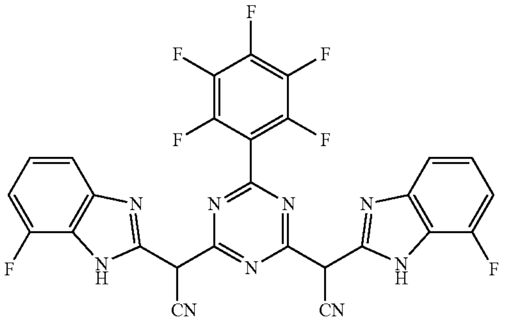

29-3

In a flask, the compound 29-2 (10 g, 0.021 mol) and 3-fluorobenzene-1,2-diamine (11 g, 0.087 mol) were stirred and reacted at 200° C. for 12 hrs. After completion of reaction, the resultant was extracted and re-crystalized to obtain the compound 29-3. (9.5 g, yield=72%)

(4) Compound 29

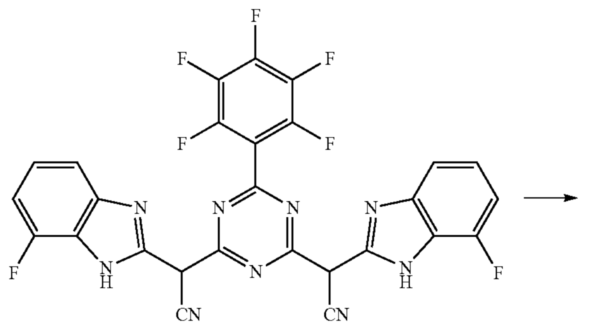

29-3

-continued

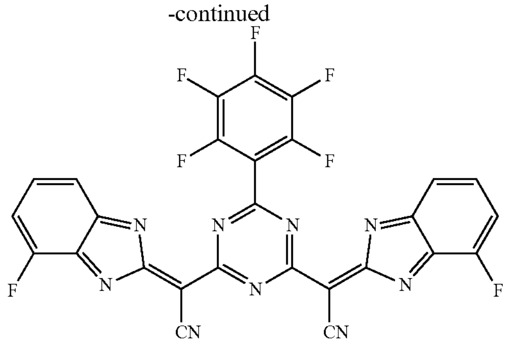

29

The compound 29-3 (10 g, 0.017 mol), potassium hydroxide (14.2 g, 0.252 mol), $H_2O$ (25 ml) and 1,4-dioxane (500 ml) were put into a flask. After $K_3Fe(CN)_6$ (55.5 g, 0.168 mol) and $H_2O$ (690 ml) was added, the mixture was stirred and reacted at 100° C. for 12 hrs. After completion of reaction, the resultant was extracted and column-refined to obtain the compound 29. (3.2 g, yield=32.2%)

H-NMR (200 MHz, $CDCl_3$): δ ppm, 2H (7.99/d, 7.86/d, 6.1/d), LC/MS: m/z=589[$(M+1)^+$]

8. Synthesis of Compound 40

(1) Compound 40-1

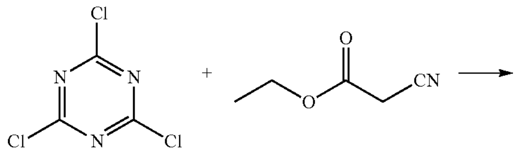

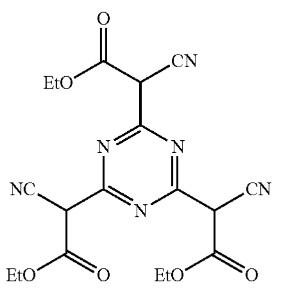

40-1

In a flask, ethyl-2-cyanoacetate (22.08 g, 0.195 mol) and THF (400 ml) were cooled at 0° C. After sodium hydride (5.60 g, 0.233 mol) was slowly added, the mixture was stirred for 1 hr. 2,4,6-trichloro-1,3,5-triazine (10 g, 0.054 mol) dissolved in THF (60 ml) was added into the mixture, and the mixture was stirred and reacted under the room temperature for 12 hrs. After completion of reaction, the resultant was extracted and column-refined to obtain the compound 40-1. (17 g, yield=75.6%)

(2) Compound 40-2

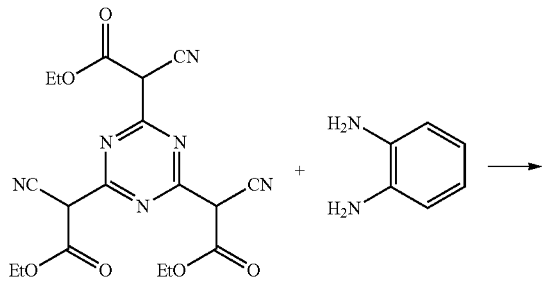

40-1

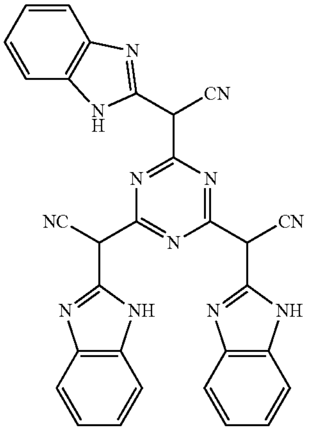

40-2

In a flask, the compound 40-1 (10 g, 0.024 mol) and o-phenylenediamine (15.66 g, 0.145 mol) were stirred and reacted at 200° C. for 12 hrs. After completion of reaction, the resultant was extracted and re-crystalized to obtain the compound 40-2. (9.5 g, yield=72%)

(3) Compound 40

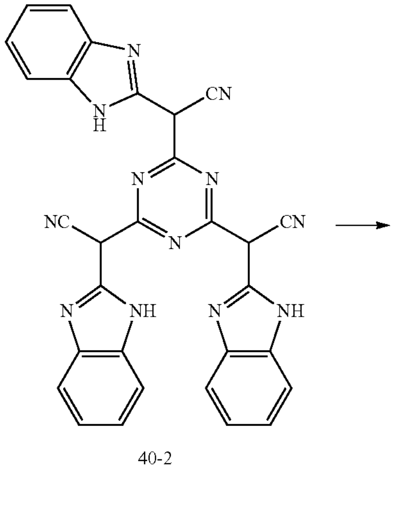

40-2

-continued

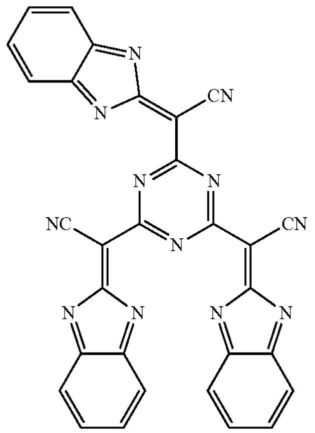

40

The compound 40-2 (10 g, 0.018 mol), potassium hydroxide (15.4 g, 0.274 mol), $H_2O$ (25 ml) and 1,4-dioxane (500 ml) were put into a flask. After $K_3Fe(CN)_6$ (60.2 g, 0.183 mol) and $H_2O$ (690 ml) was added, the mixture was stirred and reacted at 100° C. for 12 hrs. After completion of reaction, the resultant was extracted and column-refined to obtain the compound 40. (3 g, yield=30.3%)

H-NMR (200 MHz, $CDCl_3$): δ ppm, 6H (7.91/d, 7.86/d), LC/MS: m/z=540[$(M+1)^+$]

9. Synthesis of Compound 44

(1) Compound 44-1

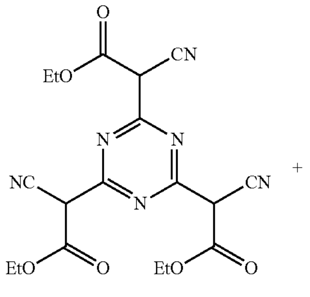

40-1

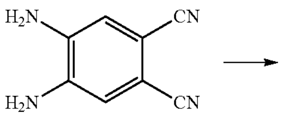

-continued

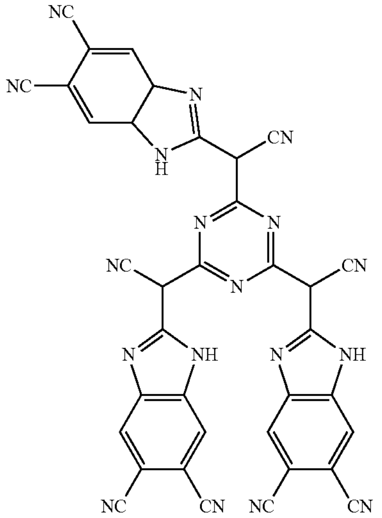

44-1

In a flask, the compound 40-1 (10 g, 0.024 mol) and 4,5-diaminophthalonitrile (23.05 g, 0.144 mol) were stirred and reacted at 200° C. for 12 hrs. After completion of reaction, the resultant was extracted and re-crystalized to obtain the compound 44-1. (12.5 g, yield=74.3%)

(2) Compound 44

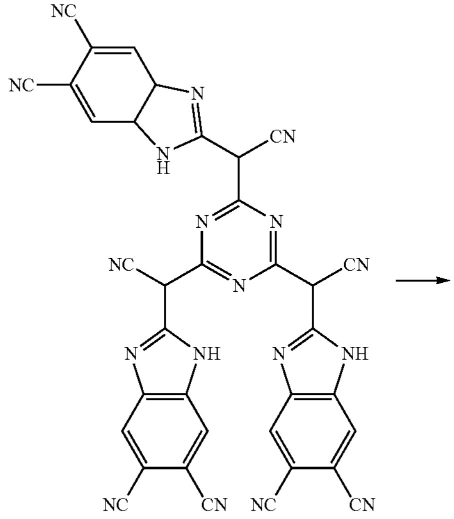

44-1

-continued

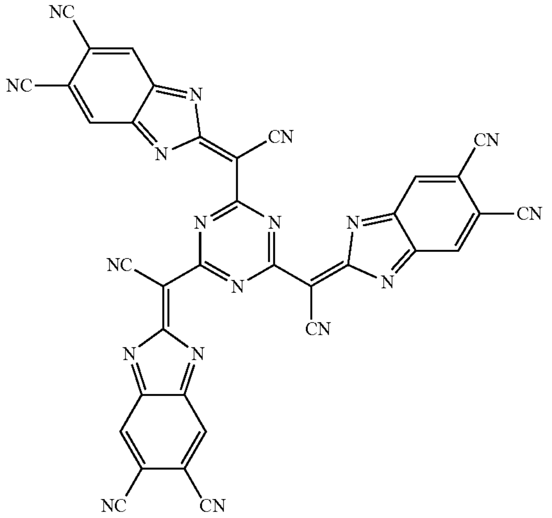

44

The compound 44-1 (10 g, 0.0144 mol), potassium hydroxide (12.04 g, 0.215 mol), $H_2O$ (20 ml) and 1,4-dioxane (500 ml) were put into a flask. After $K_3Fe(CN)_6$ (47.3 g, 0.144 mol) and $H_2O$ (400 ml) was added, the mixture was stirred and reacted at 100° C. for 12 hrs. After completion of reaction, the resultant was extracted and column-refined to obtain the compound 44. (3.3 g, yield=33.3%)

H-NMR (200 MHz, $CDCl_3$): δ ppm, 6H (6.0/s), LC/MS: m/z=690[$(M+1)^+$]

10. Synthesis of Compound 45

(1) Compound 45-1

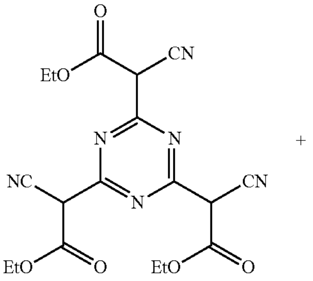

40-1

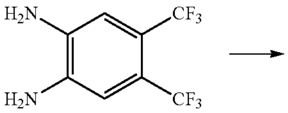

-continued

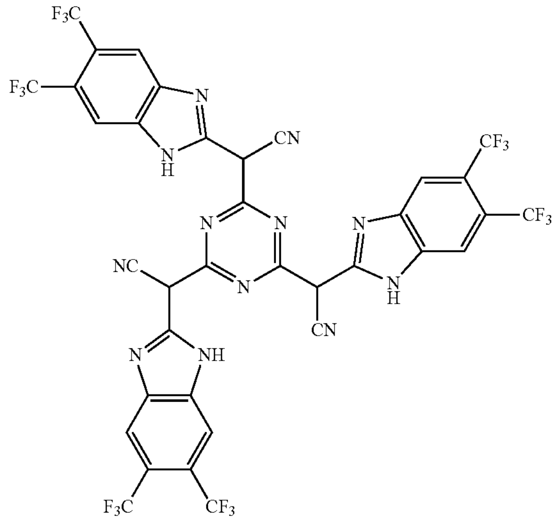

45-1

In a flask, the compound 40-1 (10 g, 0.024 mol) and 4,5-bis(trifluoromethyl)benzene-1,2-diamine (35.35 g, 0.145 mol) were stirred and reacted at 200° C. for 12 hrs. After completion of reaction, the resultant was extracted and re-crystalized to obtain the compound 45-1. (16.8 g, yield=73.4%)

(2) Compound 45

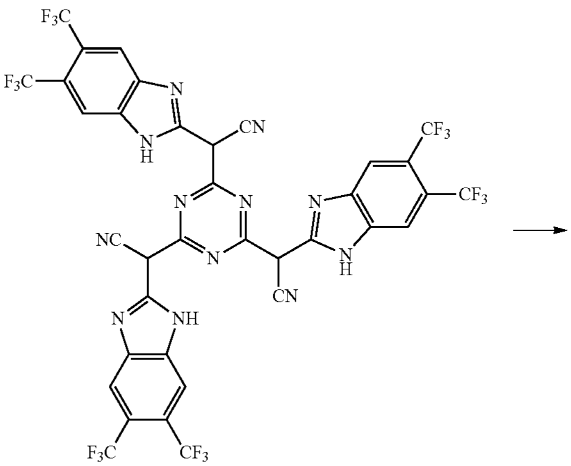

45-1

-continued

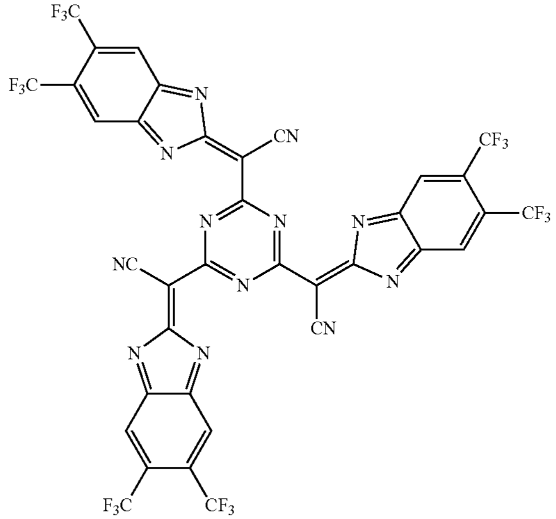

45

The compound 45-1 (10 g, 0.0105 mol), potassium hydroxide (8.82 g, 0.157 mol), $H_2O$ (15 ml) and 1,4-dioxane (500 ml) were put into a flask. After $K_3Fe(CN)_6$ (34.5 g, 0.105 mol) and $H_2O$ (350 ml) was added, the mixture was stirred and reacted at 100° C. for 12 hrs. After completion of reaction, the resultant was extracted and column-refined to obtain the compound 45. (3 g, yield=30.2%)

H-NMR (200 MHz, $CDCl_3$): δ ppm, 6H (5.58/s), LC/MS: m/z=948[$(M+1)^+$]

11. Synthesis of Compound 66

(1) Compound 66-1

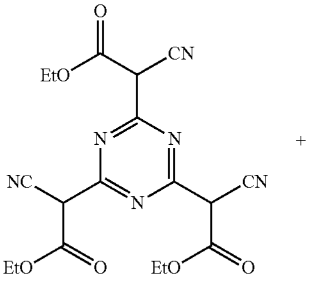

40-1

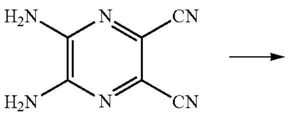

-continued

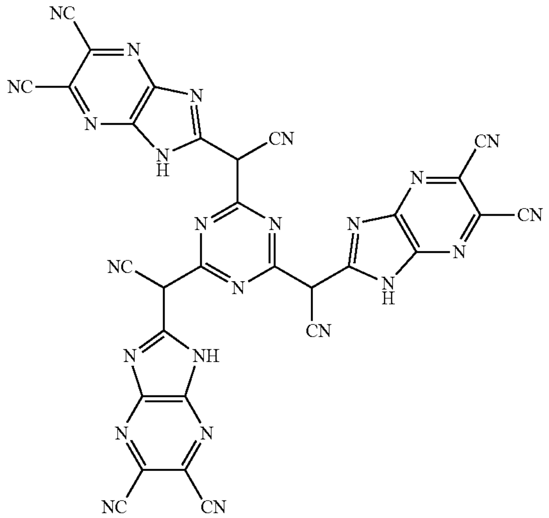

66-1

In a flask, the compound 40-1 (10 g, 0.024 mol) and 5,6-diaminopyrazine-2,3-dicarbonitrile (23.19 g, 0.145 mol, Mascot) were stirred and reacted at 200° C. for 12 hrs. After completion of reaction, the resultant was extracted and re-crystalized to obtain the compound 66-1. (12.4 g, yield=73.1%)

(2) Compound 66

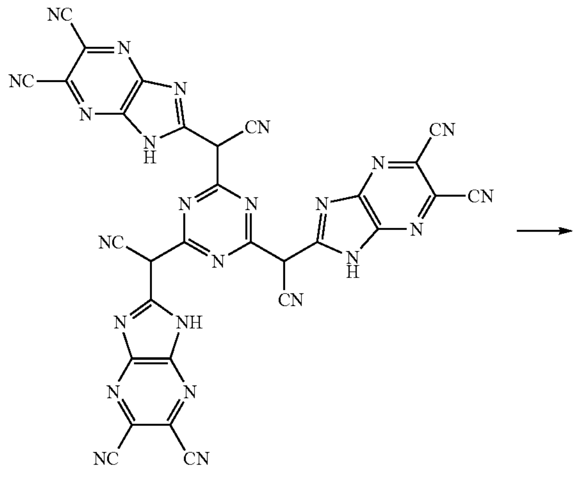

66-1

-continued

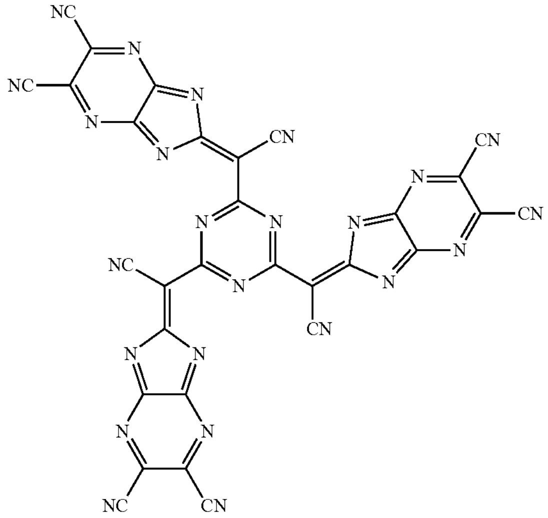

66

The compound 66-1 (10 g, 0.0142 mol), potassium hydroxide (11.98 g, 0.213 mol), $H_2O$ (15 ml) and 1,4-dioxane (500 ml) were put into a flask. After $K_3Fe(CN)_6$ (46.86 g, 0.142 mol) and $H_2O$ (470 ml) was added, the mixture was stirred and reacted at 100° C. for 12 hrs. After completion of reaction, the resultant was extracted and column-refined to obtain the compound 66. (3.1 g, yield=31%)

H-NMR (200 MHz, $CDCl_3$): δ ppm, 6H (5.58/s), LC/MS: m/z=948[$(M+1)^+$]

12. Synthesis of Compound 68

(1) Compound 68-1

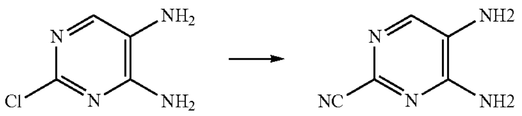

68-1

In a flask, 2-chloropyrimidine-4,5-diamine (10 g, 0.069 mol), copper(I) cyanide (19.6 g, 0.145 mol) and DMF (400 ml) were stirred and reacted at 100° C. for 5 hrs. After completion of reaction, the mixture was cooled into the room temperature. The resultant was extracted and column-refined to obtain the compound 68-1. (6.5 g, yield=69.5%)

(2) Compound 68-2

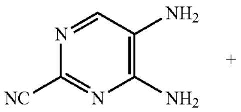

68-1

-continued

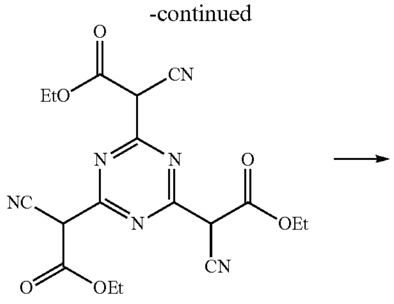

40-1

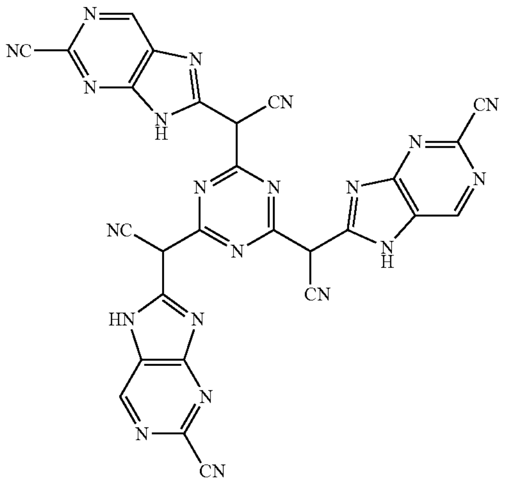

68-2

In a flask, the compound 40-1 (10 g, 0.024 mol) and the compound 68-1 (15.66 g, 0.145 mol) were stirred and reacted at 200° C. for 12 hrs. After completion of reaction, the resultant was extracted and re-crystalized to obtain the compound 68-2. (9.5 g, yield=72%)

(3) Compound 68

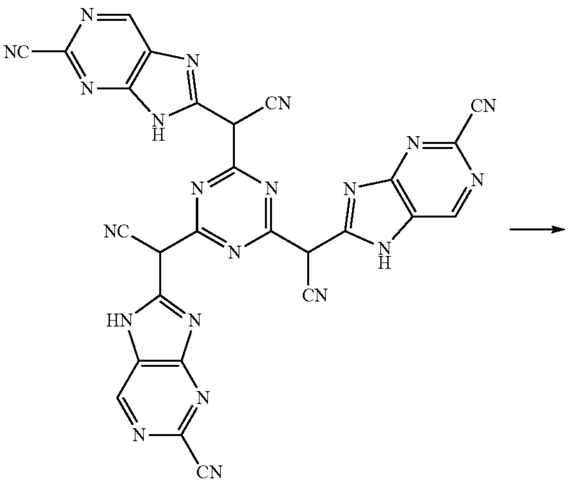

68-2

-continued

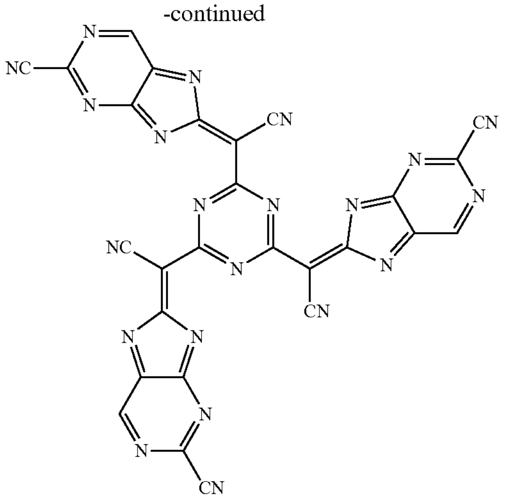

68

The compound 68-2 (10 g, 0.016 mol), potassium hydroxide (13.4 g, 0.24 mol), $H_2O$ (15 ml) and 1,4-dioxane (300 ml) were put into a flask. After $K_3Fe(CN)_6$ (52.5 g, 0.159 mol) and $H_2O$ (270 ml) was added, the mixture was stirred and reacted at 100° C. for 9 hrs. After completion of reaction, the resultant was extracted and column-refined to obtain the compound 68. (3.1 g, yield=31.1%)

H-NMR (200 MHz, $CDCl_3$): δ ppm, 4H (7.99/d), 2H (7.86/m, 6.5/d), LC/MS: m/z=640[$(M+1)^+$]

13. Synthesis of Compound 74

(1) Compound 74-1

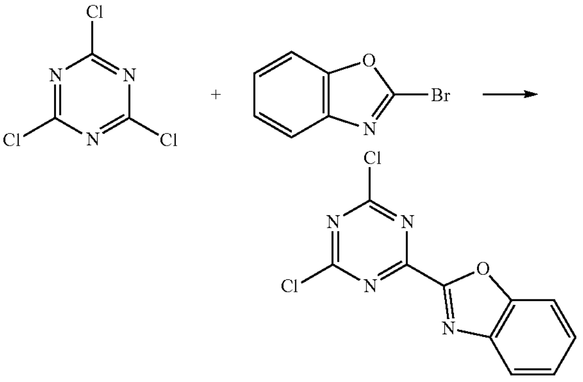

74-1

In a flask, magnesium (1.85 g, 0.076 mol), iodine (0.83 g, 0.003 mol) and THF (15 ml) were stirred, and 2-bromobenzoxazole (11.19 g, 0.065 mol) dissolved in THF (100 ml) was slowly added. The mixture was refluxed/stirred and reacted for 1 hr. After completion of reaction, the mixture was cooled into the room temperature to obtain the Grignard reagent. In another flask, 2,4,6-trichloro-1,3,5-triazine (10 g, 0.054 mol) and THF (100 ml) were added, and the mixture was cooled into 0° C. Grignard reagent was added into the mixture, and the mixture was stirred and reacted under the room temperature for 2 hrs. After completion of reaction, cool water was added at 0° C. to finish the reaction. The solid product was filtered and column-refined to obtain the compound 74-1. (9.4 g, yield=64.9%)

(2) Compound 74

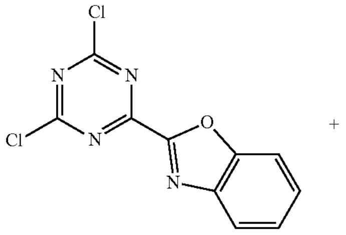

74-1

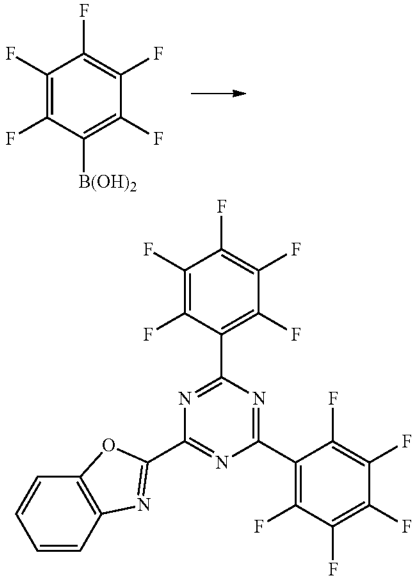

74

In a flask, the compound 74-1 (10 g, 0.037 mol), perfluorophenylboronic acid (18.25 g, 0.086 mol), potassium carbonate (25.88 g, 0.187 mol), $Pd(PPh_3)_4$ (2.16 g, 0.0019 mol), toluene (200 ml), ethanol (40 ml) and $H_2O$ (20 ml) were refluxed/stirred and reacted for 8 hrs. After completion of reaction, the resultant was extracted and column-refined to obtain the compound 74. (13 g, yield=65.4%)

H-NMR (200 MHz, $CDCl_3$): δ ppm, 2H (7.74/d, 7.39/d), LC/MS: m/z=530[$(M+1)^+$]

14. Synthesis of Compound 86

(1) Compound 86-1

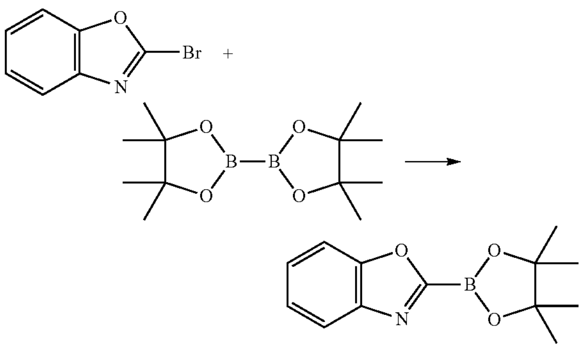

86-1

In a flask, 2-bromobenzoxazole (10 g, 0.050 mol), bis(pinacolato)diboron (16.4 g, 0.065 mol), potassium acetate (9.91 g, 0.101 mol), $PdCl_2$(dppf) (1.1 g, 0.001 mol) and 1,4-dioxane (200 ml) were stirred and reacted at 95° C. for 12 hrs. After completion of reaction, the resultant was extracted and column-refined to obtain the compound 86-1. (9.2 g, yield=74.3%)

(2) Compound 86-2

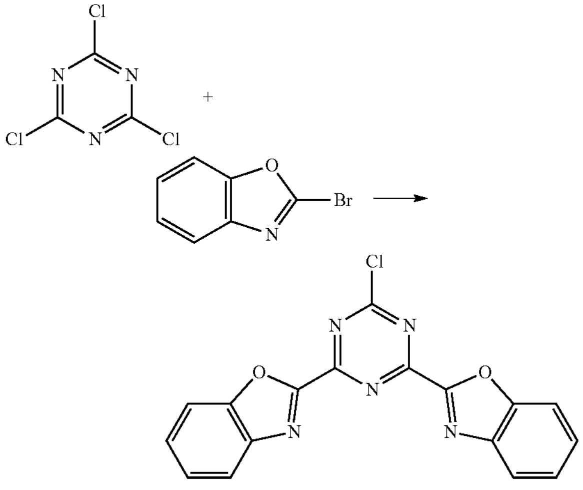

86-2

In a flask, magnesium (3.69 g, 0.152 mol), iodine (1.38 g, 0.005 mol) and THF (30 ml) were stirred, and 2-bromobenzoxazole (17.8 g, 0.09 mol) dissolved in THE (200 ml) was slowly added. The mixture was refluxed/stirred and reacted for 1 hr. After completion of reaction, the mixture was cooled into the room temperature to obtain the Grignard reagent. In another flask, 2,4,6-trichloro-1,3,5-triazine (10 g, 0.054 mol) and TH (100 ml) were added, and the mixture was cooled into 0° C. Grignard reagent was added into the mixture, and the mixture was stirred and reacted under the room temperature for 2 hrs. After completion of reaction, cool water was added at 0° C. to finish the reaction. The solid product was filtered and column-refined to obtain the compound 86-2. (10 g, yield=67%)

(3) Compound 86

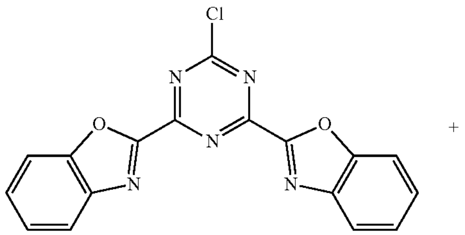

86-2

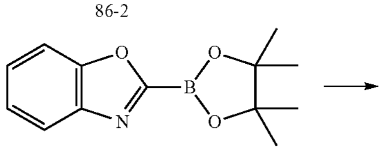

86-1

-continued

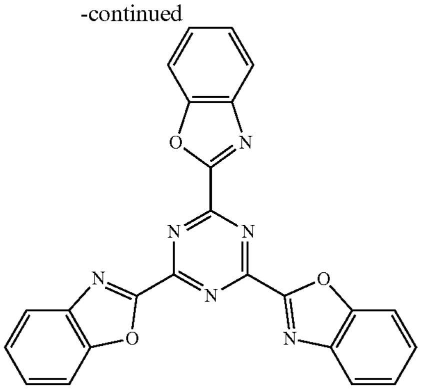

86

In a flask, the compound 86-2 (10 g, 0.029 mol), the compound 86-1 (15.9 g, 0.064 mol), potassium carbonate (23.9 g, 0.174 mol), $Pd(PPh_3)_4$ (4.95 g, 0.003 mol), toluene (200 ml), ethanol (40 ml) and $H_2O$ (20 ml) were refluxed/stirred and reacted for 7 hrs. After completion of reaction, the resultant was extracted and column-refined to obtain the compound 86. (8.7 g, yield=70.4%)

H-NMR (200 MHz, $CDCl_3$): δ ppm, 6H (7.74/m, 7.39/d), LC/MS: m/z=432[$(M+1)^+$]

15. Synthesis of Compound 90

(1) Compound 90-1

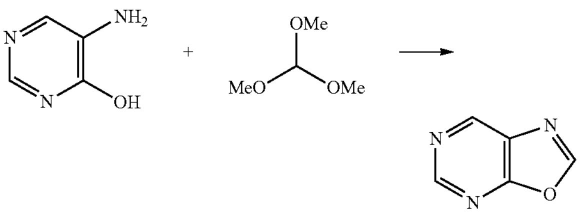

90-1

In a flask, 5-aminopyrimidin-4-ol (10 g, 0.090 mol), trimethyl orthoformate (19.1 g, 0.180 mol) and acetic acid (21.6 g, 0.360 mol) were reacted at 85° C. for 2 hrs. After completion of reaction, the resultant was extracted and column-refined to obtain the compound 90-1. (7.9 g, yield=72.5%)

(2) Compound 90-2

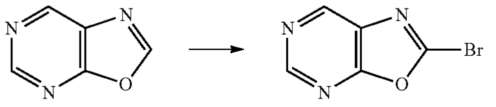

90-1 90-2

In a flask, carbon tetrabromide (30.1 g, 0.091 mol) and sodium t-butoxide (31.7 g, 0.330 mol) were added to DMF (35 ml), where the compound 90-1 (10 g, 0.083 mol) was dissolved, and the mixture was stirred under the room temperature for 5 hrs. After completion of reaction, the resultant was extracted using $CH_2Cl_2$ and column-refined to obtain the compound 90-2. (13.5 g, yield=81.8%)

(3) Compound 90-3

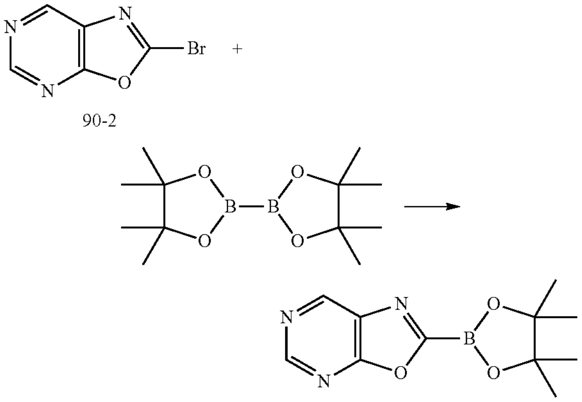

90-2

90-3

In a flask, the compound 90-2 (10 g, 0.050 mol), bis(pinacolato)diboron (16.5 g, 0.065 mol), potassium acetate (9.81 g, 0.100 mol), $PdCl_2(dppf)$ (1.1 g, 0.001 mol) and 1,4-dioxane (200 ml) were stirred and reacted at 95° C. for 12 hrs. After completion of reaction, the resultant was extracted and column-refined to obtain the compound 90-3. (9.2 g, yield=74.5%)

(4) Compound 90-4

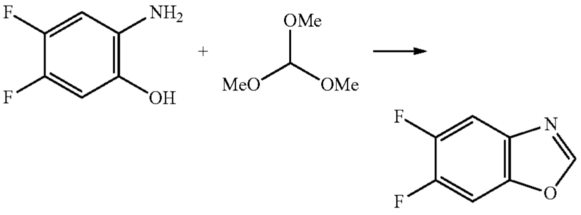

90-4

In a flask, 2-amino-4,5-difluorophenol (10 g, 0.069 mol), trimethyl orthoformate (14.6 g, 0.138 mol) and acetic acid (16.5 g, 0.276 mol) were reacted at 85° C. for 2 hrs. After completion of reaction, the resultant was extracted and column-refined to obtain the compound 90-4. (8.1 g, yield=75.8%)

(5) Compound 90-5

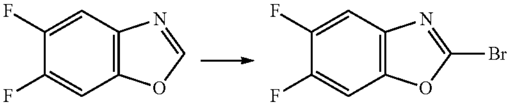

90-4 90-5

In a flask, carbon tetrabromide (23.5 g, 0.071 mol) and sodium t-butoxide (24.8 g, 0.258 mol) were added to DMF (35 ml), where the compound 90-4 (10 g, 0.059 mol) was dissolved, and the mixture was stirred under the room temperature for 5 hrs. After completion of reaction, the resultant was extracted using $CH_2Cl_2$ and column-refined to obtain the compound 90-5. (12.4 g, yield=82.1%)

(6) Compound 90-6

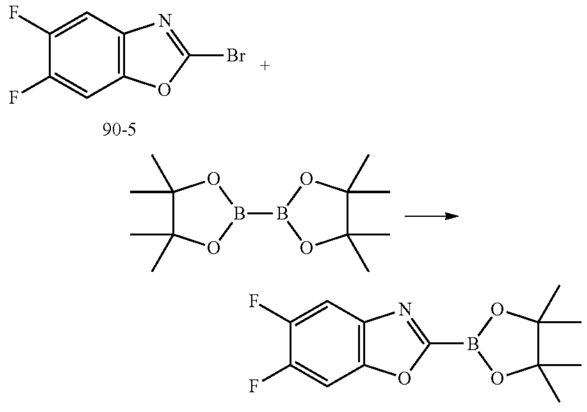

90-5

90-6

In a flask, the compound 90-5 (10 g, 0.043 mol), bis (pinacolato)diboron (14.1 g, 0.056 mol), potassium acetate (8.39 g, 0.085 mol), $PdCl_2$(dppf) (0.94 g, 0.001 mol) and 1,4-dioxane (200 ml) were stirred and reacted at 95° C. for 12 hrs. After completion of reaction, the resultant was extracted and column-refined to obtain the compound 90-6. (9.1 g, yield=75.8%)

(7) Compound 90-7

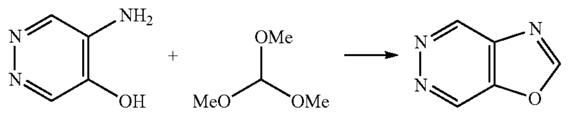

90-7

In a flask, 5-aminopyridazin-4-ol (10 g, 0.090 mol), trimethyl orthoformate (19.1 g, 0.180 mol) and acetic acid (21.6 g, 0.360 mol) were reacted at 85° C. for 2 hrs. After completion of reaction, the resultant was extracted and column-refined to obtain the compound 90-7. (7.8 g, yield=71.6%)

(8) Compound 90-8

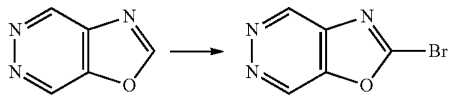

90-7 90-8

In a flask, carbon tetrabromide (30.1 g, 0.091 mol) and sodium t-butoxide (31.7 g, 0.330 mol) were added to DMF (35 ml), where the compound 90-7 (10 g, 0.083 mol) was dissolved, and the mixture was stirred under the room temperature for 5 hrs. After completion of reaction, the resultant was extracted using $CH_2Cl_2$ and column-refined to obtain the compound 90-8. (13.8 g, yield=83.6%)

(9) Compound 90-9

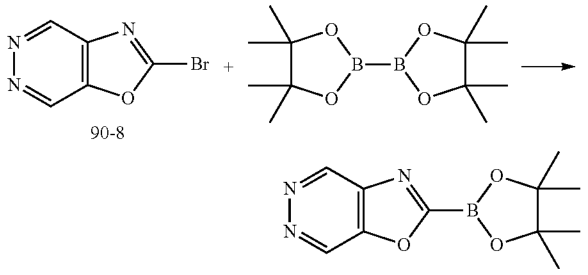

90-8

90-9

In a flask, the compound 90-8 (10 g, 0.050 mol), bis (pinacolato)diboron (16.5 g, 0.065 mol), potassium acetate (9.81 g, 0.100 mol), $PdCl_2$(dppf) (1.1 g, 0.001 mol) and 1,4-dioxane (200 ml) were stirred and reacted at 95° C. for 12 hrs. After completion of reaction, the resultant was extracted and column-refined to obtain the compound 90-9. (8.8 g, yield=71.2%)

(10) Compound 90-10

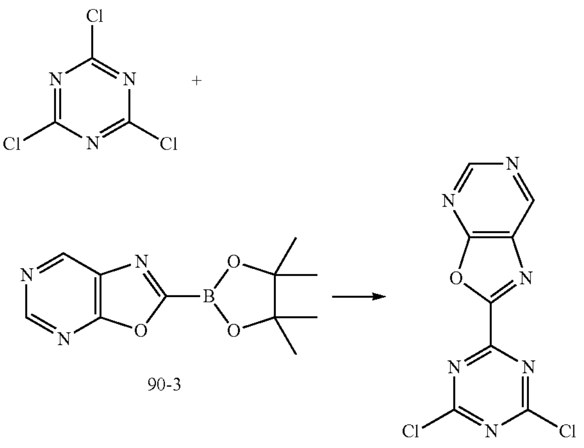

90-3

90-10

In a flask, 2,4,6-trichloro-1,3,5-triazine (10 g, 0.054 mol), the compound 90-3 (16.1 g, 0.065 mol), potassium carbonate (18.7 g, 0.136 mol), $Pd(PPh_3)_4$ (3.13 g, 0.0027 mol), toluene (200 ml), ethanol (40 ml) and $H_2O$ (20 ml) were refluxed/stirred and reacted for 8 hrs. After completion of reaction, the resultant was extracted and column-refined to obtain the compound 90-10. (9.9 g, yield=67.9%)

(11) Compound 90-11

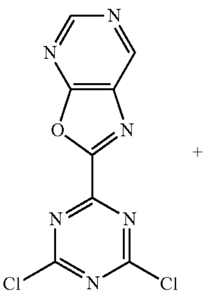

90-10

-continued

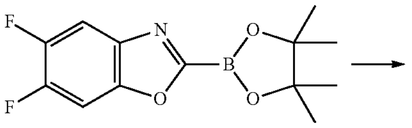

90-6

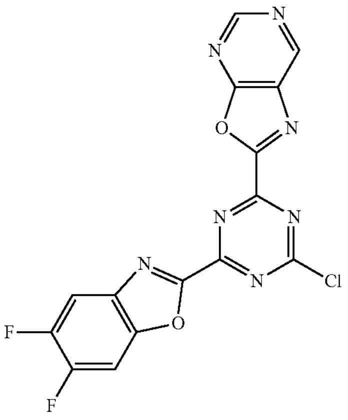

90-11

In a flask, the compound 90-10 (10 g, 0.037 mol), the compound 90-6 (12.5 g, 0.045 mol), potassium carbonate (12.8 g, 0.093 mol), $Pd(PPh_3)_4$ (2.15 g, 0.0019 mol), toluene (200 ml), ethanol (40 ml) and $H_2O$ (20 ml) were stirred and reacted for 8 hrs. After completion of reaction, the resultant was extracted and column-refined to obtain the compound 90-11. (8.7 g, yield=60.4%)

(12) Compound 90

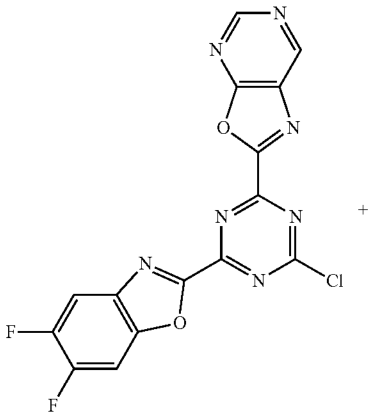

90-11

+

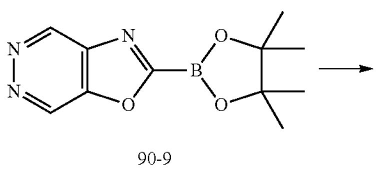

90-9

-continued

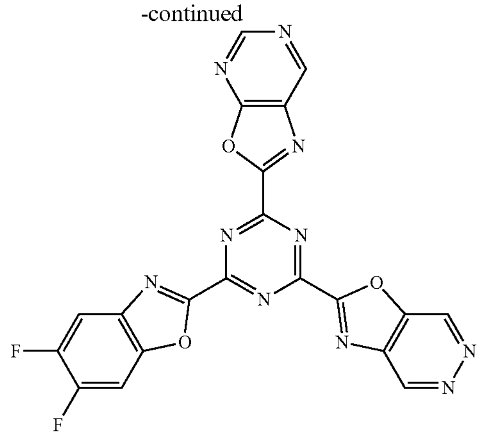

90

In a flask, the compound 90-11 (10 g, 0.026 mol), the compound 90-9 (7.65 g, 0.031 mol), potassium carbonate (8.9 g, 0.064 mol), $Pd(PPh_3)_4$ (1.49 g, 0.0013 mol), toluene (200 ml), ethanol (40 ml) and $H_2O$ (20 ml) were stirred and reacted for 8 hrs. After completion of reaction, the resultant was extracted and column-refined to obtain the compound 90. (7.6 g, yield=62.3%)

H-NMR (200 MHz, $CDCl_3$): δ ppm, 1H (9.26/s, 8.78/s) 2H (9.24/s, 6.95/s), LC/MS: m/z=472[$(M+1)^+$]

16. Synthesis of Compound 91

(1) Compound 91-1

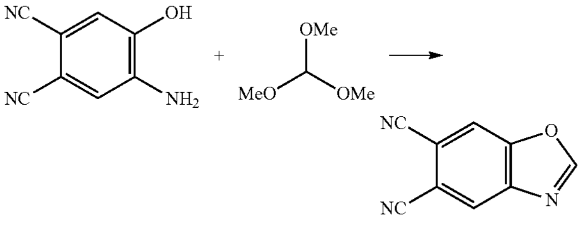

91-1

In a flask, 4-amino-5-hydroxyphthalonitrile (10 g, 0.063 mol), trimethyl orthoformate (13.3 g, 0.126 mol) and acetic acid (15.1 g, 0.251 mol) were reacted at 85° C. for 2 hrs. After completion of reaction, the resultant was extracted and column-refined to obtain the compound 91-1. (7.7 g, yield=72.4%)

(2) Compound 91-2

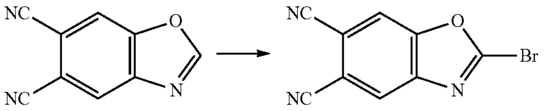

91-1 91-2

In a flask, carbon tertrabromide (21.57 g, 0.065 mol) and sodium t-butoxide (22.73 g, 0.237 mol) were added to DMF (35 ml), where the compound 91-1 (10 g, 0.059 mol) was dissolved, and the mixture was stirred under the room temperature for 5 hrs. After completion of reaction, the resultant was extracted using $CH_2Cl_2$ and column-refined to obtain the compound 91-2. (12.1 g, yield=82.5%)

(3) Compound 91-3

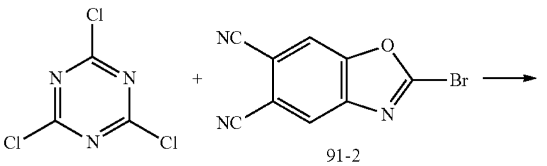

91-2

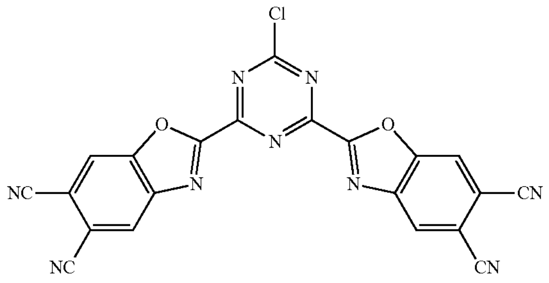

91-3

In a flask, magnesium (3.67 g, 0.151 mol), iodine (1.15 g, 0.005 mol) and THF (15 ml) were stirred, and 2-bromobenzoxazole (22.2 g, 0.091 mol) dissolved in THF (200 ml) was slowly added. The mixture was refluxed/stirred and reacted for 1 hr. After completion of reaction, the mixture was cooled into the room temperature to obtain the Grignard reagent. In another flask, 2,4,6-trichloro-1,3,5-triazine (10 g, 0.054 mol) and TH (100 ml) were added, and the mixture was cooled into 0° C. Grignard reagent was added into the mixture, and the mixture was stirred and reacted under the room temperature for 2 hrs. After completion of reaction, cool water was added at 0° C. to finish the reaction. The solid product was filtered and column-refined to obtain the compound 91-3. (15.3 g, yield=62.7%)

(4) Compound 91-4

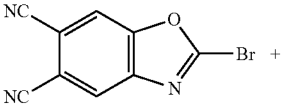

91-2

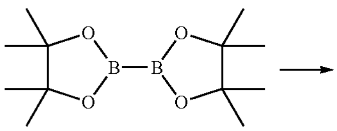

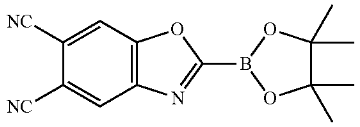

91-4

In a flask, the compound 91-2 (10 g, 0.040 mol), bis (pinacolato)diboron (13.3 g, 0.052 mol), potassium acetate (7.91 g, 0.081 mol), $PdCl_2$(dppf) (0.89 g, 0.001 mol) and 1,4-dioxane (200 ml) were stirred and reacted at 95° C. for 12 hrs. After completion of reaction, the resultant was extracted and column-refined to obtain the compound 91-4. (8.9 g, yield=74.8%)

(5) Compound 91

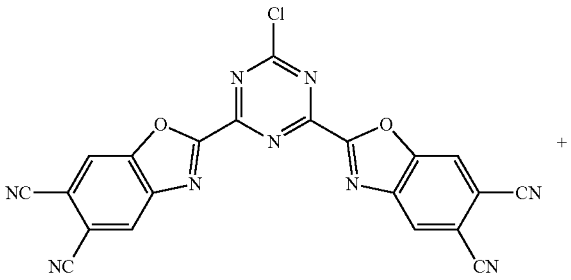

91-3

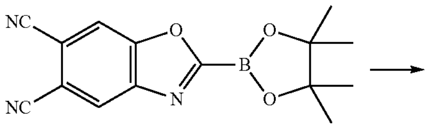

91-4

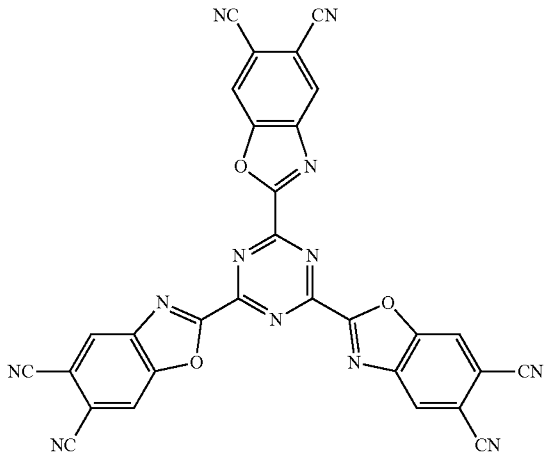

91

In a flask, the compound 91-3 (10 g, 0.022 mol), the compound 91-4 (7.87, 0.024 mol), potassium carbonate (9.05 g, 0.066 mol), $Pd(PPh_3)_4$ (1.28 g, 0.0011 mol), toluene (200 ml), ethanol (40 ml) and $H_2O$ (20 ml) were stirred and reacted for 8 hrs. After completion of reaction, the resultant was extracted and column-refined to obtain the compound 91. (8.1 g, yield=62.5%)

H-NMR (200 MHz, $CDCl_3$): δ ppm, 6H (7.69/s), LC/MS: m/z=582[$(M+1)^+$]

17. Synthesis of Compound 95

(1) Compound 95-1

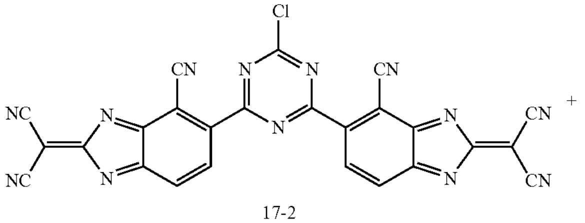

17-2

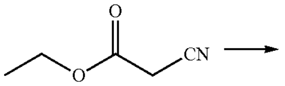

-continued

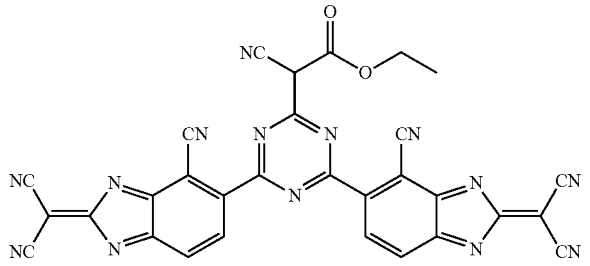

95-1

In a flask, ethyl-2-cyanoacetate (5.2 g, 0.046 mol) and THF (30 ml) were cooled at 0° C. After sodium hydride (1.28 g, 0.053 mol) was slowly added, the mixture was stirred for 1 hr. The compound 17-2 (10 g, 0.019 mol) dissolved in TH (60 ml) was added into the mixture, and the mixture was stirred and reacted under the room temperature for 12 hrs. After completion of reaction, the resultant was extracted and column-refined to obtain the compound 95-1. (8.5 g, yield=74.1%)

(2) Compound 95-2

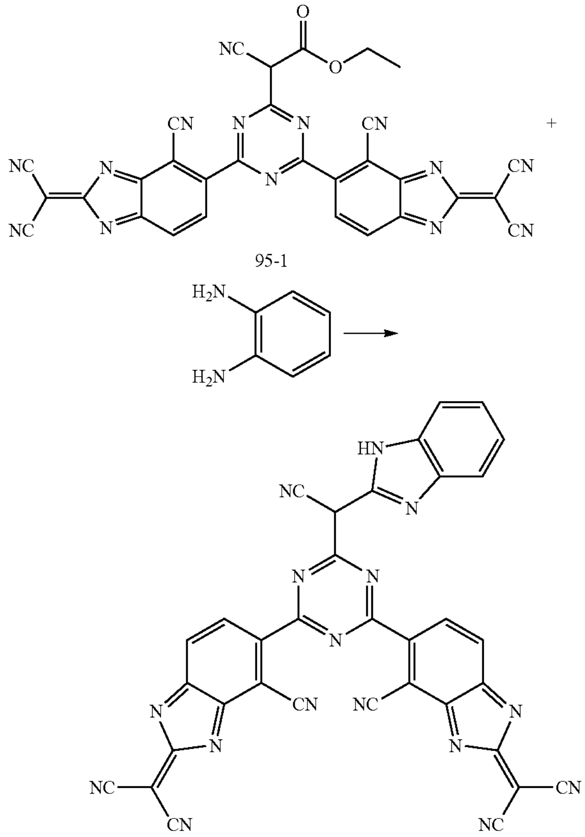

95-1

95-2

In a flask, the compound 95-1 (10 g, 0.017 mol) and o-phenylenediamine (3.61 g, 0.033 mol) were stirred and reacted at 200° C. for 10 hrs. After completion of reaction, the resultant was extracted and re-crystalized to obtain the compound 95-2. (7.8 g, yield=72.6%)

(3) Compound 95

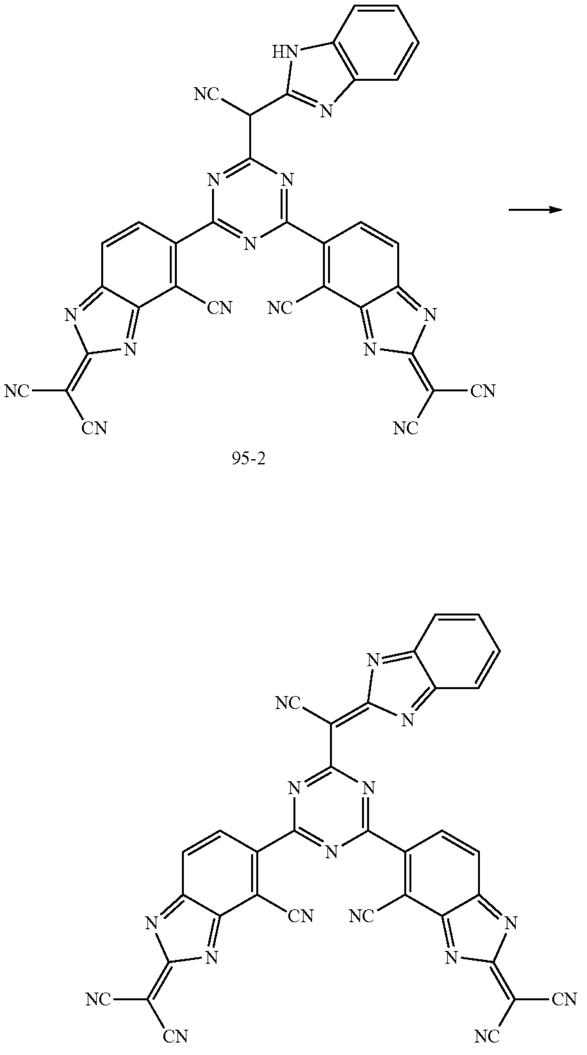

95-2

95

The compound 95-2 (10 g, 0.016 mol), potassium hydroxide (13.4 g, 0.24 mol), $H_2O$ (15 ml) and 1,4-dioxane (300 ml) were put into a flask. After $K_3Fe(CN)_6$ (52.5 g, 0.159 mol) and $H_2O$ (270 ml) was added, the mixture was stirred and reacted at 100° C. for 9 hrs. After completion of reaction, the resultant was extracted and column-refined to obtain the compound 95. (3.1 g, yield=31.1%)

H-NMR (200 MHz, $CDCl_3$): δ ppm, 4H (7.99/d), 2H (7.86/m, 6.5/d), LC/MS: m/z=640[$(M+1)^+$]

18. Synthesis of Compound 98

(1) Compound 98-1

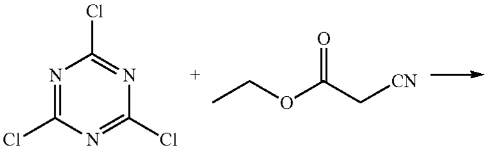

-continued

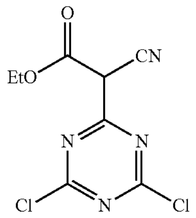

98-1

In a flask, ethyl-2-cyanoacetate (7.36 g, 0.065 mol) and THF (100 ml) were cooled at 0° C. After sodium hydride (1.82 g, 0.076 mol) was slowly added, the mixture was stirred for 1 hr. 2,4,6-trichloro-1,3,5-triazine (10 g, 0.054 mol) dissolved in THF (60 ml) was added into the mixture, and the mixture was stirred and reacted under the room temperature for 12 hrs. After completion of reaction, the resultant was extracted and column-refined to obtain the compound 98-1. (10.7 g, yield=75.5%)

(2) Compound 98-2

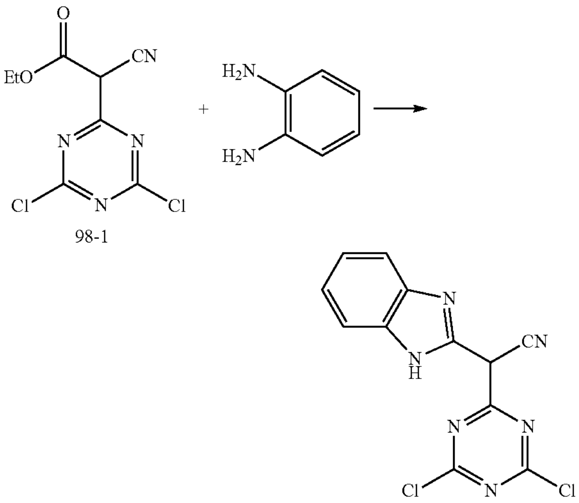

98-1

98-2

In a flask, the compound 98-1 (10 g, 0.038 mol) and o-phenylenediamine (8.28 g, 0.076 mol) were stirred and reacted at 200° C. for 12 hrs. After completion of reaction, the resultant was extracted and re-crystalized to obtain the compound 98-2. (7.3 g, yield=73%)

(3) Compound 98-3

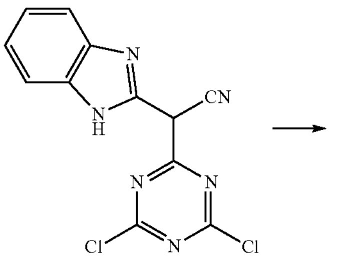

98-2

-continued

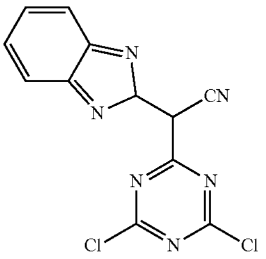

98-3

The compound 98-2 (10 g, 0.033 mol), potassium hydroxide (6.44 g, 0.114 mol), $H_2O$ (15 ml) and 1,4-dioxane (500 ml) were put into a flask. After $K_3Fe(CN)_6$ (26.98 g, 0.082 mol) and $H_2O$ (270 ml) was added, the mixture was stirred and reacted at 100° C. for 12 hrs. After completion of reaction, the resultant was extracted and column-refined to obtain the compound 98-3. (3.4 g, yield=34.2%)

(4) Compound 98-4

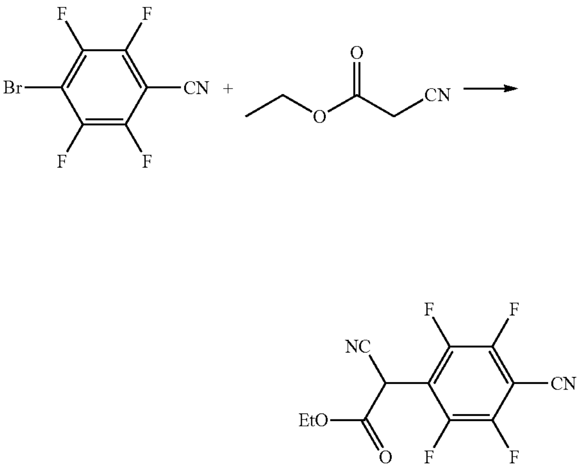

98-4

In a flask, ethyl-2-cyanoacetate (5.35 g, 0.047 mol) and THF (100 ml) were cooled at 0° C. After sodium hydride (1.32 g, 0.055 mol) was slowly added, the mixture was stirred for 1 hr. 4-bromo-2,3,5,6-tetrafluorobenzonitrile (10 g, 0.039 mol) dissolved in TH (60 ml) was added into the mixture, and the mixture was stirred and reacted under the room temperature for 12 hrs. After completion of reaction, the resultant was extracted and column-refined to obtain the compound 98-4. (8.6 g, yield=76.3%)

(5) Compound 98-5

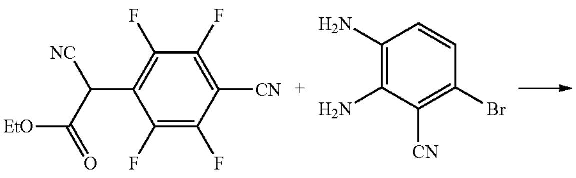

98-4

-continued

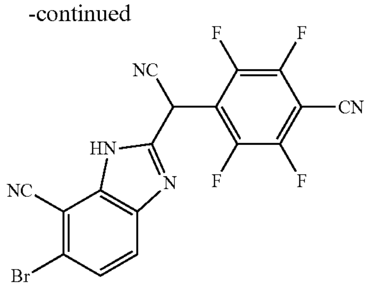

98-5

In a flask, the compound 98-4 (10 g, 0.035 mol) and 2,3-diamino-6-bromobenzonitrile (14.82 g, 0.07 mol) were stirred and reacted at 200° C. for 12 hrs. After completion of reaction, the resultant was extracted and re-crystalized to obtain the compound 98-5. (11.6 g, yield=76.4%)

(6) Compound 98-6

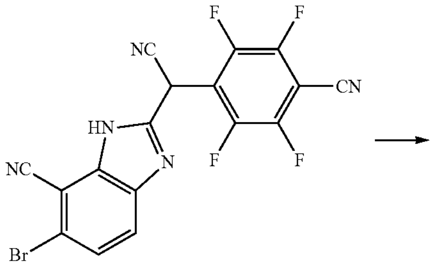

98-5

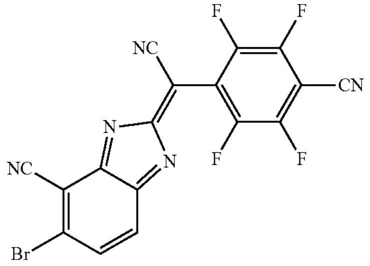

98-6

The compound 98-5 (10 g, 0.023 mol), potassium hydroxide (19.4 g, 0.346 mol), $H_2O$ (20 ml) and 1,4-dioxane (500 ml) were put into a flask. After $K_3Fe(CN)_6$ (75.8 g, 0.230 mol) and $H_2O$ (270 ml) was added, the mixture was stirred and reacted at 100° C. for 12 hrs. After completion of reaction, the resultant was extracted and column-refined to obtain the compound 98-6. (3.2 g, yield=32.1%)

(7) Compound 98-7

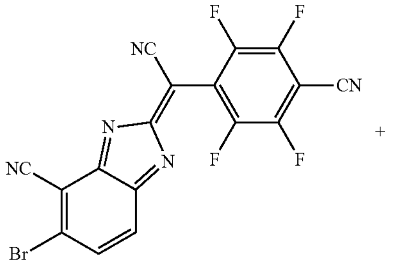

98-6

-continued

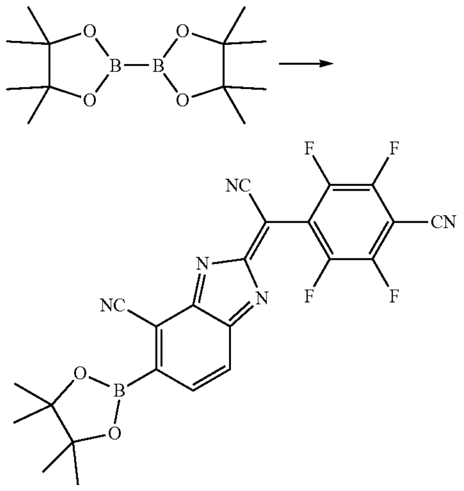

98-7

In a flask, the compound 98-6 (10 g, 0.023 mol), bis(pinacolato)diboron (7.64 g, 0.030 mol), potassium acetate (4.54 g, 0.046 mol), $PdCl_2(dppf)$ (0.51 g, 0.0007 mol) and 1,4-dioxane (200 ml) were stirred and reacted at 95° C. for 12 hrs. After completion of reaction, the resultant was extracted and column-refined to obtain the compound 98-7. (8 g, yield=72.1%)

(8) Compound 98-8

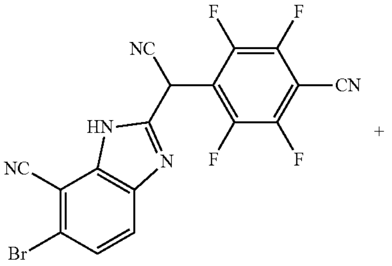

98-5

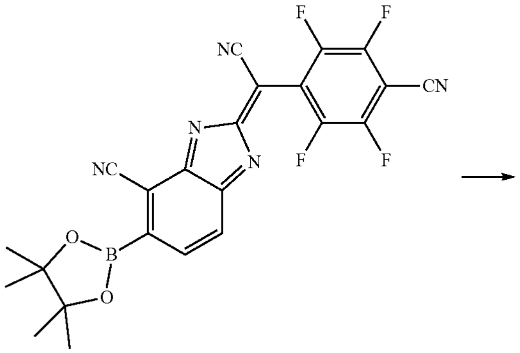

98-7

-continued

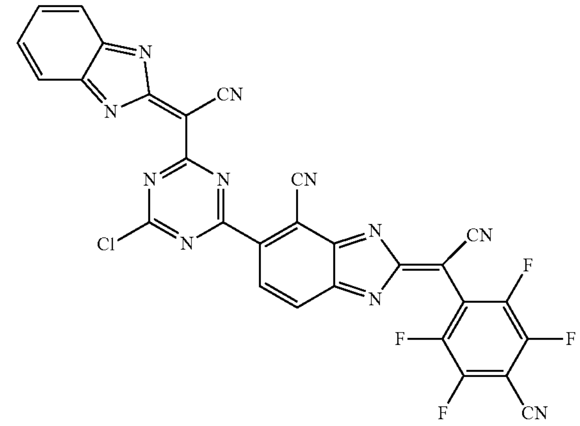

98-8

-continued

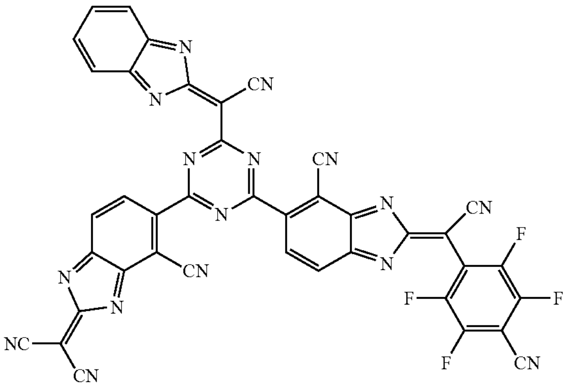

98

In a flask, the compound 98-5 (10 g, 0.023 mol), the compound 98-7 (12.14 g, 0.025 mol), potassium carbonate (9.55 g, 0.069 mol), $Pd(PPh_3)_4$ (1.33 g, 0.0012 mol), toluene (200 ml), ethanol (40 ml) and $H_2O$ (20 ml) were stirred and reacted for 8 hrs. After completion of reaction, the resultant was extracted and column-refined to obtain the compound 98-8. (10.6 g, yield=74.2%)

(9) Compound 98

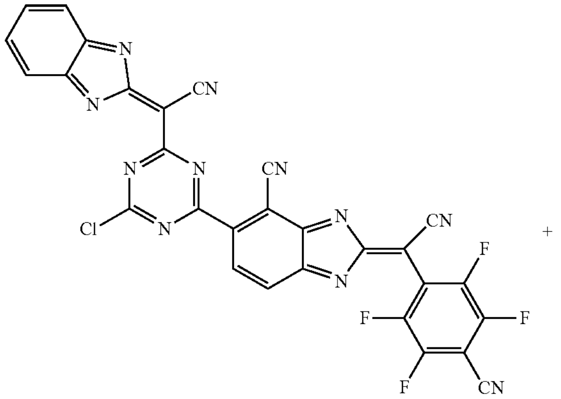

98-8

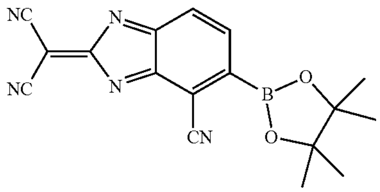

17-1

THF (200 ml) and water (50 ml) were added to the mixture of the compound 98-8 (10 g, 0.016 mol), the compound 17-1 (5.88 g, 0.018 mol), potassium carbonate (6.69 g, 0.048 mol) and $Pd(PPh_3)_4$ (0.93 g, 0.0008 mol), and the mixture was stirred and reacted at 60° C. for 8 hrs. After completion of reaction, the resultant was extracted and column-refined to obtain the compound 98. (9 g, yield=70.7%)

H-NMR (200 MHz, $CDCl_3$): δ ppm, 2H (7.86/m, 6.5/d) 4H (7.99/d), LC/MS: m/z=788[$(M+1)^+$]

19. Synthesis of Compound 102

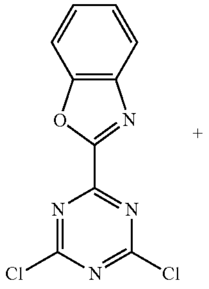

74-1

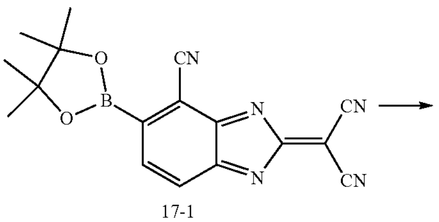

17-1

-continued

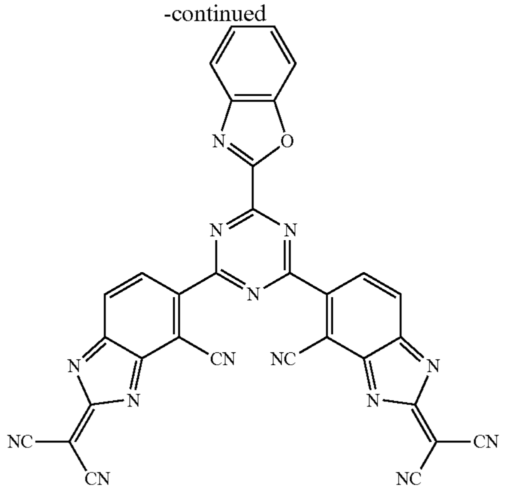

102

THF (200 ml) and water (50 ml) were added to the mixture of the compound 74-1 (10 g, 0.037 mol), the compound 17-1 (27.3 g, 0.082 mol), potassium carbonate (25.8 g, 0.187 mol) and $Pd(PPh_3)_4$ (2.1 g, 0.0019 mol), and the mixture was stirred and reacted at 60° C. for 8 hrs. After completion of reaction, the resultant was extracted and column-refined to obtain the compound 102. (16.1 g, yield=71.1%)

H-NMR (200 MHz, $CDCl_3$): δ ppm, 2H (7.99/d, 7.74/d, 7.39/d, 6.5/d), LC/MS: m/z=604[$(M+1)^+$]

20. Synthesis of Compound 103

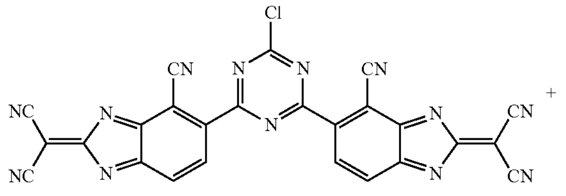

17-2

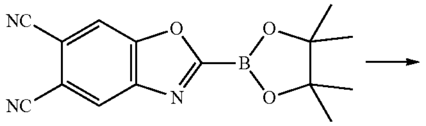

91-4

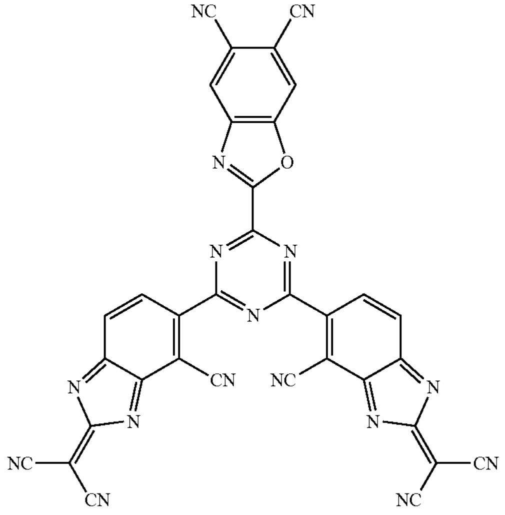

103

In a flask, the compound 17-2 (10 g, 0.019 mol), the compound 91-4 (6.22, 0.021 mol), potassium carbonate (7.95 g, 0.057 mol), $Pd(PPh_3)_4$ (1.11 g, 0.001 mol), toluene (200 ml), ethanol (40 ml) and $H_2O$ (20 ml) were stirred and reacted for 8 hrs. After completion of reaction, the resultant was extracted and column-refined to obtain the compound 103. (8.2 g, yield=65.4%)

H-NMR (200 MHz, $CDCl_3$): δ ppm, 2H (7.99/d, 7.69/s, 6.5/d), LC/MS: m/z=654[$(M+1)^+$]

21. Synthesis of Compound 109

(1) Compound 109-1

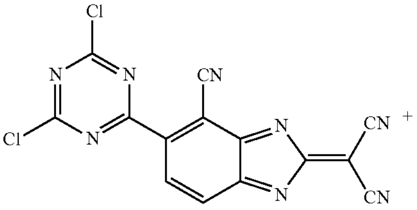

4-4

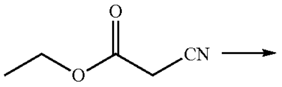

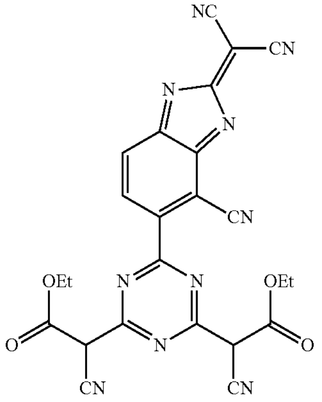

109-1

In a flask, ethyl-2-cyanoacetate (7.56 g, 0.067 mol) and TH (500 ml) were cooled at 0° C. After sodium hydride (13.1 g, 0.078 mol) was slowly added, the mixture was stirred for 1 hr. The compound 4-4 (10 g, 0.028 mol) dissolved in THE (60 ml) was added into the mixture, and the mixture was stirred and reacted under the room temperature for 12 hrs. After completion of reaction, the resultant was extracted and column-refined to obtain the compound 109-1. (10.3 g, yield=71.8%)

(2) Compound 109-2

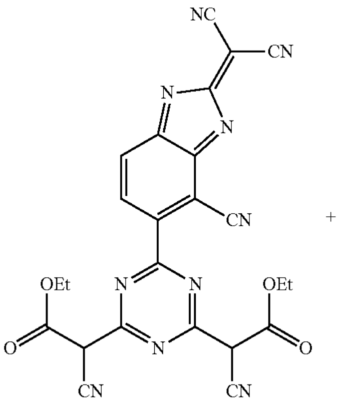

109-1

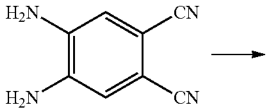

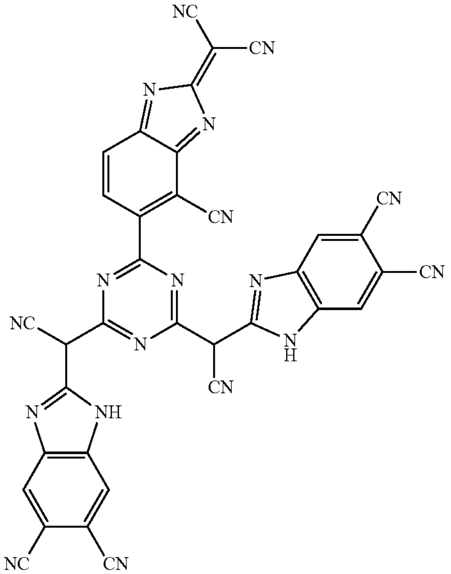

109-2

In a flask, the compound 109-1 (10 g, 0.0197 mol) and 4,5-diaminophthalonitrile (12.5 g, 0.079 mol) were stirred and reacted at 200° C. for 14 hrs. After completion of reaction, the resultant was extracted and re-crystalized to obtain the compound 109-2. (9.7 g, yield=73.3%)

(3) Compound 109

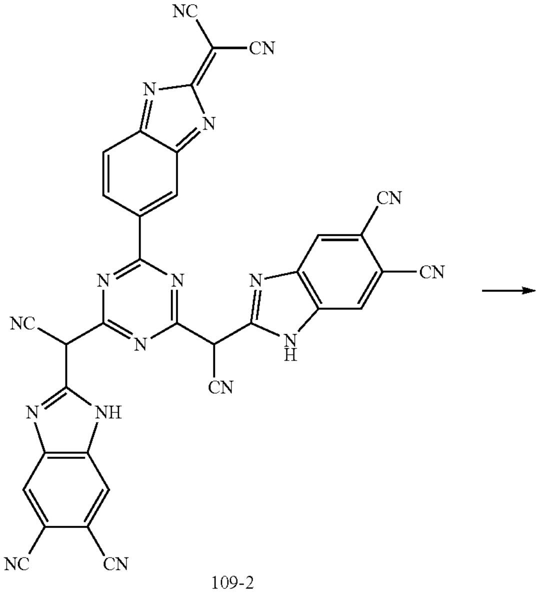

109-2

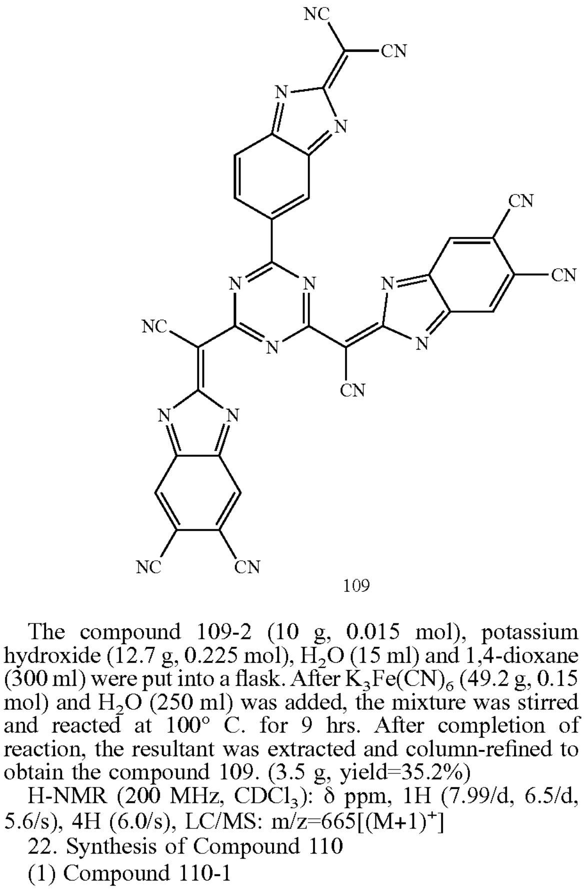

109

The compound 109-2 (10 g, 0.015 mol), potassium hydroxide (12.7 g, 0.225 mol), $H_2O$ (15 ml) and 1,4-dioxane (300 ml) were put into a flask. After $K_3Fe(CN)_6$ (49.2 g, 0.15 mol) and $H_2O$ (250 ml) was added, the mixture was stirred and reacted at 100° C. for 9 hrs. After completion of reaction, the resultant was extracted and column-refined to obtain the compound 109. (3.5 g, yield=35.2%)

H-NMR (200 MHz, $CDCl_3$): δ ppm, 1H (7.99/d, 6.5/d, 5.6/s), 4H (6.0/s), LC/MS: m/z=665[$(M+1)^+$]

22. Synthesis of Compound 110

(1) Compound 110-1

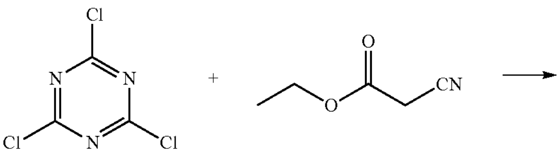

-continued

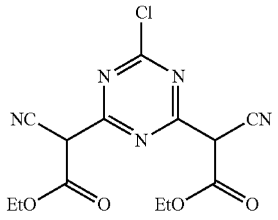

110-1

In a flask, ethyl-2-cyanoacetate (12.8 g, 0.113 mol) and THF (300 ml) were cooled at 0° C. After sodium hydride (3.62 g, 0.151 mol) was slowly added, the mixture was stirred for 1 hr. 2,4,6-trichloro-1,3,5-triazine (10 g, 0.054 mol) dissolved in THF (60 ml) was added into the mixture, and the mixture was stirred and reacted under the room temperature for 12 hrs. After completion of reaction, the resultant was extracted and column-refined to obtain the compound 110-1. (14 g, yield=76.4%)

(2) Compound 110-2

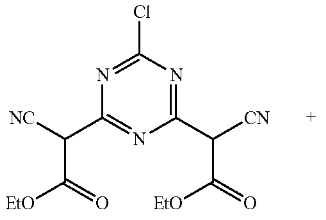

110-1

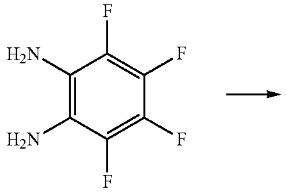

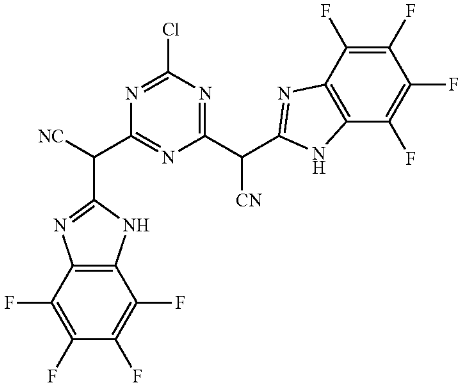

110-2

In a flask, the compound 110-1 (10 g, 0.029 mol) and 3,4,5,6-tetrafluorobenzene-1,2-diamine (10.67 g, 0.059 mol) were stirred and reacted at 200° C. for 12 hrs. After completion of reaction, the resultant was extracted and re-crystalized to obtain the compound 110-2. (12 g, yield=71.1%)

(3) Compound 110-3

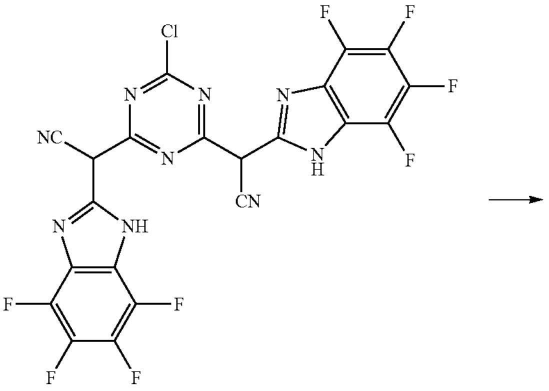

110-2

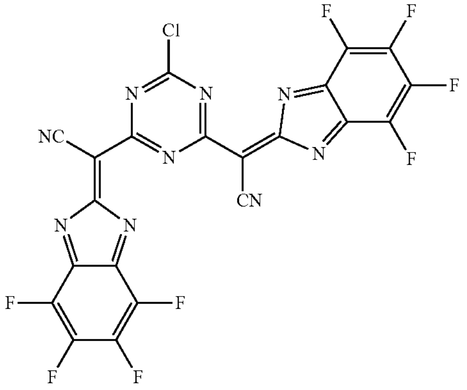

110-3

The compound 110-2 (10 g, 0.018 mol), potassium hydroxide (9.85 g, 0.176 mol), $H_2O$ (20 ml) and 1,4-dioxane (300 ml) were put into a flask. After $K_3Fe(CN)_6$ (40.45 g, 0.123 mol) and $H_2O$ (400 ml) was added, the mixture was stirred and reacted at 100° C. for 12 hrs. After completion of reaction, the resultant was extracted and column-refined to obtain the compound 110-3. (3.2 g, yield=32.2%)

(4) Compound 110-4

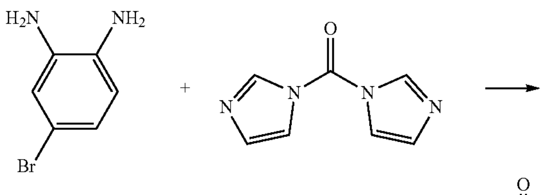

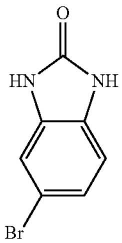

110-4

In a flask, 4-bromobenzene-1,2-diamine (10 g, 0.053 mol), 1,1'-carbonyldiimidazole (10.53 g, 0.064 mol) and DMF (200 ml) were stirred and reacted under the room temperature for 24 hrs. After completion of reaction, the resultant was extracted and re-crystalized to obtain the compound 110-4. (8.6 g, yield=75.5%)

(5) Compound 110-5

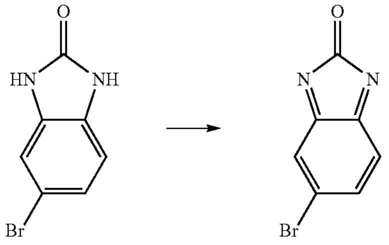

110-4 110-5

The compound 110-4 (10 g, 0.047 mol), potassium hydroxide (13.17 g, 0.235 mol), $H_2O$ (25 ml) and 1,4-dioxane (500 ml) were put into a flask. After $K_3Fe(CN)_6$ (46.37 g, 0.141 mol) and $H_2O$ (470 ml) was added, the mixture was stirred and reacted at 100° C. for 12 hrs. After completion of reaction, the resultant was extracted and column-refined to obtain the compound 110-5. (3.2 g, yield=32.3%)

(6) Compound 110-6

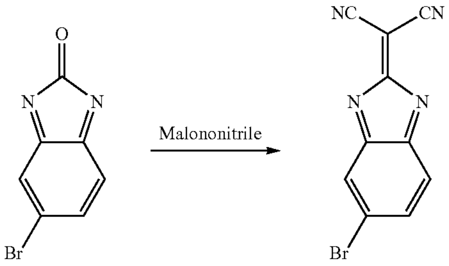

110-5 110-6

The compound 110-5 (10 g, 0.042 mol), malononitrile (4.69 g, 0.071 mol) and methylene chloride (300 ml) were put into a flask and cooled in an ice-bath. $TiCl_4$ (13.48 g, 0.0711 mol) was slowly dropped, and pyridine (11.25 g, 0.142 mol) was very slowly added. After 1 hr, the ice-bath was removed. The mixture was stirred and reacted for 24 hrs. After completion of reaction, the resultant was extracted using hydrochloric acid aqueous solution and column-refined to obtain the compound 110-6. (7.7 g, yield=62.7%)

(7) Compound 110-7

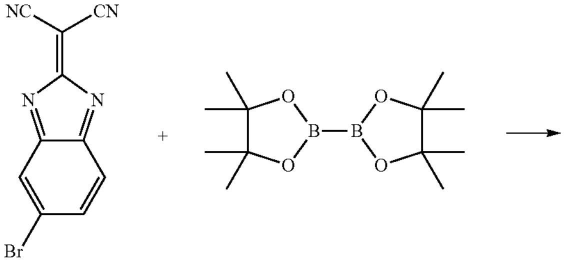

110-6

-continued

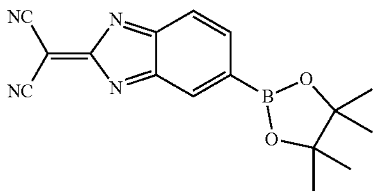

110-7

In a flask, the compound 110-6 (10 g, 0.0386 mol), bis(pinacolato)diboron (12.74 g, 0.050 mol), potassium acetate (7.58 g, 0.077 mol), $PdCl_2$(dppf) (0.85 g, 0.0012 mol) and 1,4-dioxane (200 ml) were stirred and reacted at 95° C. for 12 hrs. After completion of reaction, the resultant was extracted and column-refined to obtain the compound 110-7. (8.6 g, yield=72.7%)

(8) Compound 110

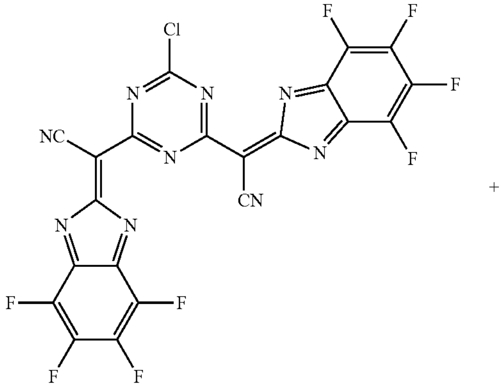

110-3

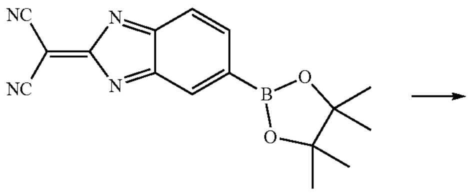

110-7

-continued

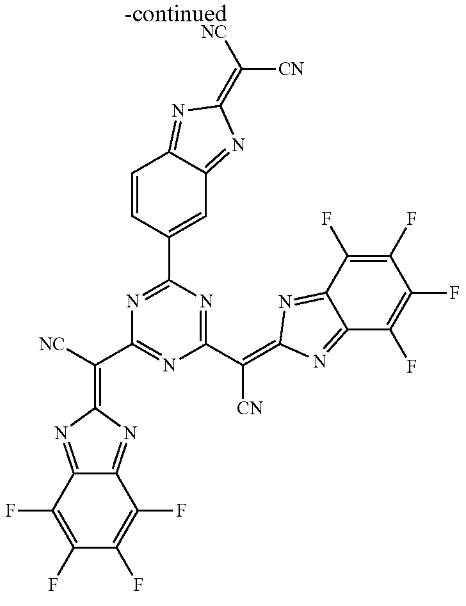

110

THF (200 ml) and water (50 ml) were added to the mixture of the compound 110-3 (10 g, 0.017 mol), the compound 110-7 (6.49 g, 0.021 mol), potassium carbonate (7.33 g, 0.053 mol) and $Pd(PPh_3)_4$ (1.02 g, 0.0009 mol), and the mixture was stirred and reacted at 60° C. for 8 hrs. After completion of reaction, the resultant was extracted and column-refined to obtain the compound 110. (9 g, yield=71.7%)

H-NMR (200 MHz, $CDCl_3$): δ ppm, 1H (7.99/d, 6.5/d, 5.6/s), LC/MS: m/z=709[$(M+1)^+$]

23. Synthesis of Compound 117

(1) Compound 117-1

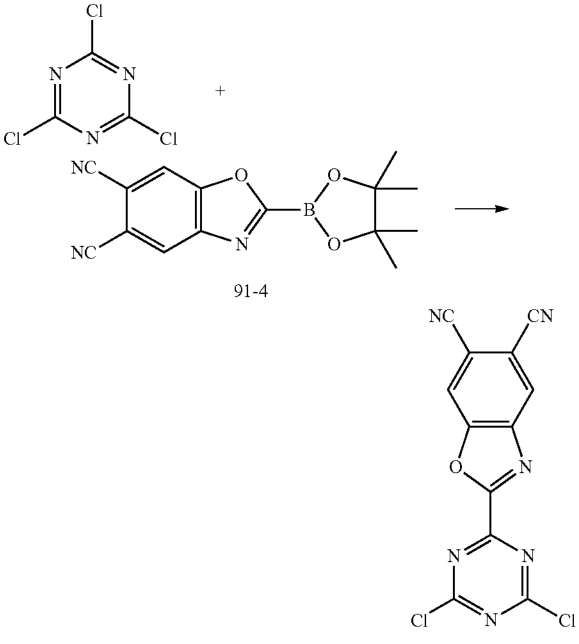

91-4

117-1

2,4,6-trichloro-1,3,5-triazine (10 g, 0.054 mol), the compound 91-4 (19.2 g, 0.065 mol), potassium carbonate (22.4 g, 0.163 mol), $Pd(PPh_3)_4$ (3.13 g, 0.003 mol), toluene (300 ml), ethanol (50 ml) and $H_2O$ (30 ml) were stirred for 10 hr. After completion of reaction, the resultant was extracted and column-refined to obtain the compound 117-1. (11.6 g, yield=67.4%)

(2) Compound 117-2

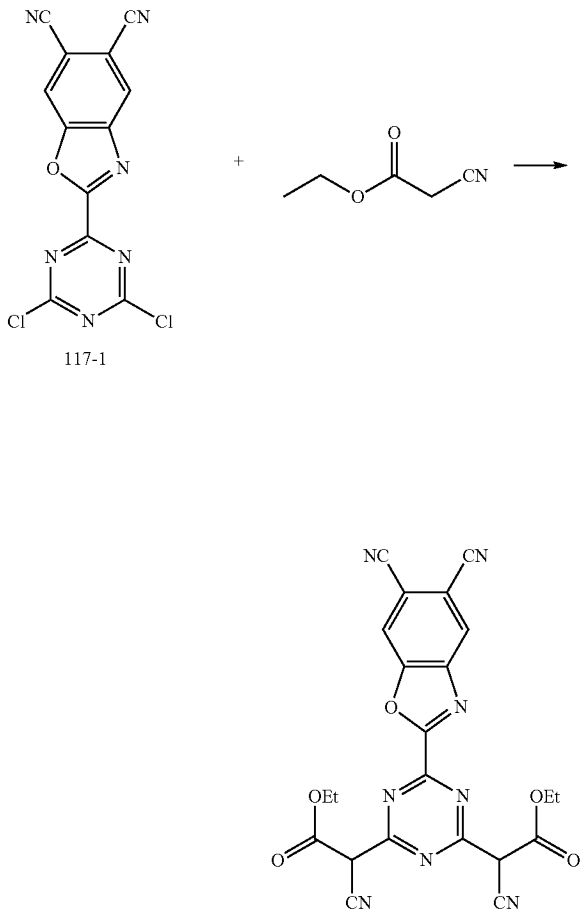

117-1

117-2

In a flask, ethyl-2-cyanoacetate (8.4 g, 0.074 mol) and THF (300 ml) were cooled at 0° C. After sodium hydride (3.4 g, 0.087 mol) was slowly added, the mixture was stirred for 1 hr. The compound 117-1 (10 g, 0.031 mol) dissolved in THF (60 ml) was added into the mixture, and the mixture was stirred and reacted under the room temperature for 12 hrs. After completion of reaction, the resultant was extracted and column-refined to obtain the compound 117-2. (11.3 g, yield=76.1%)

(3) Compound 117-3

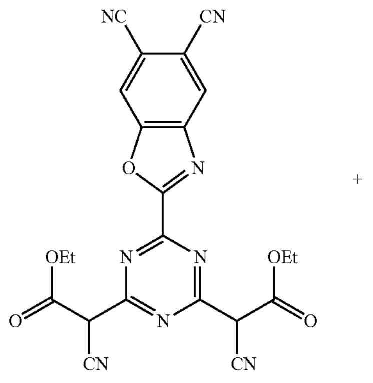

117-2

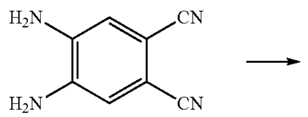

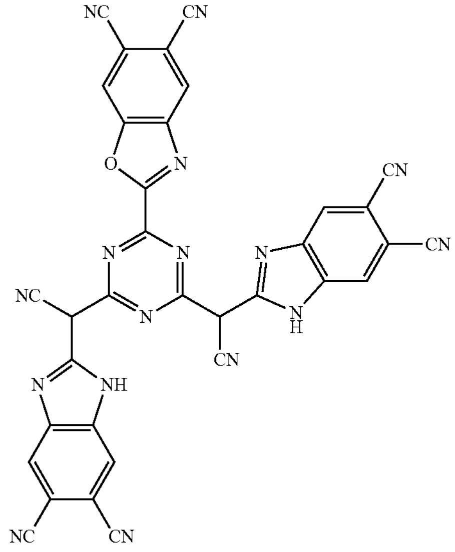

117-3

In a flask, the compound 117-2 (10 g, 0.021 mol) and 4,5-diaminophthalonitrile (20.2 g, 0.084 mol) were stirred and reacted at 200° C. for 10 hrs. After completion of reaction, the resultant was extracted and re-crystalized to obtain the compound 117-3. (10.7 g, yield=76.4%)

(4) Compound 117

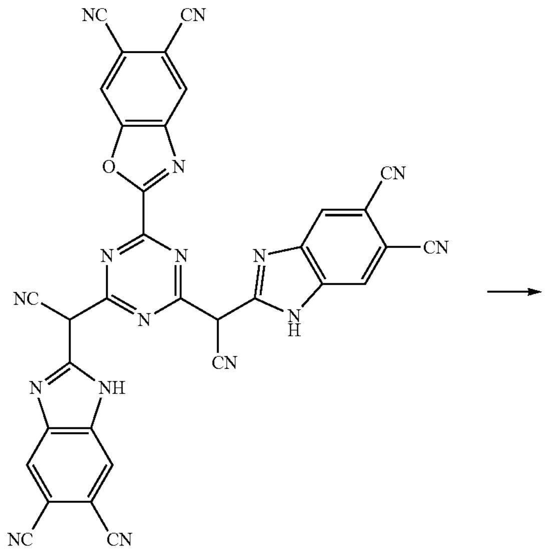

117-3

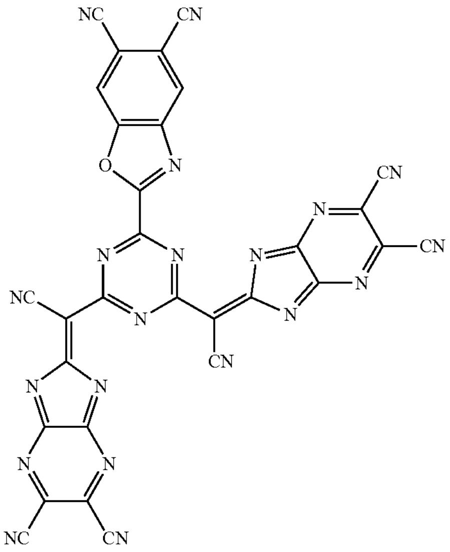

117

The compound 117-3 (10 g, 0.0152 mol), potassium hydroxide (12.8 g, 0.228 mol), $H_2O$ (20 ml) and 1,4-dioxane (500 ml) were put into a flask. After $K_3Fe(CN)_6$ (49.9 g, 0.152 mol) and $H_2O$ (400 ml) was added, the mixture was stirred and reacted at 100° C. for 12 hrs. After completion of reaction, the resultant was extracted and column-refined to obtain the compound 117. (3.2 g, yield=32%)

H-NMR (200 MHz, $CDCl_3$): δ ppm, 2H (7.69/s), LC/MS: m/z=658[$(M+1)^+$]

24. Synthesis of Compound 120

(1) Compound 120-1

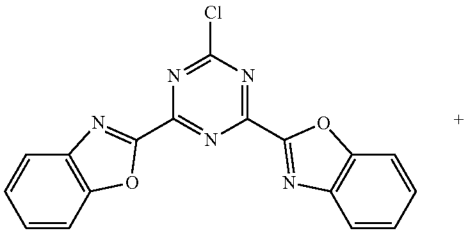

86-2

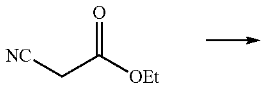

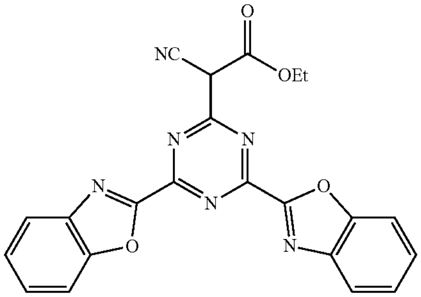

120-1

In a flask, ethyl-2-cyanoacetate (6.9 g, 0.061 mol) and THF (30 ml) were cooled at 0° C. After sodium hydride (0.96 g, 0.040 mol) was slowly added, the mixture was stirred for 1 hr. The compound 86-2 (1 g, 0.029 mol) dissolved in THF (60 ml) was added into the mixture, and the mixture was stirred and reacted under the room temperature for 12 hrs. After completion of reaction, the resultant was extracted and column-refined to obtain the compound 120-1. (9.1 g, yield=74.6%)

(2) Compound 120-2

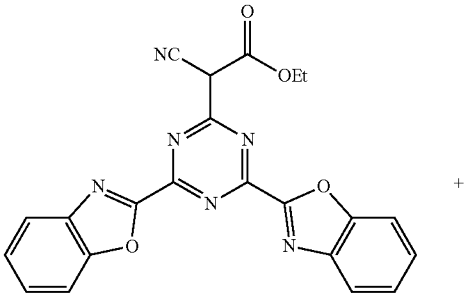

120-1

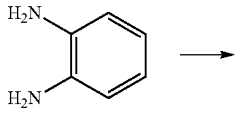

-continued

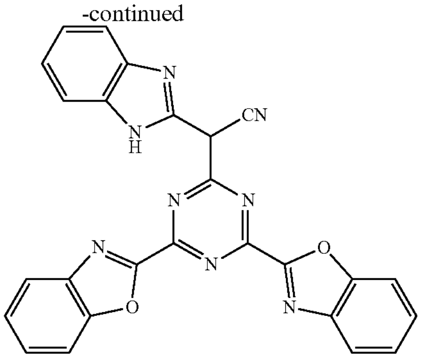

120-2

In a flask, the compound 120-1 (0 g, 0.023 mol) and o-phenylenediamine (5.3 g, 0.049 mol) were stirred and reacted at 200° C. for 10 hrs. After completion of reaction, the resultant was extracted and re-crystalized to obtain the compound 120-2. (8.3 g, yield=75.2%)

(3) Compound 120

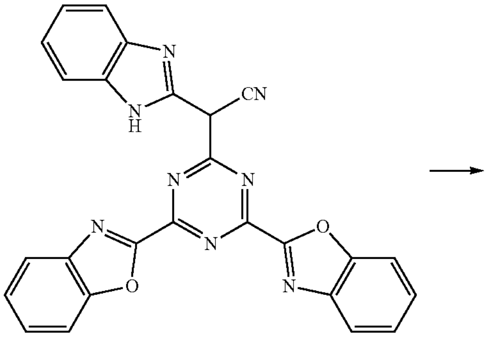

120-2

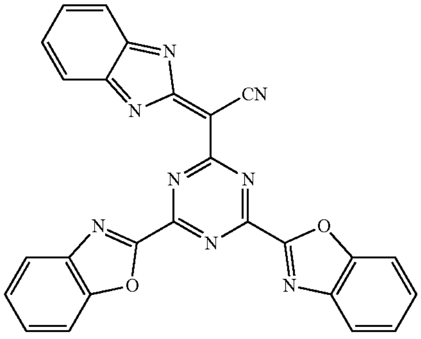

120

The compound 120-2 (10 g, 0.021 mol), potassium hydroxide (17.9 g, 0.319 mol), $H_2O$ (30 ml) and 1,4-dioxane (300 ml) were put into a flask. After $K_3Fe(CN)_6$ (69.9 g, 0.213 mol) and $H_2O$ (400 ml) was added, the mixture was stirred and reacted at 100° C. for 12 hrs. After completion of reaction, the resultant was extracted and column-refined to obtain the compound 120. (3.3 g, yield=33.1%)

H-NMR (200 MHz, $CDCl_3$): δ ppm, 2H (7.99/d, 7.86/m), 4H (7.74/m, 7.39/d), LC/MS: m/z=654[$(M+1)^+$]

25. Synthesis of Compound 123

(1) Compound 123-1

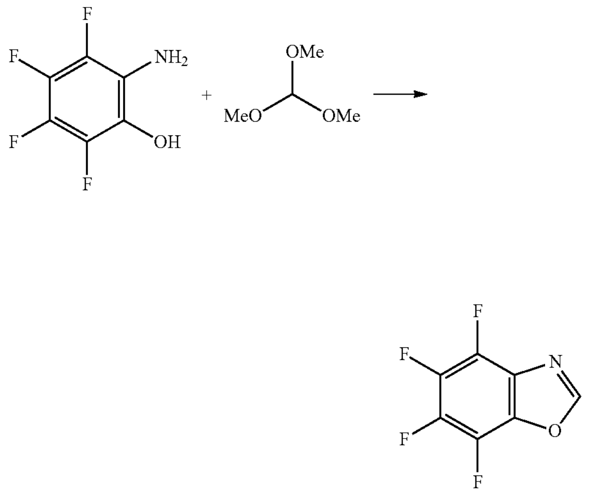

123-1

In a flask, 2-amino-3,4,5,6-tetrafluorophenol (10 g, 0.055 mol), trimethyl orthoformate (11.7 g, 0.110 mol) and acetic acid (13.3 g, 0.221 mol) were reacted at 85° C. for 2 hrs. After completion of reaction, the resultant was extracted and column-refined to obtain the compound 123-1. (7.9 g, yield=74.8%)

(2) Compound 123-2

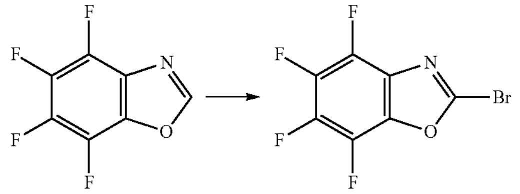

123-1 123-2

In a flask, carbon tetrabromide (19.1 g, 0.058 mol) and sodium t-butoxide (20.1 g, 0.209 mol) were added to DMF (35 ml), where the compound 123-1 (10 g, 0.052 mol) was dissolved, and the mixture was stirred under the room temperature for 5 hrs. After completion of reaction, the resultant was extracted using $CH_2Cl_2$ and column-refined to obtain the compound 123-2. (11.1 g, yield=78.5%)

(3) Compound 123-3

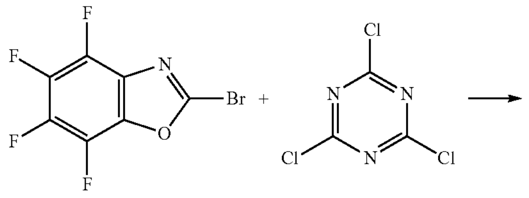

123-2

-continued

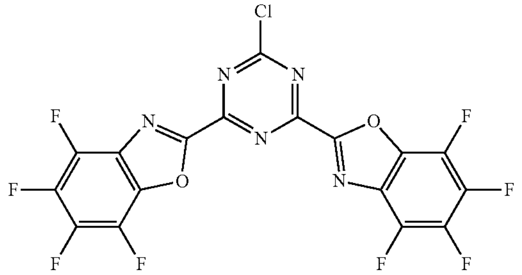

123-3

In a flask, magnesium (3.69 g, 0.152 mol), iodine (1.38 g, 0.005 mol) and THF (15 ml) were stirred, and the compound 123-2 (24.3 g, 0.089 mol) dissolved in TH (100 ml) was slowly added. The mixture was refluxed/stirred and reacted for 1 hr. After completion of reaction, the mixture was cooled into the room temperature to obtain the Grignard reagent. In another flask, 2,4,6-trichloro-1,3,5-triazine (10 g, 0.054 mol) and THF (100 ml) were added, and the mixture was cooled into 0° C. Grignard reagent was added into the mixture, and the mixture was stirred and reacted under the room temperature for 2 hrs. After completion of reaction, cool water was added at 0° C. to finish the reaction. The solid product was filtered and column-refined to obtain the compound 123-3. (16.6 g, yield=62.0%)

(4) Compound 123-4

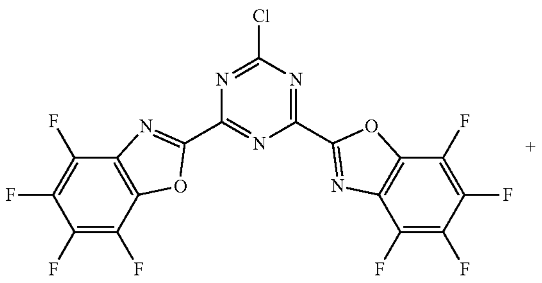

123-3

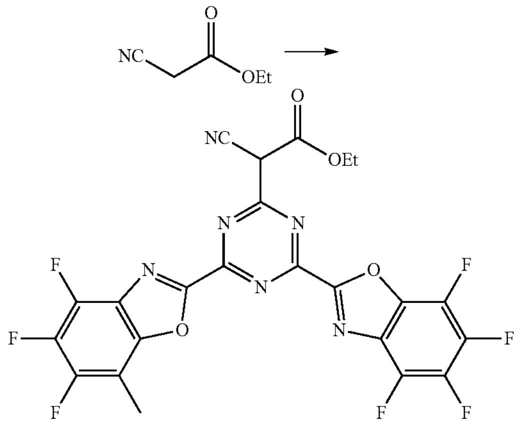

123-4

In a flask, ethyl-2-cyanoacetate (2.7 g, 0.024 mol) and THF (30 ml) were cooled at 0° C. After sodium hydride (0.68 g, 0.028 mol) was slowly added, the mixture was stirred for 1 hr. The compound 123-3 (10 g, 0.020 mol) dissolved in THE (60 ml) was added into the mixture, and the mixture was stirred and reacted under the room temperature for 12 hrs. After completion of reaction, the resultant was extracted and column-refined to obtain the compound 123-4. (8.5 g, yield=73.6%)

(5) Compound 123-5

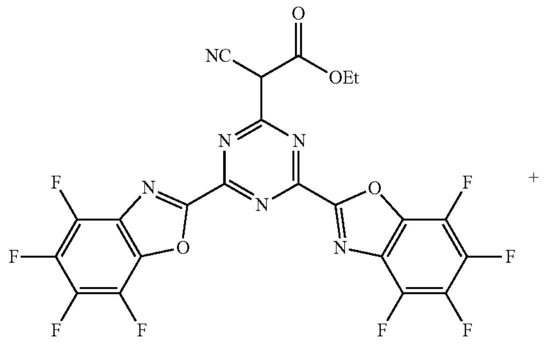

123-4

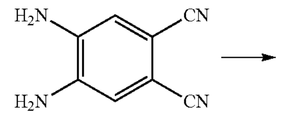

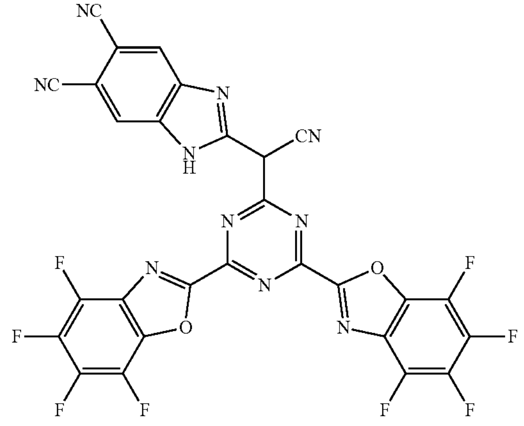

123-5

In a flask, the compound 123-4 (10 g, 0.017 mol) and 4,5-diaminophthalonitrile (4.9 g, 0.034 mol) were stirred and reacted at 200° C. for 12 hrs. After completion of reaction, the resultant was extracted and re-crystalized to obtain the compound 123-5. (9.1 g, yield=78.1%)

(6) compound 123

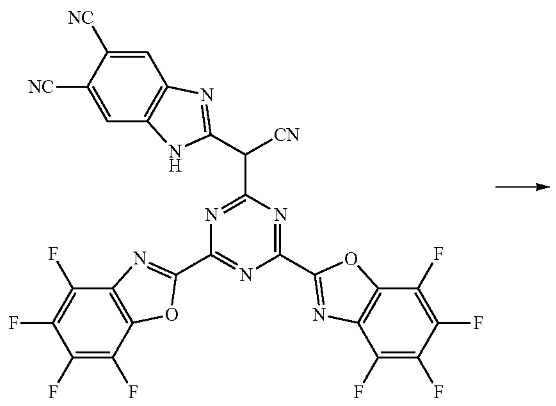

123-5

-continued

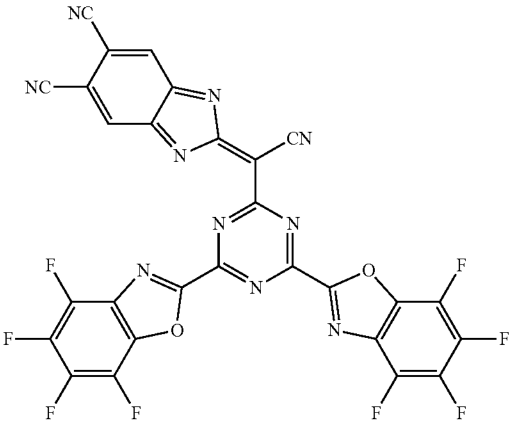

123

The compound 123-5 (10 g, 0.015 mol), potassium hydroxide (12.7 g, 0.226 mol), $H_2O$ (30 ml) and 1,4-dioxane (300 ml) were put into a flask. After $K_3Fe(CN)_6$ (49.6 g, 0.151 mol) and $H_2O$ (400 ml) was added, the mixture was stirred and reacted at 100° C. for 12 hrs. After completion of reaction, the resultant was extracted and column-refined to obtain the compound 123. (3.3 g, yield=33.1%)

H-NMR (200 MHz, $CDCl_3$): δ ppm, 2H (6.0/s), LC/MS: m/z=662[$(M+1)^+$]

26. Synthesis of Compound 146

(1) Compound 146-1

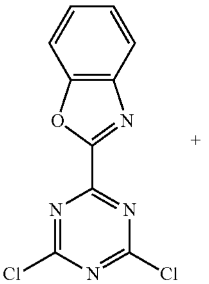

102-1

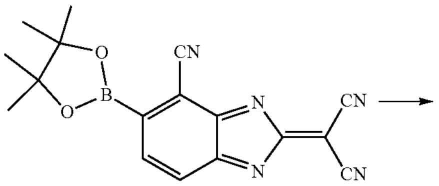

17-1

-continued

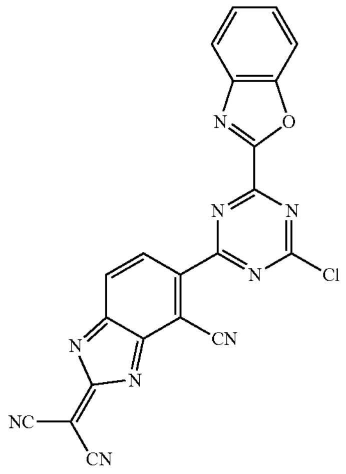

146-1

In a flask, the compound 102-1 (10 g, 0.037 mol), the compound 17-1 (14.9 g, 0.049 mol), potassium carbonate (15.5 g, 0.112 mol), $Pd(PPh_3)_4$ (2.16 g, 0.002 mol), toluene (200 ml), ethanol (40 ml) and $H_2O$ (20 ml) were stirred and reacted for 7 hrs. After completion of reaction, the resultant was extracted and column-refined to obtain the compound 146-1. (10.3 g, yield=63.1%)

(2) Compound 146-2

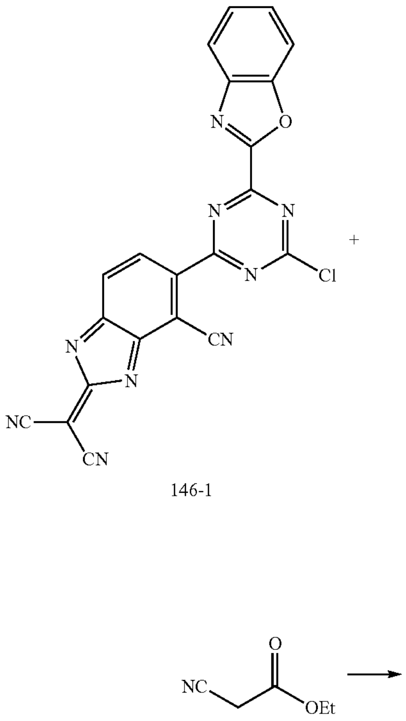

-continued

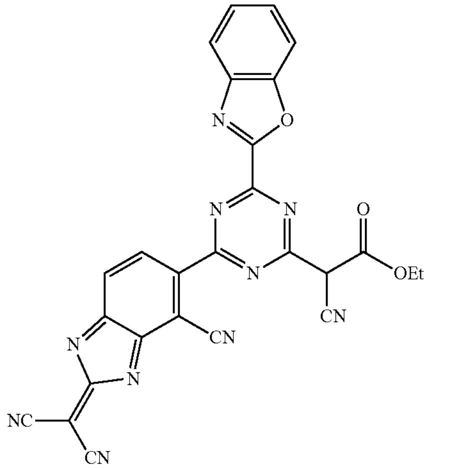

146-2

In a flask, ethyl-2-cyanoacetate (5.5 g, 0.048 mol) and THF (200 ml) were cooled at 0° C. After sodium hydride (0.77 g, 0.032 mol) was slowly added, the mixture was stirred for 1 hr. The compound 146-1 (10 g, 0.023 mol) dissolved in THF (60 ml) was added into the mixture, and the mixture was stirred and reacted under the room temperature for 12 hrs. After completion of reaction, the resultant was extracted and column-refined to obtain the compound 146-2. (8.7 g, yield=73.9%)

(3) Compound 146-3

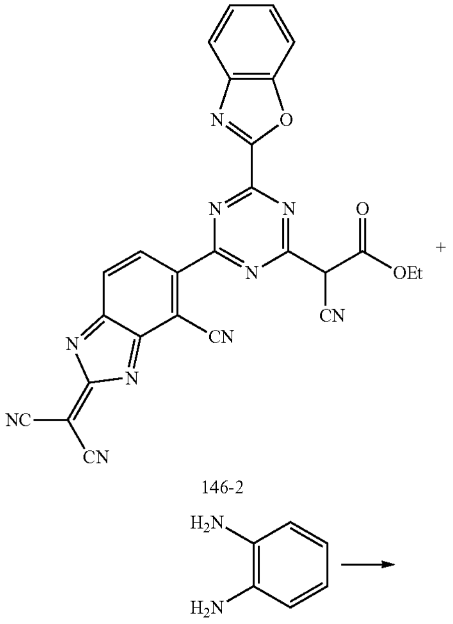

-continued

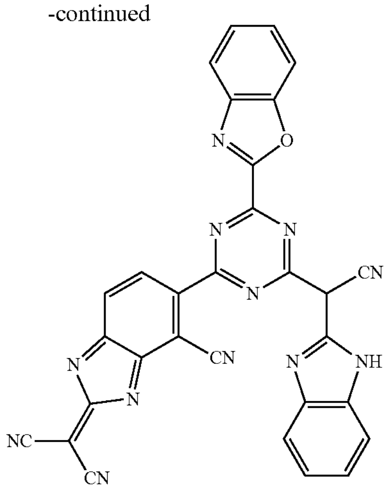

146-3

In a flask, the compound 146-2 (10 g, 0.019 mol) and o-Phenylenediamine (4.1 g, 0.038 mol) were stirred and reacted at 200° C. for 12 hrs. After completion of reaction, the resultant was extracted and re-crystalized to obtain the compound 146-3. (8.5 g, yield=78.2%)

(4) Compound 146

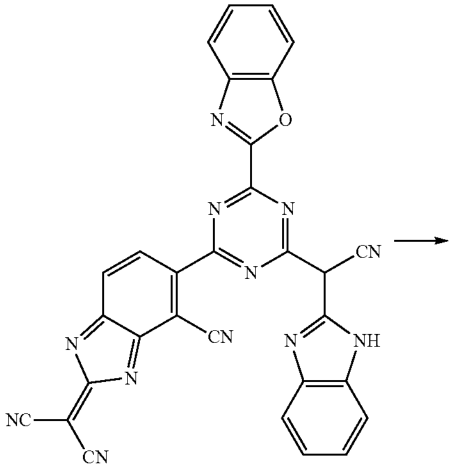

146-3

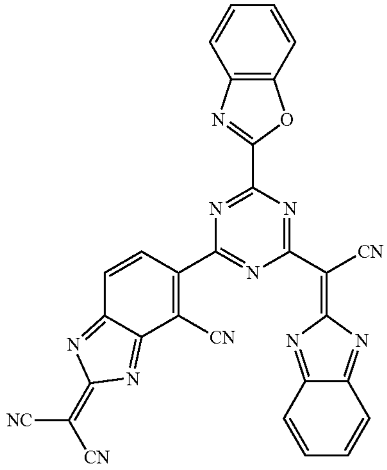

146

The compound 146-3 (10 g, 0.018 mol), potassium hydroxide (15.1 g, 0.269 mol), $H_2O$ (30 ml) and 1,4-dioxane (300 ml) were put into a flask. After $K_3Fe(CN)_6$ (59.2 g, 0.179 mol) and $H_2O$ (400 ml) was added, the mixture was stirred and reacted at 100° C. for 12 hrs. After completion of reaction, the resultant was extracted and column-refined to obtain the compound 146. (3.2 g, yield=32.1%)

H-NMR (200 MHz, $CDCl_3$): δ ppm, 1H (7.99/d, 6.5/d), 2H (7.69/s, 6.0/s), LC/MS: m/z=654[$(M+1)^+$]

27. Synthesis of Compound 151

(1) Compound 151-1

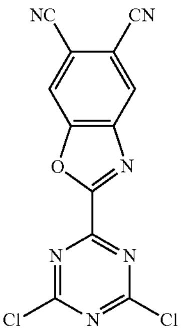

117-1

+

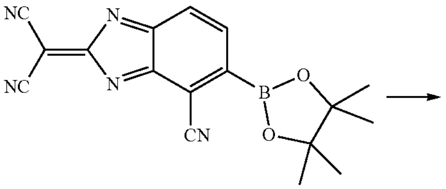

17-1

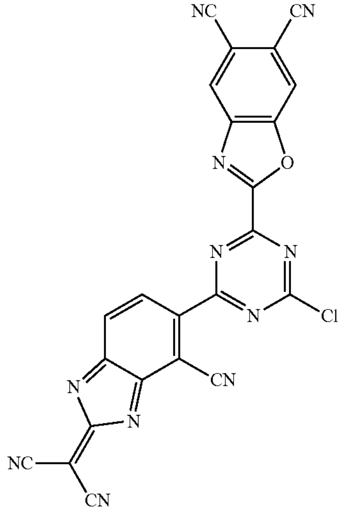

151-1

In a flask, the compound 117-1 (10 g, 0.031 mol), the compound 17-1 (12.5 g, 0.038 mol), potassium carbonate (13.1 g, 0.095 mol), $Pd(PPh_3)_4$ (1.82 g, 0.002 mol), toluene (200 ml), ethanol (40 ml) and $H_2O$ (20 ml) were stirred and reacted for 7 hrs. After completion of reaction, the resultant was extracted and column-refined to obtain the compound 151-1. (10.7 g, yield=69.8%)

(2) Compound 151-2

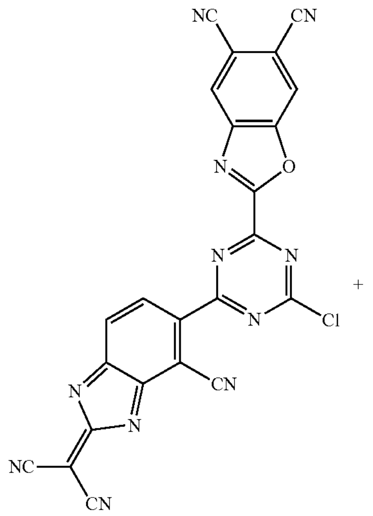

151-1

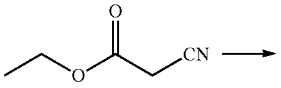

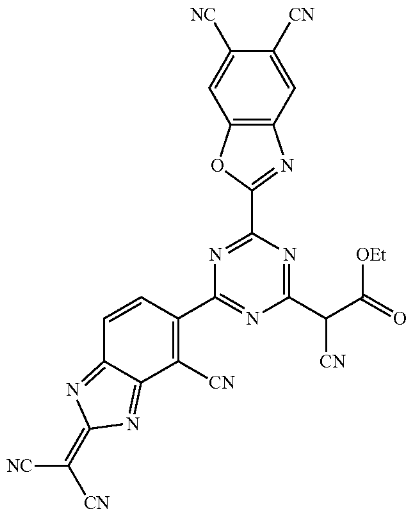

151-2

In a flask, ethyl-2-cyanoacetate (5.1 g, 0.046 mol) and THF (200 ml) were cooled at 0° C. After sodium hydride (1.15 g, 0.029 mol) was slowly added, the mixture was stirred for 1 hr. The compound 151-1 (10 g, 0.021 mol) dissolved in THE (60 ml) was added into the mixture, and the mixture was stirred and reacted under the room temperature for 12 hrs. After completion of reaction, the resultant was extracted and column-refined to obtain the compound 151-2. (8.6 g, yield=74.2%)

(3) Compound 151-3

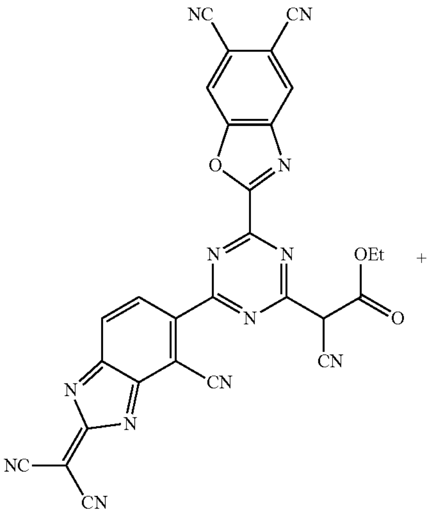

151-2

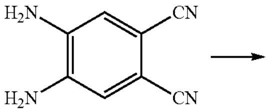

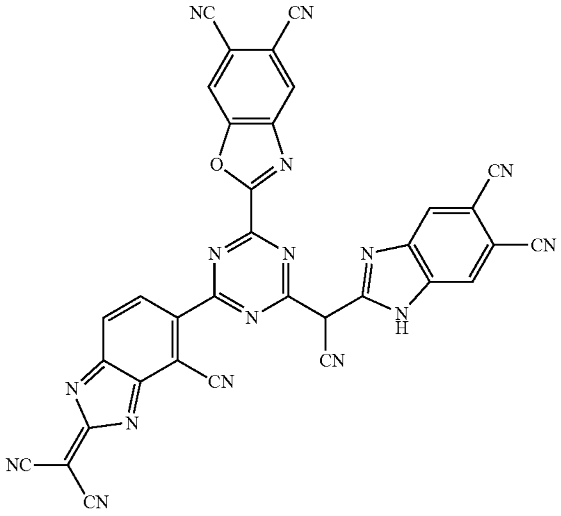

151-3

In a flask, the compound 151-2 (10 g, 0.018 mol) and 4,5-diaminophthalonitrile (5.62 g, 0.036 mol) were stirred and reacted at 200° C. for 12 hrs. After completion of reaction, the resultant was extracted and re-crystalized to obtain the compound 151-3. (9.1 g, yield=77.9%)

(4) Compound 151

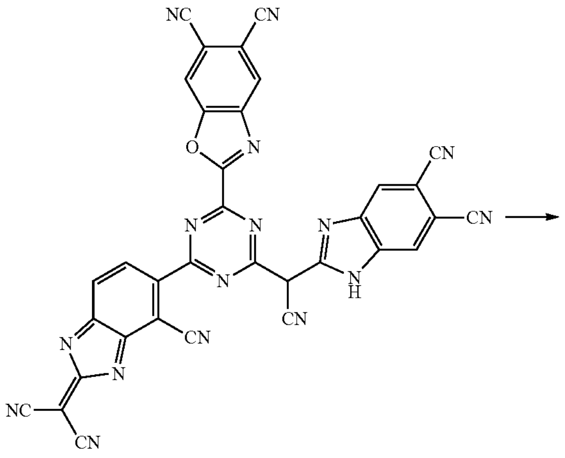

151-3

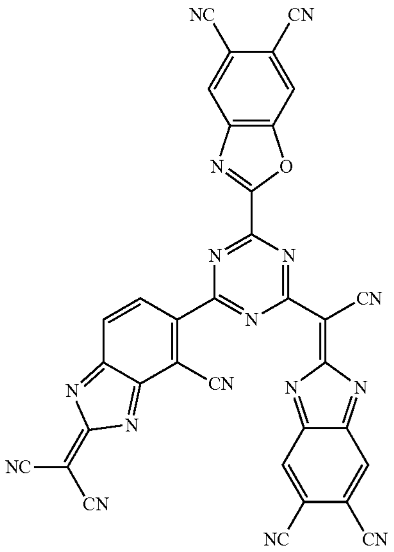

151

The compound 151-3 (10 g, 0.015 mol), potassium hydroxide (12.8 g, 0.229 mol), $H_2O$ (30 ml) and 1,4-dioxane (300 ml) were put into a flask. After $K_3Fe(CN)_6$ (50.1 g, 0.152 mol) and $H_2O$ (400 mol) was added, the mixture was stirred and reacted at 100° C. for 12 hrs. After completion of reaction, the resultant was extracted and column-refined to obtain the compound 151. (2.9 g, yield=29.1%)

H-NMR (200 MHz, $CDCl_3$): δ ppm, 1H (7.99/d, 6.5/d), 2H (7.69/s, 6.0/s), LC/MS: m/z=654[$(M+1)^+$]

28. Synthesis of Compound 159

(1) Compound 159-1

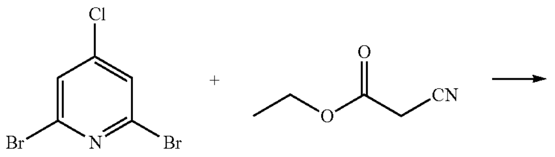

-continued

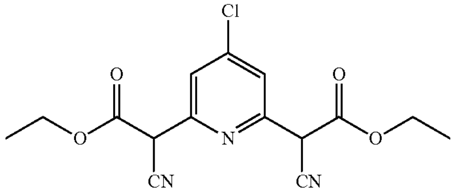

159-1

In a flask, 2,6-dibromo-4-chloropyridine (10 g, 0.037 mol), CuI (1.40 g, 0.007 mol), picolinic acid (5.31 g, 0.015 mol), $Cs_2CO_3$ (19.5 g, 0.155 mol), ethyl 2-cyanoacetate (17.5 g, 0.155 mol) and 1,4-dioxane (400 ml) were stirred and reacted at 80° C. for 15 hrs. After completion of reaction, the mixture was cooled into the room temperature. The resultant was extracted and column-refined to obtain the compound 159-1. (8.4 g, yield=67.9%)

(2) Compound 159-2

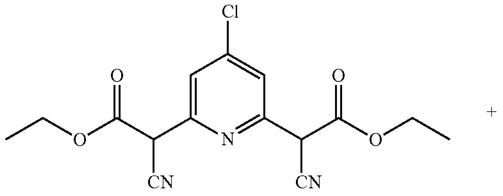

159-1

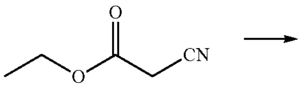

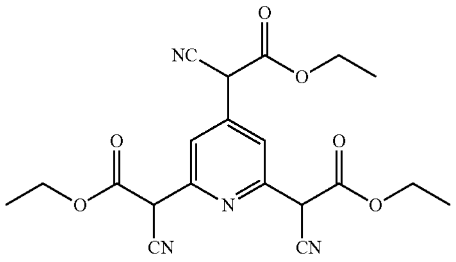

159-2

In a flask, ethyl-2-cyanoacetate (4.4 g, 0.039 mol) and THF (200 ml) were cooled at 0° C. After sodium hydride (1.0 g, 0.042 mol) was slowly added, the mixture was stirred for 1 hr. The compound 159-1 (10 g, 0.029 mol) dissolved in THE (60 ml) was added into the mixture, and the mixture was stirred and reacted under the room temperature for 12 hrs. After completion of reaction, the resultant was extracted and column-refined to obtain the compound 159-2. (9.1 g, yield=74.1%)

(3) Compound 159-3

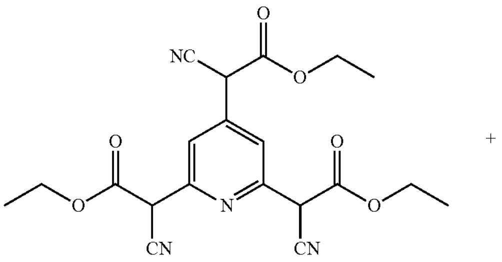

159-2

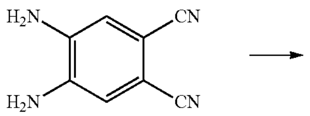

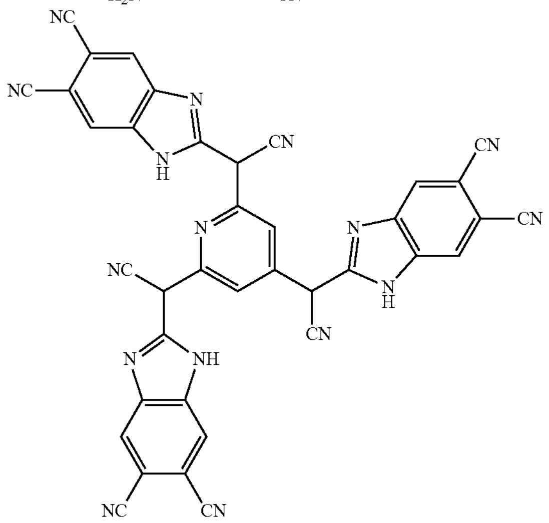

159-3

In a flask, the compound 159-2 (10 g, 0.024 mol) and 4,5-diaminophthalonitrile (23.0 g, 0.146 mol) were stirred and reacted at 200° C. for 10 hrs. After completion of reaction, the resultant was extracted and re-crystalized to obtain the compound 159-3. (12.6 g, yield=74.8%)

(4) Compound 159

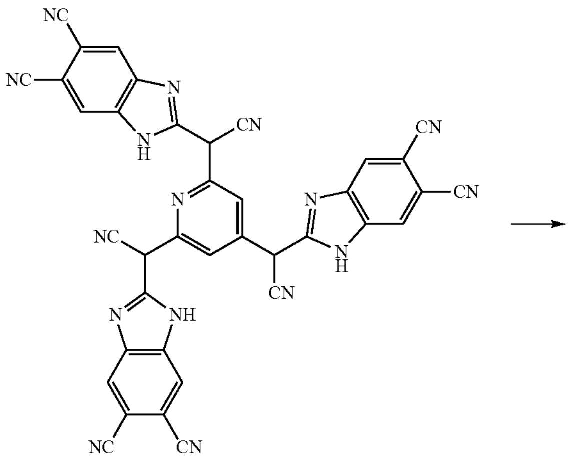

159-3

-continued

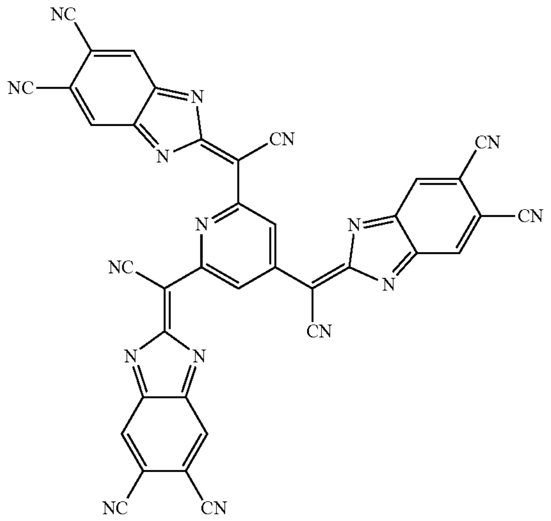

159

The compound 159-3 (10 g, 0.014 mol), potassium hydroxide (12.1 g, 0.216 mol), $H_2O$ (30 ml) and 1,4-dioxane (300 ml) were put into a flask. After $K_3Fe(CN)_6$ (47.4 g, 0.144 mol) and $H_2O$ (400 ml) was added, the mixture was stirred and reacted at 100° C. for 12 hrs. After completion of reaction, the resultant was extracted and column-refined to obtain the compound 159. (2.9 g, yield=29.1%)

H-NMR (200 MHz, $CDCl_3$): δ ppm, 2H (7.51/s), 6H (6.0/s), LC/MS: m/z=654[$(M+1)^+$]

29. Synthesis of Compound 161

(1) Compound 161-1

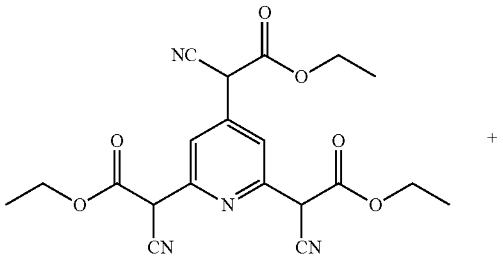

159-2

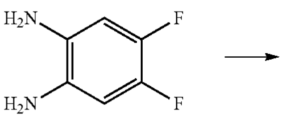

-continued

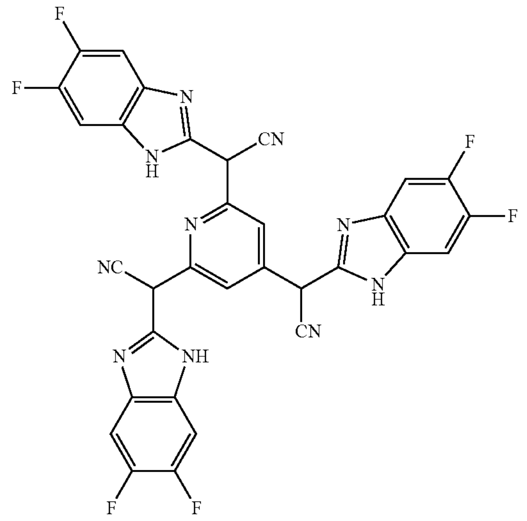

161-1

In a flask, the compound 159-2 (10 g, 0.024 mol) and 4,5-difluorobenzene-1,2-diamine (21.0 g, 0.145 mol) were stirred and reacted at 200° C. for 12 hrs. After completion of reaction, the resultant was extracted and re-crystalized to obtain the compound 161-1. (12.1 g, yield=76.5%)

(2) Compound 161

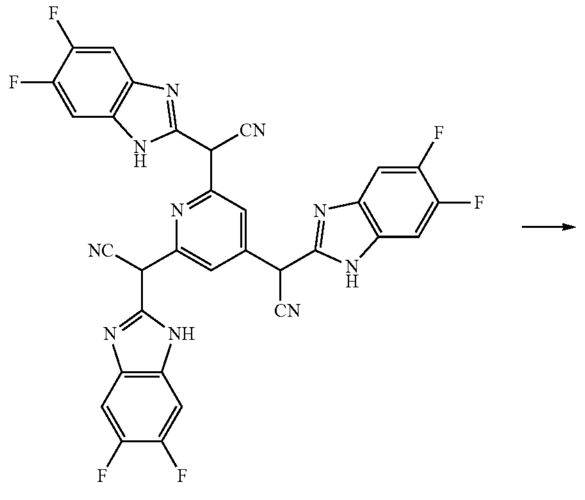

161-1

-continued

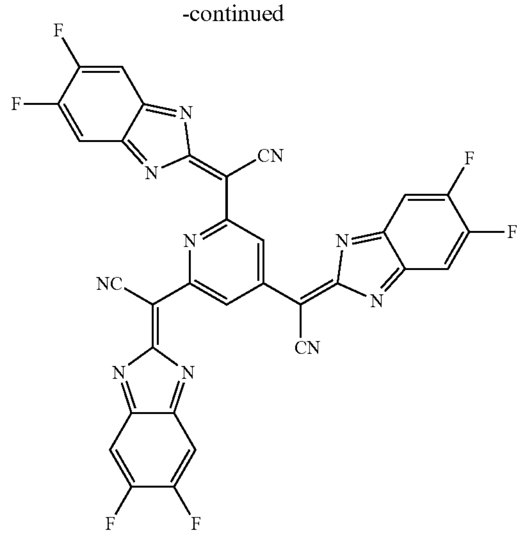

161

The compound 161-1 (10 g, 0.015 mol), potassium hydroxide (12.9 g, 0.230 mol), $H_2O$ (30 ml) and 1,4-dioxane (300 ml) were put into a flask. After $K_3Fe(CN)_6$ (50.5 g, 0.153 mol) and $H_2O$ (400 ml) was added, the mixture was stirred and reacted at 100° C. for 12 hrs. After completion of reaction, the resultant was extracted and column-refined to obtain the compound 161. (3.2 g, yield=32.3%)

H-NMR (200 MHz, $CDCl_3$): δ ppm, 2H (7.51/s), 6H (4.8/s), LC/MS: m/z=646[$(M+1)^+$]

30. Synthesis of Compound 162

(1) Compound 162-1

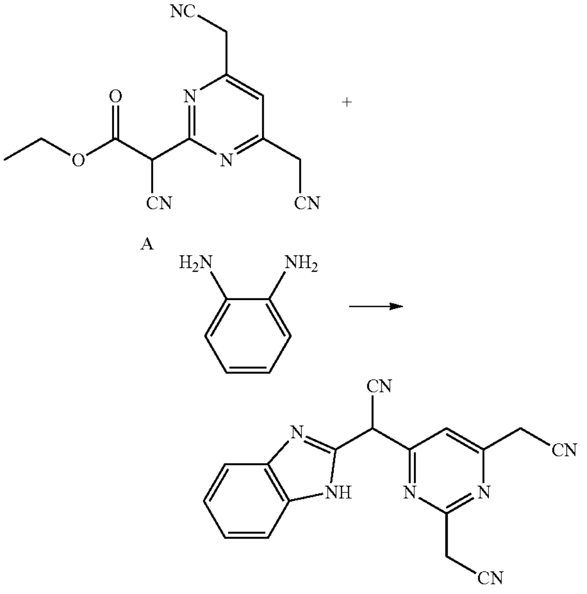

A 162-1

In a flask, the compound A (10 g, 0.037 mol) and o-phenylenediamine (7.9 g, 0.074 mol) were stirred and reacted at 200° C. for 12 hrs. After completion of reaction, the resultant was extracted and re-crystalized to obtain the compound 162-1. (9.2 g, yield=79.1%)

(2) Compound 161-2

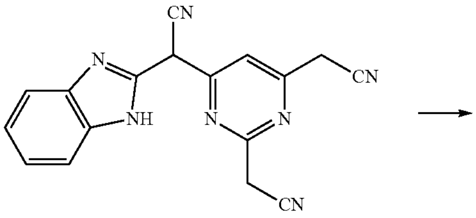

162-1

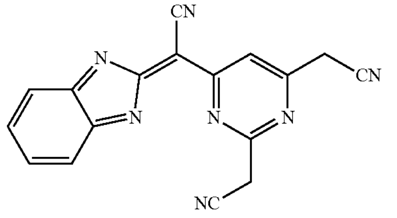

162-2

The compound 162-1 (10 g, 0.032 mol), potassium hydroxide (26.8 g, 0.479 mol), $H_2O$ (30 ml) and 1,4-dioxane (300 ml) were put into a flask. After $K_3Fe(CN)_6$ (105 g, 0.319 mol) and $H_2O$ (400 ml) was added, the mixture was stirred and reacted at 100° C. for 12 hrs. After completion of reaction, the resultant was extracted and column-refined to obtain the compound 162-2. (3.2 g, yield=32.2%)

(3) Compound 162

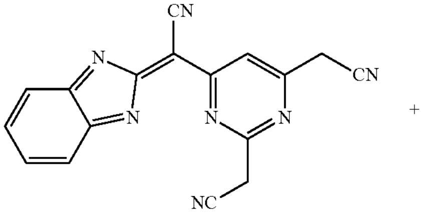

162-2

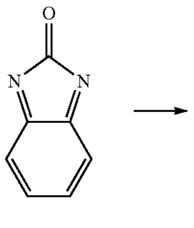

-continued

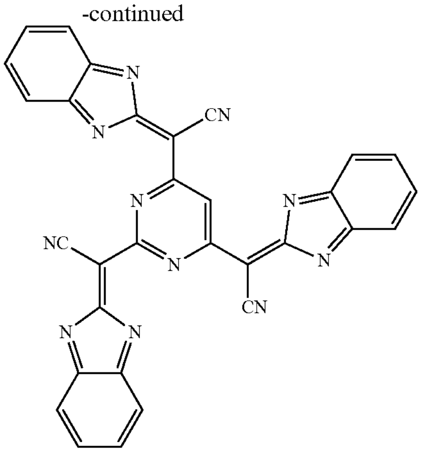

162

The compound 162-2 (10 g, 0.028 mol), benzimidazol-2-one (9.3 g, 0.071 mol) and methylene chloride (500 ml) were put into a flask and cooled in an ice-bath. $TiCl_4$ (12.2 g, 0.064 mol) was slowly dropped, and pyridine (7.62 g, 0.096 mol) was very slowly added. After 1 hr, the ice-bath was removed. The mixture was stirred and reacted for 24 hrs. After completion of reaction, the resultant was extracted using hydrochloric acid aqueous solution and column-refined to obtain the compound 162. (11.5 g, yield=66.3%)

H-NMR (200 MHz, $CDCl_3$): δ ppm, 1H (7.47/s), 6H (7.99/d, 7.86/m), LC/MS: m/z=539[$(M+1)^+$]

31. Synthesis of Compound 163

(1) Compound 163-1

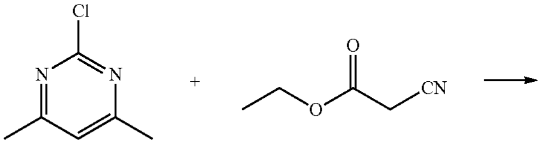

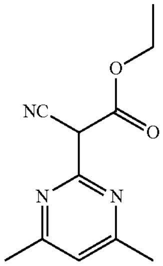

163-1

In a flask, 2-chloro-4,6-dimethylpyrimidine (10 g, 0.070 mol), CuI (1.34 g, 0.007 mol), picolinic acid (5.06 g, 0.014 mol), $Cs_2CO_3$ (18.1 g, 0.148 mol), ethyl 2-cyanoacetate (16.7 g, 0.147 mol) and 1,4-dioxane (300 ml) were stirred and reacted at 80° C. for 14 hrs. After completion of reaction, the mixture was cooled into the room temperature. The resultant was extracted and column-refined to obtain the compound 163-1. (10.3 g, yield=66.9%)

(2) Compound 163-2

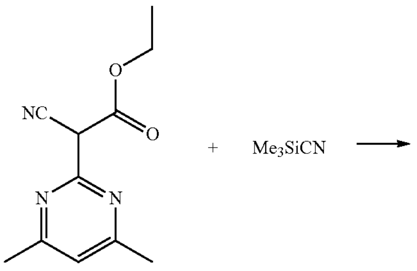

163-1

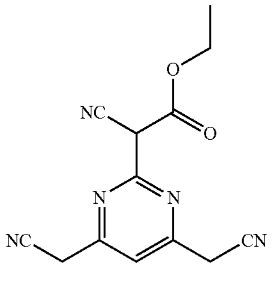

163-2

$Me_3SiCN$ (13.6 g, 0.137 mol) and t-BuOK (15.35 g, 0.137 mol) were added into THE (300 ml), and the mixture was reacted under the room temperature for 3 hrs. After the compound 163-1 (10 g, 0.046 mol) was added, the mixture was stirred and reacted for 12 hrs. After completion of reaction, the mixture was cooled into the room temperature. The resultant was extracted and column-refined to obtain the compound 163-2. (58.6 g, yield=58.6%)

(3) Compound 163-3

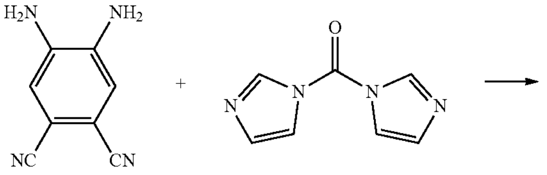

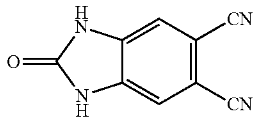

163-3

In a flask, 4,5-diaminophthalonitrile (10 g, 0.063 mol), 1,1'-carbonyldiimidazole (12.3 g, 0.076 mol) and DMF (200 ml) were stirred and reacted under the room temperature for 24 hrs. After completion of reaction, the resultant was extracted and re-crystalized to obtain the compound 163-3. (8.9 g, yield=76.4%)

(4) Compound 163-4

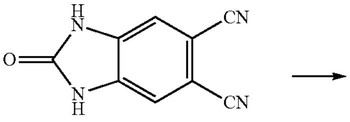

163-3

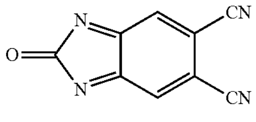

163-4

The compound 163-3 (10 g, 0.054 mol), potassium hydroxide (15.2 g, 0.271 mol), $H_2O$ (30 ml) and 1,4-dioxane (500 ml) were added into a flask, and $K_3Fe(CN)_6$ (53.6 g, 0.163 mol) and $H_2O$ (490 ml) were dropped. The mixture was stirred and reacted at 100° C. for 12 hrs. After completion of reaction, the resultant was extracted and column-refined to obtain the compound 163-4. (5.8 g, yield=39.7%)

(5) Compound 163-5

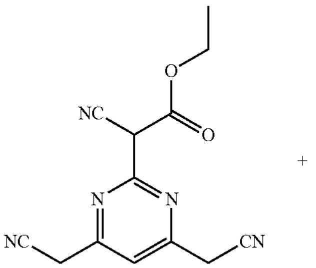

163-2

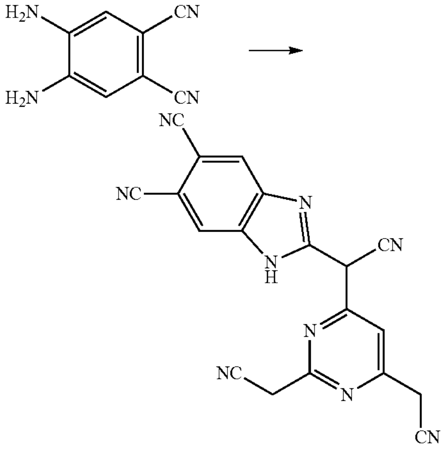

163-5

In a flask, the compound 163-2 (10 g, 0.037 mol) and 4,5-diaminophthalonitrile (11.75 g, 0.074 mol) were stirred and reacted at 200° C. for 12 hrs. After completion of reaction, the resultant was extracted and re-crystalized to obtain the compound 163-5. (70.2 g, yield=75.6%)

(6) Compound 163-6

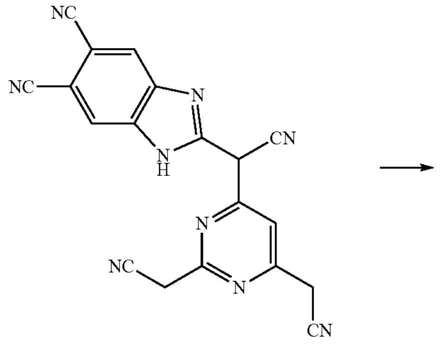

163-5

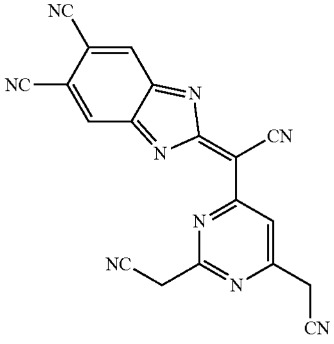

163-6

The compound 163-5 (10 g, 0.027 mol), potassium hydroxide (22.5 g, 0.405 mol), $H_2O$ (20 ml) and 1,4-dioxane (500 ml) were added into a flask, and $K_3Fe(CN)_6$ (88.5 g, 0.27 mol) and $H_2O$ (470 ml) were dropped. The mixture was stirred and reacted at 100° C. for 12 hrs. After completion of reaction, the resultant was extracted and column-refined to obtain the compound 163-6. (3.3 g, yield=33.2%)

(7) Compound 163

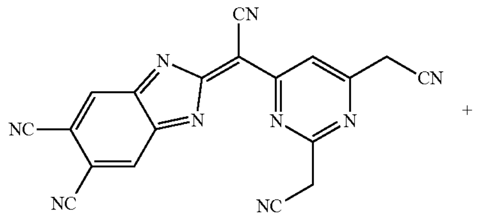

163-8

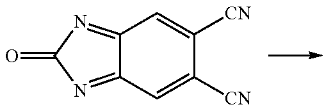

163-4

-continued

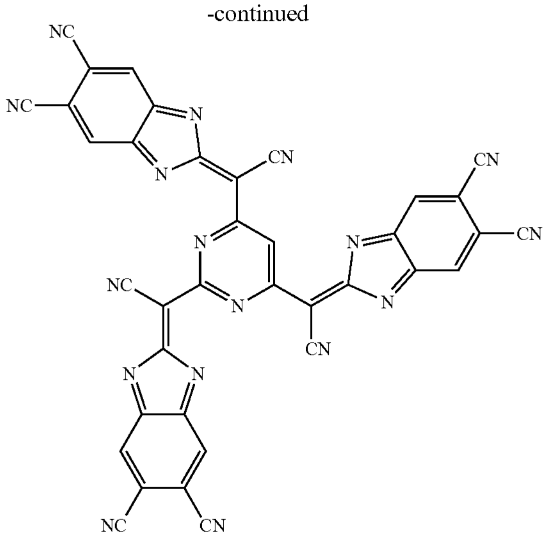

163

The compound 163-6 (10 g, 0.028 mol), the compound 163-4 (11.1 g, 0.061 mol) and methylene chloride (500 ml) were put into a flask and cooled in an ice-bath. $TiCl_4$ (7.87 g, 0.041 mol) was slowly dropped, and pyridine (6.57 g, 0.083 mol) was very slowly added. After 1 hr, the ice-bath was removed. The mixture was stirred and reacted for 24 hrs. After completion of reaction, the resultant was extracted using hydrochloric acid aqueous solution and column-refined to obtain the compound 163. (12.8 g, yield=67.1%)

H-NMR (200 MHz, $CDCl_3$): δ ppm, 1H (7.47/s), 6H (6.0/s), LC/MS: m/z=654[$(M+1)^+$]

32. Synthesis of Compound 170

(1) Compound 170-1

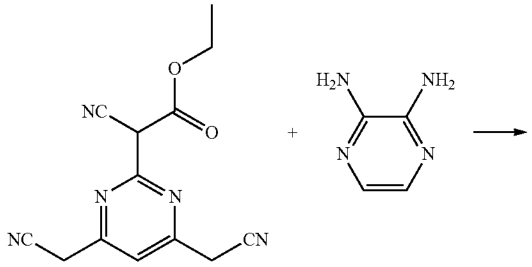

163-2

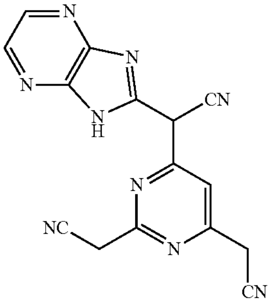

170-1

(8.2 g, 0.074 mol) were stirred and reacted at 200° C. for 12 hrs. After completion of reaction, the resultant was extracted and re-crystalized to obtain the compound 170-1. (9.1 g, yield=77.7%)

(2) Compound 170-2

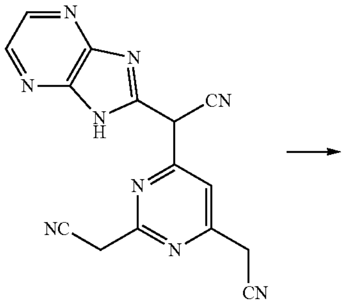

170-1

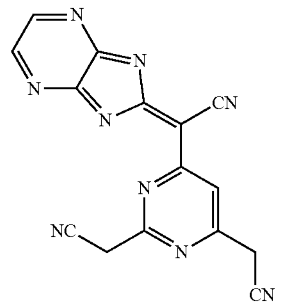

170-2

The compound 1 (g, 0.032 mol), potassium hydroxide (26.7 g, 0.476 mol), $H_2O$ (20 ml) and 1,4-dioxane (500 ml) were added into a flask, and $K_3Fe(CN)$ (104.5 g, 0.317 mol) and $H_2O$ (500 ml) were dropped. The mixture was stirred and reacted at 100° C. for 14 hrs. After completion of reaction, the resultant was extracted and column-refined to obtain the compound 170-2. (2.9 g, yield=29.2%)

(3) Compound 170

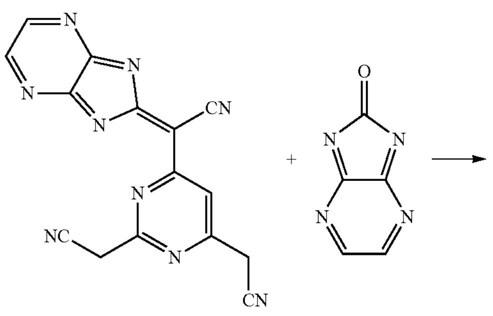

170-2

-continued

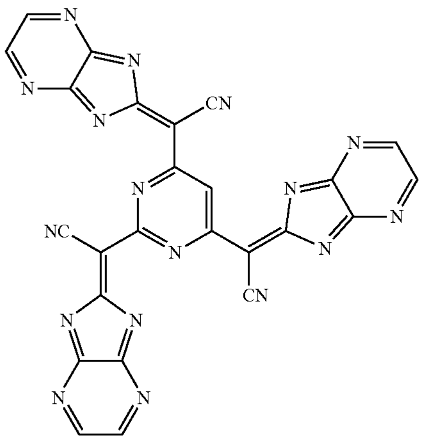

170

The compound 170-2 (10 g, 0.032 mol), imidazopyrazinone (9.0 g, 0.067 mol) and methylene chloride (500 ml) were put into a flask and cooled in an ice-bath. $TiCl_4$ (12.1 g, 0.064 mol) was slowly dropped, and pyridine (7.57 g, 0.096 mol) was very slowly added. After 1 hr, the ice-bath was removed. The mixture was stirred and reacted for 24 hrs. After completion of reaction, the resultant was extracted using hydrochloric acid aqueous solution and column-refined to obtain the compound 170. (11.6 g, yield=66.6%)

H-NMR (200 MHz, $CDCl_3$): δ ppm, 1H (7.47/s), 2H (7.50/d), 4H (8.68/d), LC/MS: m/z=545[$(M+1)^+$]

33. Synthesis of Compound 171

(1) Compound 171-1

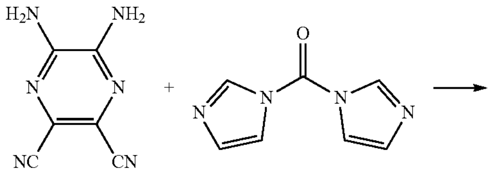

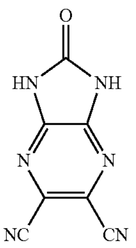

171-1

In a flask, 5,6-diaminopyrazine-2,3-dicarbonitrile (10 g, 0.062 mol), 1,1'-carbonyldiimidazole (12.1 g, 0.075 mol) and DMF (200 ml) were stirred and reacted under the room temperature for 24 hrs. After completion of reaction, the resultant was extracted and re-crystalized to obtain the compound 171-1. (8.4 g, yield=72.3%)

(2) Compound 171-2

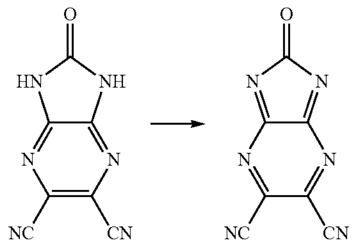

171-1 171-2

The compound 171-1 (10 g, 0.054 mol), potassium hydroxide (15.1 g, 0.269 mol), $H_2O$ (30 ml) and 1,4-dioxane (400 ml) were added into a flask, and $K_3Fe(CN)_6$ (53.1 g, 0.161 mol) and $H_2O$ (420 ml) were dropped. The mixture was stirred and reacted at 100° C. for 12 hrs. After completion of reaction, the resultant was extracted and column-refined to obtain the compound 171-2. (3.8 g, yield=38.4%)

(3) Compound 171-3

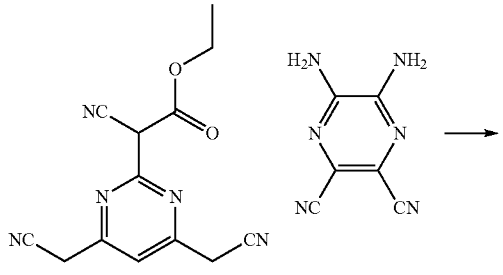

163-2

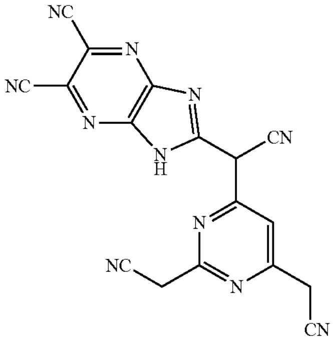

171-3

In a flask, the compound 163-2 (10 g, 0.037 mol) and 5,6-diaminopyrazine-2,3-dicarbonitrile (11.9 g, 0.074 mol) were stirred and reacted at 200° C. for 12 hrs. After completion of reaction, the resultant was extracted and re-crystalized to obtain the compound 171-3. (10.3 g, yield=75.9%)

(4) Compound 171-4

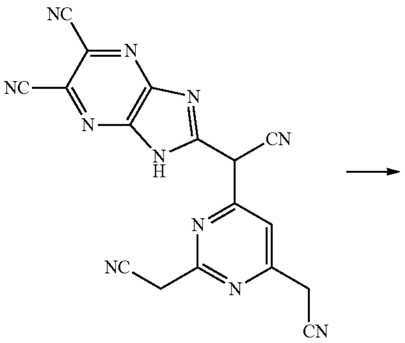

171-3

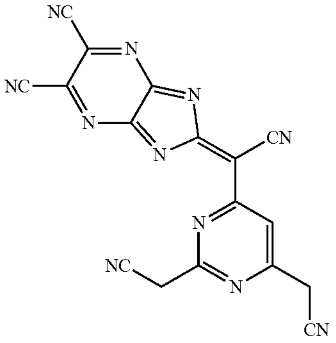

171-4

The compound 171-3 (10 g, 0.027 mol), potassium hydroxide (7.7 g, 0.137 mol), $H_2O$ (30 ml) and 1,4-dioxane (400 ml) were added into a flask, and $K_3Fe(CN)_6$ (27.04 g, 0.082 mol) and $H_2O$ (420 ml) were dropped. The mixture was stirred and reacted at 100° C. for 12 hrs. After completion of reaction, the resultant was extracted and column-refined to obtain the compound 171-4. (3.3 g, yield=33.2%)

(5) Compound 171

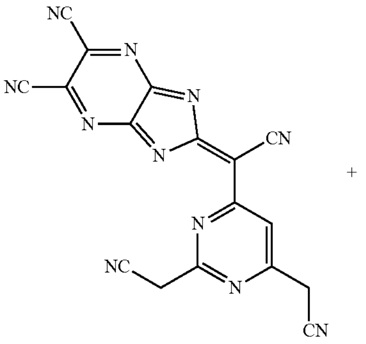

171-4

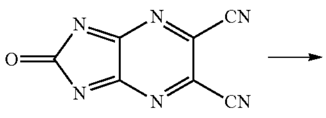

171-2

-continued

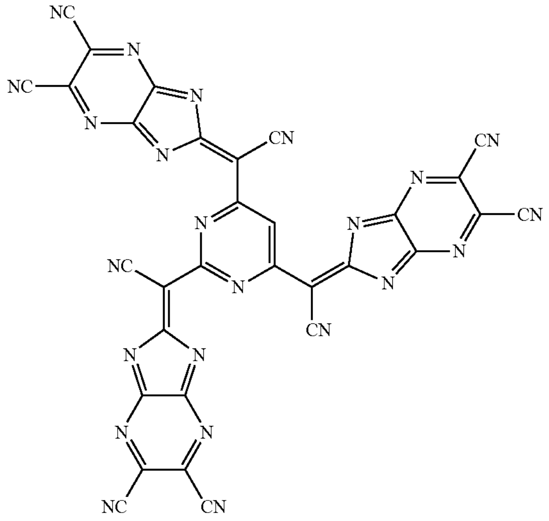

171

The compound 171-4 (10 g, 0.027 mol), the compound 171-2 (11.1 g, 0.061 mol) and methylene chloride (300 ml) were put into a flask and cooled in an ice-bath. $TiCl_4$ (15.3 g, 0.08 mol) was slowly dropped, and pyridine (12.7 g, 0.162 mol) was very slowly added. After 1 hr, the ice-bath was removed. The mixture was stirred and reacted for 24 hrs. After completion of reaction, the resultant was extracted using hydrochloric acid aqueous solution and column-refined to obtain the compound 171. (11.7 g, H-NM/R (200 MHz, $CDCl_3$): δ ppm, 1H (7.47/LC/MS: m/z=695[$(M+1)^+$]

34. Synthesis of Compound 174

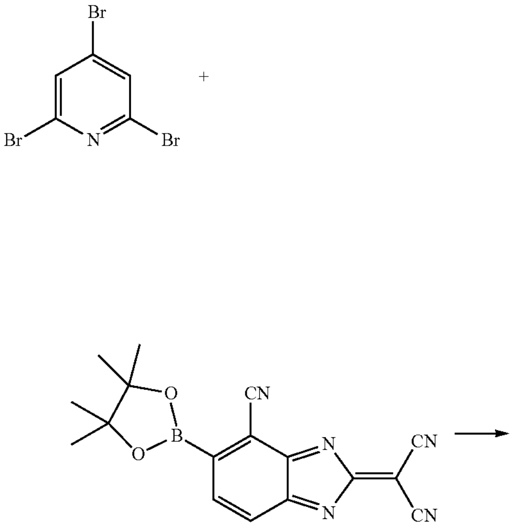

17-1

-continued

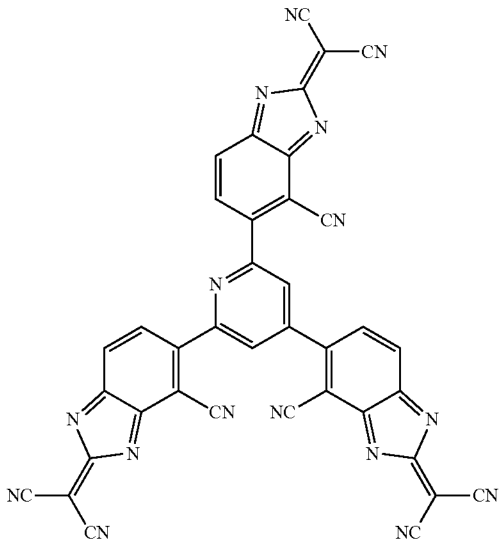

174

In a flask, 2,4,6-tribromopyridine (10 g, 0.032 mol), the compound 17-1 (34.6 g, 0.104 mol), potassium carbonate (26.3 g, 0.190 mol), $Pd(PPh_3)_4$ (1.83 g, 0.0016 mol), toluene (300 ml), ethanol (40 ml) and $H_2O$ (20 ml) were refluxed/stirred and reacted for 9 hrs. After completion of reaction, the resultant was extracted and column-refined to obtain the compound 174. (16.6 g, yield=76.1%)

H-NMR (200 MHz, $CDCl_3$): δ ppm, 2H (7.51/s), 3H (7.99/d, 6.5/d), LC/MS: m/z=688[$(M+1)^+$]

35. Synthesis of Compound 176

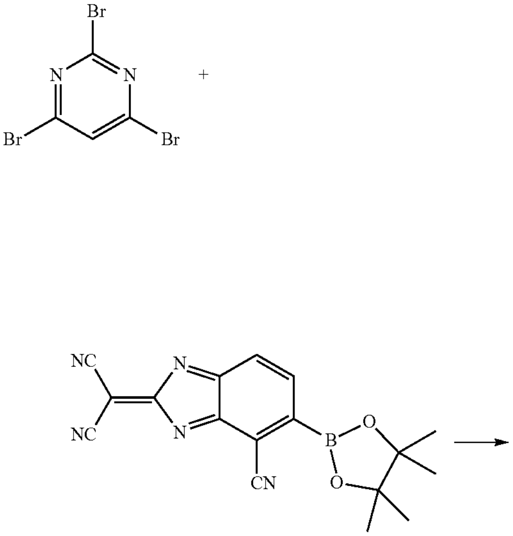

17-1

-continued

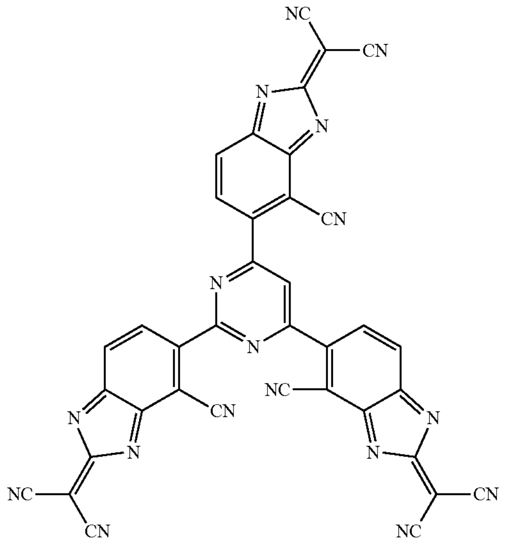

176

In a flask, 2,4,6-tribromopyrimidine (10 g, 0.032 mol), the compound 17-1 (33.4 g, 0.101 mol), potassium carbonate (21.8 g, 0.158 mol), $Pd(PPh_3)_4$ (1.82 g, 0.0016 mol), toluene (300 ml), ethanol (40 ml) and $H_2O$ (20 ml) were refluxed/stirred and reacted for 9 hrs. After completion of reaction, the resultant was extracted and column-refined to obtain the compound 176. (15.7 g, yield=72.1%)

H-NMR (200 MHz, $CDCl_3$): δ ppm, 1H (7.47/s), 3H (7.99/d, 6.5/d), LC/MS: m/z=689[$(M+1)^+$]

36. Synthesis of Compound 177

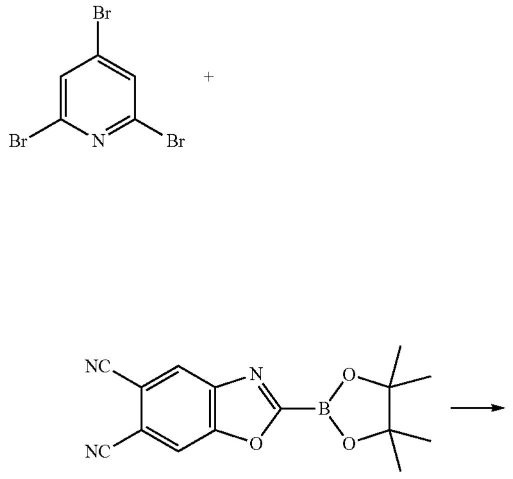

91-4

-continued

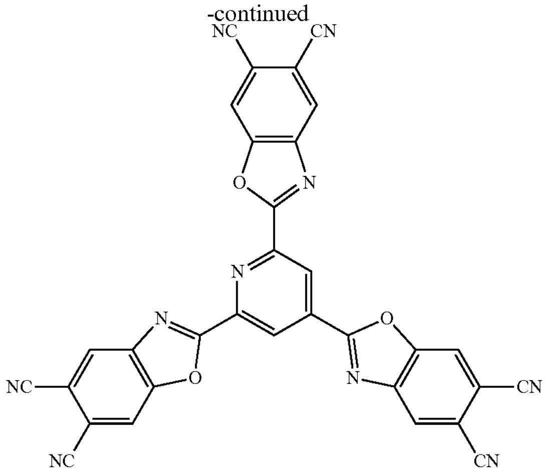

177

In a flask, 2,4,6-tribromopyridine (10 g, 0.032 mol), the compound 91-4 (29.9 g, 0.101 mol), potassium carbonate (21.9 g, 0.158 mol), $Pd(PPh_3)_4$ (1.83 g, 0.0016 mol), toluene (400 ml), ethanol (50 ml) and $H_2O$ (30 ml) were refluxed/stirred and reacted for 9 hrs. After completion of reaction, the resultant was extracted and column-refined to obtain the compound 177. (13.3 g, yield=72.4%)

H-NMR (200 MHz, $CDCl_3$): δ ppm, 2H (8.47/s), 6H (7.69/s), LC/MS: m/z=580[$(M+1)^+$]

37. Synthesis of Compound 178

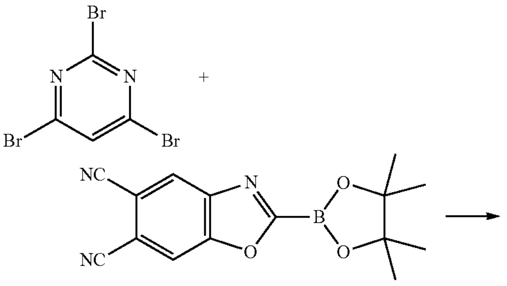

91-4

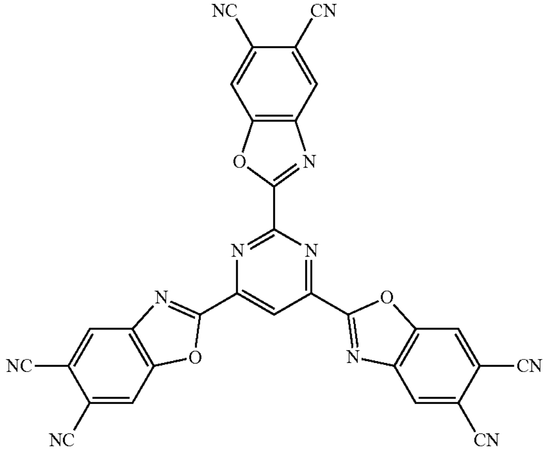

178

In a flask, 2,4,6-tribromopyrimidine (10 g, 0.032 mol), the compound 91-4 (29.8 g, 0.101 mol), potassium carbonate (21.8 g, 0.158 mol), $Pd(PPh_3)_4$ (1.82 g, 0.0016 mol), toluene (400 ml), ethanol (50 ml) and $H_2O$ (30 ml) were refluxed/stirred and reacted for 9 hrs. After completion of reaction, the resultant was extracted and column-refined to obtain the compound 178. (13.1 g, yield=71.4%)

H-NMR (200 MHz, $CDCl_3$): δ ppm, 1H (8.71/s), 6H (7.69/s), LC/MS: m/z=581 [$(M+1)^+$]

Referring back to FIG. 3, the HIL 171 has a first thickness, and the HTL 173 may have a second thickness being greater than the first thickness. For example, in some embodiments, the first thickness may be about 1 to 50 nm, and the second thickness may be about 50 to 150 nm.

A host of the HIL 171 may be the same as or different from a material of the HTL 173. For example, the host of the HIL 171 and the material of the HTL 173 may be independently selected from the group consisting of NPD (or NPB, N,N'-bis(naphthalen-1-yl)-N,N'-bis(phenyl)-2,2'-dimethylbenzidine), TPD (N,N'-bis-(3-methylphenyl)-N,N'-bis-(phenyl)-benzidine), spiro-TAD (2,2',7,7'-tetrakis(N,N-diphenylamino)-9,9'-spirofluorene) and MTDATA (4,4',4"-tris(N-3-methylphenyl-N-phenylamino)-triphenylamine), but it is not limited thereto. The dopant 190 may have a volume ratio of about 1 to 30 with respect to the host.

The EML 177 includes a host and a dopant. For example, in some embodiments, each of the host and the dopant may be a fluorescent compound, a phosphorescent compound or a delayed fluorescent compound.

The electron auxiliary layer 179 may include an electron transporting layer (ETL) and an electron injection layer (EIL) between the ETL and the second electrode 180.

Although not shown, an electron blocking layer (EBL) may be formed between the hole auxiliary layer 175 and the EML 177, and a hole blocking layer (HBL) may be formed between the EML 177 and the electron auxiliary layer 179.

As mentioned above, the hole auxiliary layer 175, e.g., the HIL 171, includes the host and the organic compound of the present disclosure as the dopant 190. Since the LUMO level of the organic compound is equal to or has relatively small difference from the HOMO level of a material in adjacent layer, e.g., the HTL 173, the hole injection property is improved. For example, in some embodiments, a difference between the LUMO level of the organic compound and the HOMO level of the host may be about 0.1 eV or less. In this instance, the HTL 173 may be formed of the same material as the host of the HIL 171 without the dopant.

Accordingly, the organic light emitting diode D and the OLED device 100 including the organic compound as the dopant in the hole auxiliary layer 175 have advantages in the emitting efficiency and the driving voltage.

[Organic Light Emitting Diode]

An ITO transparent electrode having an emitting area of 2 mm*2 mm is formed on a glass substrate and is cleaned. In the vacuum chamber of about 10-6 Torr, layers are sequentially deposited on an ITO transparent electrode.

(1) HIL (host (Formula 6)+p-type dopant (5 vol %), 5 nm), (2) HTL (Formula 6, 100 nm), (3) EBL (Formula 7, 10 nm), (4) EML (host (Formula 8)+dopant (Formula 9, 3 vol %) 20 nm)), (5) ETL (Formula 10+Liq (50 vol %), 30 nm), (6) EIL (LiF, mm), and (7) Cathode (Al, 100 nm)

[Formula 6]

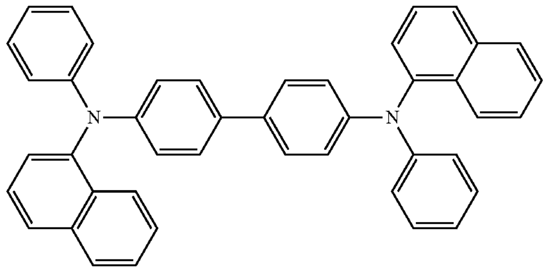

[Formula 7]

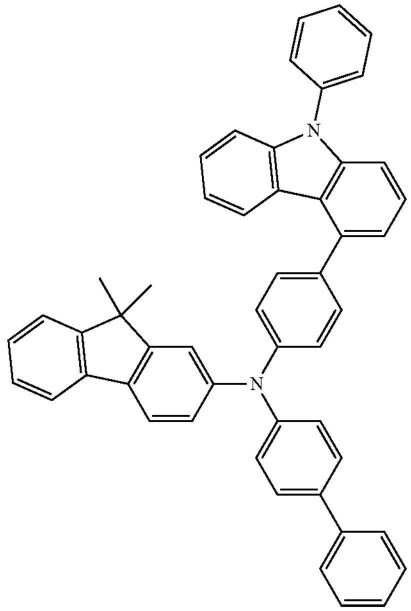

[Formula 8]

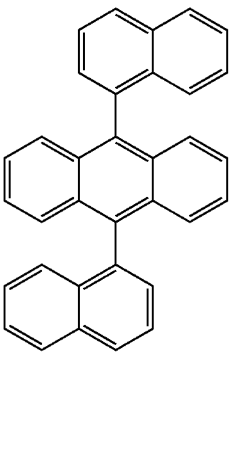

-continued

[Formula 9]

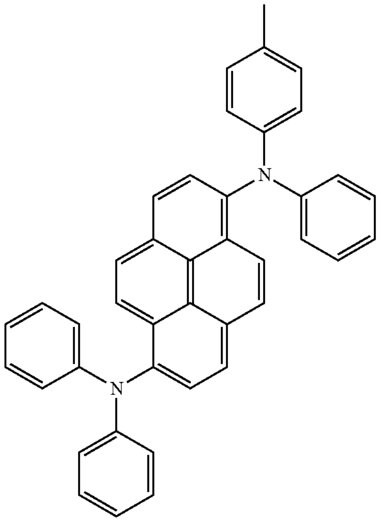

[Formula 10]

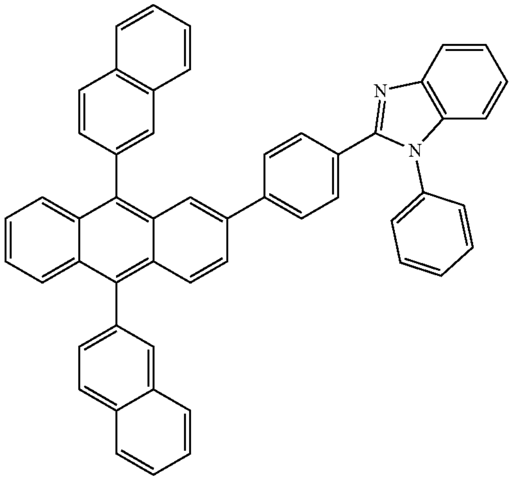

(1) Examples 1 to 37 (Ex1 to Ex37)

The compounds 4, 14, 15, 17, 21, 22, 29, 40, 44, 45, 66, 68, 74, 86, 90, 91, 95, 98, 102, 103, 109, 110, 117, 120, 123, 146, 151, 159, 161, 162, 163, 170, 171, 174, 176, 177 and 178 in Formula 5 is used as the p-type dopant in the HIL.

(2) Comparative Example (Ref)

The HIL is formed without the p-type dopant.

The properties, i.e., the driving voltage, the emitting efficiency and the color coordinate index, of the organic light emitting diodes of Examples 1 to 37 and Comparative Example are measured using Source meter (Model 237, Keithley) and Luminance meter (PR-650, Photo Research) and listed in Table 1. The driving voltage means a voltage with a current density of 10 $mA/cm^2$.

TABLE 1

| | P-dopant | V | cd/A | CIEx | CIEy |
|---|---|---|---|---|---|
| Ex 1 | compound 4 | 5.53 | 7.01 | 0.135 | 0.132 |
| Ex 2 | compound 14 | 5.38 | 7.02 | 0.135 | 0.133 |
| Ex 3 | compound 15 | 5.74 | 7.01 | 0.132 | 0.129 |
| Ex 4 | compound 17 | 5.44 | 7.01 | 0.134 | 0.138 |
| Ex 5 | compound 21 | 5.87 | 7.05 | 0.132 | 0.130 |
| Ex 6 | compound 22 | 5.61 | 7.05 | 0.132 | 0.132 |
| Ex 7 | compound 29 | 5.69 | 7.07 | 0.135 | 0.135 |
| Ex 8 | compound 40 | 4.94 | 7.16 | 0.133 | 0.132 |
| Ex 9 | compound 44 | 5.62 | 7.09 | 0.133 | 0.130 |
| Ex 10 | compound 45 | 4.90 | 7.08 | 0.134 | 0.133 |
| Ex 11 | compound 66 | 4.93 | 7.14 | 0.134 | 0.134 |
| Ex 12 | compound 68 | 5.15 | 7.17 | 0.132 | 0.136 |
| Ex 13 | compound 74 | 5.00 | 7.09 | 0.135 | 0.135 |
| Ex 14 | compound 86 | 5.80 | 6.94 | 0.132 | 0.131 |
| Ex 15 | compound 90 | 5.77 | 7.12 | 0.138 | 0.130 |
| Ex 16 | compound 91 | 5.72 | 6.98 | 0.131 | 0.130 |
| Ex 17 | compound 95 | 5.66 | 7.09 | 0.133 | 0.130 |
| Ex 18 | compound 98 | 5.56 | 7.13 | 0.134 | 0.134 |
| Ex 19 | compound 102 | 5.78 | 7.11 | 0.132 | 0.135 |
| Ex 20 | compound 103 | 5.81 | 7.03 | 0.132 | 0.131 |
| Ex 21 | compound 109 | 5.74 | 7.06 | 0.132 | 0.129 |
| Ex 22 | compound 110 | 5.39 | 7.08 | 0.135 | 0.135 |
| Ex 23 | compound 117 | 5.76 | 7.02 | 0.132 | 0.131 |
| Ex 24 | compound 120 | 5.63 | 7.11 | 0.133 | 0.133 |
| Ex 25 | compound 123 | 5.67 | 7.13 | 0.134 | 0.133 |
| Ex 26 | compound 146 | 5.68 | 6.99 | 0.131 | 0.130 |
| Ex 27 | compound 151 | 5.62 | 7.12 | 0.132 | 0.130 |
| Ex 28 | compound 159 | 5.68 | 7.15 | 0.135 | 0.133 |
| Ex 29 | compound 161 | 5.31 | 7.09 | 0.135 | 0.135 |
| Ex 30 | compound 162 | 5.72 | 6.85 | 0.132 | 0.132 |
| Ex 31 | compound 163 | 5.78 | 6.92 | 0.130 | 0.131 |
| Ex 32 | compound 170 | 5.18 | 7.12 | 0.133 | 0.131 |
| Ex 33 | compound 171 | 5.59 | 6.98 | 0.131 | 0.131 |
| Ex 34 | compound 174 | 5.62 | 7.02 | 0.133 | 0.132 |
| Ex 35 | compound 176 | 5.78 | 7.07 | 0.131 | 0.130 |
| Ex 36 | compound 177 | 5.82 | 7.06 | 0.132 | 0.131 |
| Ex 37 | compound 178 | 5.85 | 7.01 | 0.132 | 0.130 |
| Ref | — | 6.03 | 6.81 | 0.131 | 0.131 |

As shown in Table 1, in comparison to the organic light emitting diodes of Ref, the emitting efficiency of the organic light emitting diodes of Ex1 to Ex37 using the organic compounds of the present disclosure as the p-type dopant in the HIL is significantly increased. In addition, the driving voltage of the organic light emitting diode of the present disclosure is significantly reduced.

Figure 4:
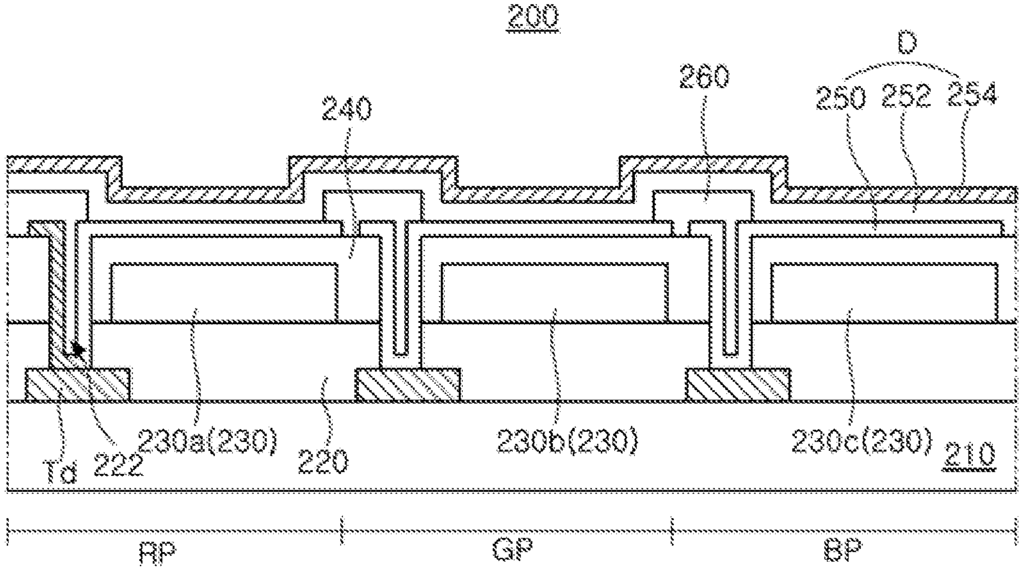
FIG. 4 is a schematic cross-sectional view of an OLED device according to a second embodiment of the present disclosure.

FIG. 4 is a schematic cross-sectional view of an OLED device according to a second embodiment of the present disclosure.

As shown in FIG. 4, the OLED device 200 includes a substrate 210, an emitting diode D over the substrate 210, a driving TFT Td, which is positioned between the substrate 210 and the organic light emitting diode D and connected to the organic light emitting diode D, and a color filter 230 between the substrate 210 and the organic light emitting diode D.

The substrate 210 may be a glass substrate or a plastic substrate. For example, in some embodiments, the substrate 210 may be a polyimide substrate.

A red pixel region RP, a green pixel region GP and a blue pixel region BP are defined on the substrate 210, and the driving TFT Td is disposed in each of the red, green and blue pixel regions RP, GP and BP. A white pixel region (not shown) may be further defined on the substrate 210. In this instance, the driving TFT Td is also disposed in the white pixel region.

For example, in some embodiments, the driving TFT Td may include a semiconductor layer on the substrate 210, a gate electrode, which is disposed over the semiconductor layer and overlaps the semiconductor layer, a source electrode, which is disposed over the gate electrode and connected one end of the semiconductor layer, and a drain electrode, which is disposed over the gate electrode and connected to the other end of the semiconductor layer. The source and drain electrodes are spaced apart from each other.

A first insulating layer 220 is formed on the driving TFT Td, and the color filter 230 is formed on the first insulating layer 220. The color filter 230 includes a red color filter pattern 230*a* corresponding to the red pixel region RP, a green color filter pattern 230*b* corresponding to the green pixel region GP and a blue color filter pattern 230*c* corresponding to the blue pixel region BP.

A second insulating layer 240 is formed on the color filter 230. A contact hole 222, which exposes an electrode, e.g., the drain electrode, of the driving TFT Td, is formed through the first and second insulating layers 220 and 240.

Namely, the color filter 230 is positioned between the first and second insulating layers 220 and 240 such that the first and second insulating layers 220 and 240 are spaced apart from each other in an emission area of the red, green and blue pixel regions RP, GP and BP. When the white pixel regions is further defined, there is no color filter in the white pixel region such that the first and second insulating layers 220 and 240 contact each other in an entire of the white pixel region.

A first electrode 250, which is connected to the driving TFT Td through the contact hole 222, is formed on the second insulating layer 240. The first electrode 250 is separated in each of the red, green and blue pixel regions RP, GP and BP. The first electrode 250 may serve as an anode and include a conductive material having relatively high work function. For example, in some embodiments, the first electrode 250 may be formed or include a transparent conductive material such as indium-tin-oxide (ITO), indium-zinc-oxide (IZO) or zinc oxide (ZnO).

A bank layer 260 covering an edge of the first electrode 250 is formed on the second insulating layer 240. The bank layer 260 exposes a center of the first electrode 250 in the red, green and blue pixel regions RP, GP and BP.

An organic emitting layer 252 is formed on the first electrode 250. The organic emitting layer 252 emits white light and is continuously formed on an entire display area, which include the red, green and blue pixel regions RP, GP and BP, as one body. Namely, the organic emitting layer 252 is formed to cover an entire surface of the bank layer 260 such that the organic emitting layer 252 in adjacent pixel regions is continuous.

A second electrode 254 is formed over the substrate 210 including the organic emitting layer 252. The second electrode 254 covers an entire display area. The second electrode 254 may be formed of or include a conductive material having relatively low work function to serve as a cathode. For example, in some embodiments, the second electrode 254 may be formed of aluminum (Al), magnesium (Mg) or Al—Mg alloy.

The first electrode 250, the organic emitting layer 252 and the second electrode 254 constitute the organic light emitting diode D.

Although not shown, an encapsulation film may be formed on the second electrode 254 to prevent penetration of moisture into the organic light emitting diode D. The encapsulation film may include a first inorganic insulating layer, an organic insulating layer and a second inorganic insulating layer sequentially stacked, but it is not limited thereto. In addition, a polarization plate for reducing an ambient light reflection may be disposed at an outer side of the substrate 210. For example, in some embodiments, the polarization plate may be a circular polarization plate.

A cover window (not shown) may be attached on an outer side of the substrate 210 or the polarization plate. The substrate 210 and the cover window may have flexibility such that a flexible OLED device may be provided.

The OLED device of FIG. 4 is a bottom-emission type. Namely, the light from the organic emitting layer 252 passes through the first electrode 250 and the color filter 230 such that an image is displayed on a side of the substrate 210.

Namely, the first electrode 250 is a transparent electrode, and the second electrode 254 is a reflective electrode. The light from the organic emitting layer 252 may directly pass through the first electrode 250 or indirectly pass through the first electrode 250 after being reflected on the second electrode 254.

In FIG. 4, the color filter 230 is positioned between the first and second insulating layers 220 and 240. However, a position of the color filter 230 is not restricted thereto in a space between the organic light emitting diode D and the substrate 210. For example, in some embodiments, the color filter 230 may be positioned between the substrate 210 and the first insulating layer 220. In this instance, the second insulating layer 240 may be omitted.

Since the white light from the organic light emitting diode D passes through the color filter 230, the OLED device 200 displays a full color image.

Figure 5:
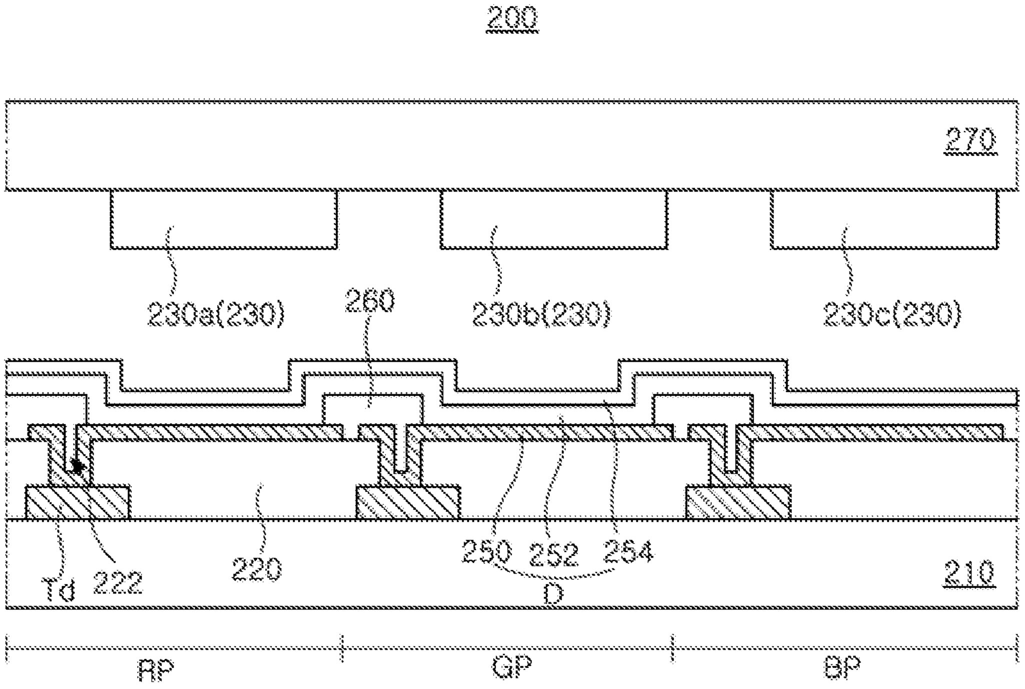
FIG. 5 is a schematic cross-sectional view of an OLED device according to a third embodiment of the present disclosure.

FIG. 5 is a schematic cross-sectional view of an OLED device according to a third embodiment of the present disclosure.

As shown in FIG. 5, the OLED device 200 includes a first substrate 210, a second electrode 270 facing the first electrode 210, an organic light emitting diode D over the first substrate 210, a driving TFT Td, which is positioned between the first substrate 210 and the organic light emitting diode D and connected to the organic light emitting diode D, and a color filter 230 between the second substrate 270 and the organic light emitting diode D.

Each of the first and second substrates 210 and 270 may be a glass substrate or a plastic substrate. For example, in some embodiments, each of the first and second substrates 210 and 270 may be a polyimide substrate.

A red pixel region RP, a green pixel region GP and a blue pixel region BP are defined on the first substrate 210, and the driving TFT Td is disposed in each of the red, green and blue pixel regions RP, GP and BP. A white pixel region (not shown) may be further defined on the first substrate 210. In this instance, the driving TFT Td is also disposed in the white pixel region.

For example, in some embodiments, the driving TFT Td may include a semiconductor layer on the first substrate 210, a gate electrode, which is disposed over the semiconductor layer and overlaps the semiconductor layer, a source electrode, which is disposed over the gate electrode and connected one end of the semiconductor layer, and a drain electrode, which is disposed over the gate electrode and connected to the other end of the semiconductor layer. The source and drain electrodes are spaced apart from each other.

An insulating layer 220 is formed on the driving TFT Td, and a contact hole 222, which exposes an electrode, e.g., the drain electrode, of the driving TFT Td, is formed through the insulating layer 220.

A first electrode 250, which is connected to the driving TFT Td through the contact hole 222, is formed on the insulating layer 220. The first electrode 250 is separated in each of the red, green and blue pixel regions RP, GP and BP. The first electrode 250 may serve as an anode and include a conductive material having relatively high work function. For example, in some embodiments, the first electrode 250 may include a transparent electrode layer, which may be formed or include a transparent conductive material such as indium-tin-oxide (ITO), indium-zinc-oxide (IZO) or zinc oxide (ZnO), and a reflection electrode layer (or reflection layer). The first electrode 250 may have a triple-layered structure of upper and lower layers of ITO and a middle layer of aluminum-palladium-copper (APC) alloy.

A bank layer 260 covering an edge of the first electrode 250 is formed on the insulating layer 220. The bank layer 260 exposes a center of the first electrode 250 in the red, green and blue pixel regions RP, GP and BP.

An organic emitting layer 252 is formed on the first electrode 250. The organic emitting layer 252 emits white light and is continuously formed on an entire display area, which include the red, green and blue pixel regions RP, GP and BP, as one body. Namely, the organic emitting layer 252 is formed to cover an entire surface of the bank layer 260 such that the organic emitting layer 252 in adjacent pixel regions is continuous.

A second electrode 254 is formed over the substrate 210 including the organic emitting layer 252. The second electrode 254 covers an entire display area. The second electrode 254 may be formed of or include a conductive material having relatively low work function to serve as a cathode. For example, in some embodiments, the second electrode 254 may be formed of aluminum (Al), magnesium (Mg) or Al—Mg alloy and may have a thin profile to transmit the light.

The first electrode 250, the organic emitting layer 252 and the second electrode 254 constitute the organic light emitting diode D.

A color filter 230 is formed over the organic light emitting diode D. Namely, the color filter 230 is positioned between the organic light emitting diode D and the second substrate 270. The color filter 230 includes a red color filter pattern 230*a* corresponding to the red pixel region RP, a green color filter pattern 230*b* corresponding to the green pixel region GP and a blue color filter pattern 230*c* corresponding to the blue pixel region BP.

Although not shown, a polarization plate for reducing an ambient light reflection may be disposed at an outer side of the second substrate 270. For example, in some embodiments, the polarization plate may be a circular polarization plate.

The OLED device of FIG. 5 is a top-emission type. Namely, the light from the organic emitting layer 252 passes through the second electrode 254 and the color filter 230 such that an image is displayed on a side of the second substrate 270.

Namely, the first electrode 250 is a reflective electrode, and the second electrode 254 is a transparent (semi-transparent) electrode. The light from the organic emitting layer 252 may directly pass through the second electrode 254 or indirectly pass through the second electrode 254 after being reflected on the first electrode 250.

Since the white light from the organic light emitting diode D passes through the color filter 230, the OLED device 200 displays a full color image.

Figure 6:
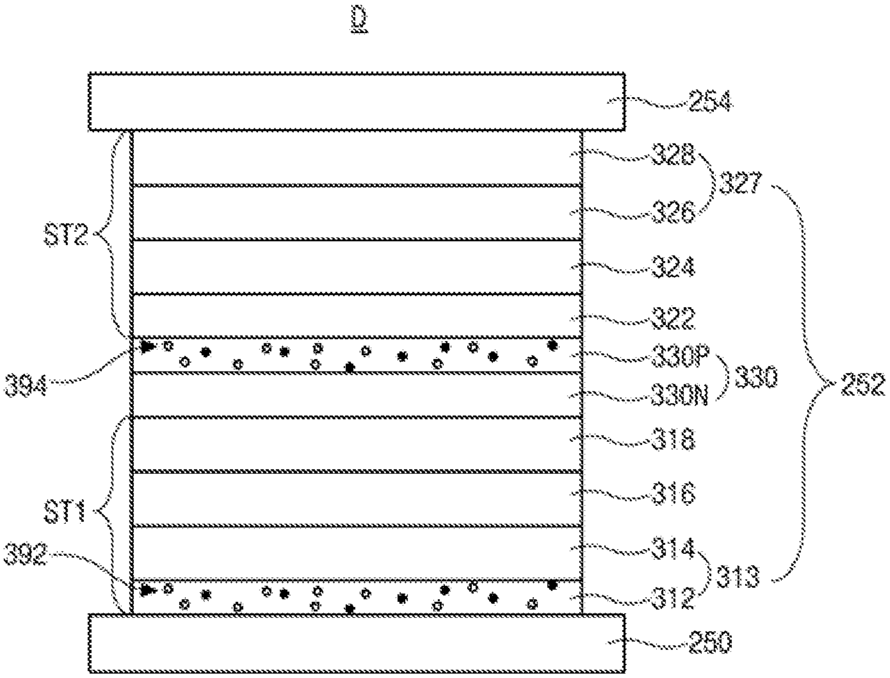
FIG. 6 is a schematic cross-sectional view of an organic light emitting diode having a two-stack structure included in the OLED device according to the second and third embodiments of the present disclosure.

FIG. 6 is a schematic cross-sectional view of an organic light emitting diode having a two-stack structure included in the OLED device according to the second and third embodiments of the present disclosure.

As shown in FIG. 6, the emitting diode D includes a first electrode 250, a second electrode 254 facing the first electrode 250 and an organic emitting layer 252 between the first and second electrodes 250 and 254, and the organic emitting layer 252 includes first and second emitting stacks ST1 and ST2 and a charge generation layer (CGL) 330.

The first electrode 250 may serve as an anode for injecting the hole and may include a conductive material having high work function, e.g., ITO, IZO or ZnO. The second electrode 254 may serve as a cathode for injecting the electron and may include a conductive material having low work function, e.g., Al, Mg or Al—Mg alloy.

When the emitting diode D is a bottom-emission type, the second electrode 254 serves as a reflection electrode. On the other hand, when the emitting diode D is a top-emission type, the first electrode 250 may further include a reflection layer or a reflection electrode, and the second electrode 254 serves as a transparent electrode.

The CGL 330 is positioned between the first and second emitting stacks ST1 and ST2, and the first emitting stack ST1, the CGL 330 and the second emitting stack ST2 are sequentially stacked on the first electrode 250. Namely, the first emitting stack ST1 is positioned between the first electrode 250 and the CGL 330, and the second emitting stack ST2 is positioned between the second electrode 254 and the CGL 330.

The first emitting stack ST1, which is positioned between the first electrode 250 and the CGL 330, may include a first EML 316, a first hole auxiliary layer 313 between the first electrode 250 and the first EML 316, and a first electron auxiliary layer 318 between the first EML 316 and the CGL 330.

The first hole auxiliary layer 313 may include an HIL 312 and a first HTL 314 between the HIL 312 and the first EML 316. In addition, the first electron auxiliary layer 318 may be a first ETL.

The second emitting stack ST2 may include a second EML 324 between the CGL 330 and the second electrode 254, a second hole auxiliary layer 322 between the CGL 330 and the second EML 324, and a second electron auxiliary layer 327 between the second EML 324 and the second electrode 254.

The second hole auxiliary layer 322 may be a second HTL. The second electron auxiliary layer 327 may include a second ETL 326 and an EIL 328 between the second ETL 326 and the second electrode 254.

The CGL 330 is positioned between the first and second emitting stacks ST1 and ST2. Namely, the first and second emitting stacks ST1 and ST2 are connected through the CGL 330. The CGL 330 may be a P-N junction CGL of an N-type CGL 330N and a P-type CGL 330P.

The N-type CGL 330N is positioned between the first electron auxiliary layer 318 and the second hole auxiliary layer 322, and the P-type CGL 330P is positioned between the N-type CGL 330N and the second hole auxiliary layer 322.

The CGL 330 generates charges or separates the holes and the electrons such that the electron and the hole are provided into the first and second emitting stacks ST1 and ST2, respectively.

Namely, the N-type CGL 330N provides the electron into the first electron auxiliary layer 318 of the first emitting stack ST1, and the first electron auxiliary layer 318 provides the electron into the first EML 316. The P-type CGL 330P provides the hole into the second hole auxiliary layer 322 of the second emitting stack ST2, and the second hole auxiliary layer 322 provides the hole into the second EML 324. Accordingly, in the organic light emitting diode D including a plurality of emitting layers, the emitting efficiency is improved, and the driving voltage is lowered.

For example, in some embodiments, the first EML 316 may be a blue EML, and the second EML 324 may be a yellow-green EML. The second EML 324 may further include a red EML to have a double-layered structure.

Each of the first and second EMLs 316 and 324 includes a host and a dopant. Each of the host and the dopant may be a fluorescent compound, a phosphorescent compound or a delayed fluorescent compound.

At least one of the first hole auxiliary layer 313, i.e., the HIL 312, and the P-type CGL 330P includes the organic compound of the present disclosure. The organic compound may be a dopant. Namely, the first hole auxiliary layer 313, i.e., the HIL 312, may include a first host (not shown) and a first dopant 392 of the organic compound of the present disclosure, and the P-type CGL 330P may include a second host (not shown) and a second dopant 394 of the organic compound of the present disclosure. On the other hand, each of the first and second HTLs 314 and 322 includes a host without a dopant. For example, in some embodiments, the first HTL 314 may include the first host, and the second HTL 322 may include the second host.

The first and second hosts may be same or different, and the first and second dopants 392 and 394 may be same or different.

For example, in some embodiments, when the HIL 312 include the organic compound as the first dopant 392, the HIL 312 has a first thickness and the first HTL 314 has a second thickness being greater than the first thickness. The first thickness may be about 1 to 50 nm, and the second thickness may be about 50 to 150 nm.

The first host of the HIL 312, the second host of the P-type CGL 330P, a material (host) of the first HTL 314 and a material (host) of the second HTL 322 may be same or different. For example, in some embodiments, each of the first host of the HIL 312, the second host of the P-type CGL 330P, the material of the first HTL 314 and the material of the second HTL 322 may be independently selected from the group consisting of NPD (or NPB, N,N'-bis(naphthalen-1-yl)-N,N'-bis(phenyl)-2,2'-dimethylbenzidine), TPD (N,N'-bis-(3-methylphenyl)-N,N'-bis-(phenyl)-benzidine), spiro-TAD (2,2',7,7'-tetrakis(N,N-diphenylamino)-9,9'-spirofluorene) and MTDATA (4,4',4"-tris(N-3-methylphenyl-N-phenylamino)-triphenylamine), but it is not limited thereto.

The first dopant 392 may have a volume ratio of about 1 to 30 with respect to the first host, and the second dopant 394 may have a volume ratio of about 1 to 30 with respect to the second host.

As mentioned above, at least one of the first hole auxiliary layer 313, e.g., the HIL 312, and the P-type CGL 330P includes the host and the organic compound of the present disclosure as the dopants 392 and 394. Since the LUMO level of the organic compound is equal to or has relatively small difference from the HOMO level of a material in adjacent layer, e.g., the first and second HTLs 314 and 322, the hole injection/transporting property is improved. For example, in some embodiments, a difference between the LUMO level of the organic compound and the HOMO level of the host, i.e., the first and second hosts, may be about 0.1 eV or less.

Accordingly, the organic light emitting diode D and the OLED device 200 including the organic compound as the dopant in the first hole auxiliary layer 313 and/or the P-type CGL 330P have advantages in the emitting efficiency and the driving voltage.

Figure 7:
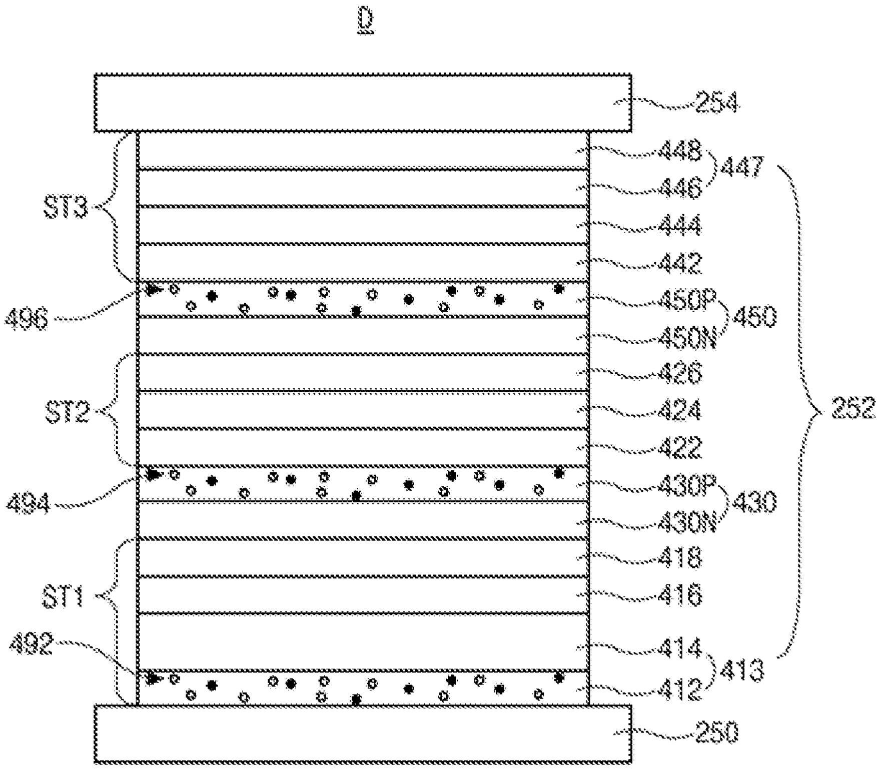
FIG. 7 is a schematic cross-sectional view of an organic light emitting diode having a three-stack structure included in the OLED device according to the second and third embodiments of the present disclosure.

FIG. 7 is a schematic cross-sectional view of an organic light emitting diode having a three-stack structure included in the OLED device according to the second and third embodiments of the present disclosure.

As shown in FIG. 7, an organic light emitting diode D includes a first electrode 250, a second electrode 254, an organic emitting layer 252 between the first and second electrodes 250 and 254, and the organic emitting layer 252 includes first to third emitting stacks ST1, ST2 and ST3 and first and second charge generation layers (CGLs) 430 and 450. Alternatively, four or more emitting stacks and three or more CGLs may be disposed between the first and second electrodes 250 and 254.

The first electrode 250 may serve as an anode for injecting the hole and may include a conductive material having high work function, e.g., ITO, IZO or ZnO. The second electrode 254 may serve as a cathode for injecting the electron and may include a conductive material having low work function, e.g., Al, Mg or Al—Mg alloy.

When the organic light emitting diode D is a bottom-emission type, the second electrode 254 serves as a reflection electrode. On the other hand, when the organic light emitting diode D is a top-emission type, the first electrode 250 may further include a reflection layer or a reflection electrode, and the second electrode 254 serves as a transparent electrode.

The first and second CGLs 430 and 450 are positioned between the first and second emitting stacks ST1 and ST2 and the second and third emitting stacks ST2 and ST3, respectively. Namely, the first emitting stack ST1, the first CGL 430, the second emitting stack ST2, the second CGL 450 and the third emitting stack ST3 are sequentially stacked on the first electrode 250. In other words, the first emitting stack ST1 is positioned between the first electrode 250 and the first CGL 430, and the second emitting stack ST2 is positioned between the First and Second CGLs 430 and 450. In addition, the third emitting stack ST3 is positioned between the second electrode 254 and the second CGL 450.

The first emitting stack ST1 may include a first EML 416, a first hole auxiliary layer 413 between the first electrode 250 and the first EML 416, and a first electron auxiliary layer 418 between the first EML 416 and the CGL 430.

The first hole auxiliary layer 413 may include an HIL 412 and a first HTL 414 between the HIL 412 and the first EML 416. In addition, the first electron auxiliary layer 418 may be a first ETL.

The second emitting stack ST2 may include a second EML 424 between the first CGL 430 and the second CGL 450, a second hole auxiliary layer 422 between the first CGL 430 and the second EML 424, and a second electron auxiliary layer 426 between the second EML 424 and the second CGL 450.

The second hole auxiliary layer 422 may be a second HTL, and the second electron auxiliary layer 426 may be a second ETL.

The third emitting stack ST3 may include a third EML 444 between the second CGL 450 and the second electrode 254, a third hole auxiliary layer 442 between the second CGL 450 and the second EML 444, and a third electron auxiliary layer 447 between the third EML 444 and the second electrode 254.

The third hole auxiliary layer 442 may be a third HTL. The third electron auxiliary layer 447 may include a third ETL 446 and an EIL 448 between the third ETL 446 and the second electrode 254.

The first CGL 430 is positioned between the first emitting stack ST1 and the second emitting stack ST2. Namely, the first and second emitting stacks ST1 and ST2 are connected through the first CGL 430. The first CGL 430 may be a P-N junction CGL of a first N-type CGL 430N and a first P-type CGL 430P.

The first N-type CGL 430N is positioned between the first electron auxiliary layer 418 and the second hole auxiliary layer 422, and the first P-type CGL 430P is positioned between the first N-type CGL 430N and the second hole auxiliary layer 422. The first P-type CGL 430P contacts the second hole auxiliary layer 422.

The second CGL 450 is positioned between the second emitting stack ST2 and the third emitting stack ST3. Namely, the second and third emitting stacks ST2 and ST3 are connected through the second CGL 450. The second CGL 450 may be a P-N junction CGL of a second N-type CGL 450N and a second P-type CGL 450P.

The second N-type CGL 450N is positioned between the second electron auxiliary layer 426 and the third hole auxiliary layer 442, and the second P-type CGL 450P is positioned between the second N-type CGL 450N and the third hole auxiliary layer 442. The second P-type CGL 450P contacts the third hole auxiliary layer 442.

The first and second CGLs 430 and 450 generate charges or separate the holes and the electrons such that the electron and the hole are provided into the first to third emitting stacks ST1 to ST3, respectively.

Namely, in the first CGL 430, the first N-type CGL 430N provides the electron into the first electron auxiliary layer 418 of the first emitting stack ST1, and the first P-type CGL 430P provides the hole into the second hole auxiliary layer 422 of the second emitting stack ST2.

In the second CGL 450, the second N-type CGL 450N provides the electron into the second electron auxiliary layer 426 of the second emitting stack ST2, and the second P-type CGL 450P provides the hole into the third hole auxiliary layer 442 of the third emitting stack ST3.

Accordingly, in the organic light emitting diode D including a plurality of emitting layers, the emitting efficiency is improved, and the driving voltage is lowered.

Each of the first and third EMLs 416 and 444 may be a blue EML, and the second EML 424 may be a yellow-green EML. As a result, the white light may be provided from the organic emitting layer 252. The second EML 424 may further include a red EML to have a double-layered structure.

Each of the first to third EMLs 416, 424 and 444 includes a host and a dopant. Each of the host and the dopant may be a fluorescent compound, a phosphorescent compound or a delayed fluorescent compound.

At least one of the first hole auxiliary layer 413, i.e., the HIL 412, and the first and second P-type CGLs 430P and 450P includes the organic compound of the present disclosure. The organic compound may be a dopant. Namely, the first hole auxiliary layer 413, i.e., the HIL 412, may include a first host (not shown) and a first dopant 492 of the organic compound of the present disclosure, and the first P-type CGL 430P may include a second host (not shown) and a second dopant 494 of the organic compound of the present disclosure. The second P-type CGL 450P may include a third host (not shown) and a third dopant 496 of the organic compound of the present disclosure.

On the other hand, each of the first to third HTLs 414, 422 and 442 includes a host without a dopant. For example, in some embodiments, the first HTL 414 may include the first host, the second HTL 422 may include the second host, and the third HTL 442 may include the third host.

The first to third hosts may be same or different, and the first to third dopants 492, 494 and 496 may be same or different.

For example, in some embodiments, when the HIL 412 include the organic compound as the first dopant 492, the HIL 412 has a first thickness and the first HTL 414 has a second thickness being greater than the first thickness. The first thickness may be about 1 to 50 nm, and the second thickness may be about 50 to 150 nm.

The first host of the HIL 412, the second host of the first P-type CGL 430P, the third host of the second P-type CGL 450P, a material (host) of the first HTL 414, a material (host) of the second HTL 422 and a material (host) of the third HTL 442 may be same or different. For example, in some embodiments, each of the first host of the HIL 412, the second host of the first P-type CGL 430P, the third host of the second P-type CGL 450P, the material of the first HTL 414, the material of the second HTL 422 and the material of the third HTL 442 may be independently selected from the group consisting of NPD (or NPB, N,N'-bis(naphthalen-1-yl)-N,N'-bis(phenyl)-2,2'-dimethylbenzidine), TPD (N,N'-bis-(3-methylphenyl)-N,N'-bis-(phenyl)-benzidine), spiro-TAD (2,2',7,7'-tetrakis(N,N-diphenylamino)-9,9'-spirofluorene) and MTDATA (4,4',4"-tris(N-3-methylphenyl-N-phenylamino)-triphenylamine), but it is not limited thereto.

The first dopant 492 may have a volume ratio of about 1 to 30 with respect to the first host, the second dopant 494 may have a volume ratio of about 1 to 30 with respect to the second host, and the third dopant 496 may have a volume ratio of about 1 to with respect to the third host.

As mentioned above, at least one of the first hole auxiliary layer 413, e.g., the HL 412, the first P-type CGL 430P and the second P-type CGL 450P includes the host and the organic compound of the present disclosure as the dopants 492, 494 and 496. Since the LUMO level of the organic compound is equal to or has relatively small difference from the HOMO level of a material in adjacent layer, e.g., the first to third second HTLs 414, 422 and 442, the hole injection/transporting property is improved. For example, in some embodiments, a difference between the LUMO level of the organic compound and the HOMO level of the host, i.e., the first to third hosts, may be about 0.1 eV or less.

Accordingly, the organic light emitting diode D and the OLED device 200 including the organic compound as the dopant in the first hole auxiliary layer 413, the first P-type CGL 430P and/or the second P-type CGL 450P have advantages in the emitting efficiency and the driving voltage.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An organic compound represented by the following Formula 1:

[Formula 1]

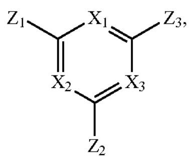

wherein:

each of $X_1$, $X_2$ and $X_3$ is independently selected from carbon (C) and nitrogen (N), provided that at least one of $X_1$ to $X_3$ is N, and each of $Z_1$, $Z_2$ and $Z_3$ is independently selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, a substituted or unsubstituted C1 to C12 ether group, halogen, cyano (CN), trimethylsilyl, Formula 2, Formula 3 and Formula 4, provided that at least one of $Z_1$ to $Z_3$ is represented by one of the following Formulas 2 to 4,

[Formula 2]

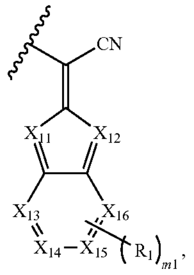

[Formula 3]

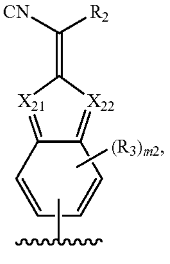

and

[Formula 4]

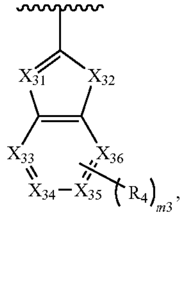

wherein in Formula 2, each of $X_{11}$ and $X_{12}$ is independently selected from C and N, provided that at least one of $X_{11}$ and $X_{12}$ is N, each of $X_{13}$ to $X_{16}$ is independently selected from C and N, $R_1$ is selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, cyano, halogen and trifluoromethyl, and m1 is an integer of 0 to 4, wherein in Formula 3, each of $X_{21}$ and $X_{22}$ is independently selected from C and N, provided that at least one of $X_{21}$ and $X_{22}$ is N, $R_2$ is selected from cyano and phenyl, $R_3$ is selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, cyano, halogen and trifluoromethyl, and m2 is an integer of 0 to 3, wherein in Formula 4, each of $X_{31}$ and $X_{32}$ is independently selected from N and oxygen (O), provided that when one of $X_{31}$ and $X_{32}$ is N, then the other one of $X_{31}$ and $X_{32}$ is O, each of $X_{33}$ to $X_{36}$ is independently selected from C and N, $R_4$ is selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, cyano, halogen and trifluoromethyl, and m3 is an integer of 0 to 4.

2. The organic compound of claim 1, wherein at least one of $X_{13}$ to $X_{16}$ is C, and $R_1$ is selected from methyl, trifluoromethyl, trifluoromethoxy, cyano and fluorine (F).

3. The organic compound of to claim 1, wherein $R_2$ is phenyl substituted by at least one of F and CN, and $R_3$ is CN.

4. The organic compound of claim 1, wherein at least one of $X_{33}$ to $X_{36}$ is C, and $R_4$ is selected from F, CN and trifluoromethyl.

5. The organic compound of claim 1, wherein the organic compound has one of the following structures:

1

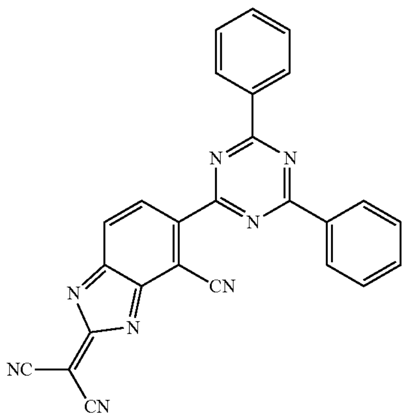

;

-continued
2
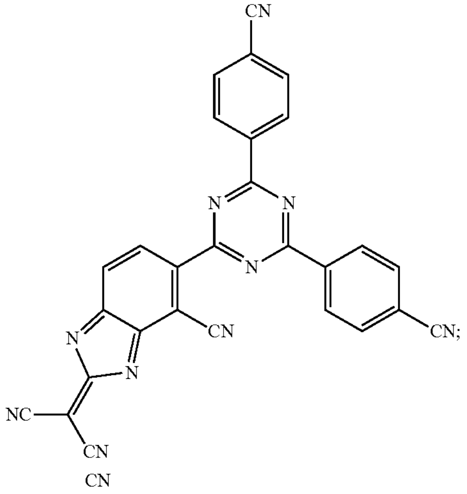
3
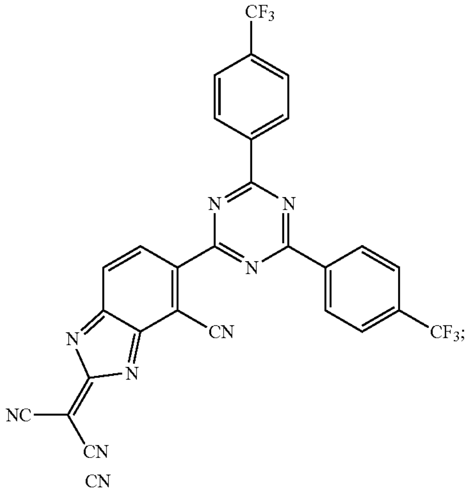
4
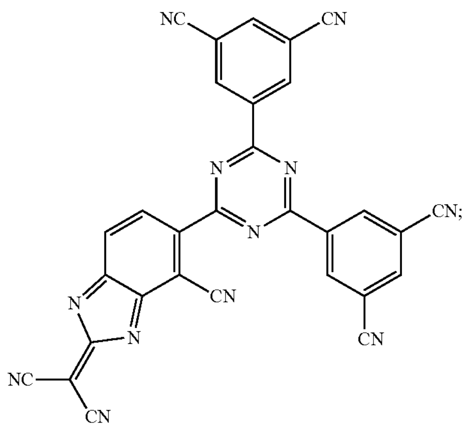
-continued
5
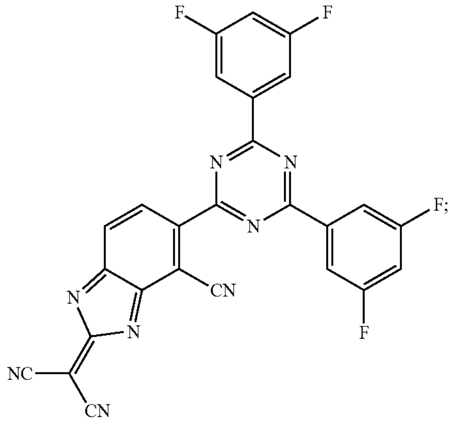
6
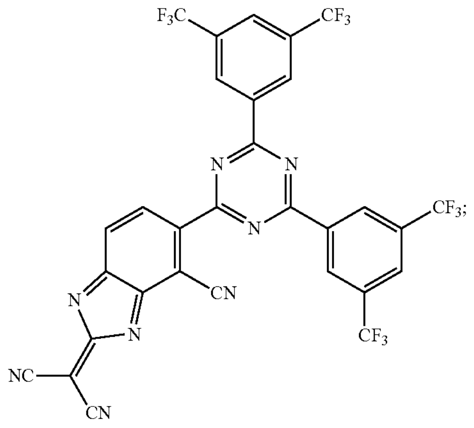
7
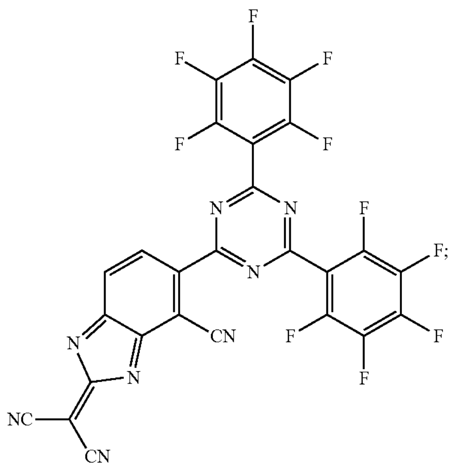

-continued
8
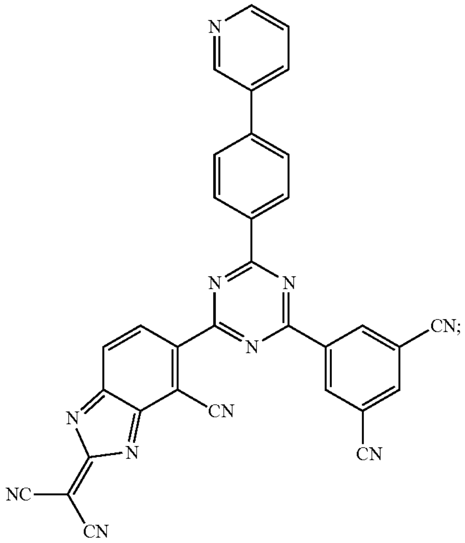
9
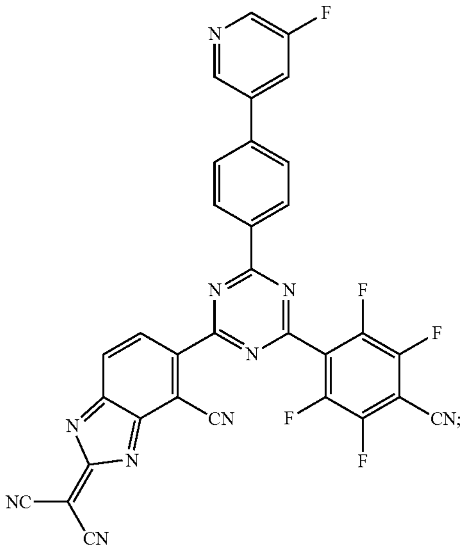
10
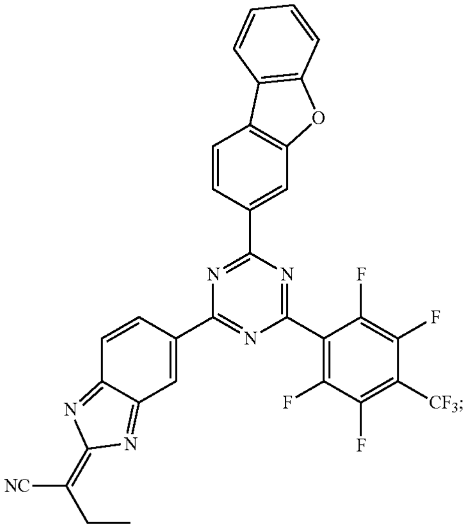
-continued
11
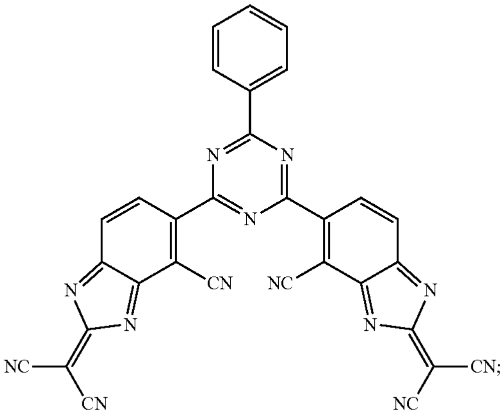
12
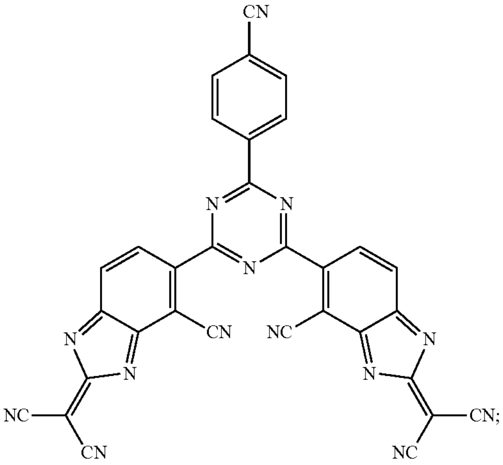
13
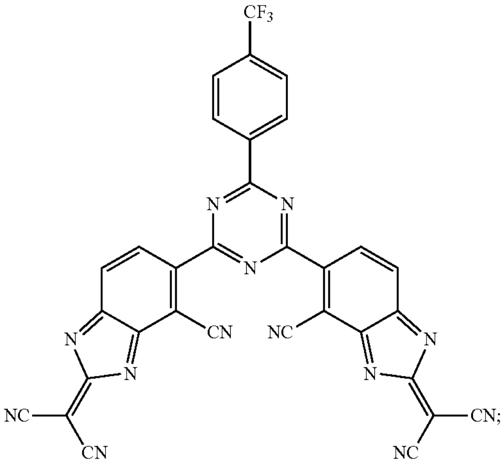

-continued
14
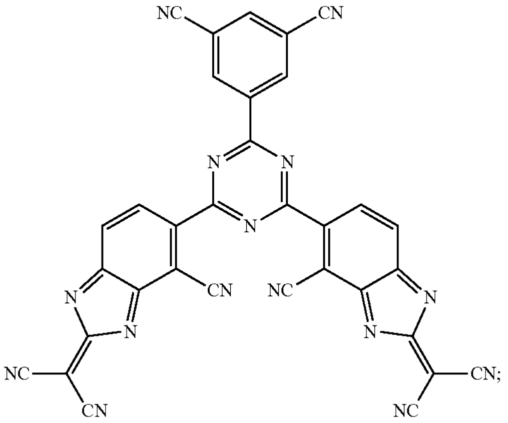
15
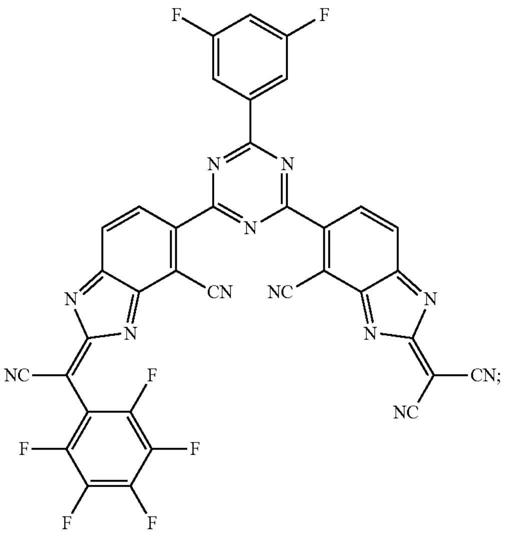
16
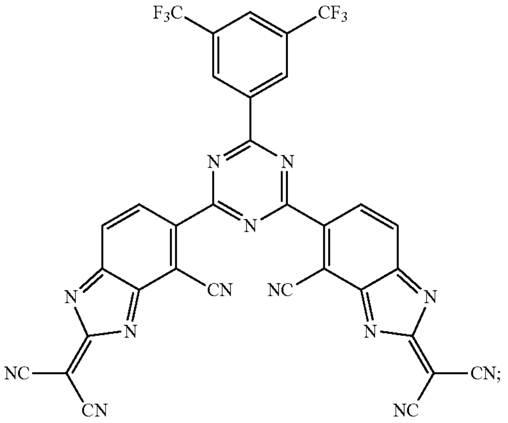
-continued
17
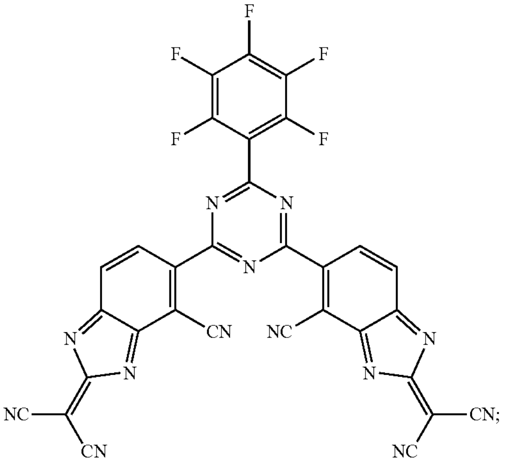
18
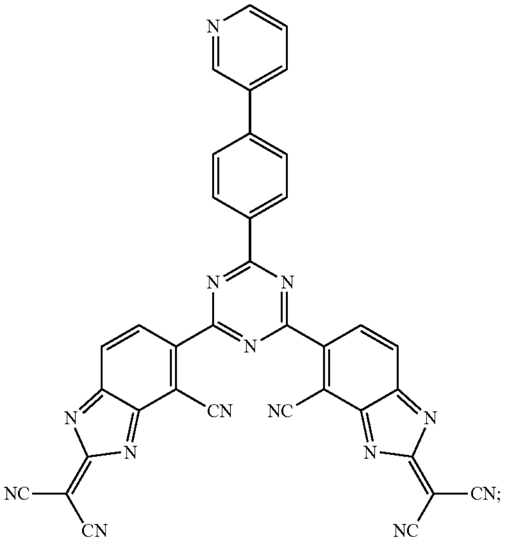
19
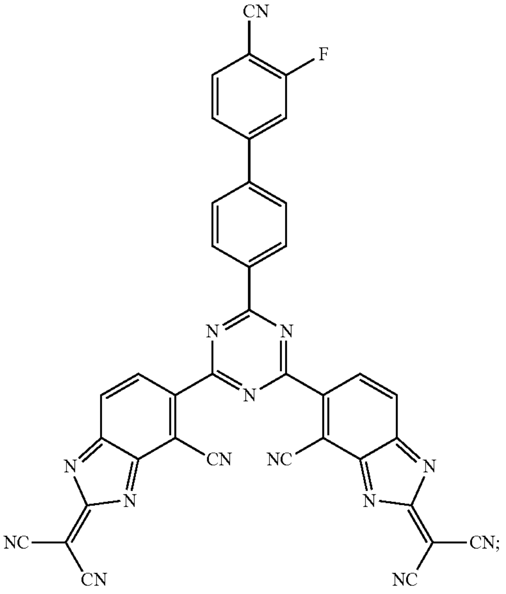

-continued
20
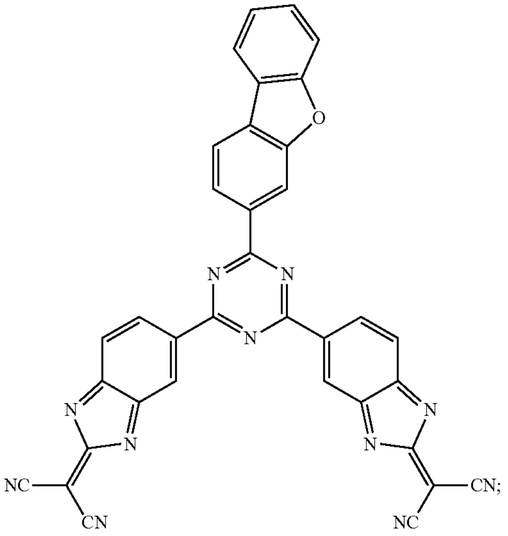
21
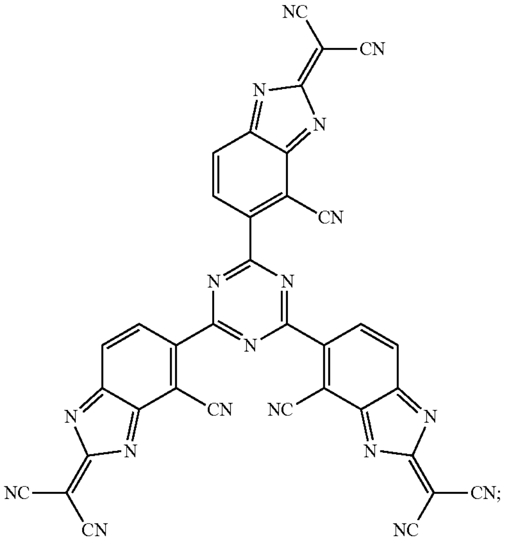
22
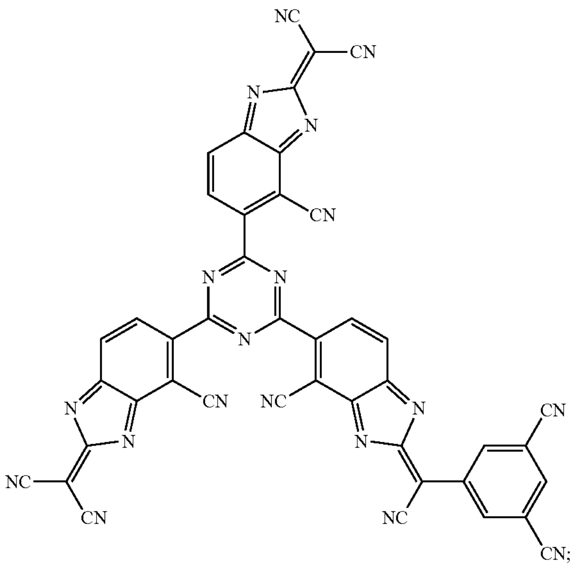
-continued
23
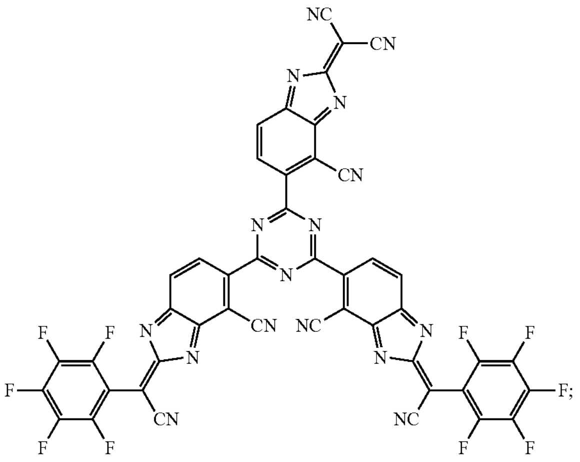
24
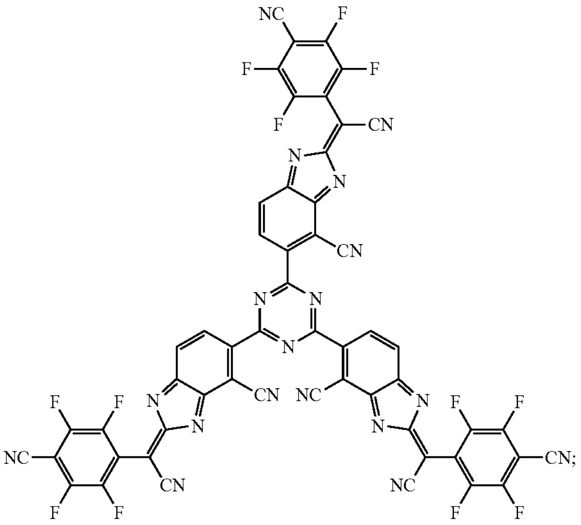
25
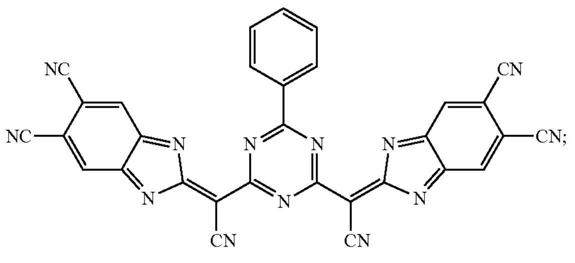
26
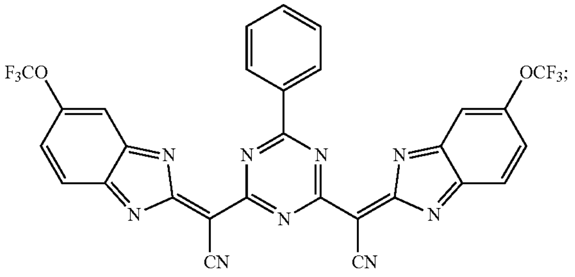

27
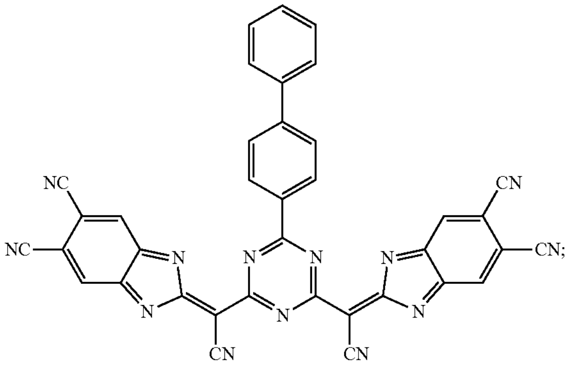
28
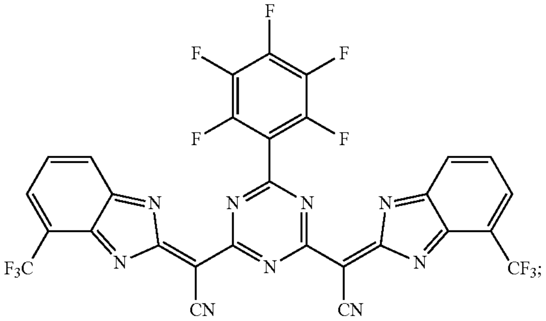
29
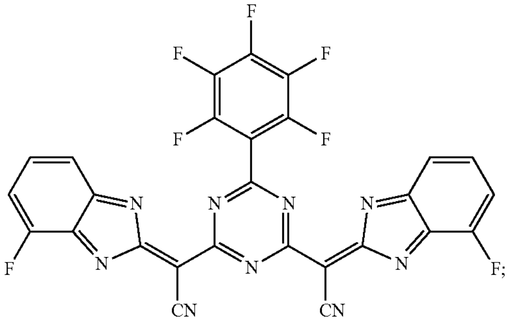
30
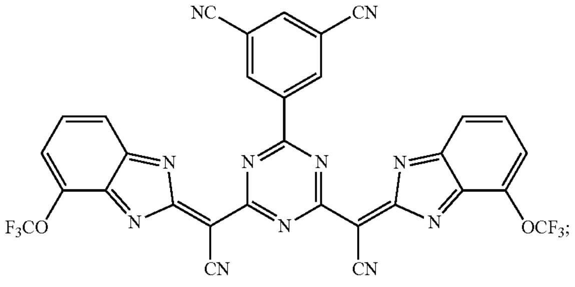
31
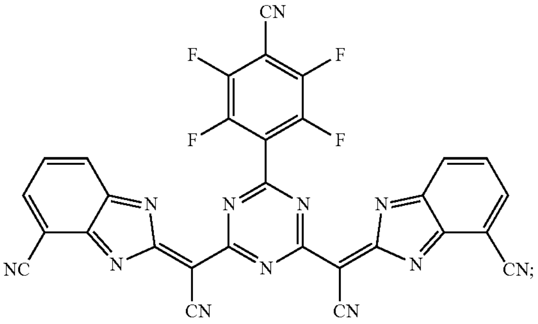
32
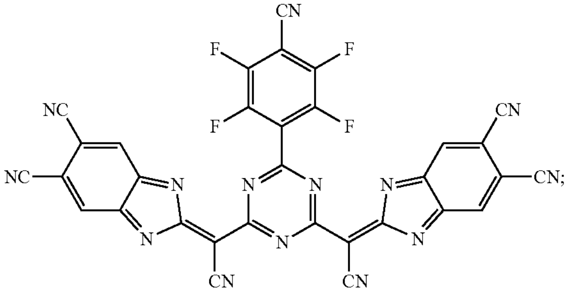
33
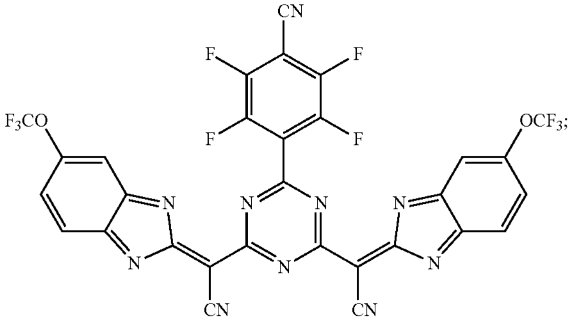
34
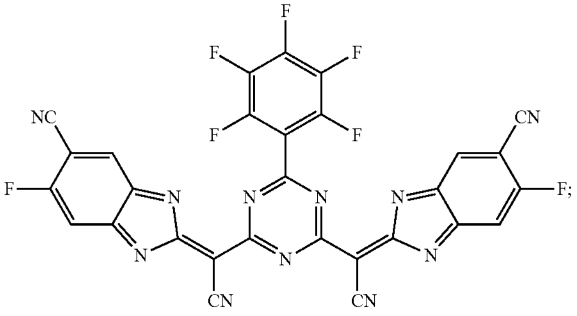

-continued
35
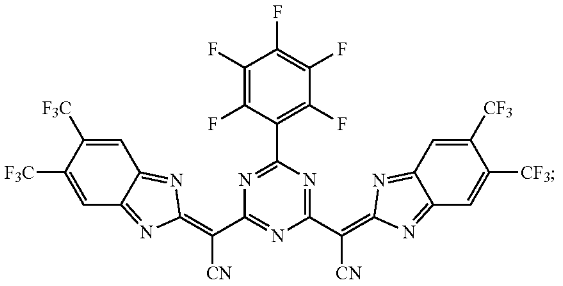
36
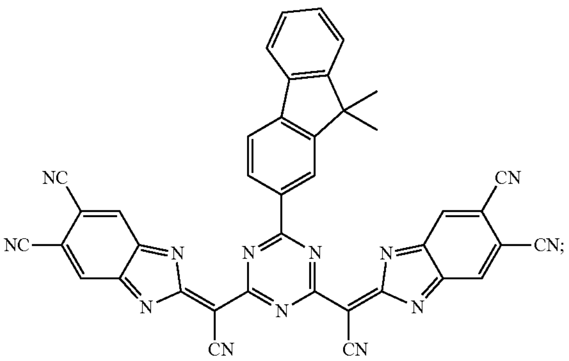
37
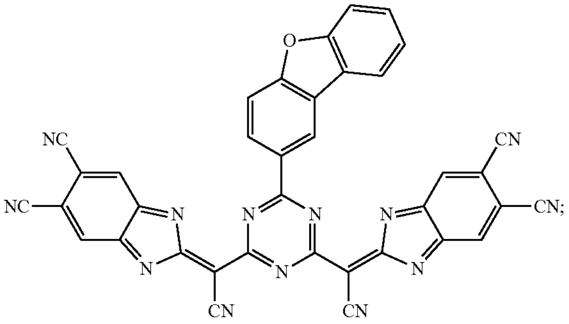
38
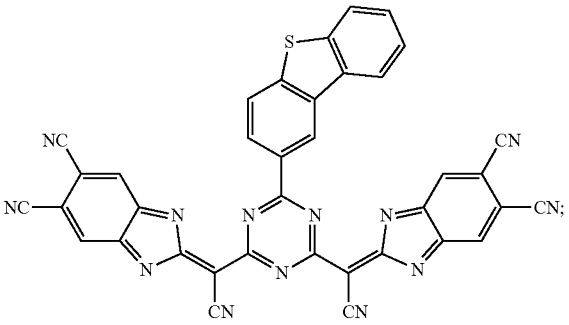
-continued
39
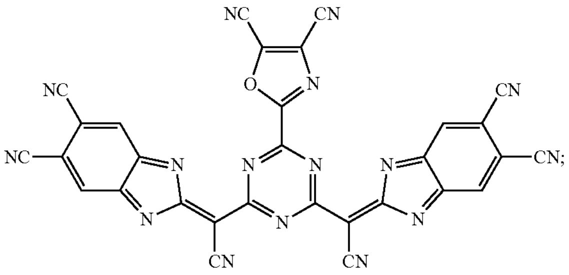
40
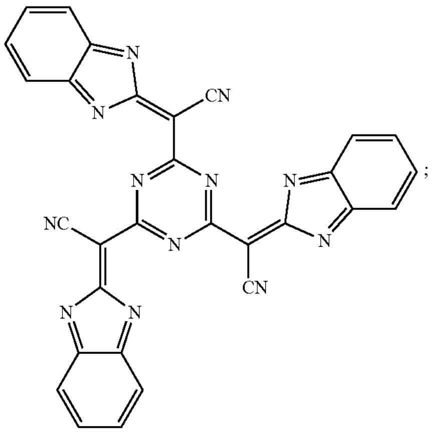
41
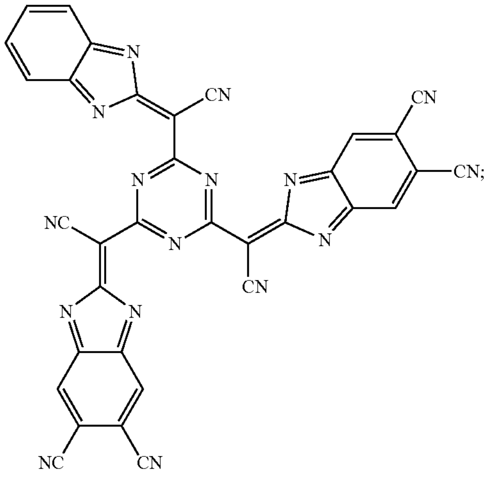

-continued
42
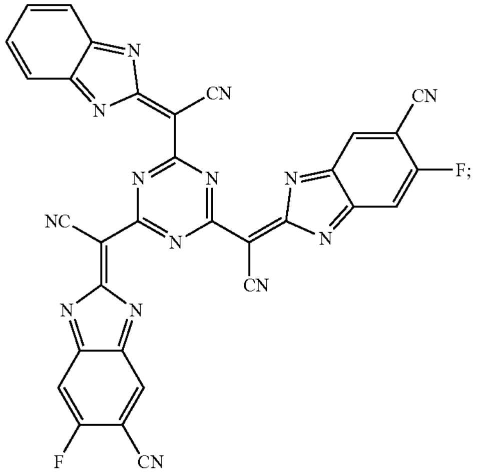
43
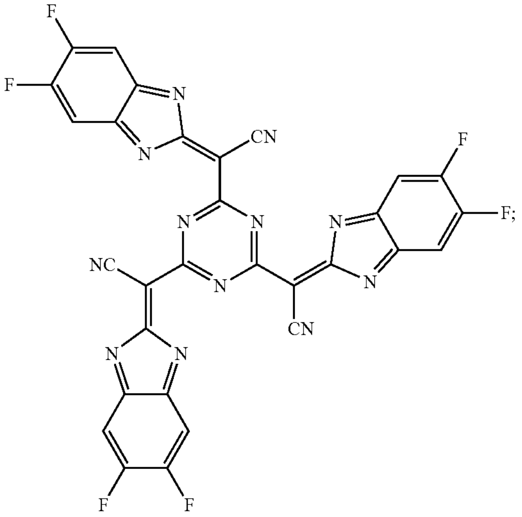
44
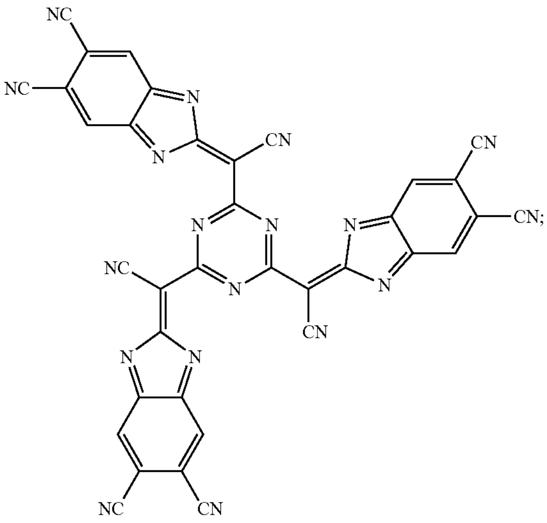
-continued
45
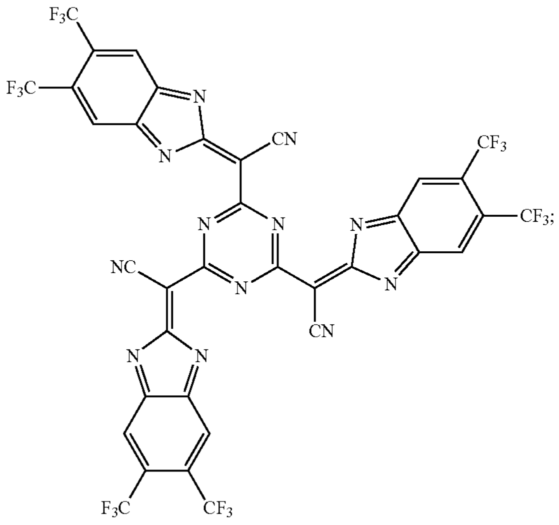
46
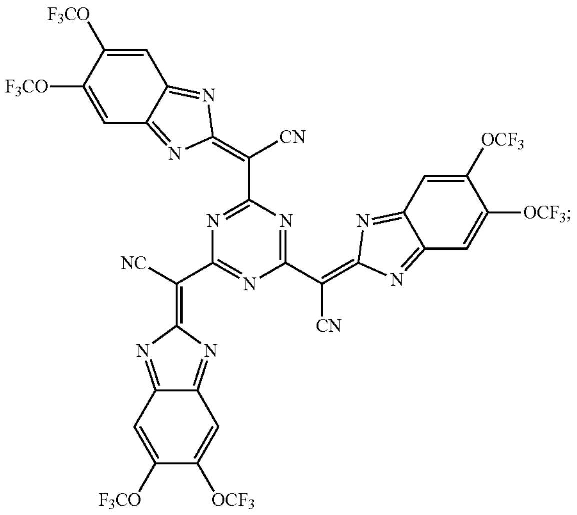
47
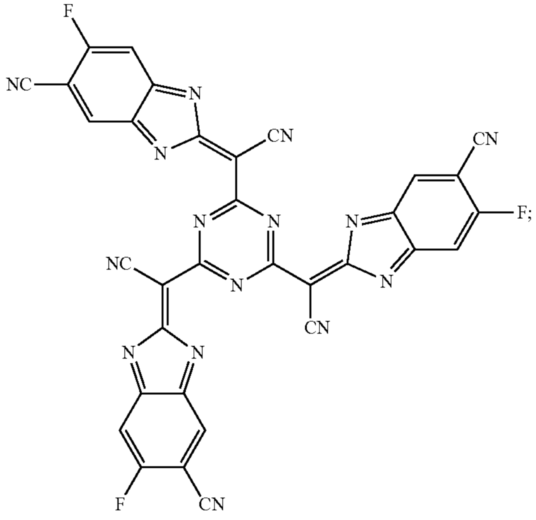

-continued
48
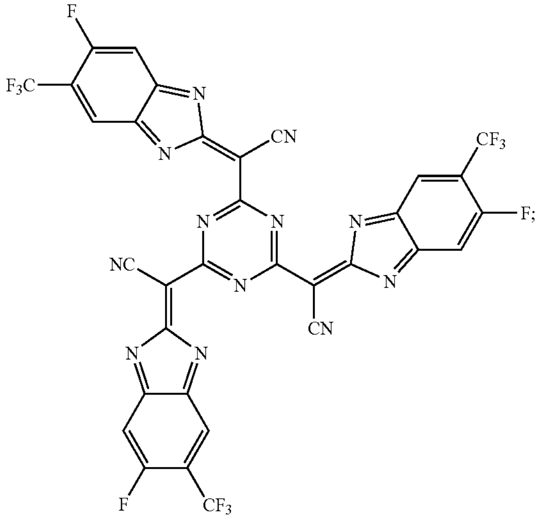
49
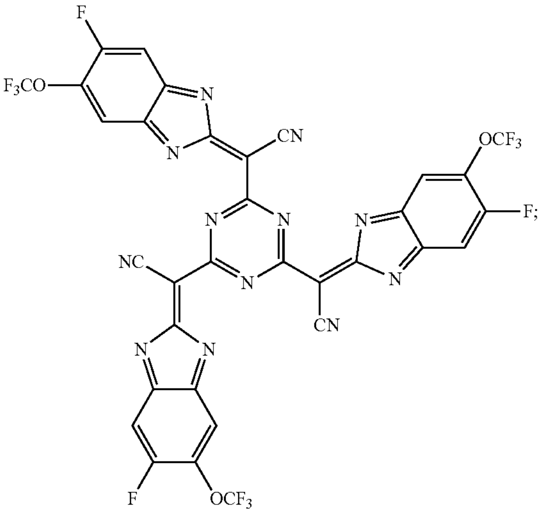
50
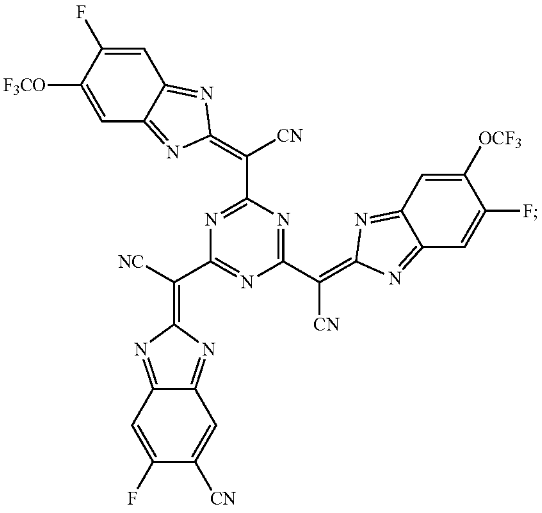
-continued
51
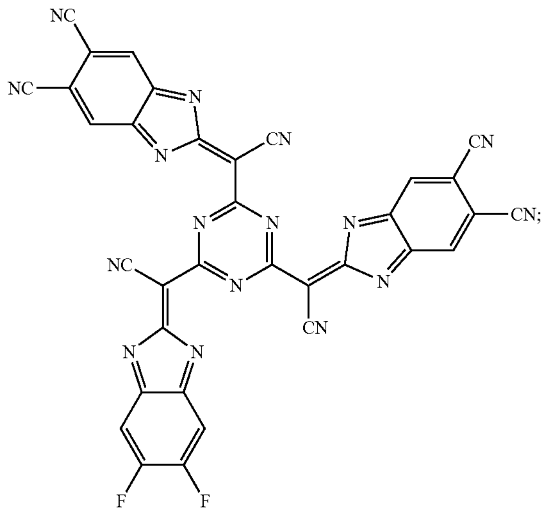
52
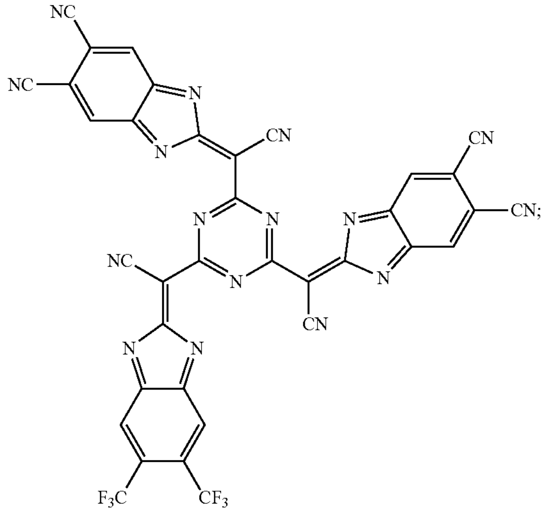
53
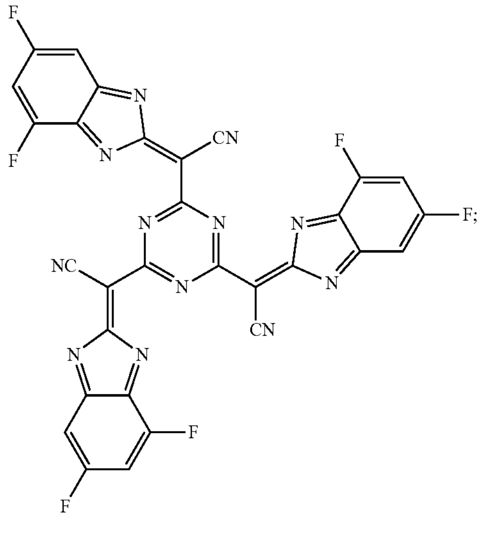

-continued
54
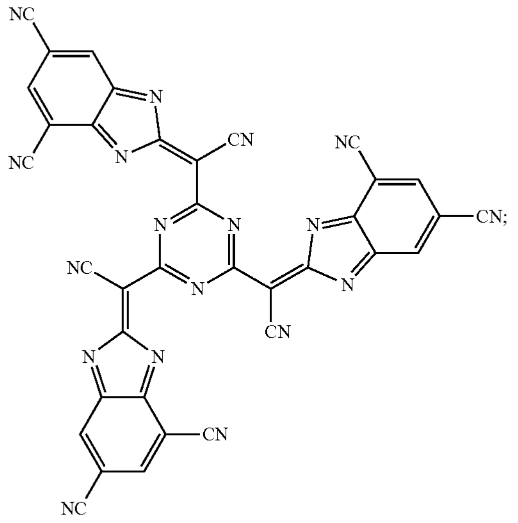
55
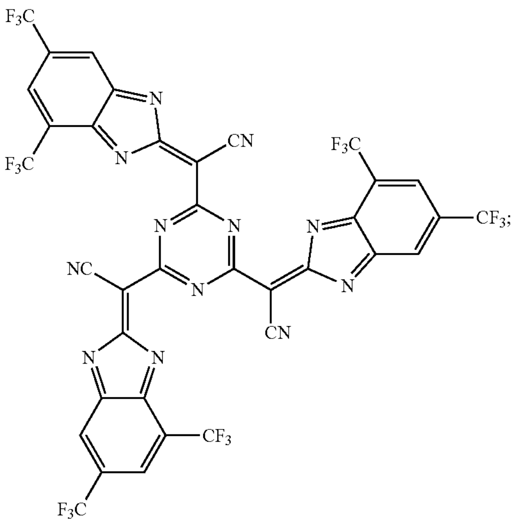
56
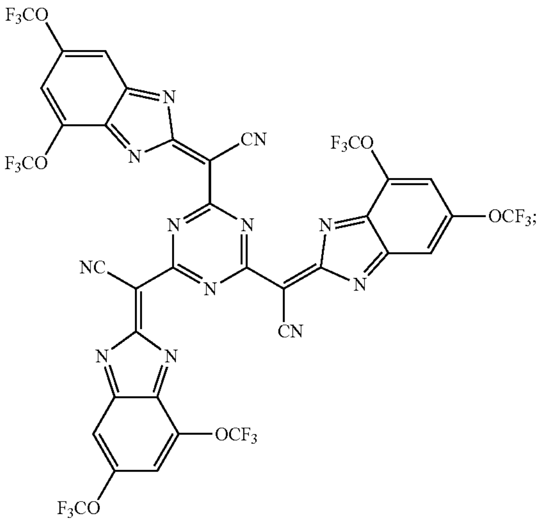
-continued
57
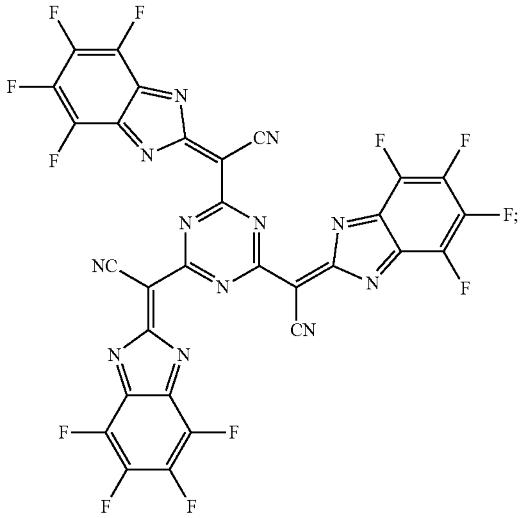
58
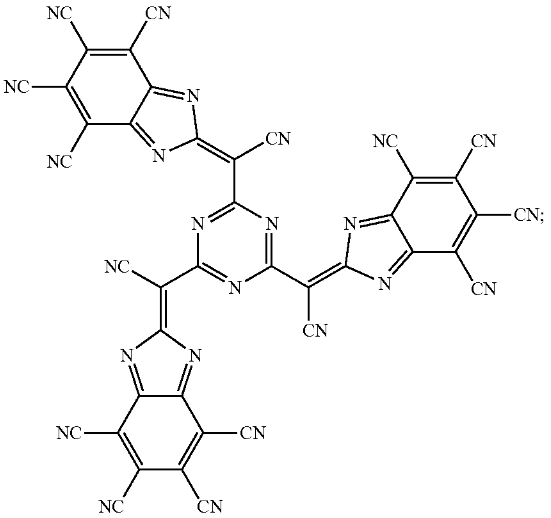
59
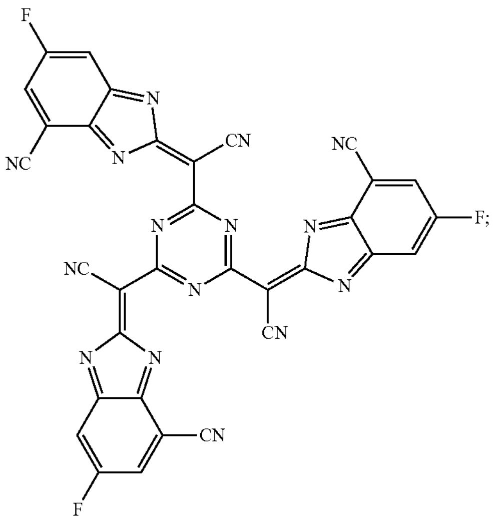

-continued
60
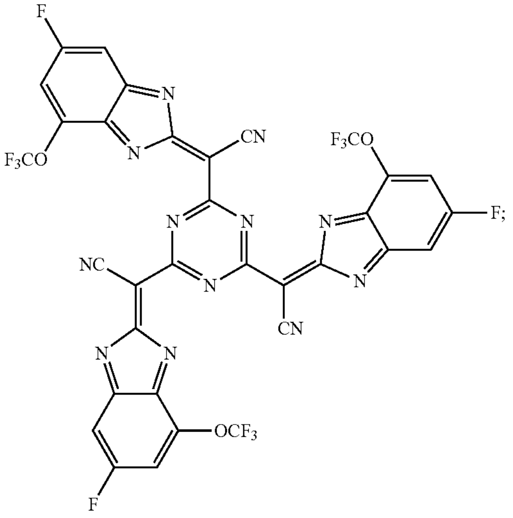
61
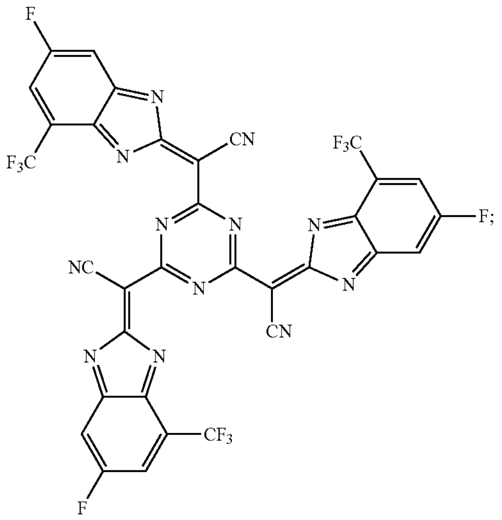
62
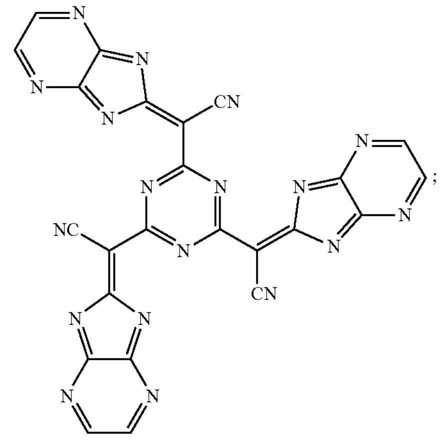
-continued
63
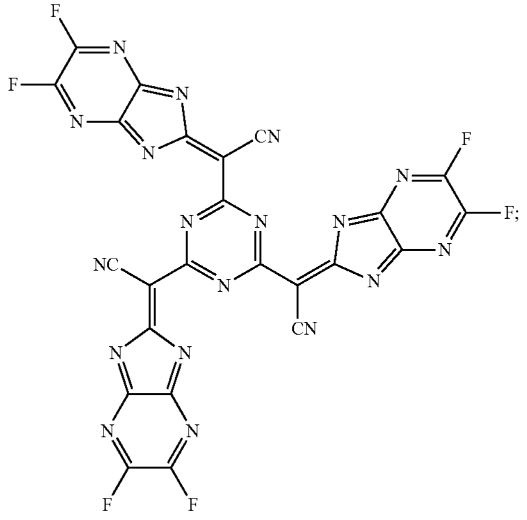
64
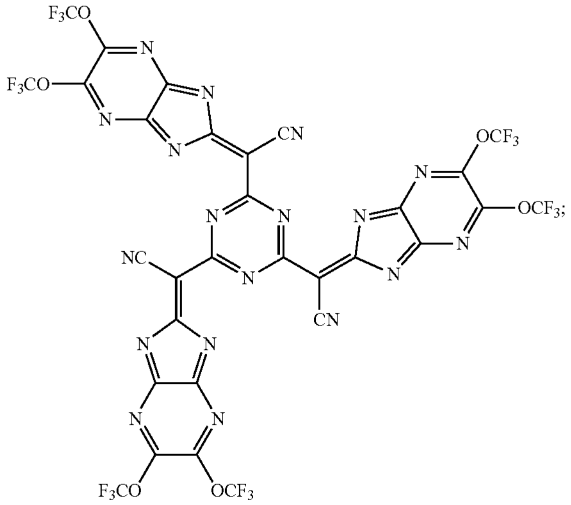
65
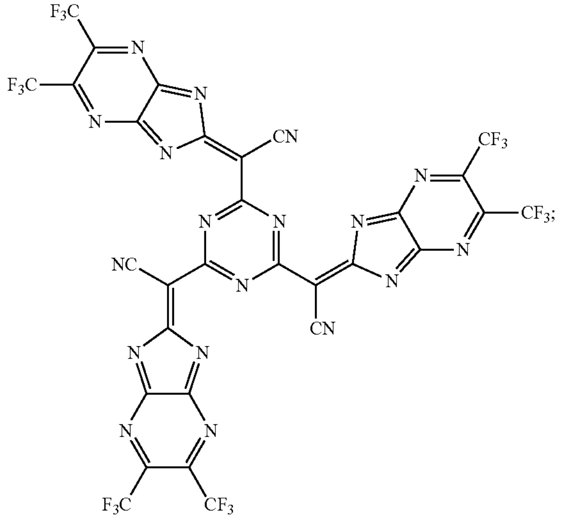

-continued
66
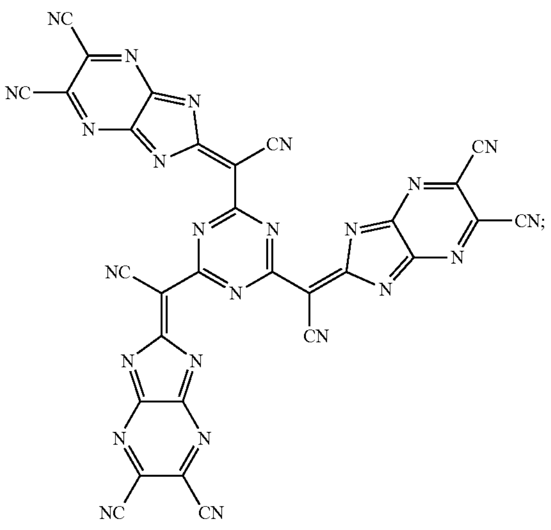
67
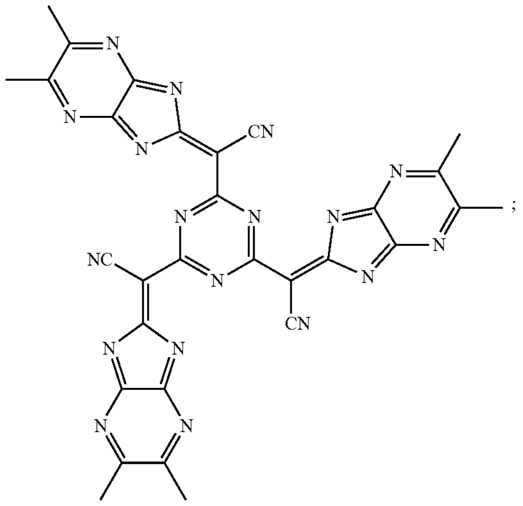
68
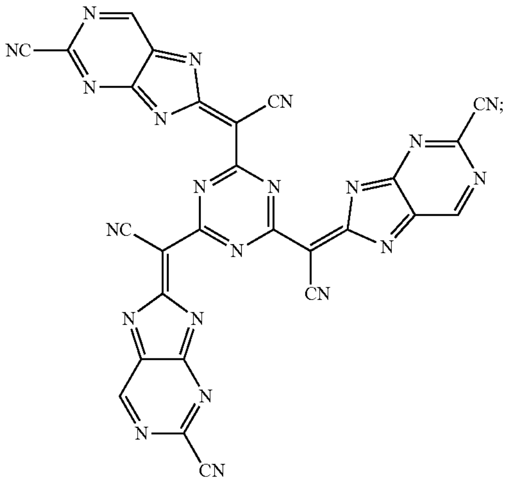
-continued
69
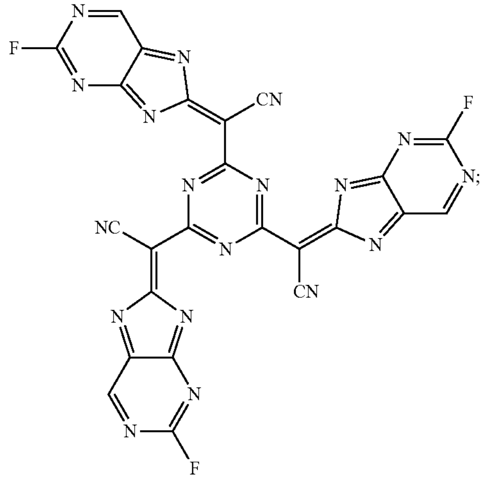
70
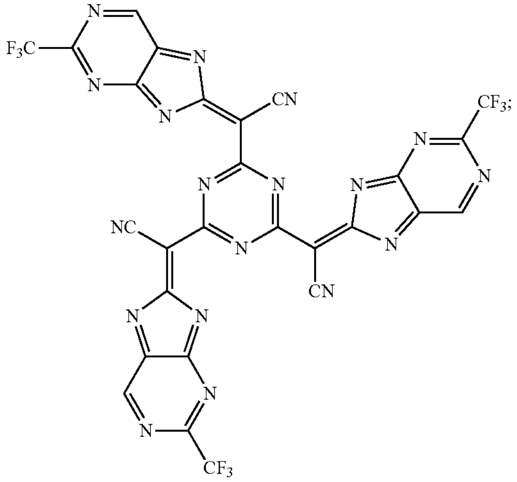
71
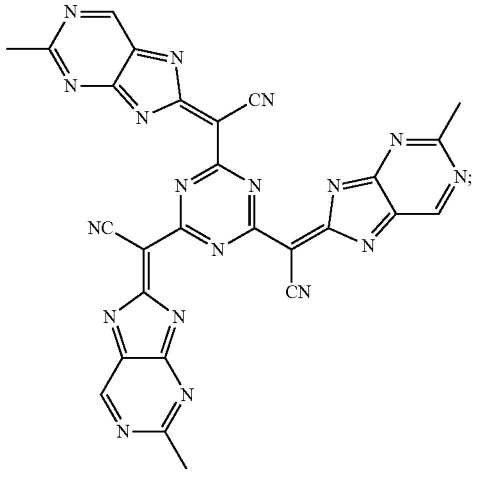

-continued
72
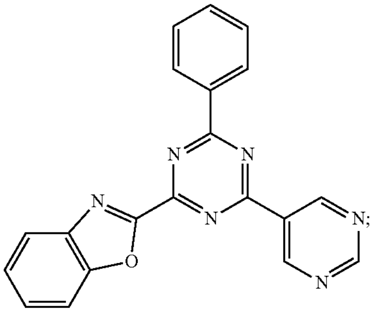
73
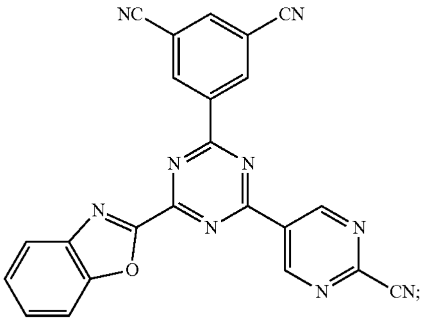
74
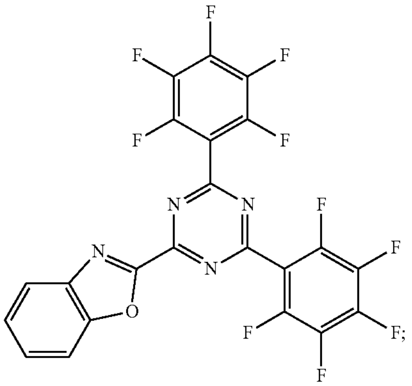
75
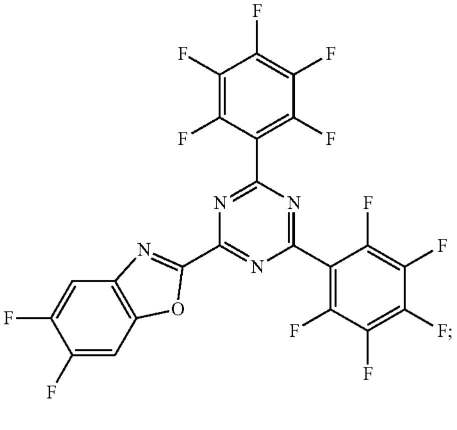
-continued
76
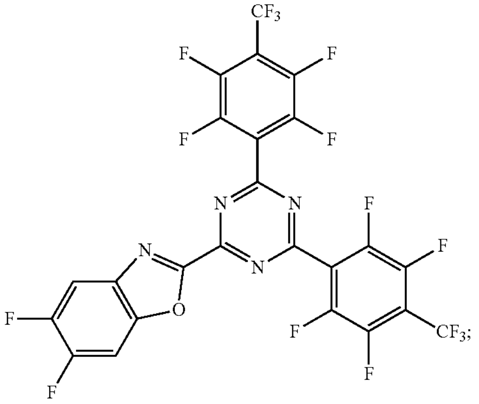
77
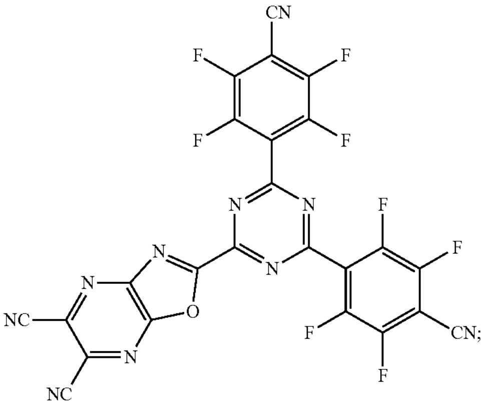
78
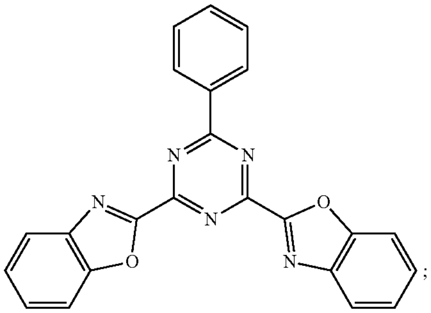
79
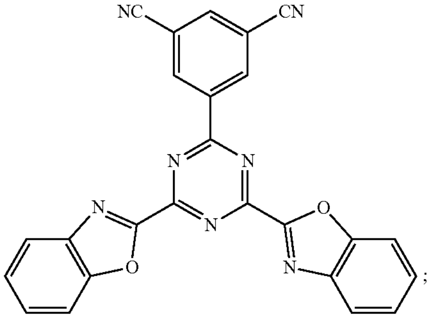

80
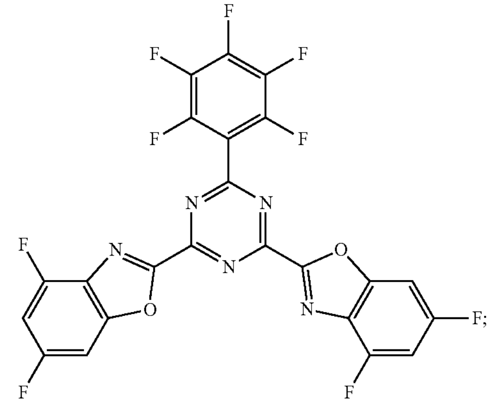
81
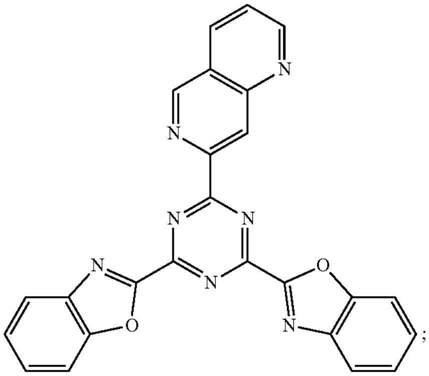
82
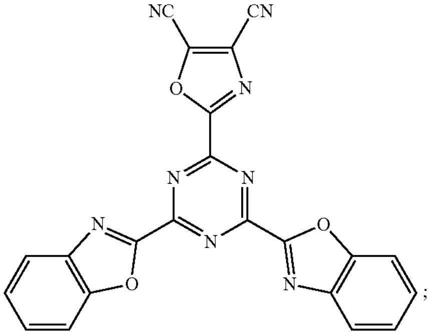
83
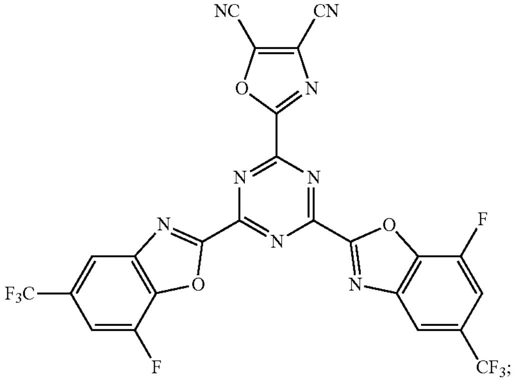
84
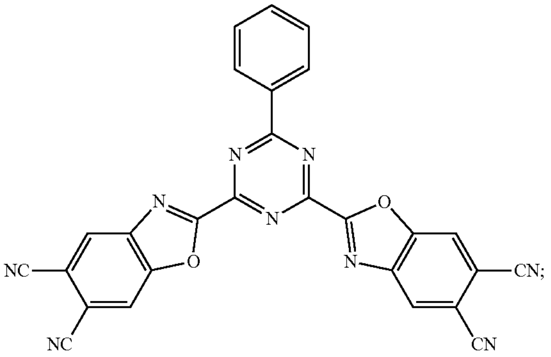
85
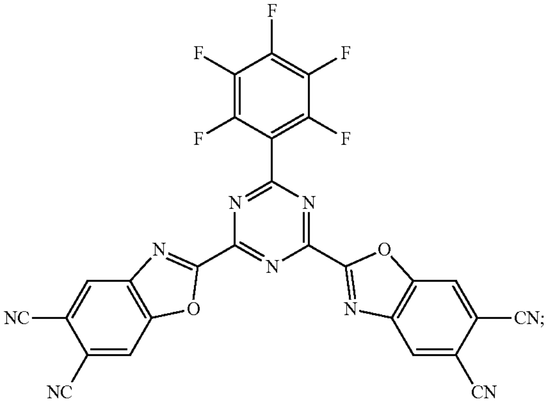
86
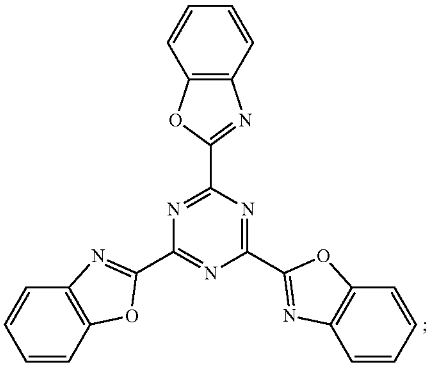
87
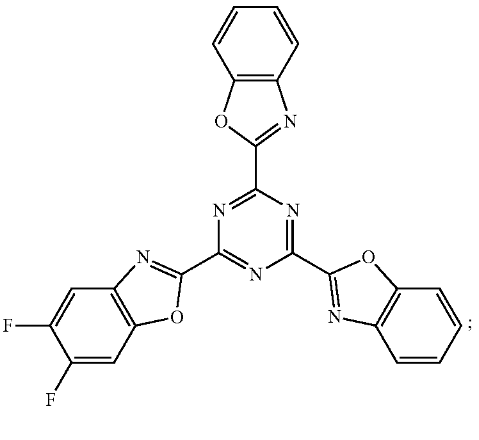

-continued
88
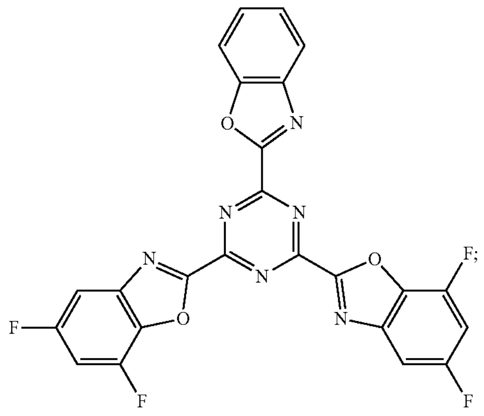
89
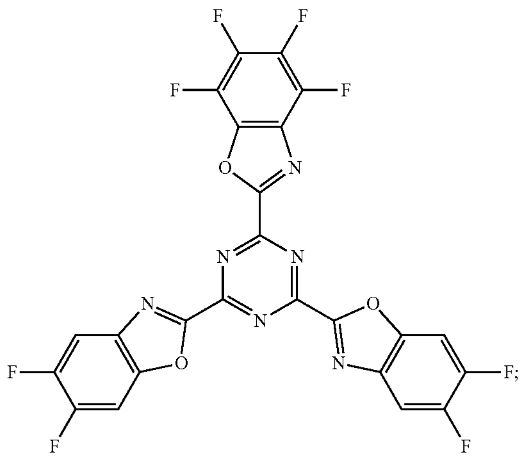
90
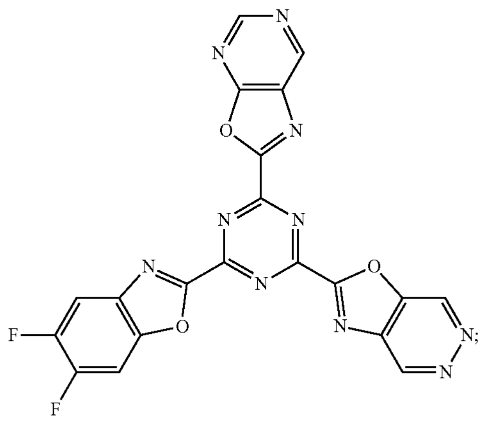
-continued
91
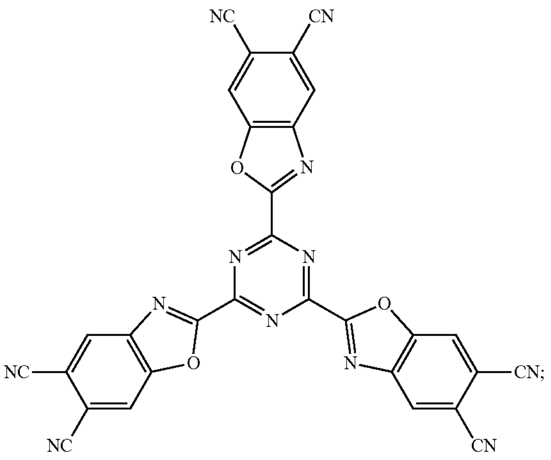
92
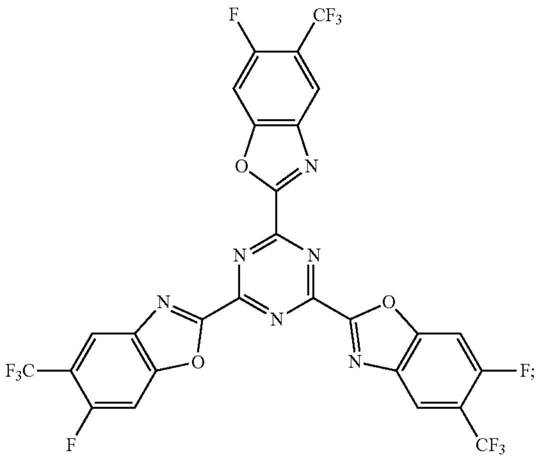
93
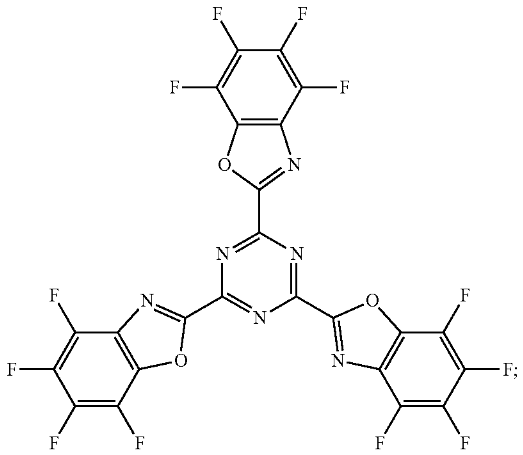

-continued
94
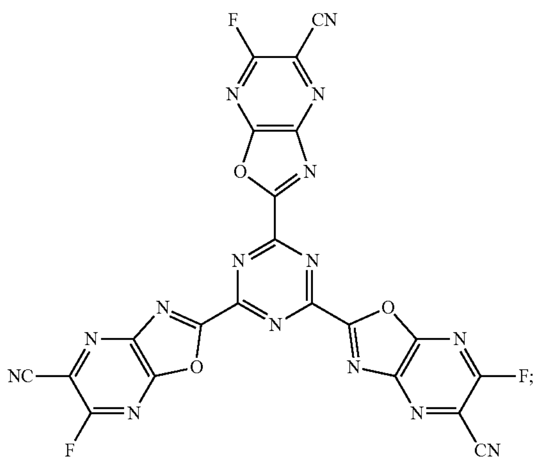
95
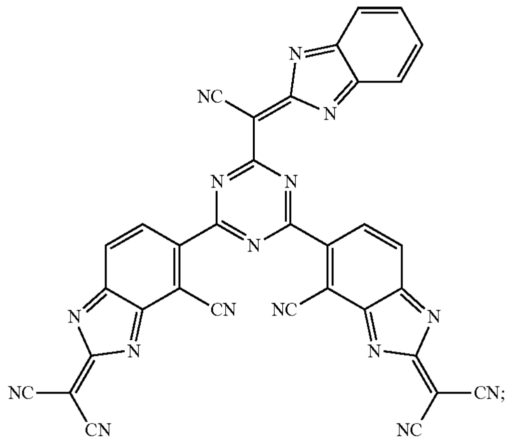
96
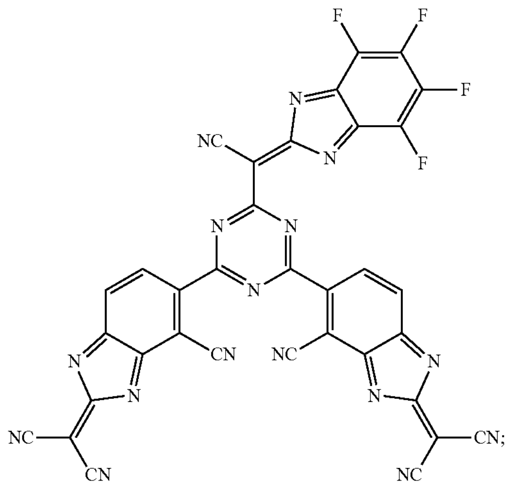
-continued
97
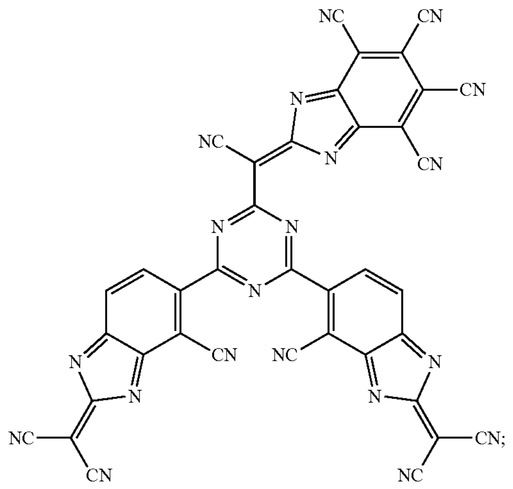
98
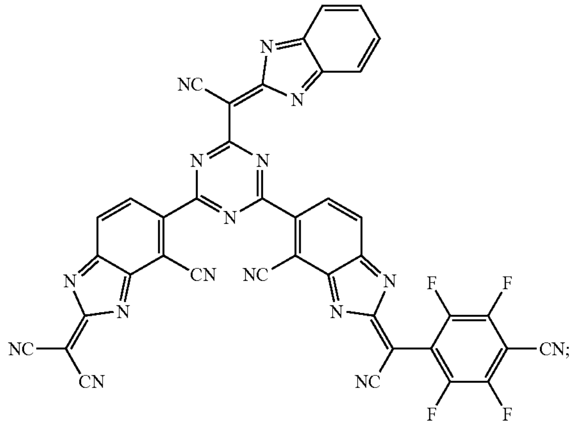
99
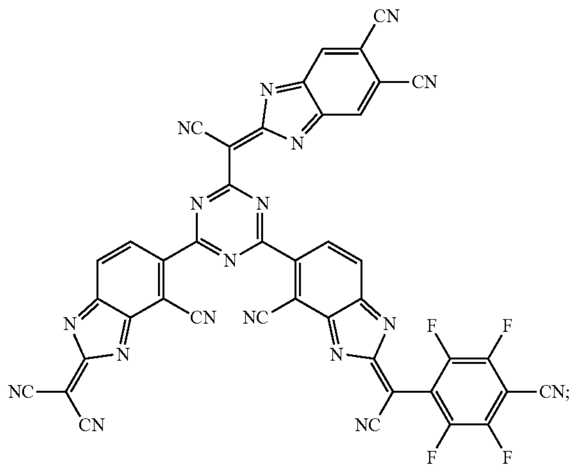

-continued
100
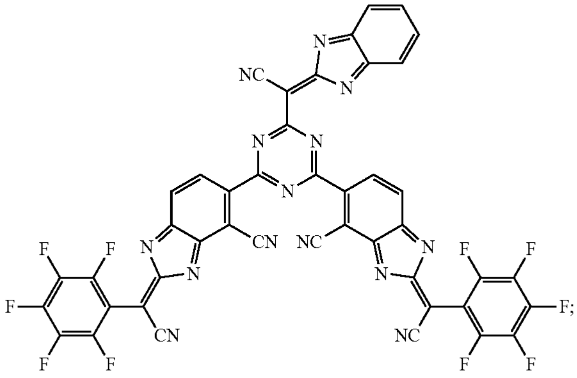
101
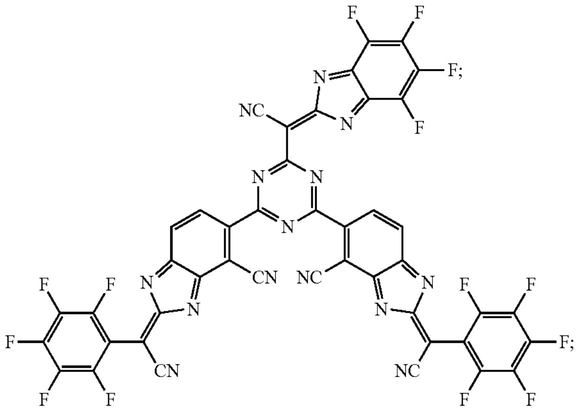
102
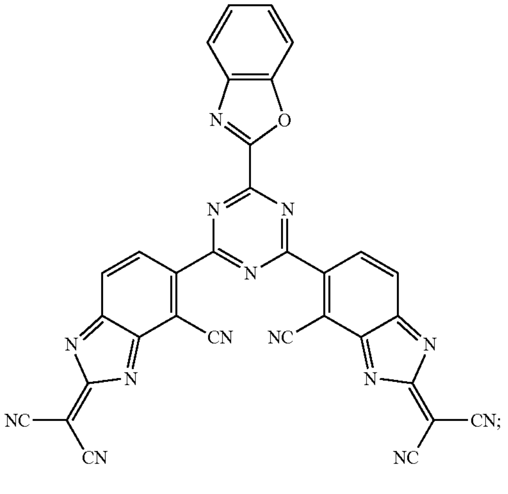
-continued
103
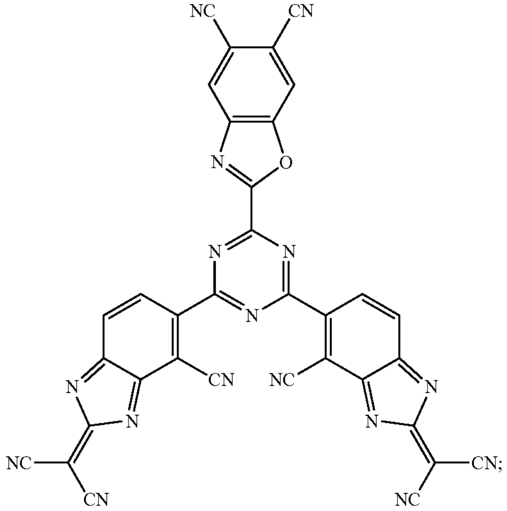
104
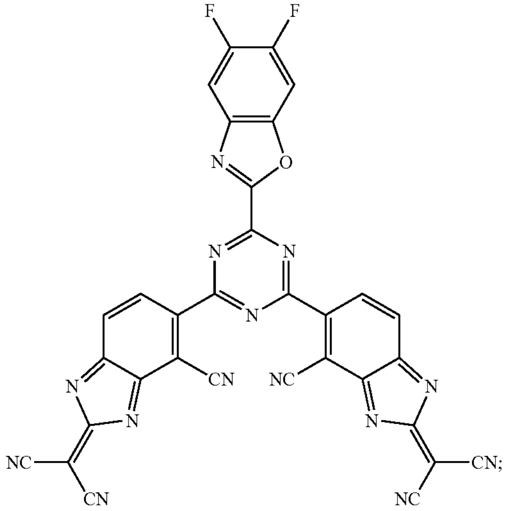
105
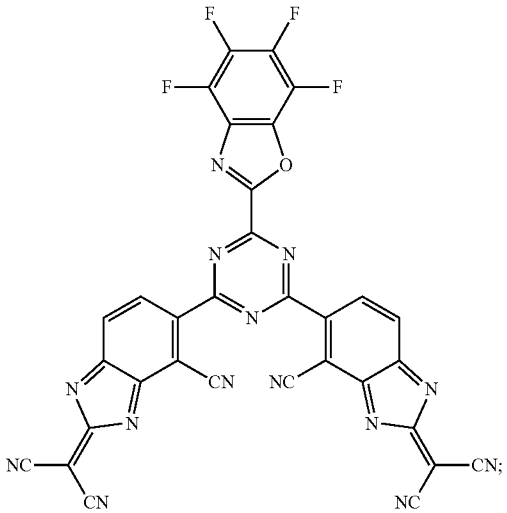

-continued
106
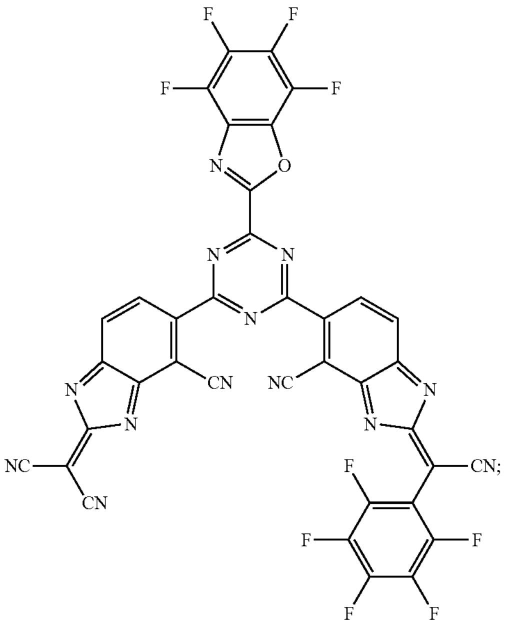
107
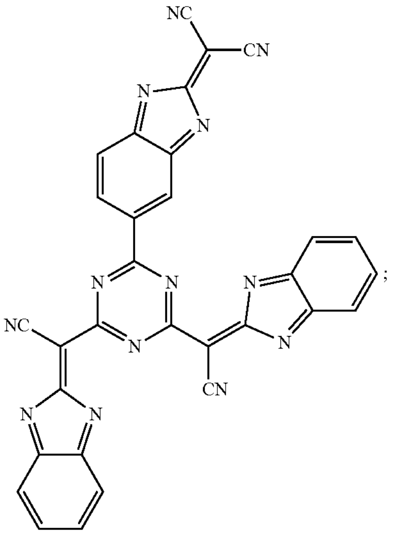
-continued
108
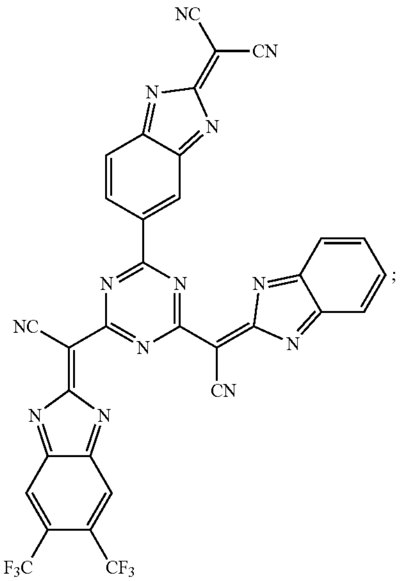
109
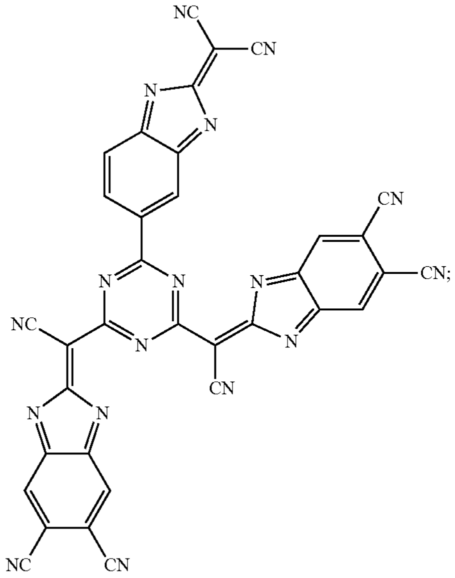

-continued
110
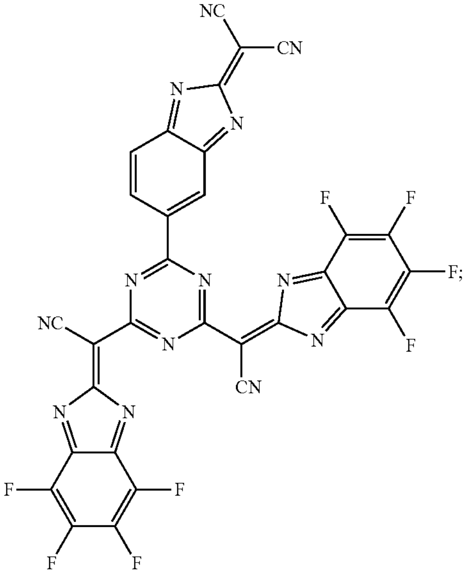
111
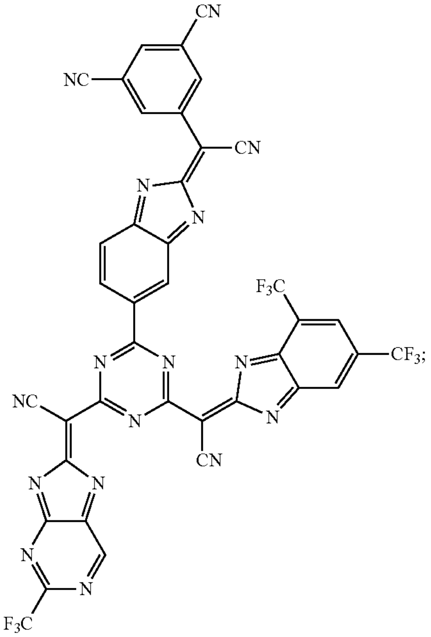
-continued
112
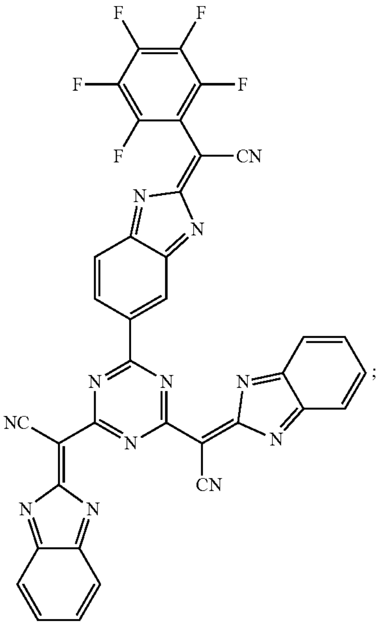
113
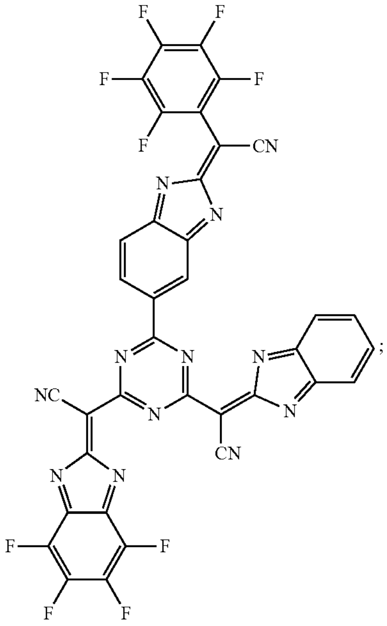

-continued
114
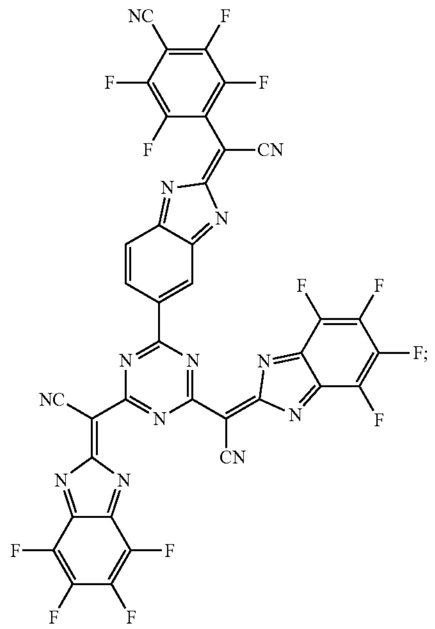
115
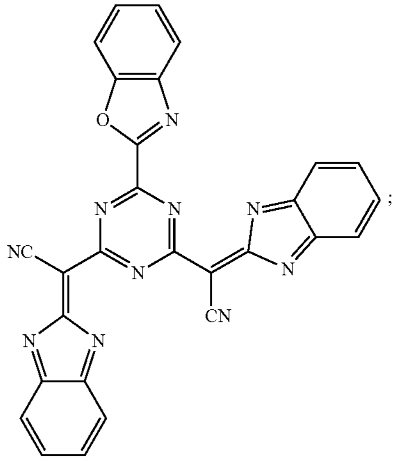
116
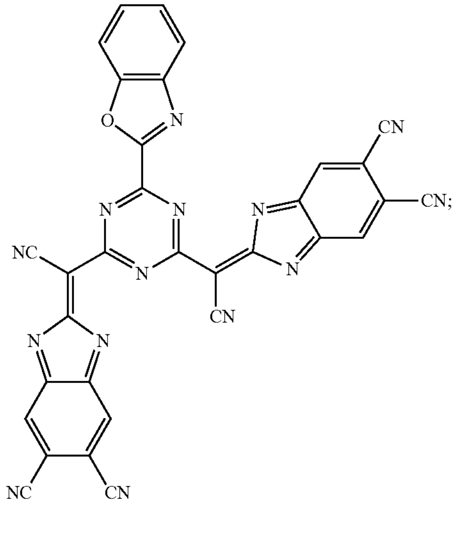
-continued
117
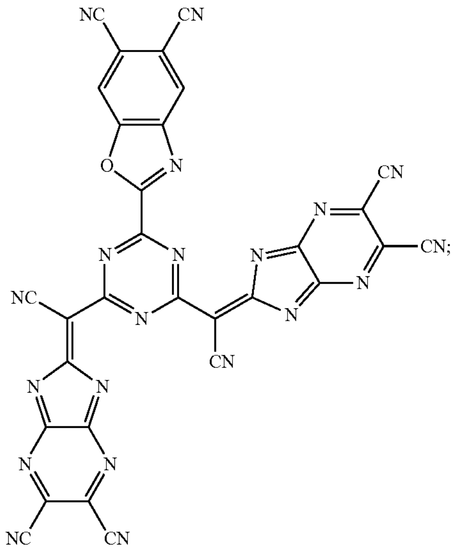
118
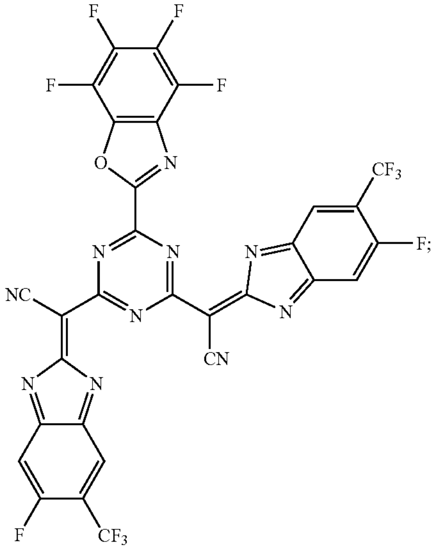
119
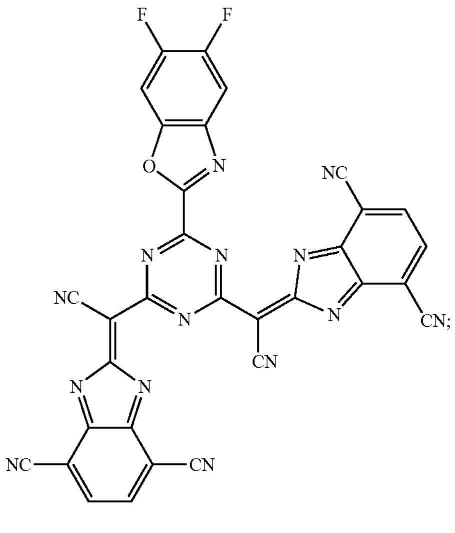

-continued
120
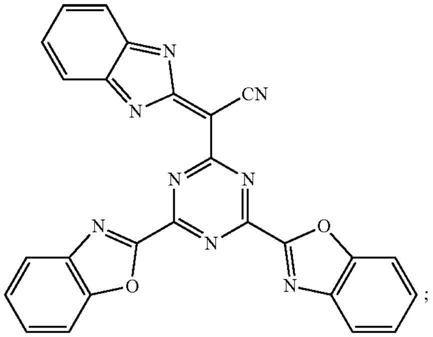
121
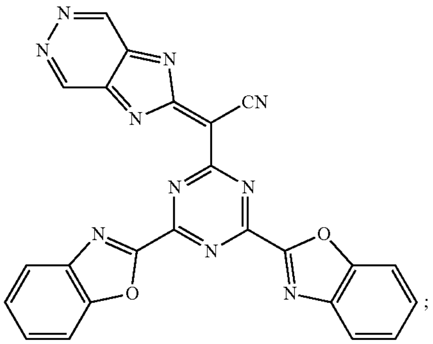
122
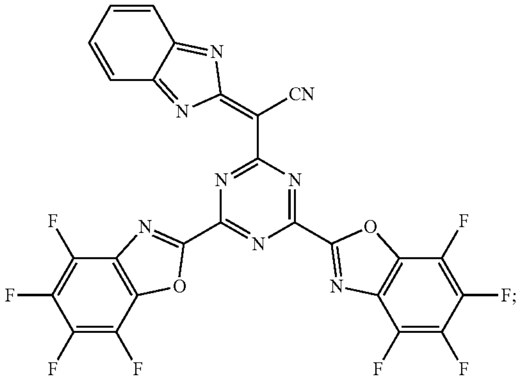
123
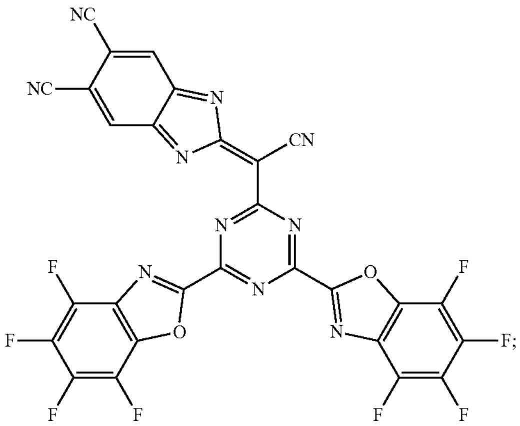
-continued
124
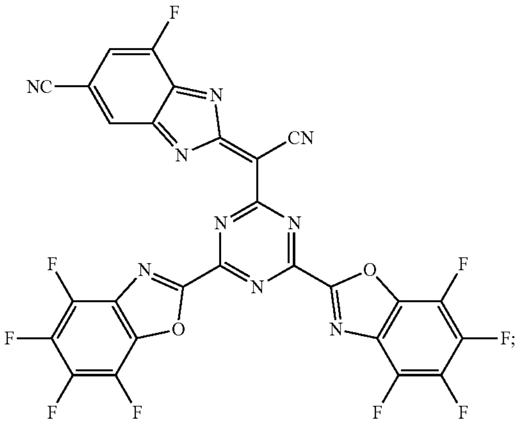
125
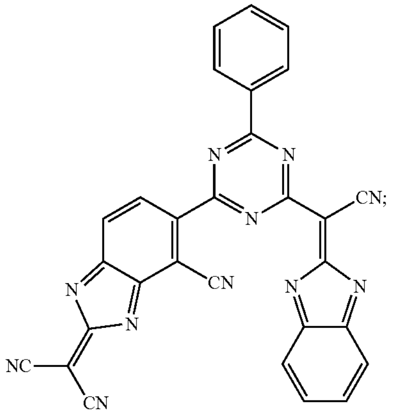
126
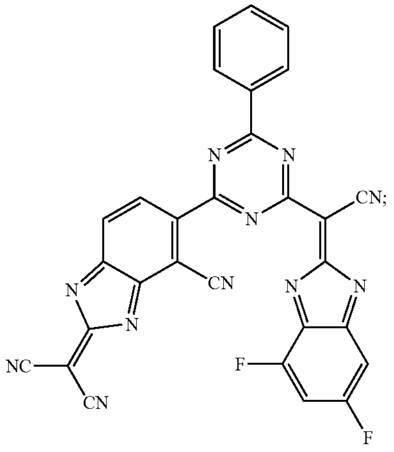

-continued
127
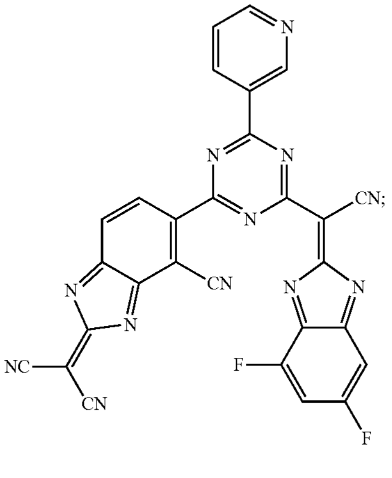
128
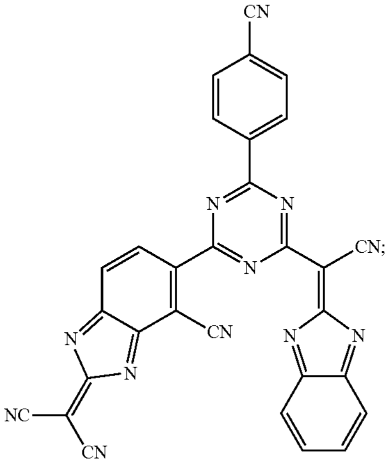
129
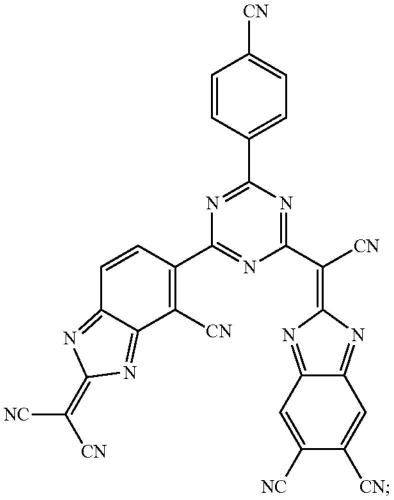
-continued
130
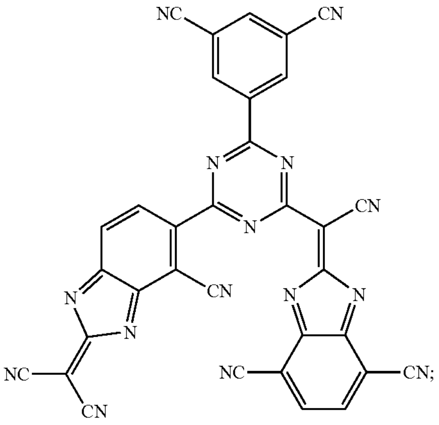
131
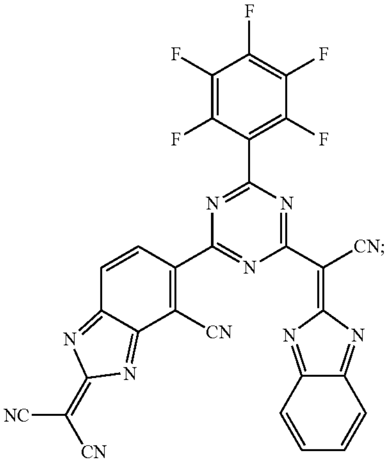
132
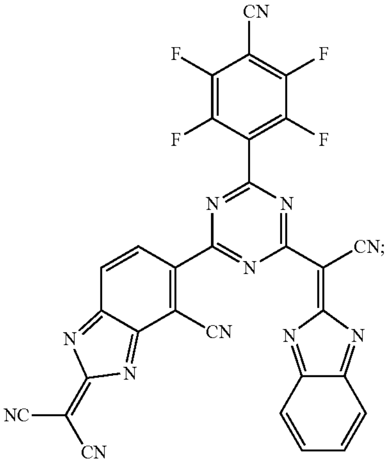

-continued
133
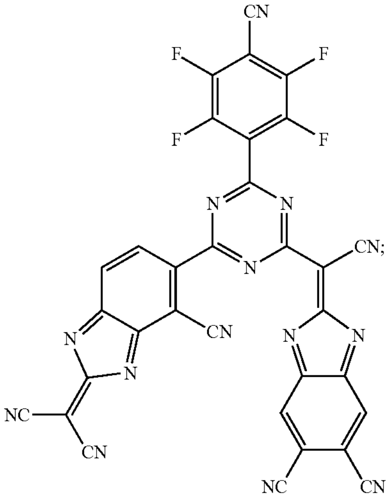
134
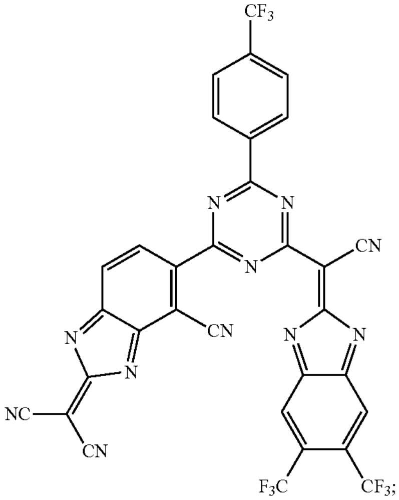
135
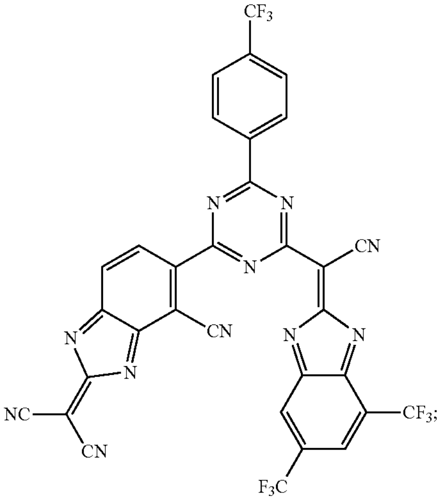
-continued
136
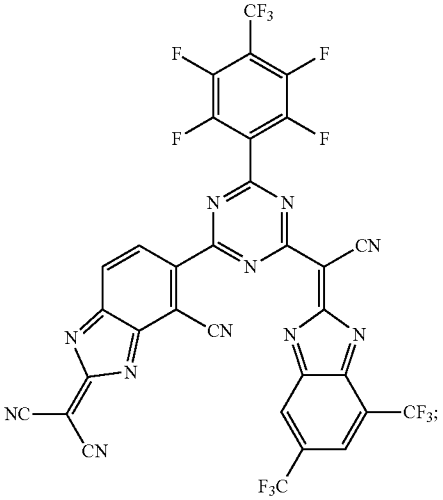
137
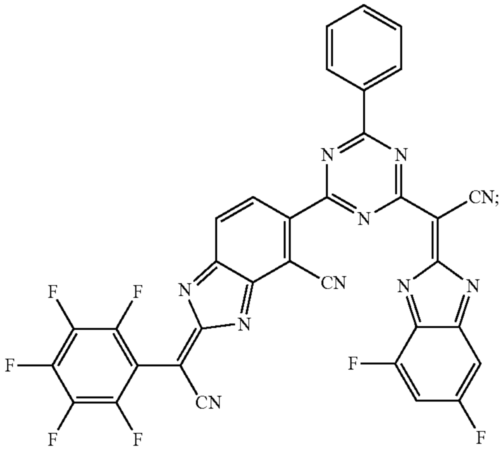
138
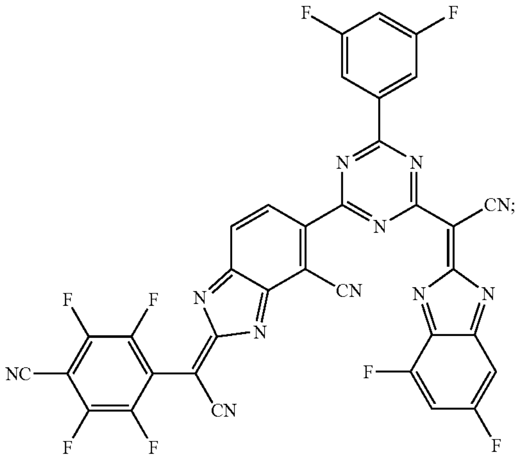

-continued
139
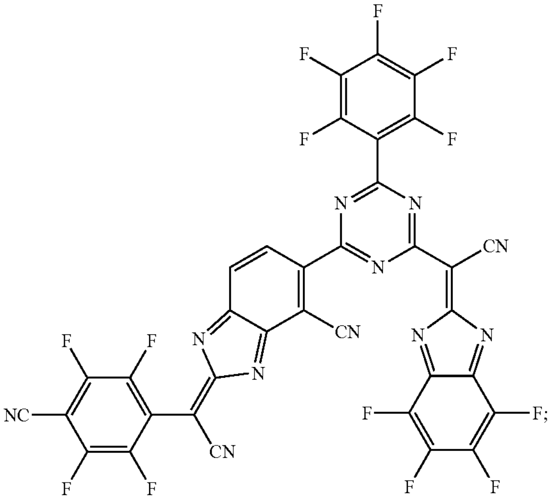
140
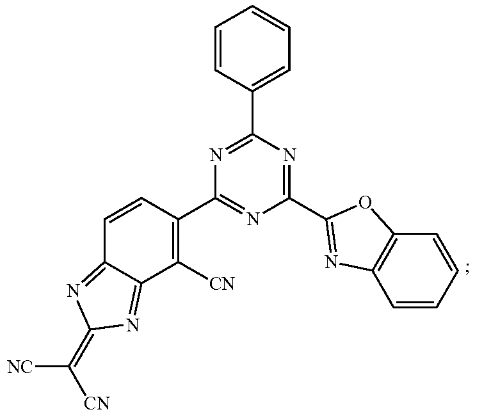
141
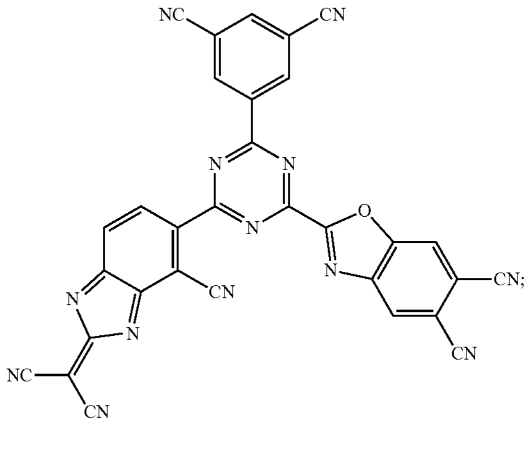
-continued
142
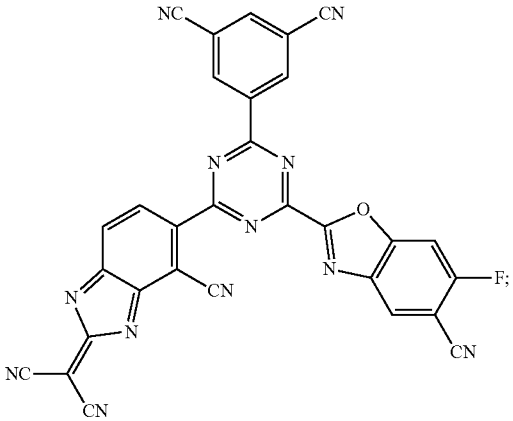
143
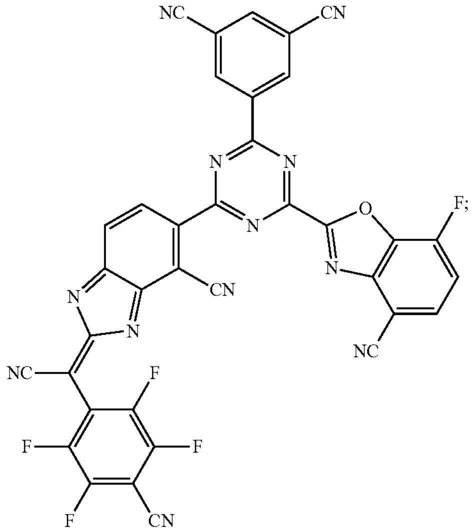
144
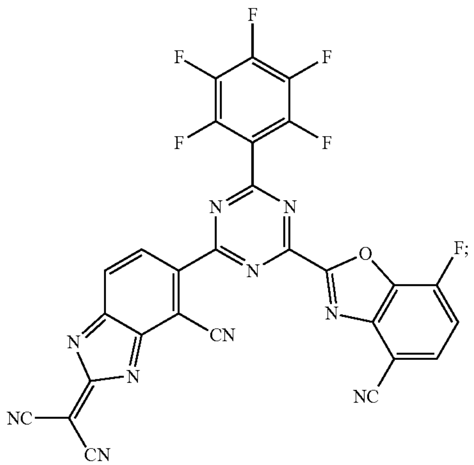

145
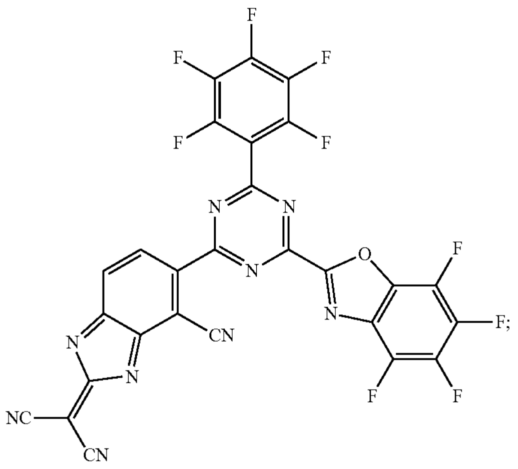
146
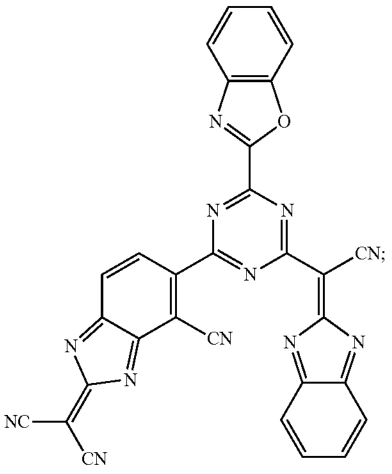
147
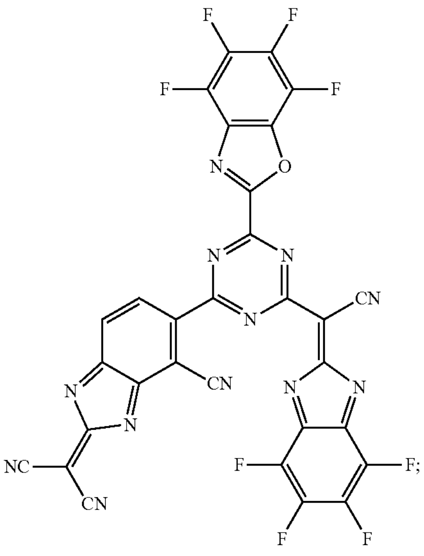
148
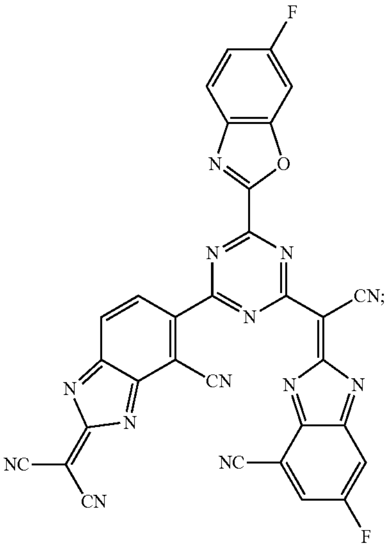
149
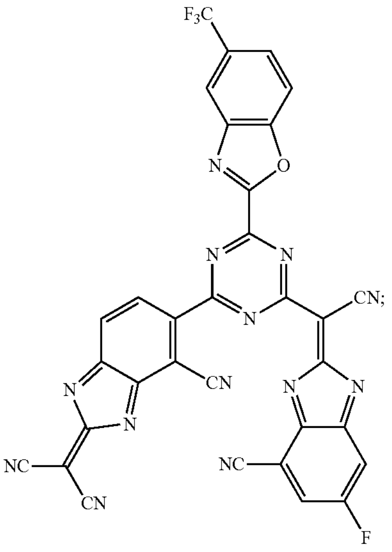
150
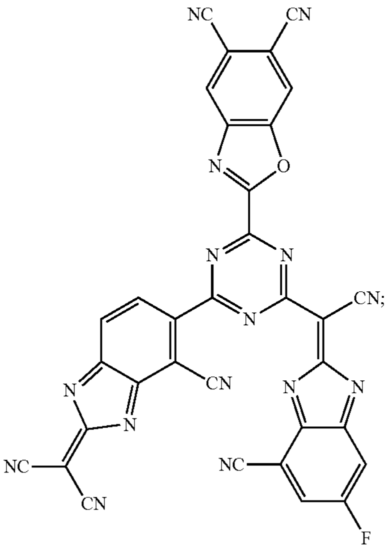

-continued
151
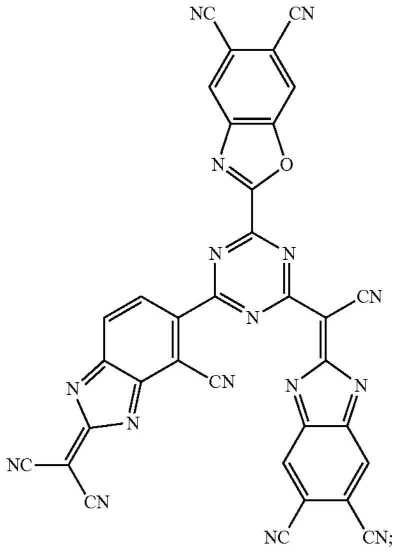
152
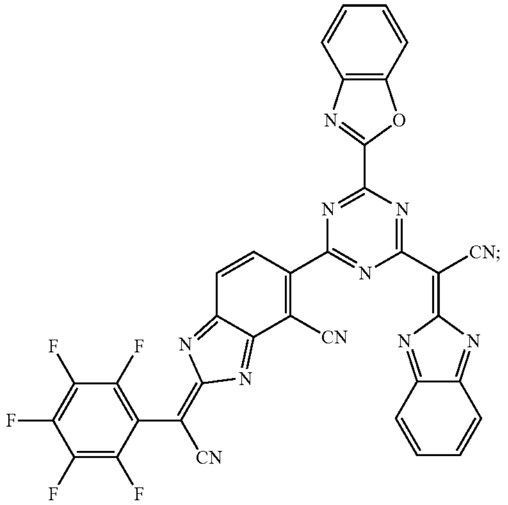
153
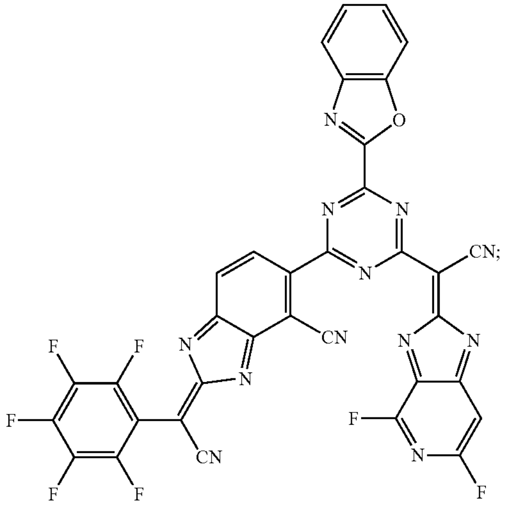
-continued
154
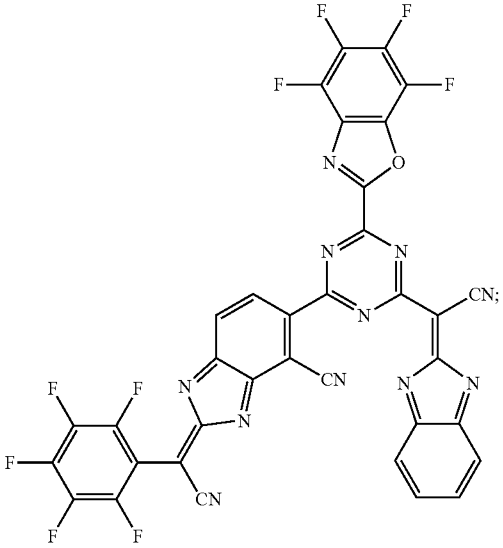
155
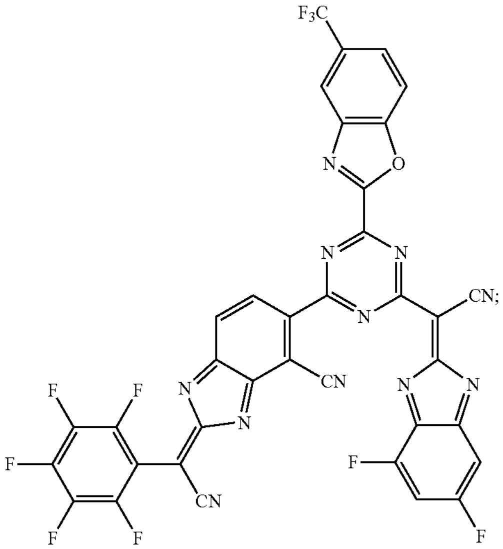
156
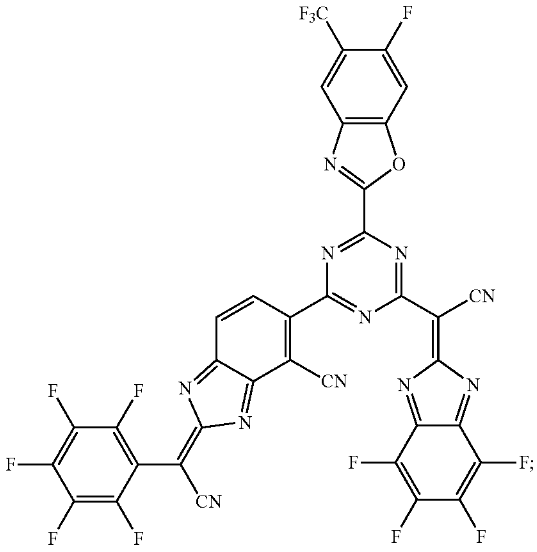

-continued
157
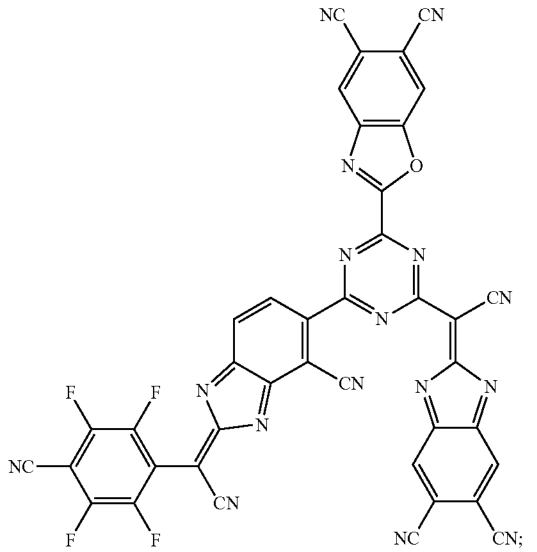
158
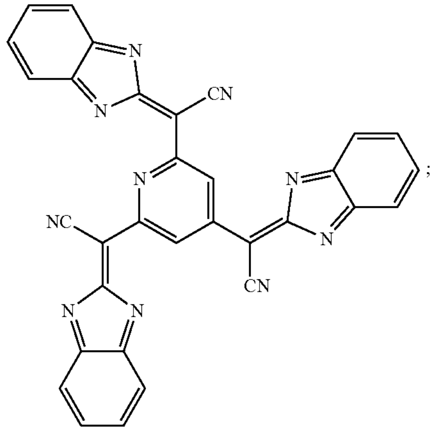
159
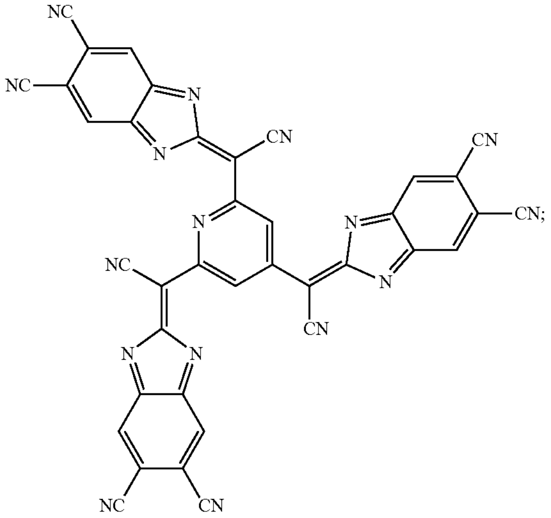
-continued
160
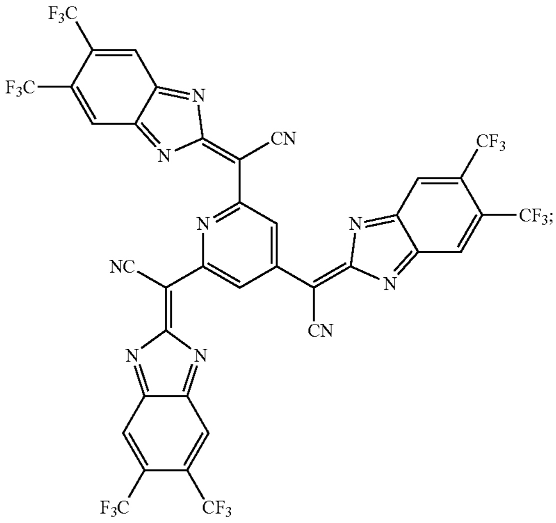
161
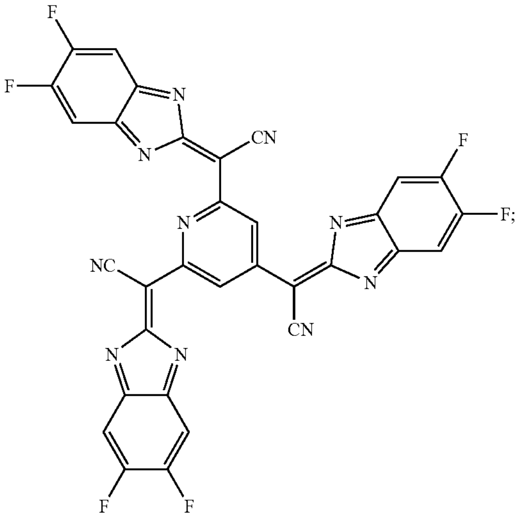
162
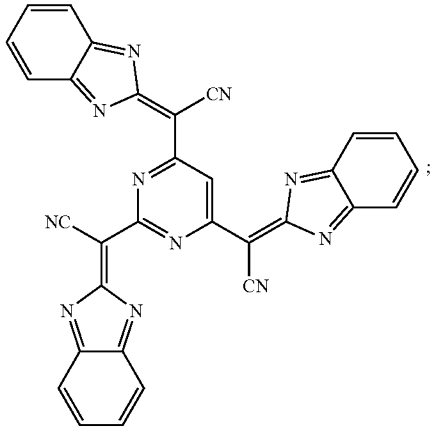

-continued
163
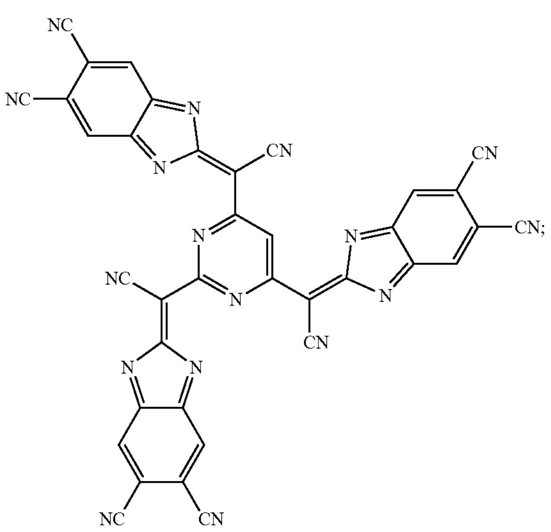
164
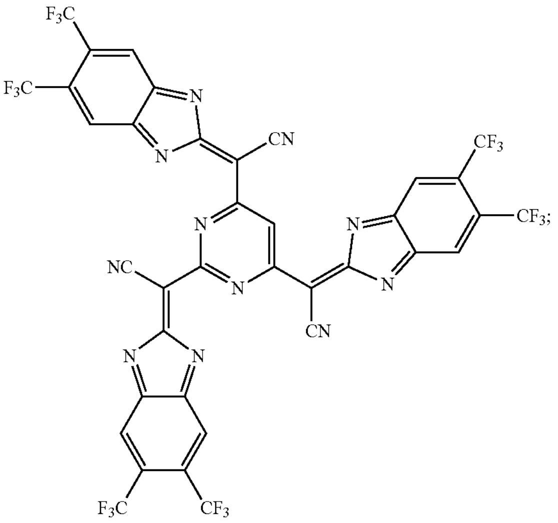
165
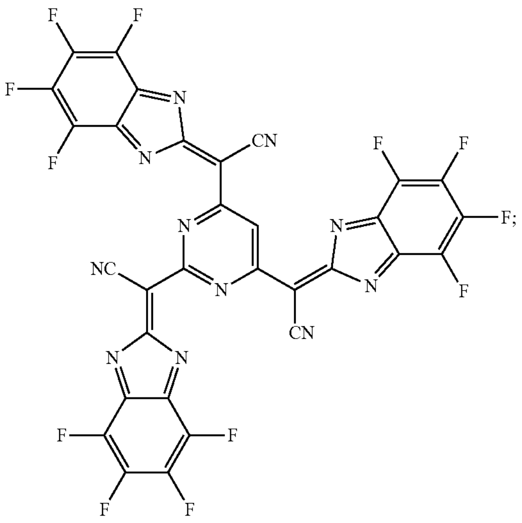
-continued
166
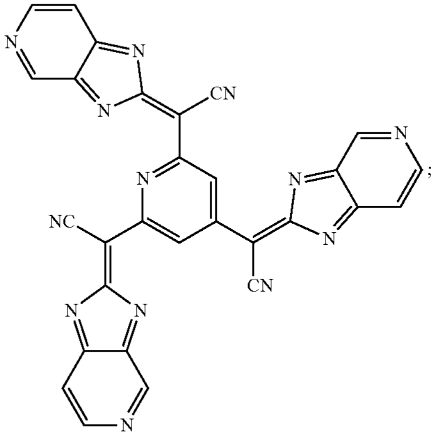
167
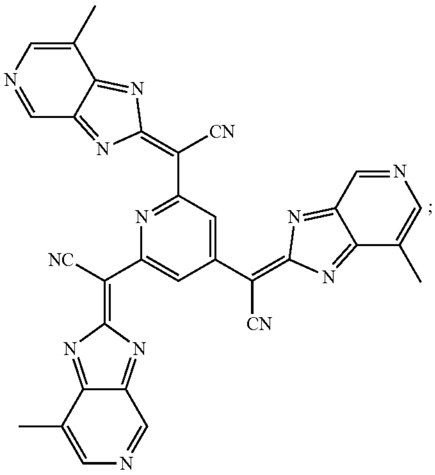
168
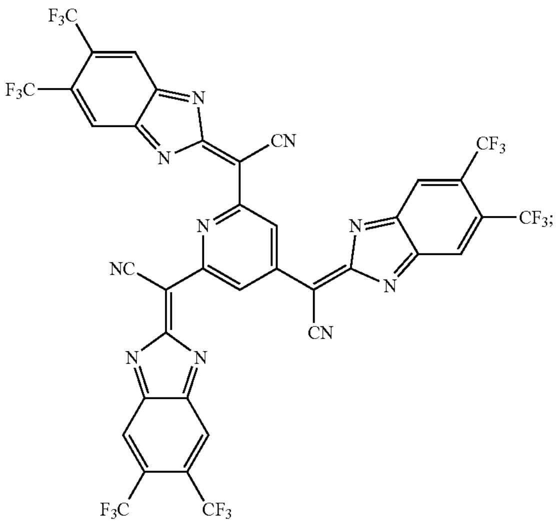

-continued
169
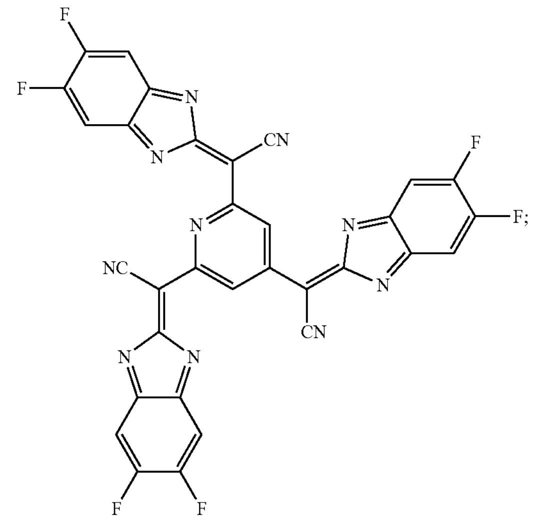
170
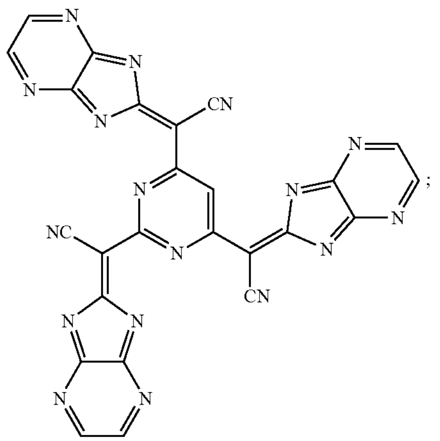
171
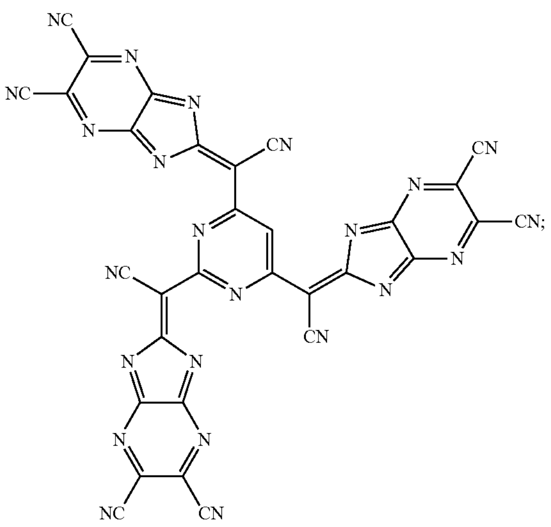
-continued
172
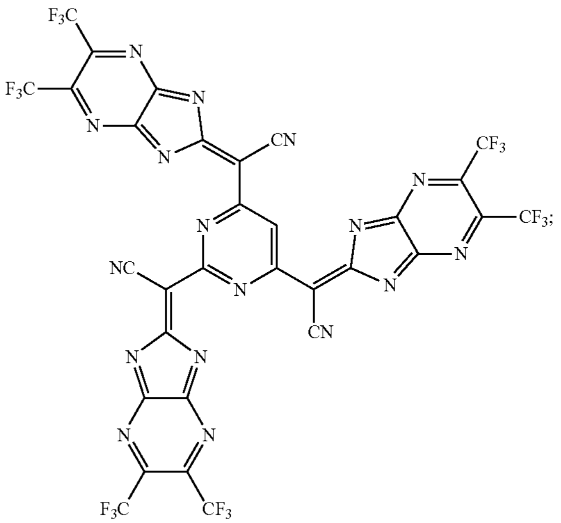
173
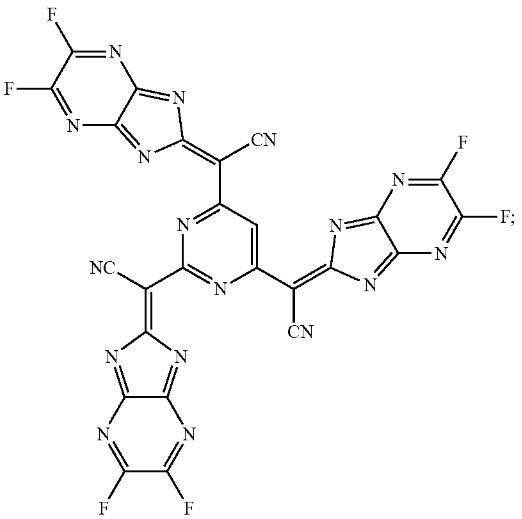
174
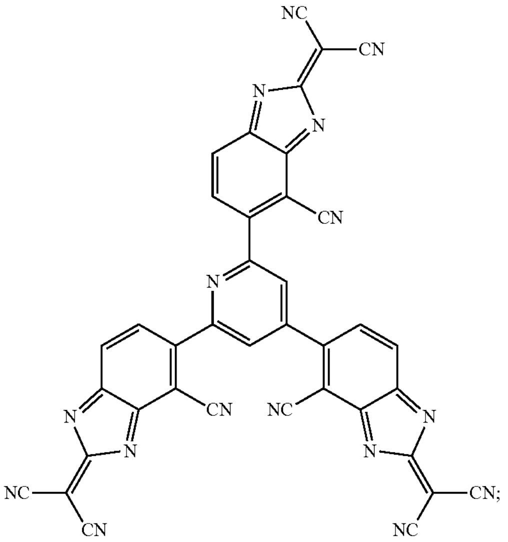

-continued

175

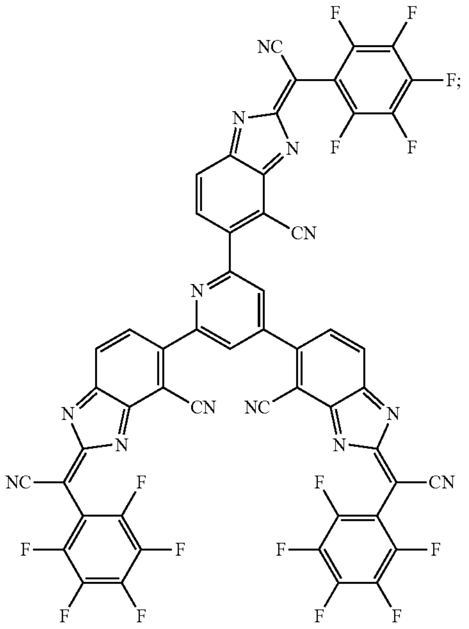

176

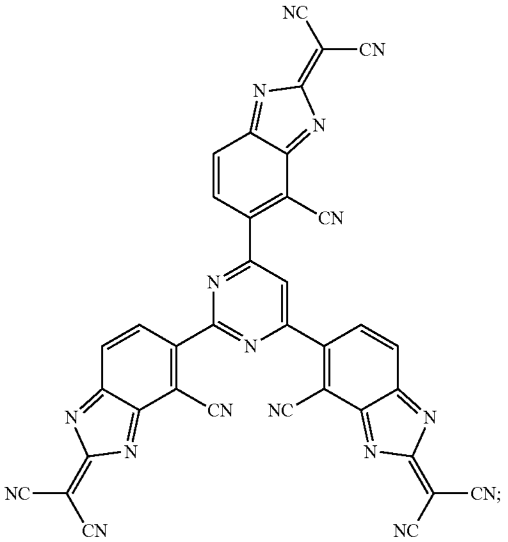

177

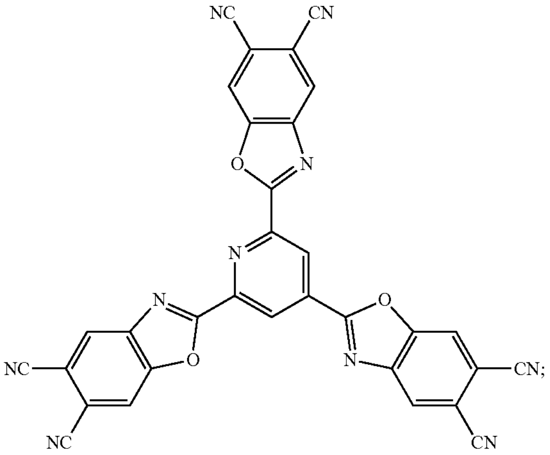

or

-continued

178

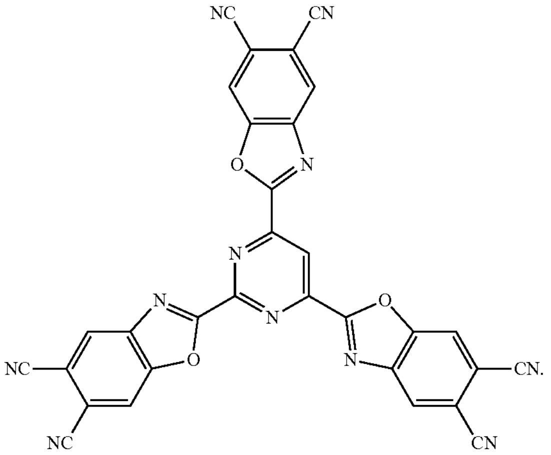

6. An organic light emitting diode, comprising:

first and second electrodes facing each other;

a first emitting material layer between the first and second electrodes;

a first hole auxiliary layer between the first electrode and the first emitting material layer; and a first electron auxiliary layer between the first emitting material layer and the second electrode, wherein the first hole auxiliary layer comprises a first host and a first dopant including an organic compound represented by the following Formula 1:

[Formula 1]

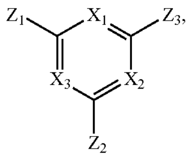

wherein:

each of $X_1$, $X_2$ and $X_3$ is independently selected from carbon (C) and nitrogen (N), provided that at least one of $X_1$ to $X_3$ is N, and each of $Z_1$, $Z_2$ and $Z_3$ is independently selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, a substituted or unsubstituted C1 to C12 ether group, halogen, cyano (CN), trimethylsilyl, Formula 2, Formula 3 and Formula 4, provided that at least one of $Z_1$ to $Z_3$ is represented by one of the following Formulas 2 to 4,

[Formula 2]

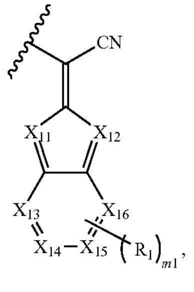

[Formula 3]

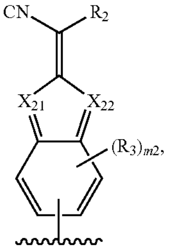

and

[Formula 4]

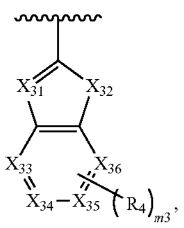

wherein in Formula 2, each of $X_{11}$ and $X_{12}$ is independently selected from C and N, provided that at least one of $X_{11}$ and $X_{12}$ is N, each of $X_{13}$ to $X_{16}$ is independently selected from C and N, $R_1$ is selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, cyano, halogen and trifluoromethyl, and m1 is an integer of 0 to 4, wherein in Formula 3, each of $X_{21}$ and $X_{22}$ is independently selected from C and N, provided that at least one of $X_{21}$ and $X_{22}$ is N, $R_2$ is selected from cyano and phenyl, $R_3$ is selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, cyano, halogen and trifluoromethyl, and m2 is an integer of 0 to 3, wherein in Formula 4, each of $X_{31}$ and $X_{32}$ is independently selected from N and oxygen (O), provided that when one of $X_{31}$ and $X_{32}$ is N, then the other one of $X_{31}$ and $X_{32}$ is O, each of $X_{33}$ to $X_{36}$ is independently selected from C and N, $R_4$ is selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, cyano, halogen and trifluoromethyl, and m3 is an integer of 0 to 4.

7. The organic light emitting diode of claim 6, wherein the first hole auxiliary layer comprises:

a hole injection layer between the first electrode and the first emitting material layer; and a first hole transporting layer between the hole injection layer and the first emitting material layer, wherein the hole injection layer includes the first host and the first dopant, and the first hole transporting layer includes the first host.

8. The organic light emitting diode of claim 6, further comprising:

a second emitting material layer between the first emitting material layer and the first electron auxiliary layer;

a first charge generation layer between the first emitting material layer and the second emitting material layer and including a first N-type charge generation layer and a first P-type charge generation layer;

a second electron auxiliary layer between the first charge generation layer and the first emitting material layer; and a second hole auxiliary layer between the first charge generation layer and the second emitting material layer.

9. The organic light emitting diode of claim 8, wherein the first P-type charge generation layer comprises a second host and a second dopant including the organic compound.

10. The organic light emitting diode of claim 9, wherein the second hole auxiliary layer comprises the second host.

11. The organic light emitting diode of claim 8, further comprising:

a third emitting material layer between the second emitting material layer and the first electron auxiliary layer;

a second charge generation layer between the second emitting material layer and the third emitting material layer and including a second N-type charge generation layer and a second P-type charge generation layer;

a third electron auxiliary layer between the second charge generation layer and the second emitting material layer; and a third hole auxiliary layer between the second charge generation layer and the third emitting material layer.

12. The organic light emitting diode of claim 11, wherein the second P-type charge generation layer includes a third host and a third dopant including the organic compound.

13. The organic light emitting diode of claim 12, wherein the third hole auxiliary layer comprises the third host.

14. An organic light emitting diode, comprising:

first and second electrodes facing each other;

a first charge generation layer between the first and second electrodes and including a first N-type charge generation layer and a first P-type charge generation layer;

a first emitting stack including a first emitting material layer between the first electrode and the first N-type charge generation layer, a first hole auxiliary layer between the first electrode and the first emitting material layer, and a first electron auxiliary layer between the first emitting material layer and the first N-type charge generation layer; and a second emitting stack including a second emitting material layer between the first P-type charge generation layer and the second electrode, a second hole auxiliary layer between the first P-type charge generation layer and the second emitting material layer, and a second electron auxiliary layer between the second emitting material layer and the second electrode, wherein the first P-type charge generation layer comprises a first host and a first dopant including an organic compound represented by the following Formula 1:

[Formula 1]

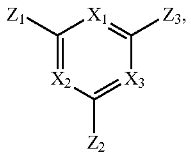

wherein:

each of $X_1$, $X_2$ and $X_3$ is independently selected from carbon (C) and nitrogen (N), provided that at least one of $X_1$ to $X_3$ is N, and each of $Z_1$, $Z_2$ and $Z_3$ is independently selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, a substituted or unsubstituted C1 to C12 ether group, halogen, cyano (CN), trimethylsilyl, Formula 2, Formula 3 and Formula 4, provided that at least one of $Z_1$ to $Z_3$ is represented by one of the following Formulas 2 to 4,

[Formula 2]

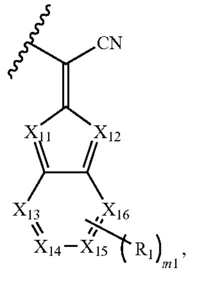

[Formula 3]

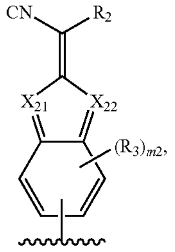

and

[Formula 4]

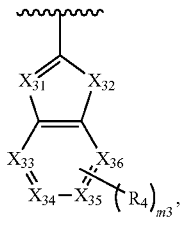

wherein in Formula 2, each of $X_{11}$ and $X_{12}$ is independently selected from C and N, provided that at least one of $X_{11}$ and $X_{12}$ is N, each of $X_{13}$ to $X_{16}$ is independently selected from C and N, $R_1$ is selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, cyano, halogen and trifluoromethyl, and m1 is an integer of 0 to 4, wherein in Formula 3, each of $X_{21}$ and $X_{22}$ is independently selected from C and N, provided that at least one of $X_{21}$ and $X_{22}$ is N, $R_2$ is selected from cyano and phenyl, $R_3$ is selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, cyano, halogen and trifluoromethyl, and m2 is an integer of 0 to 3, wherein in Formula 4, each of $X_{31}$ and $X_{32}$ is independently selected from N and oxygen (O), provided that when one of $X_{31}$ and $X_{32}$ is N, then the other one of $X_{31}$ and $X_{32}$ is O, each of $X_{33}$ to $X_{36}$ is independently selected from C and N, $R_4$ is selected from a substituted or unsubstituted C6 to C30 aryl group, a substituted or unsubstituted C5 to C30 heteroaryl group, a substituted or unsubstituted C1 to C12 alkyl group, a substituted or unsubstituted C1 to C12 alkoxy group, cyano, halogen and trifluoromethyl, and m3 is an integer of 0 to 4.

15. The organic light emitting diode of claim 14, wherein the second hole auxiliary layer comprises the first host.

16. The organic light emitting diode of claim 14, further comprising:

a second charge generation layer between the second emitting stack and the second electrode and including a second N-type charge generation layer and a second P-type charge generation layer; and a third emitting stack including a third emitting material layer between the second P-type charge generation layer and the second electrode, a third hole auxiliary layer between the second P-type charge generation layer and the third emitting material layer, and a third electron auxiliary layer between the third emitting material layer and the second electrode, wherein the second P-type charge generation layer includes a second host and a second dopant including the organic compound.

17. The organic light emitting diode of claim 16, wherein the third hole auxiliary layer comprises the second host.

18. An organic light emitting display device, comprising:

a substrate;

an organic light emitting diode of claim 6 over the substrate; and a thin film transistor positioned between the substrate and the organic light emitting diode and connected to the organic light emitting diode.

19. The organic light emitting display device of claim 18, further comprising:

red, green and blue color filter patterns respectively corresponding to red, green and blue pixel regions, wherein the organic light emitting diode corresponds to the red, green and blue pixel regions, and wherein the red, green and blue color filter patterns are positioned between the substrate and the organic light emitting diode or over the organic light emitting diode.

20. An organic light emitting display device, comprising:

a substrate;

an organic light emitting diode of claim 14 over the substrate; and a thin film transistor positioned between the substrate and the organic light emitting diode and connected to the organic light emitting diode.

21. The organic light emitting display device of claim 20, further comprising:

red, green and blue color filter patterns respectively corresponding to red, green and blue pixel regions, wherein the organic light emitting diode corresponds to the red, green and blue pixel regions, and wherein the red, green and blue color filter patterns are positioned between the substrate and the organic light emitting diode or over the organic light emitting diode.

22. The organic light emitting diode of claim 6, wherein the organic compound has one of the following structures:

1

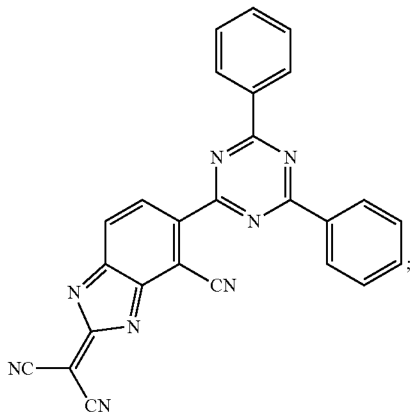

2

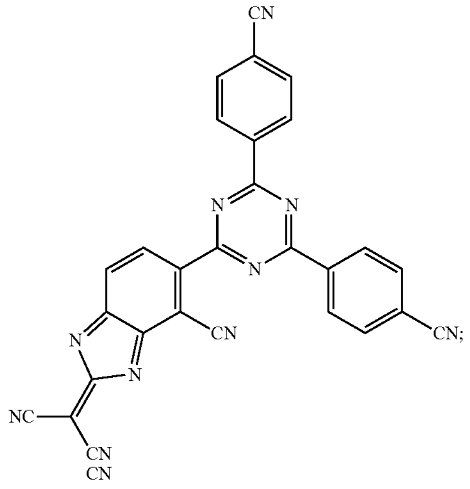

-continued

3

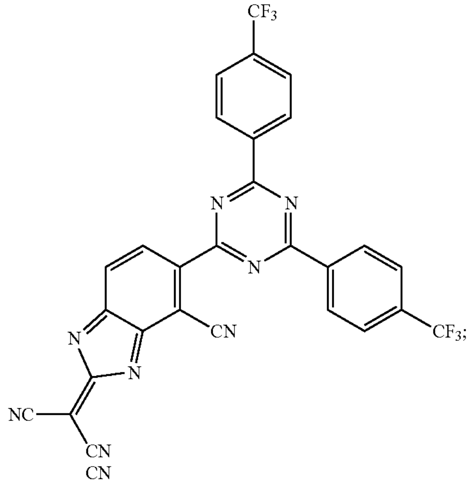

4

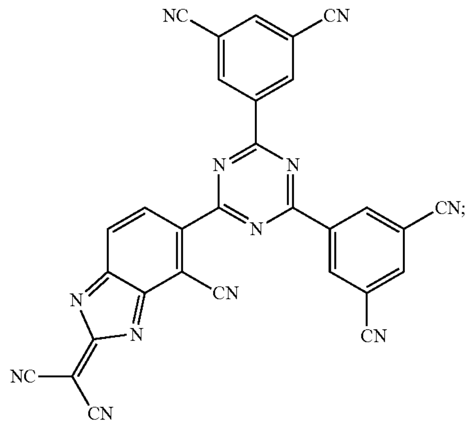

5

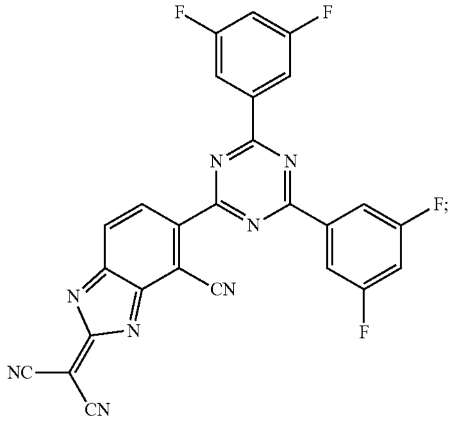

-continued
6
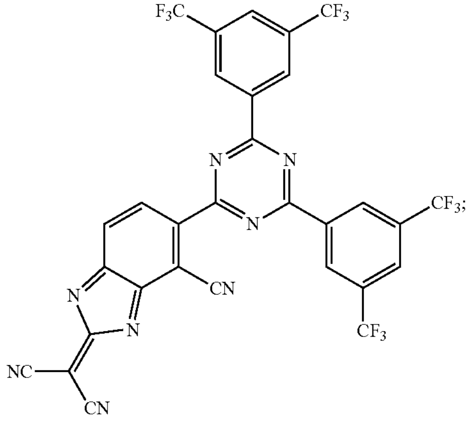
7
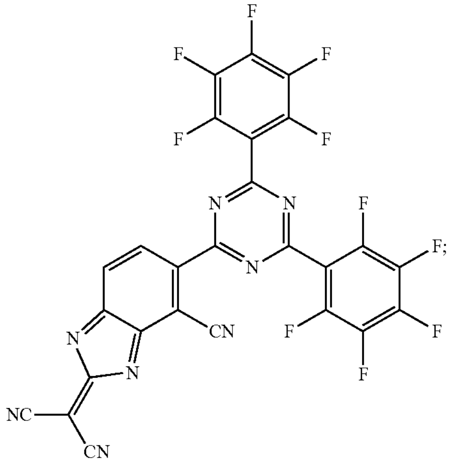
8
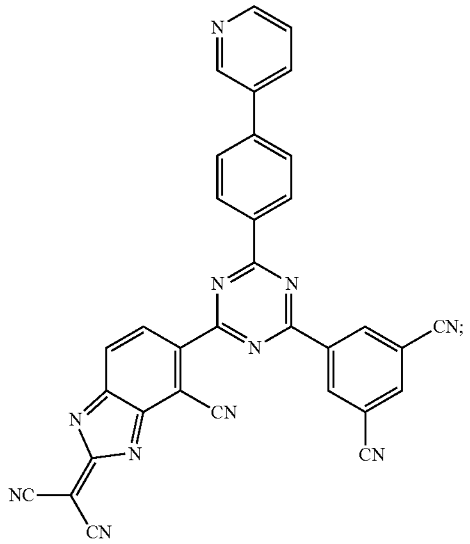
-continued
9
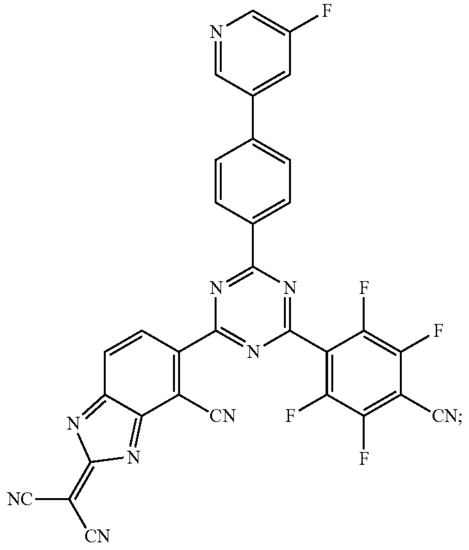
10
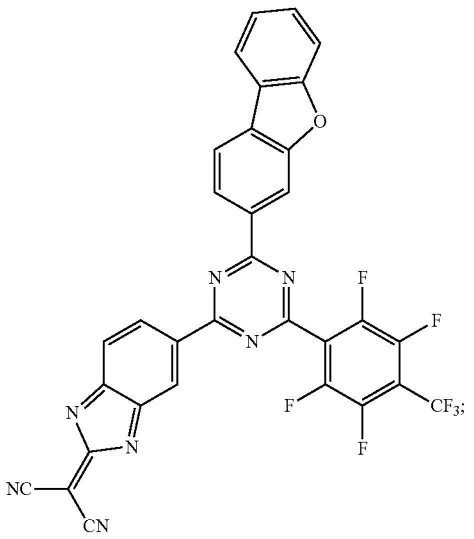
11
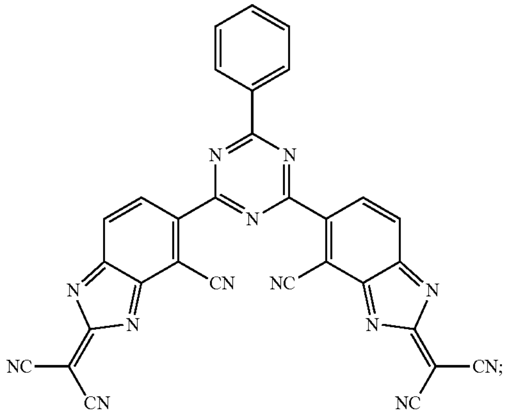

12
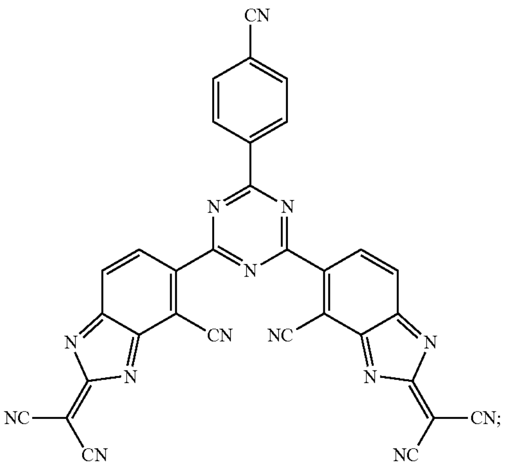
13
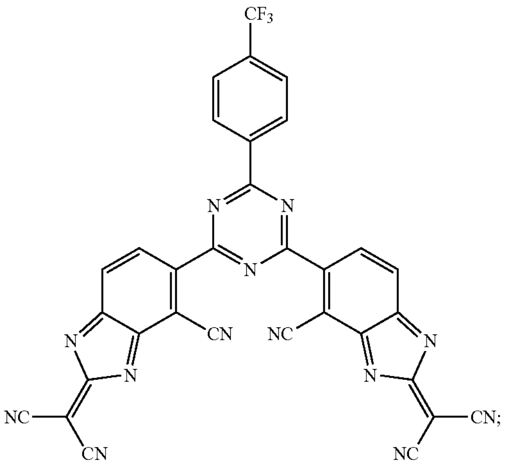
14
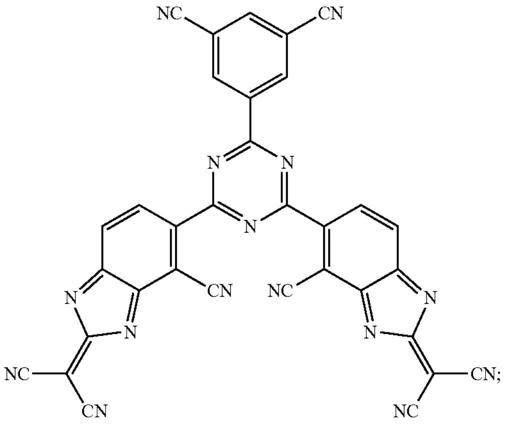
15
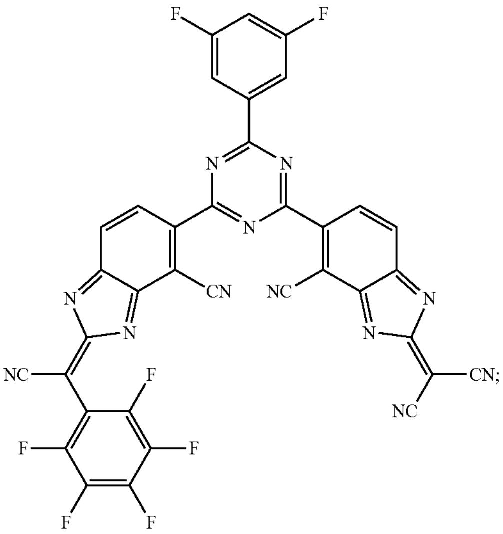
16
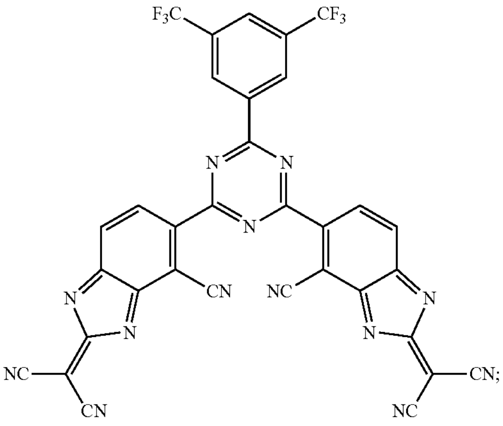
17
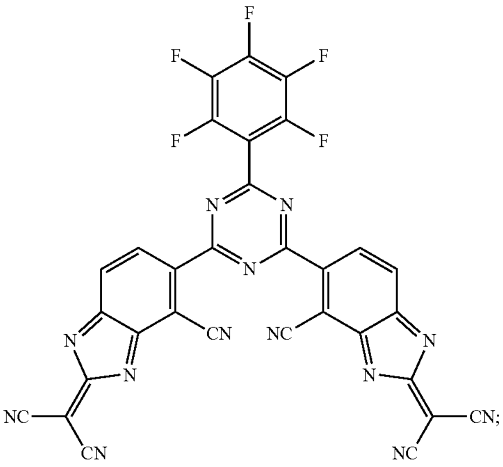

18
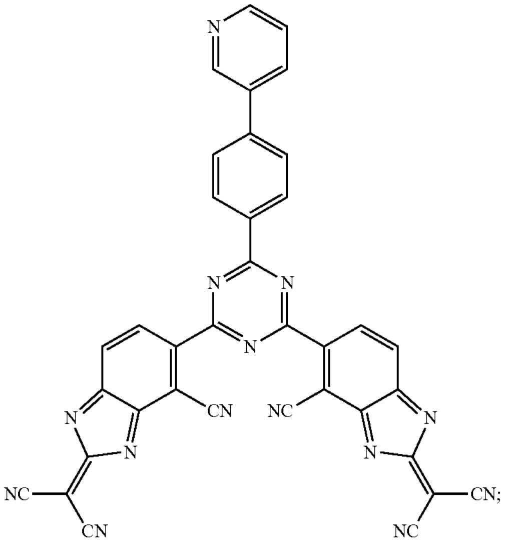
19
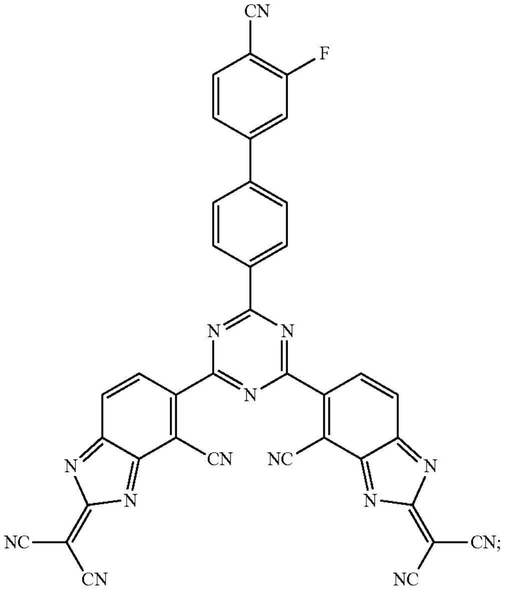
20
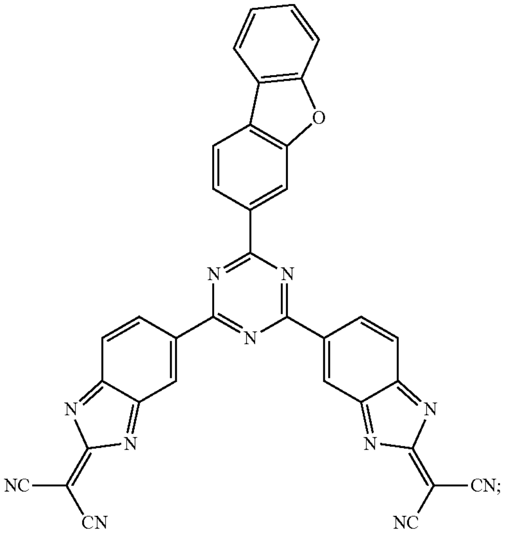
21
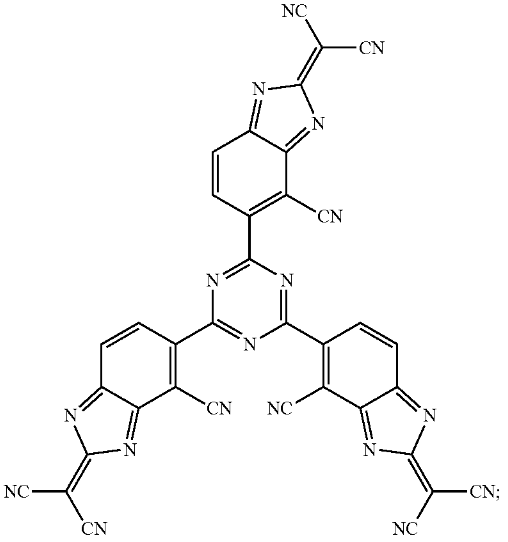
22
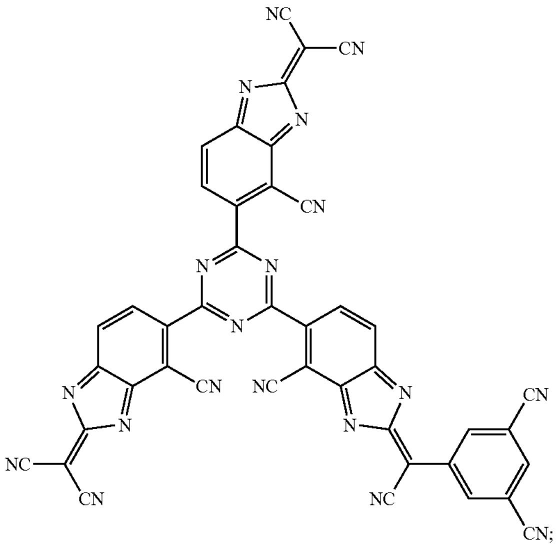
23
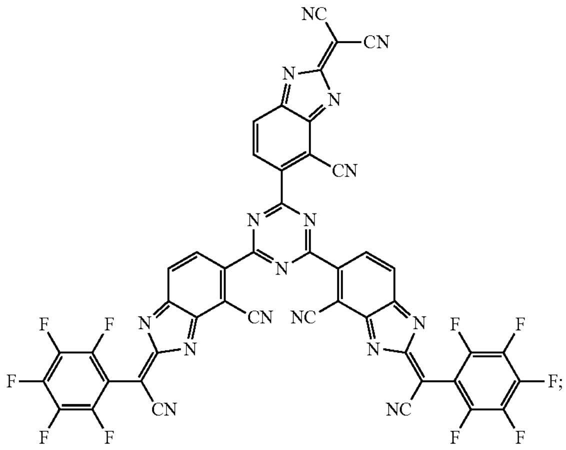

-continued
24
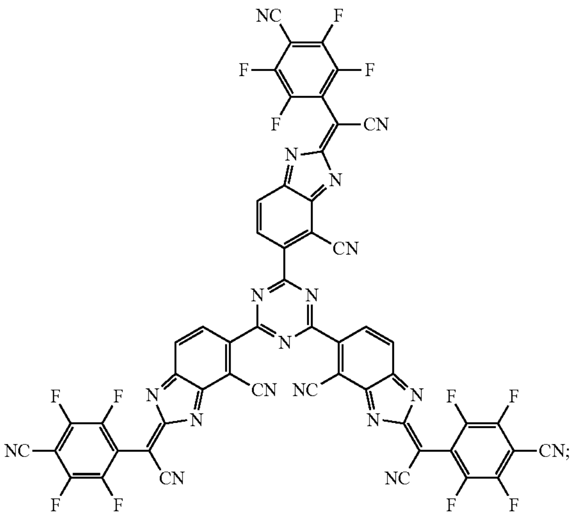
25
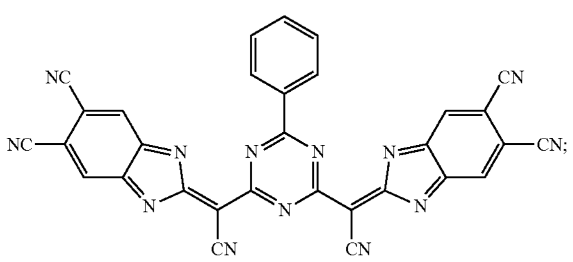
26
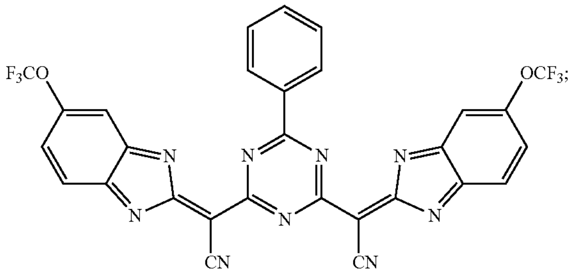
27
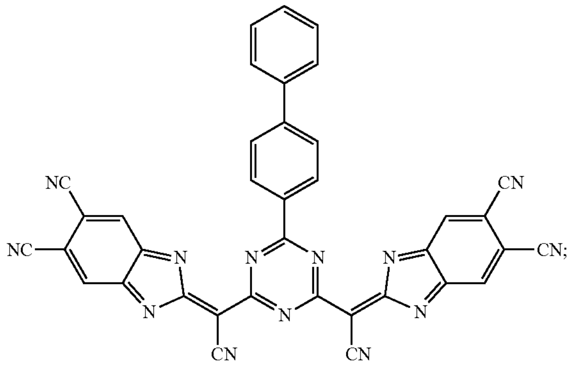
-continued
28
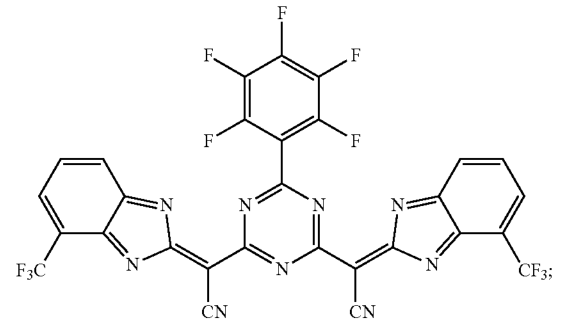
29
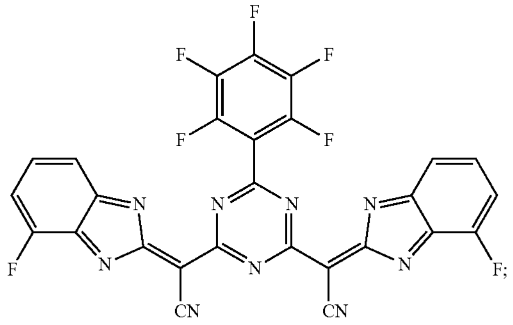
30
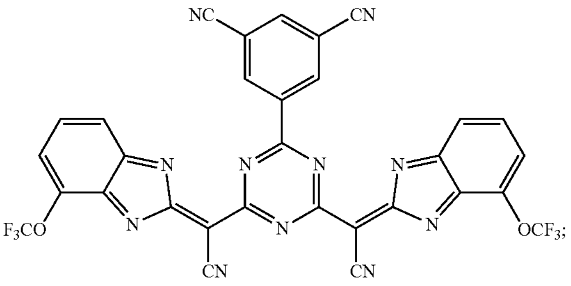
31
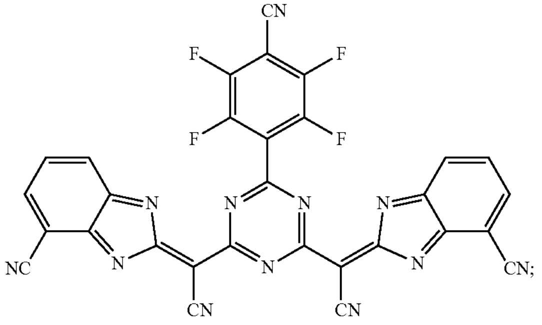
32
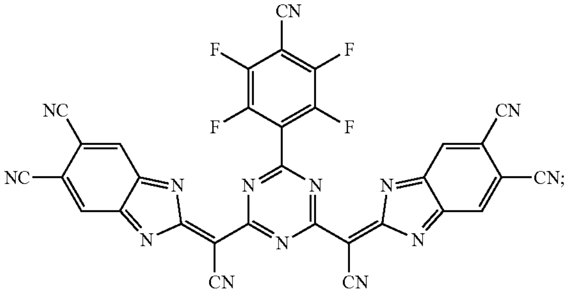

-continued
33
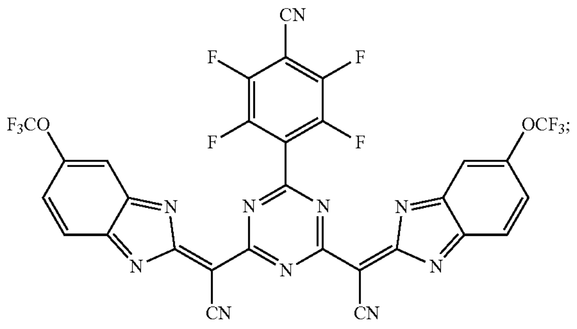
34
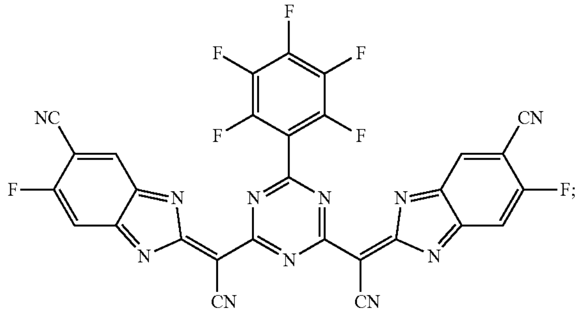
35
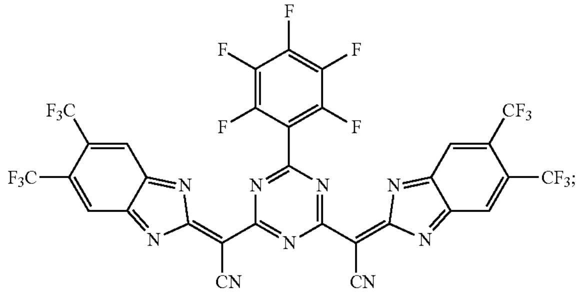
36
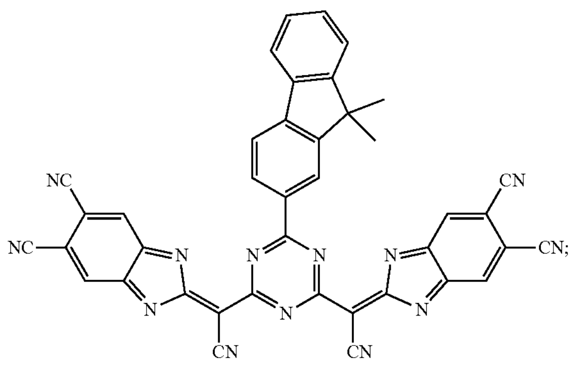
-continued
37
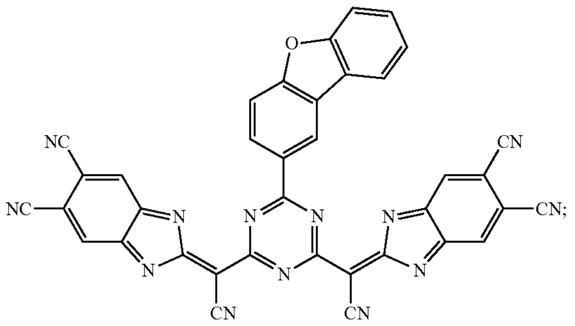
38
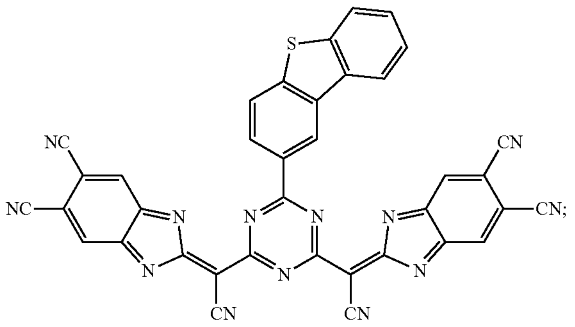
39
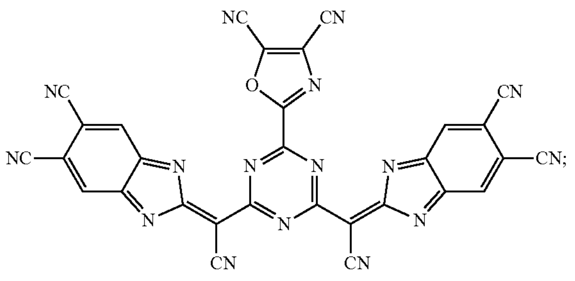
40
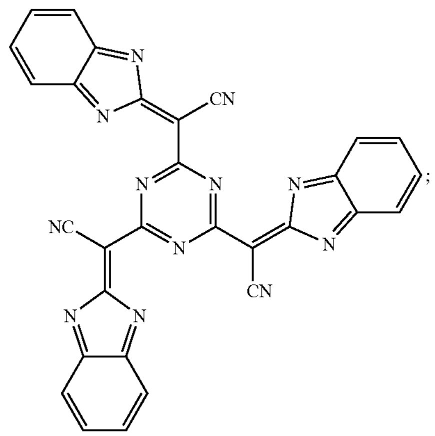

-continued
41
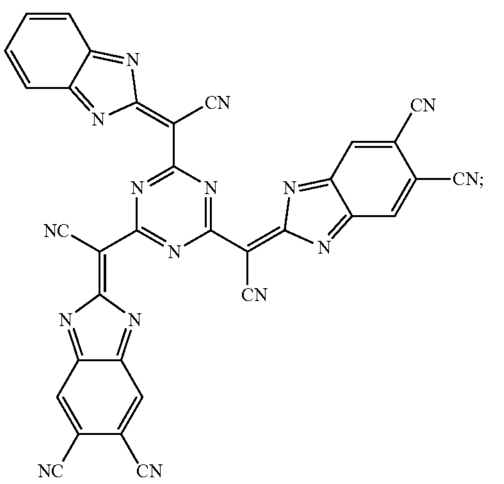
42
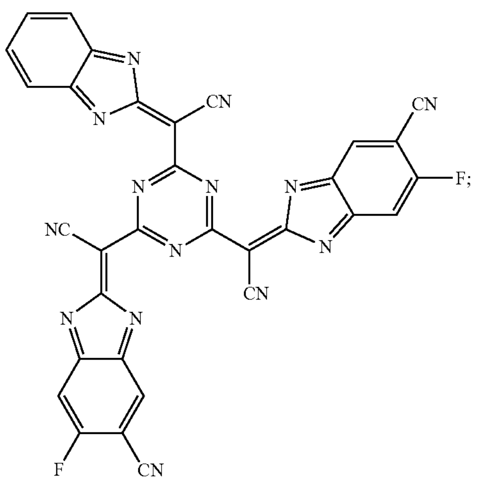
43
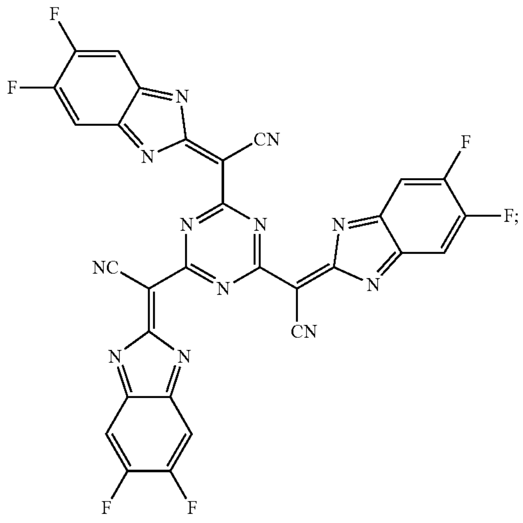
-continued
44
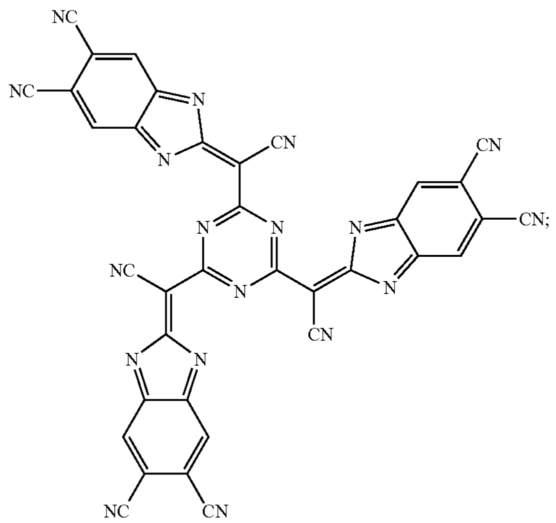
45
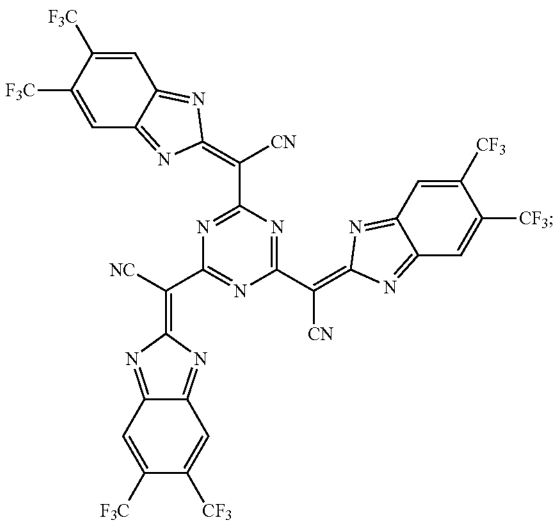
46
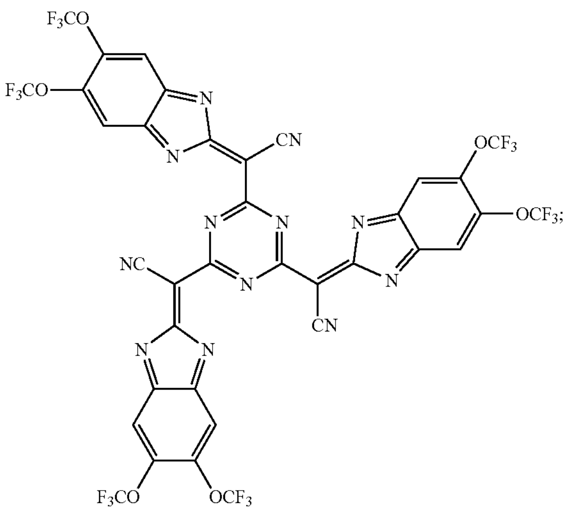

-continued
47
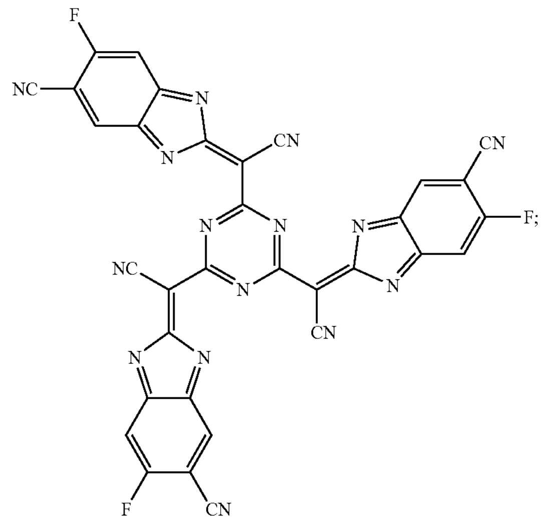
48
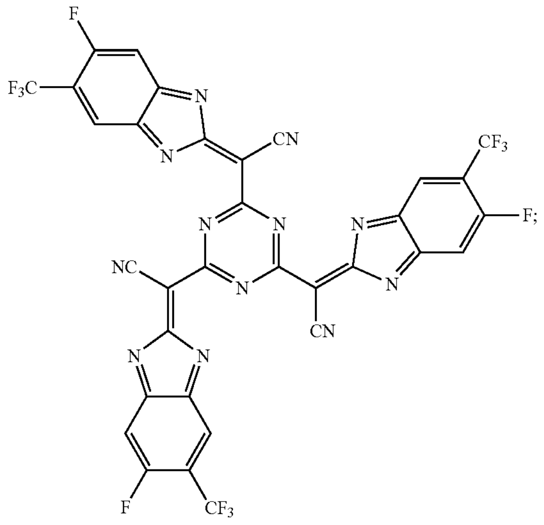
49
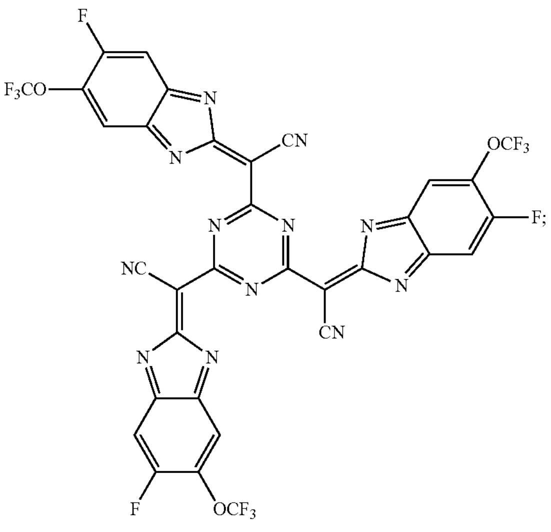
-continued
50
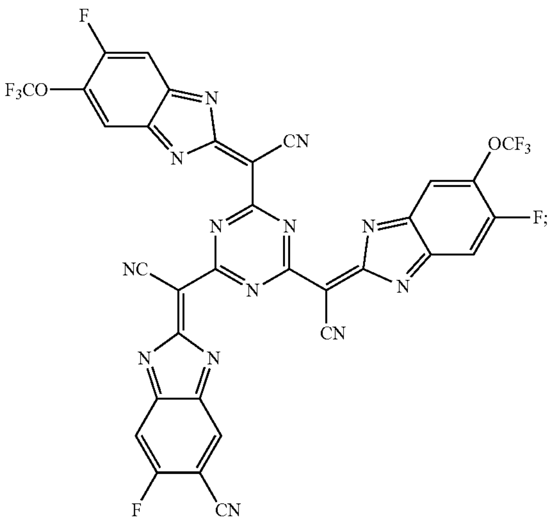
51
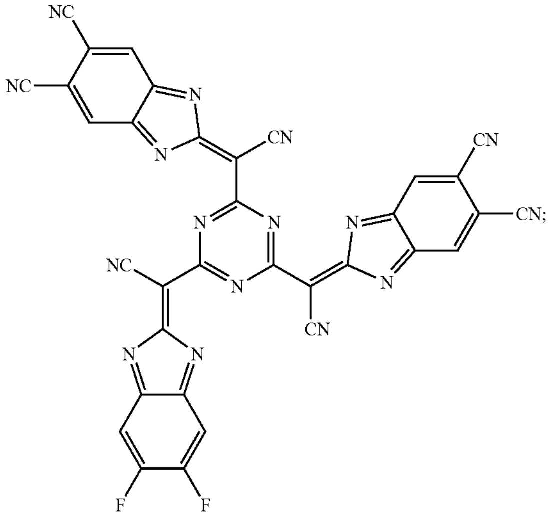
52
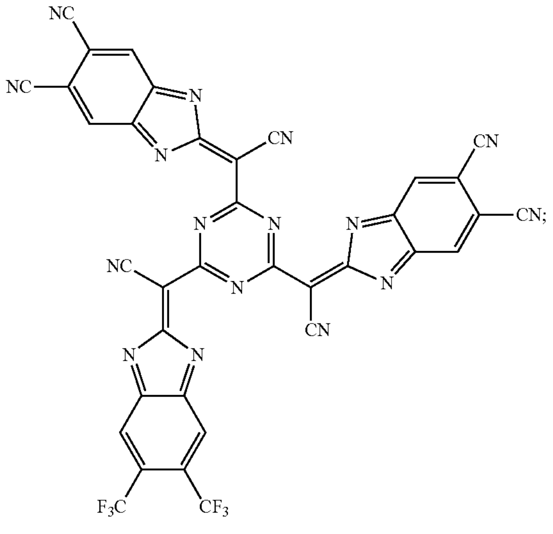

-continued
53
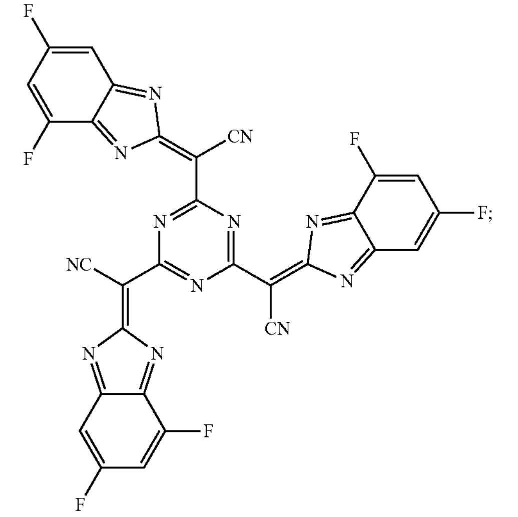
54
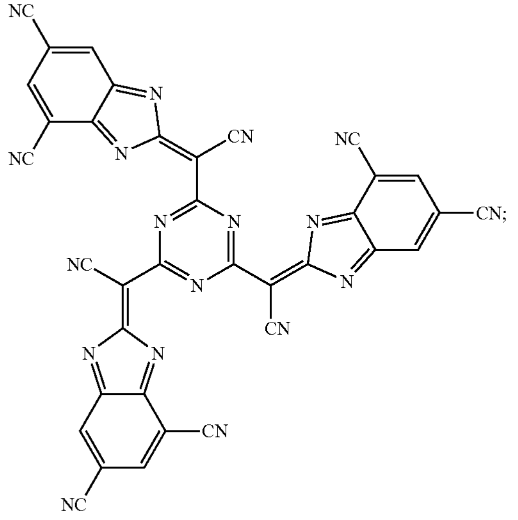
55
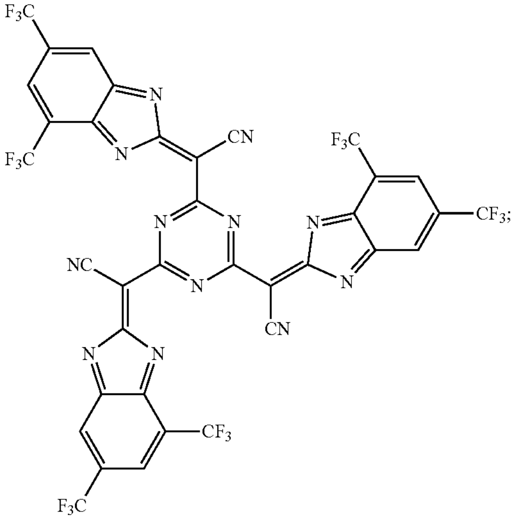
-continued
56
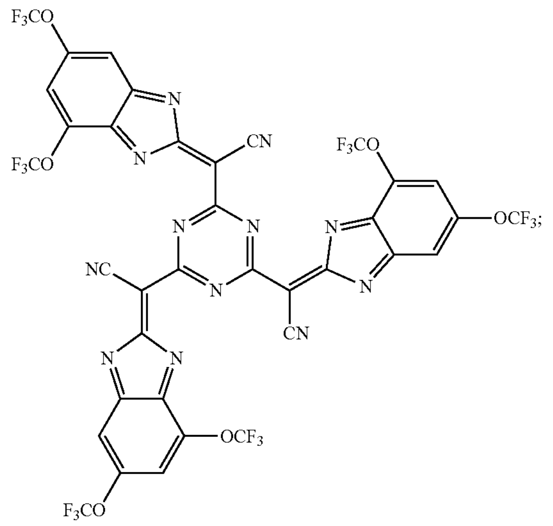
57
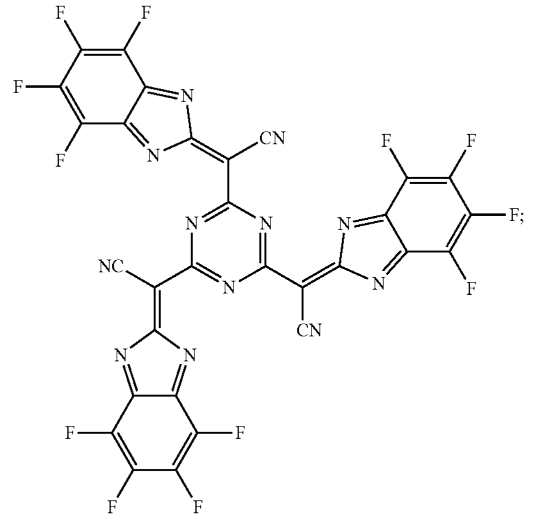
58
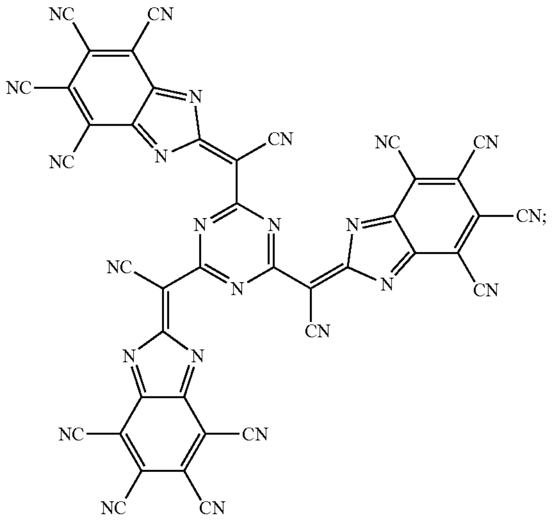

-continued
59
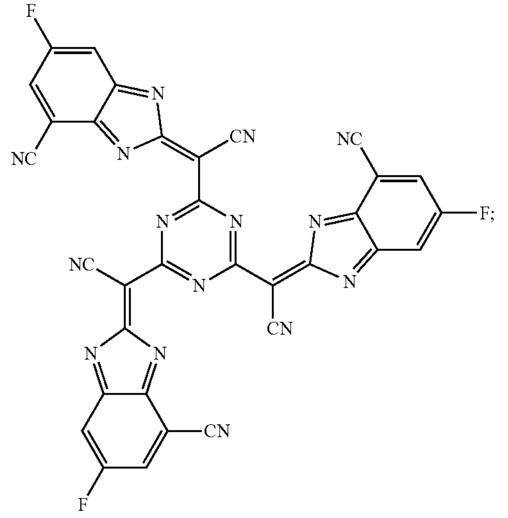
60
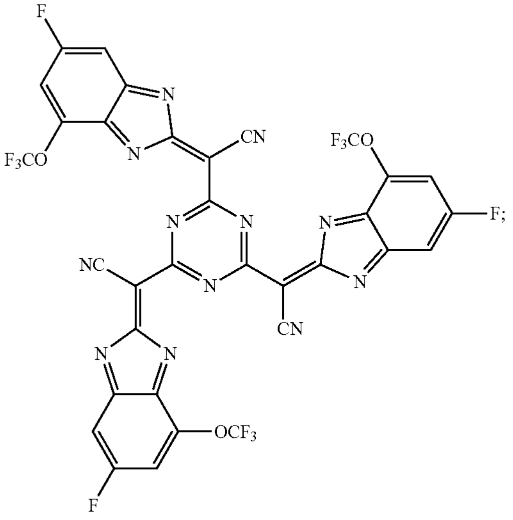
61
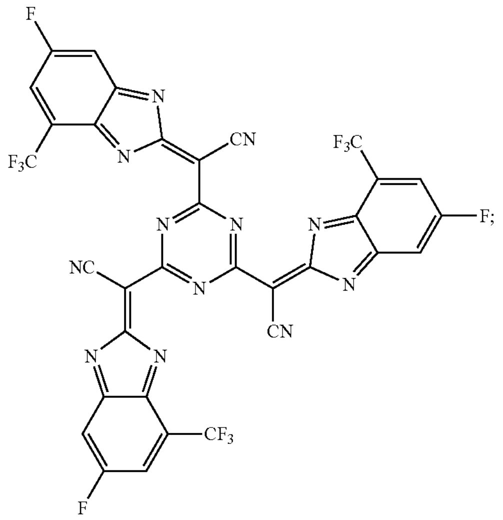
-continued
62
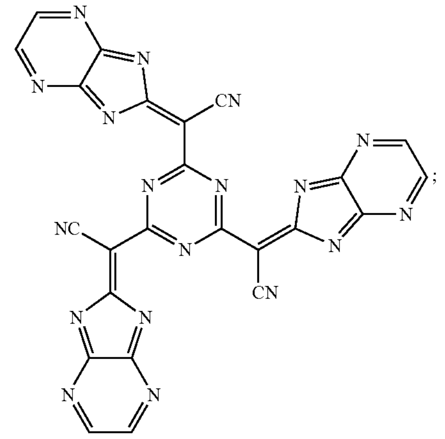
63
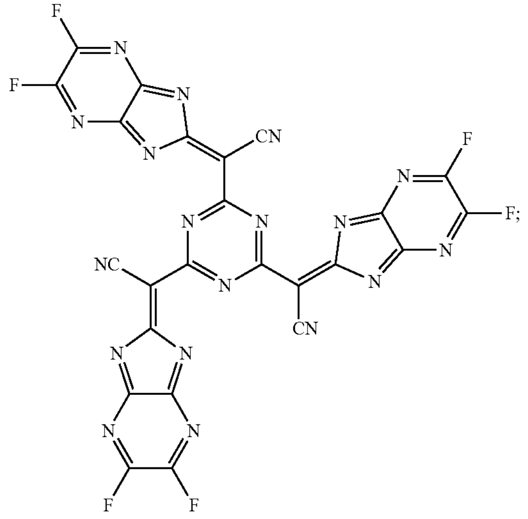
64
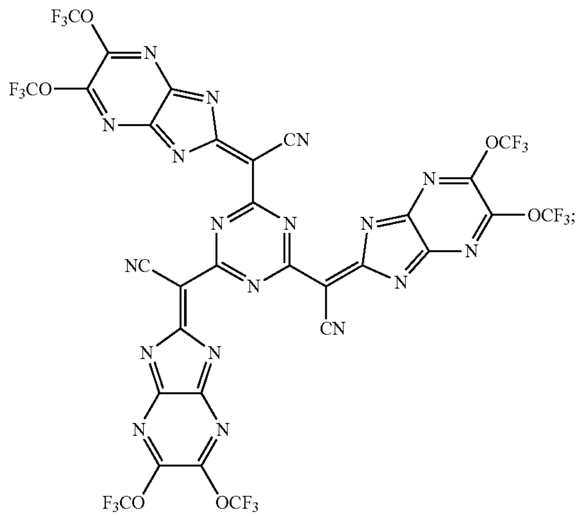

249
-continued
65
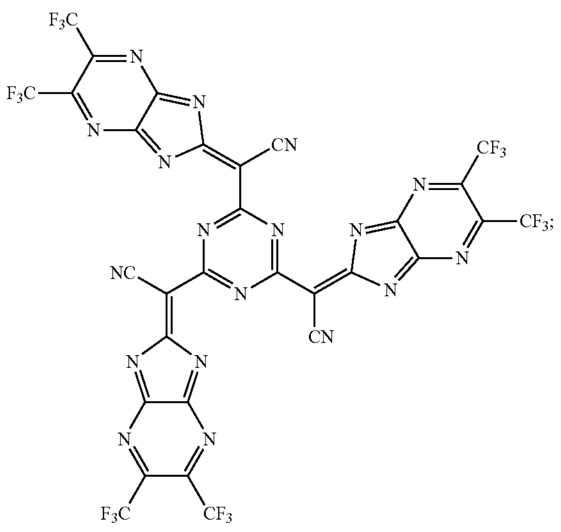
66
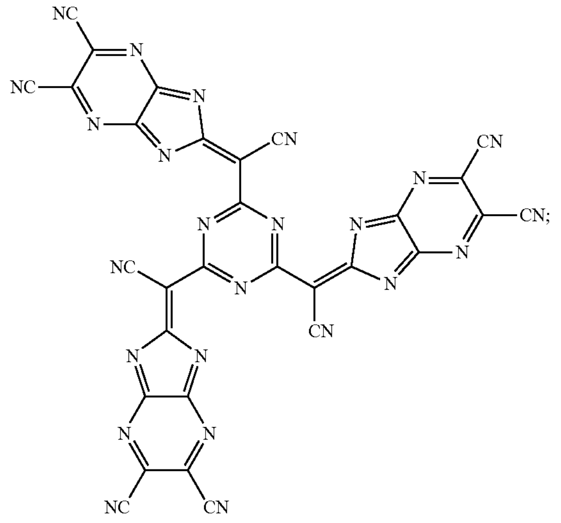
67
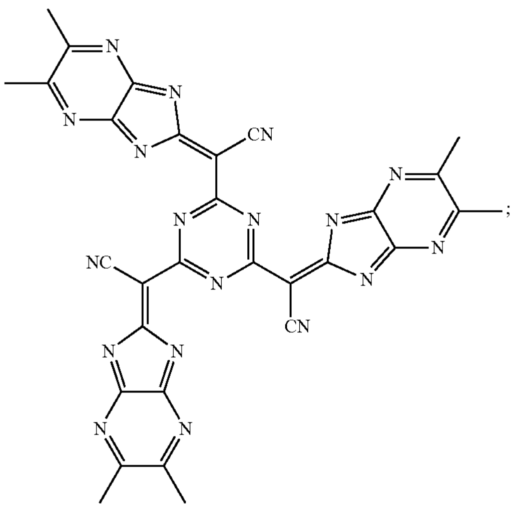
250
-continued
68
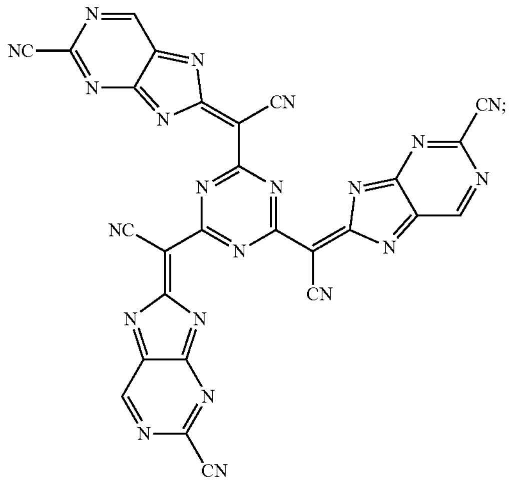
69
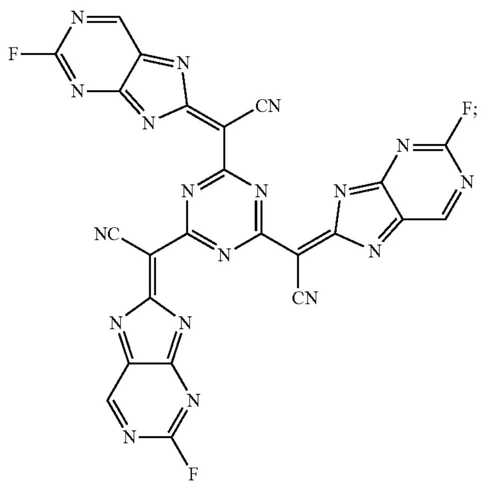
70
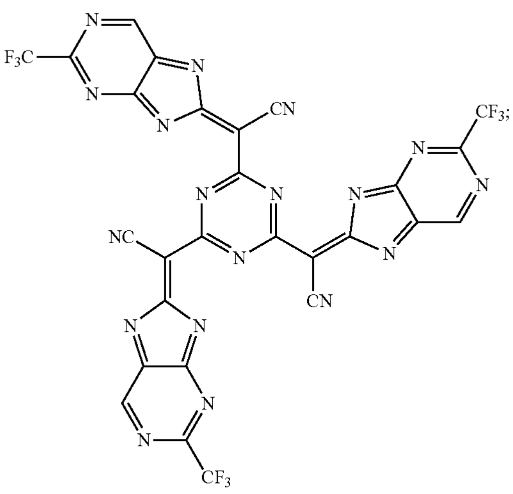

-continued
71
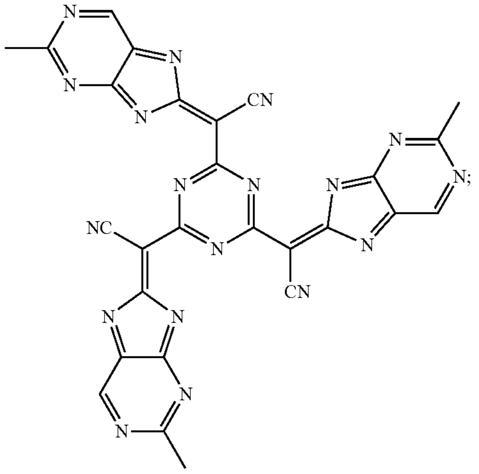
72
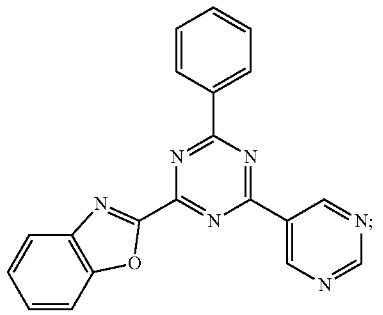
73
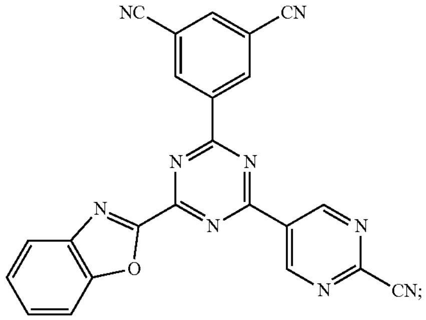
74
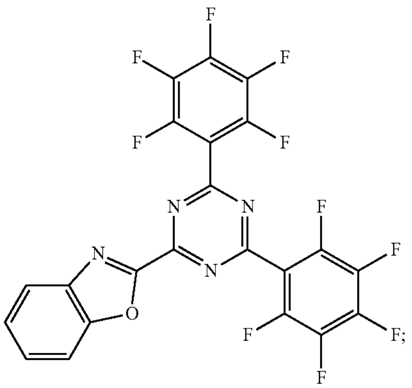
-continued
75
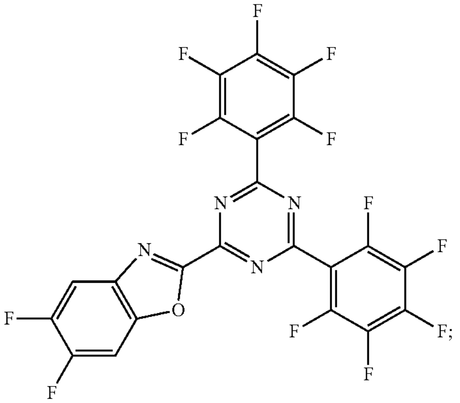
76
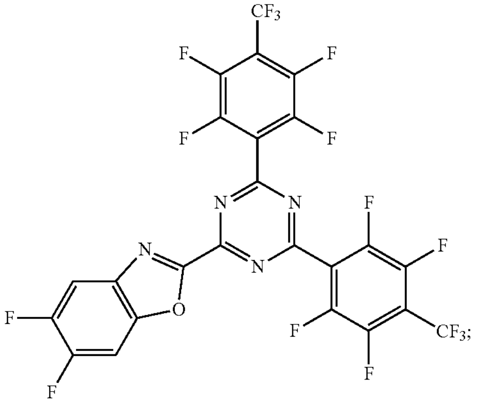
77
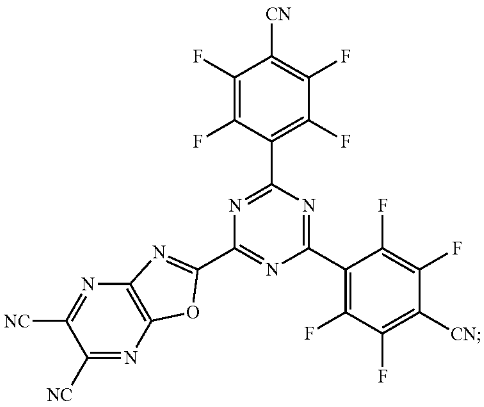
78
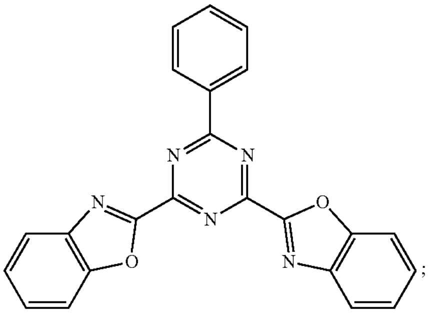

-continued
79
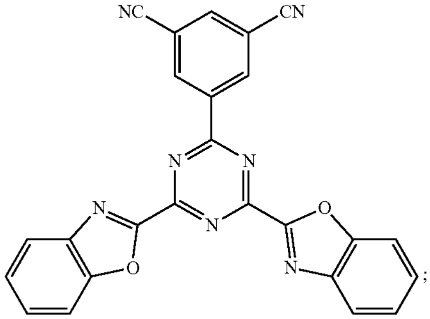
80
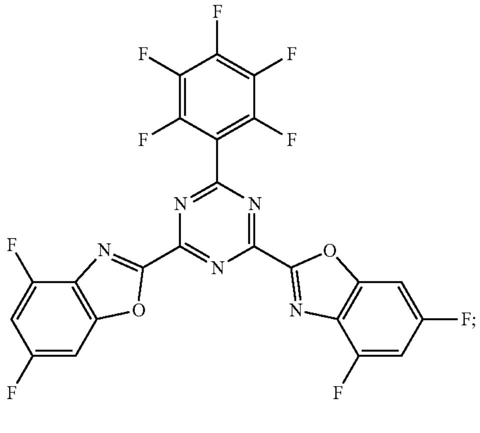
81
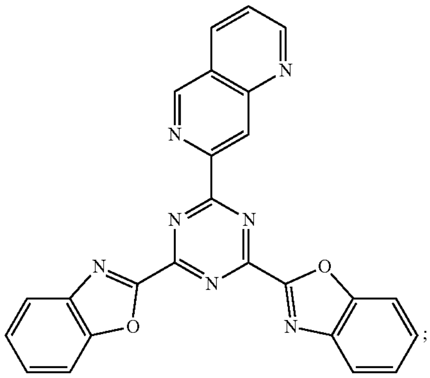
82
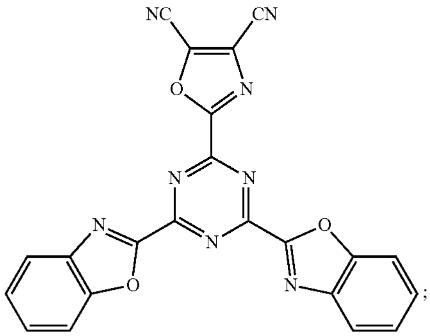
-continued
83
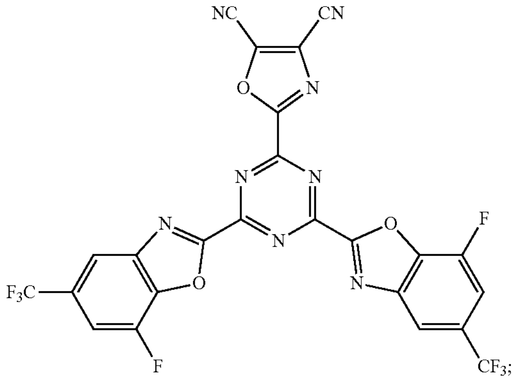
84
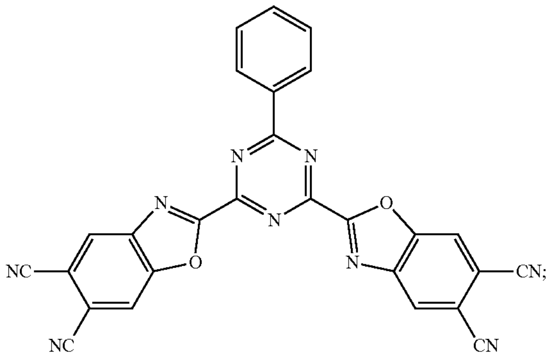
85
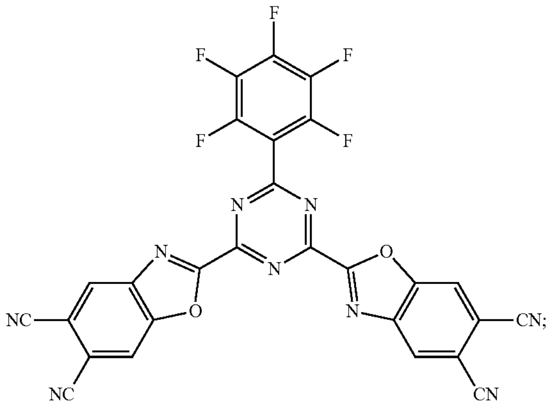
86
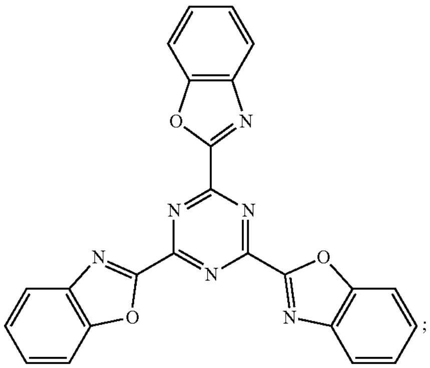

-continued
87
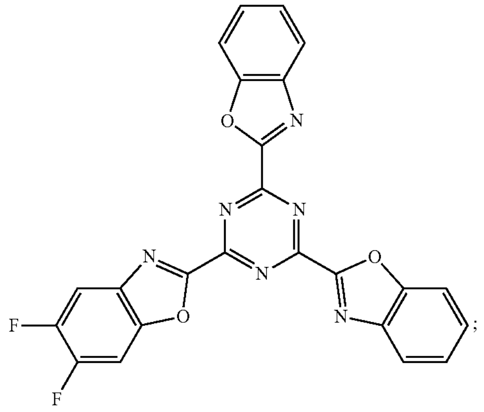
88
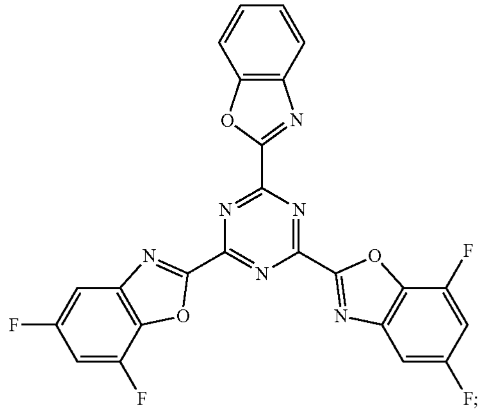
89
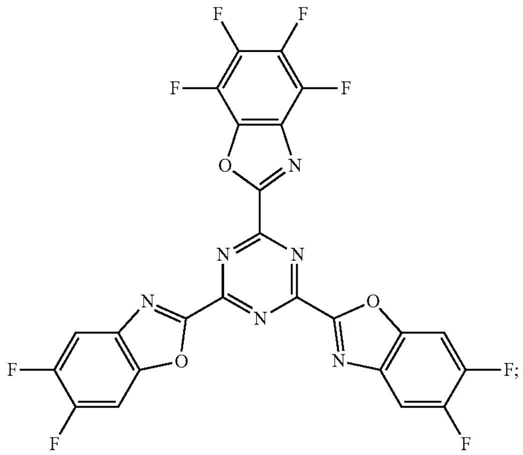
-continued
90
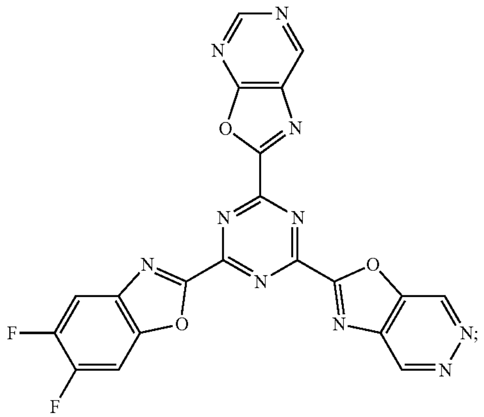
91
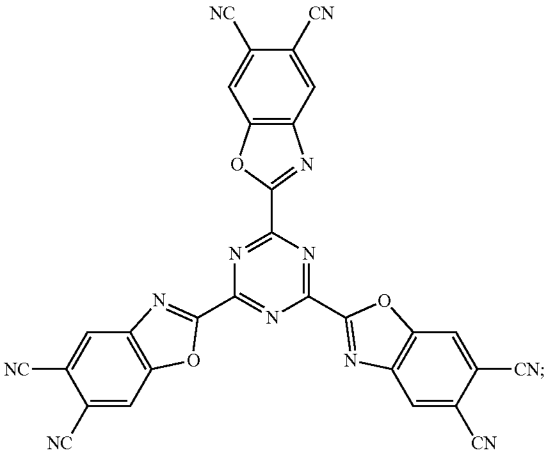
92
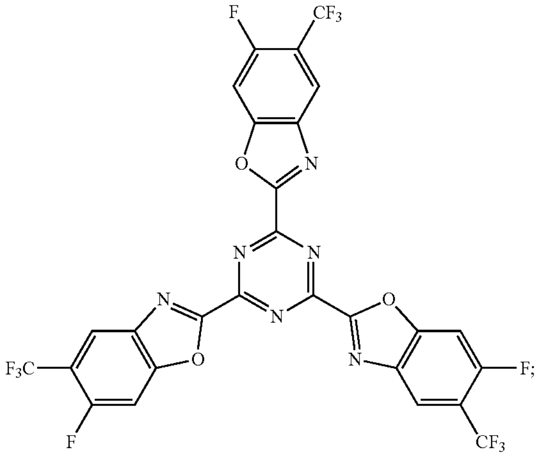

-continued
93
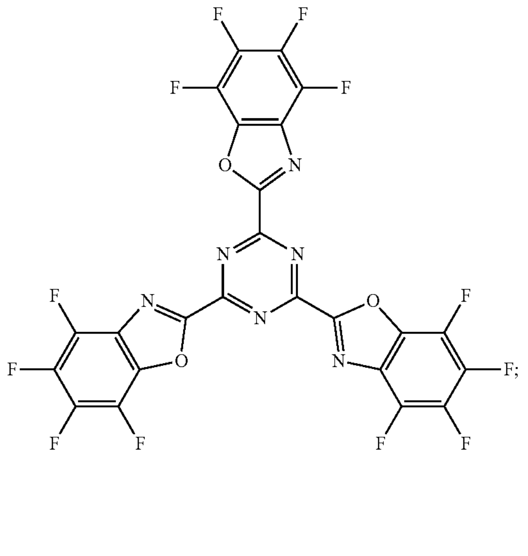
94
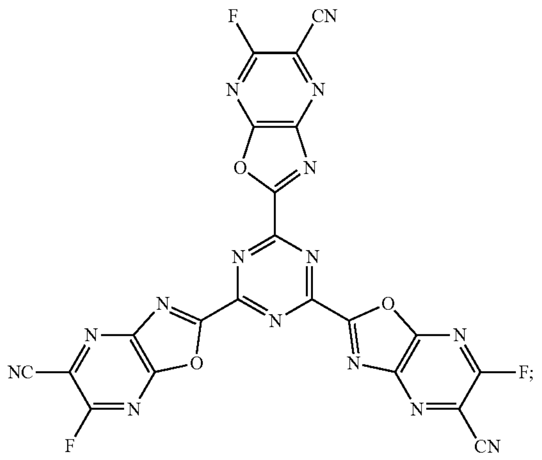
95
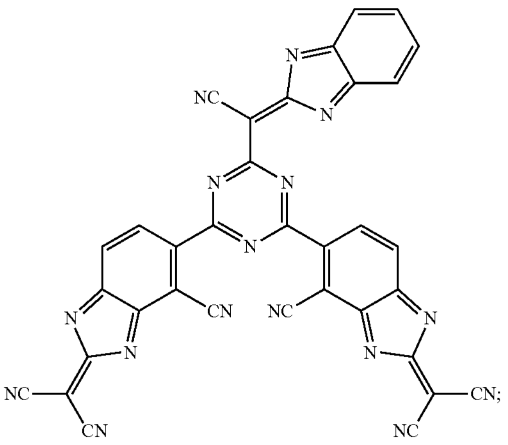
-continued
96
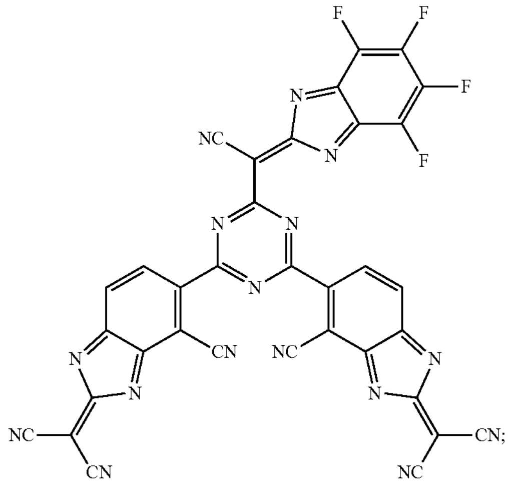
97
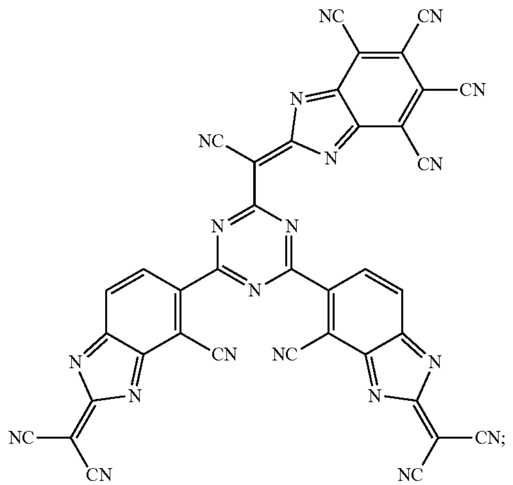
98
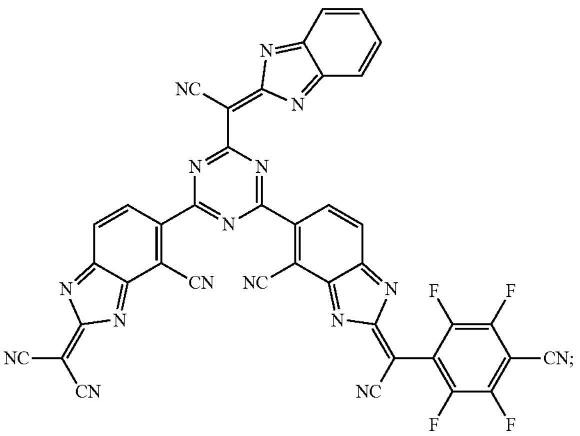

-continued
99
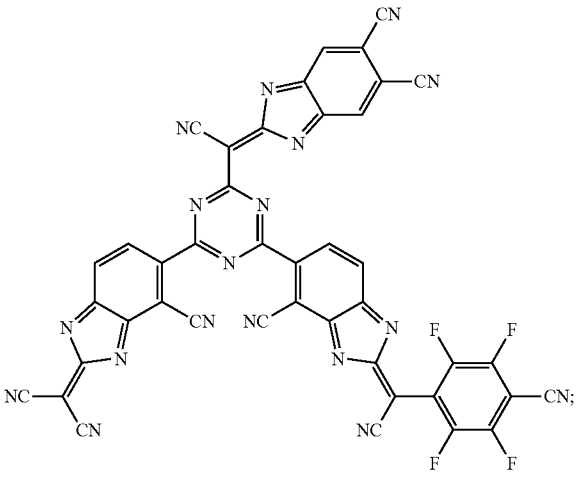
100
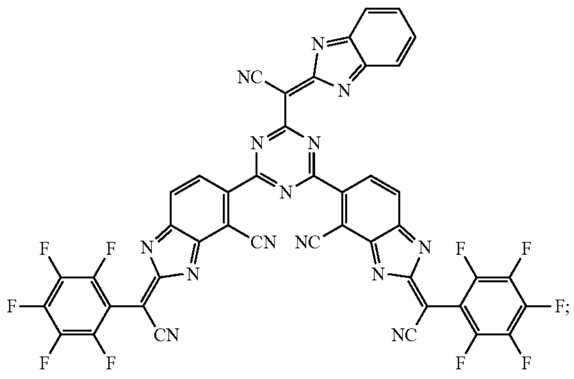
101
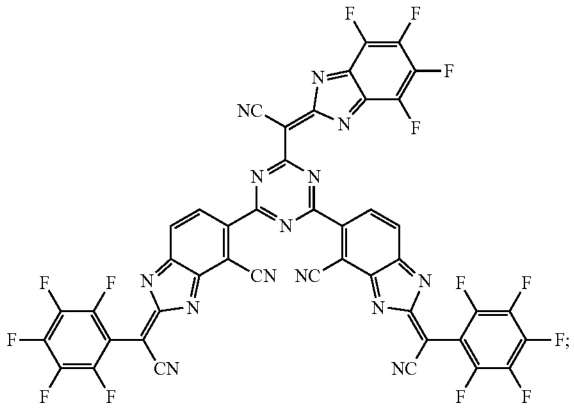
-continued
102
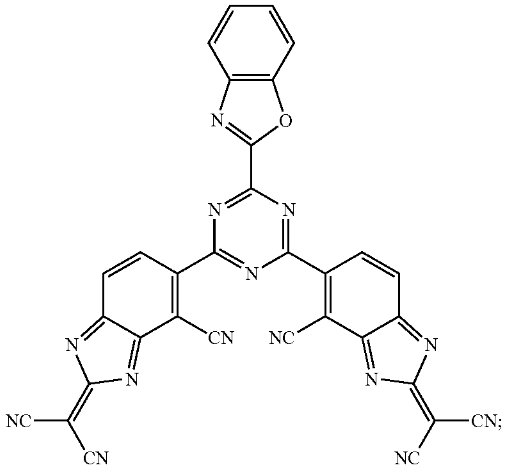
103
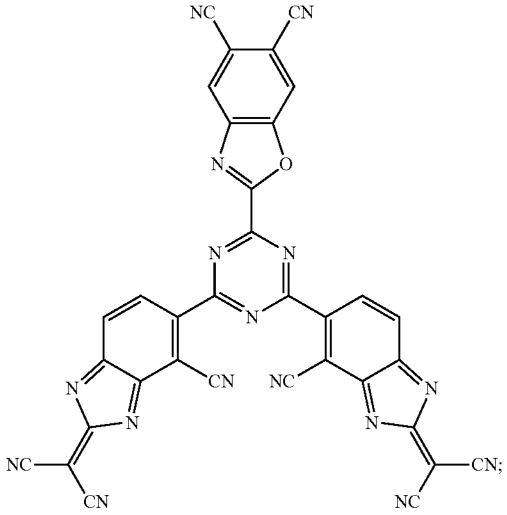
104
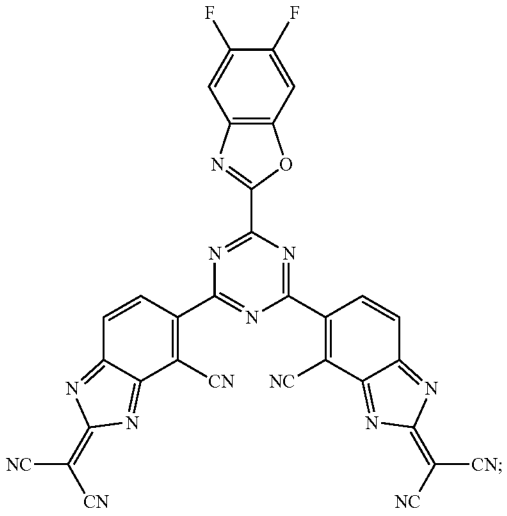

-continued
105
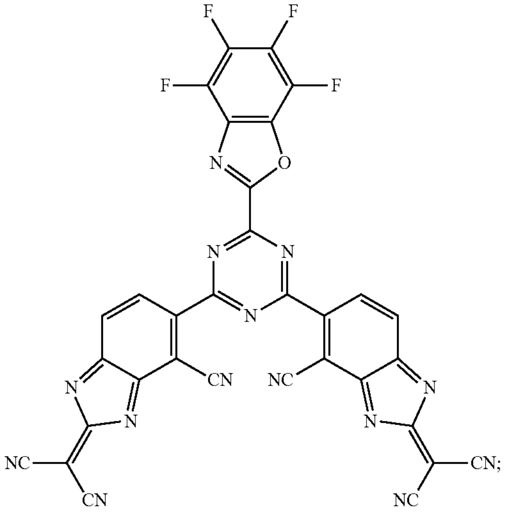
106
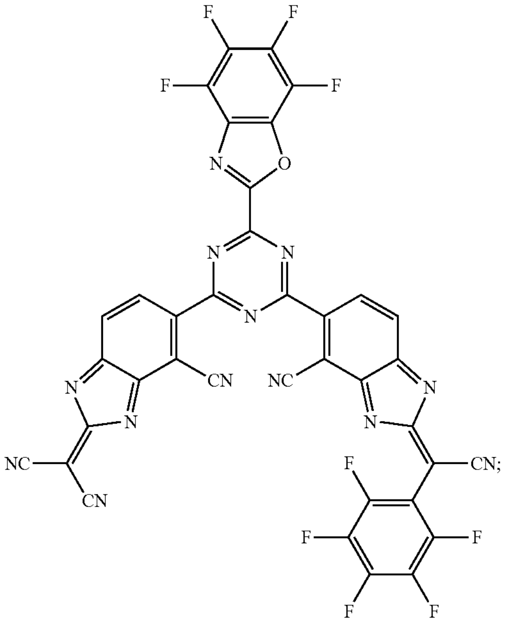
107
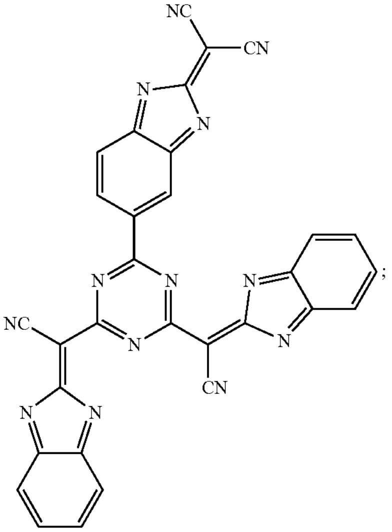
-continued
108
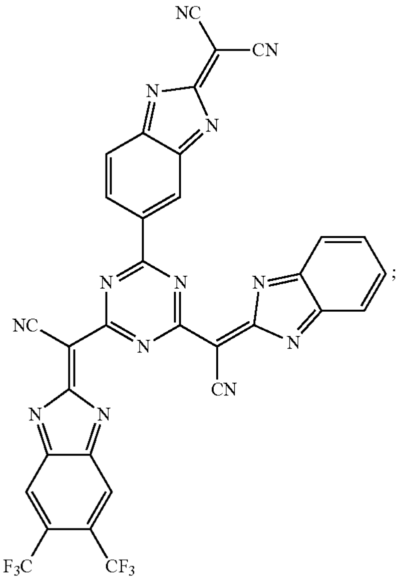
109
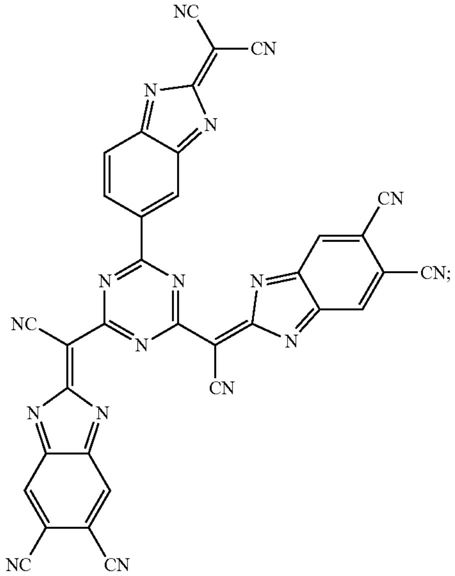

110
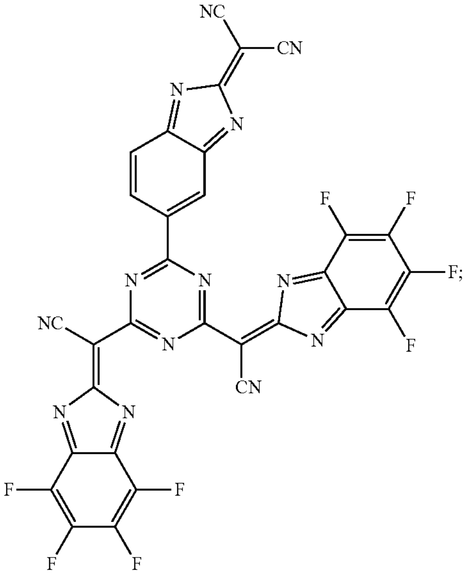
111
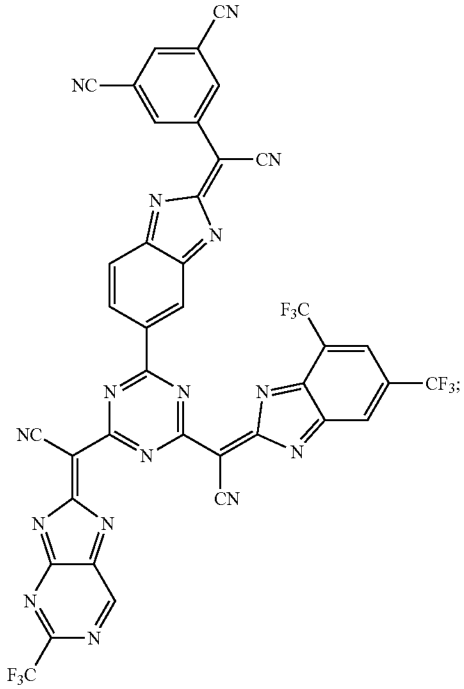
112
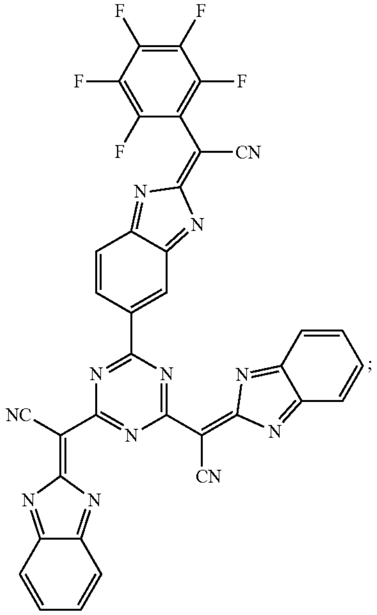
113
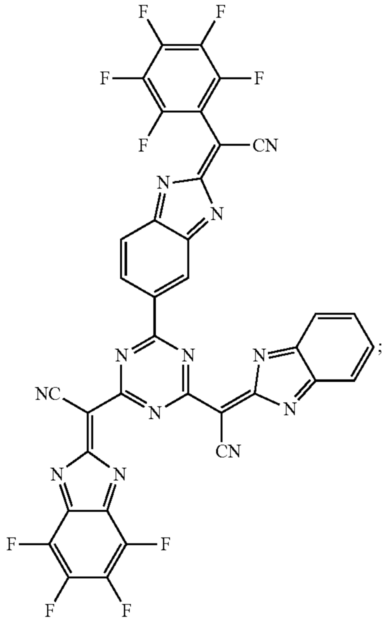

-continued
114
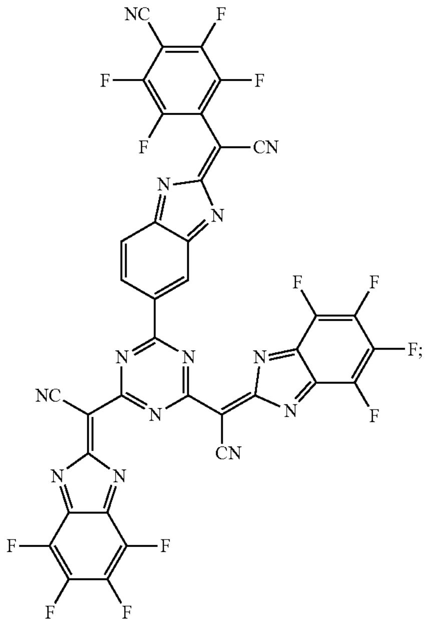
115
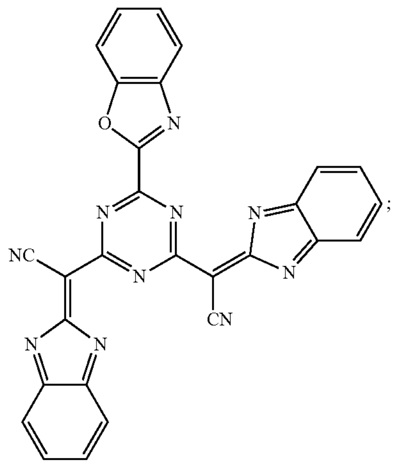
116
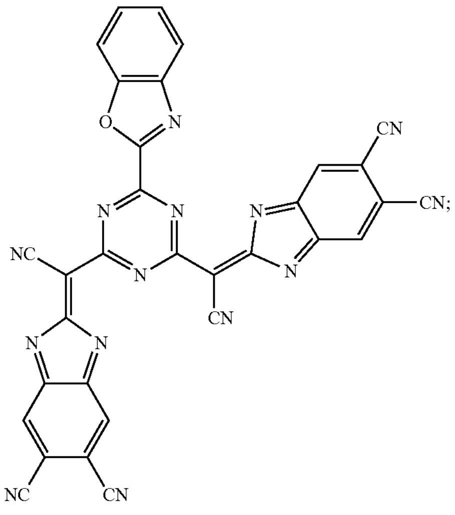
-continued
117
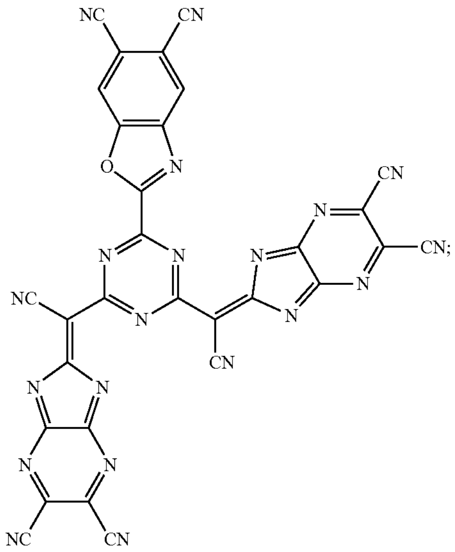
118
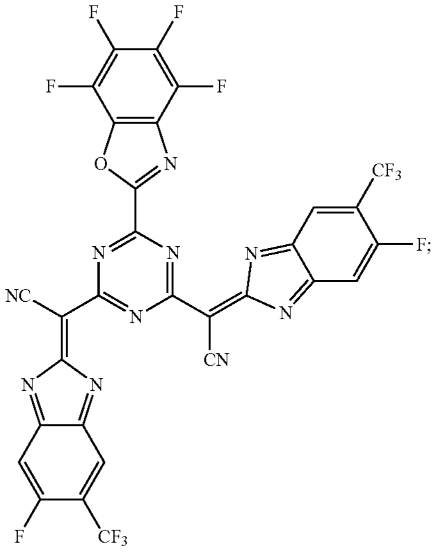
119
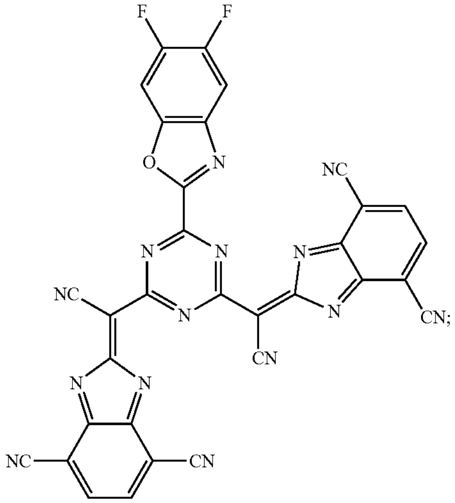

-continued
120
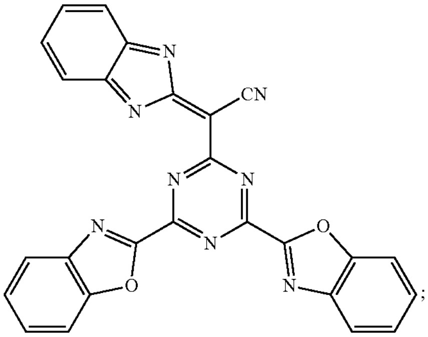
;
121
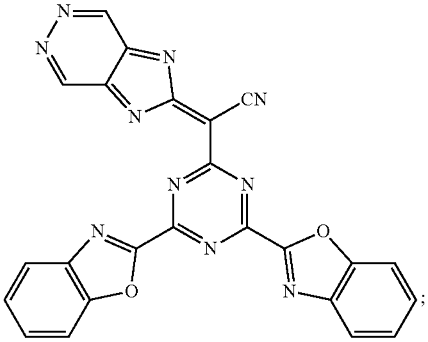
;
122
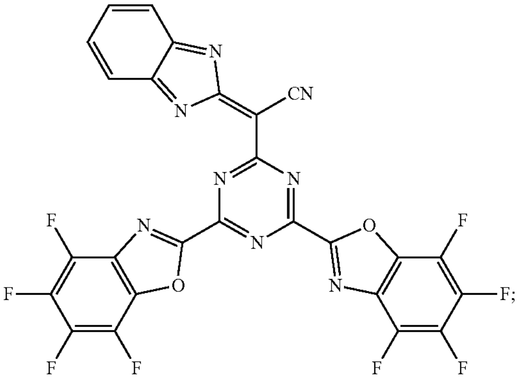
;
123
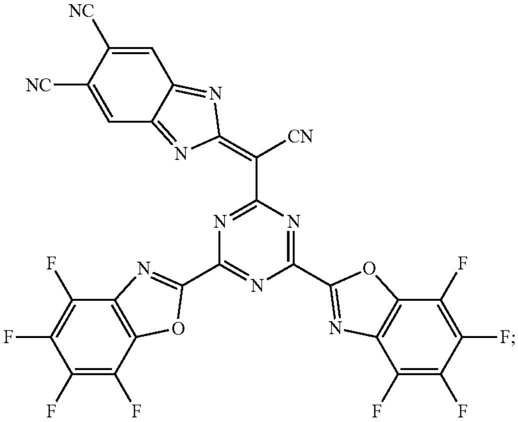
;
-continued
124
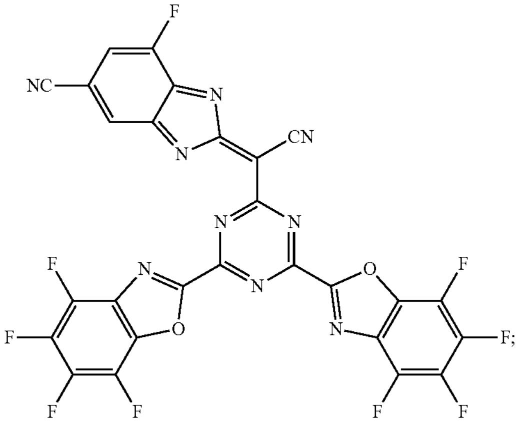
;
125
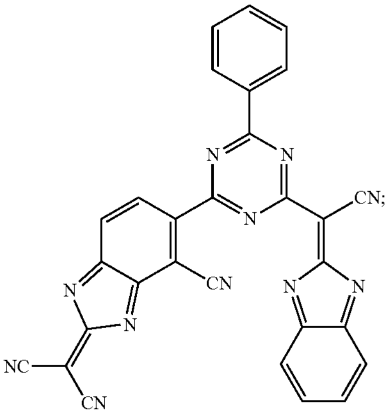
;
126
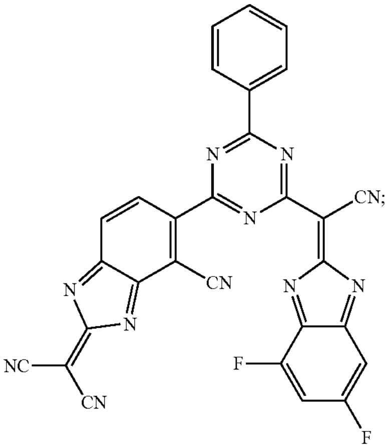
;

-continued
127
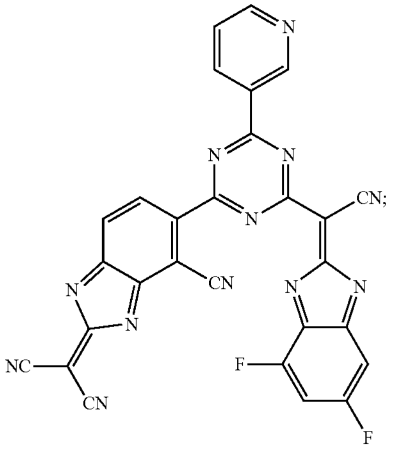
128
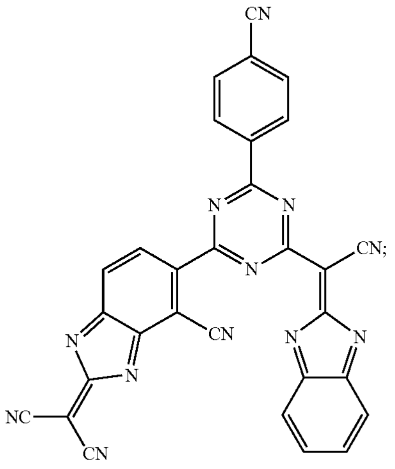
129
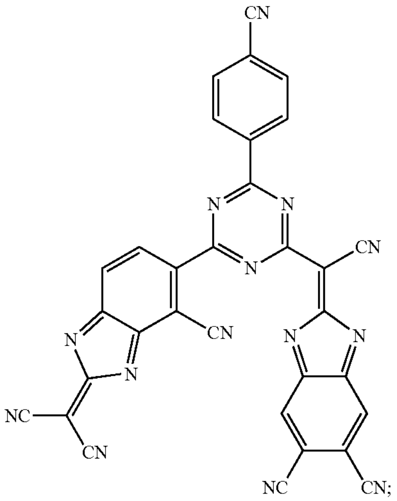
-continued
130
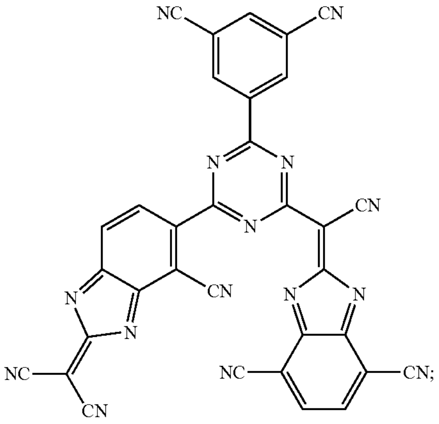
131
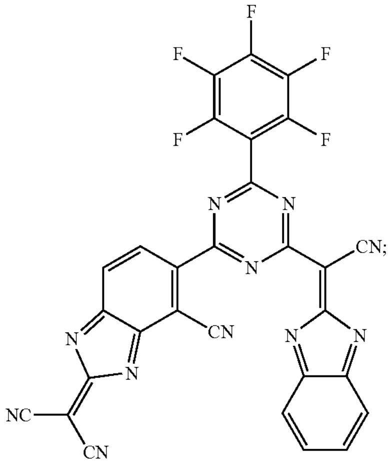
132
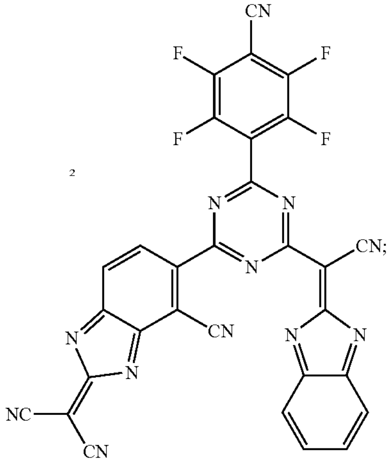

-continued
133
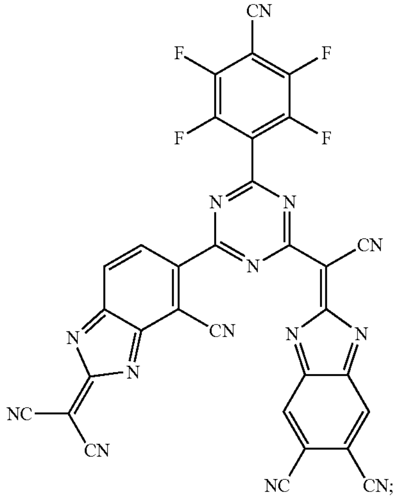
134
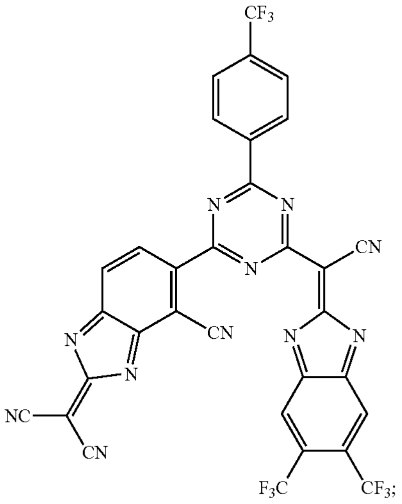
135
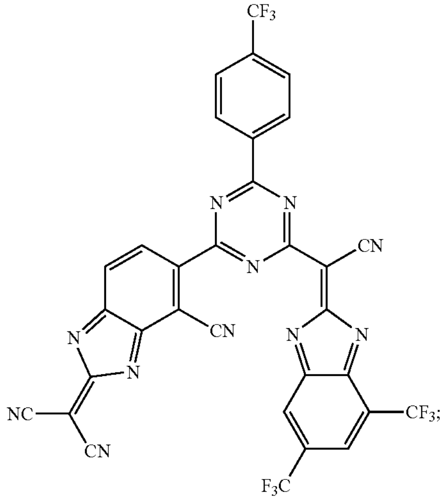
-continued
136
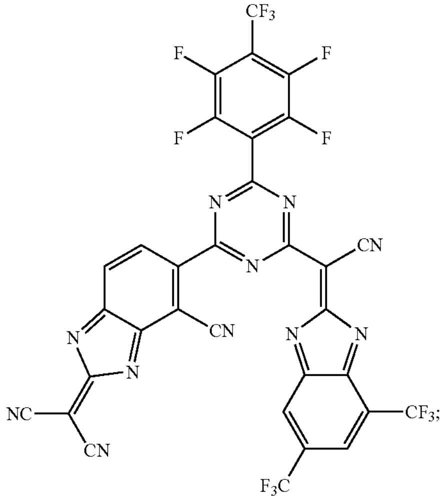
137
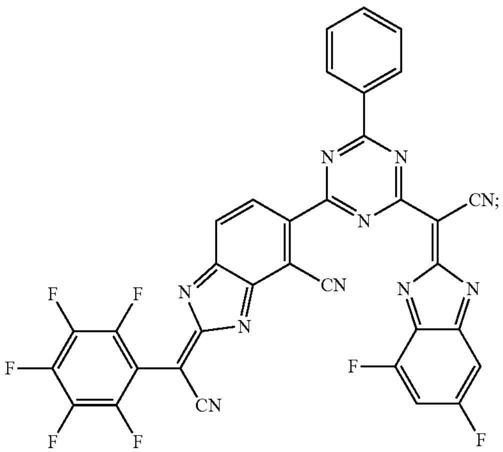
138
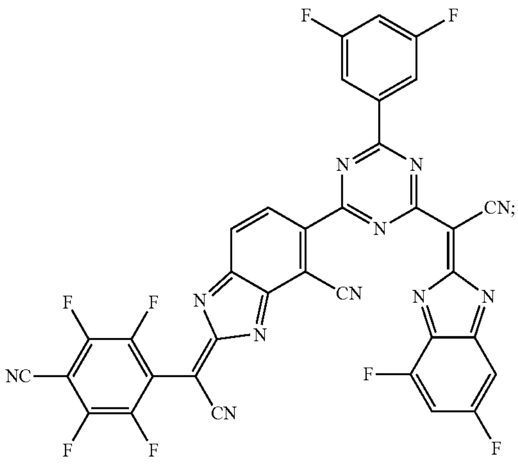

-continued
139
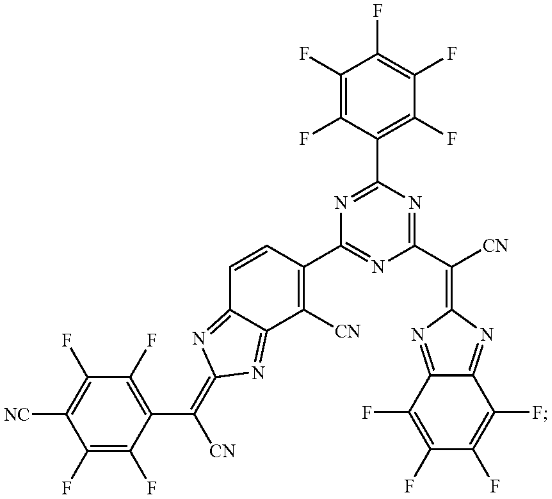
140
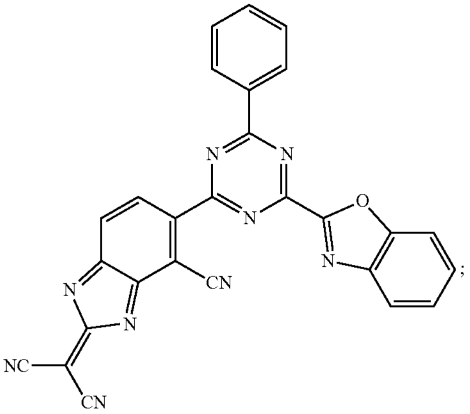
141
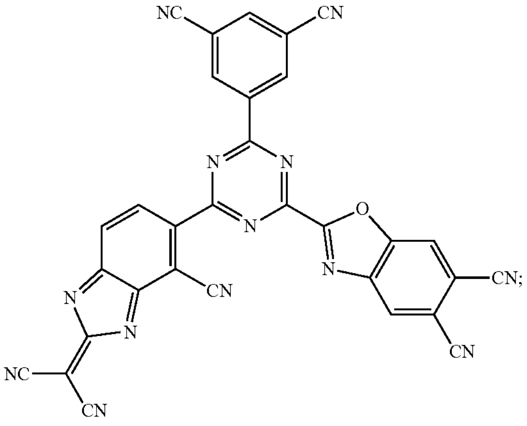
-continued
142
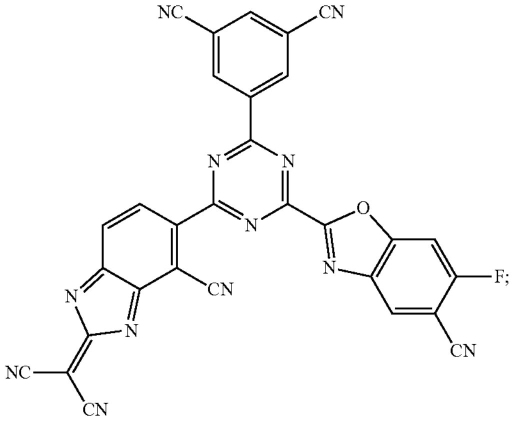
143
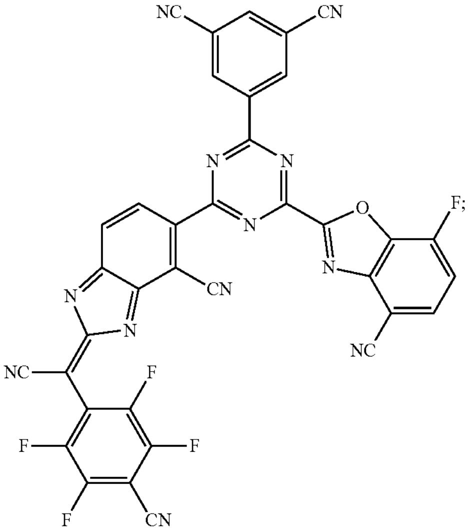
144
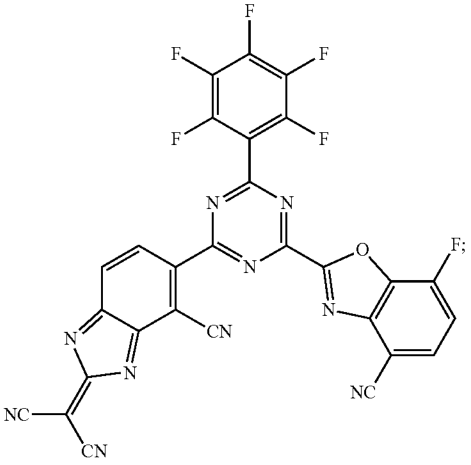

-continued
145
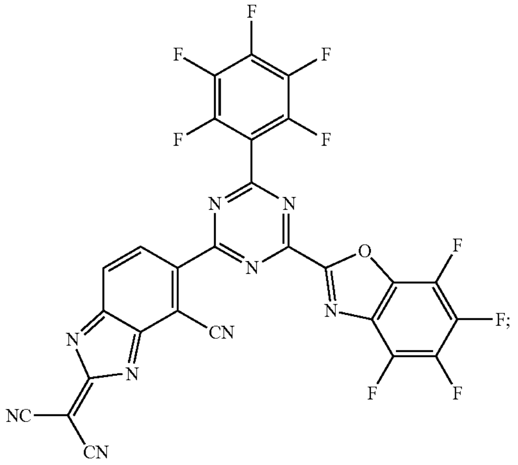
146
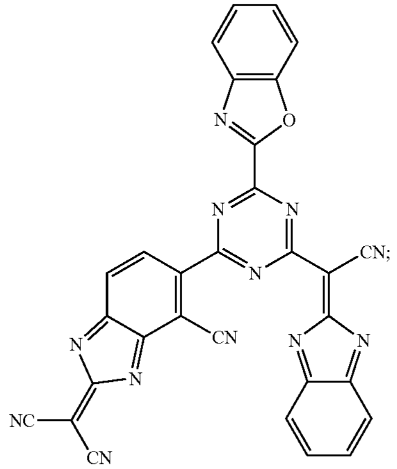
147
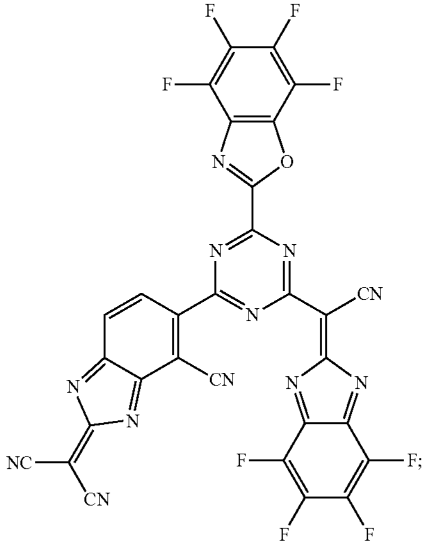
-continued
148
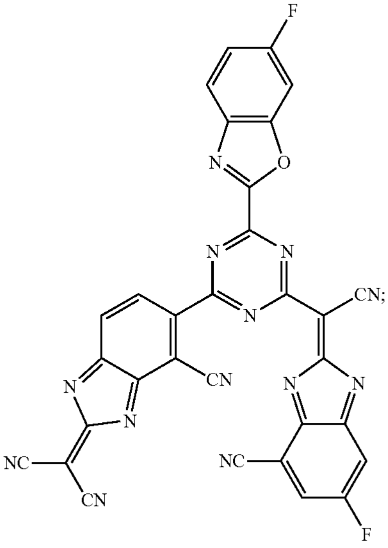
149
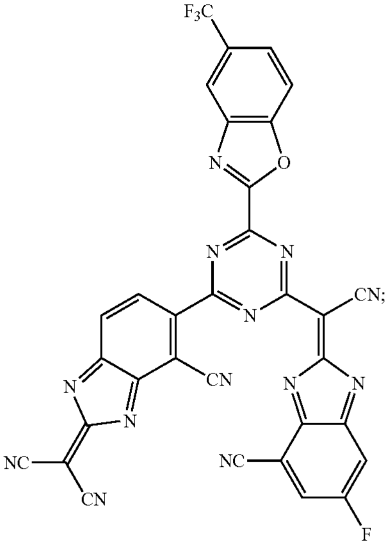
150
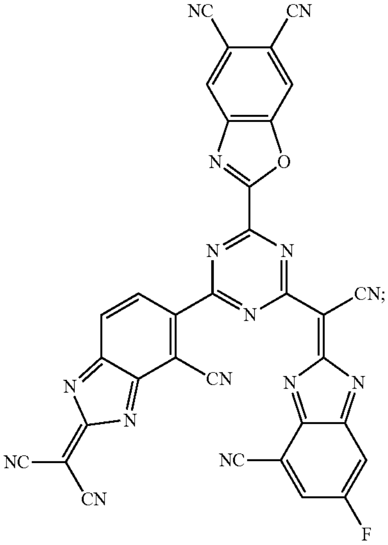

-continued
151
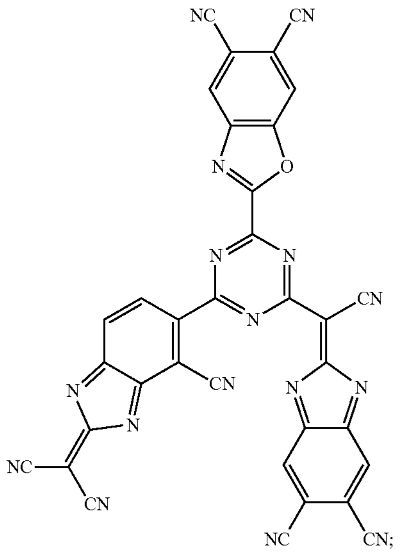
152
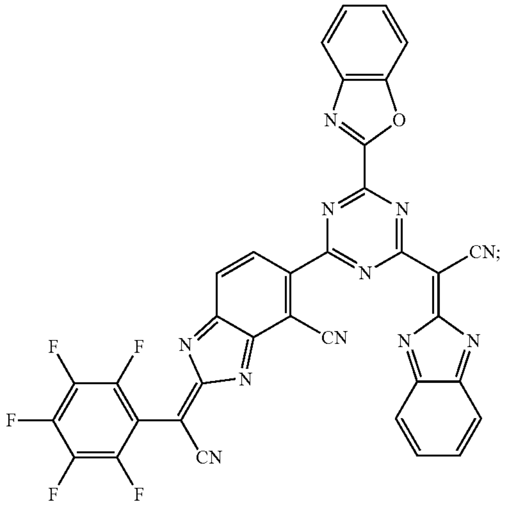
153
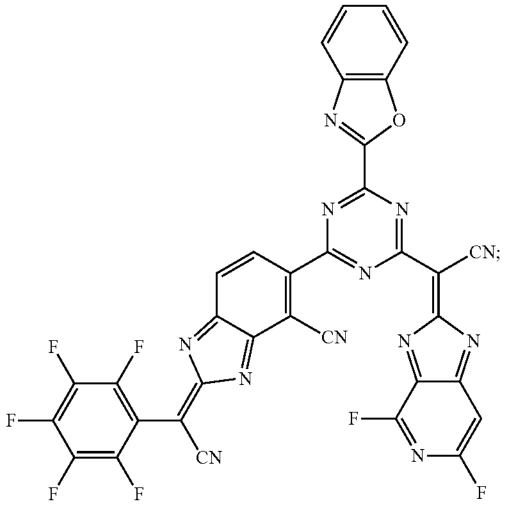
-continued
154
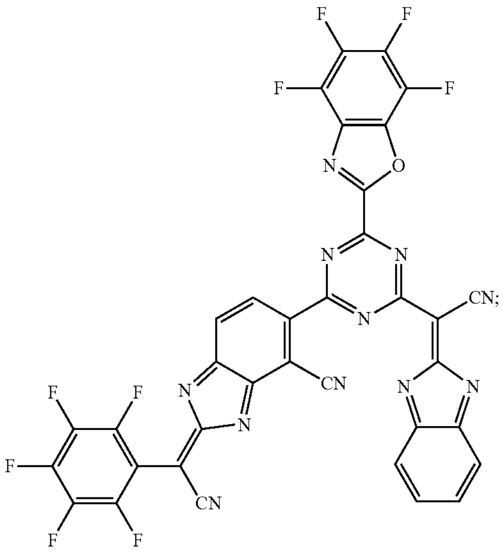
155
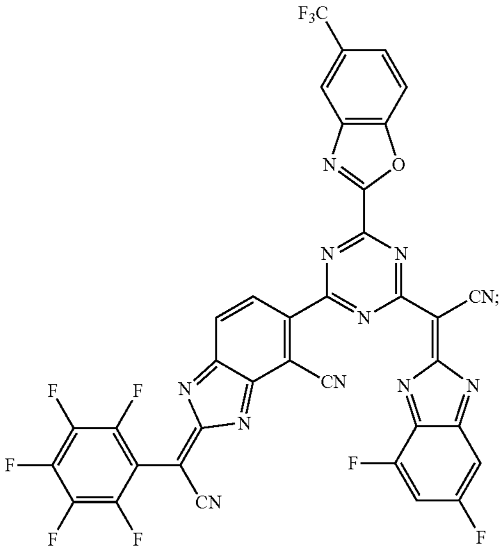
156
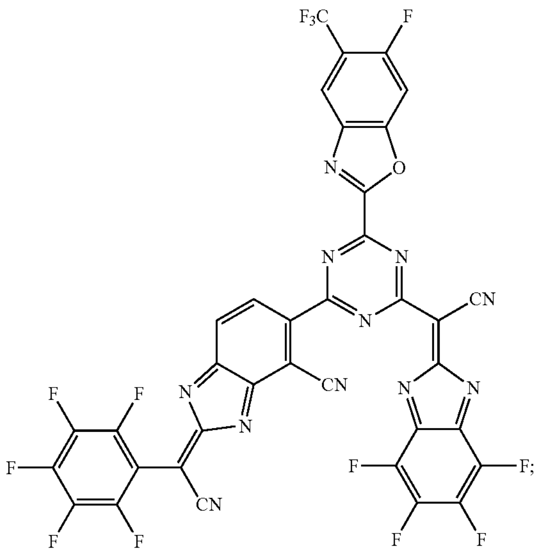

-continued
157
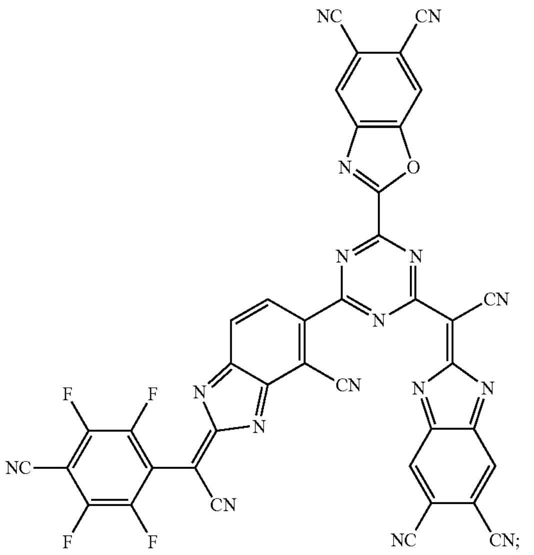
158
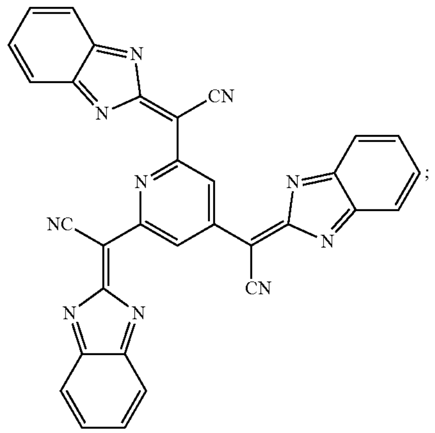
159
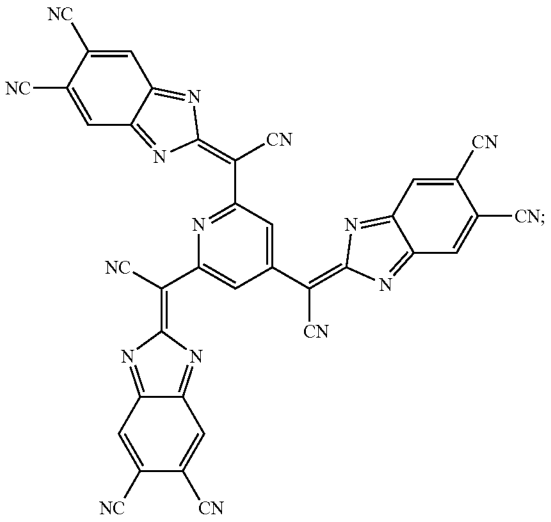
-continued
160
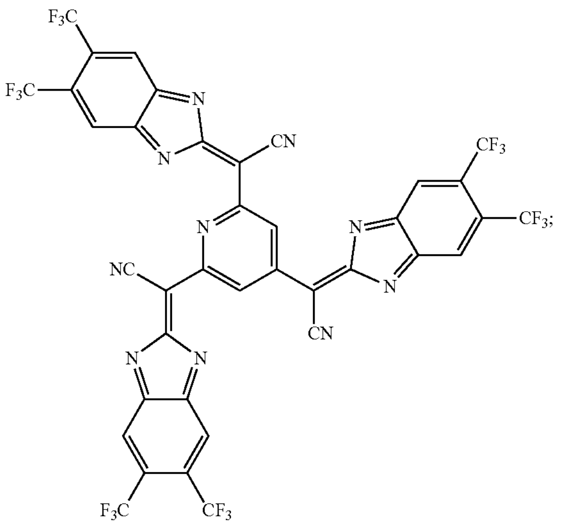
161
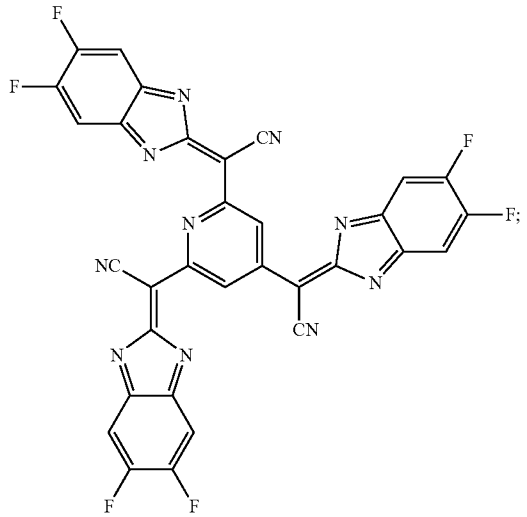
162
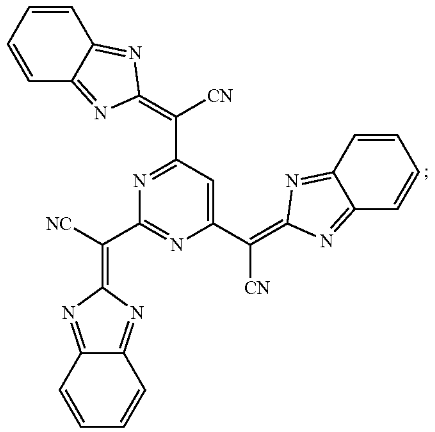

163
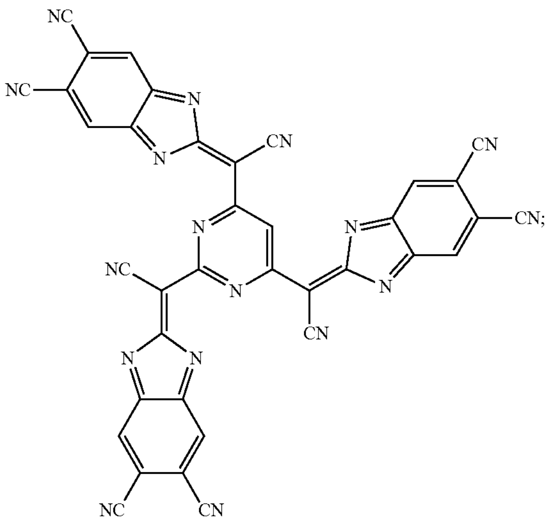
164
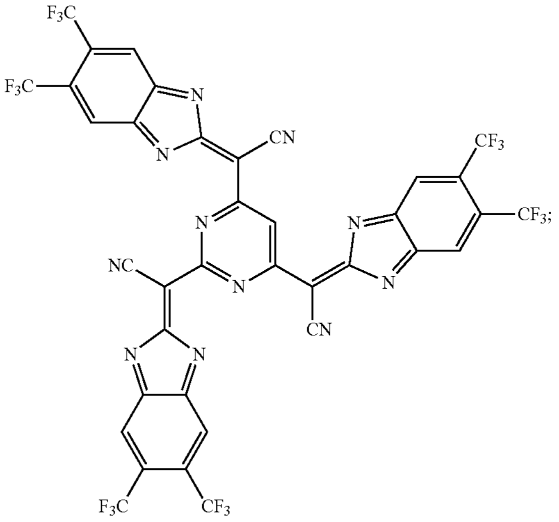
165
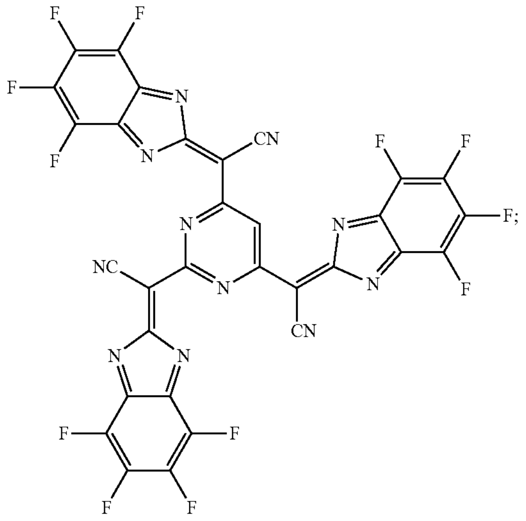
166
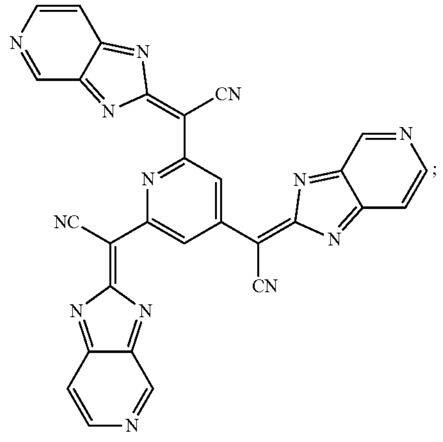
167
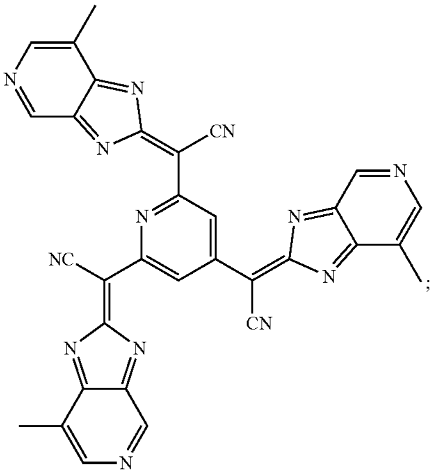
168
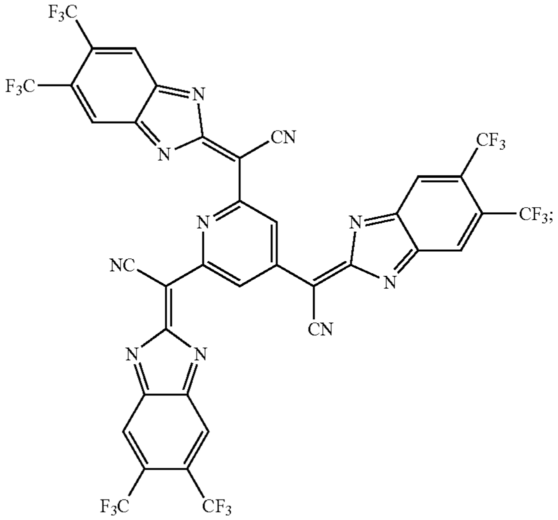

-continued
169
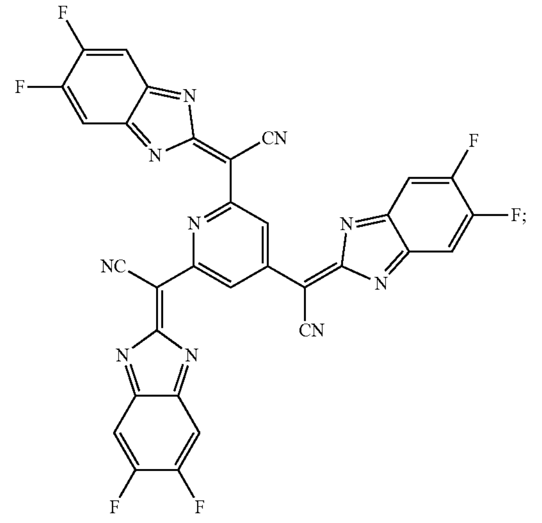
170
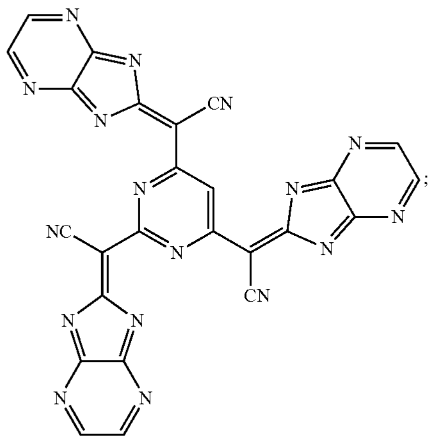
171
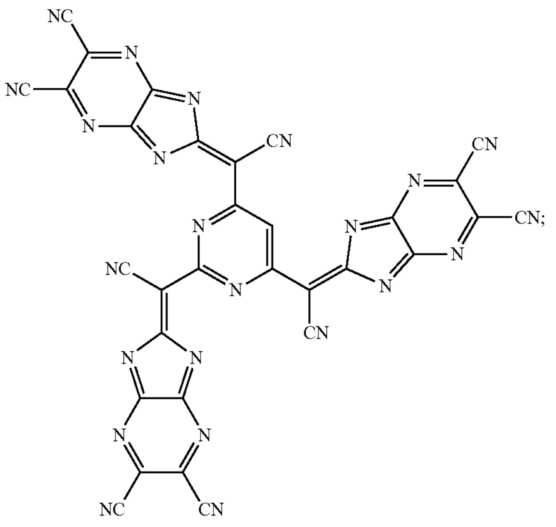
-continued
172
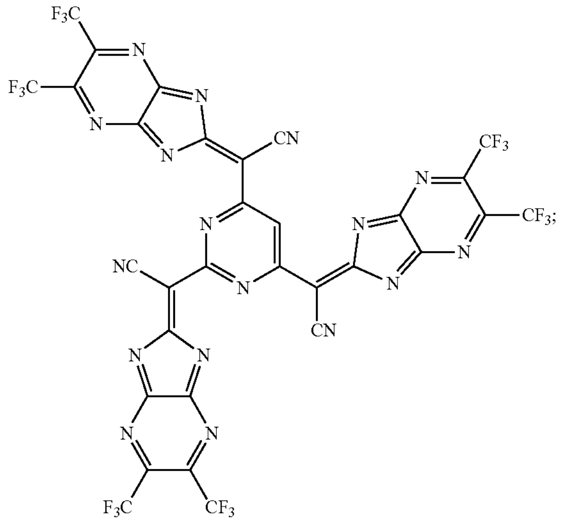
173
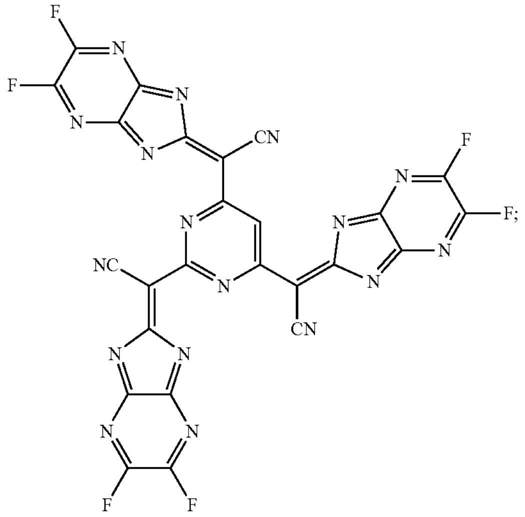
174
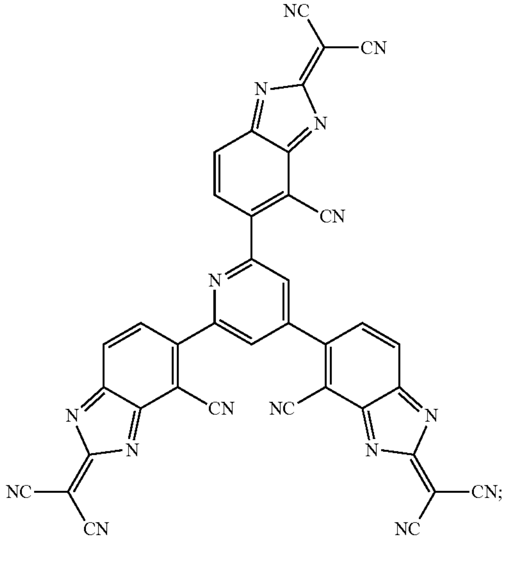

-continued
175
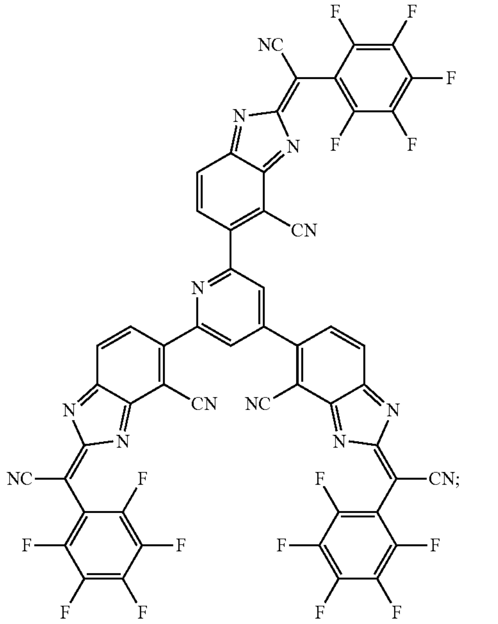
176
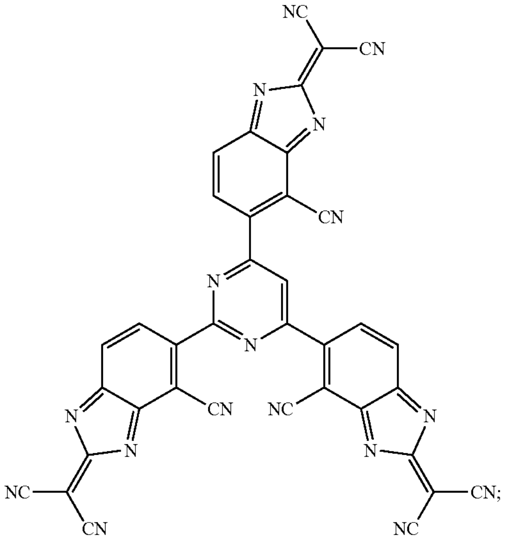
177
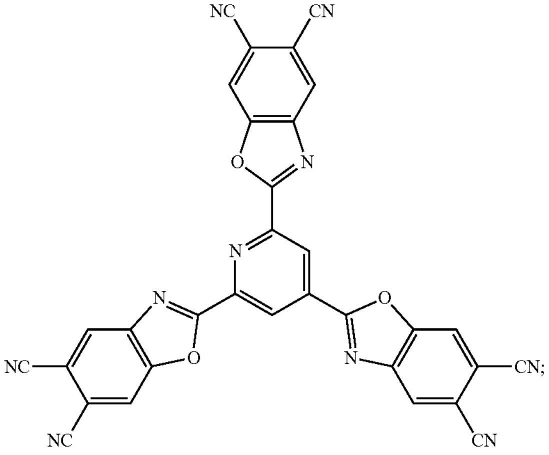
or
-continued
178
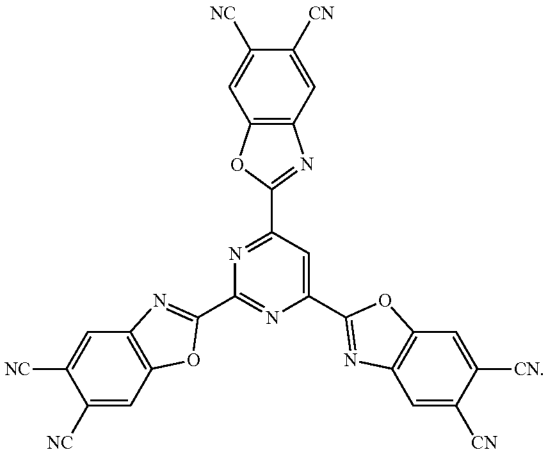
23. The organic light emitting diode of claim 14, wherein the organic compound has one of the following structures:
1
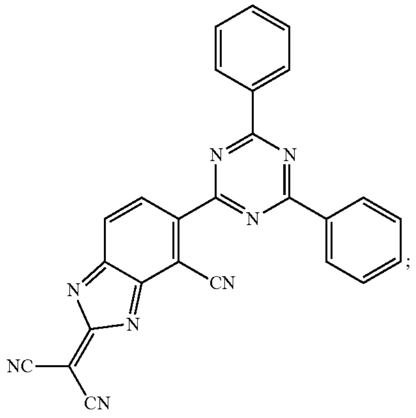
2
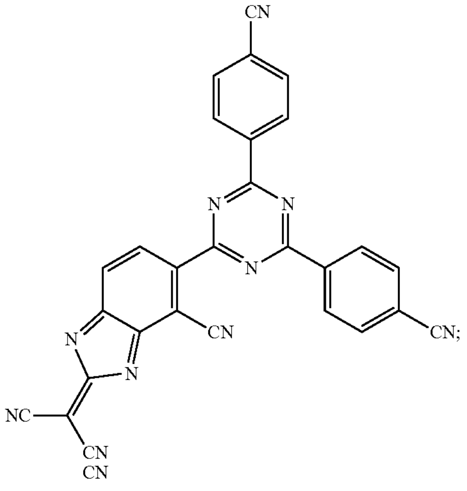

-continued
3
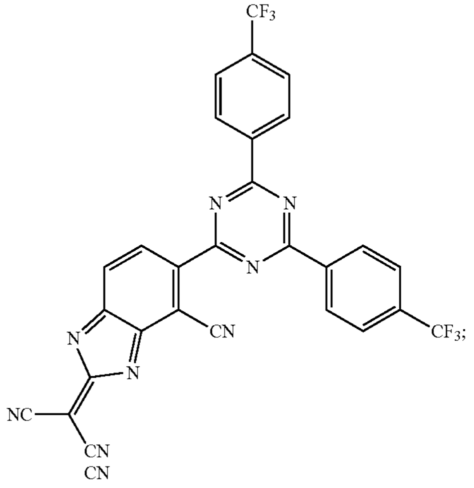
4
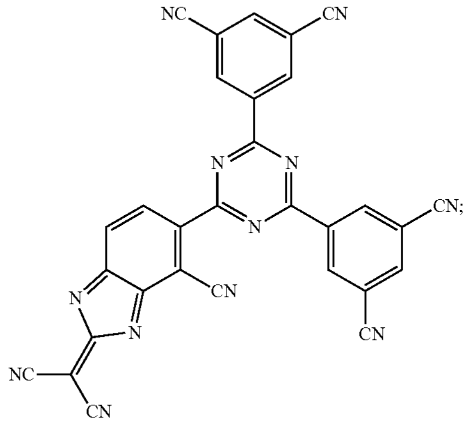
5
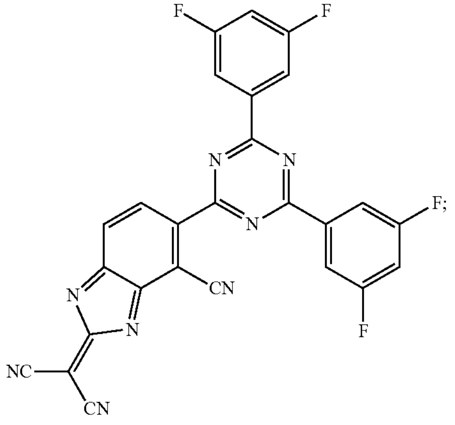
-continued
6
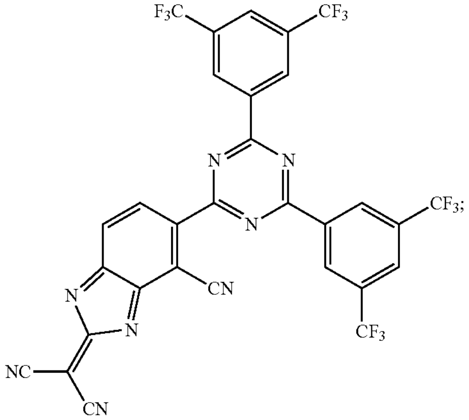
7
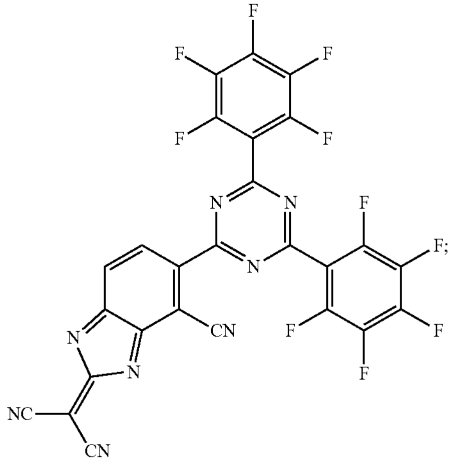
8
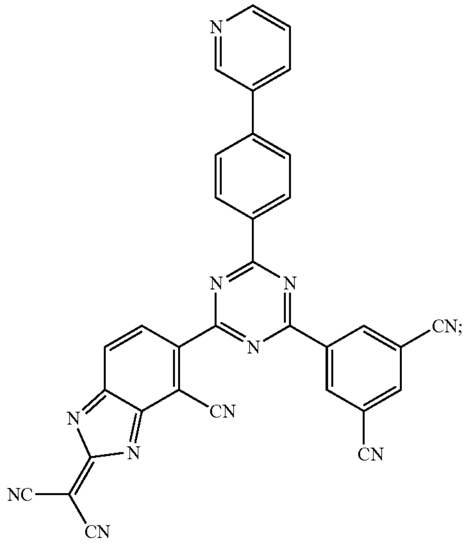

9
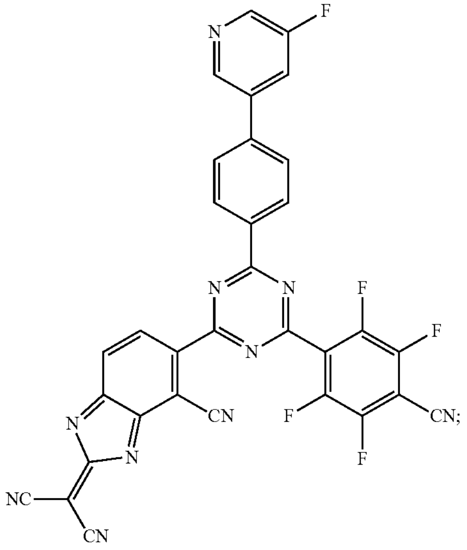
10
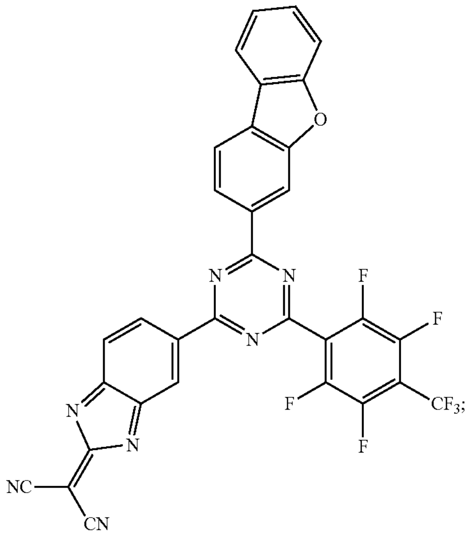
11
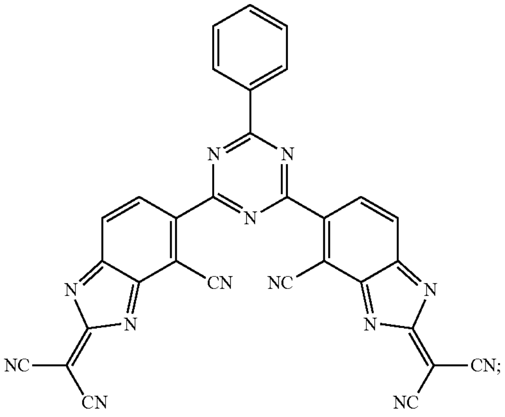
12
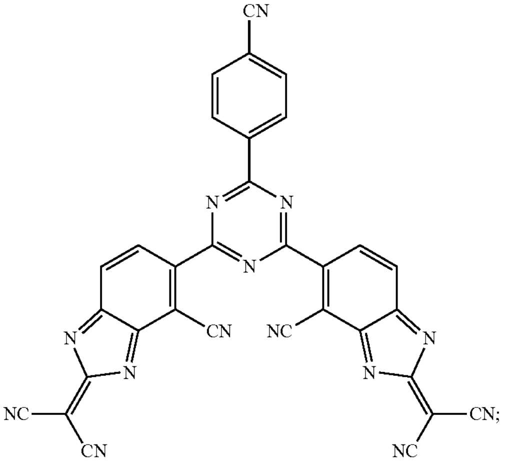
13
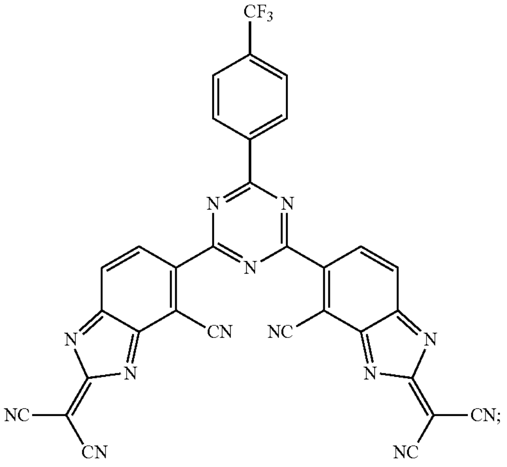
14
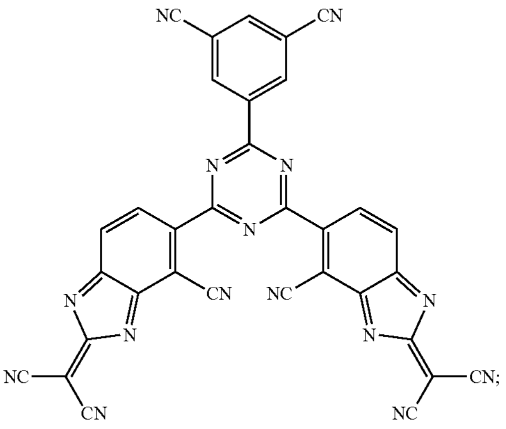

-continued
15
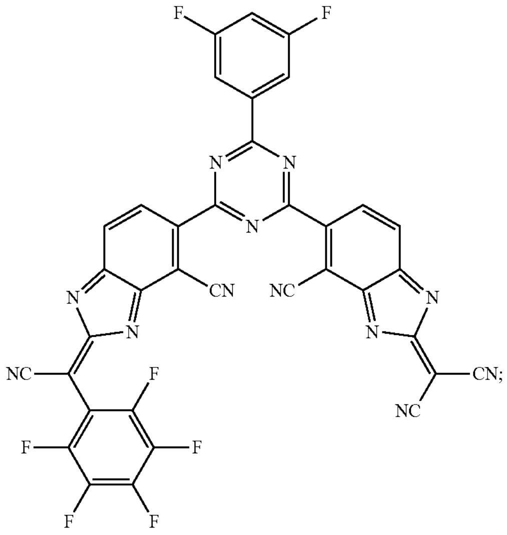
16
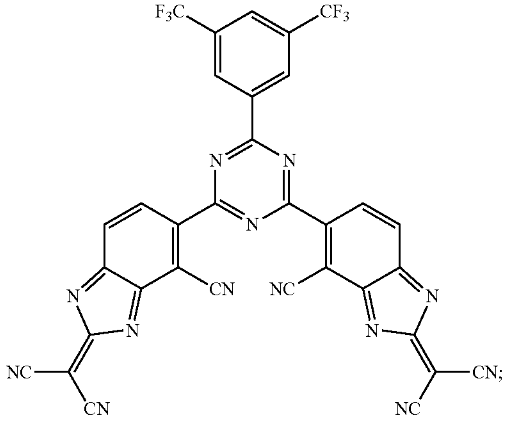
17
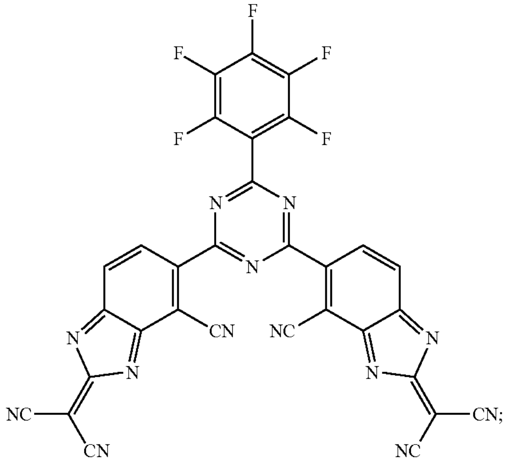
-continued
18
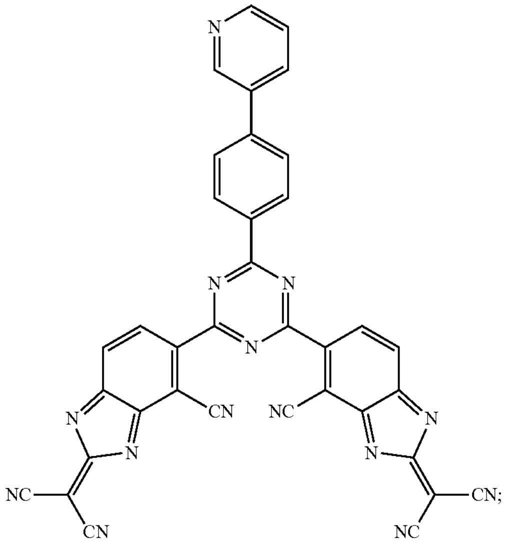
19
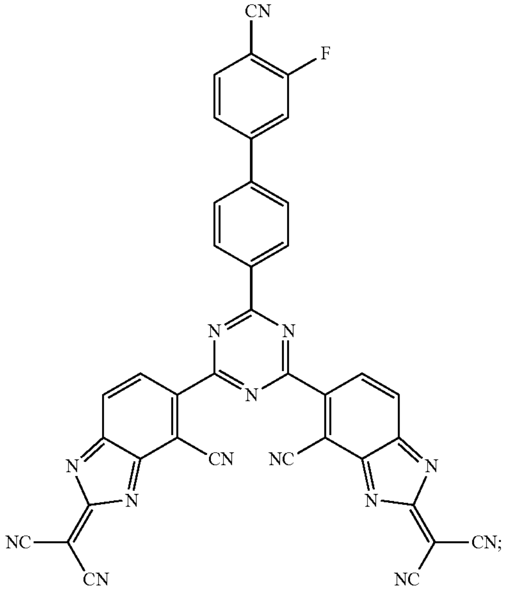
20
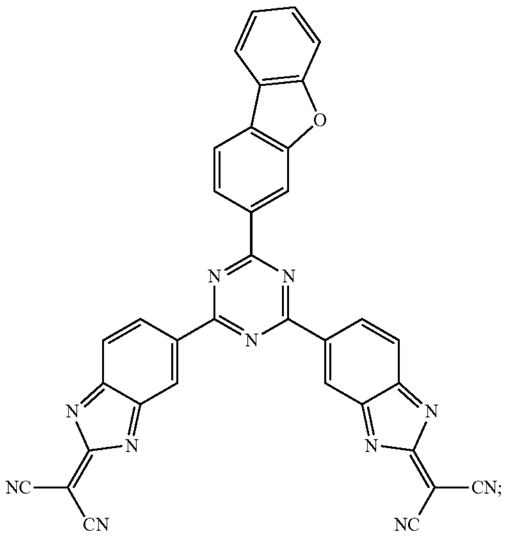

-continued
21
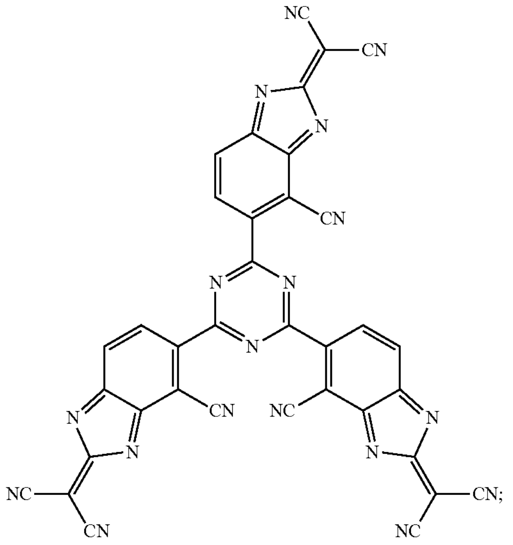
22
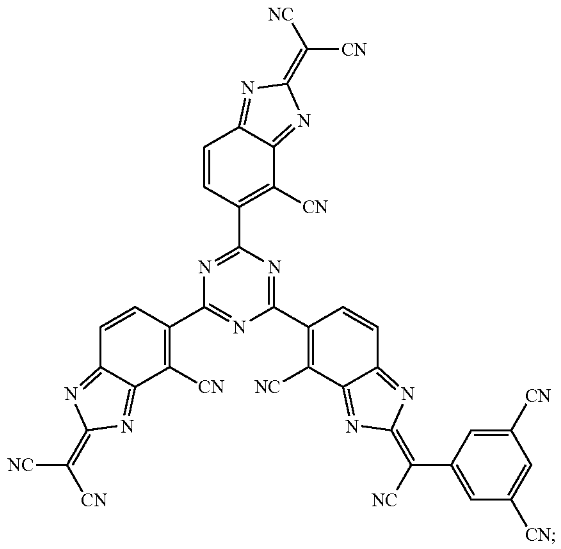
23
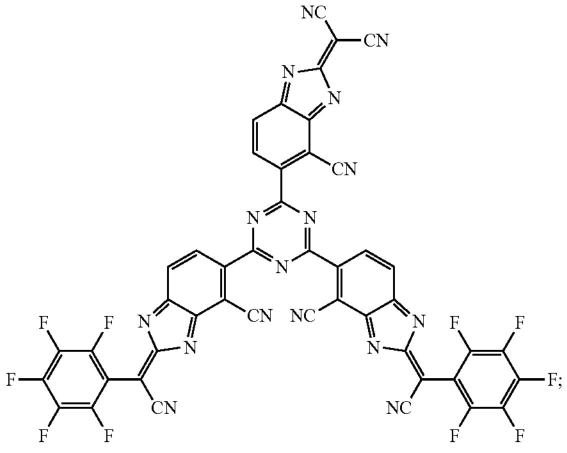
-continued
24
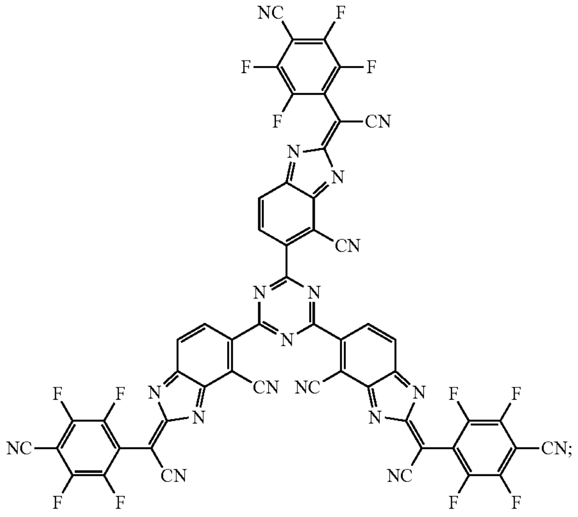
25
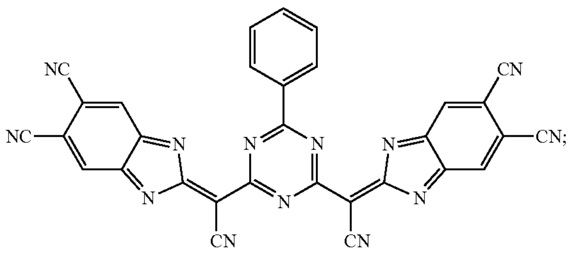
26
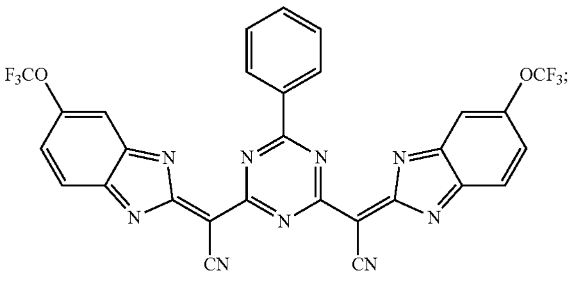
27
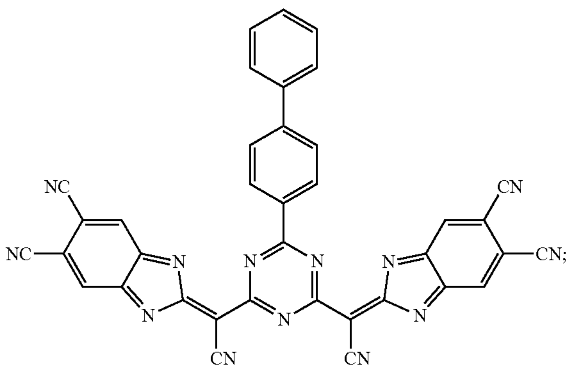

-continued
28
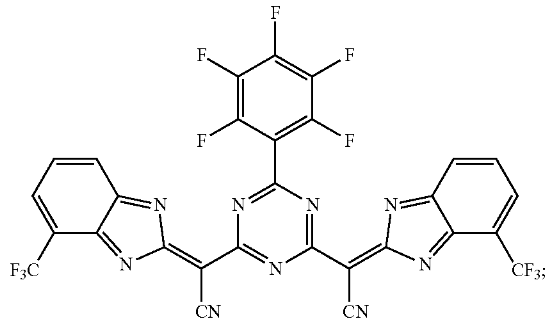
29
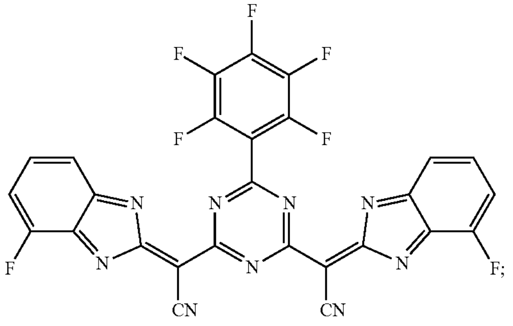
30
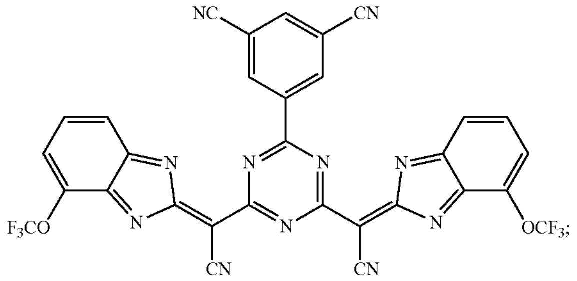
31
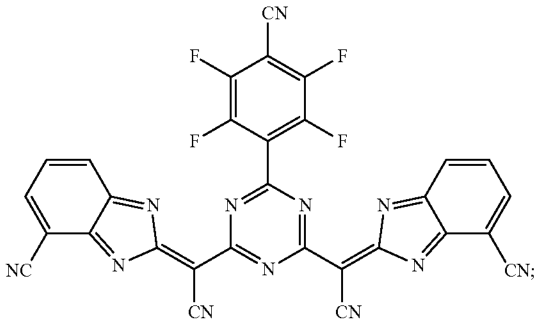
32
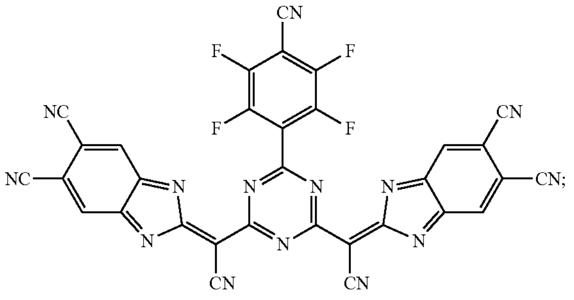
-continued
33
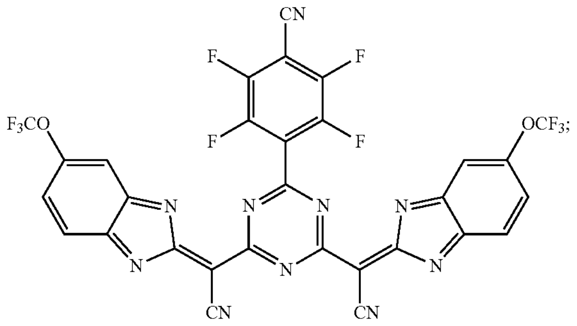
34
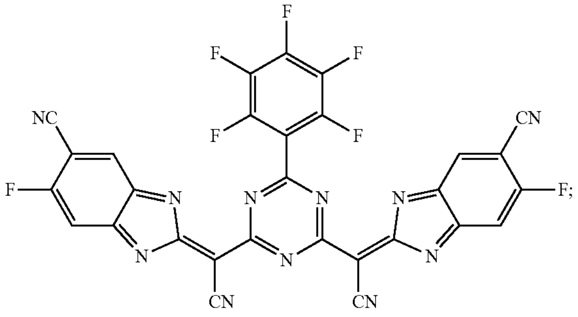
35
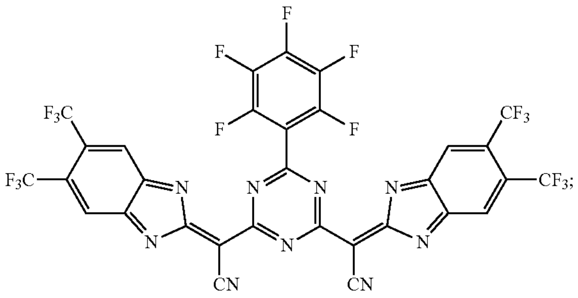
36
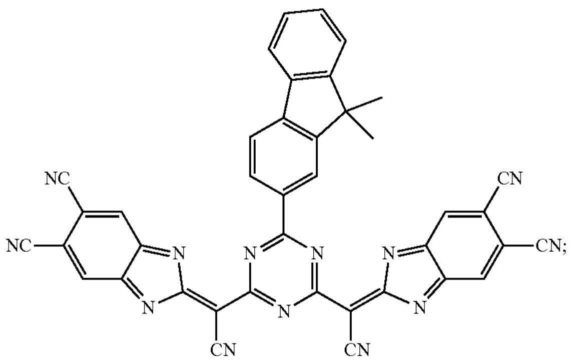

-continued
37
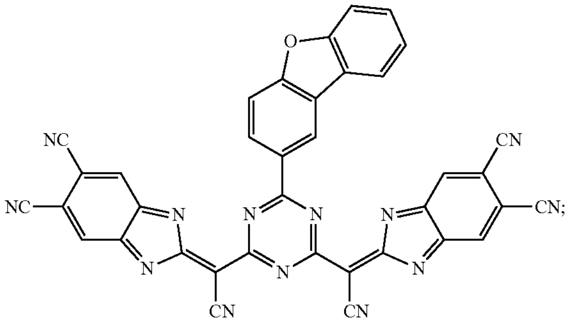
38
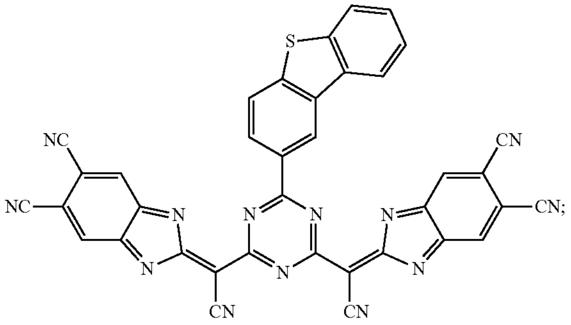
39
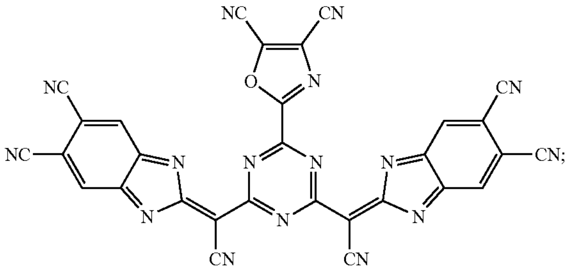
40
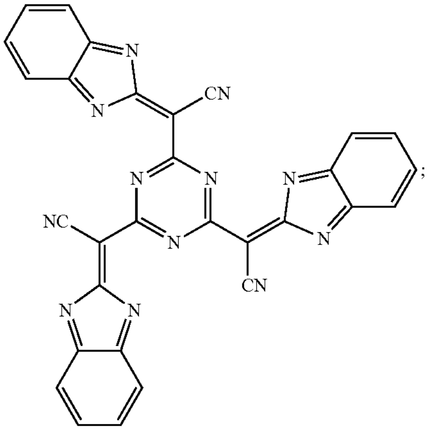
-continued
41
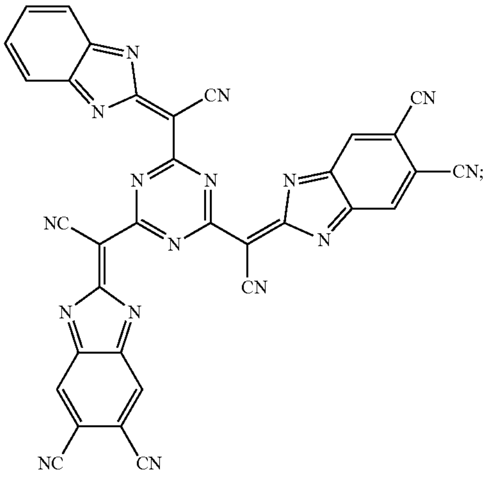
42
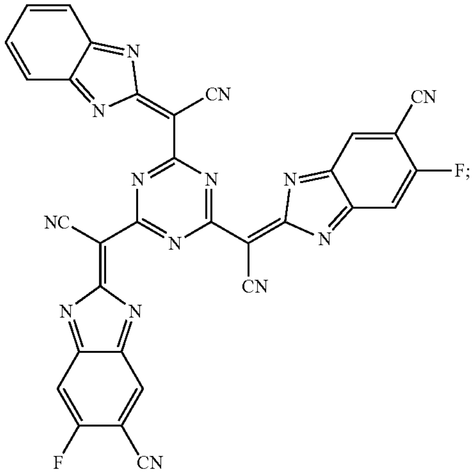
43
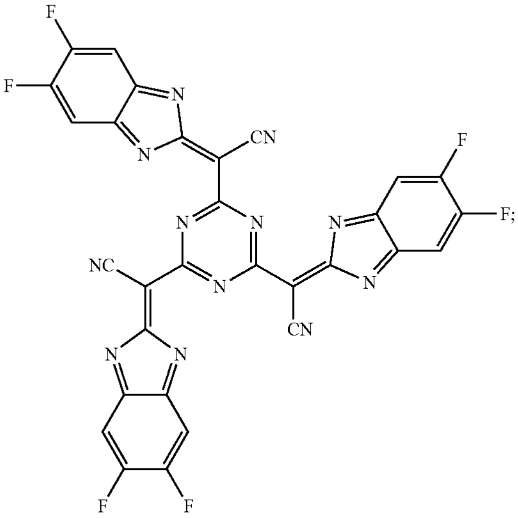

-continued
44
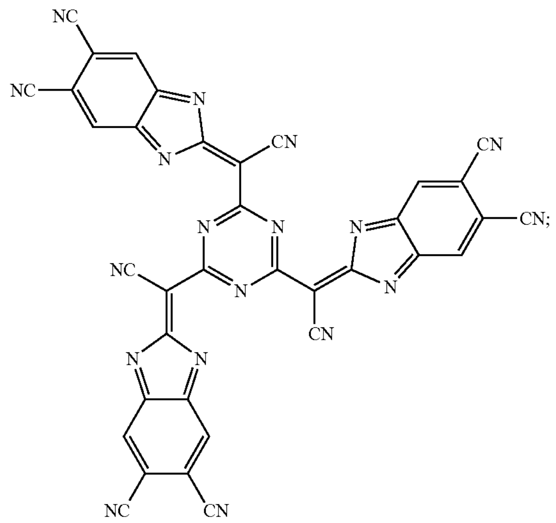
45
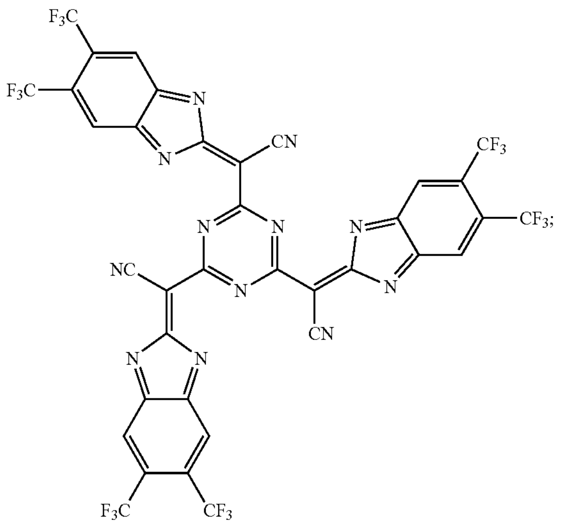
46
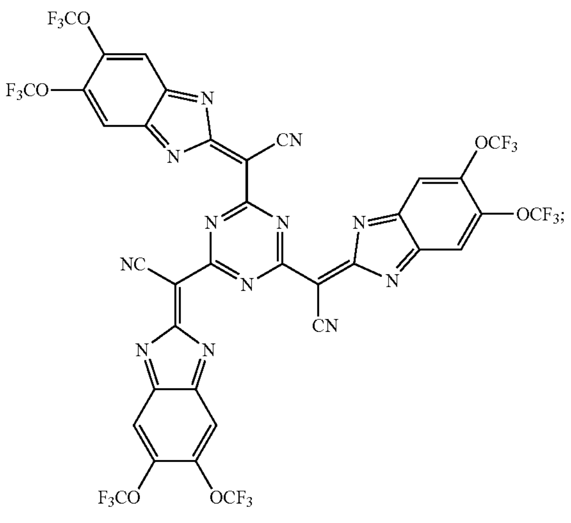
-continued
47
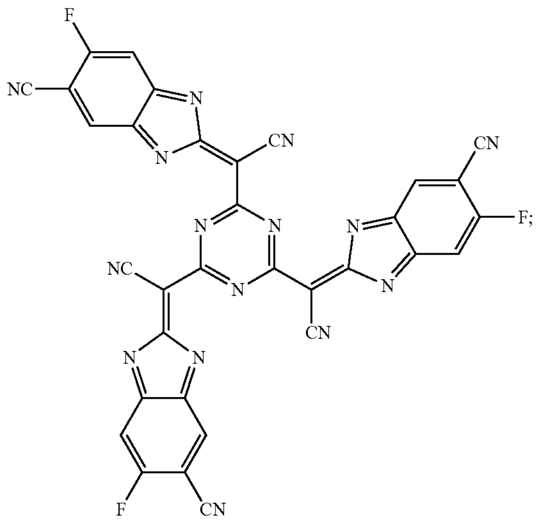
48
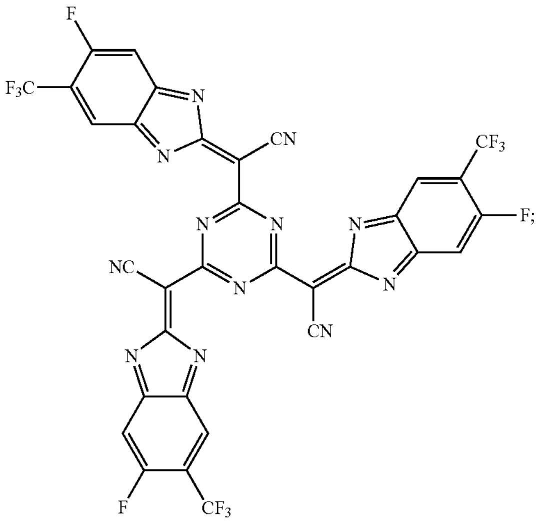
49
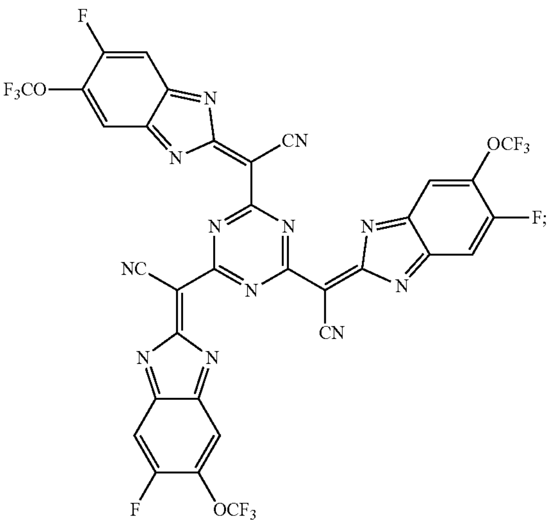

-continued
50
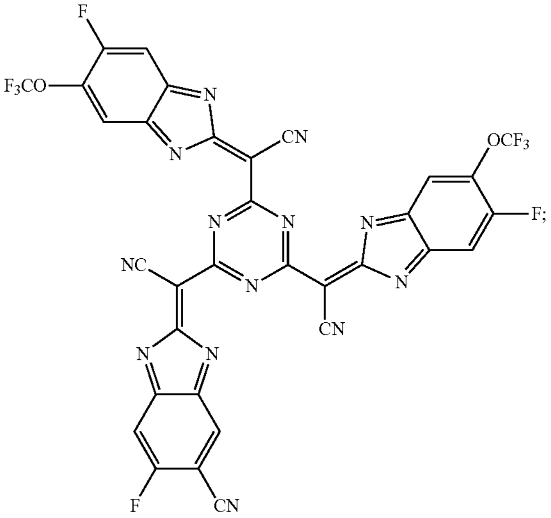
51
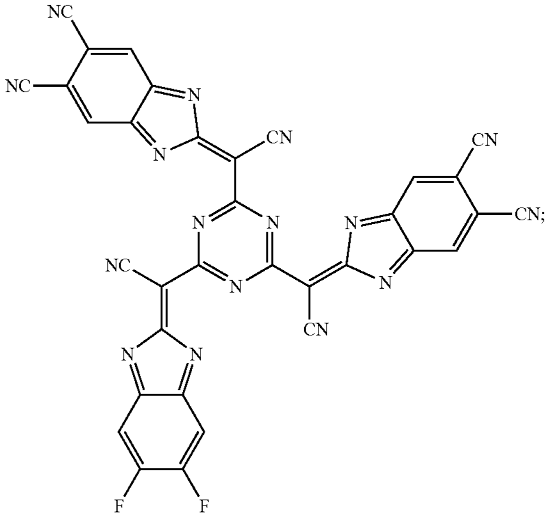
52
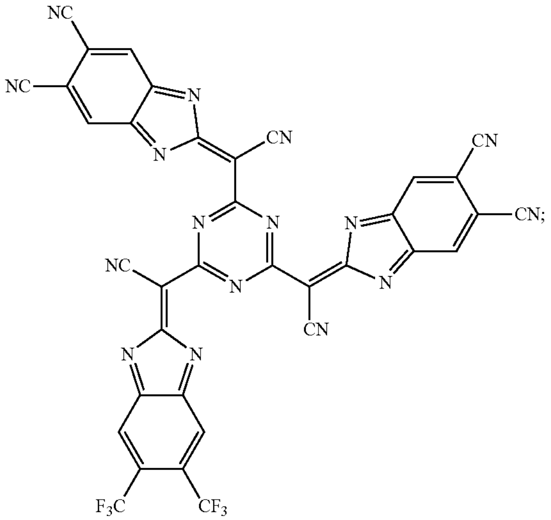
-continued
53
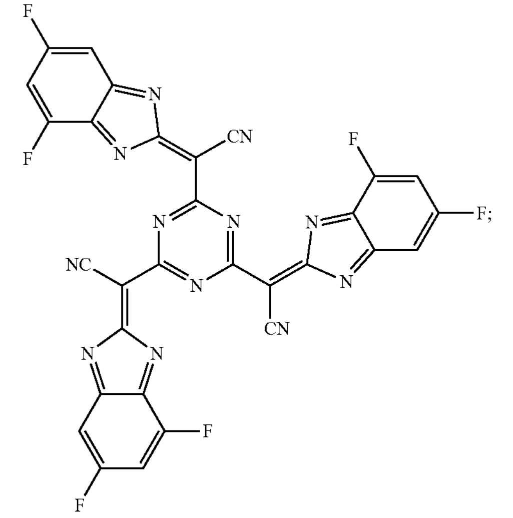
54
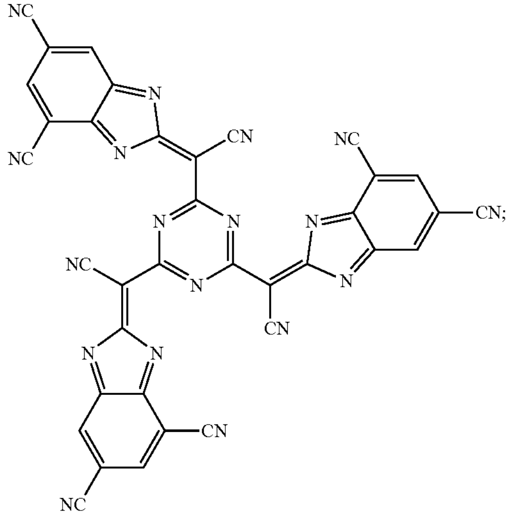
55
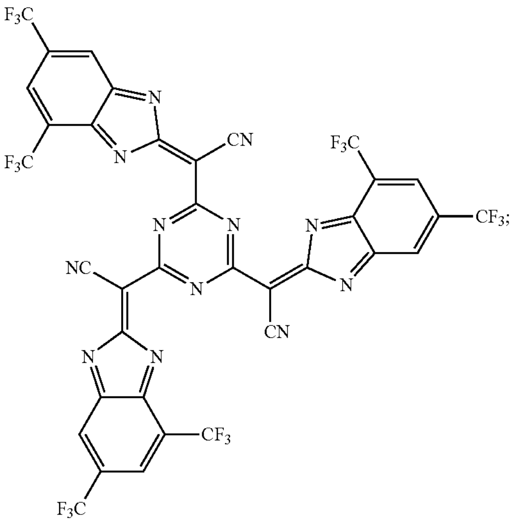

-continued
56
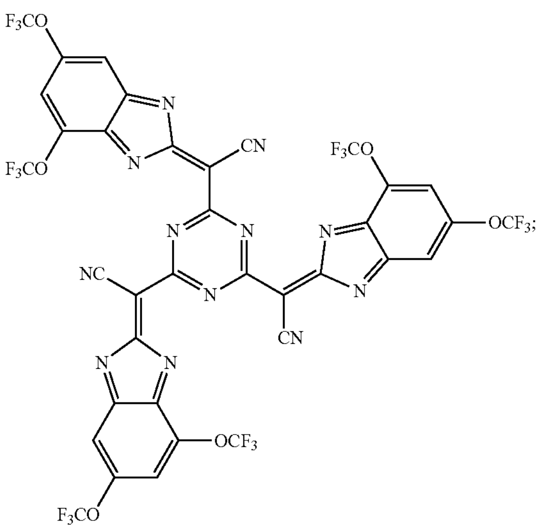
57
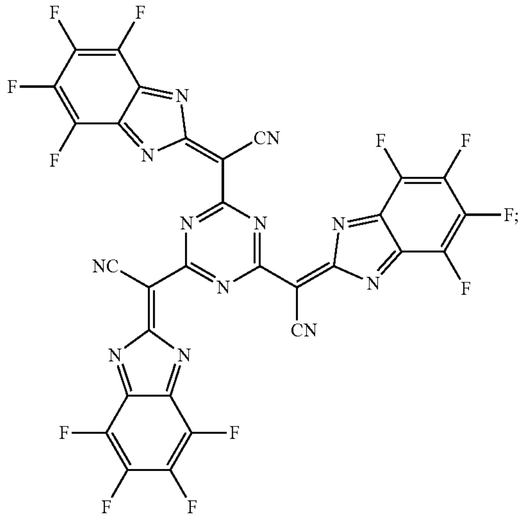
58
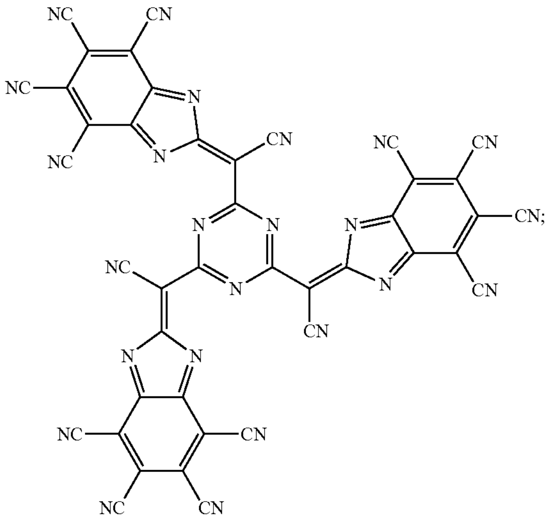
-continued
59
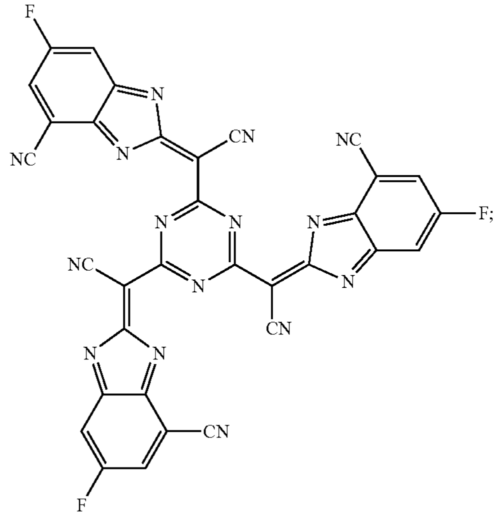
60
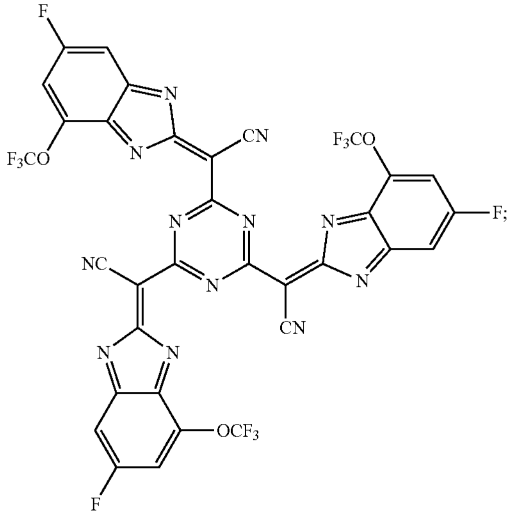
61
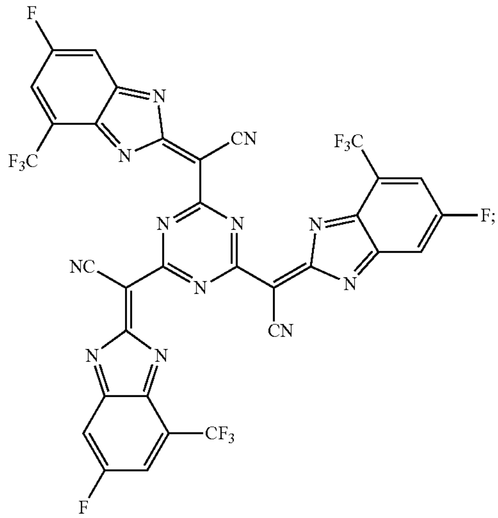

-continued
62
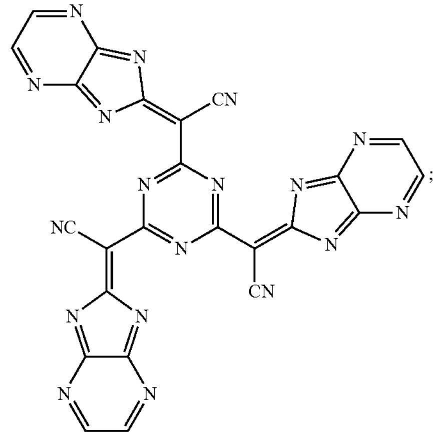
63
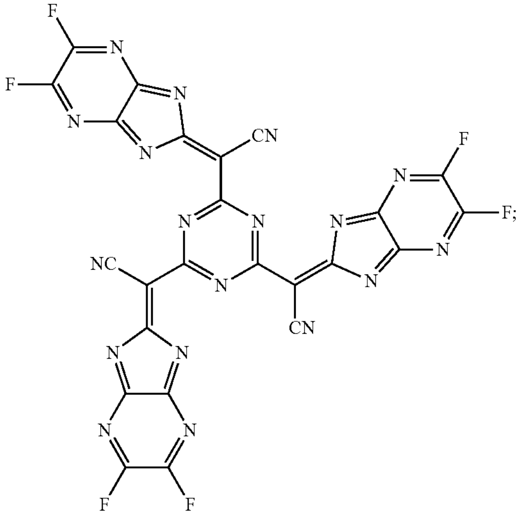
64
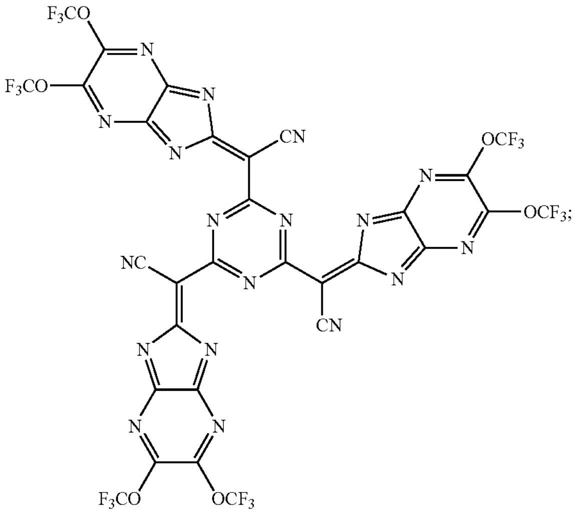
-continued
65
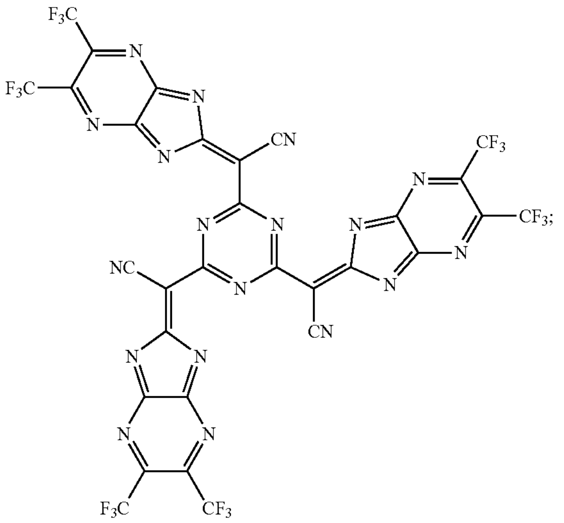
66
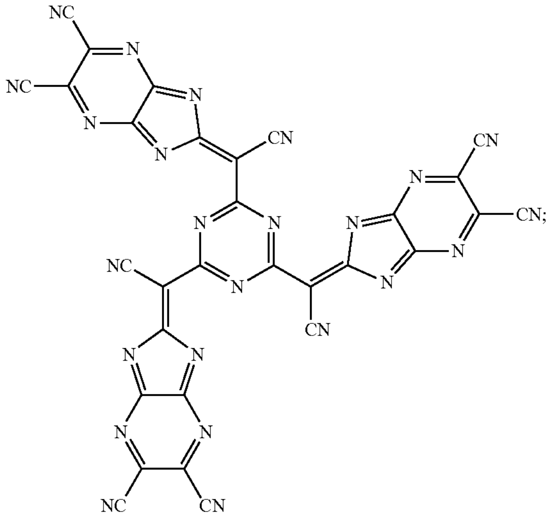
67
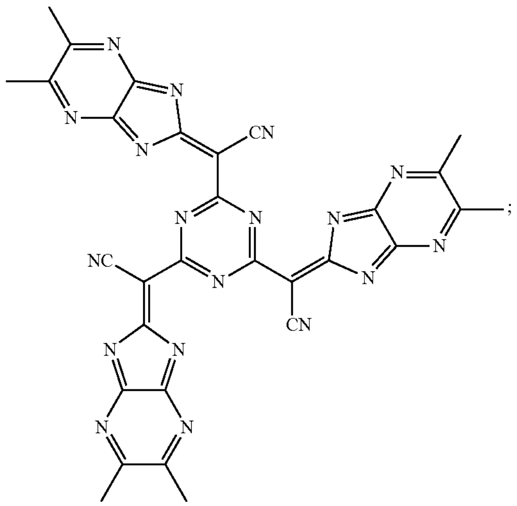

-continued
68
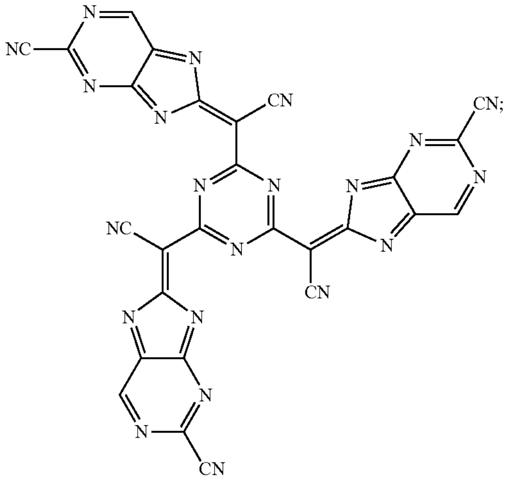
69
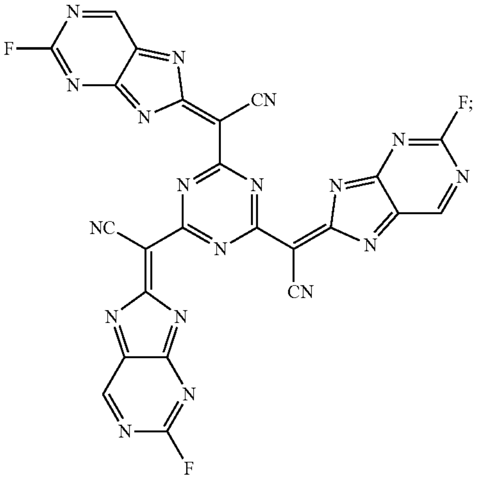
70
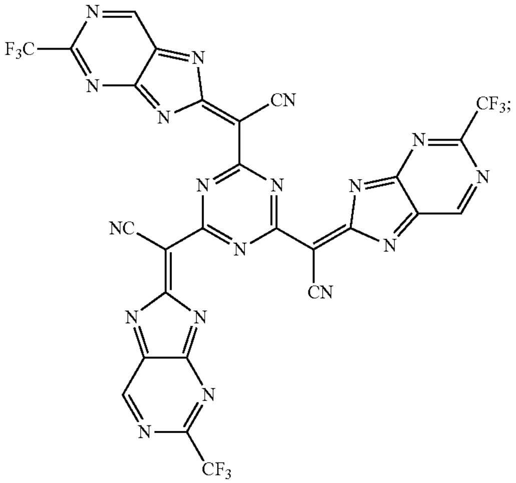
-continued
71
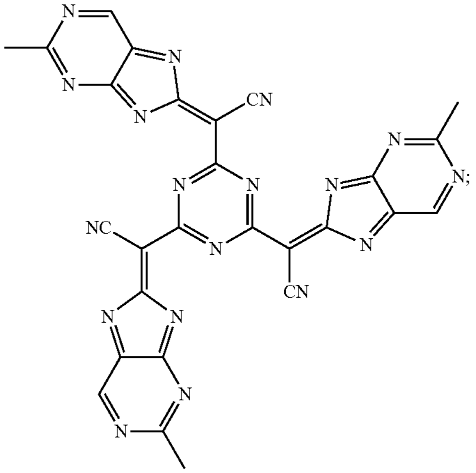
72
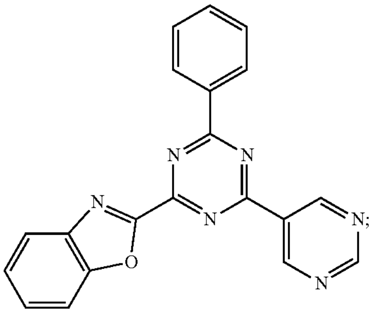
73
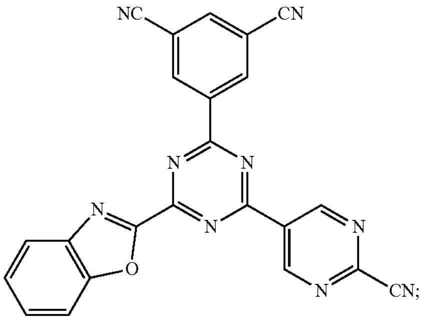
74
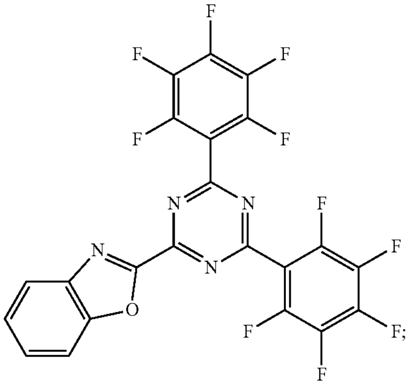

-continued
75
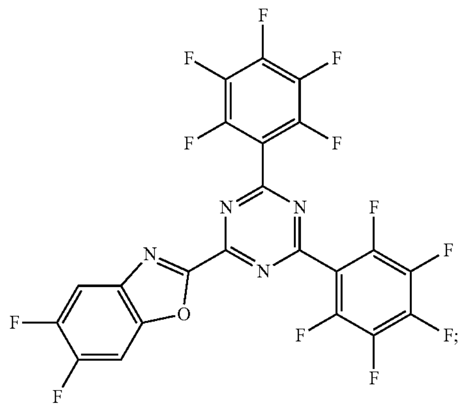
76
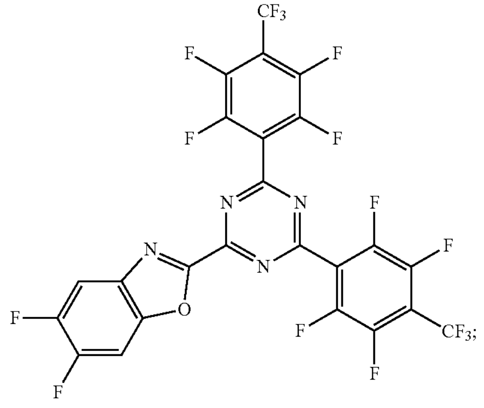
77
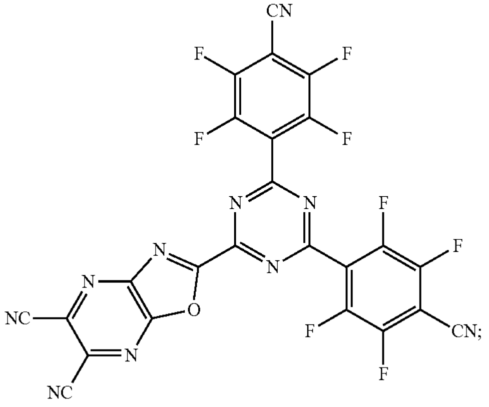
78
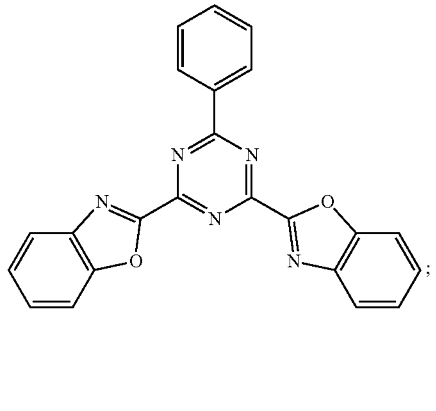
-continued
79
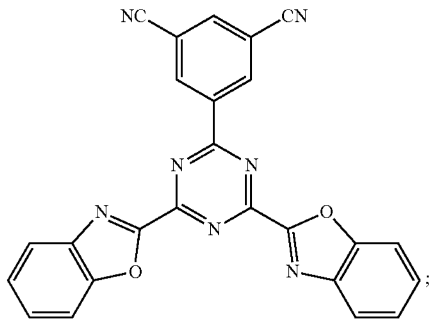
80
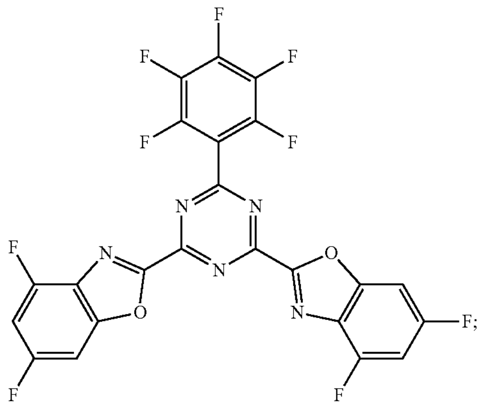
81
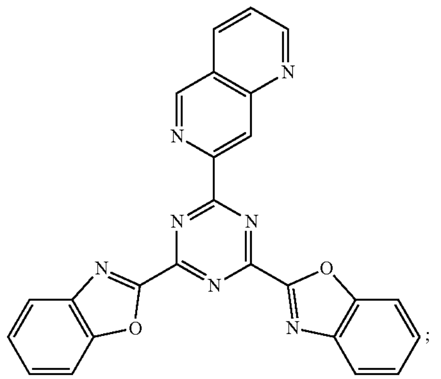
82
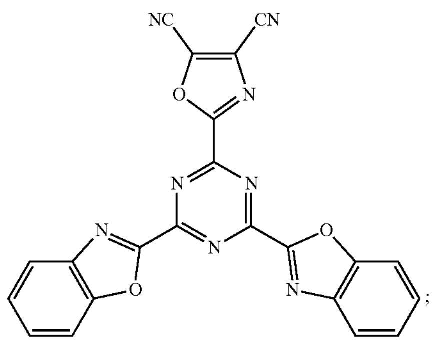

-continued
83
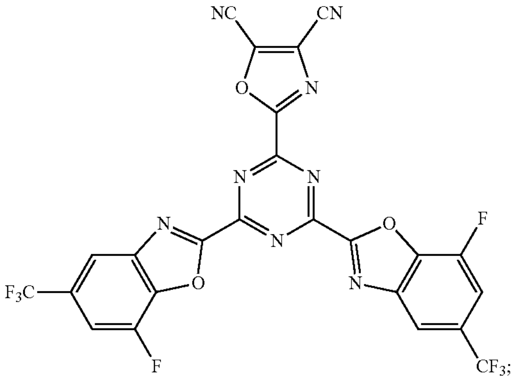
84
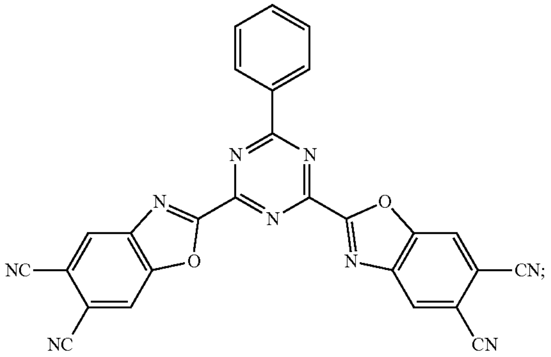
85
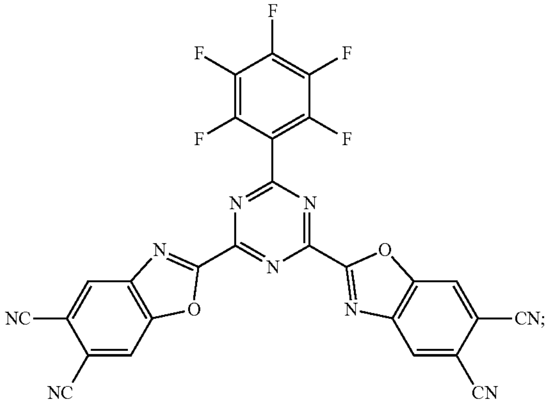
86
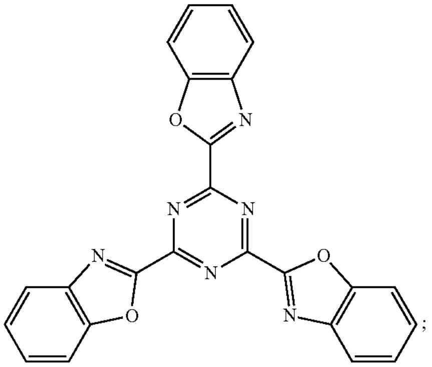
-continued
87
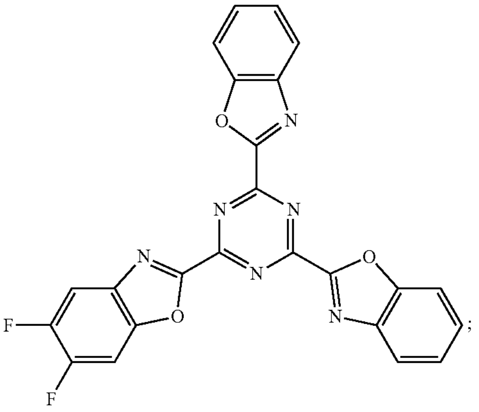
88
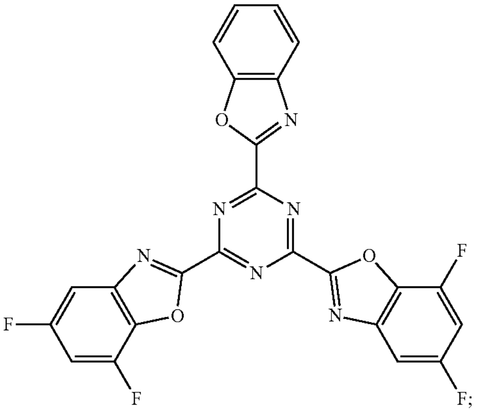
89
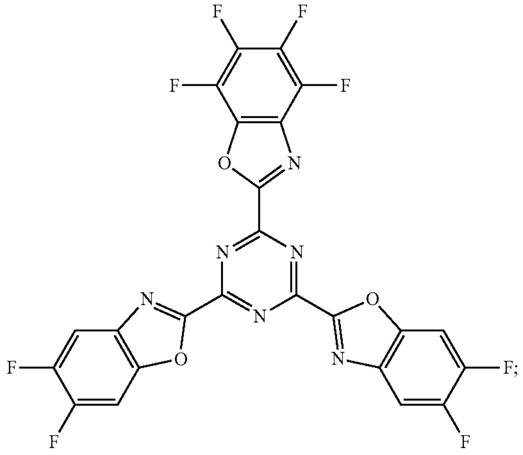

-continued
90
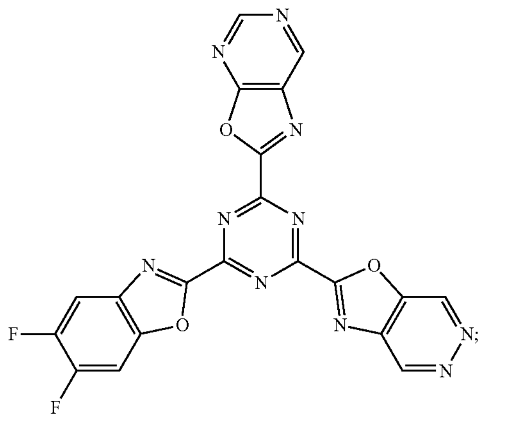
91
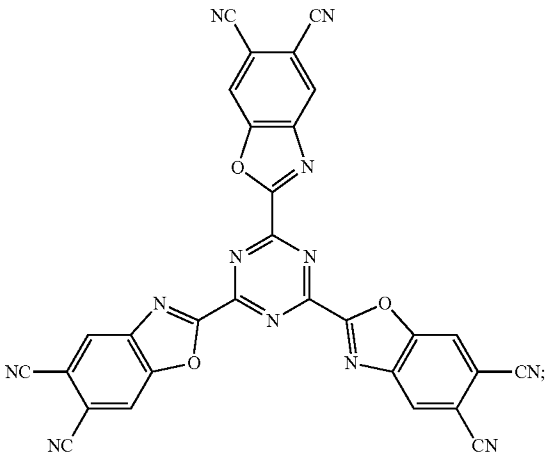
92
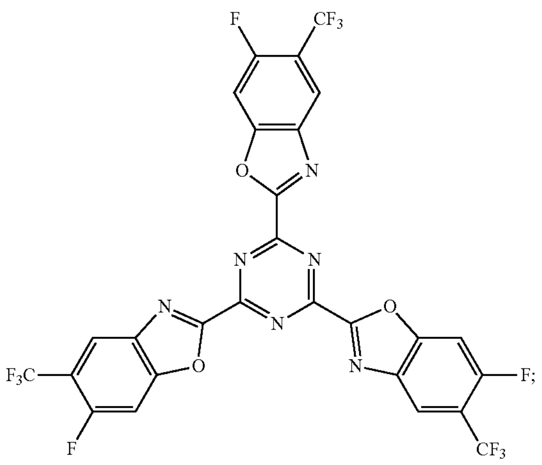
-continued
93
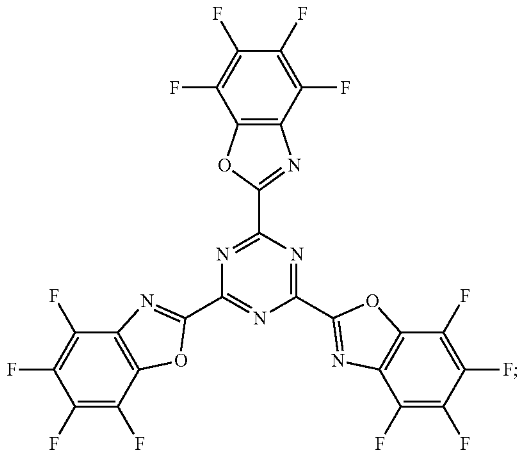
94
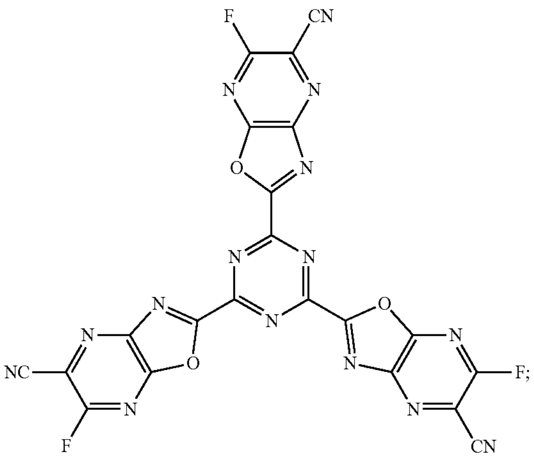
95
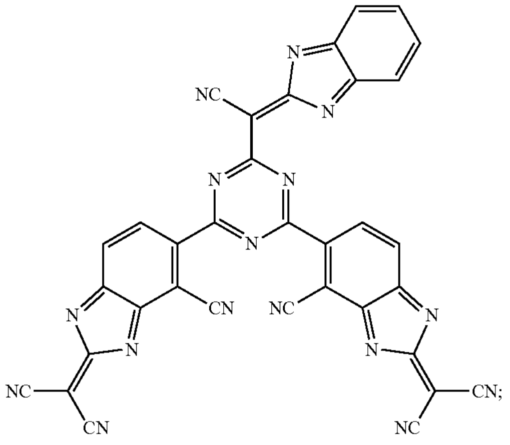

-continued
96
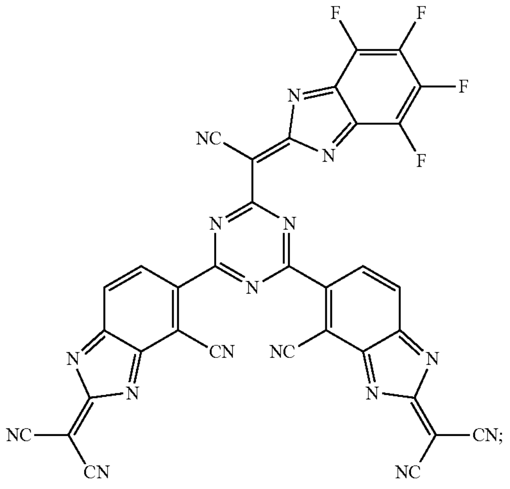
97
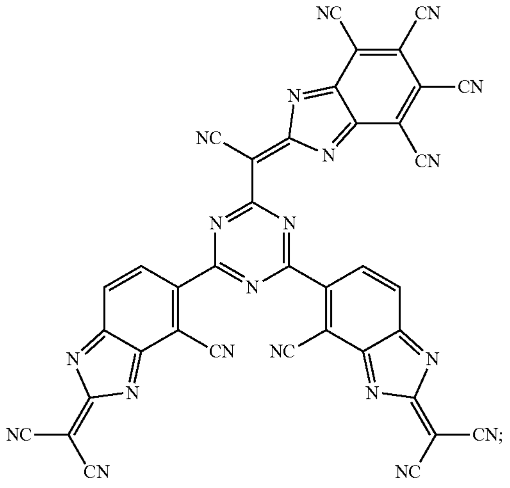
98
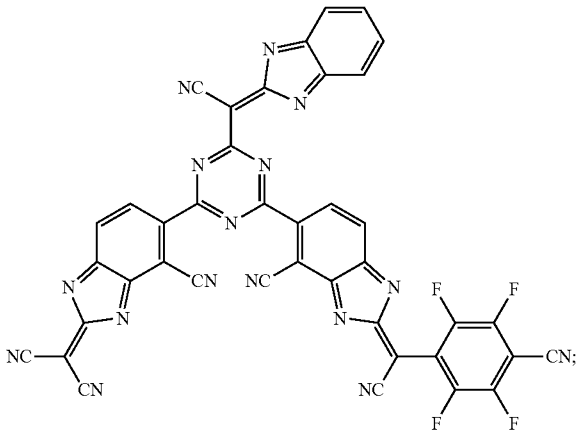
-continued
99
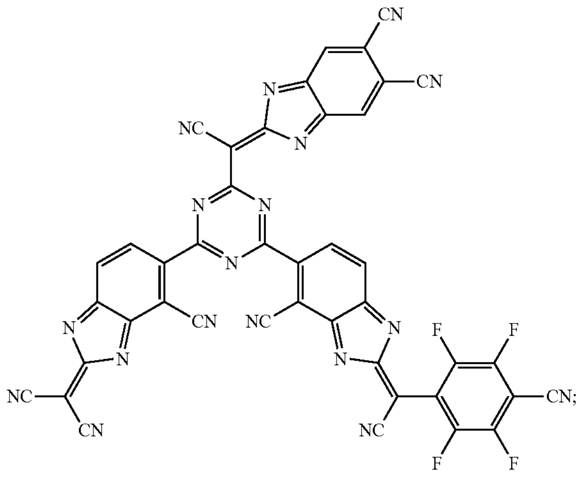
100
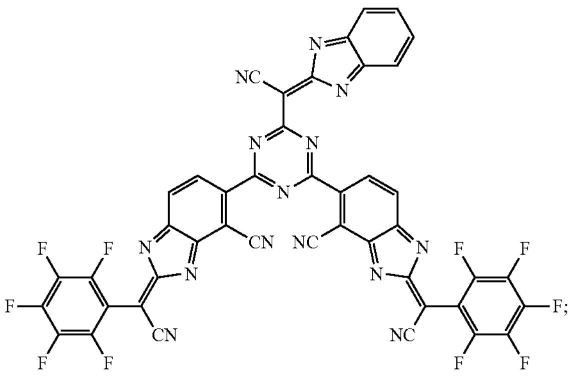
101
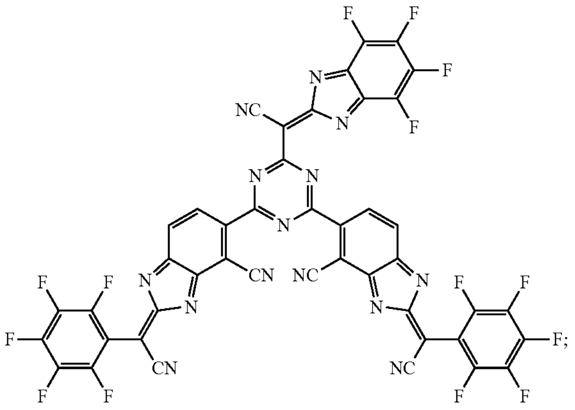

-continued
102
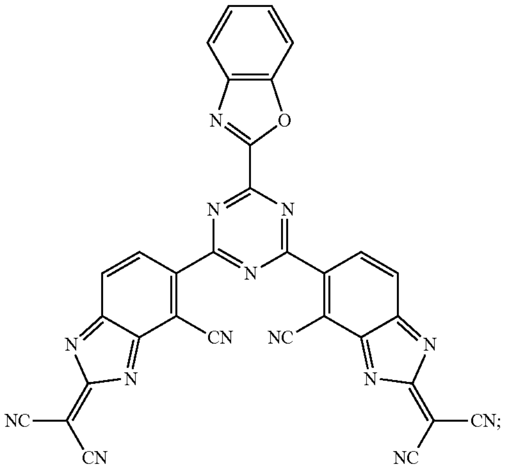
103
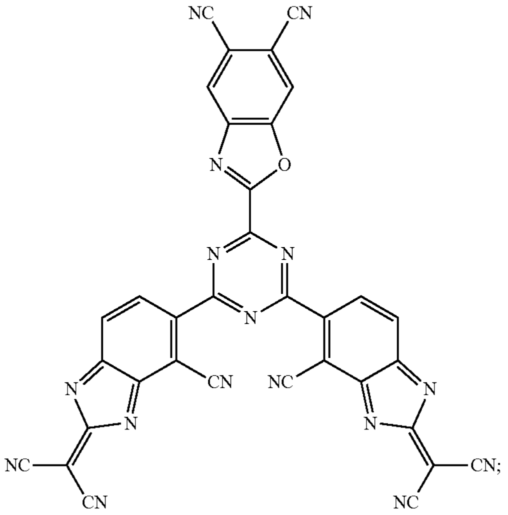
104
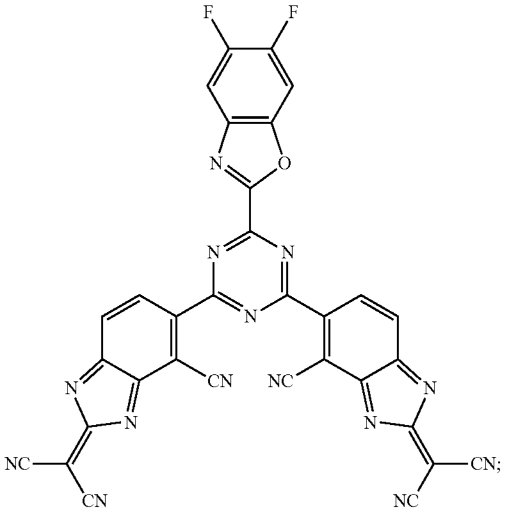
-continued
105
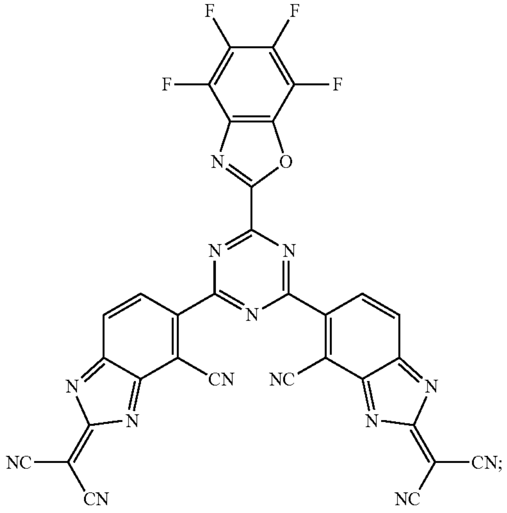
106
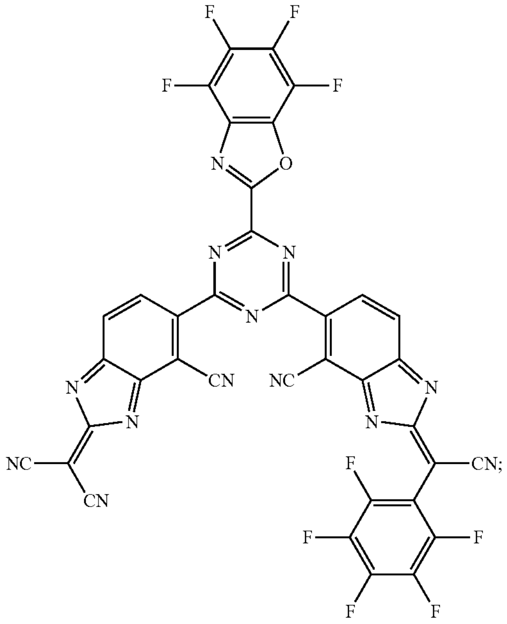
107
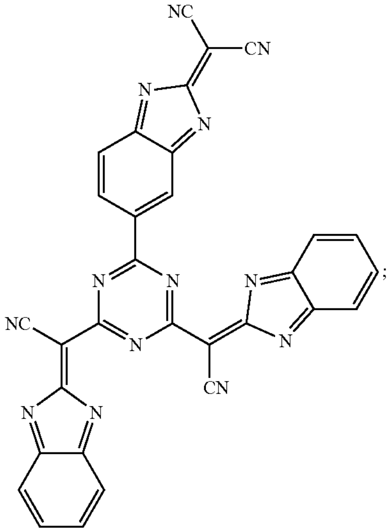

-continued
108
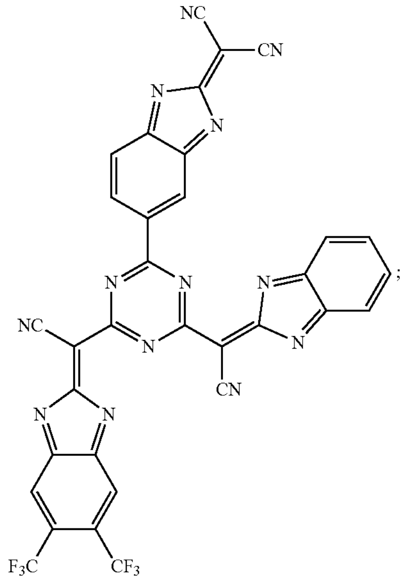
109
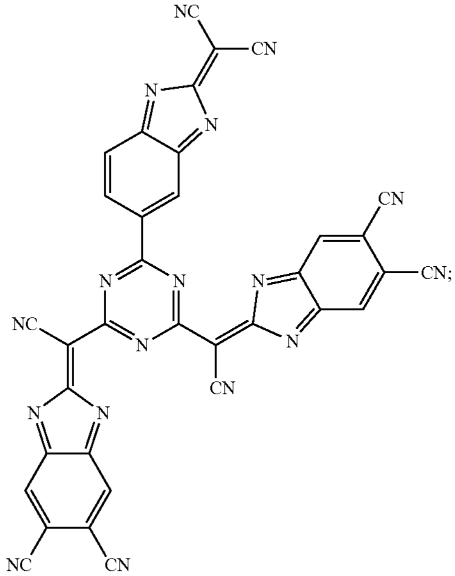
-continued
110
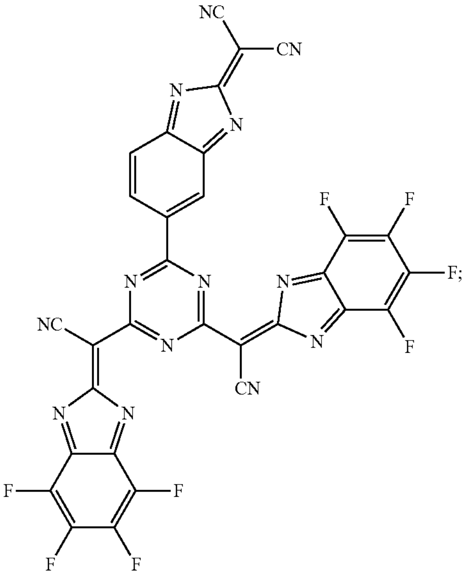
111
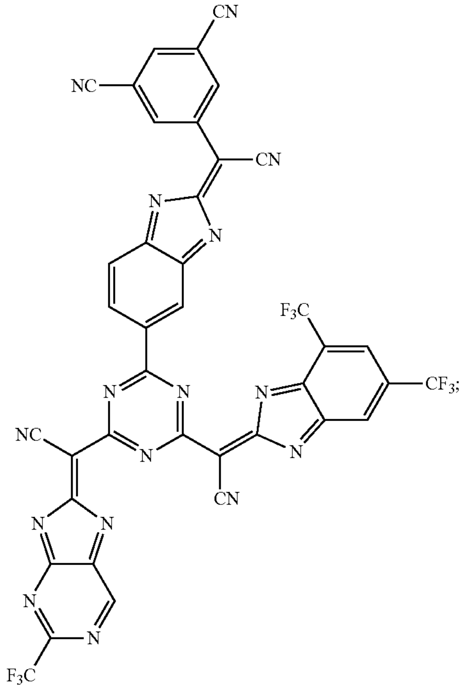

-continued
112
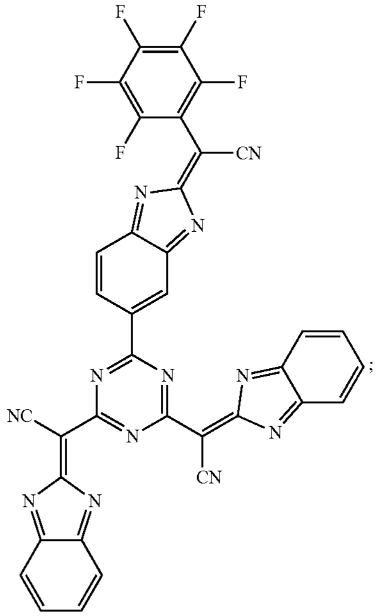
113
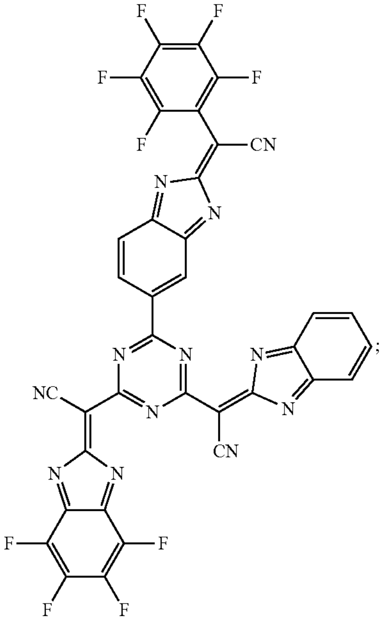
-continued
114
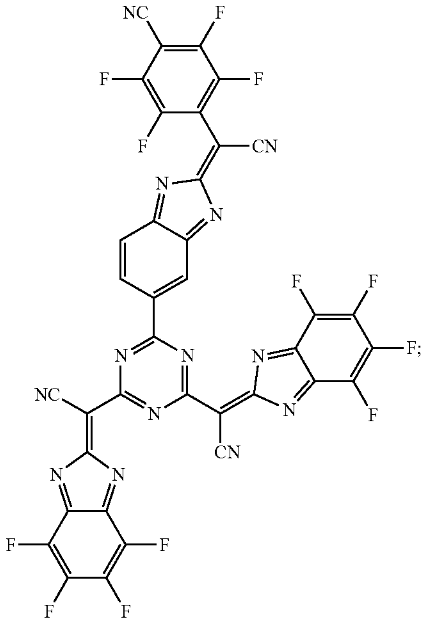
115
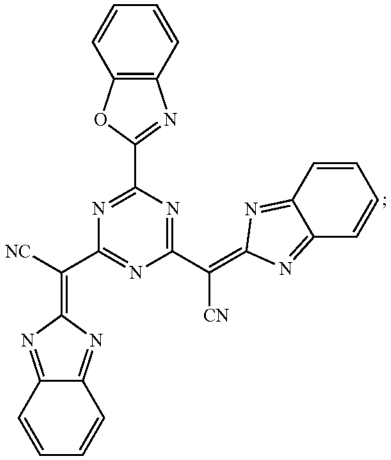
116
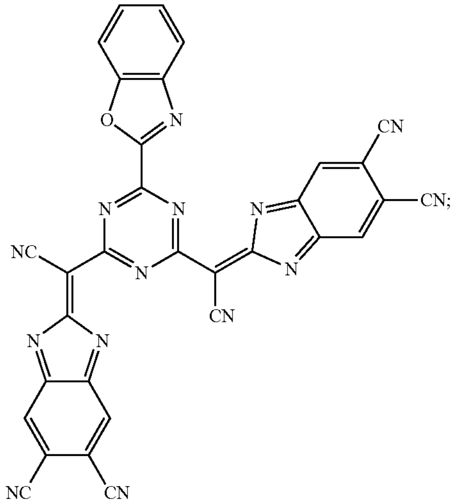

-continued
117
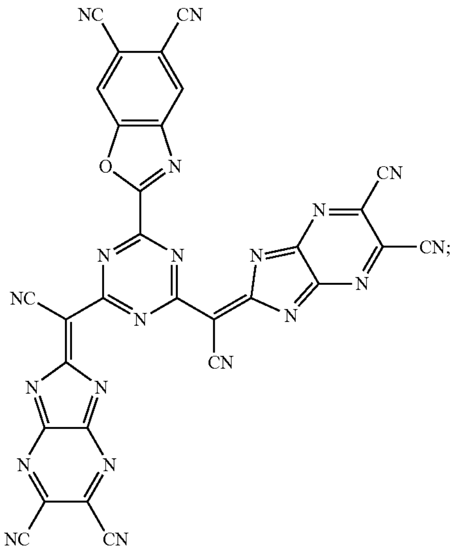
118
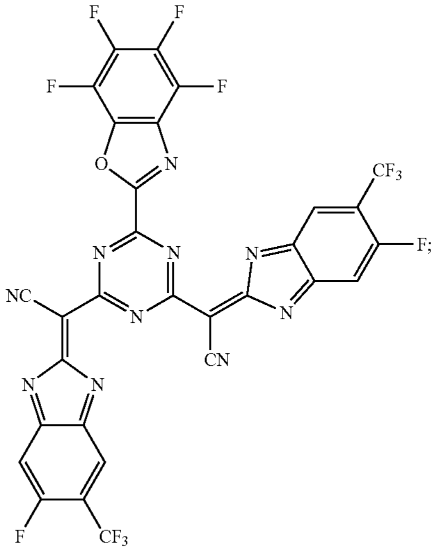
119
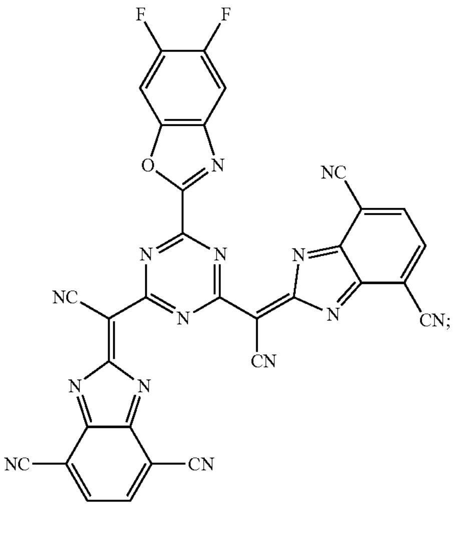
-continued
120
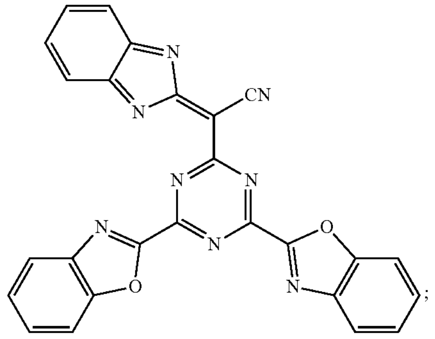
121
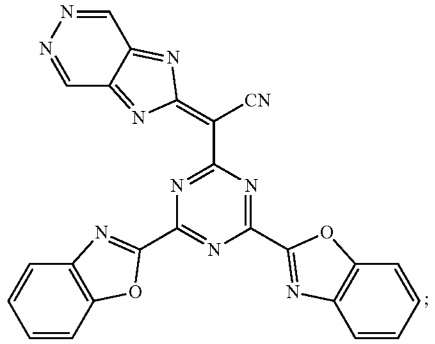
122
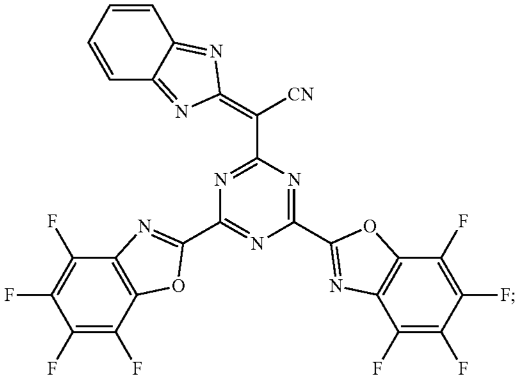
123
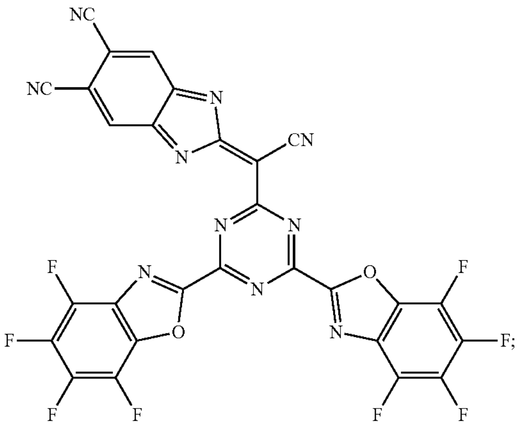

-continued
124
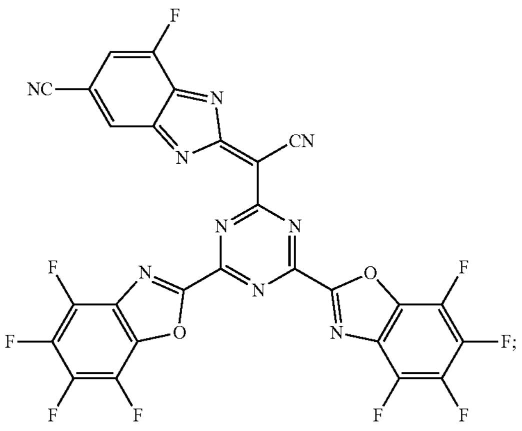
125
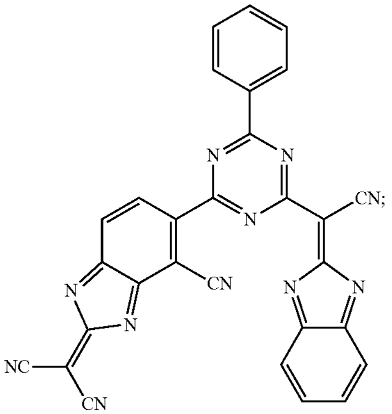
126
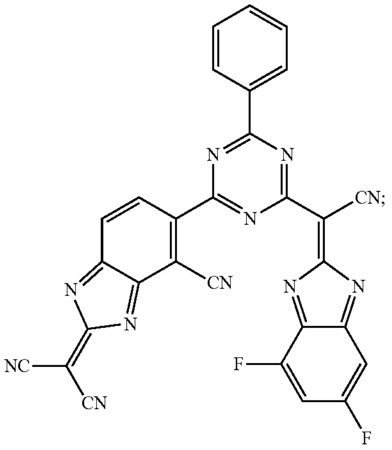
-continued
127
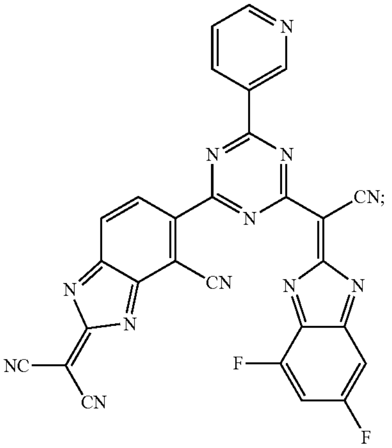
128
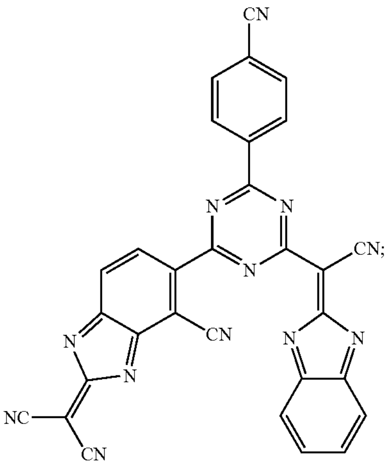
129
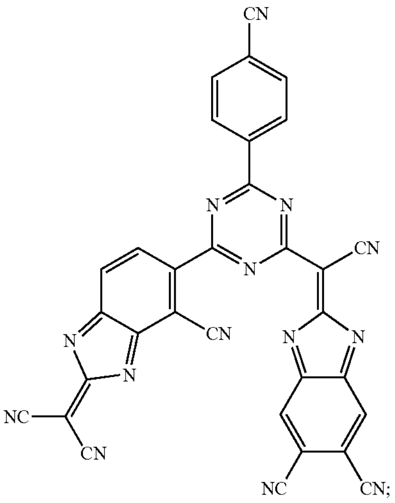

130
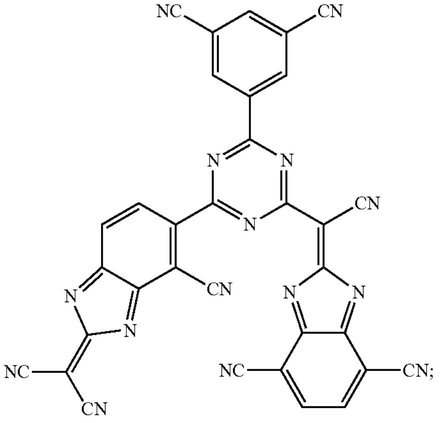
131
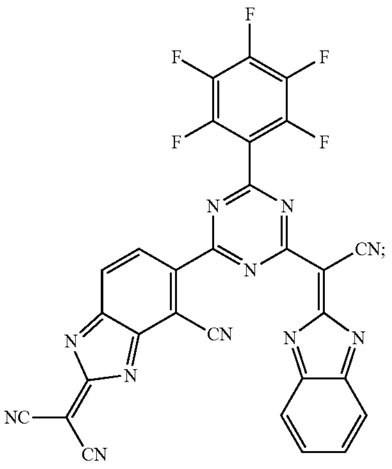
132
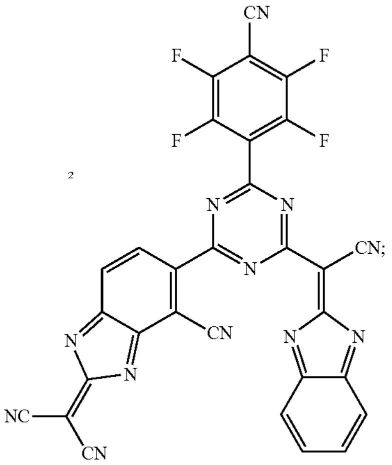
133
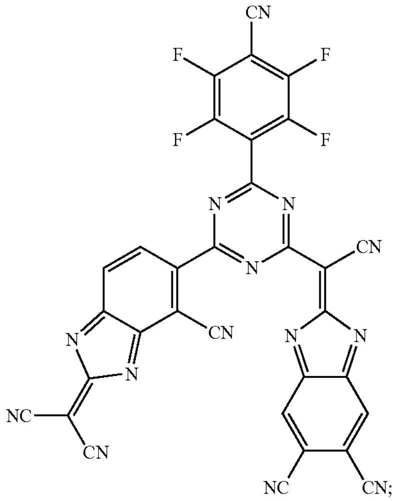
134
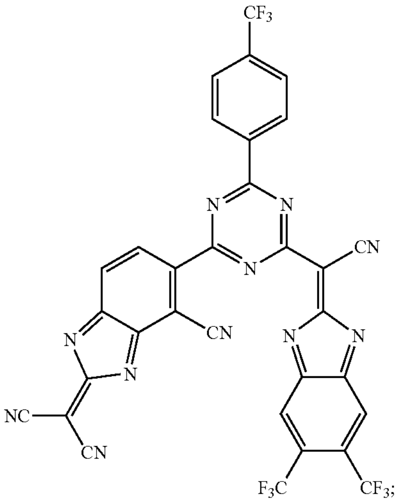
135
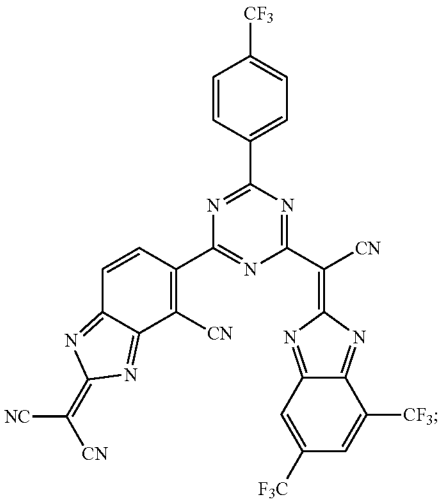

-continued
136
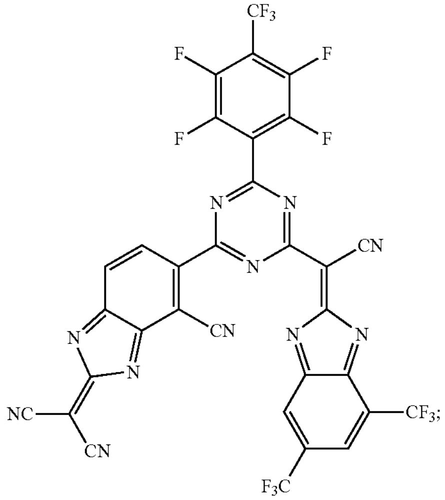
137
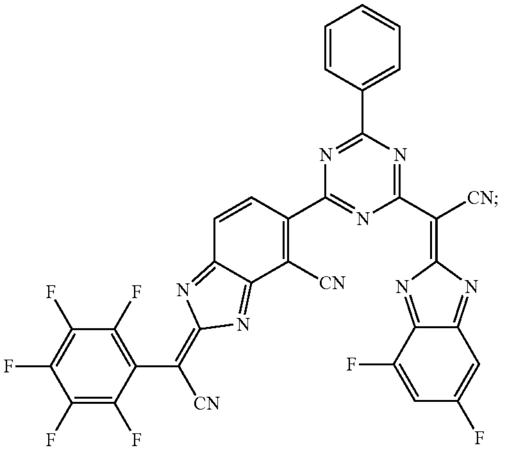
138
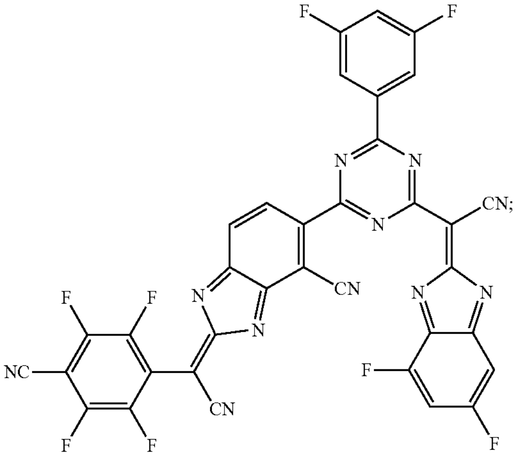
-continued
139
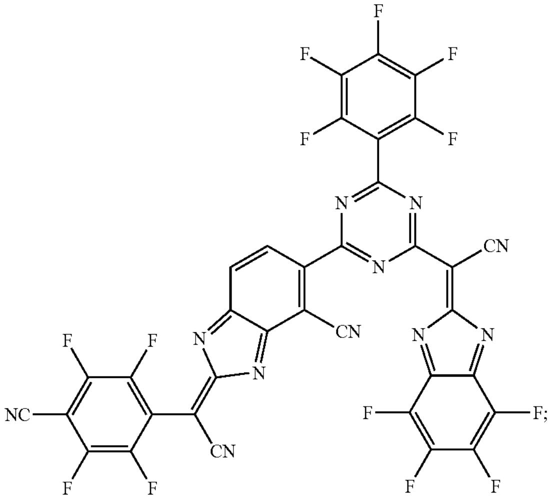
140
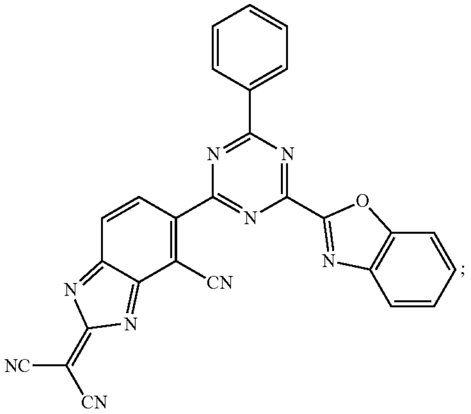
141
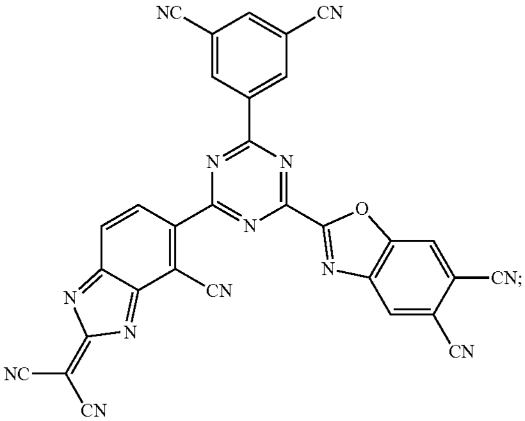

-continued
142
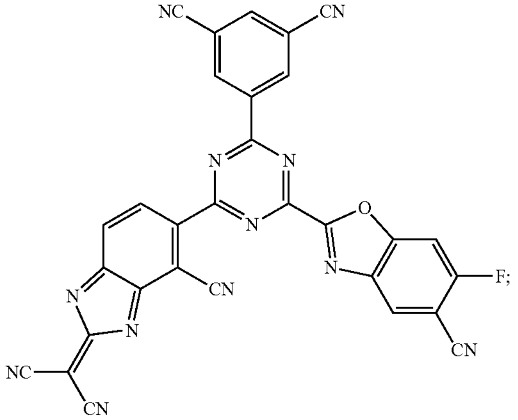
143
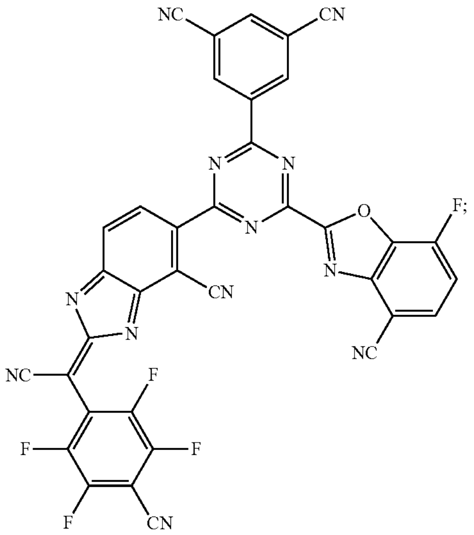
144
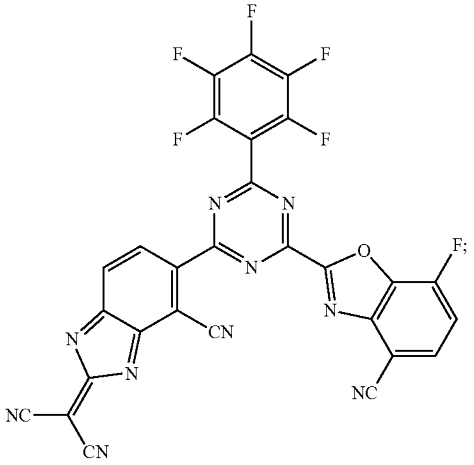
-continued
145
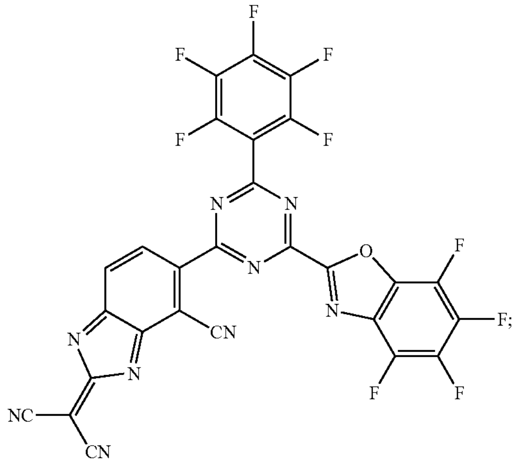
146
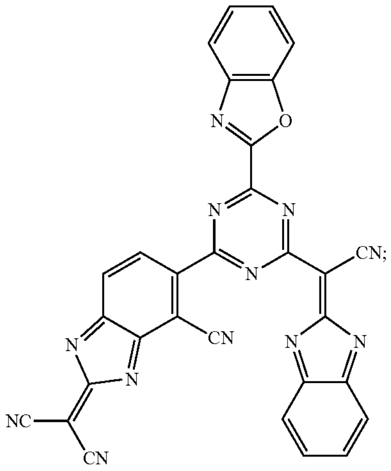
147
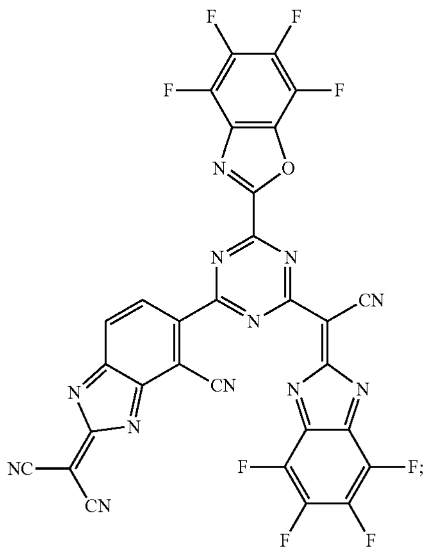

148
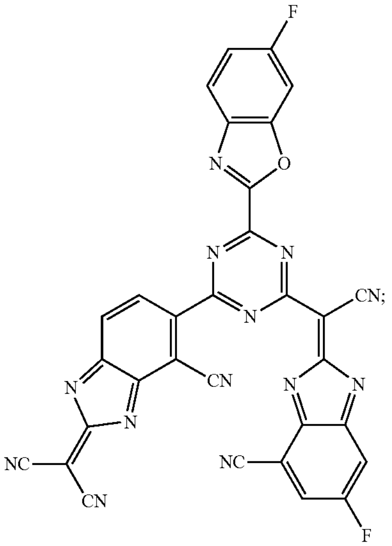
149
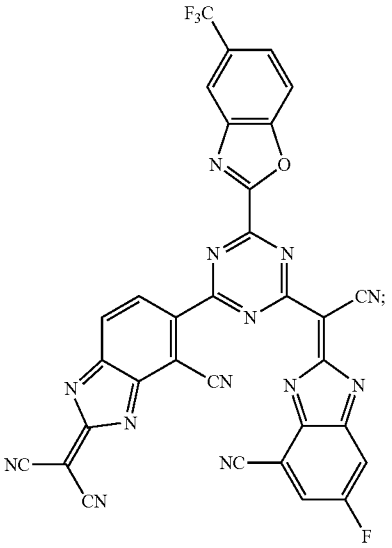
150
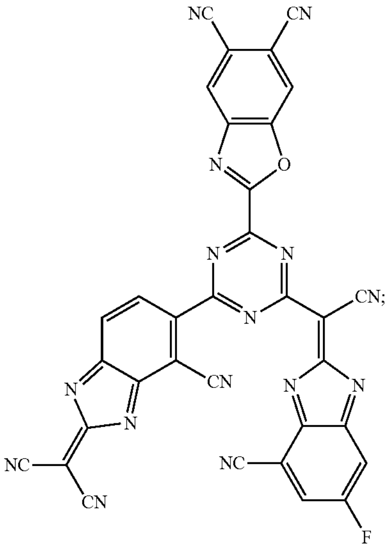
151
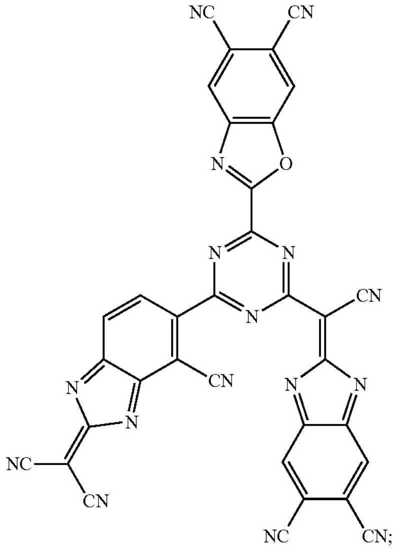
152
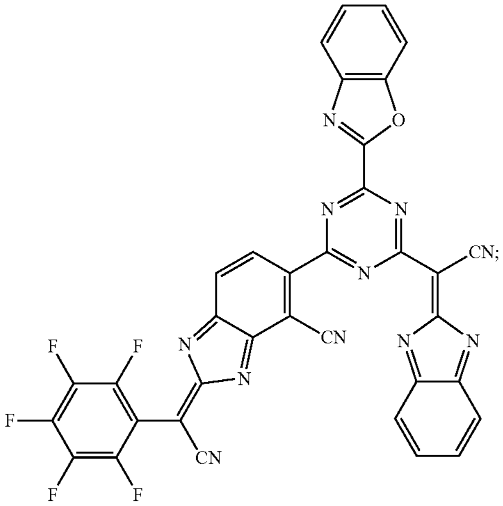
153
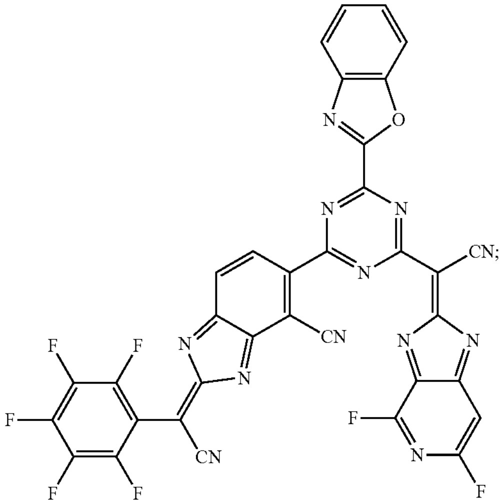

-continued
154
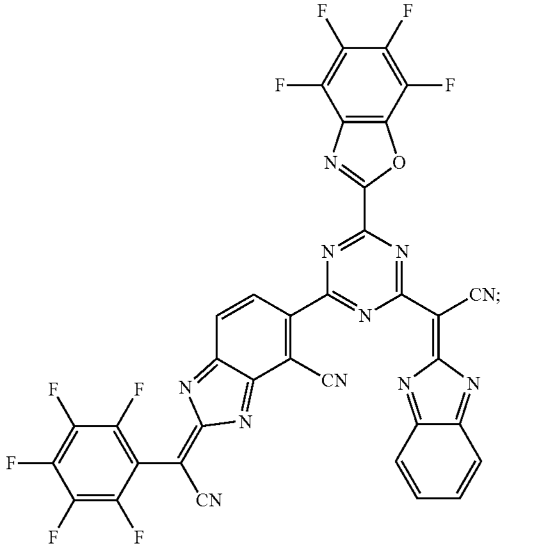
155
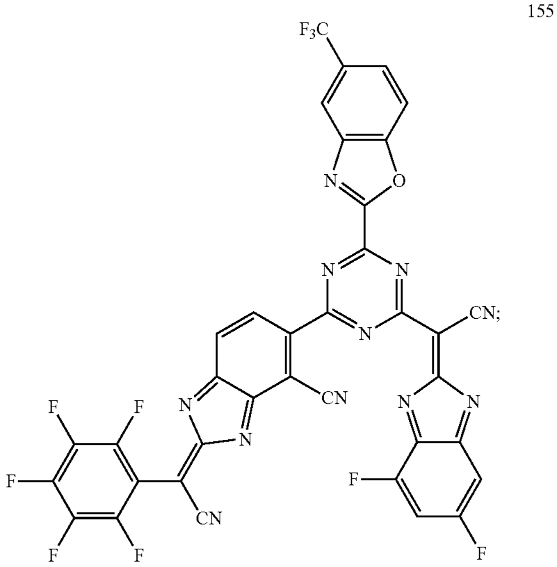
156
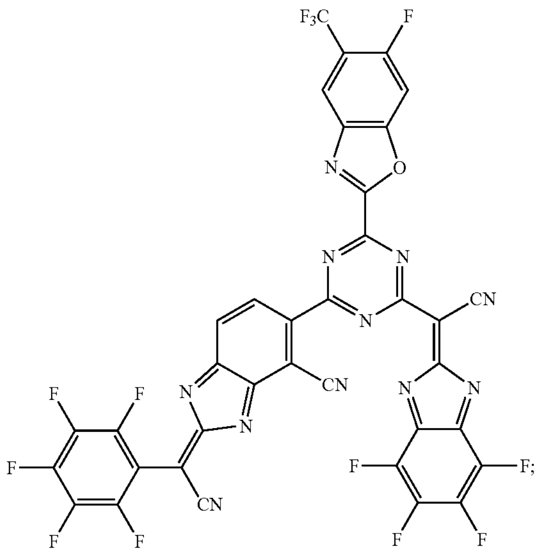
-continued
157
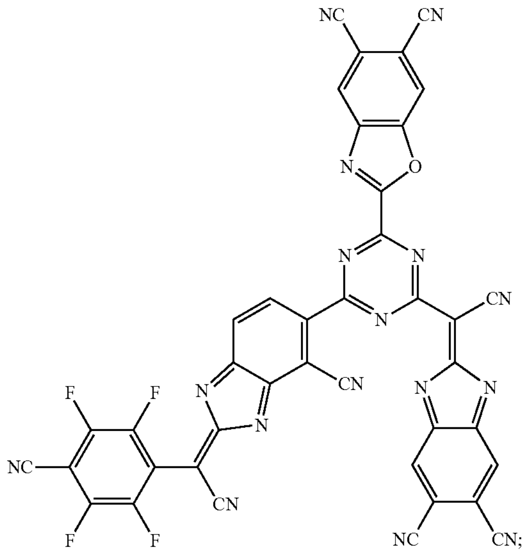
158
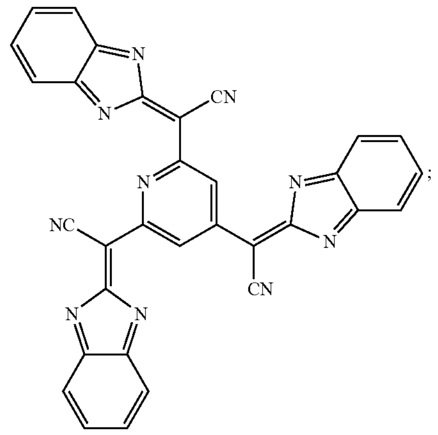
159
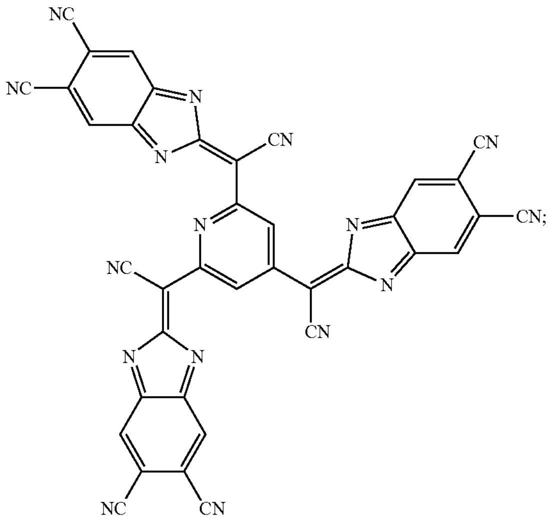

-continued
160
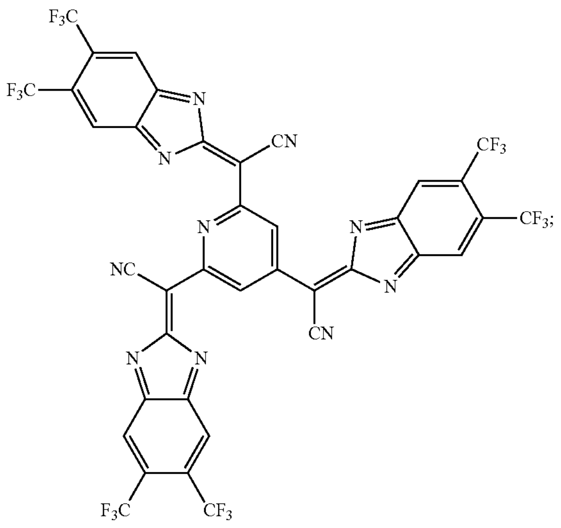
161
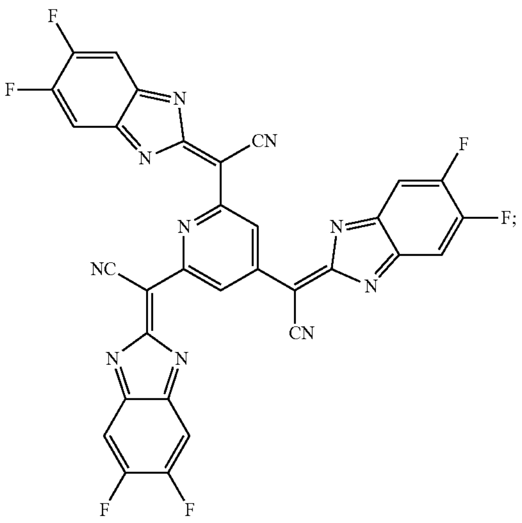
162
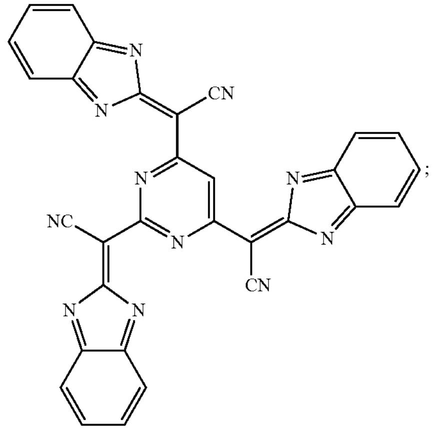
-continued
163
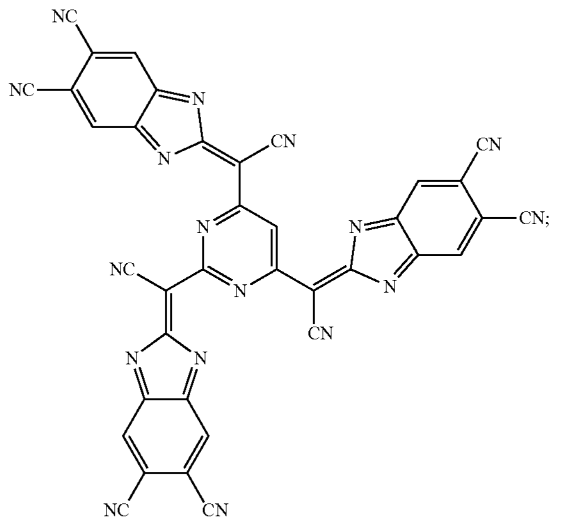
164
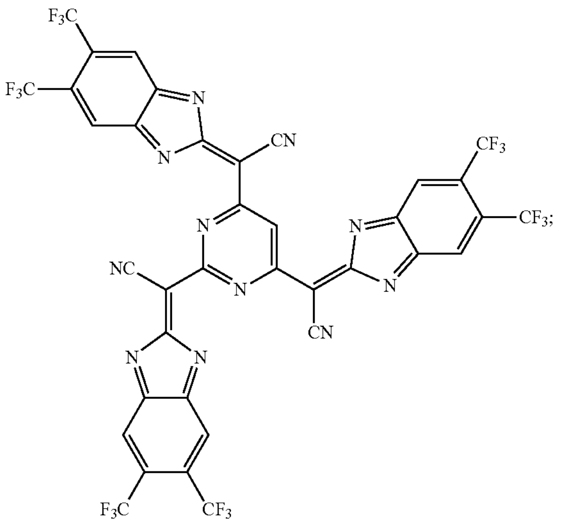
165
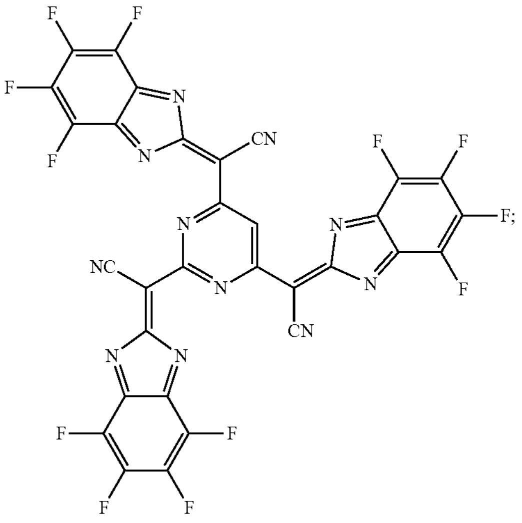

166
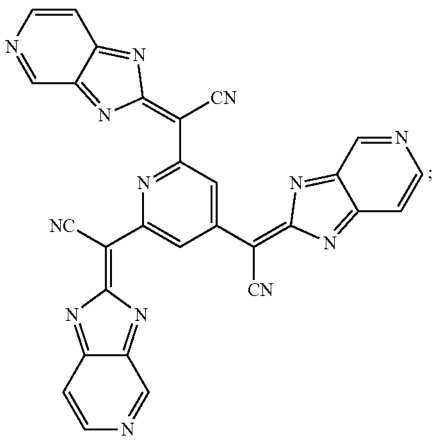
167
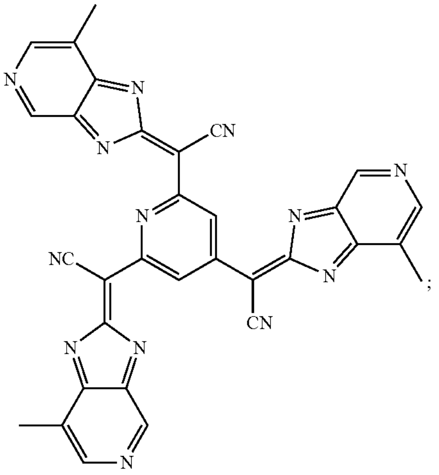
168
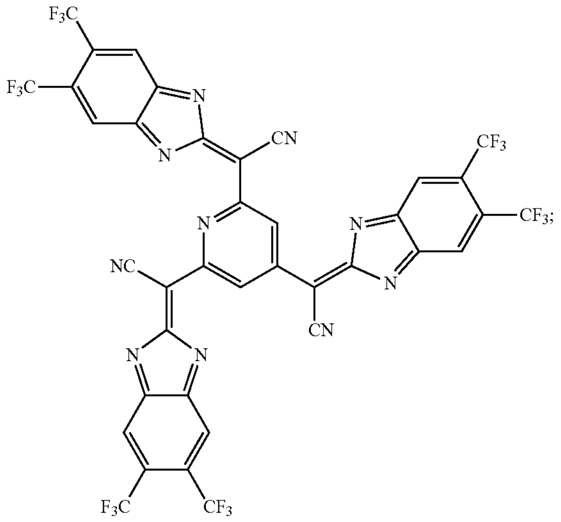
169
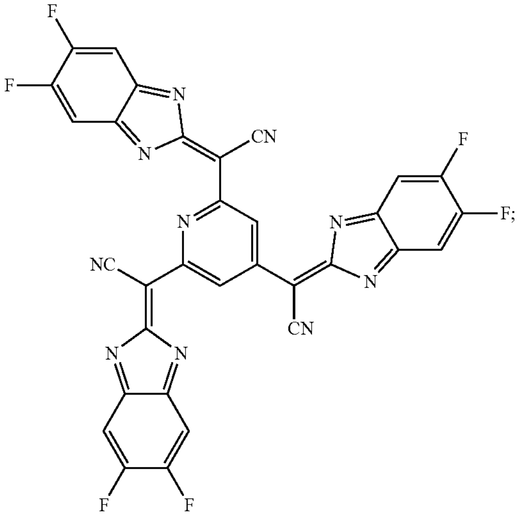
170
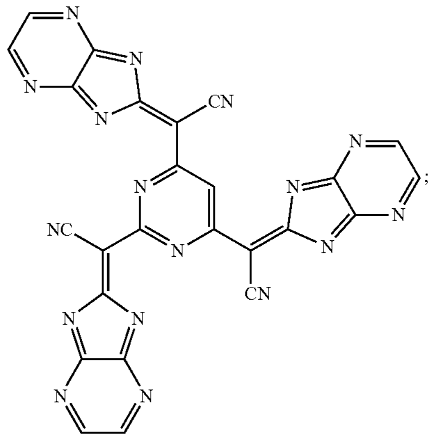
171
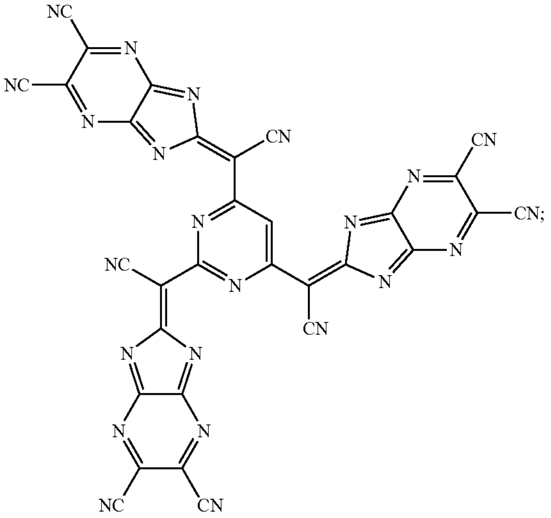

-continued
172
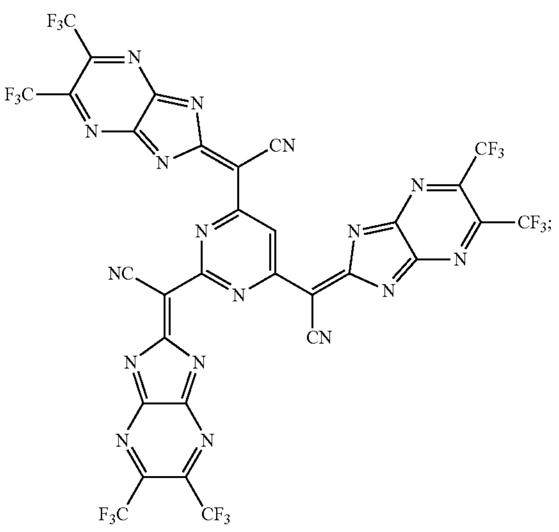
173
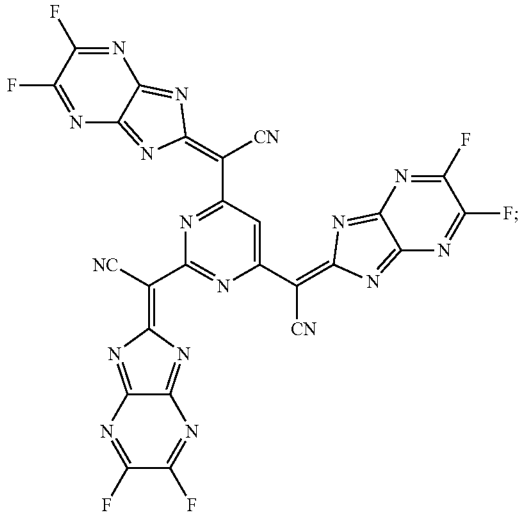
174
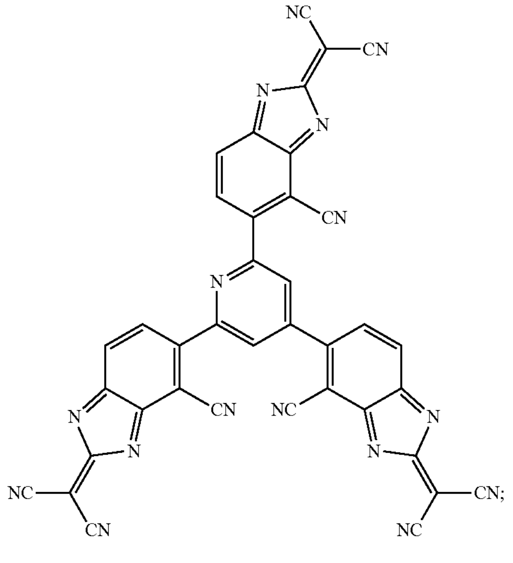
-continued
175
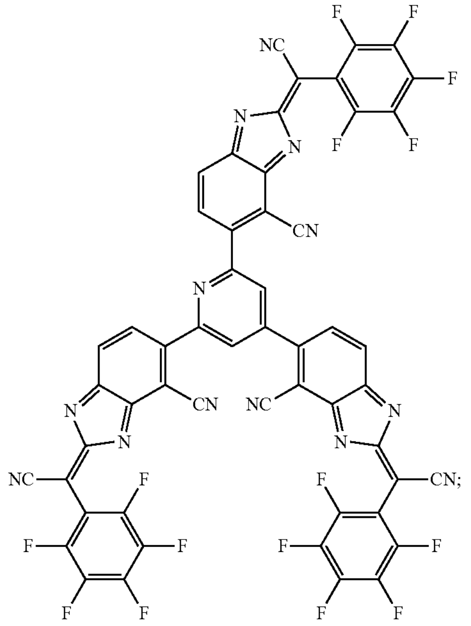
176
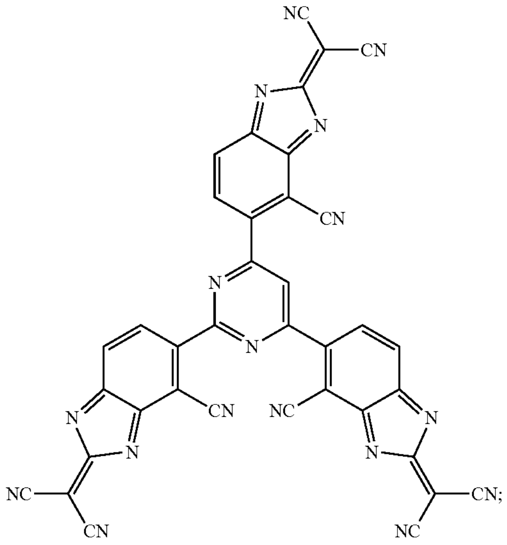
177
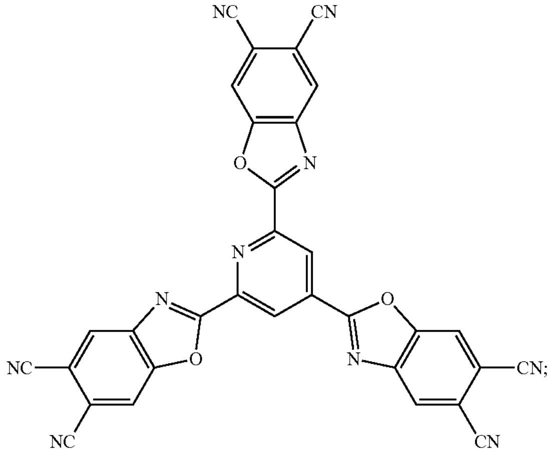
or -continued
178
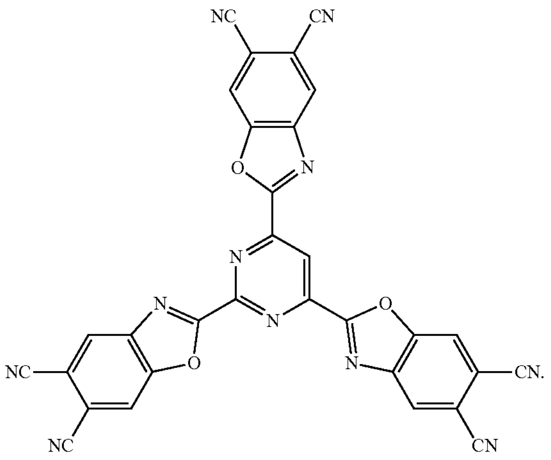
24. The organic light emitting display device of claim 18, wherein the organic compound has one of the following structures:
1
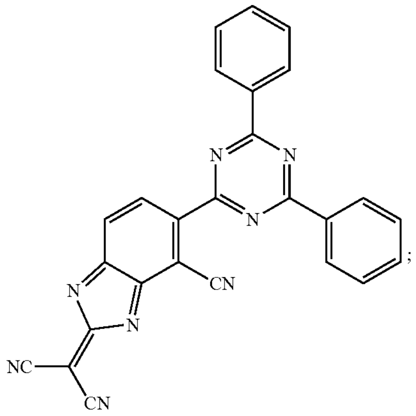
2
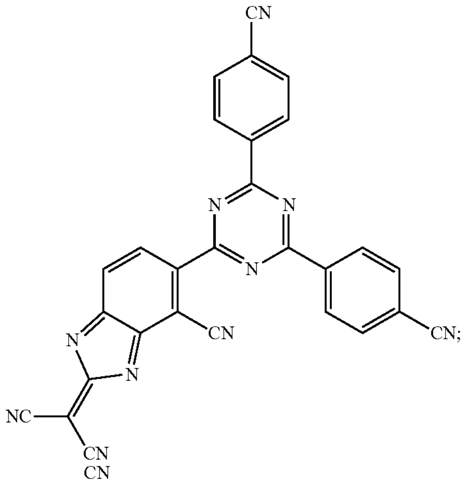
-continued
3
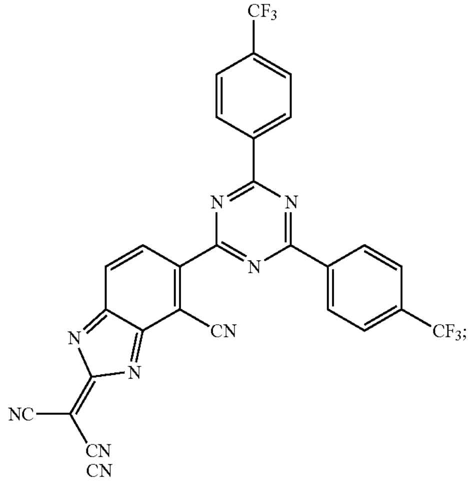
4
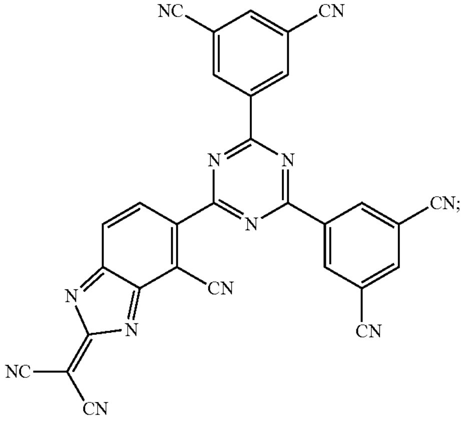
5
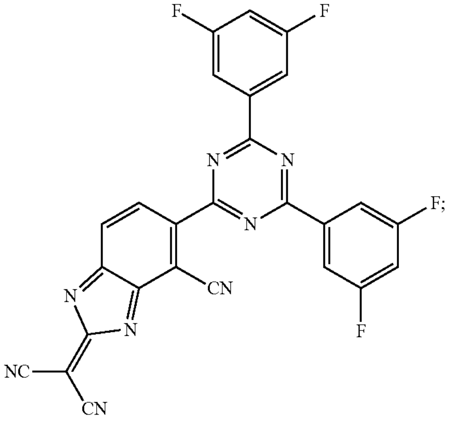

-continued
6
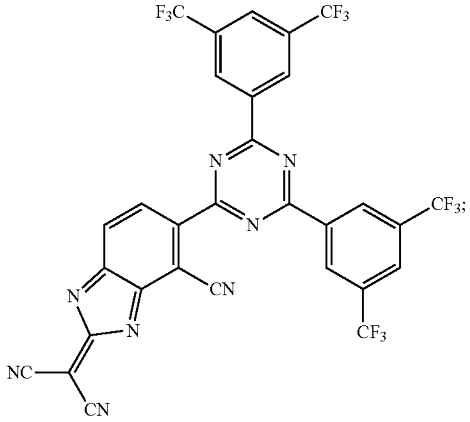
7
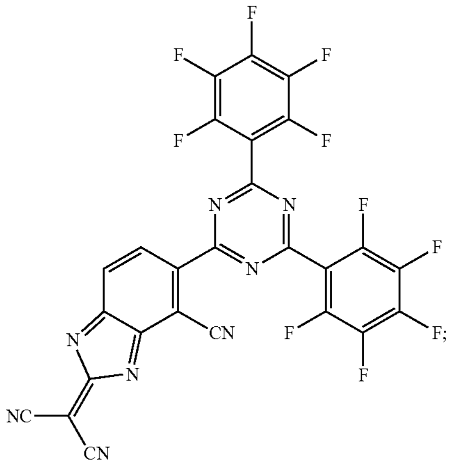
8
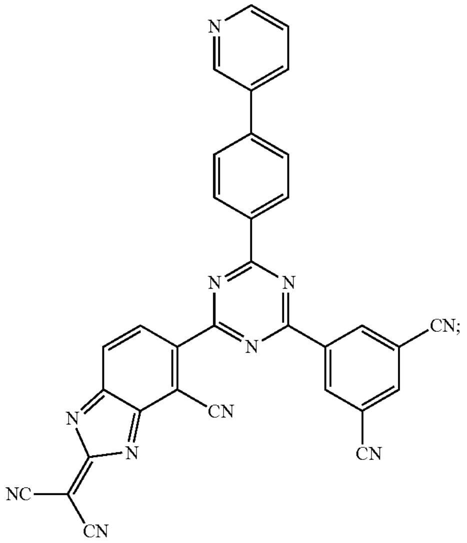
-continued
9
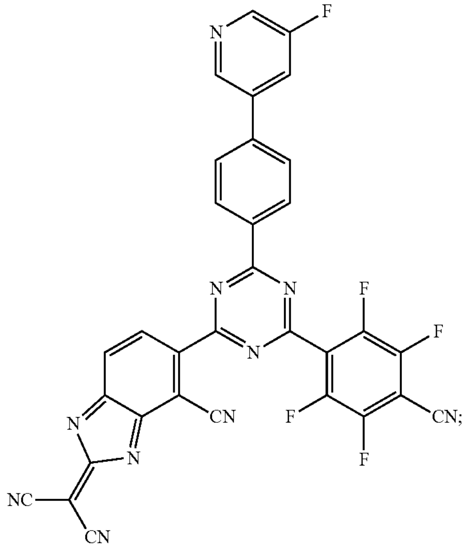
10
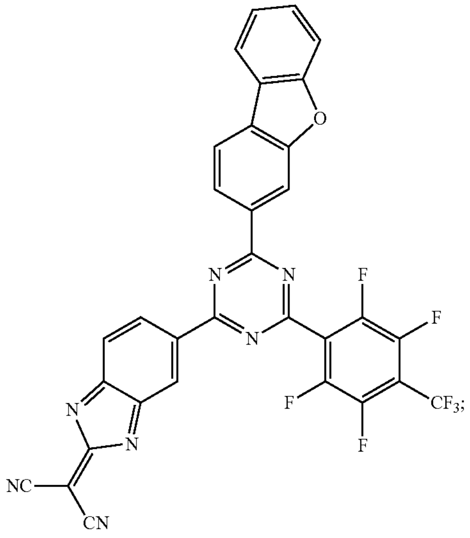
11
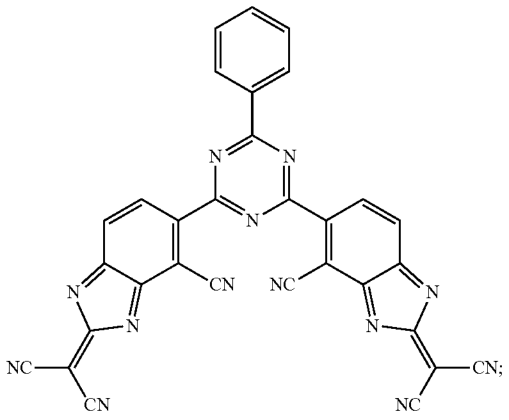

-continued
12
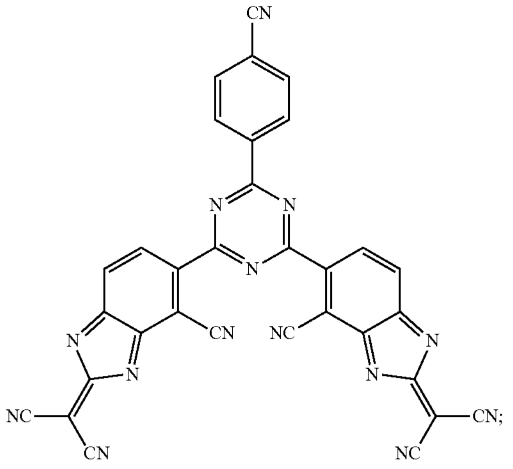
13
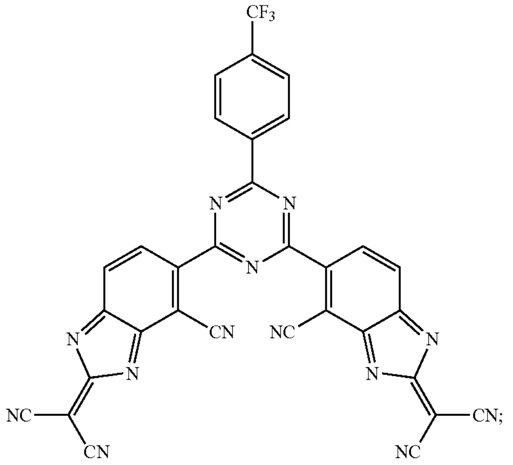
14
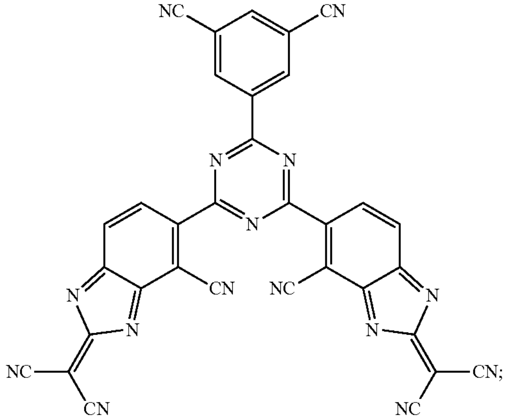
-continued
15
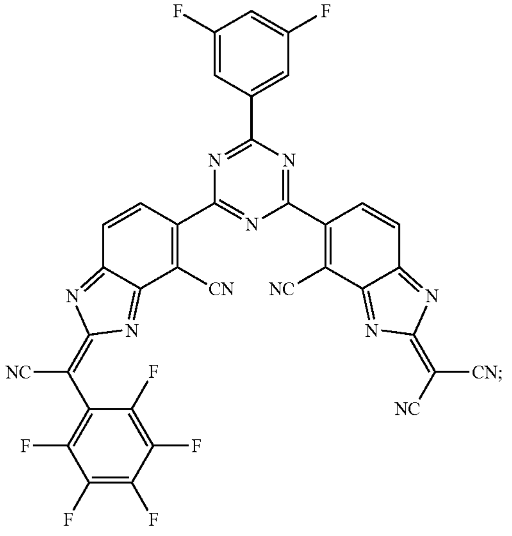
16
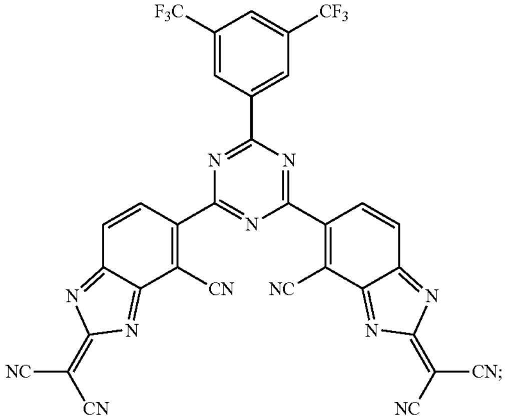
17
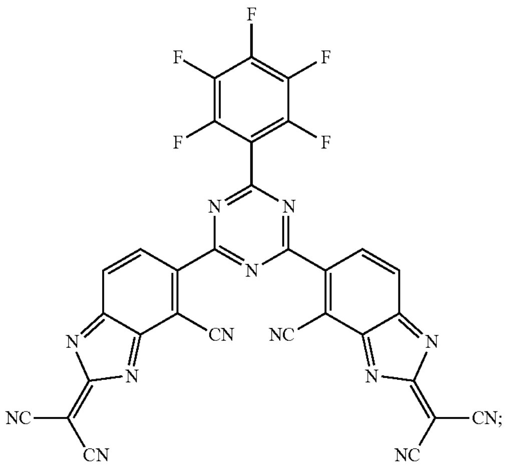

-continued
18
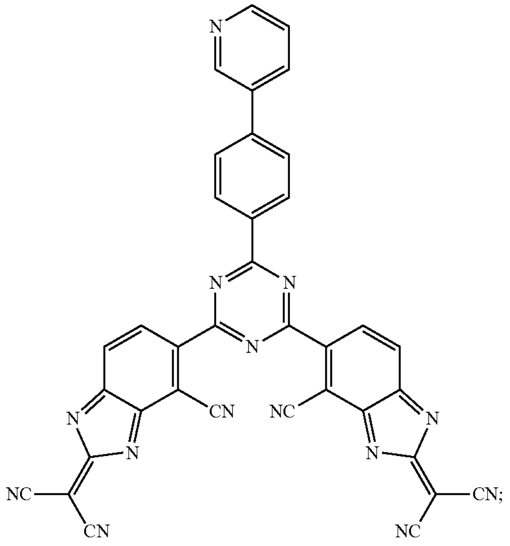
19
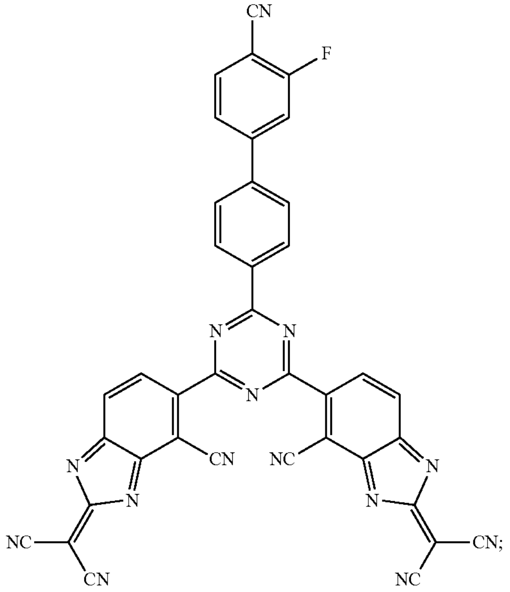
20
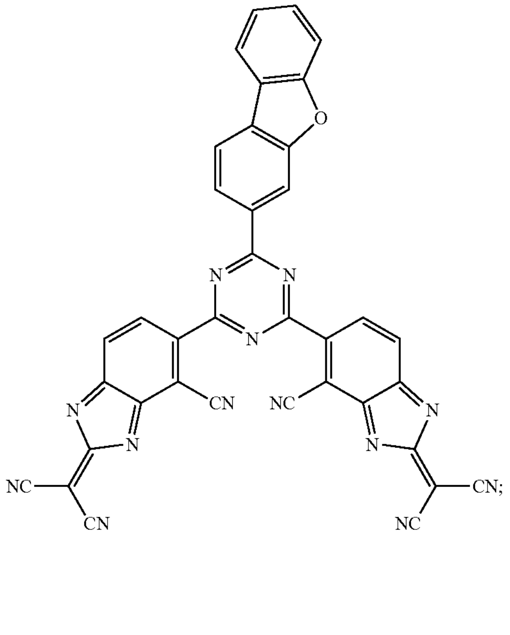
-continued
21
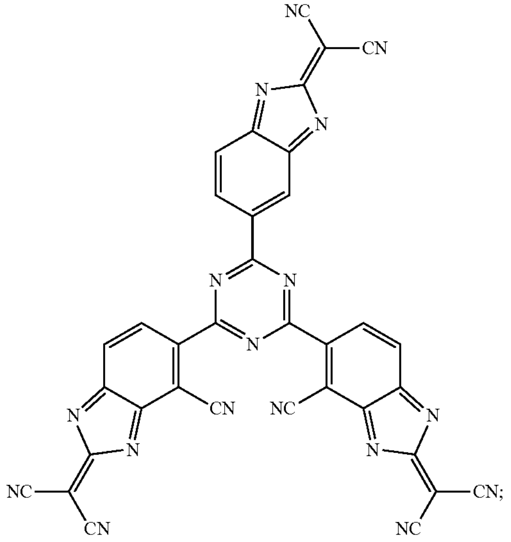
22
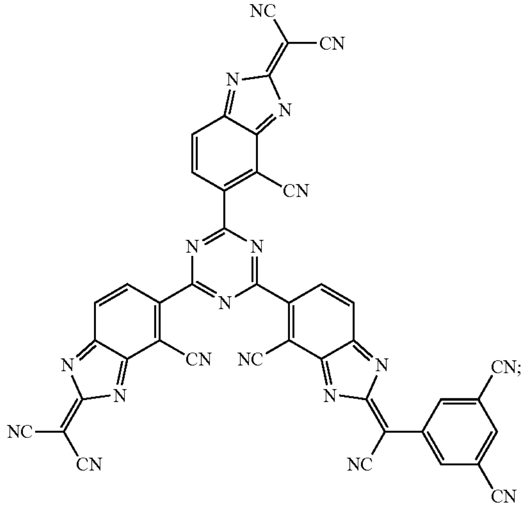
23
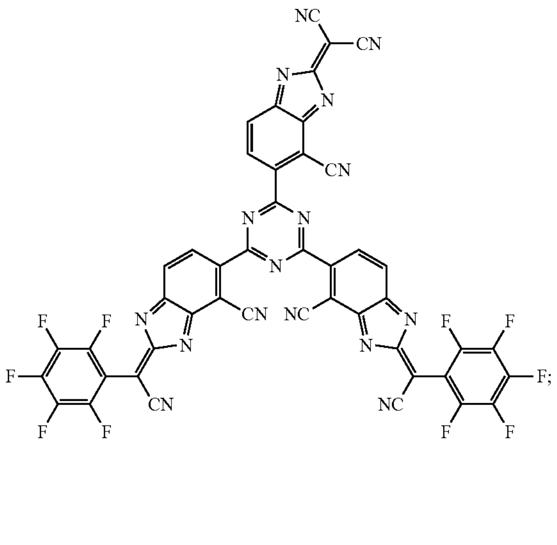

-continued
24
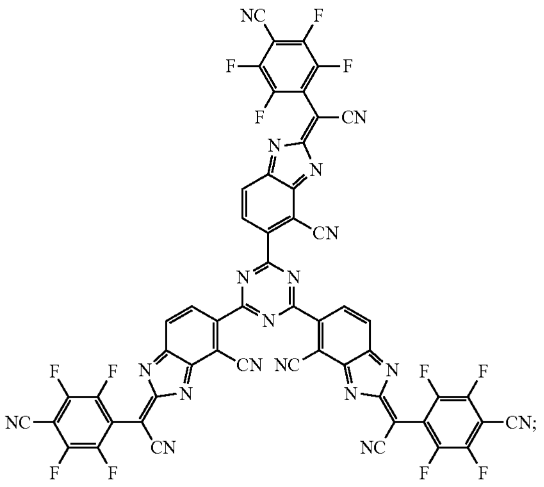
25
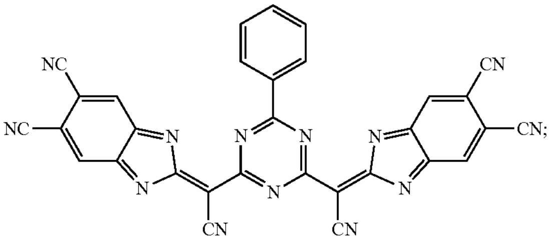
26
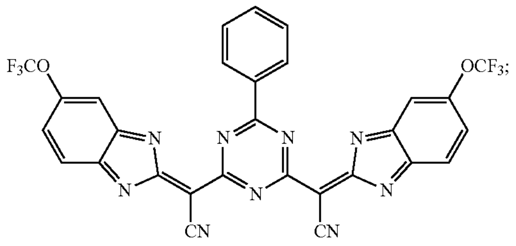
27
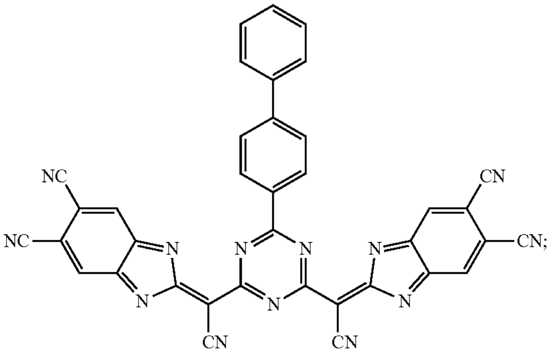
-continued
28
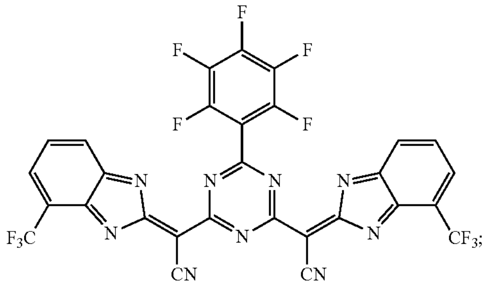
29
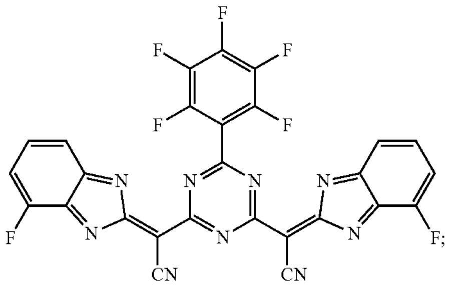
30
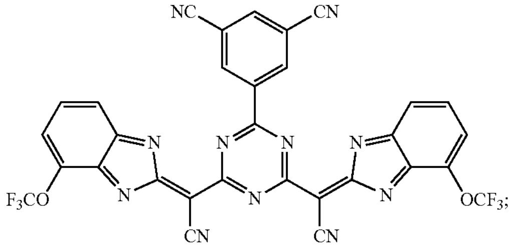
31
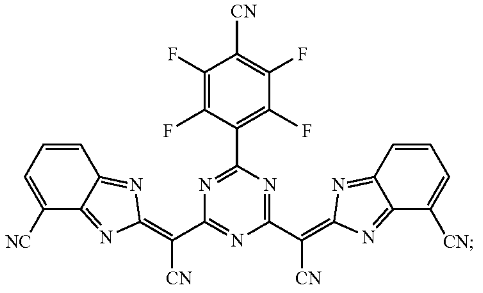
32
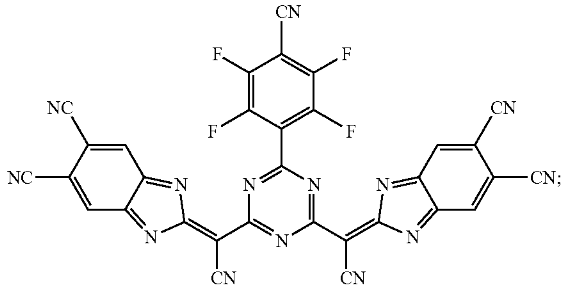

-continued
33
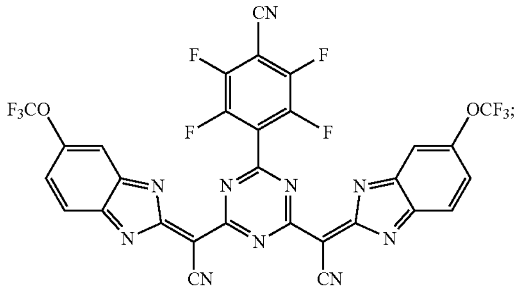
34
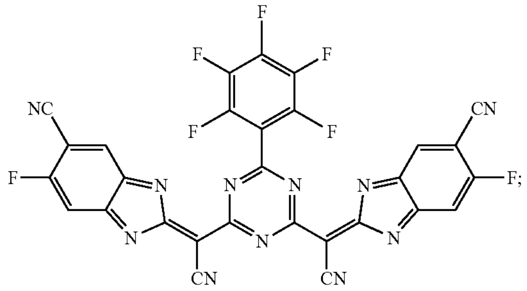
35
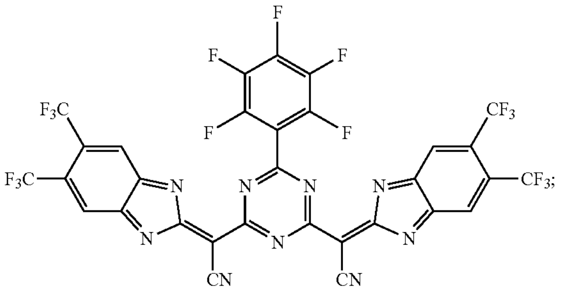
36
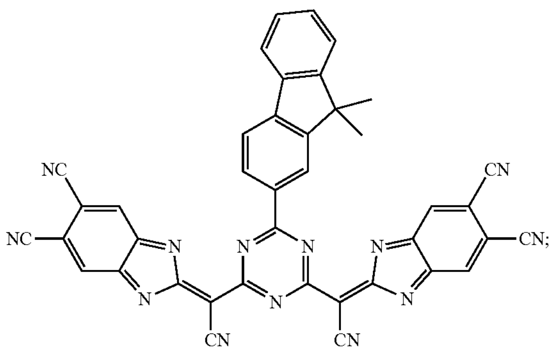
37
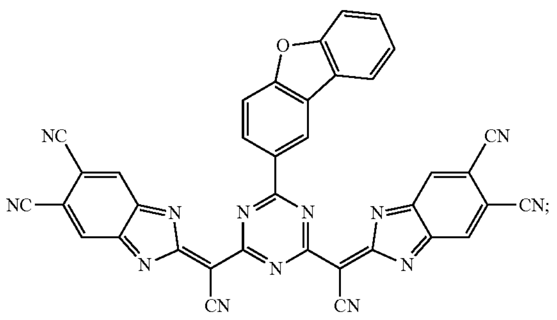
-continued
38
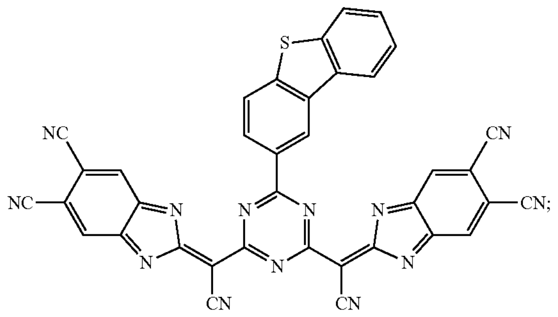
39
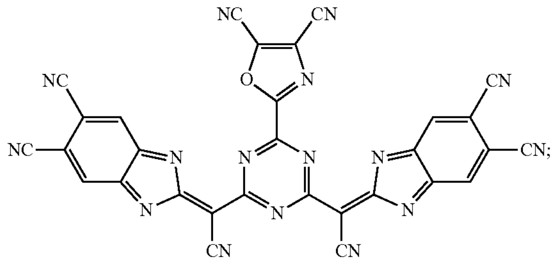
40
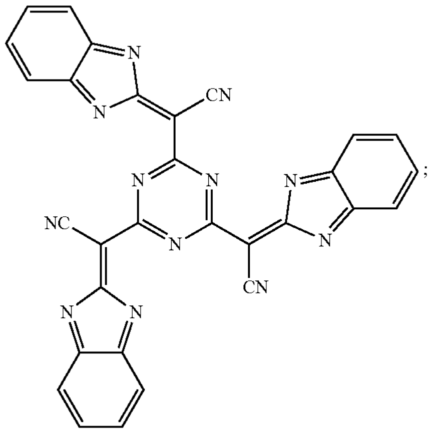
41
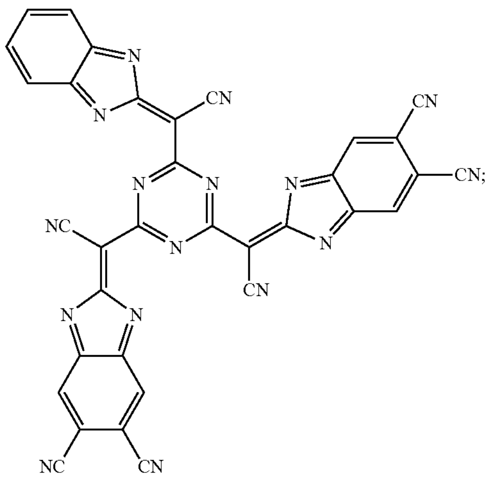

-continued
42
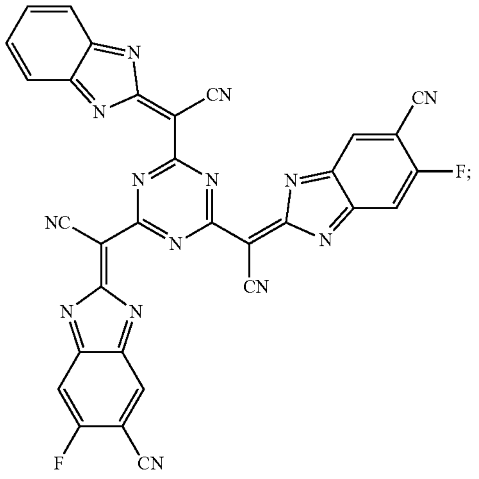
43
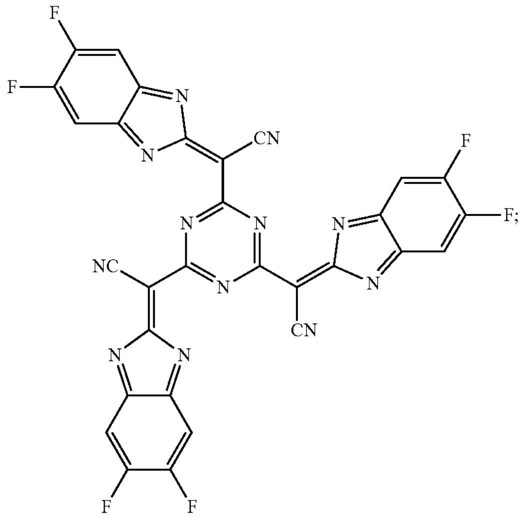
44
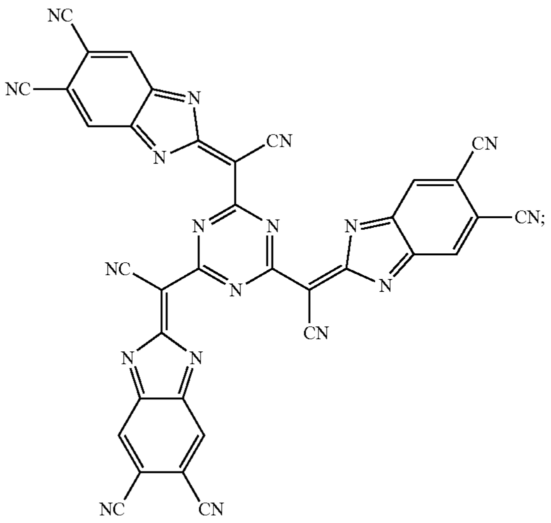
-continued
45
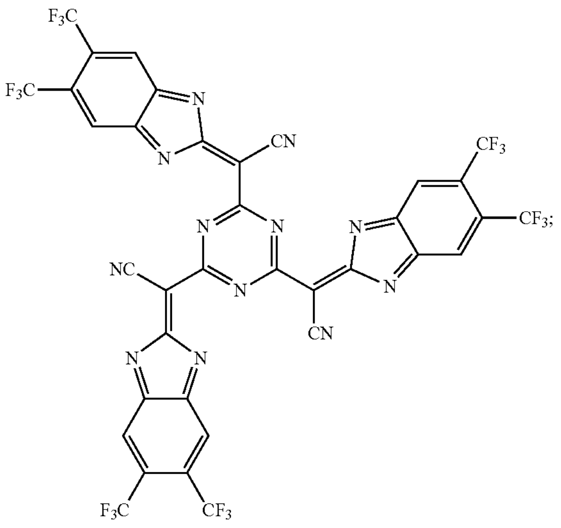
46
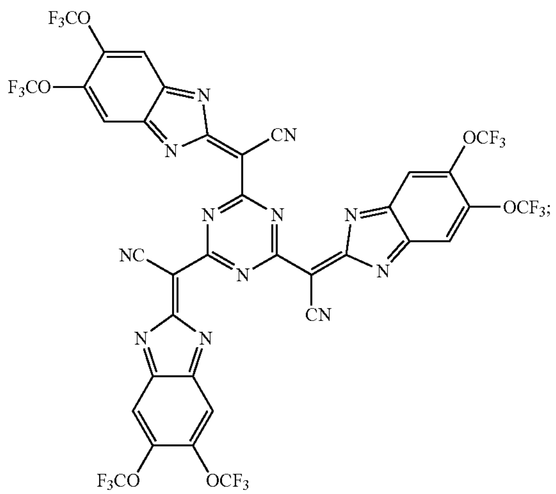
47
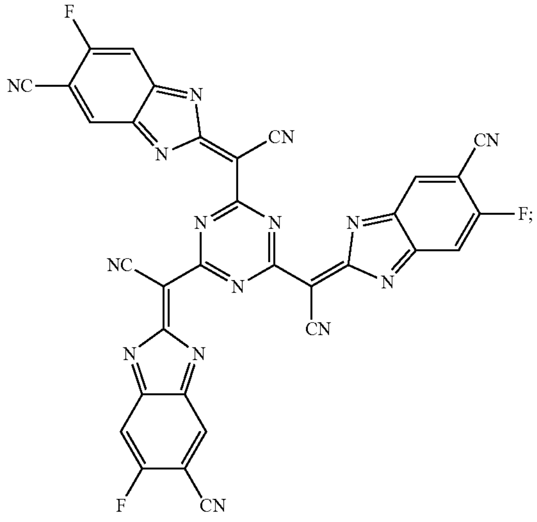

-continued
48
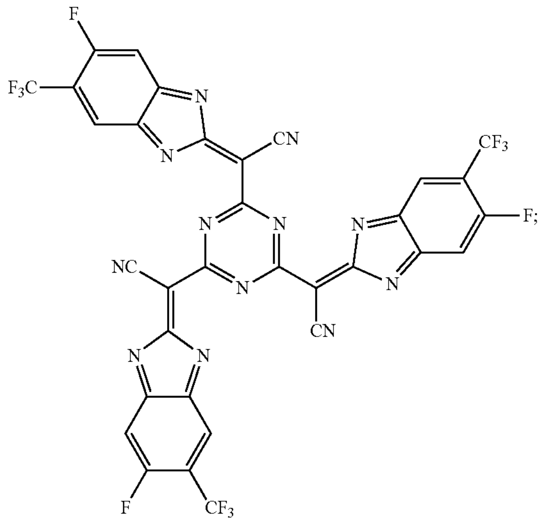
49
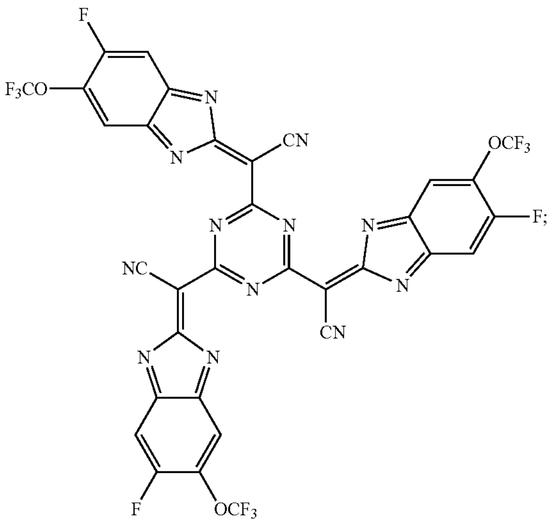
50
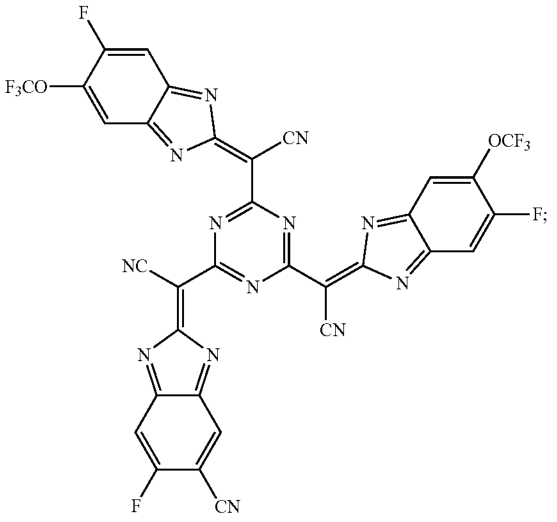
-continued
51
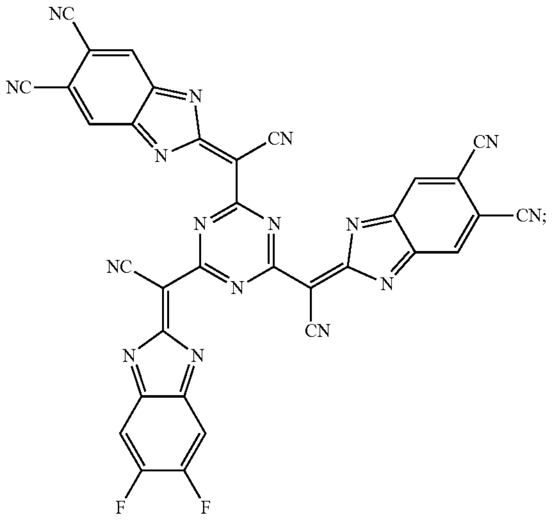
52
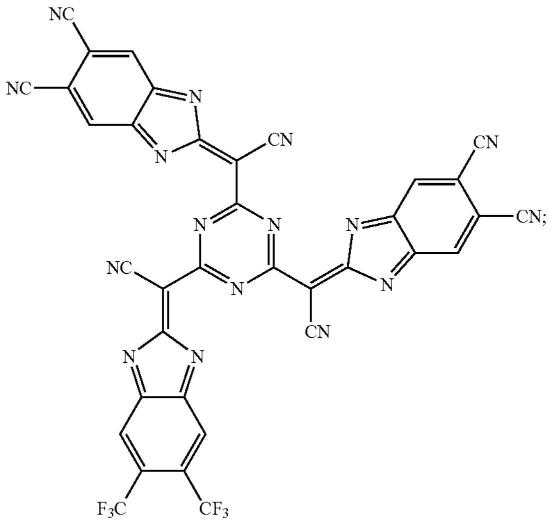
53
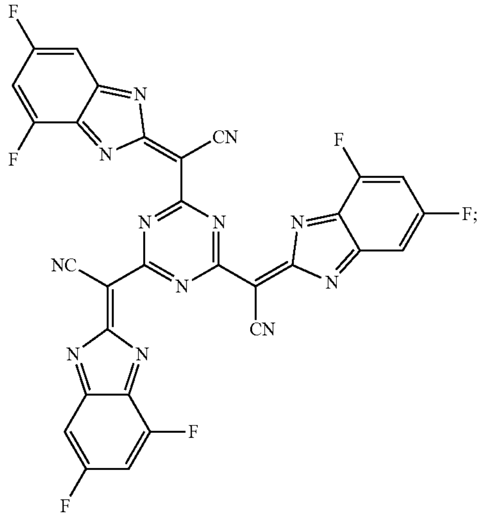

-continued
54
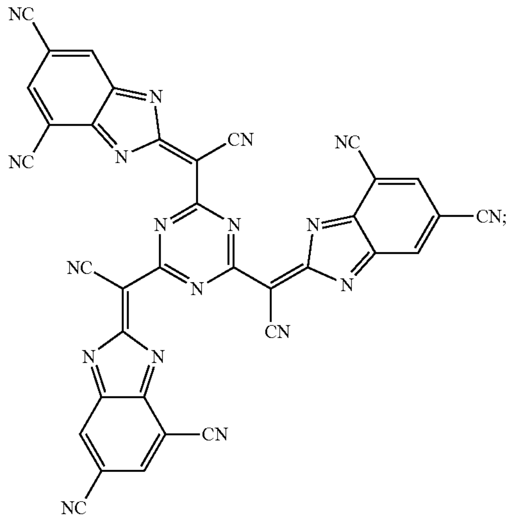
55
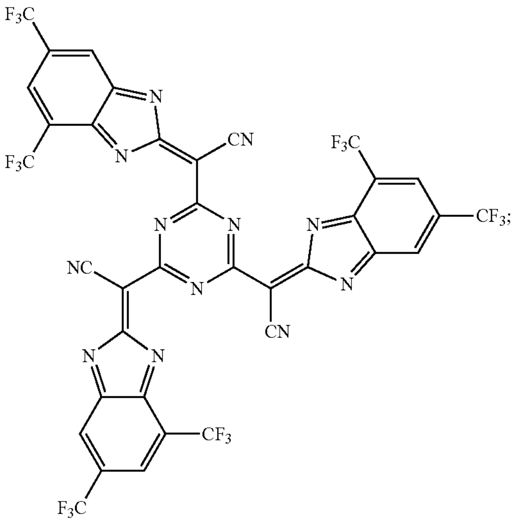
56
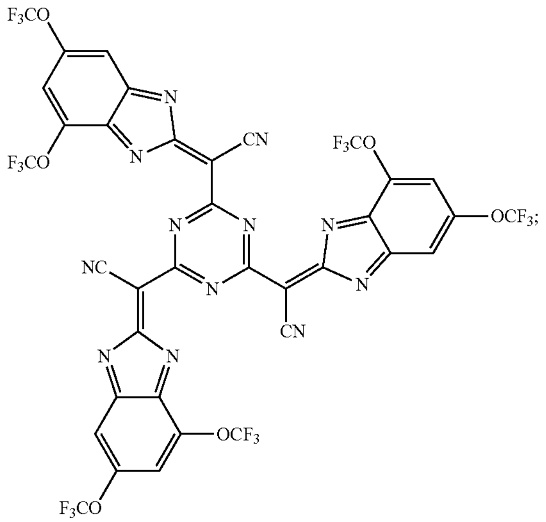
-continued
57
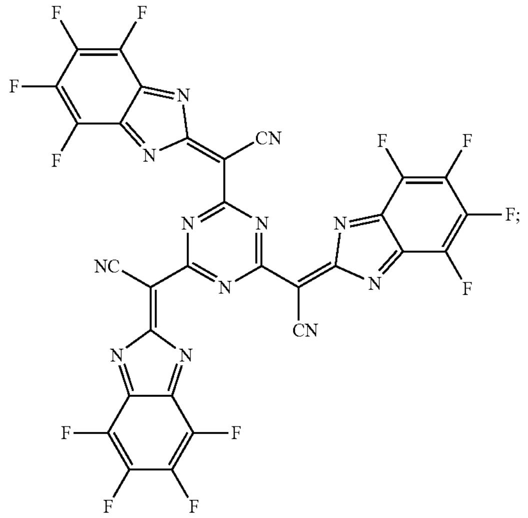
58
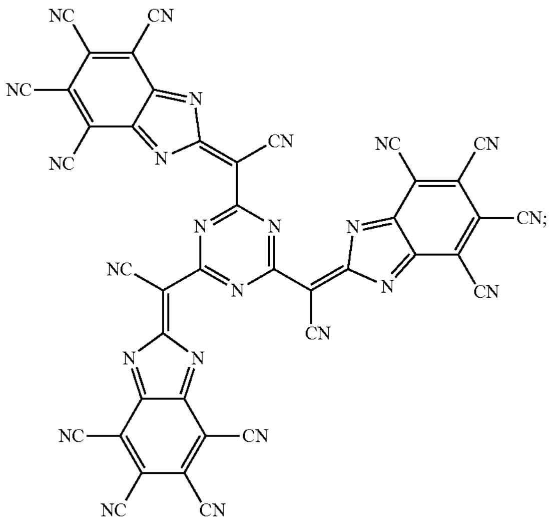
59
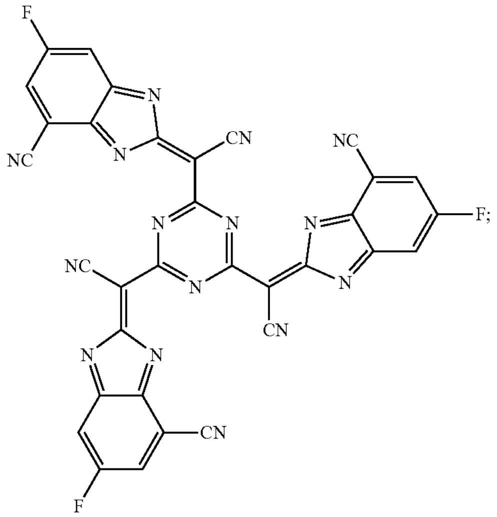

-continued
60
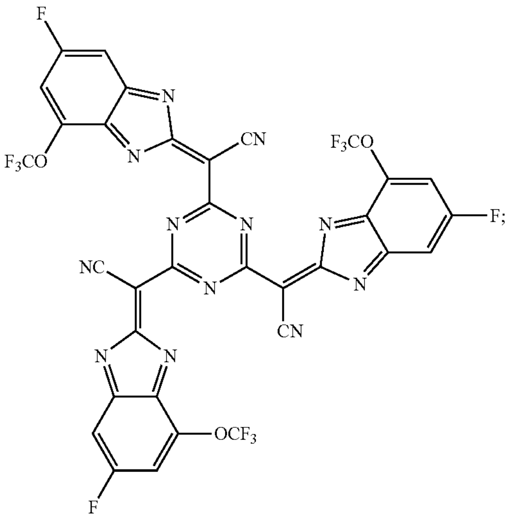
61
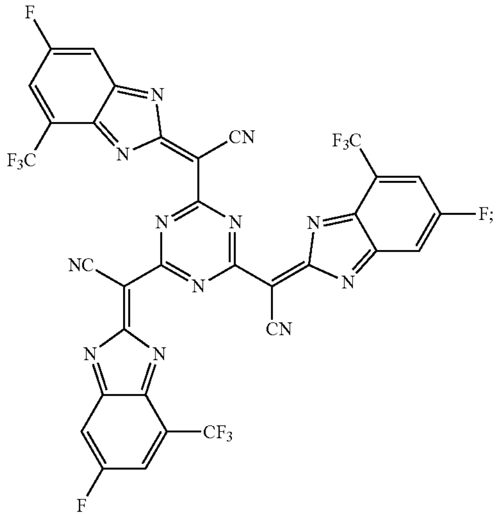
62
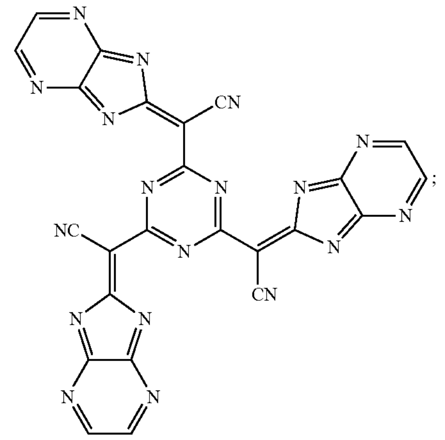
-continued
63
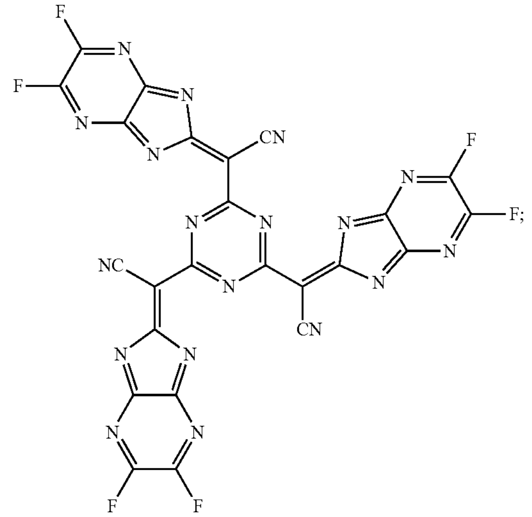
64
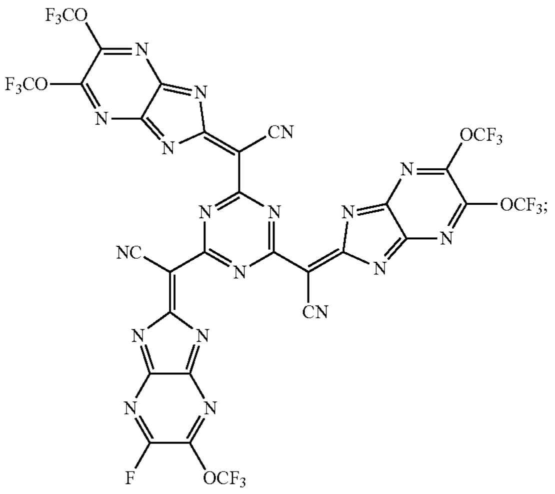
65
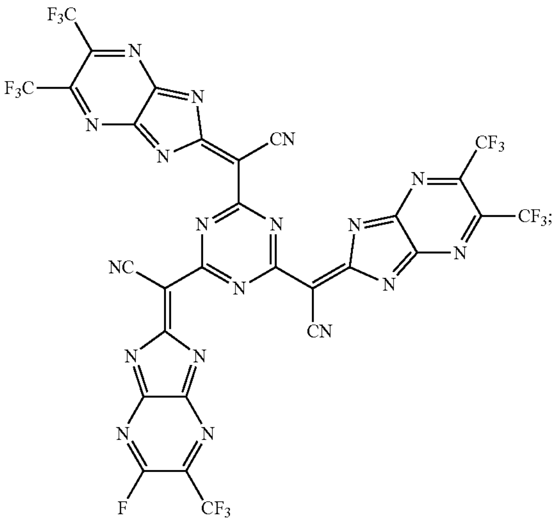

-continued
66
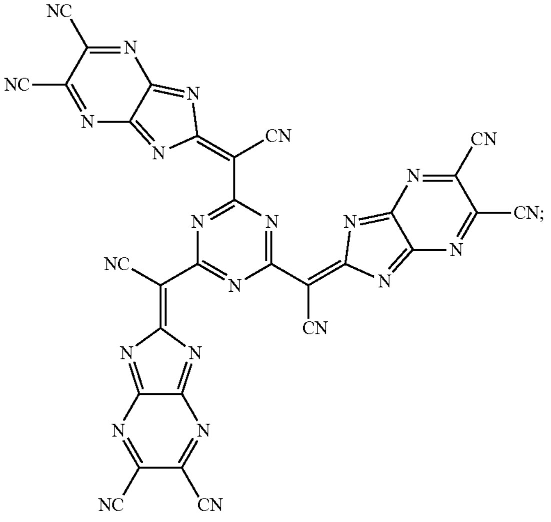
67
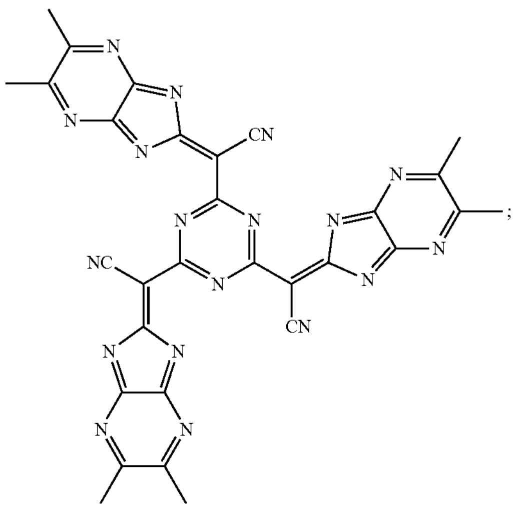
68
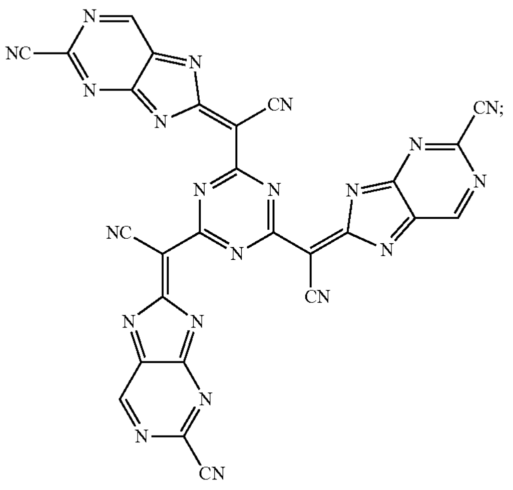
-continued
69
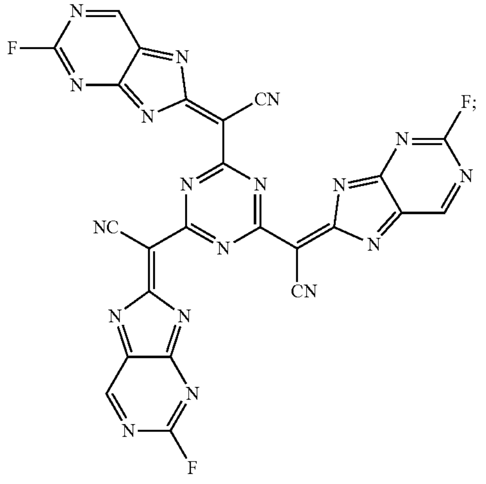
70
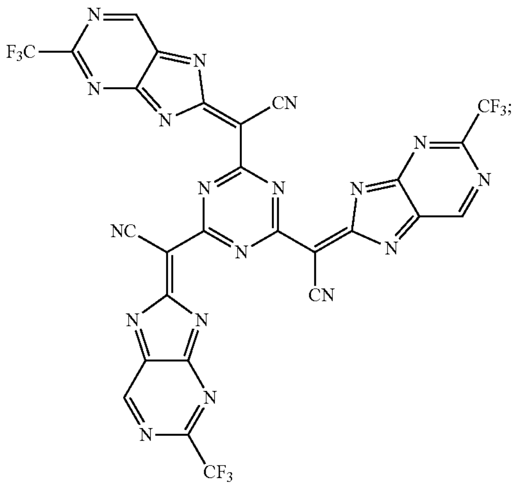
71
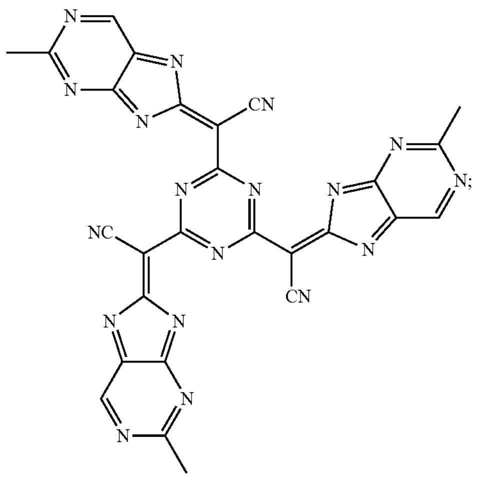

-continued
72
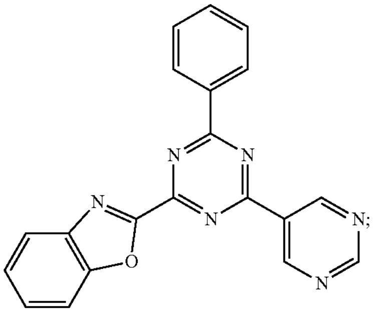
73
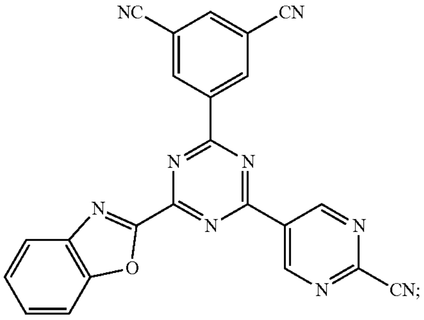
74
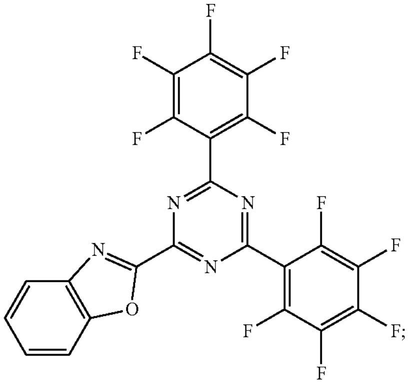
75
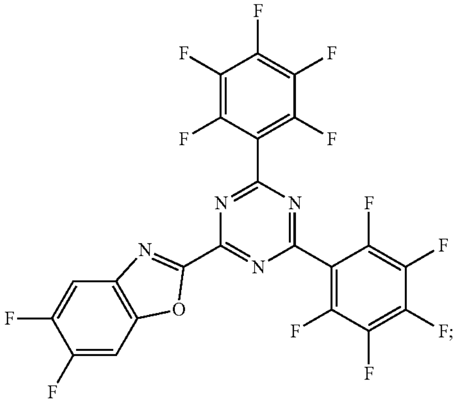
-continued
76
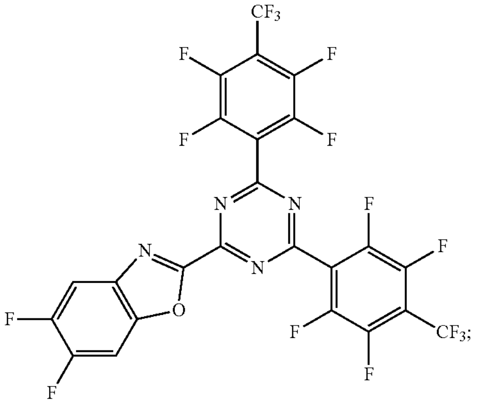
77
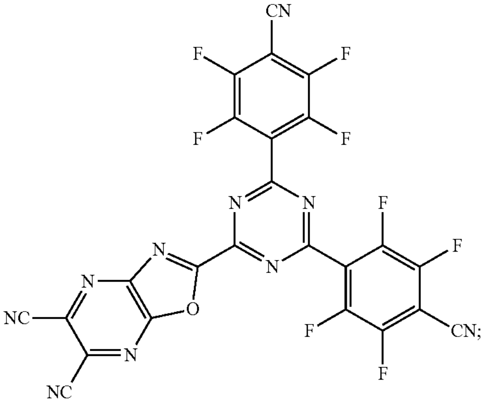
78
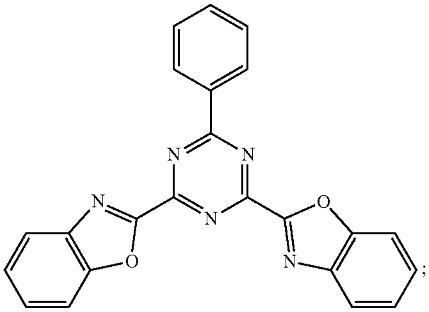
79
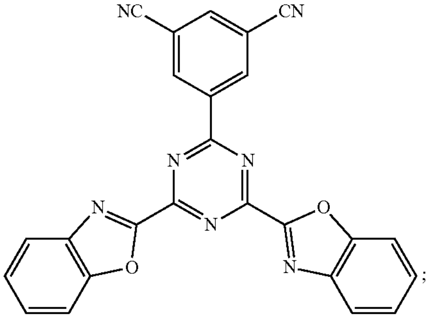

-continued
80
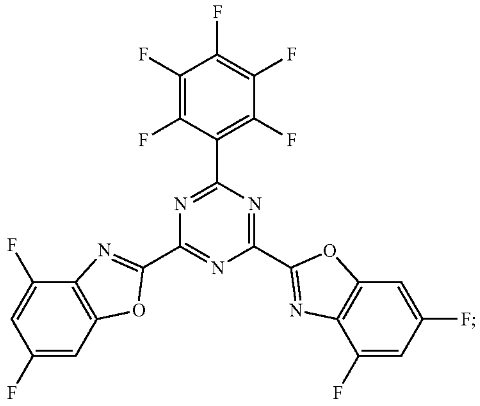
81
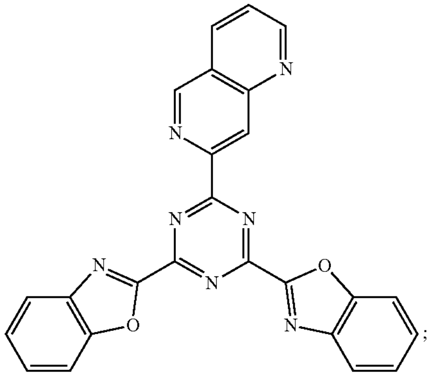
82
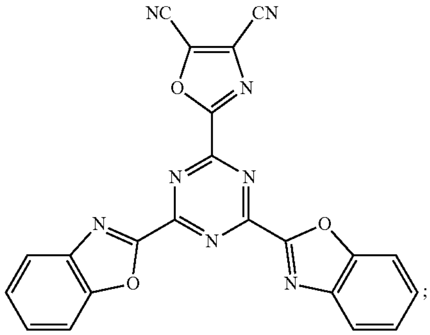
83
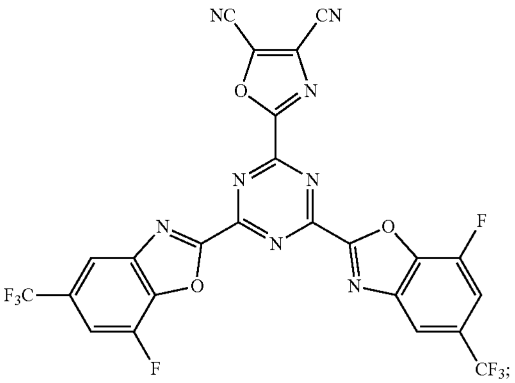
-continued
84
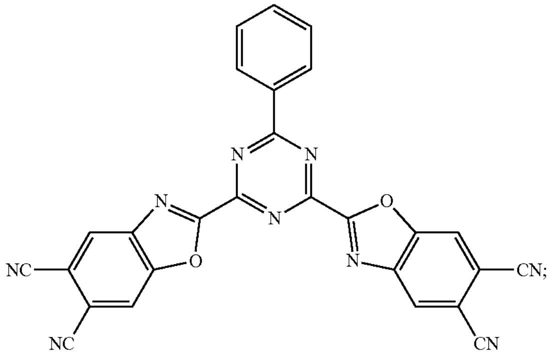
85
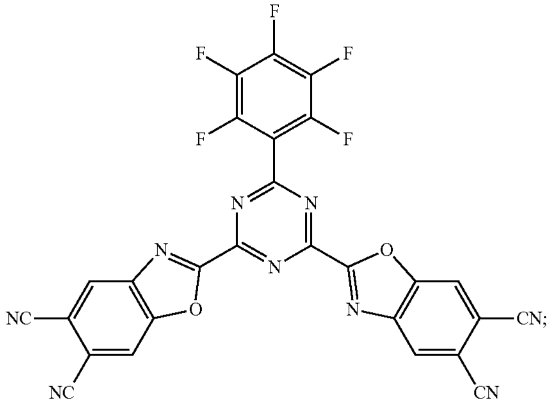
86
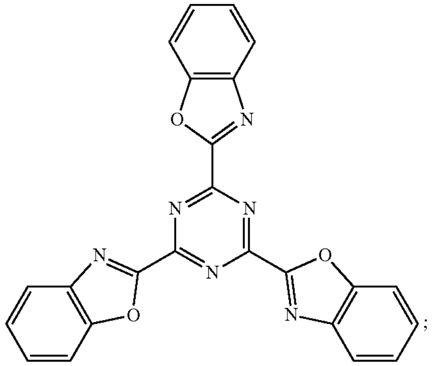
87
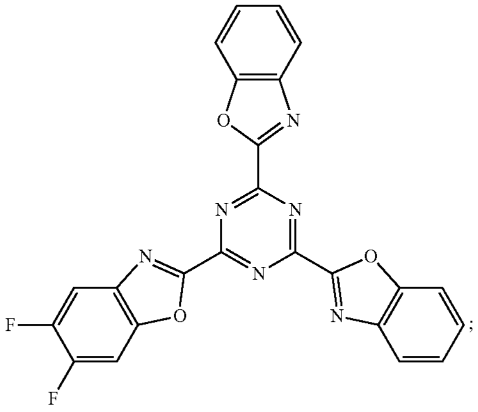

-continued
88
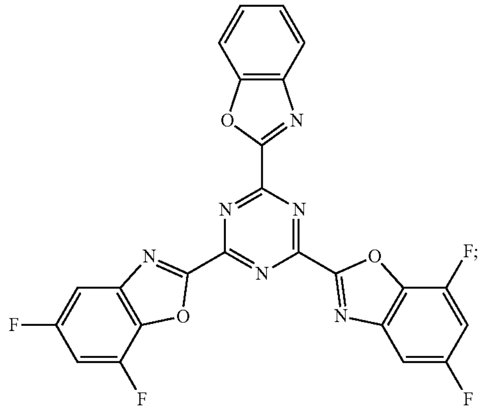
89
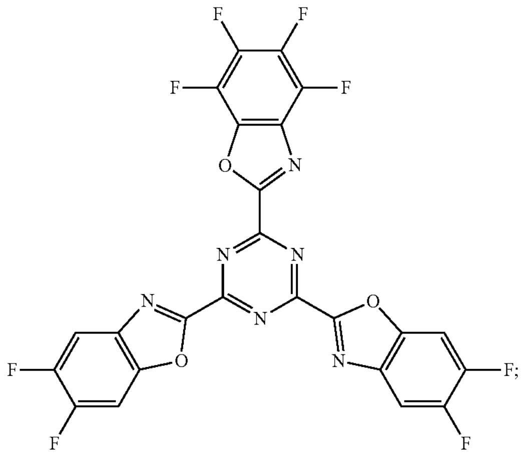
90
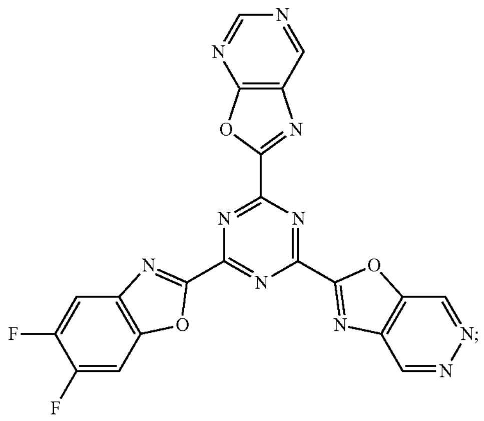
-continued
91
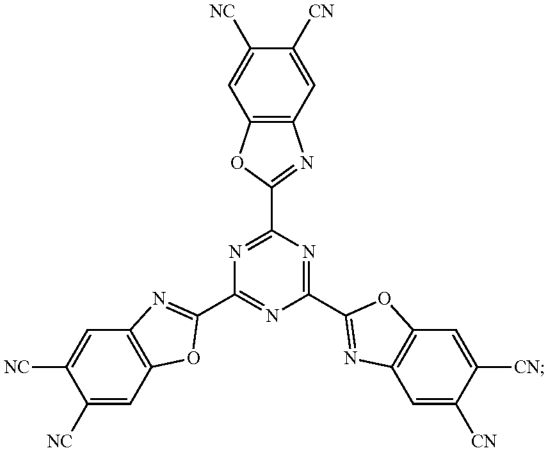
92
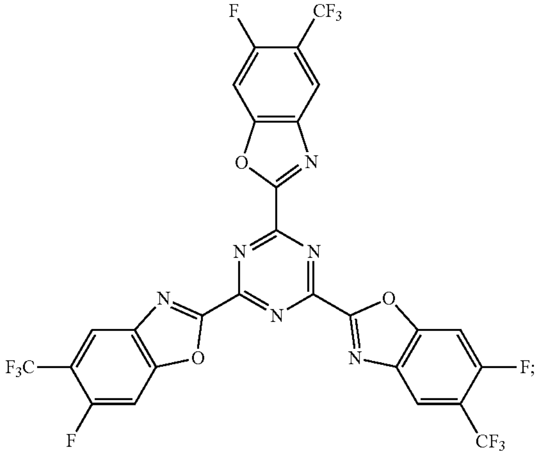
93
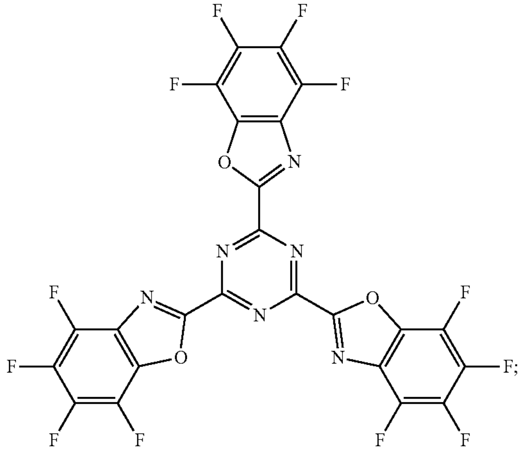

-continued
94
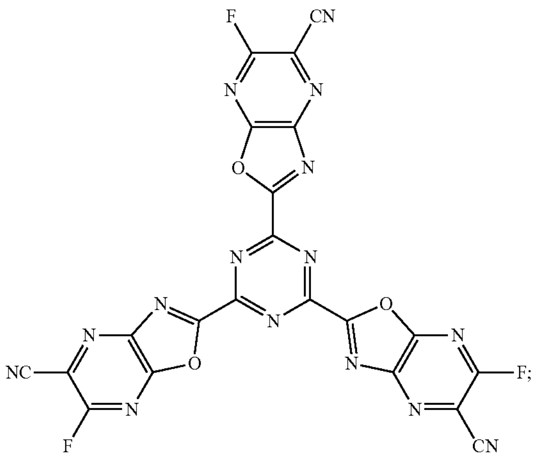
95
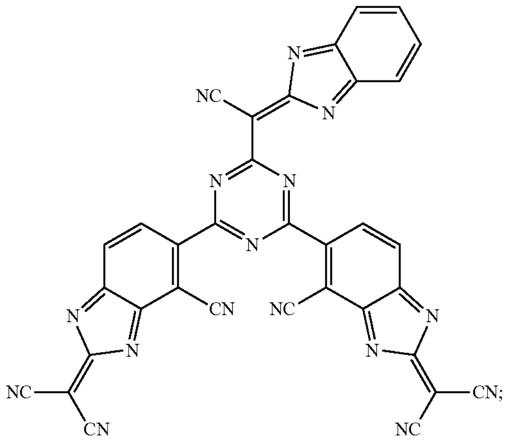
96
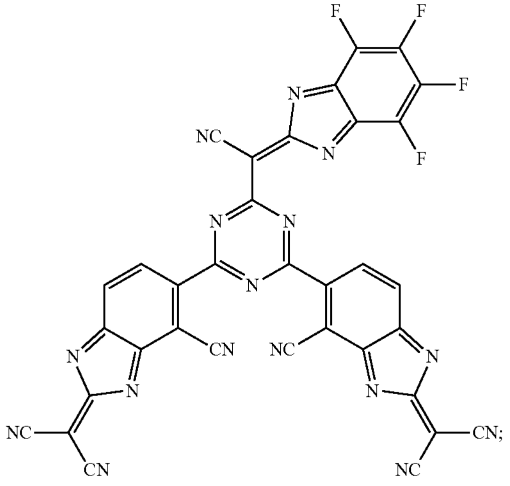
-continued
97
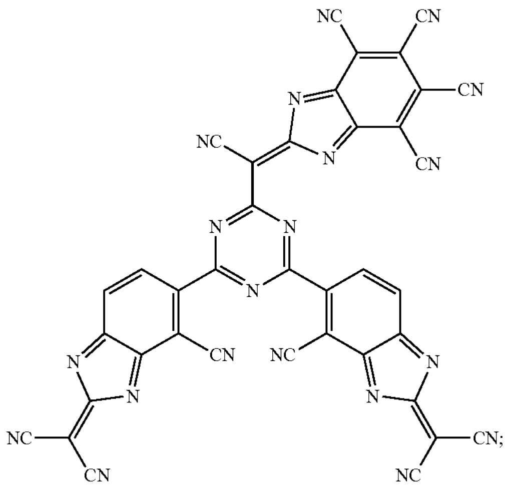
98
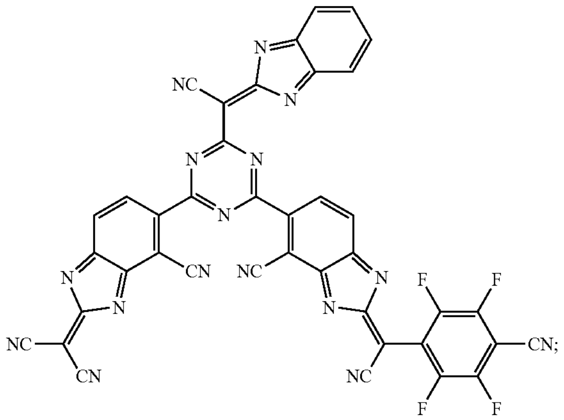
99
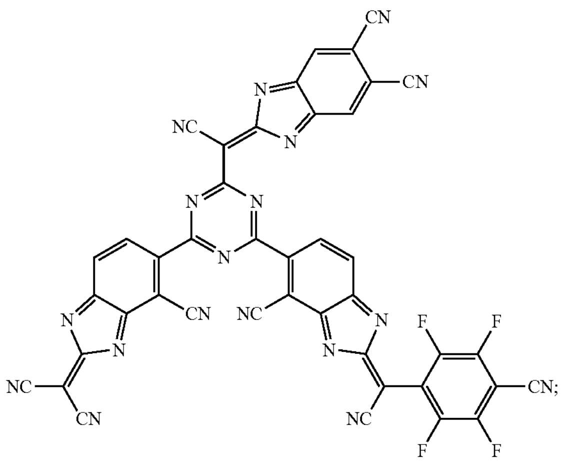

-continued
100
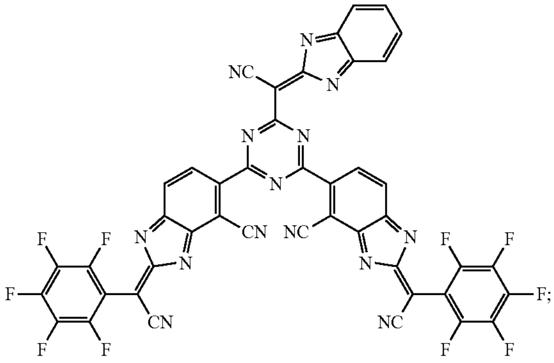
101
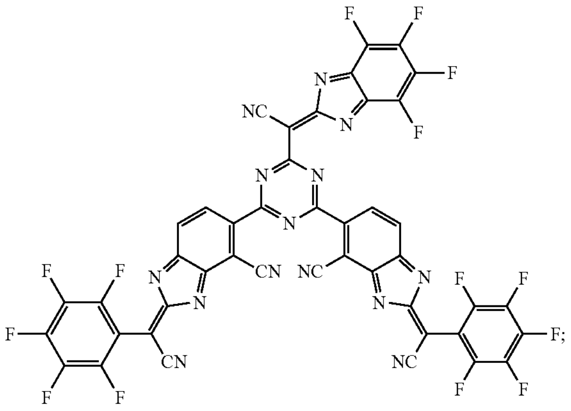
102
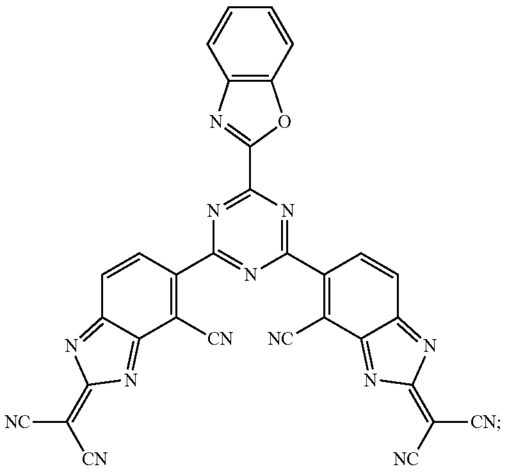
103
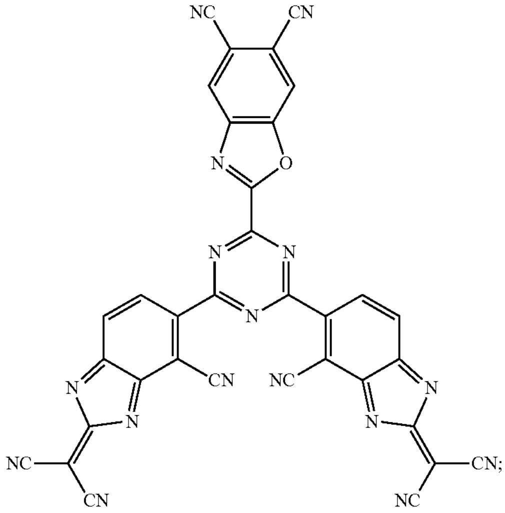
104
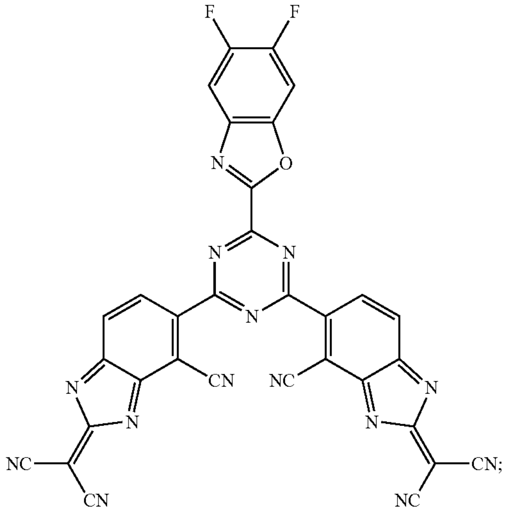
105
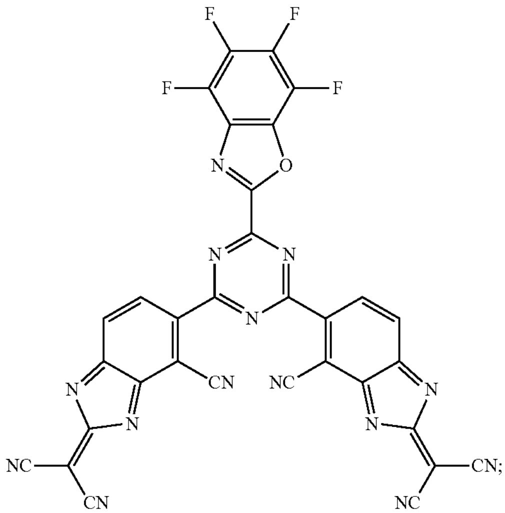

-continued
106
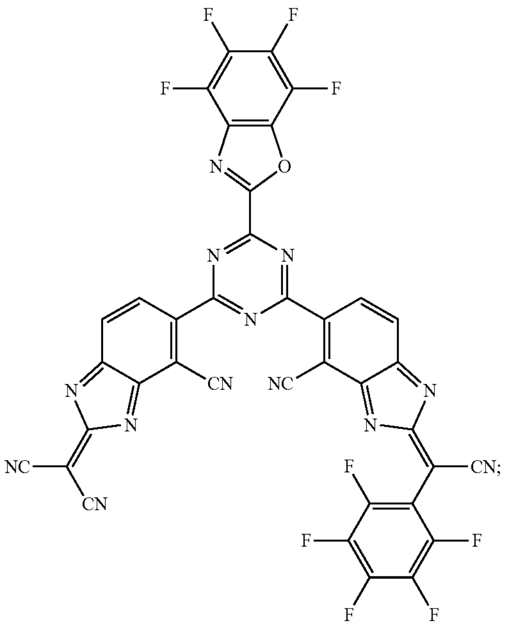
108
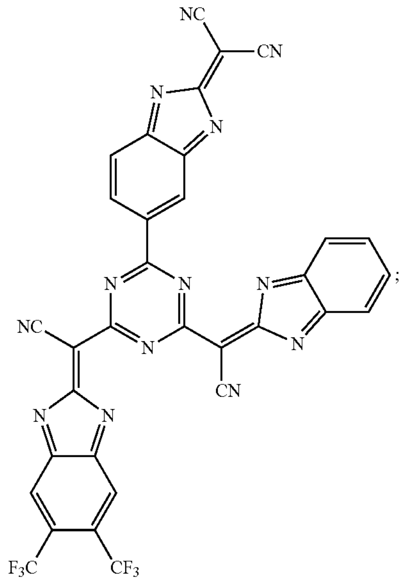
107
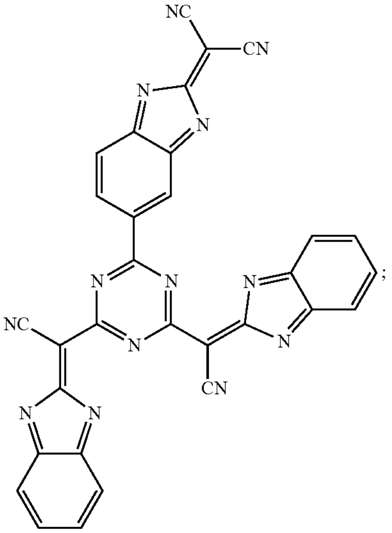
109
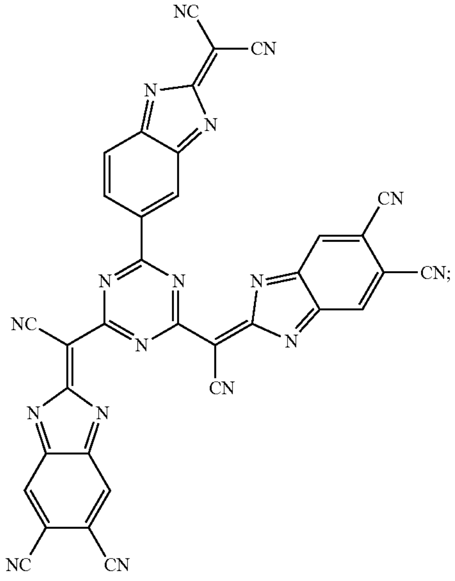

-continued
110
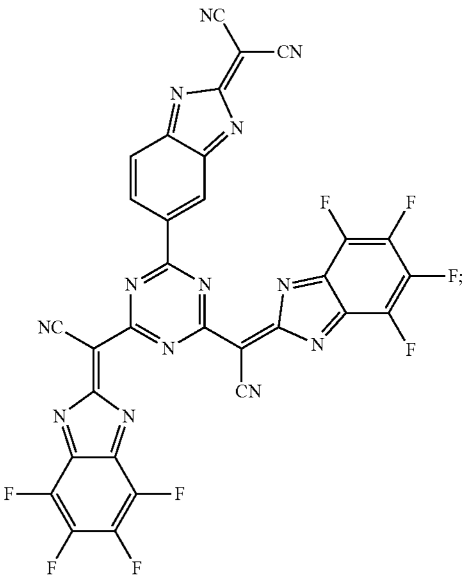
111
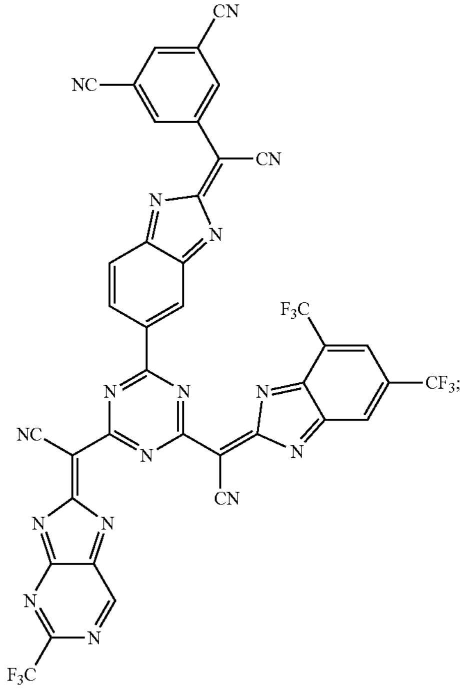
-continued
112
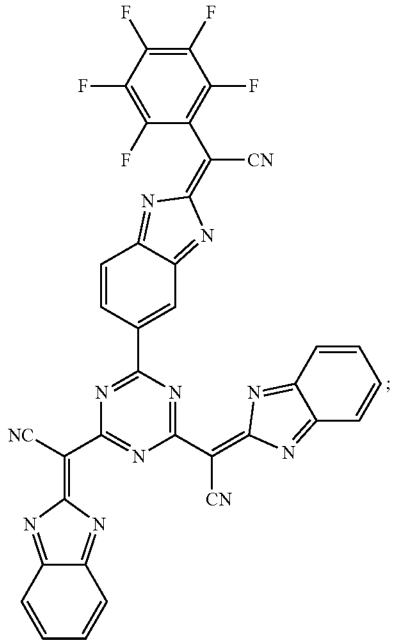
113
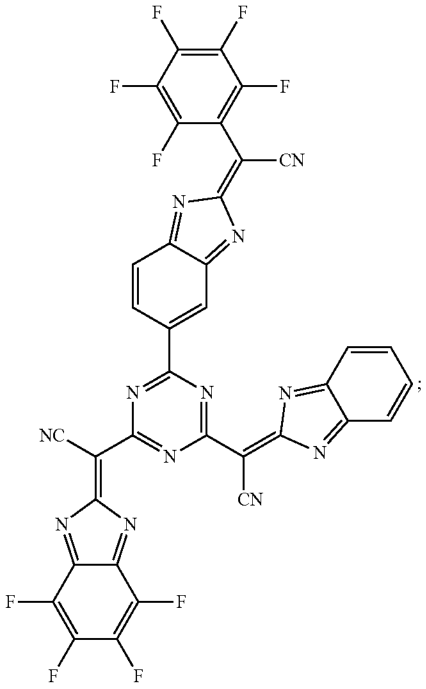

-continued
114
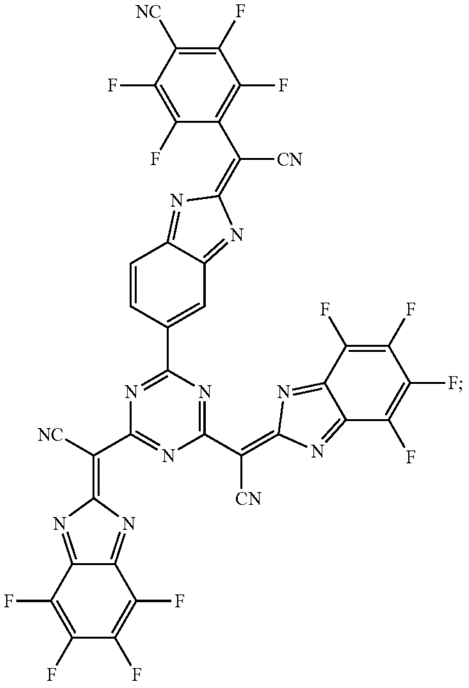
115
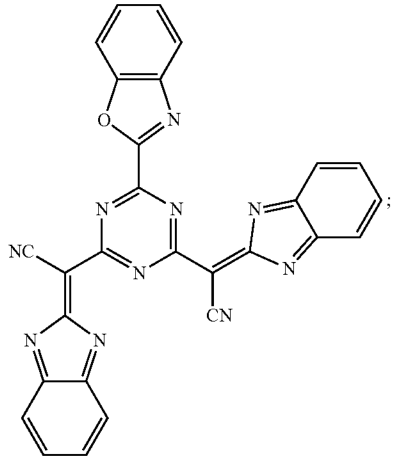
116
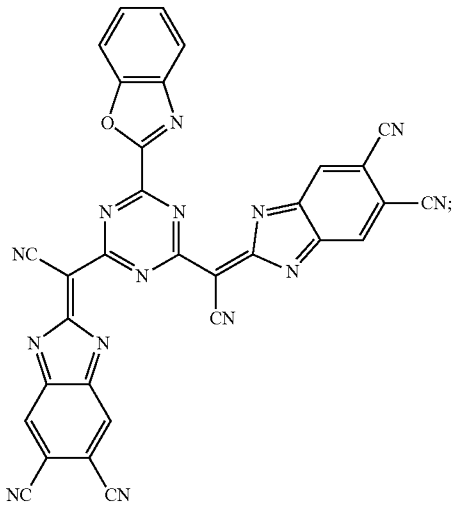
-continued
117
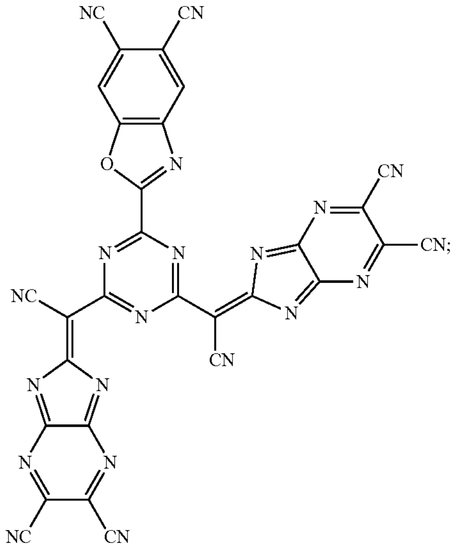
118
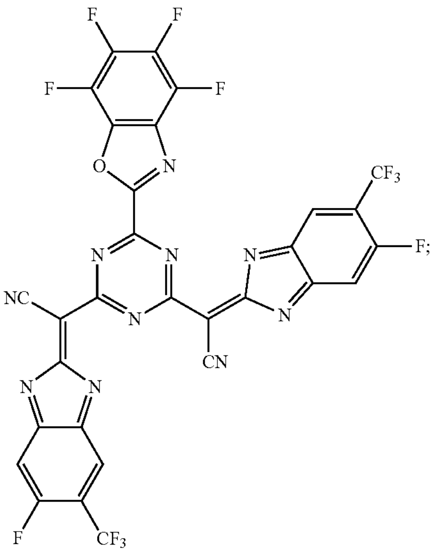
119
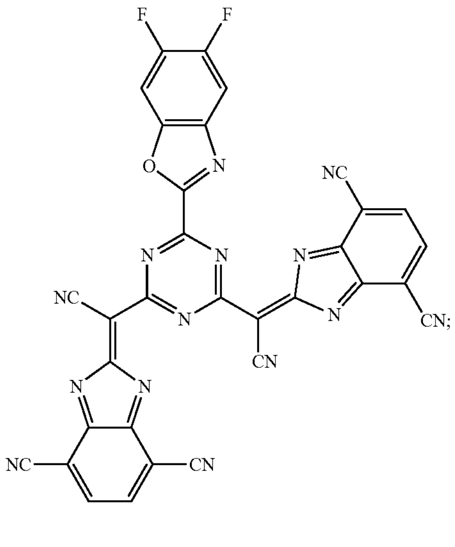

-continued
120
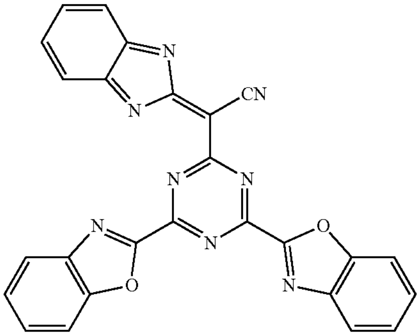
;
121
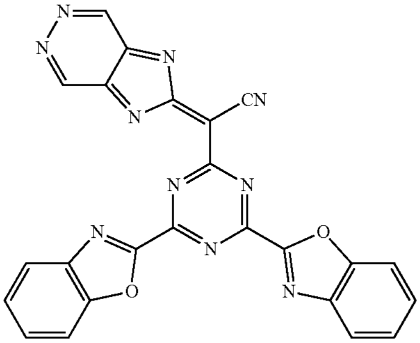
;
122
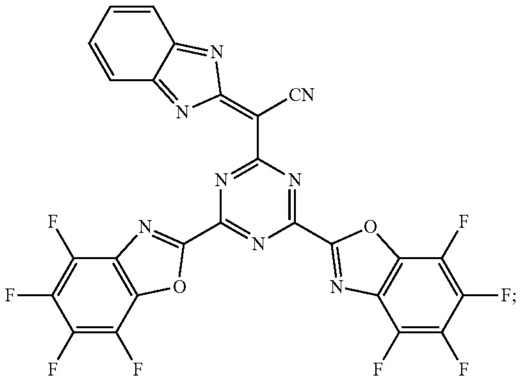
123
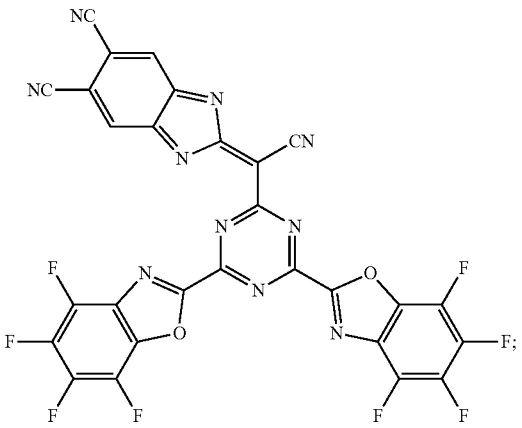
-continued
124
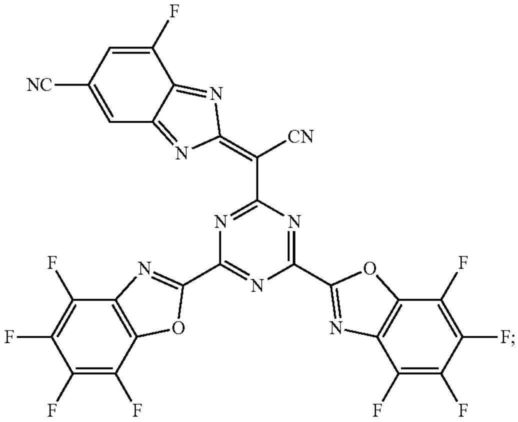
125
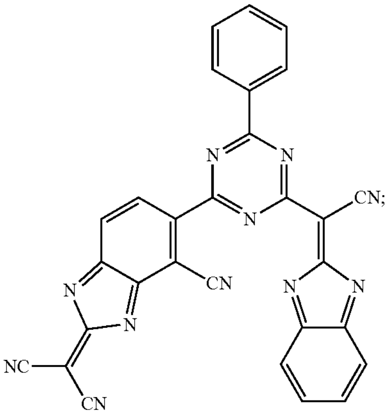
126
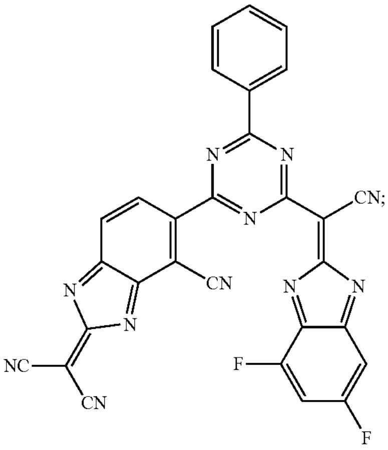

-continued
127
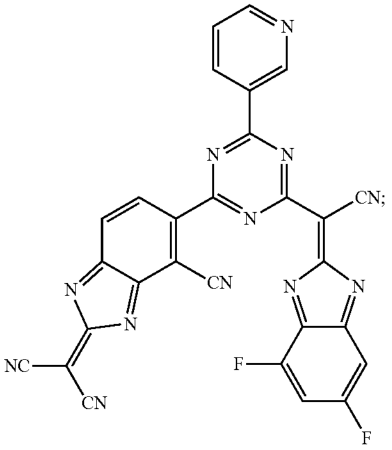
128
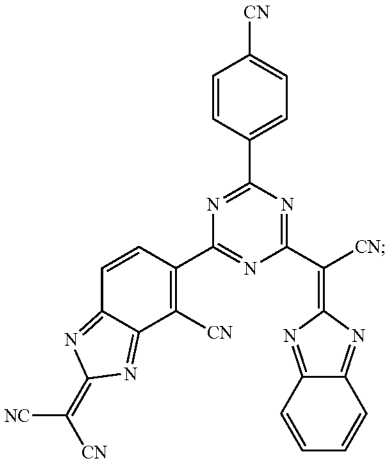
129
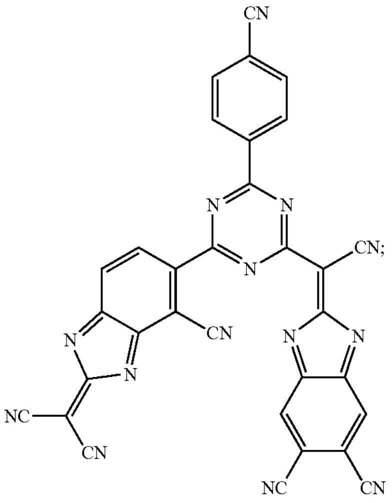
-continued
130
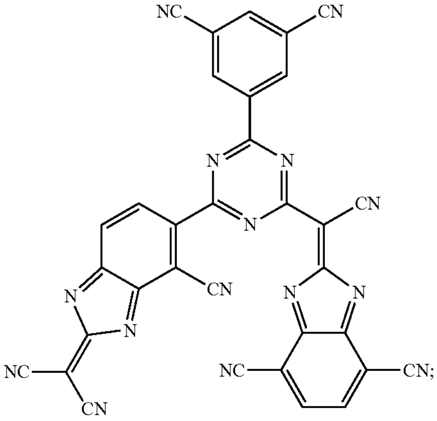
131
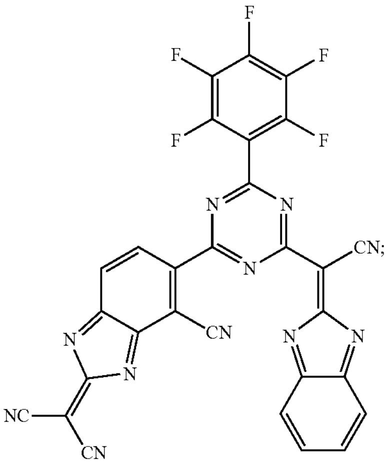
132
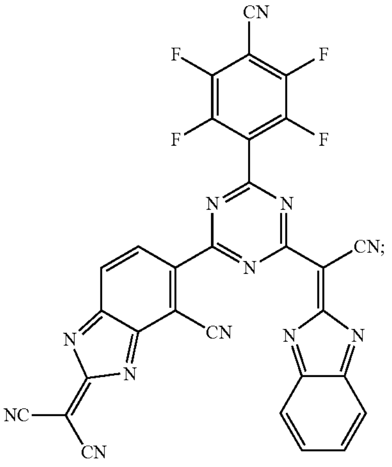

-continued
133
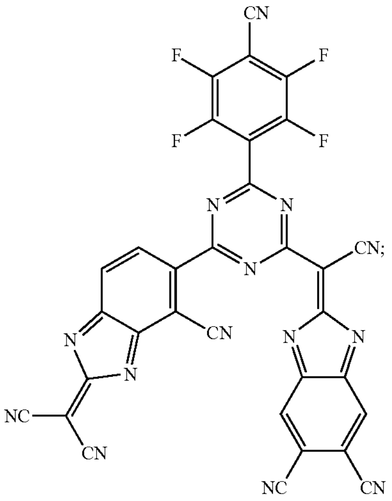
134
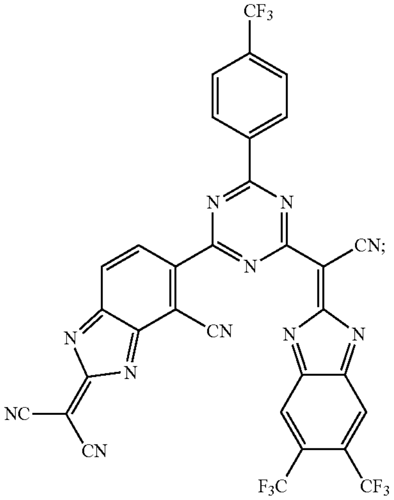
135
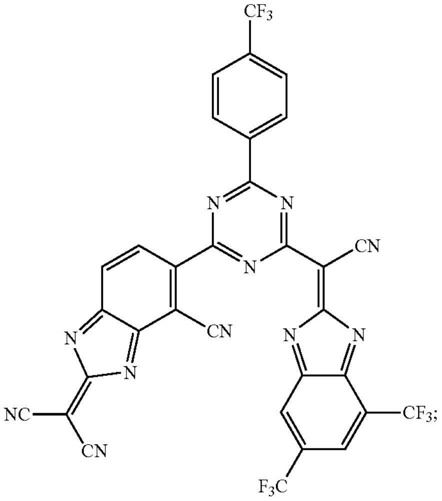
-continued
136
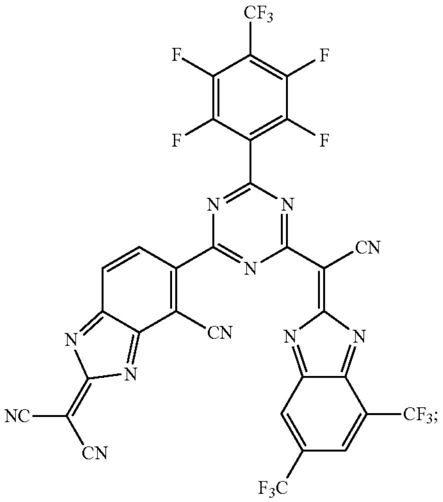
137
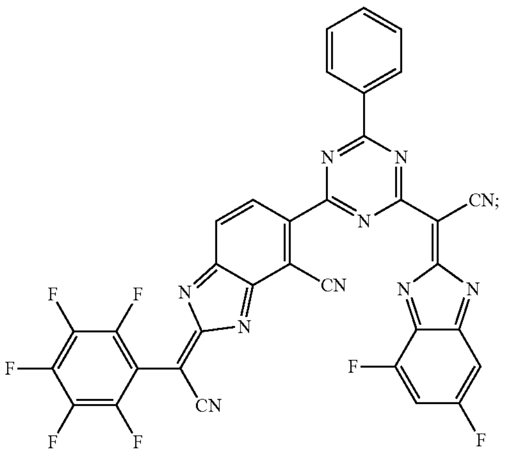
138
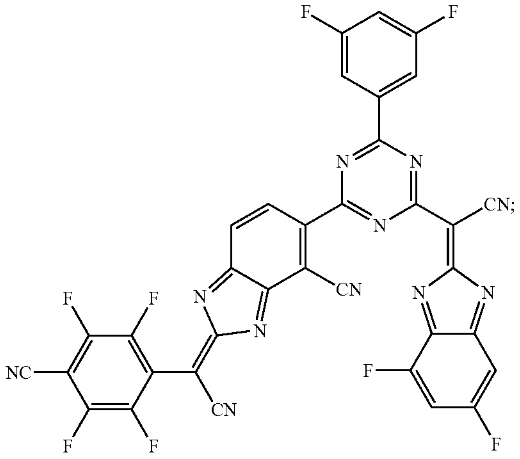

-continued
139
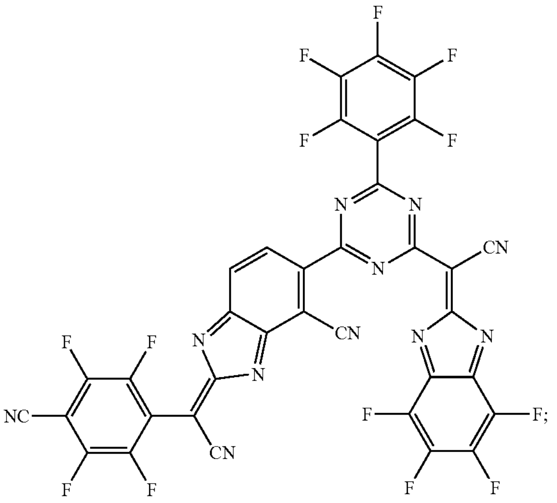
140
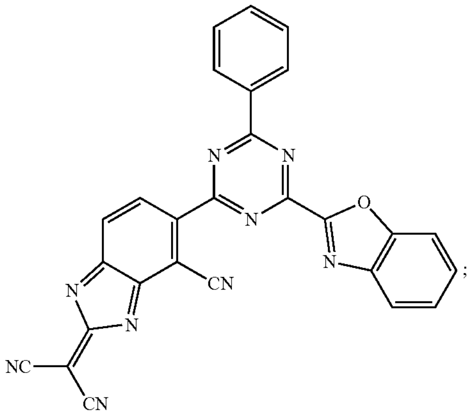
141
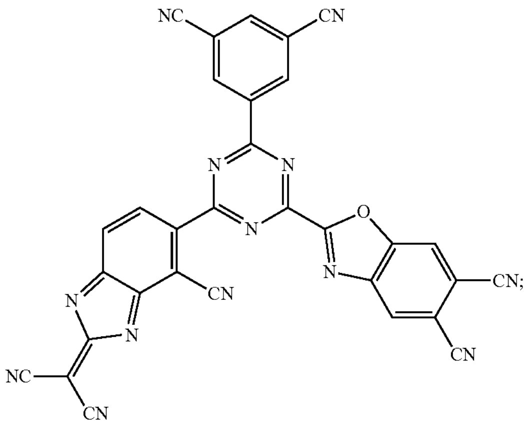
-continued
142
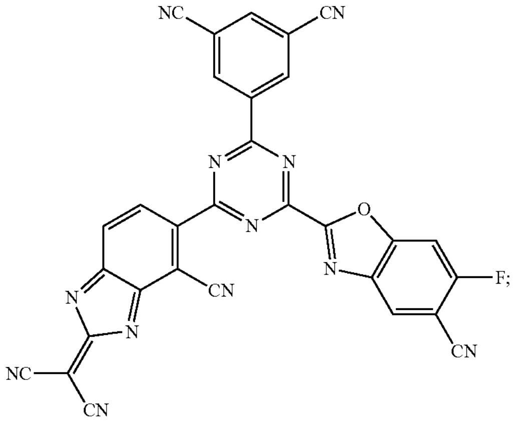
143
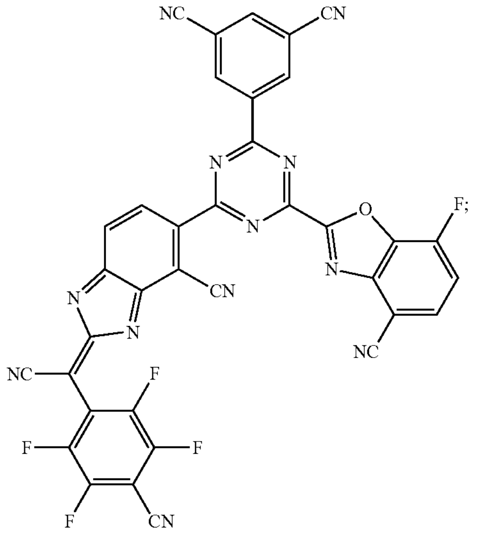
144
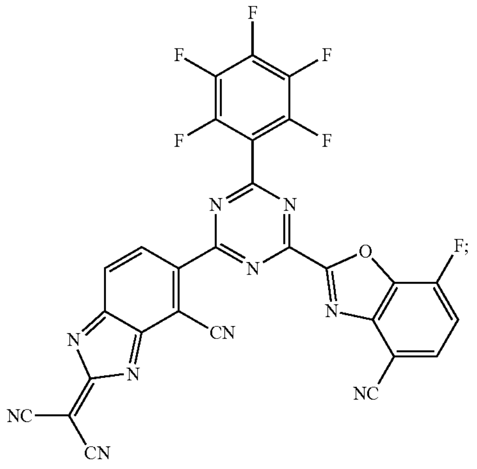

-continued
145
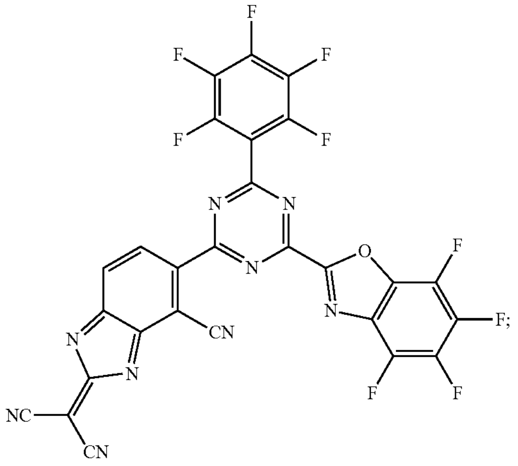
145
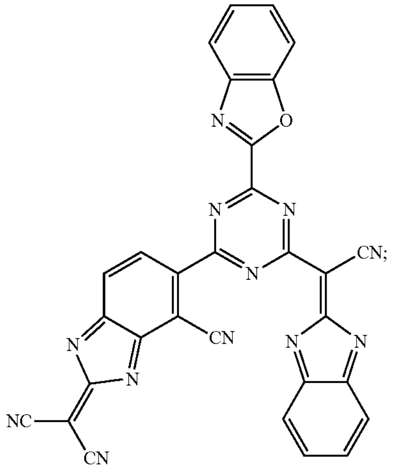
147
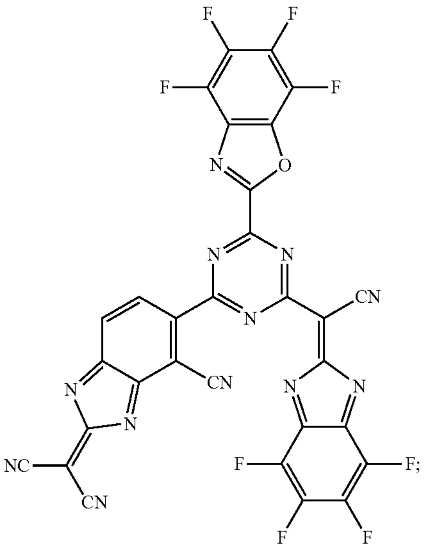
-continued
148
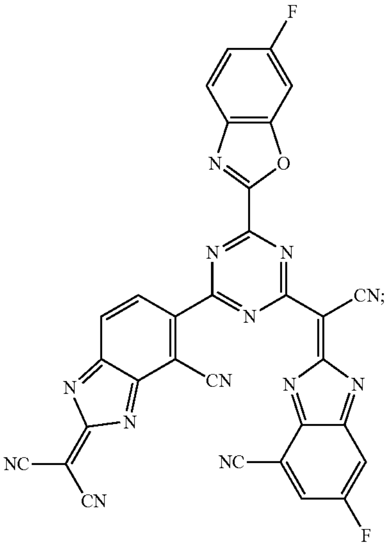
149
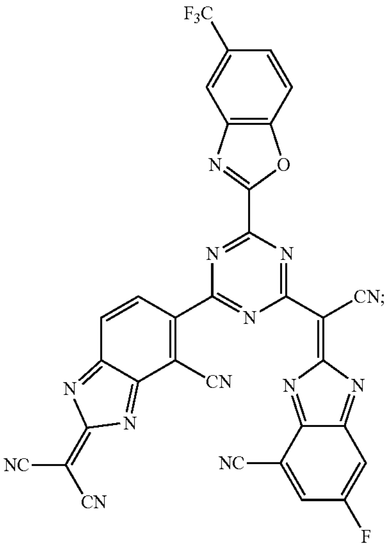
150
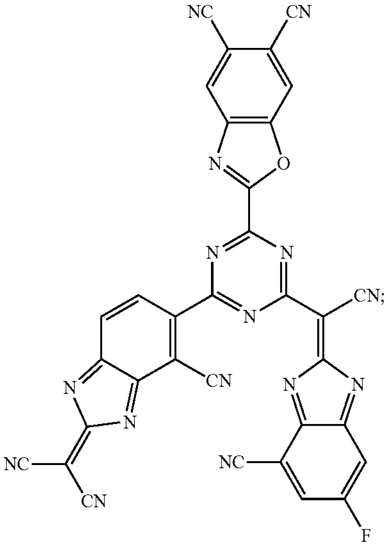

-continued
151
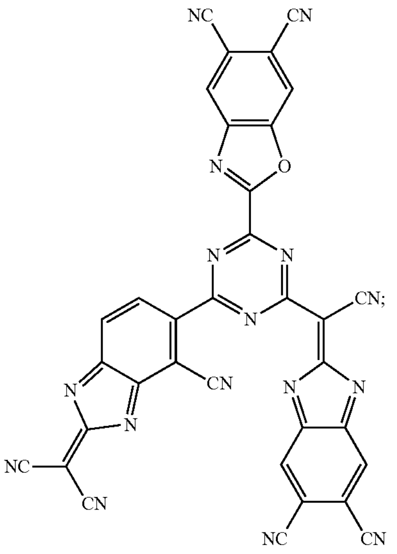
152
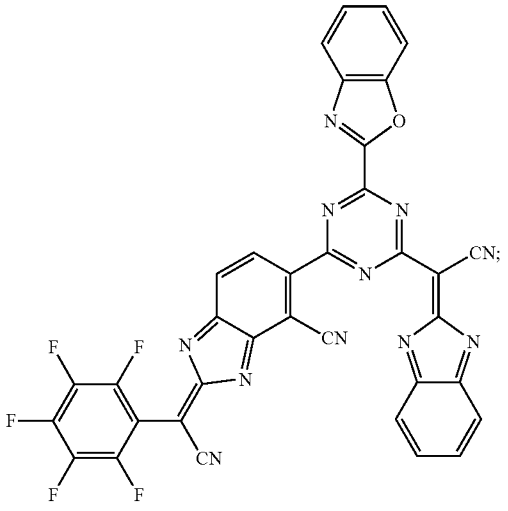
153
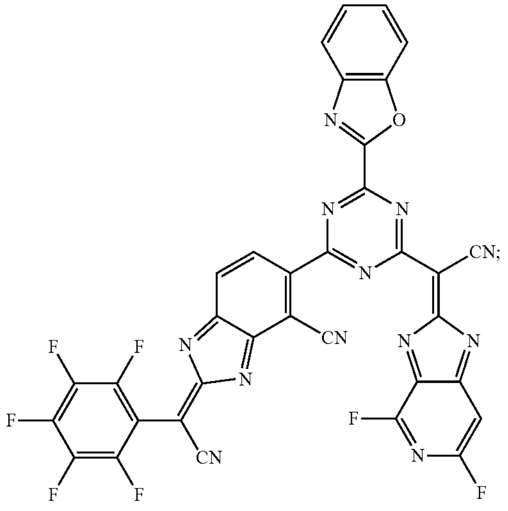
-continued
154
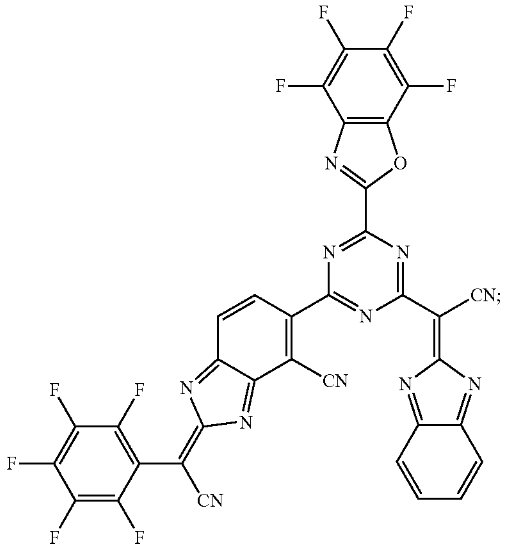
155
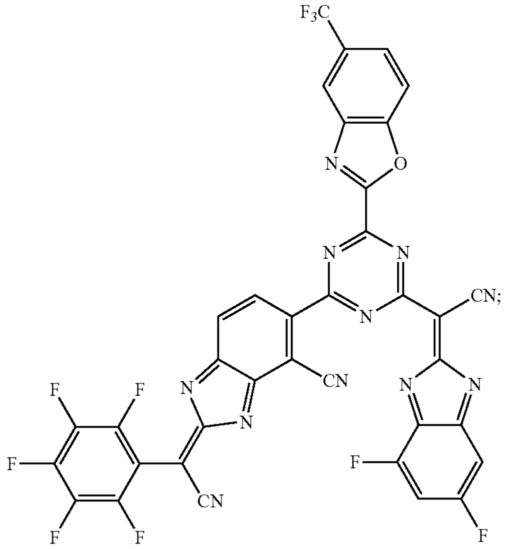
156
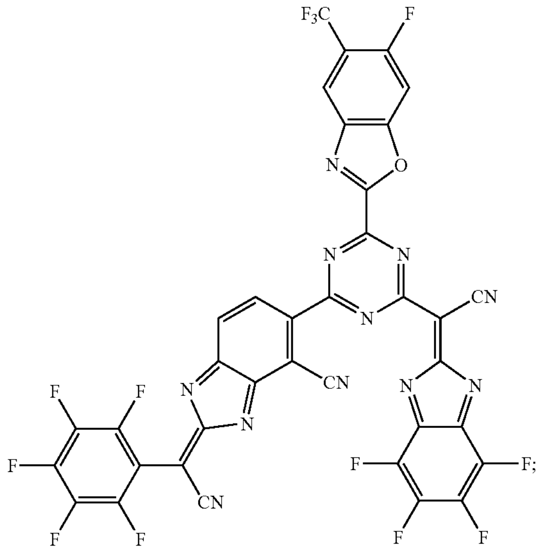

-continued
157
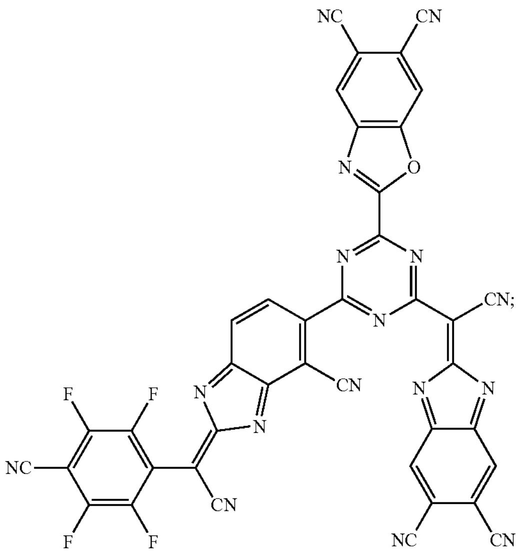
158
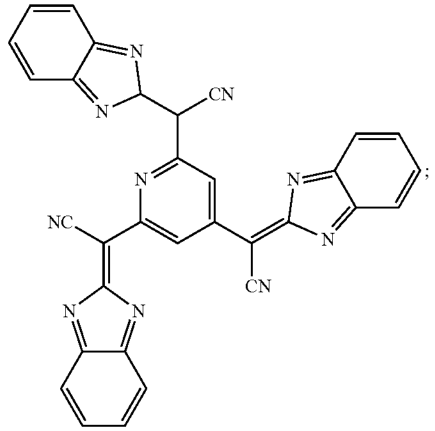
159
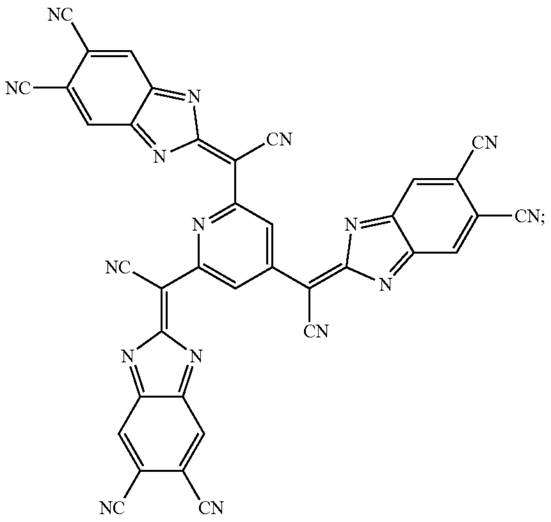
-continued
160
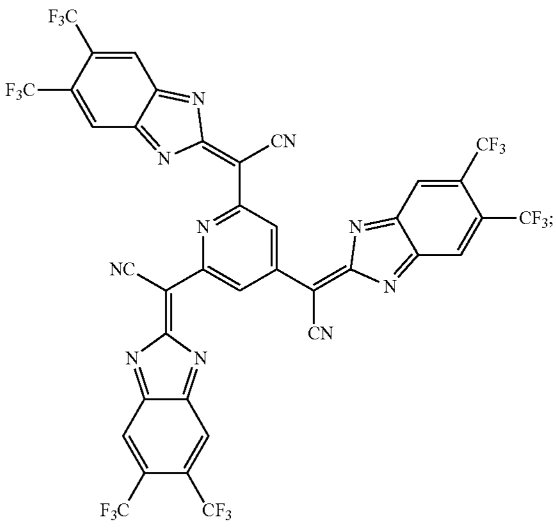
161
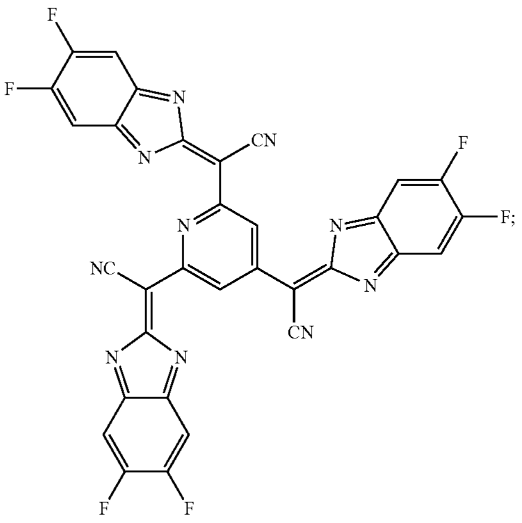
162
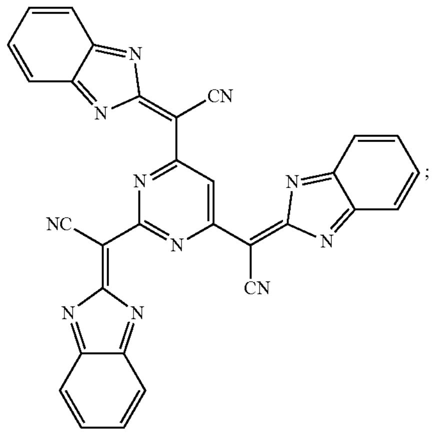

-continued
163
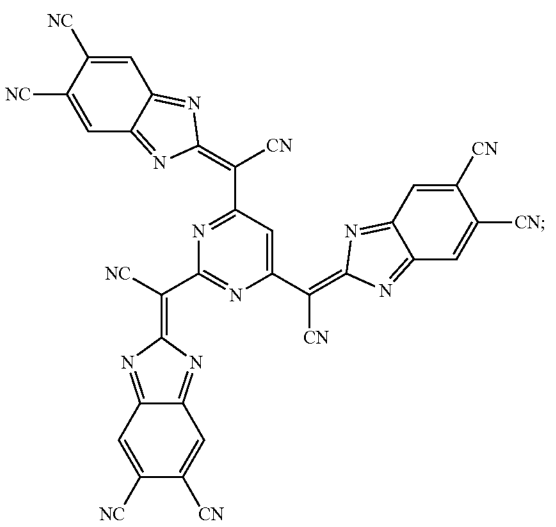
164
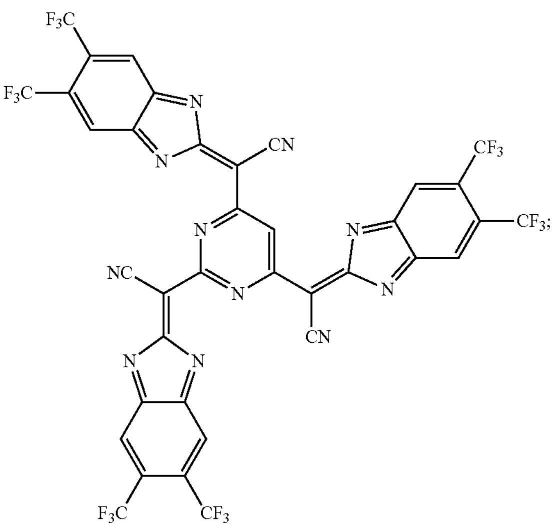
165
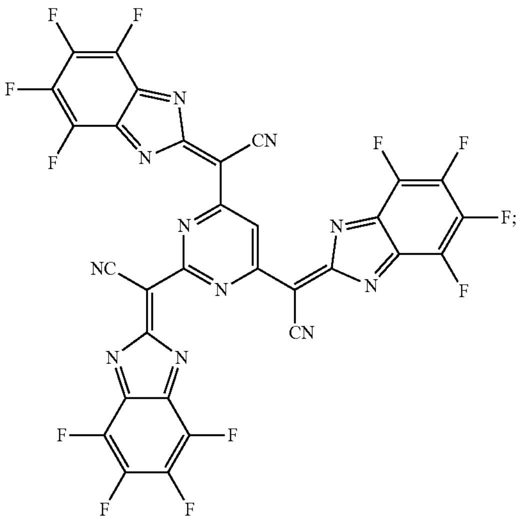
-continued
166
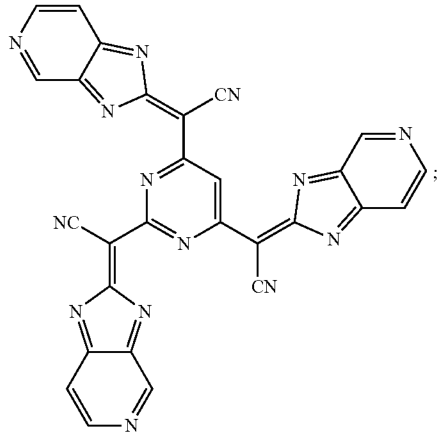
167
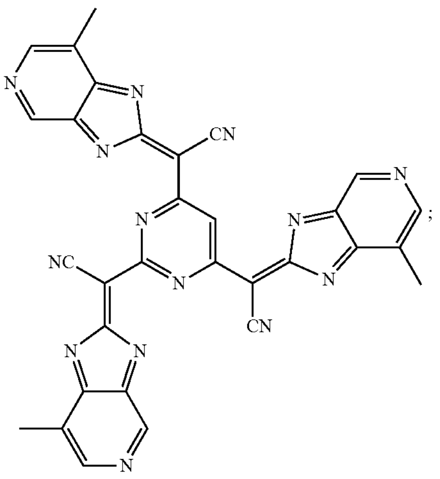
168
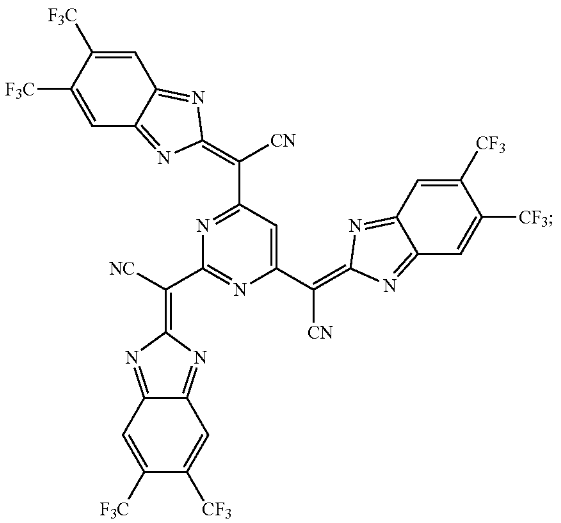

-continued
169
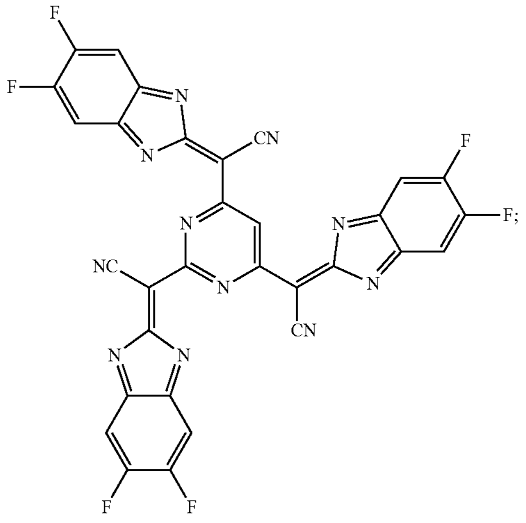
170
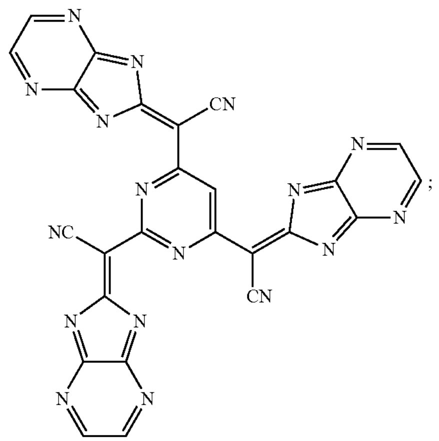
171
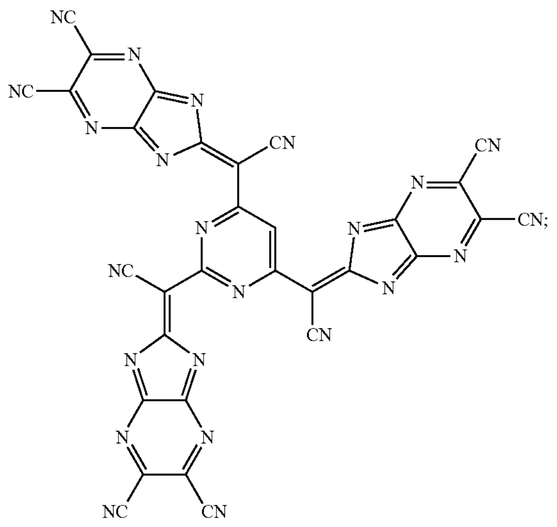
-continued
172
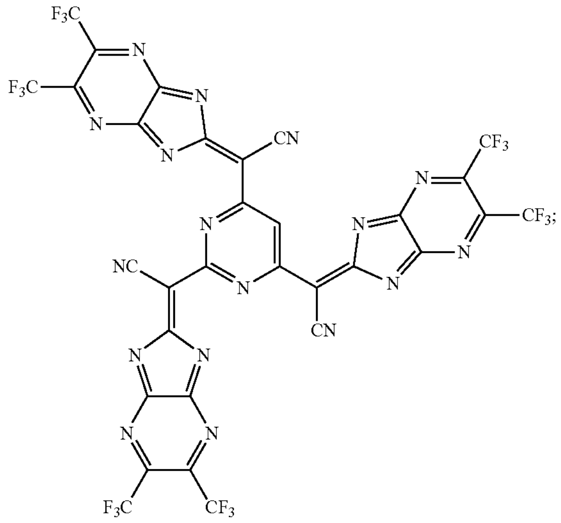
173
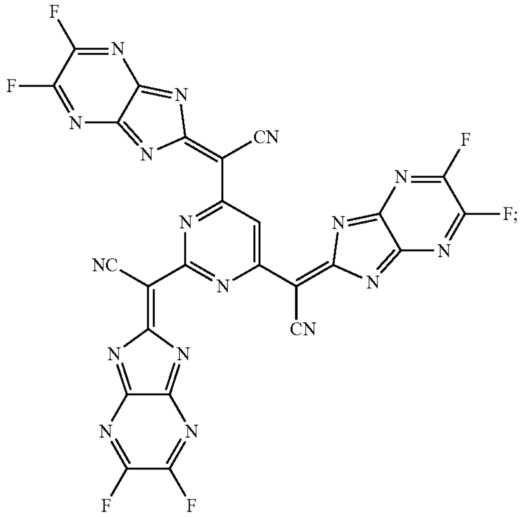
174
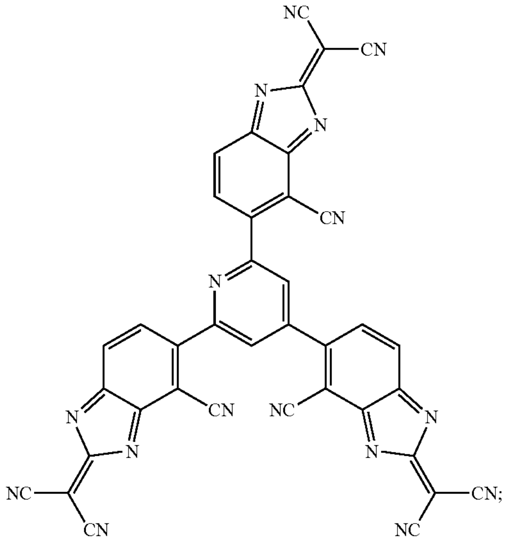

-continued
175
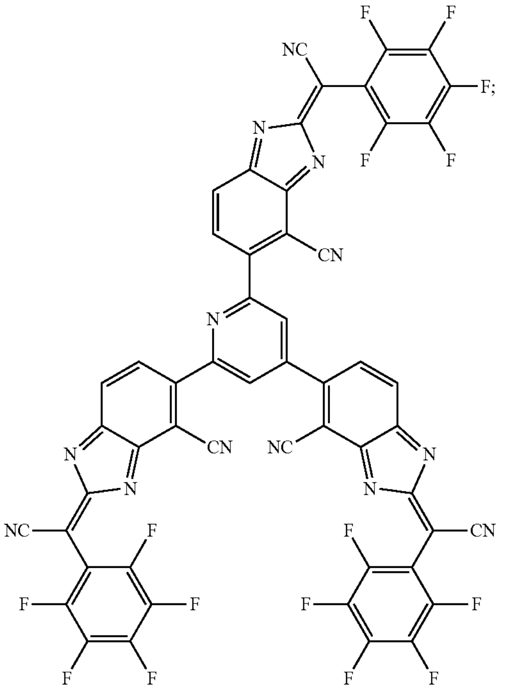
176
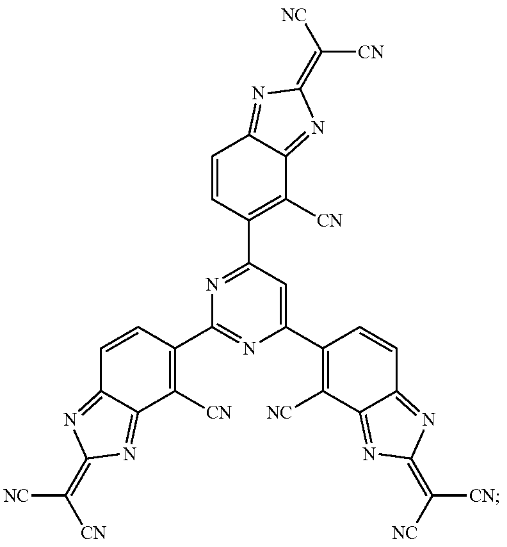
-continued
177
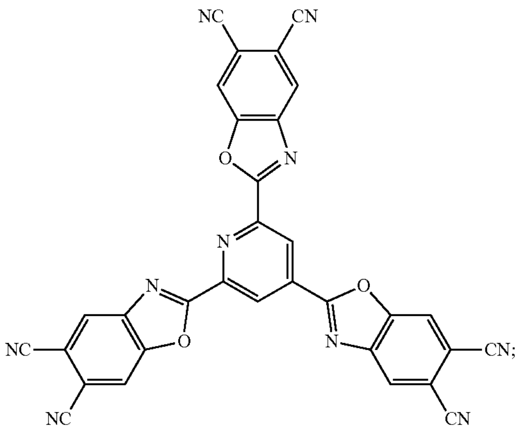
or
178
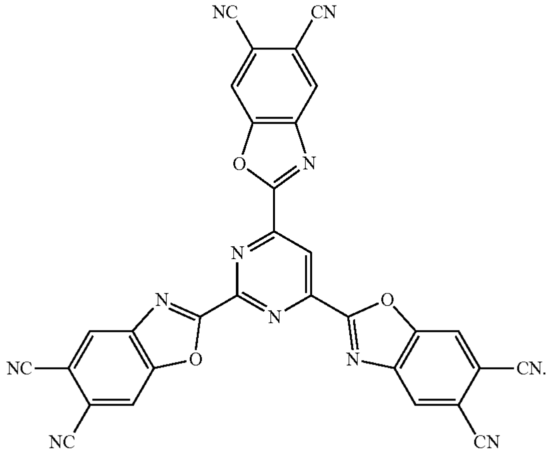
25. The organic light emitting display device of claim 20, wherein the organic compound has one of the following structures:
1
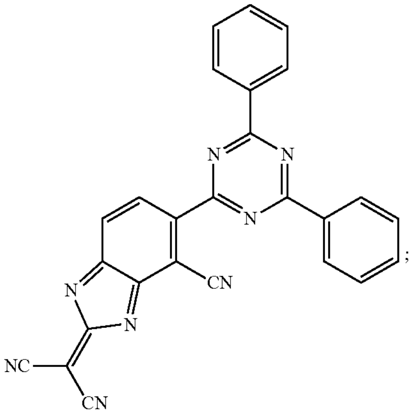

-continued
2
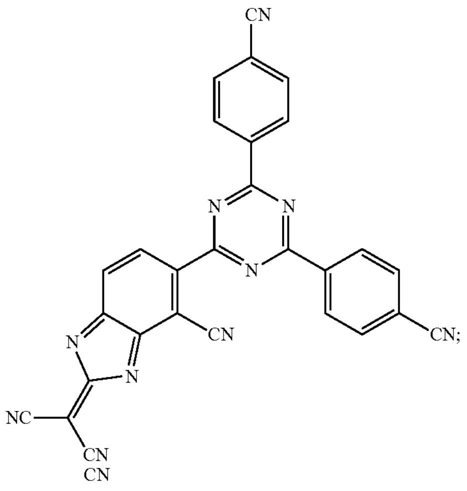
3
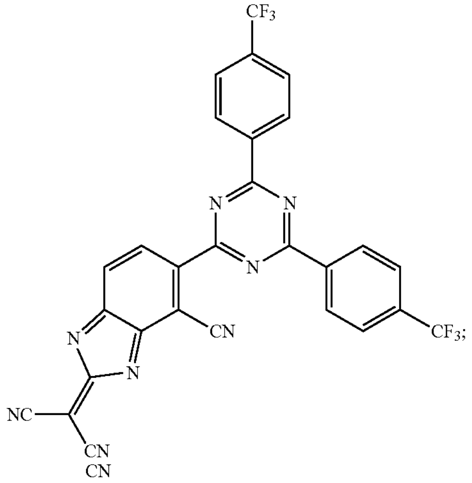
4
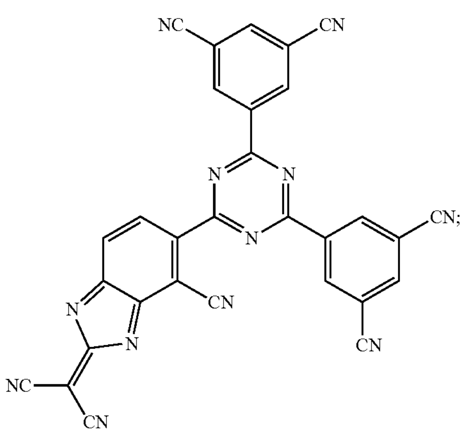
-continued
5
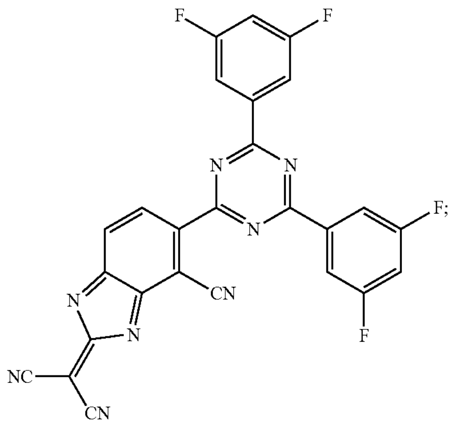
6
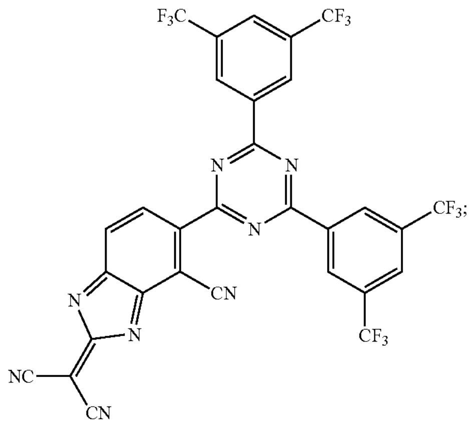
7
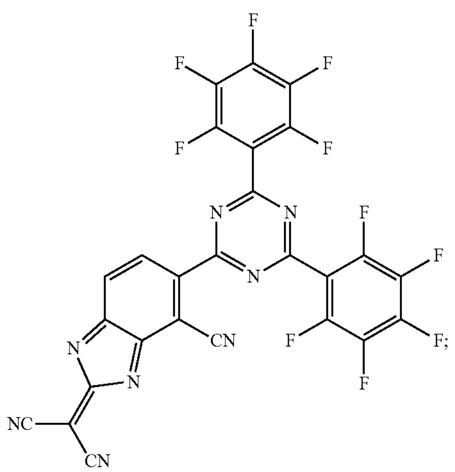

-continued
8
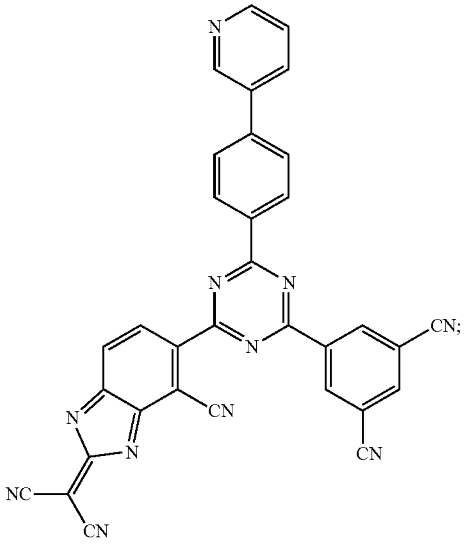
9
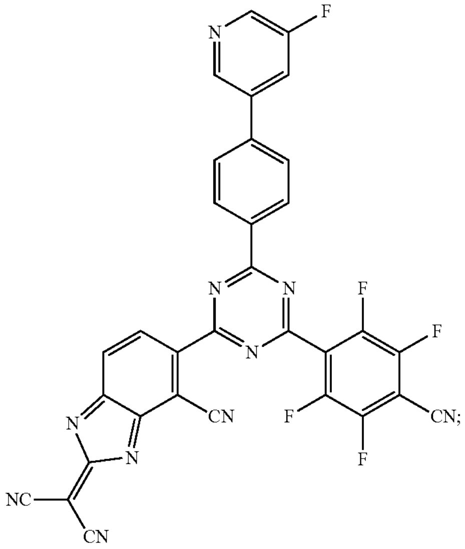
10
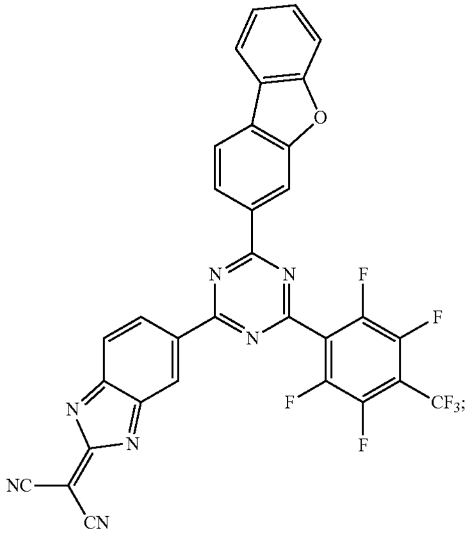
-continued
11
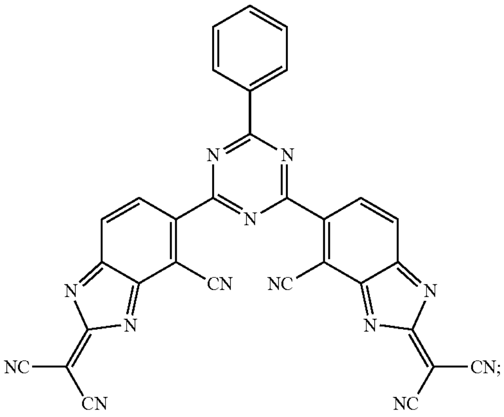
12
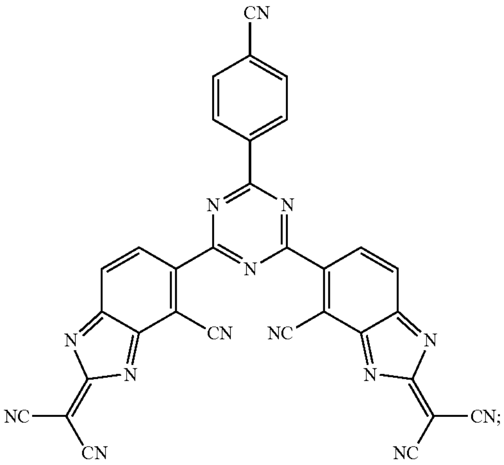
13
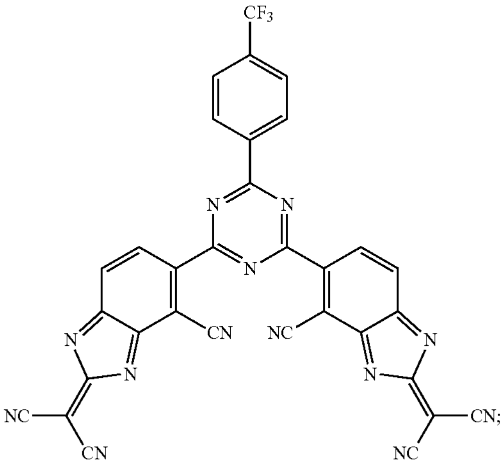

-continued
14
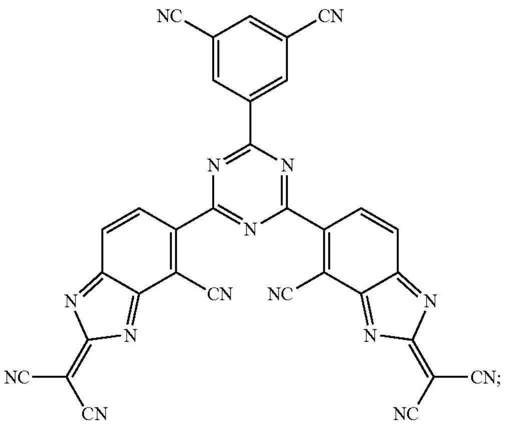
15
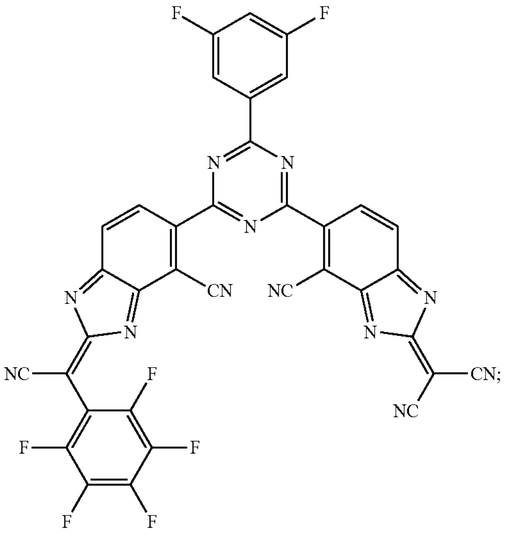
16
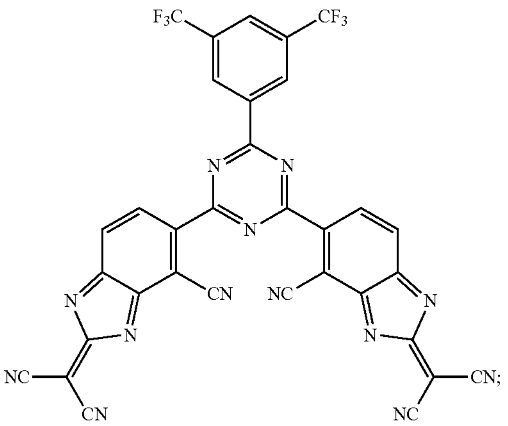
-continued
17
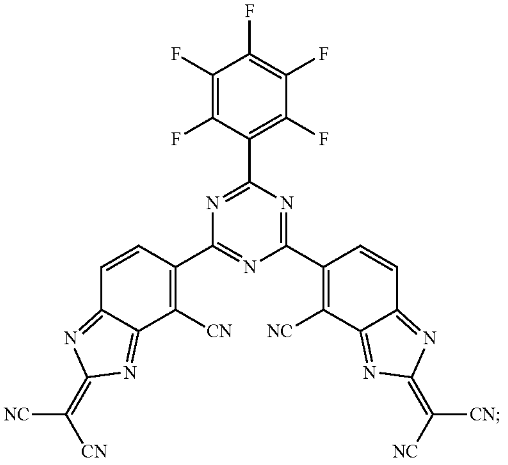
18
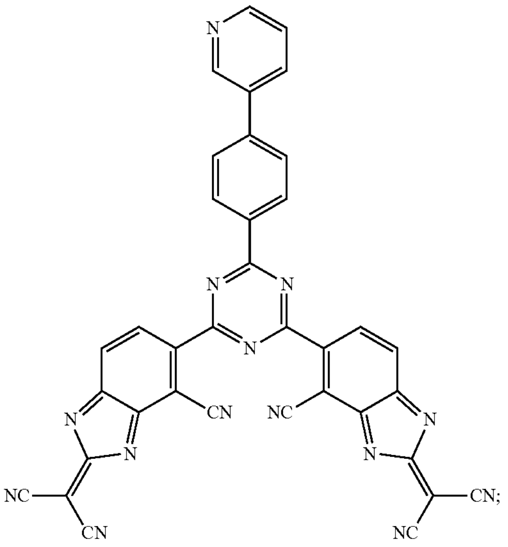
19
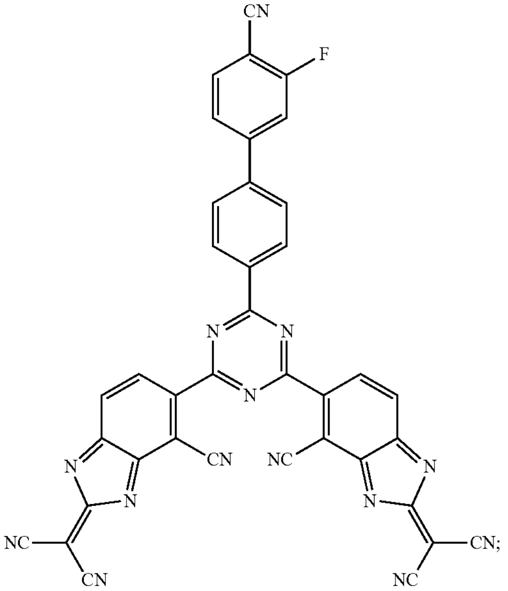

-continued
20
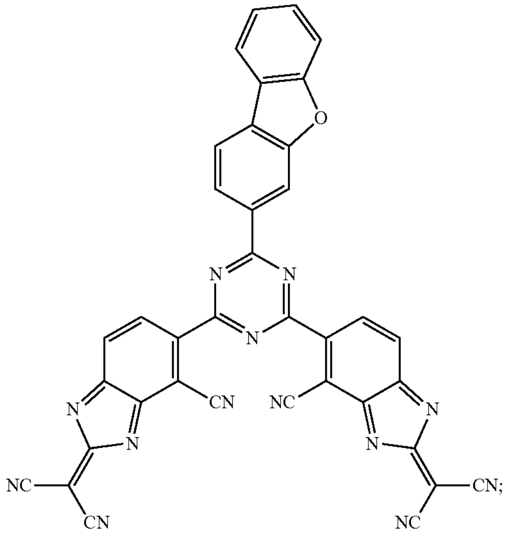
21
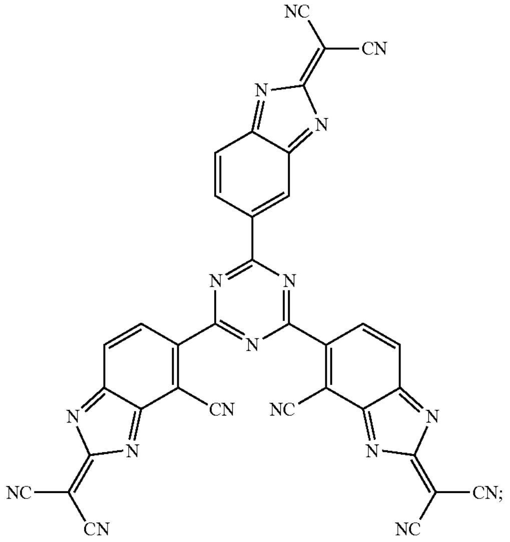
22
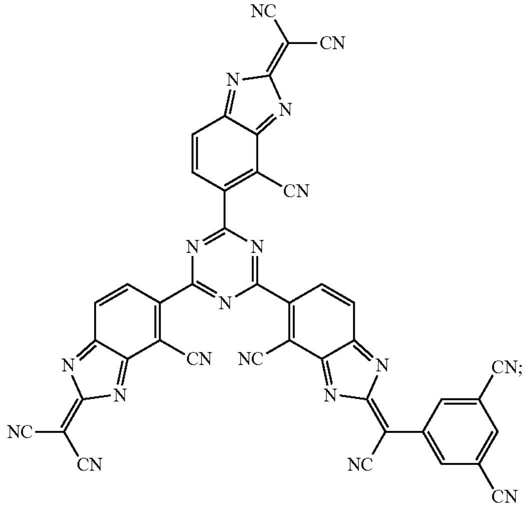
-continued
23
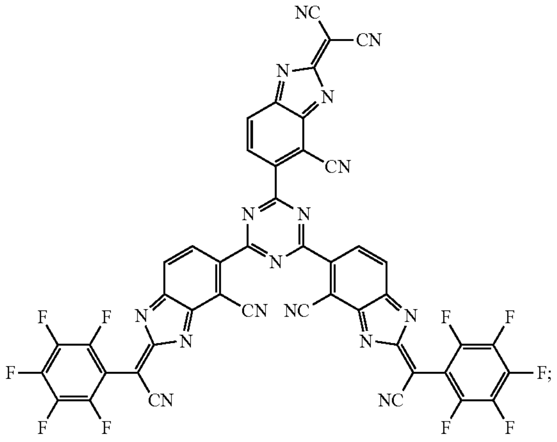
24
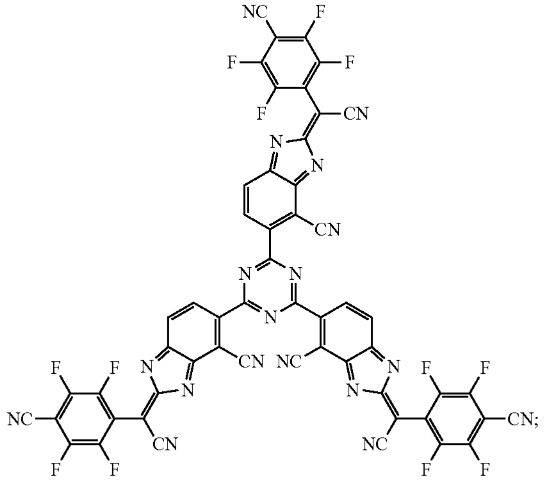
25
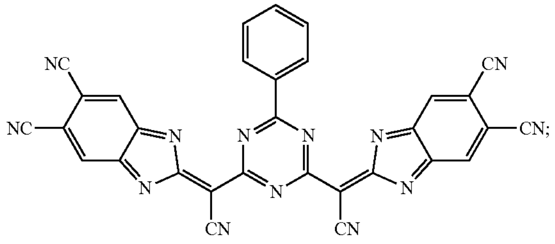
26
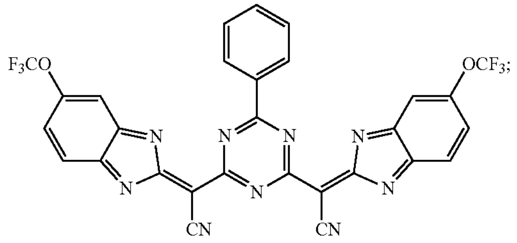

-continued
27
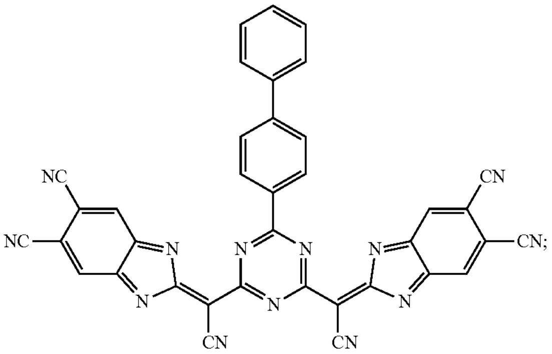
28
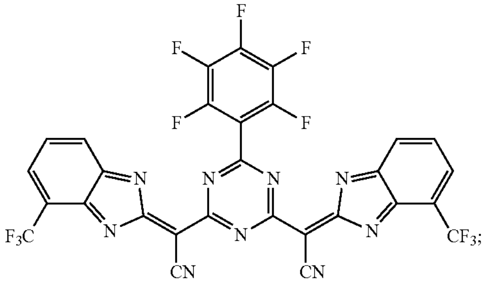
29
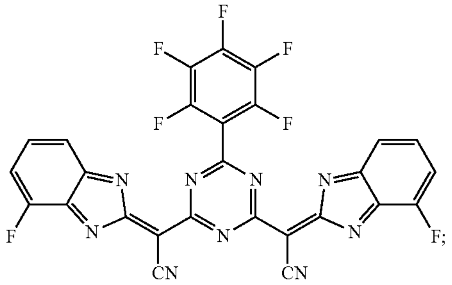
30
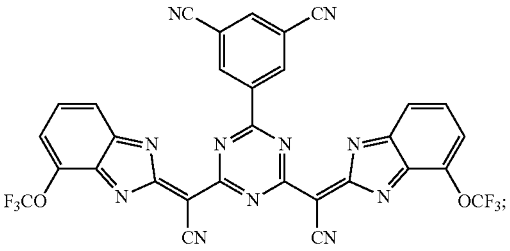
31
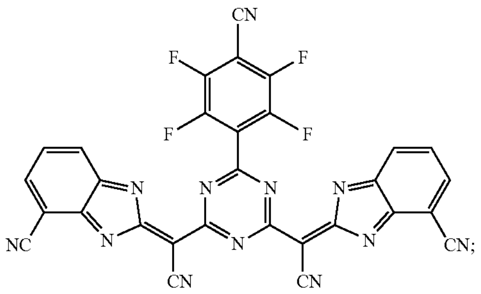
-continued
32
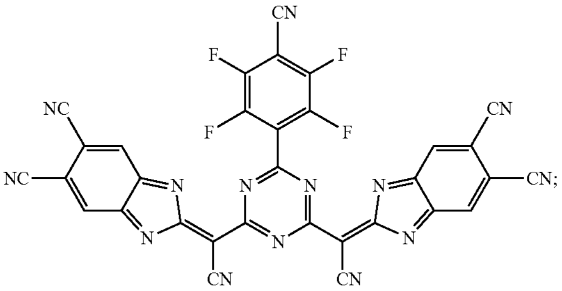
33
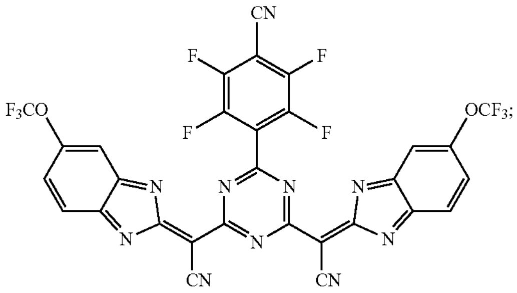
34
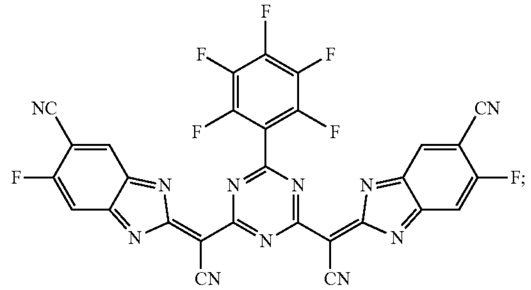
35
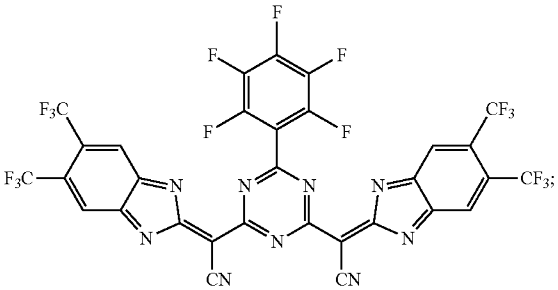
36
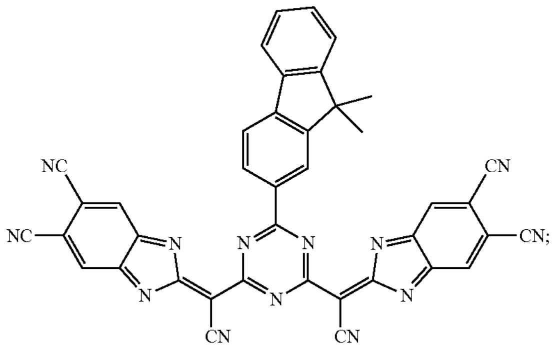

-continued
37
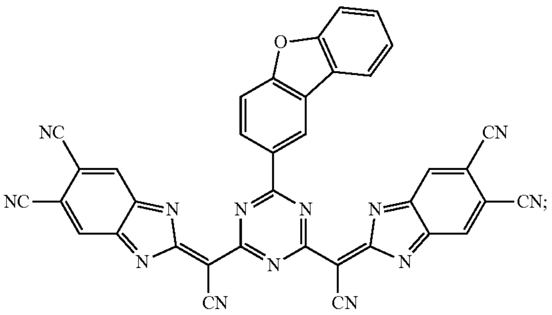
38
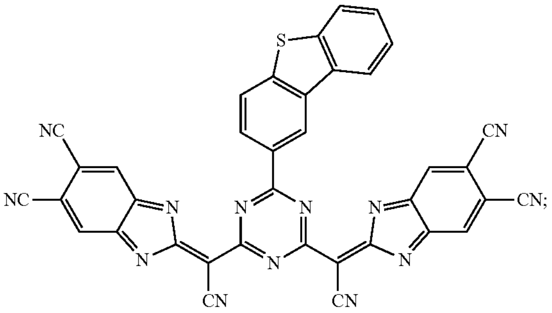
39
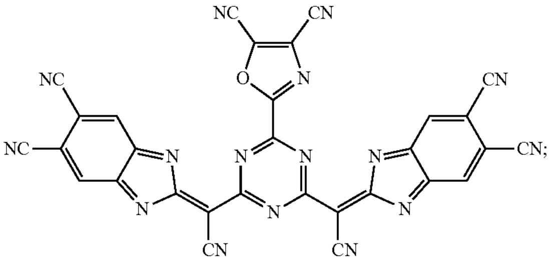
40
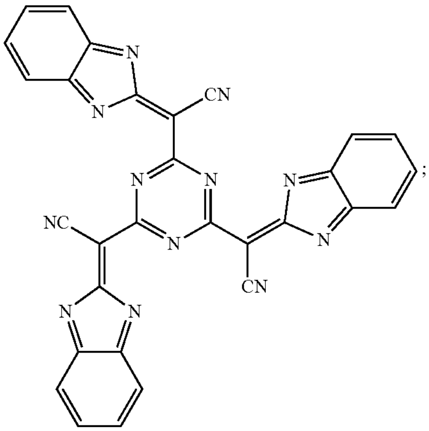
-continued
41
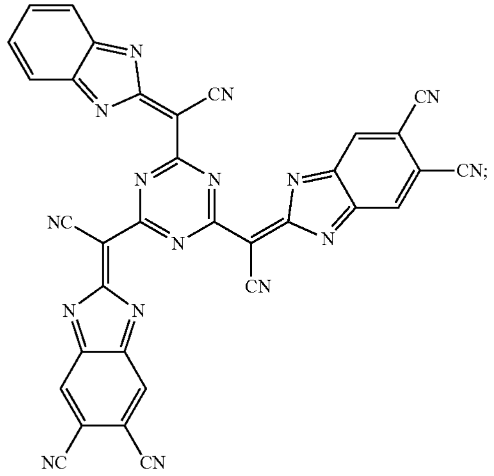
42
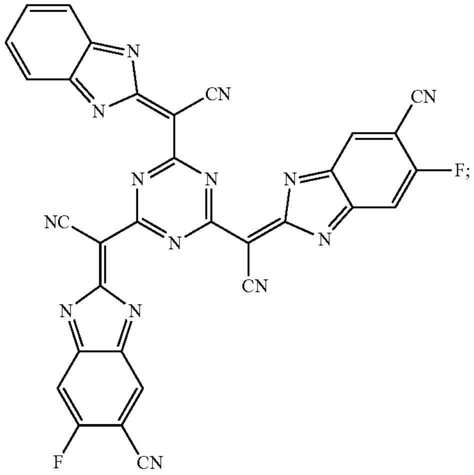
43
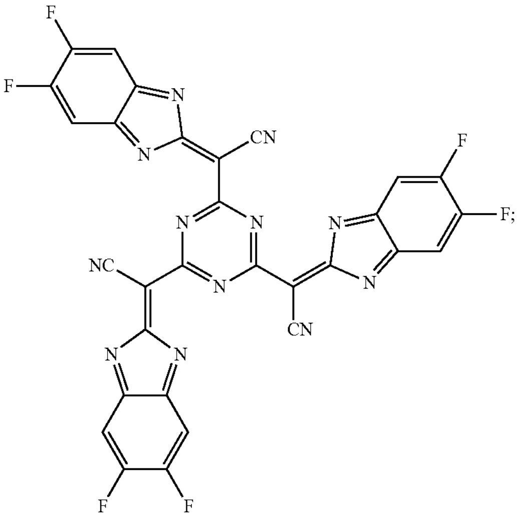

-continued
44
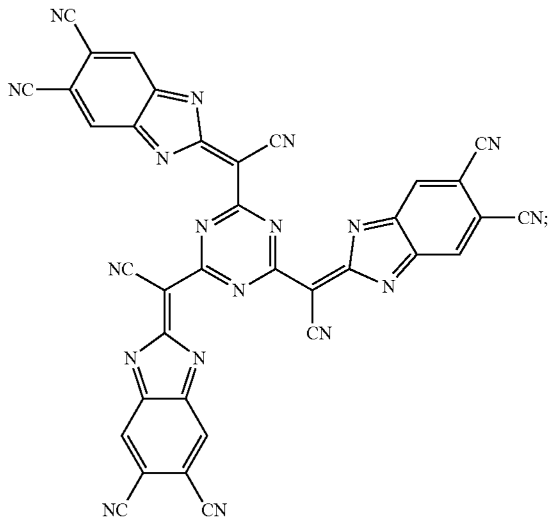
45
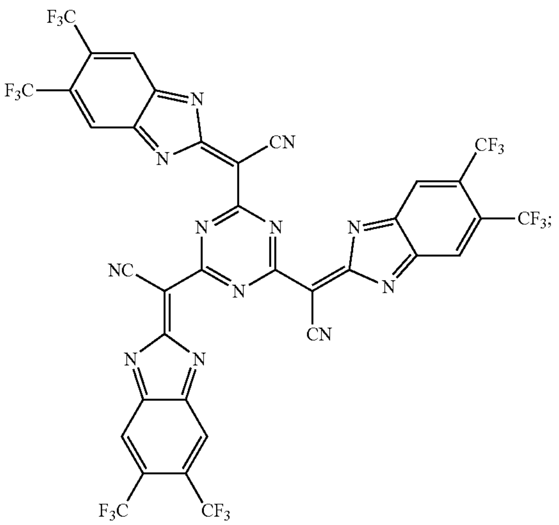
46
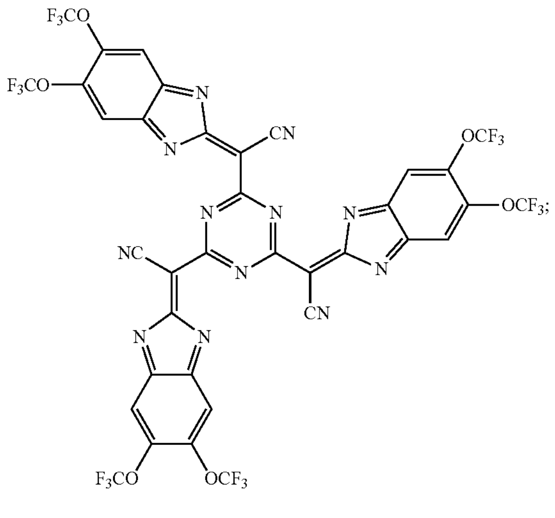
-continued
47
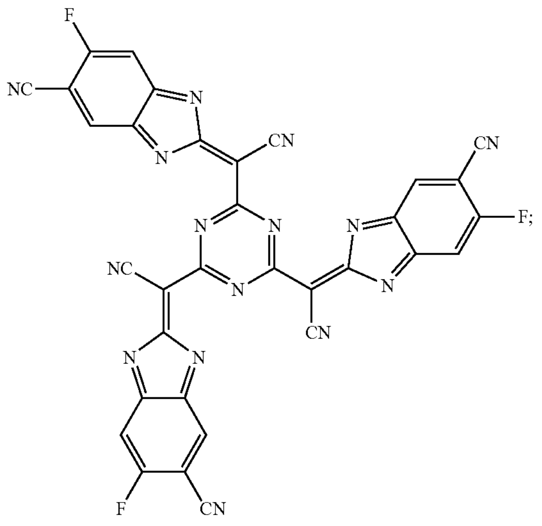
48
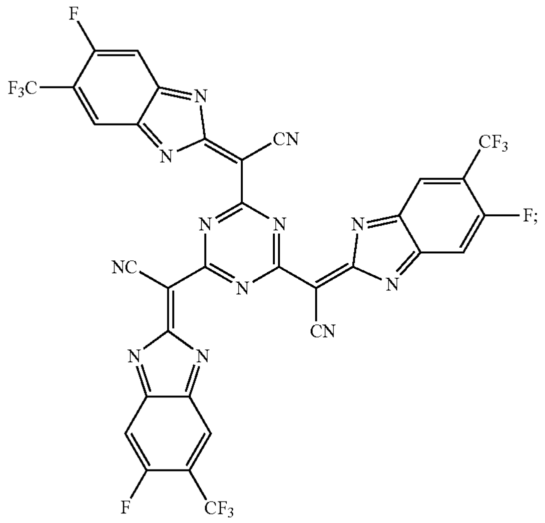
49
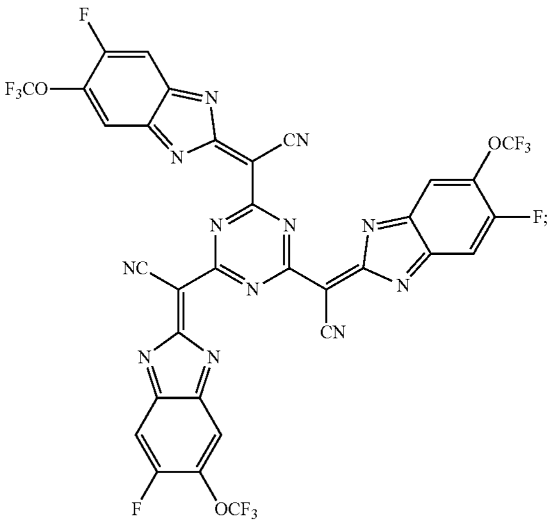

50
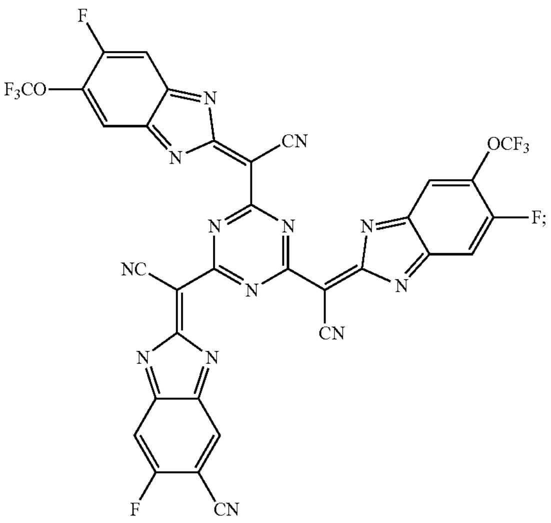
51
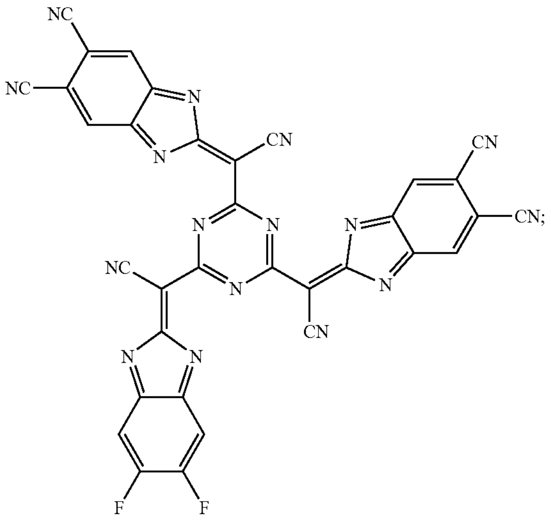
52
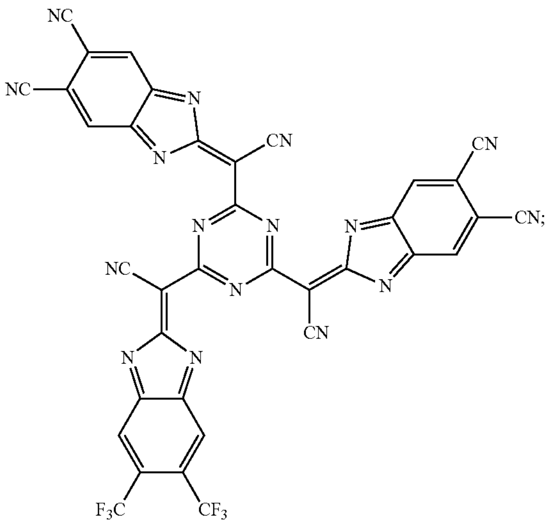
53
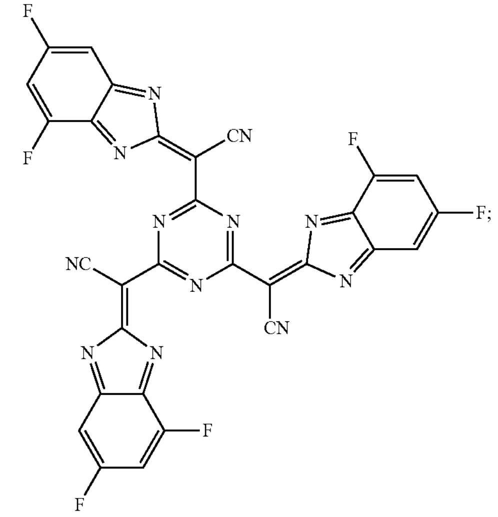
54
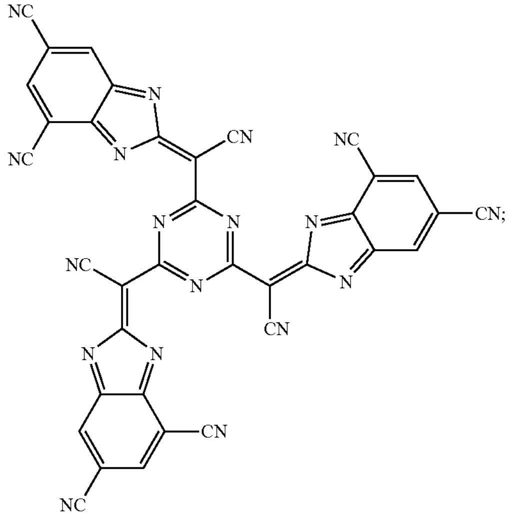
55
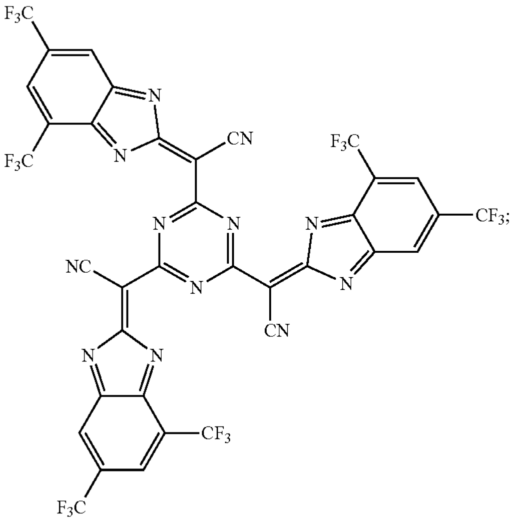

-continued
56
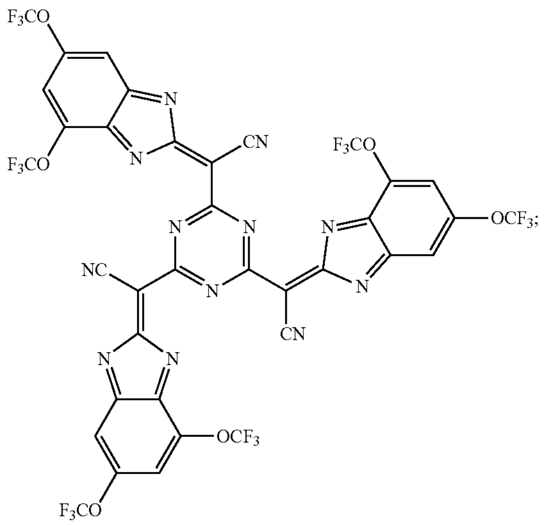
57
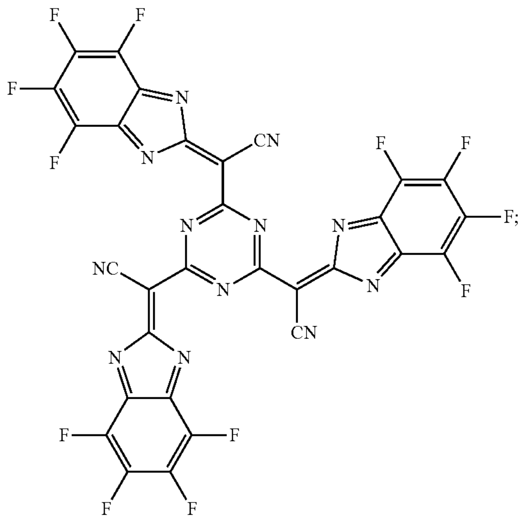
58
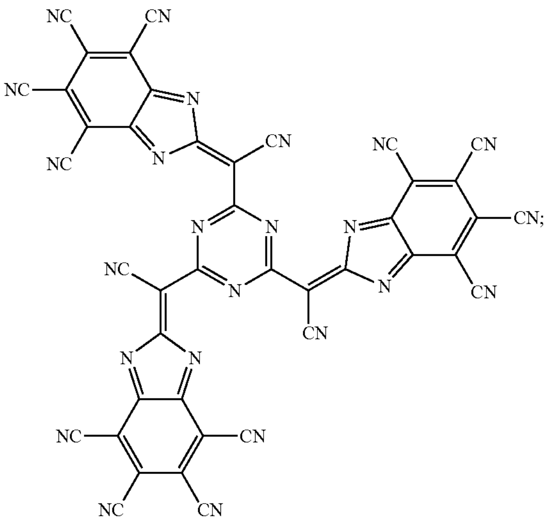
-continued
59
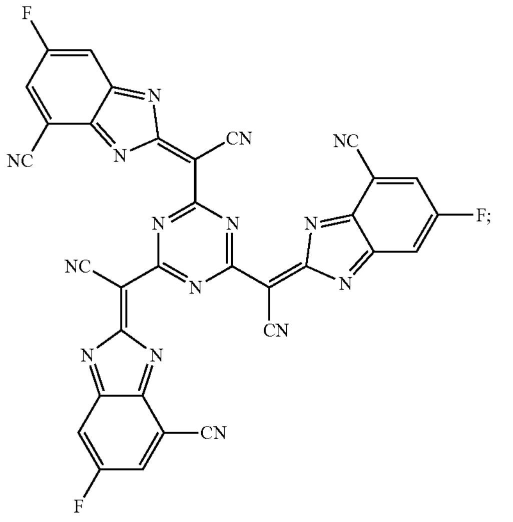
60
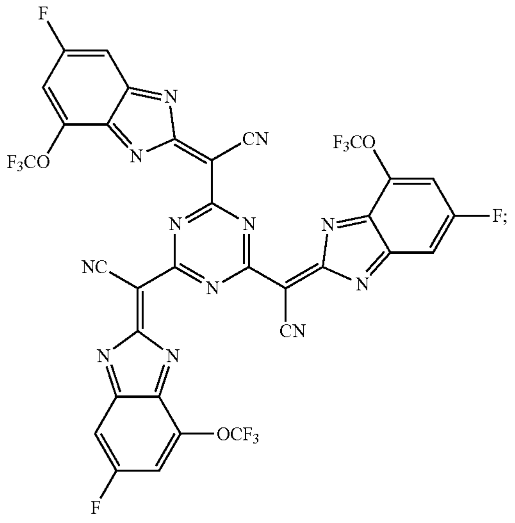
61
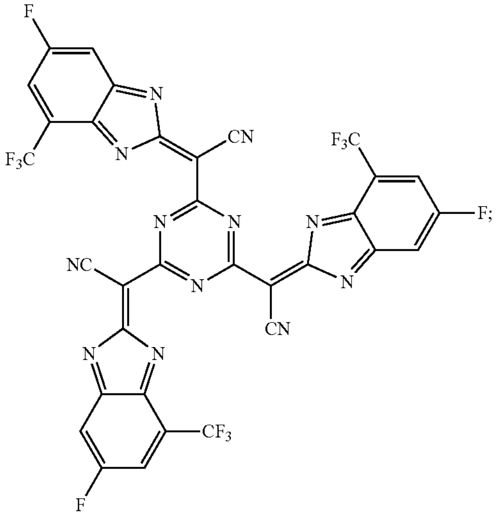

-continued
62
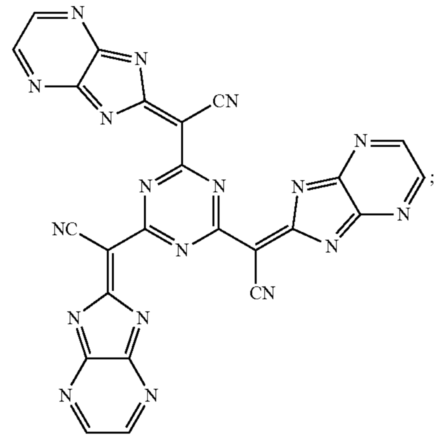
63
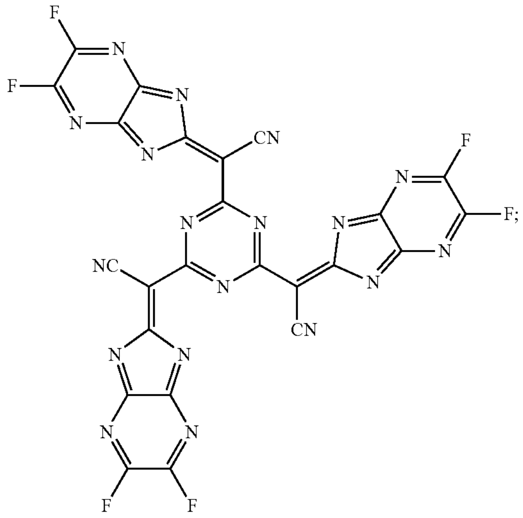
64
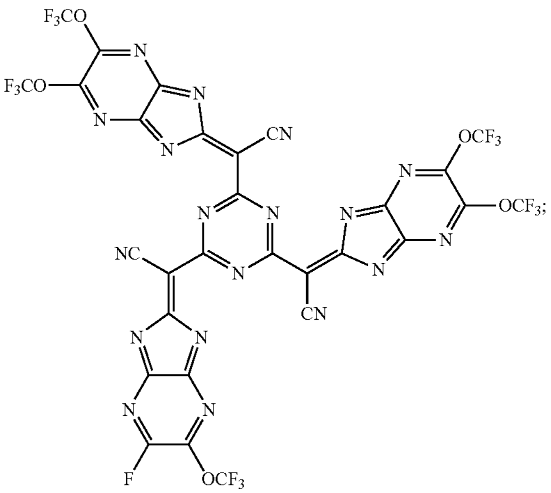
-continued
65
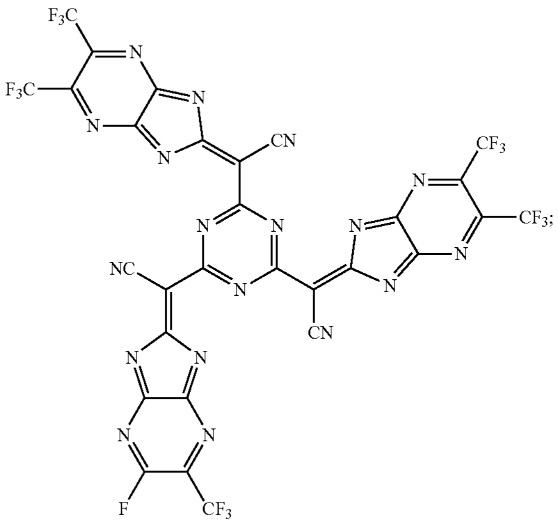
66
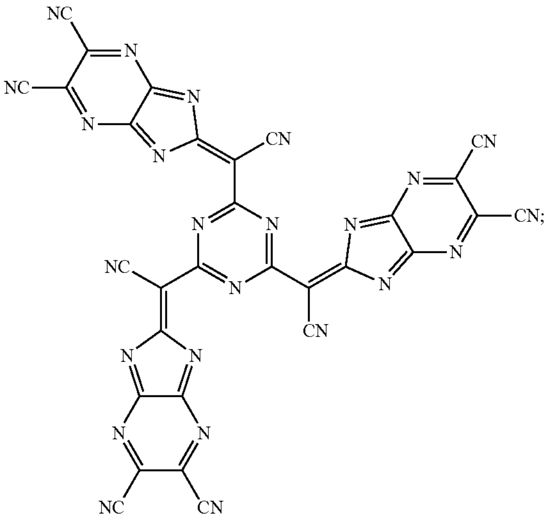
67
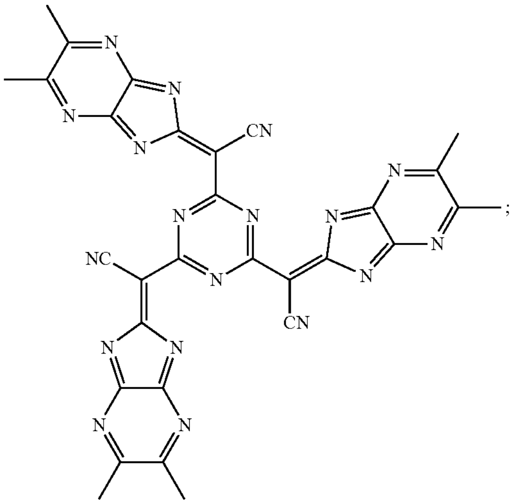

-continued
68
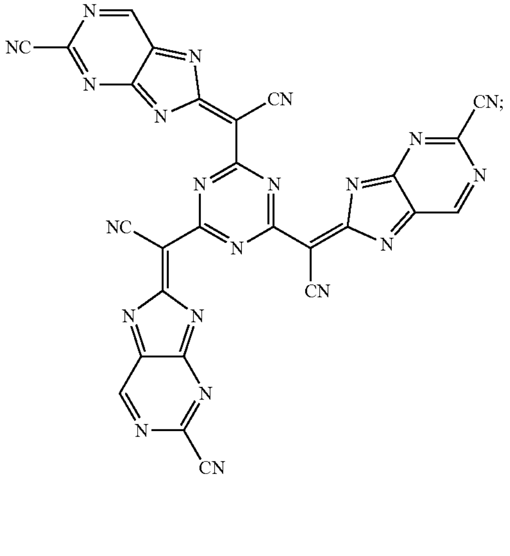
69
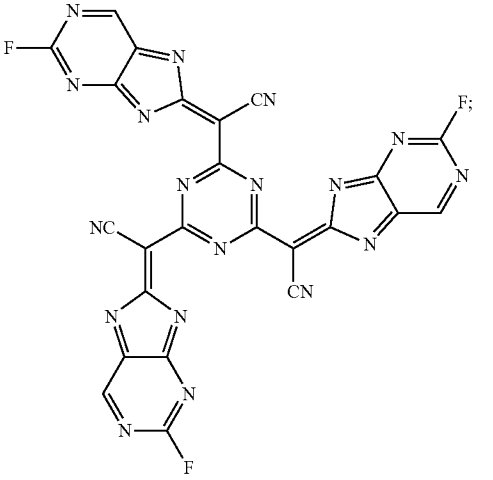
70
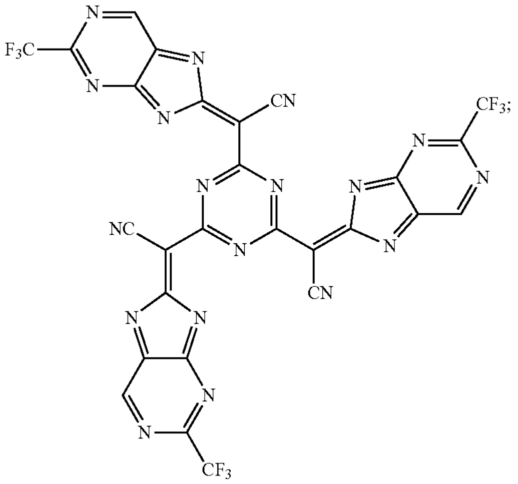
71
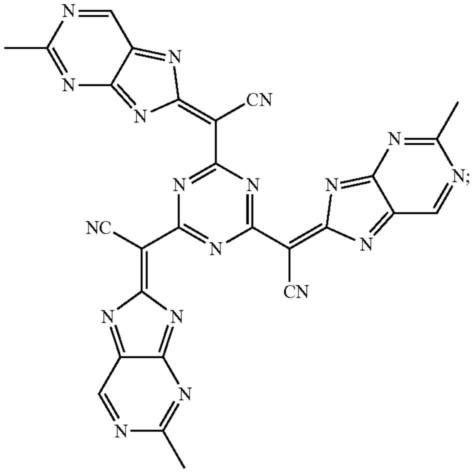
72
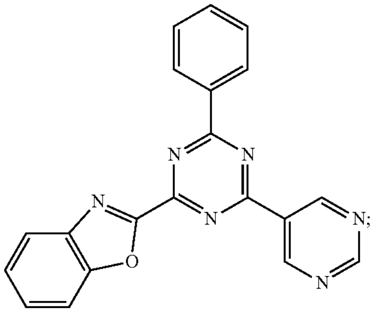
73
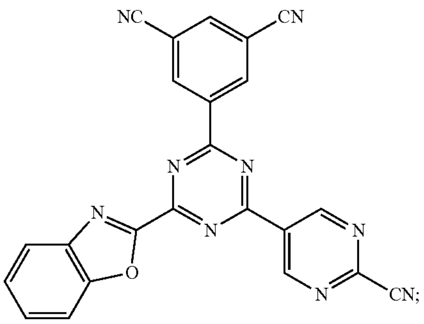
74
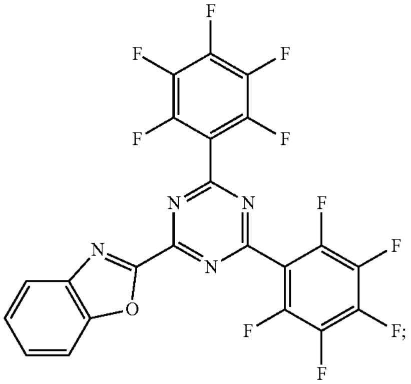

-continued
75
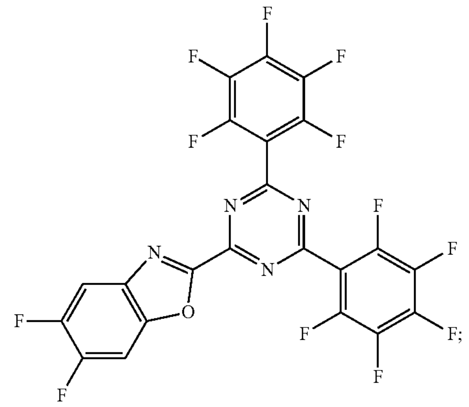
76
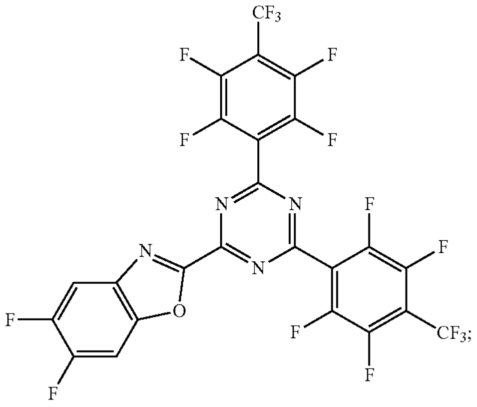
77
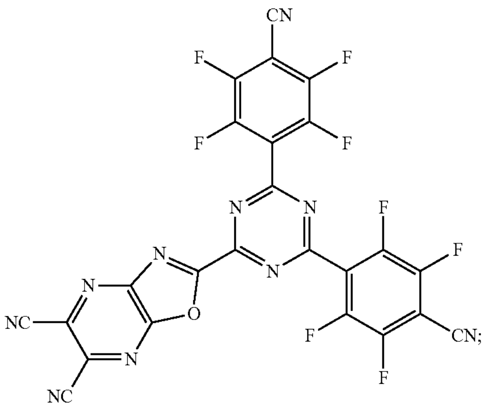
78
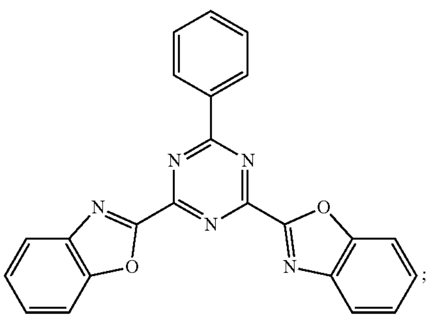
-continued
79
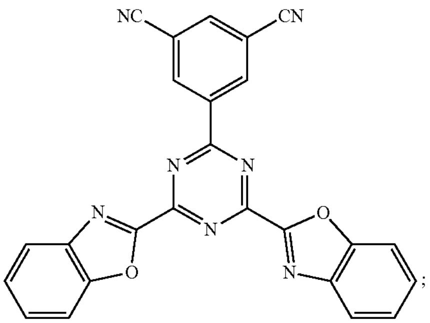
80
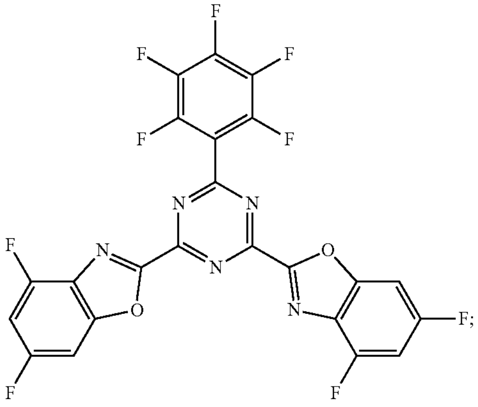
81
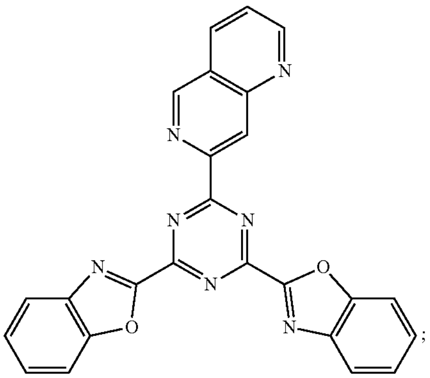
82
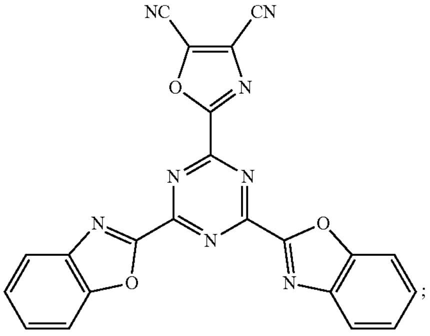

-continued
83
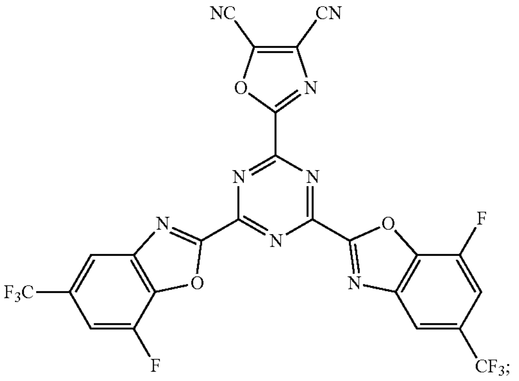
84
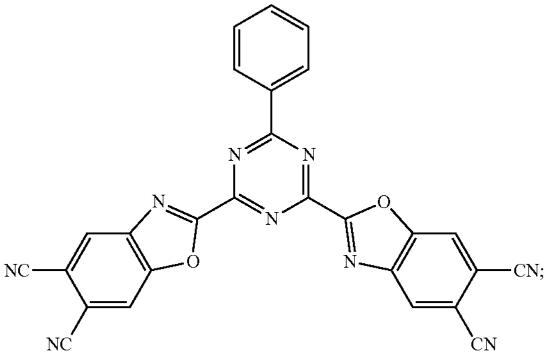
85
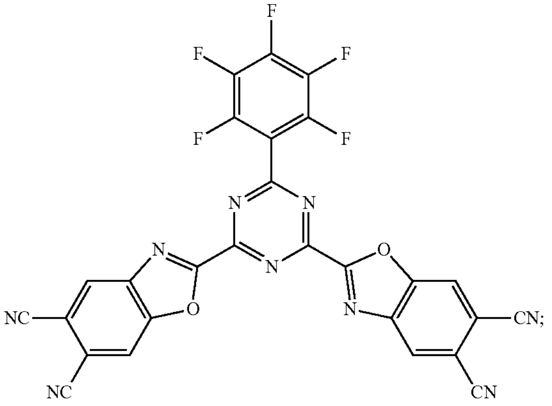
86
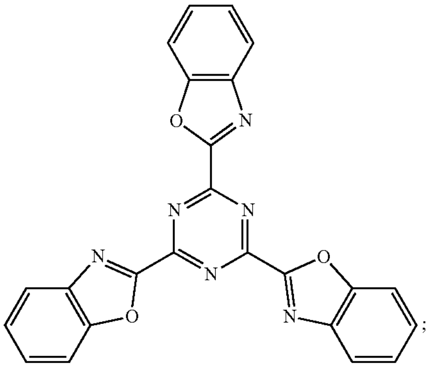
-continued
87
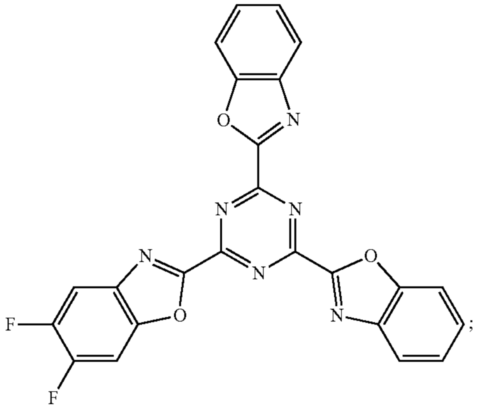
88
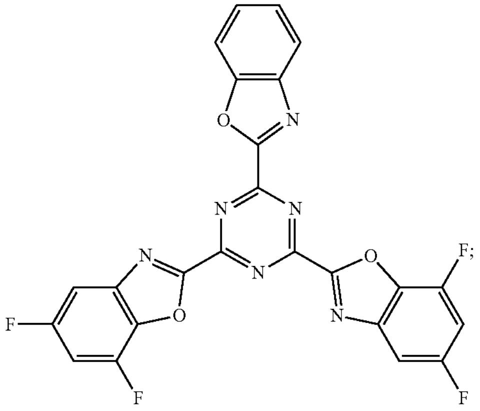
89
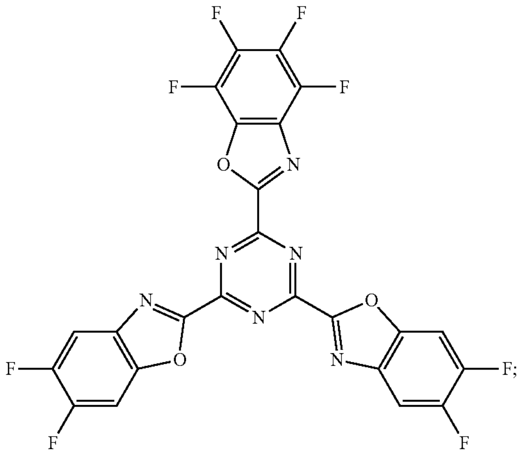

-continued
90
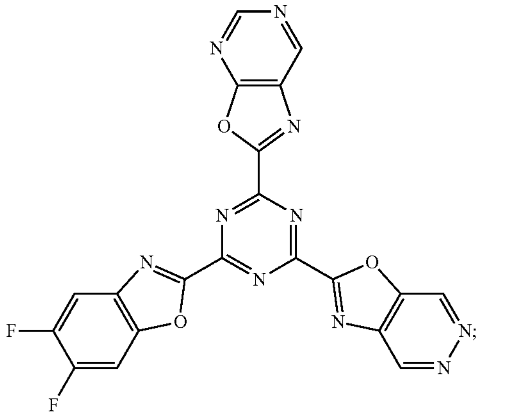
91
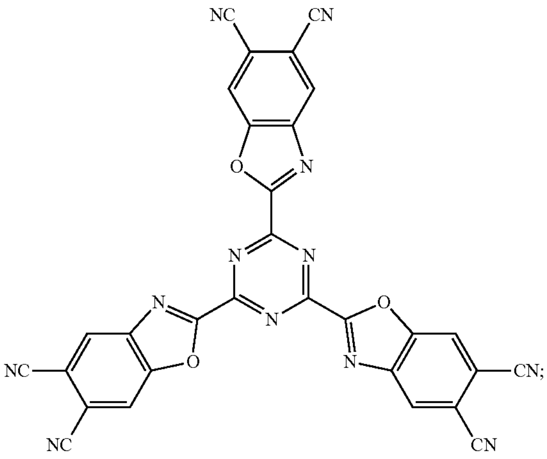
92
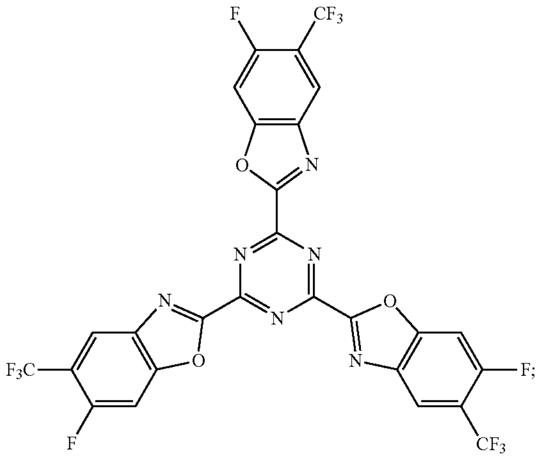
-continued
93
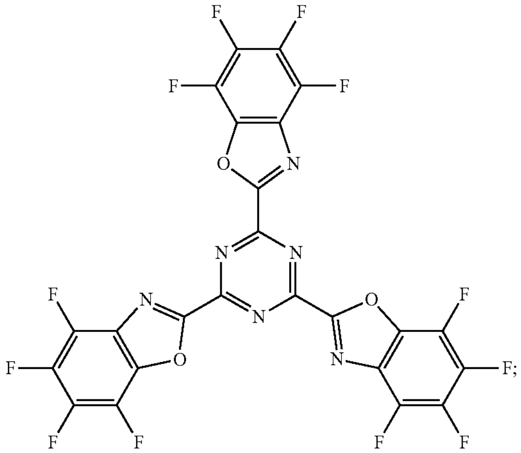
94
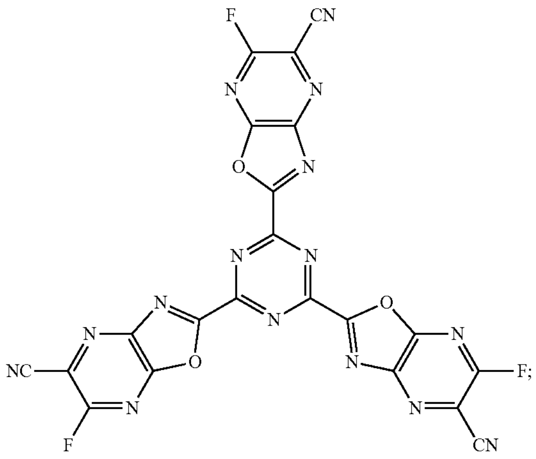
95
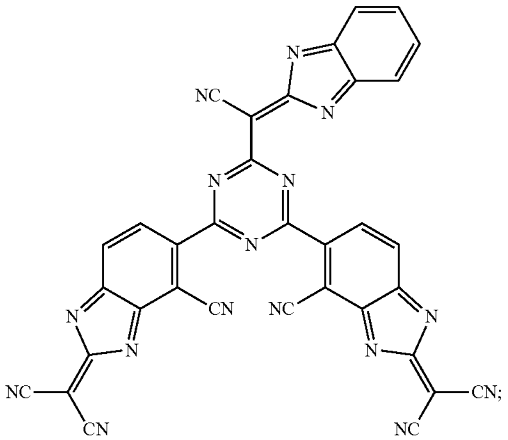

-continued
96
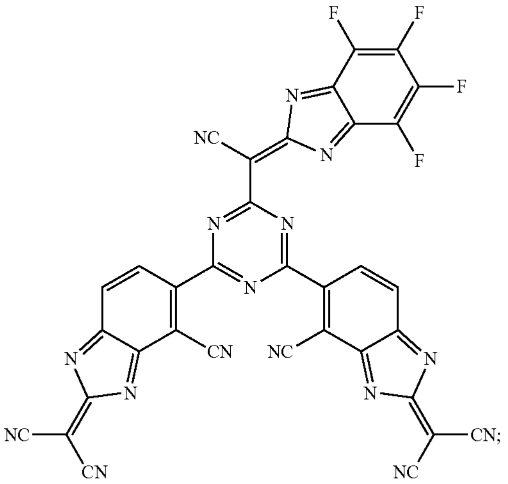
97
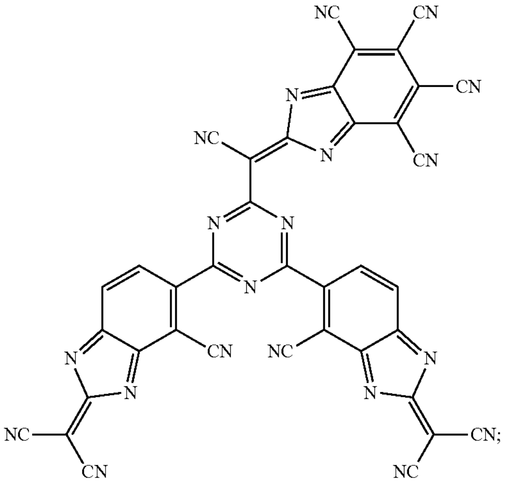
98
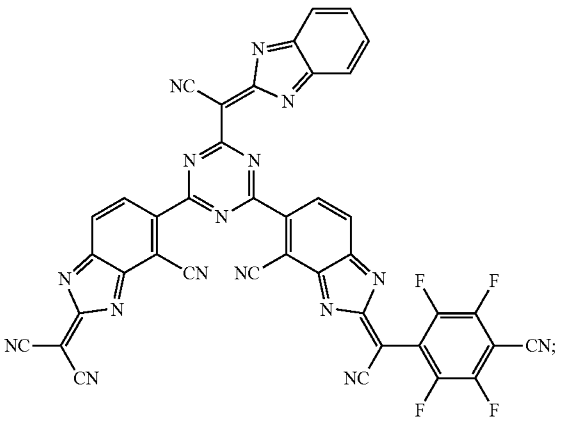
-continued
99
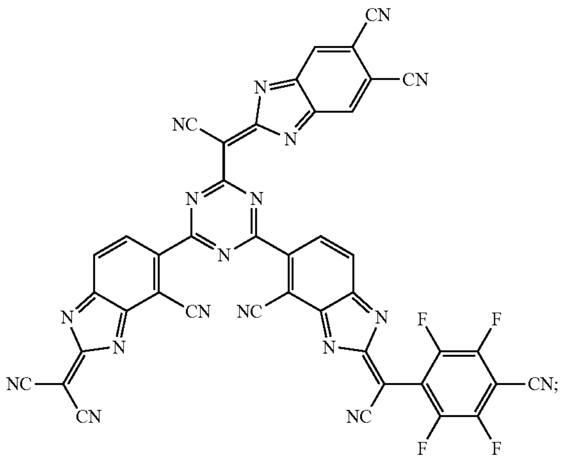
100
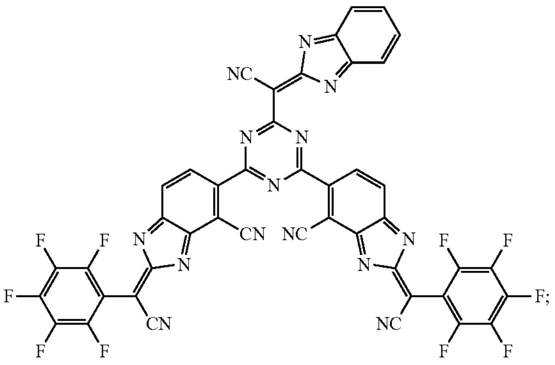
101
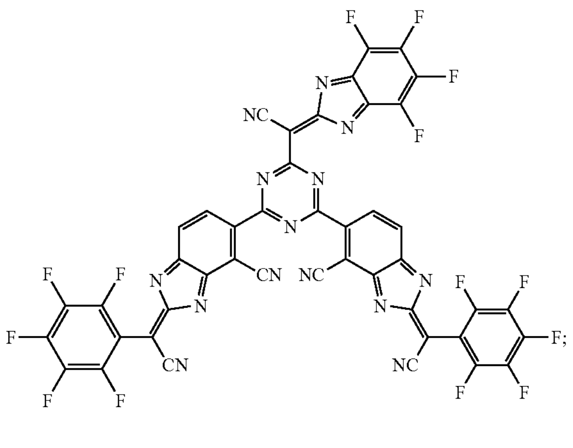

102
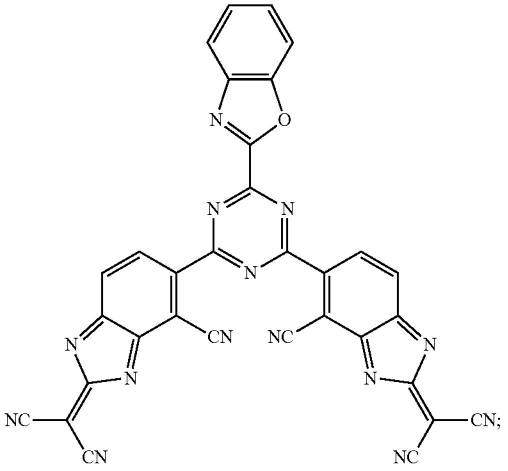
103
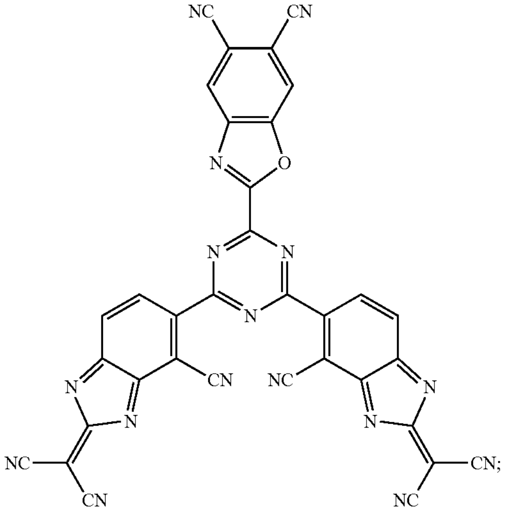
104
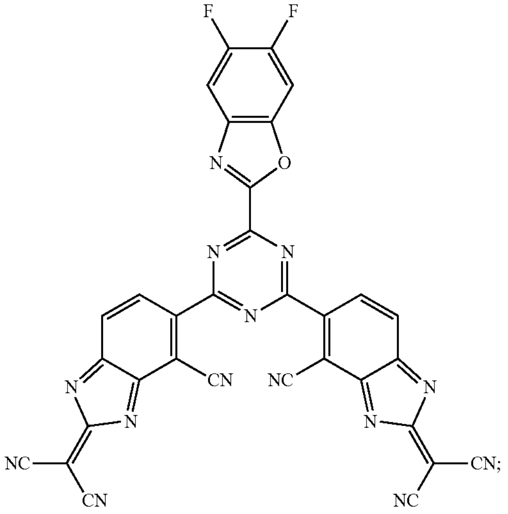
105
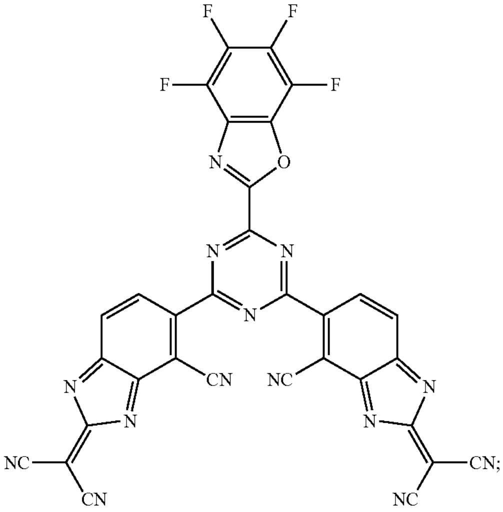
106
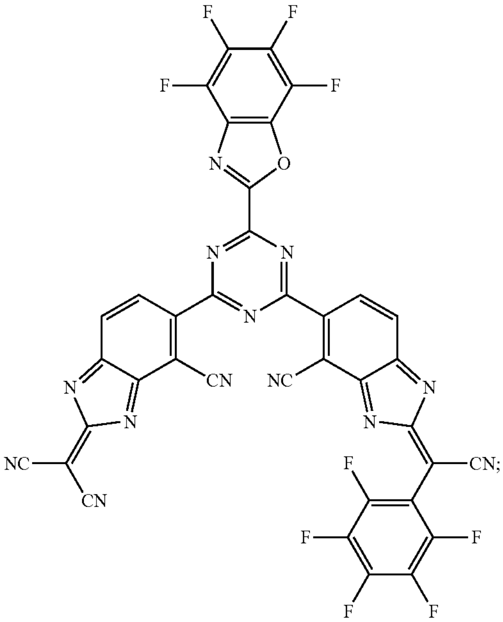
107
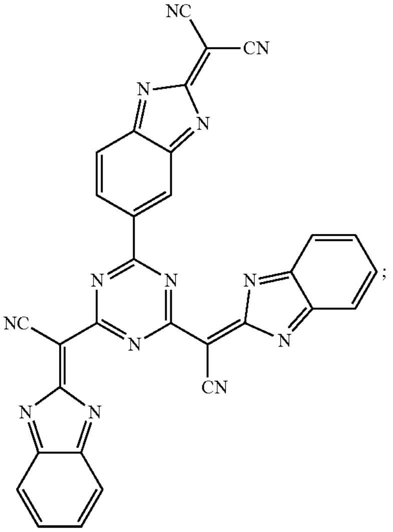

-continued
108
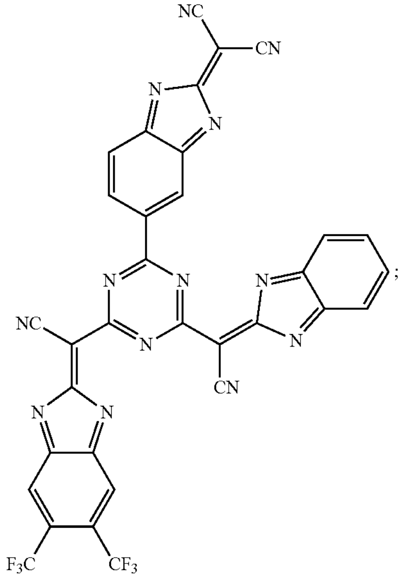
109
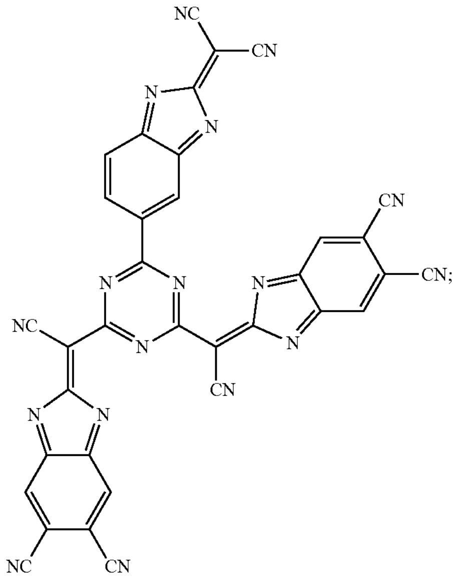
-continued
110
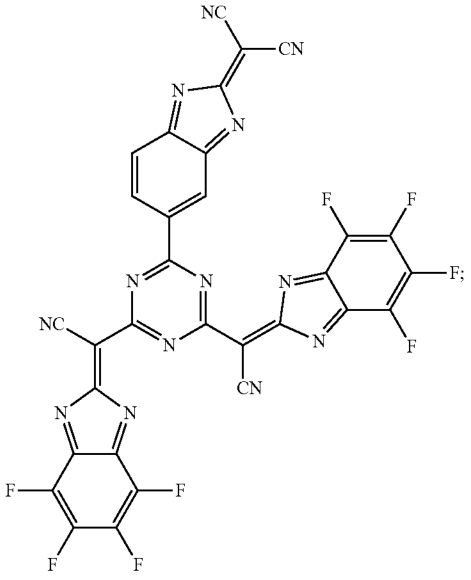
111
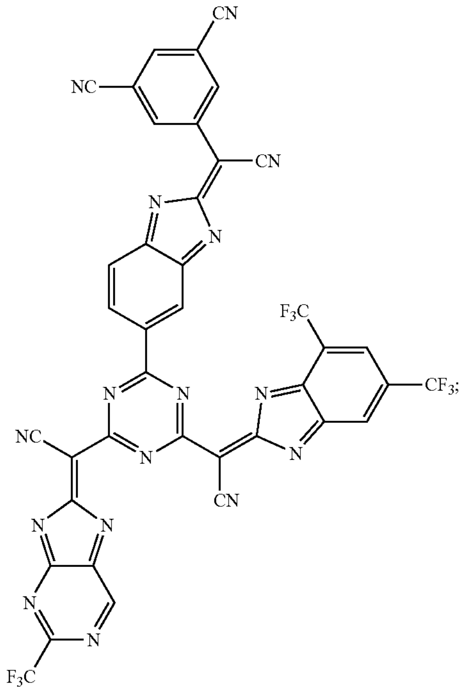

-continued
112
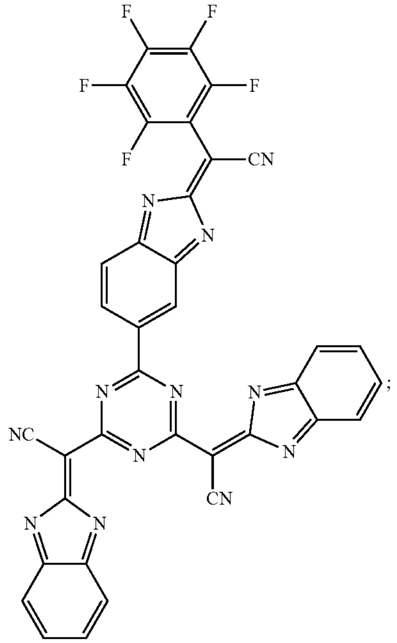
113
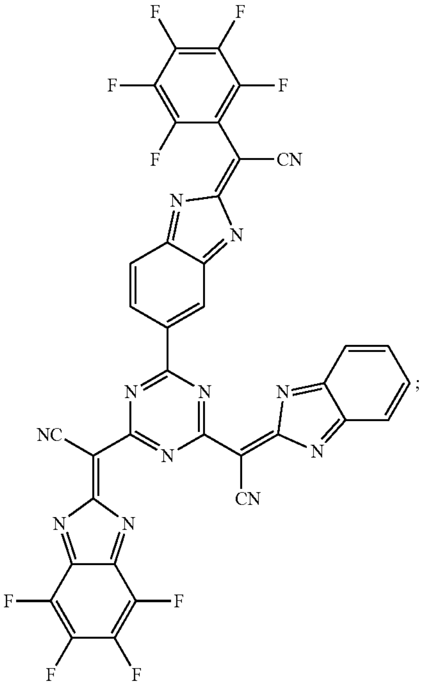
-continued
114
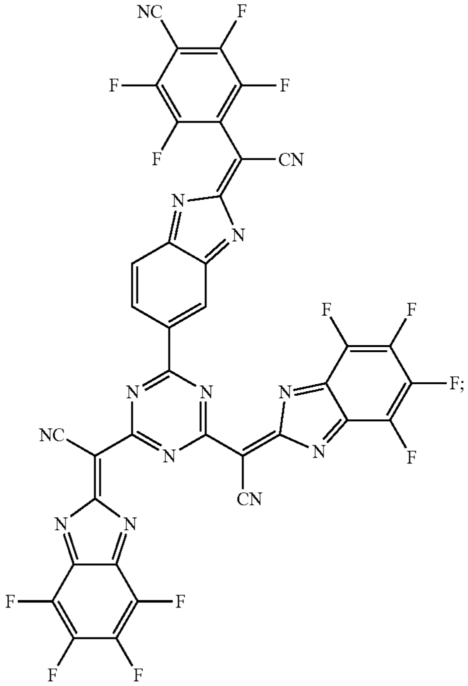
115
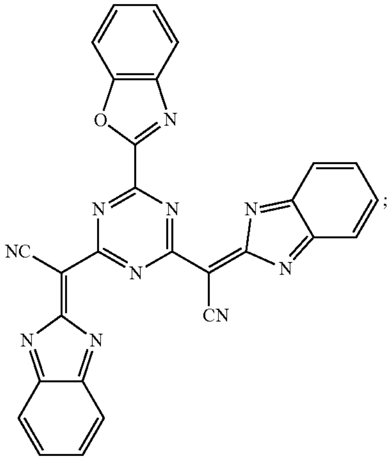
116
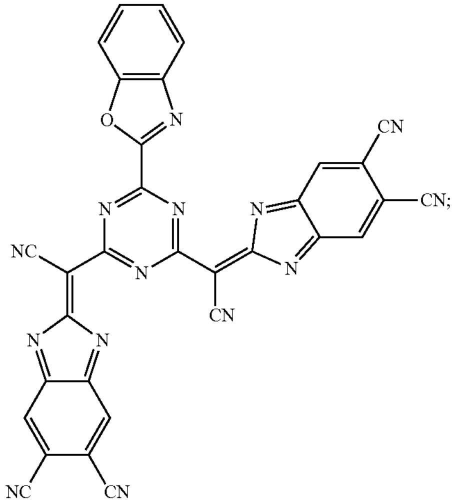

-continued
117
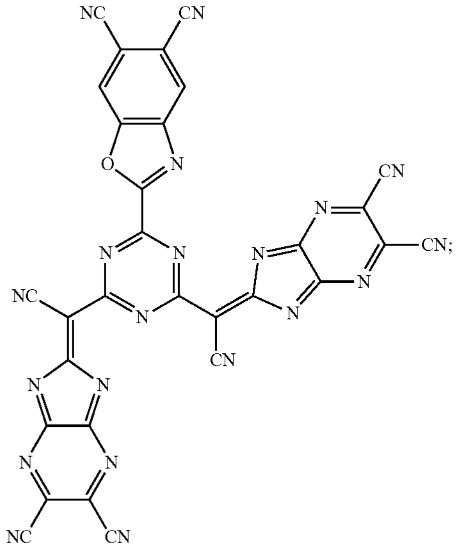
118
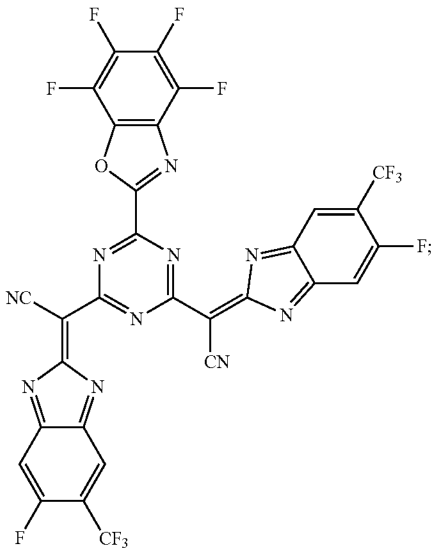
119
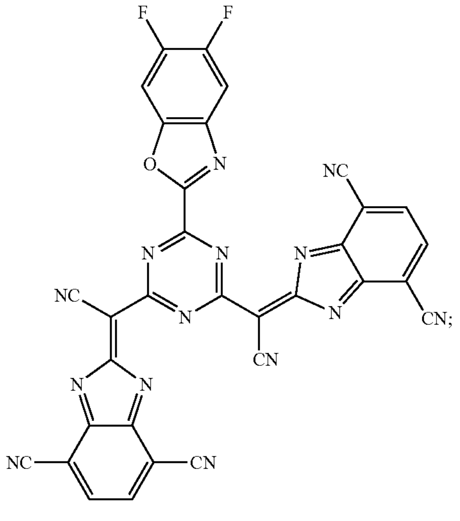
-continued
120
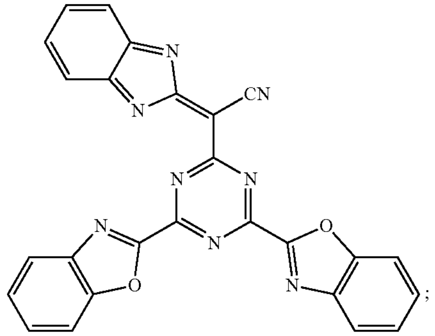
121
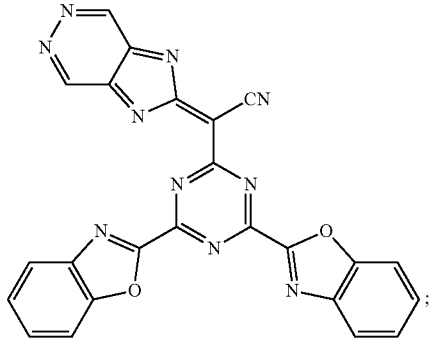
122
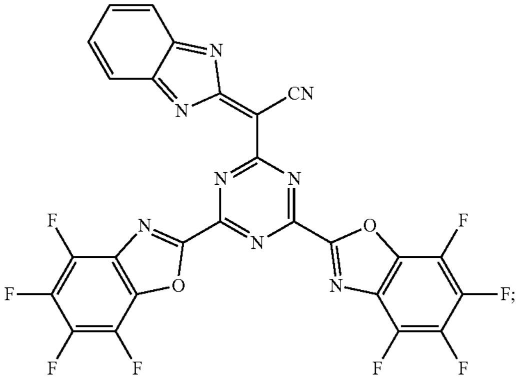
123
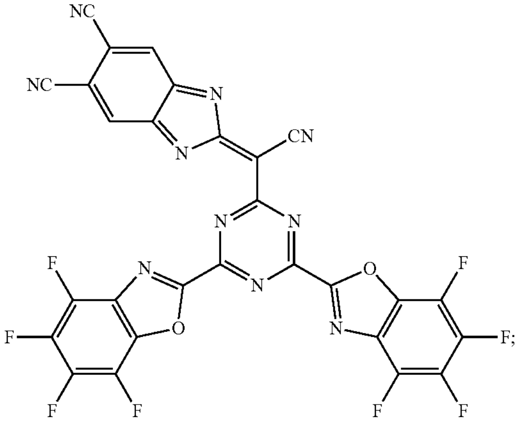

-continued
124
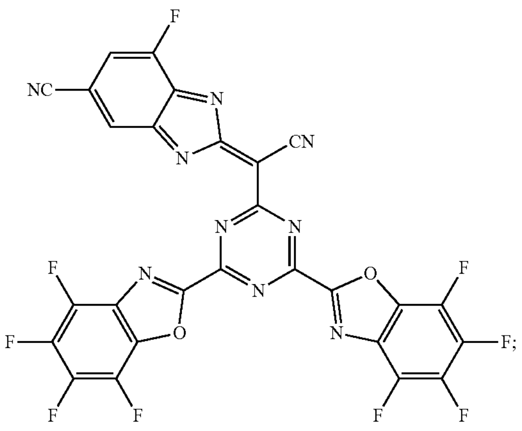
125
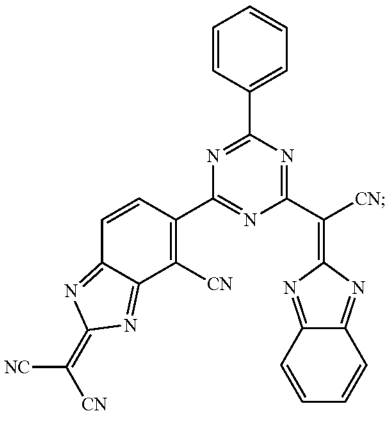
126
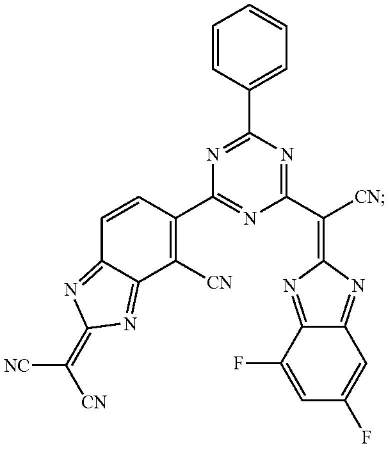
-continued
127
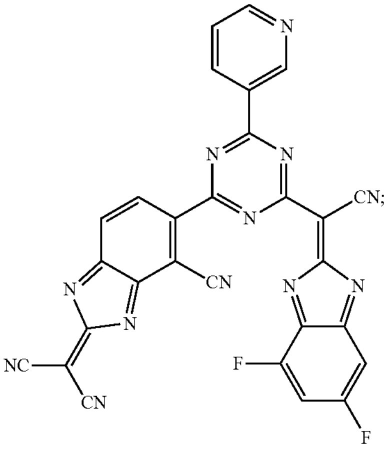
128
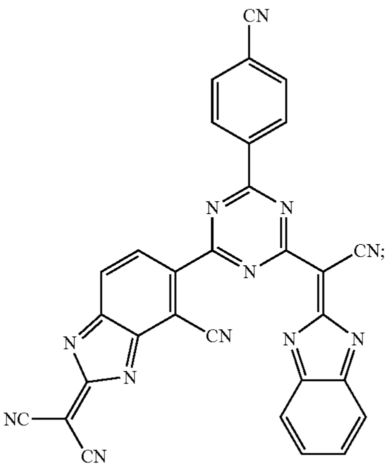
129
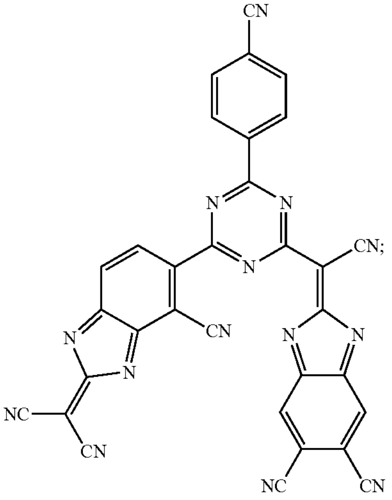

-continued
130
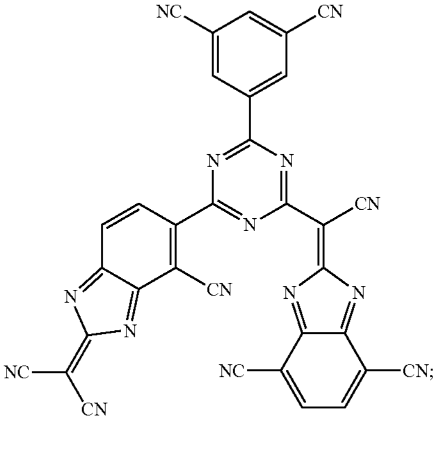
131
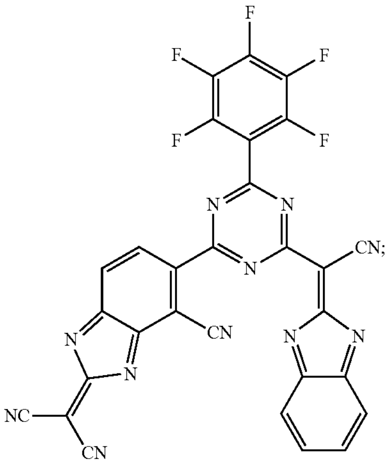
132
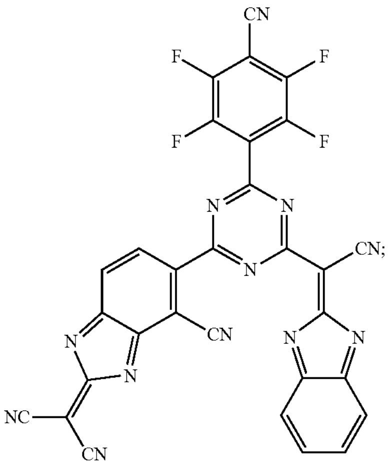
-continued
133
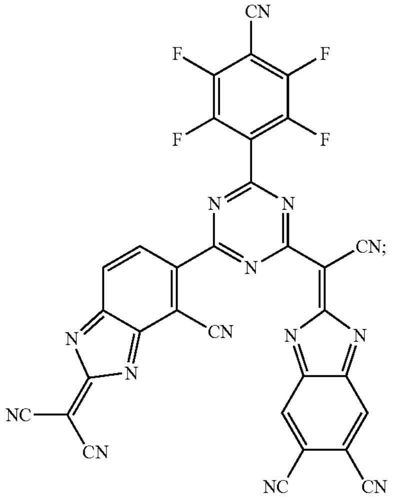
134
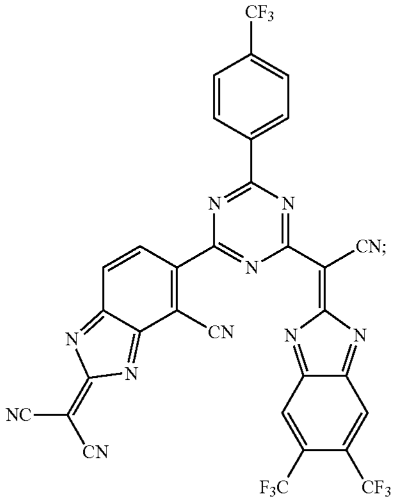
135
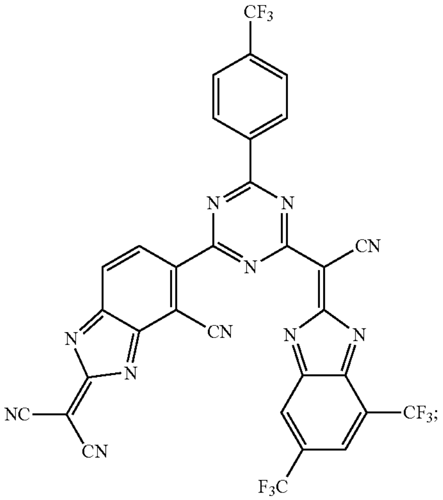

-continued
136
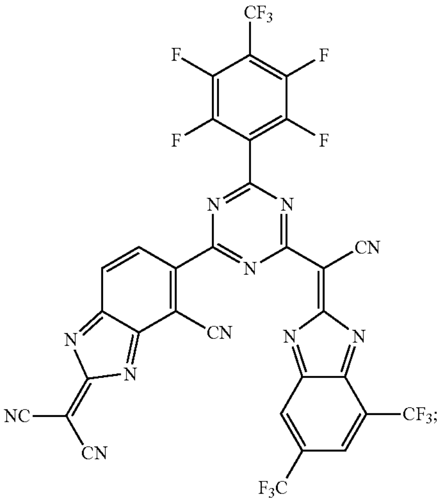
137
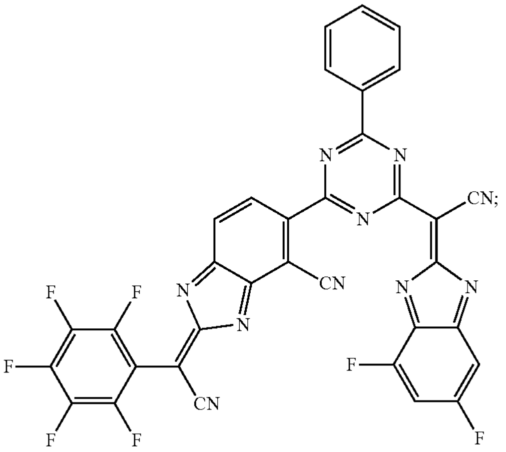
138
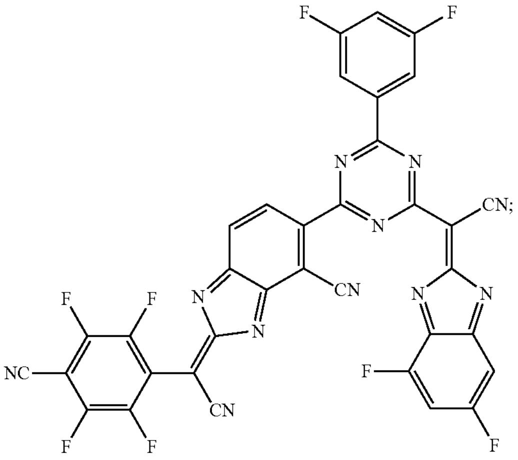
-continued
139
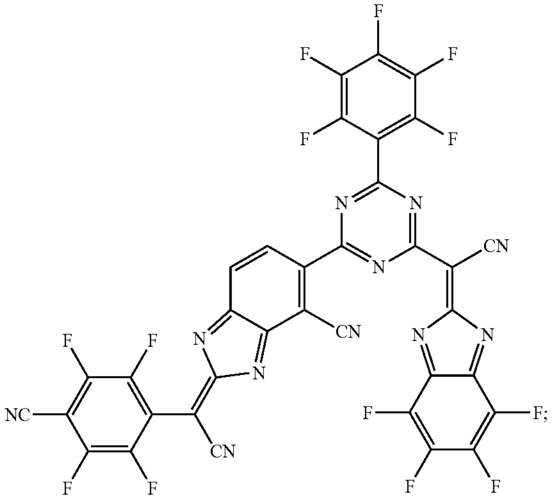
140
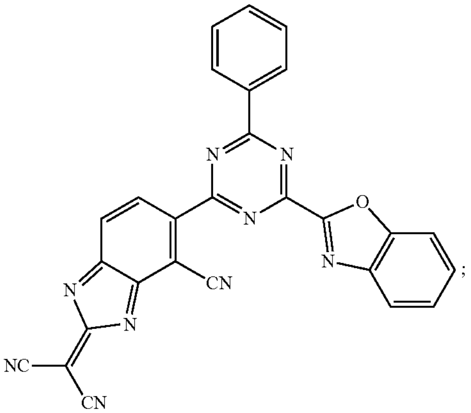
141
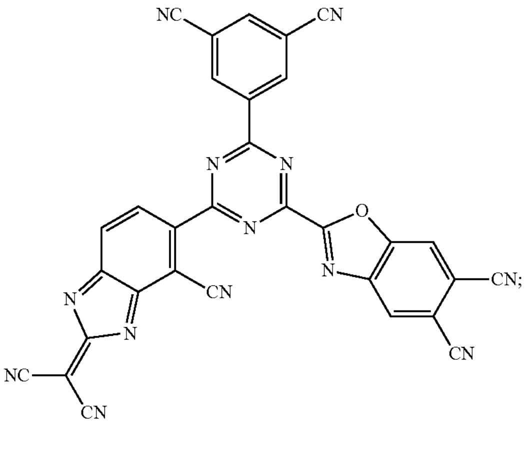

-continued
142
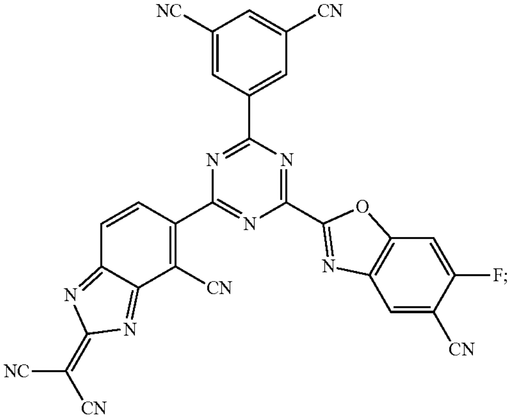
143
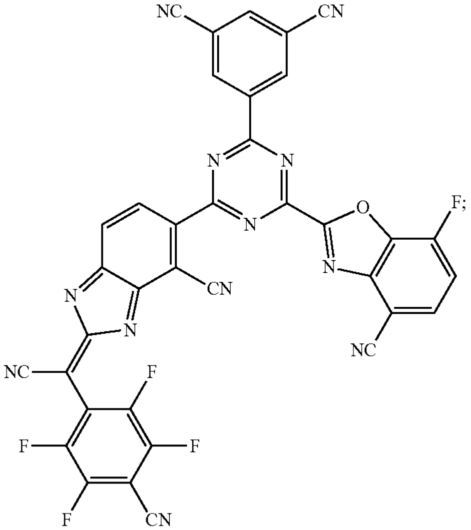
144
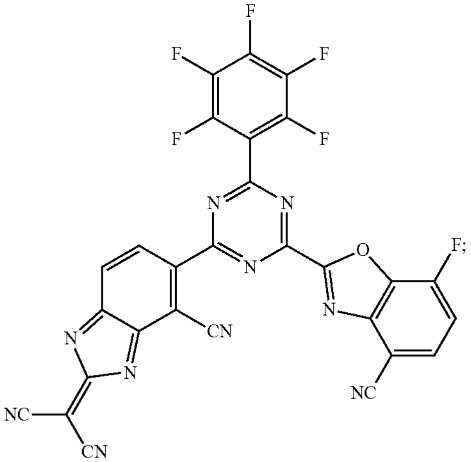
-continued
145
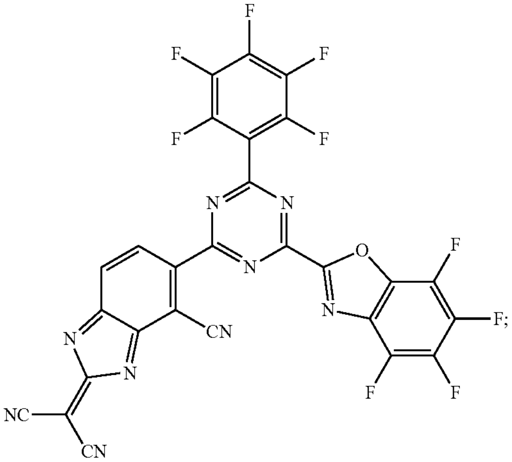
145
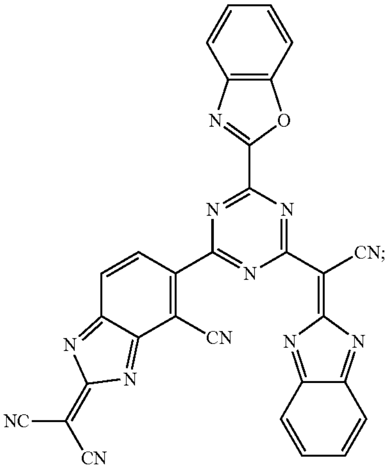
147
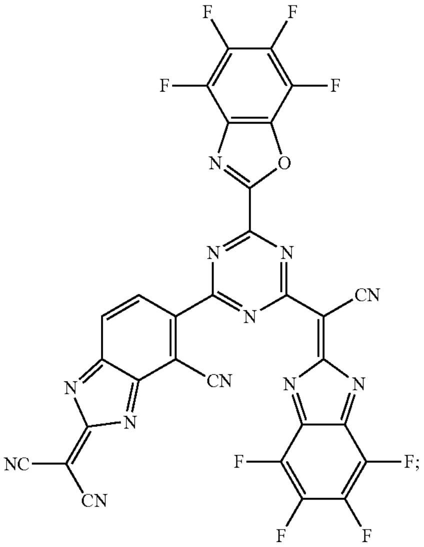

-continued
148
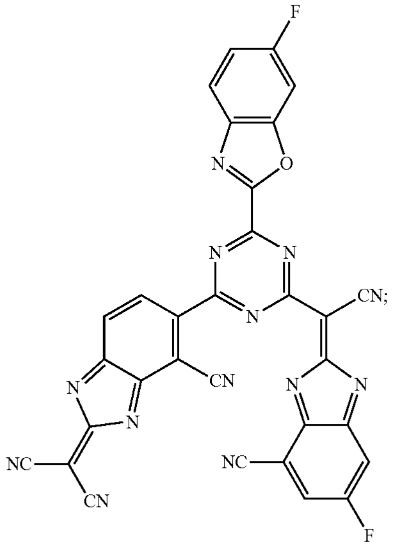
149
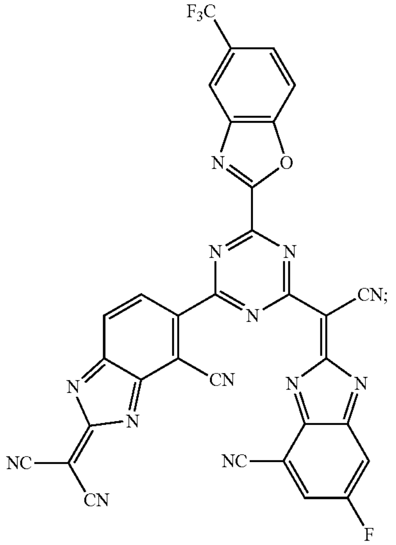
150
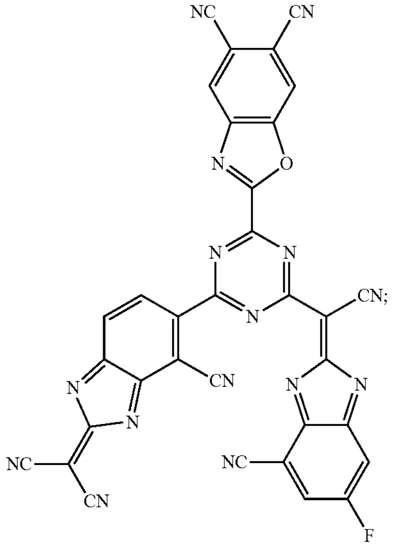
-continued
151
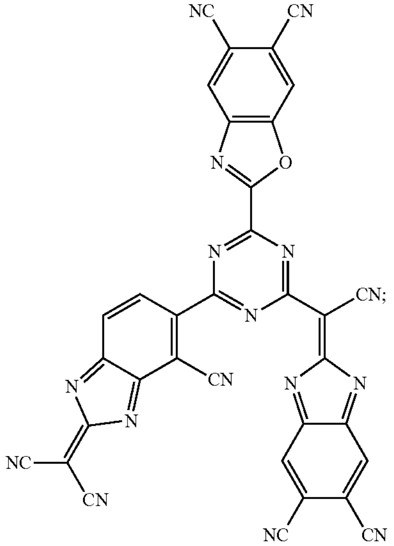
152
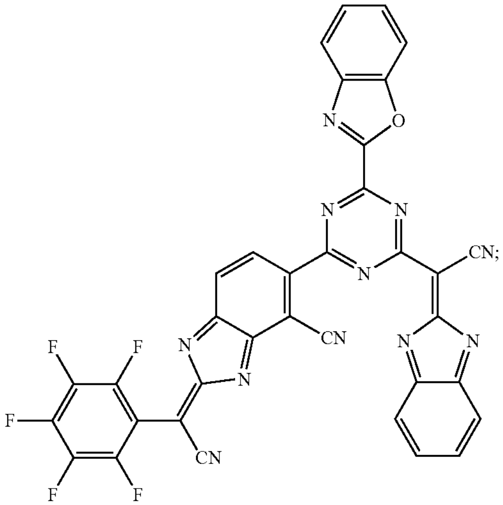
153
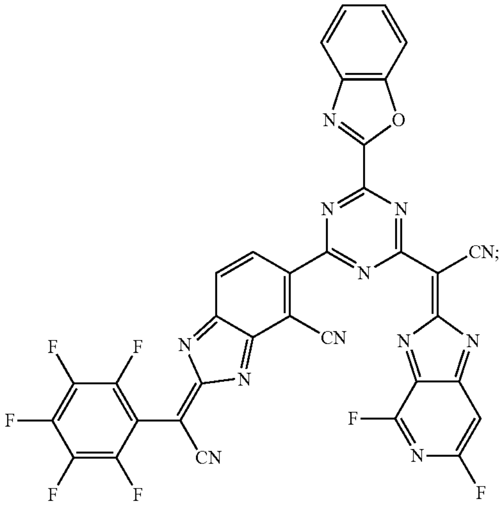

-continued
154
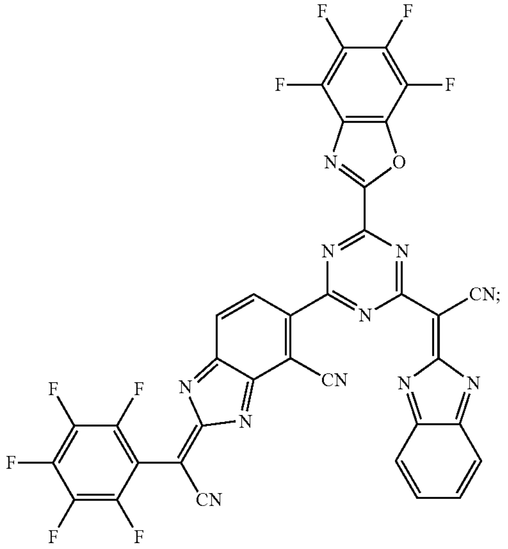
155
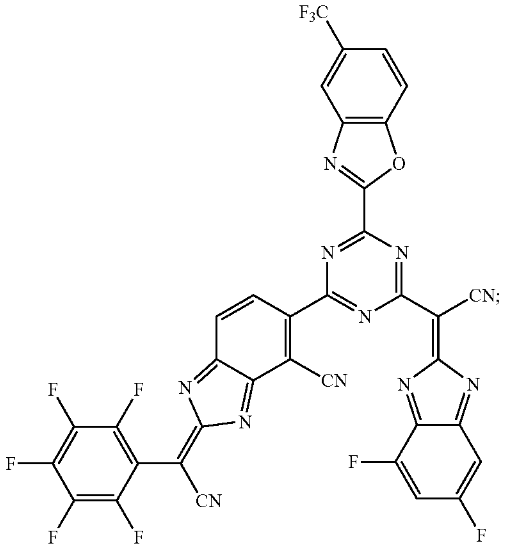
156
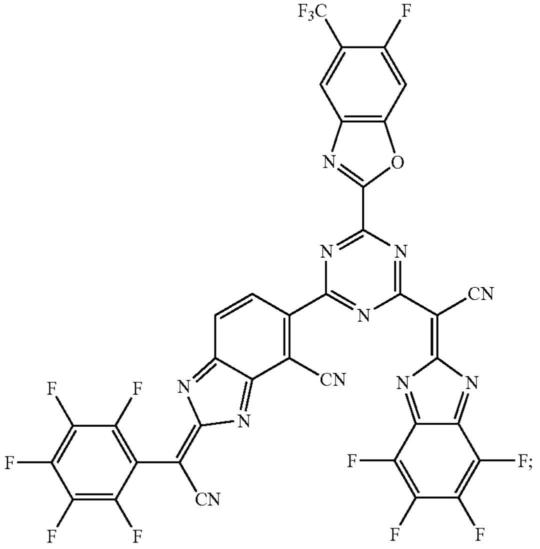
-continued
157
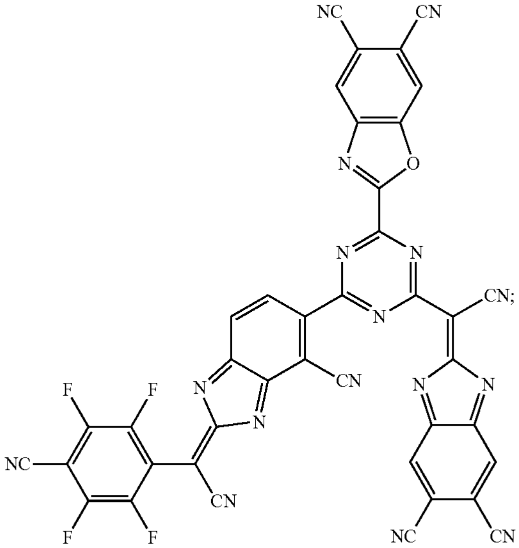
158
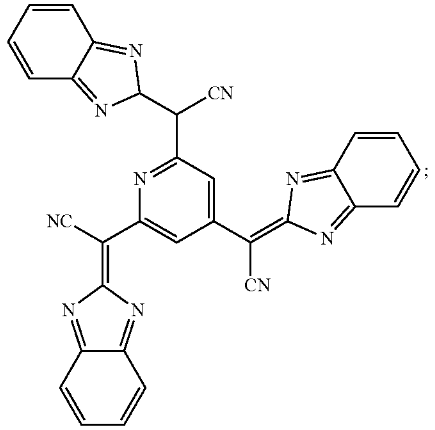
159
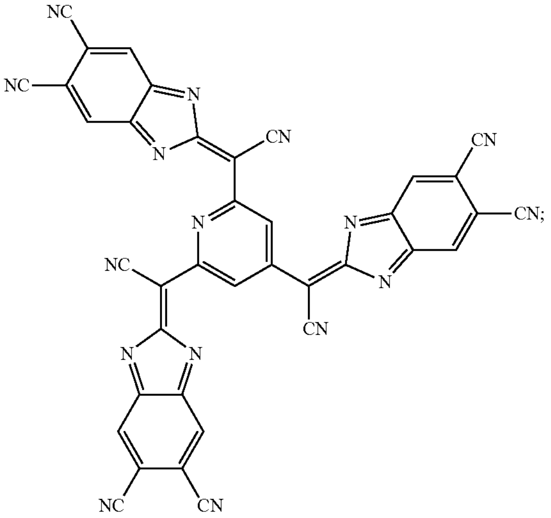

-continued
160
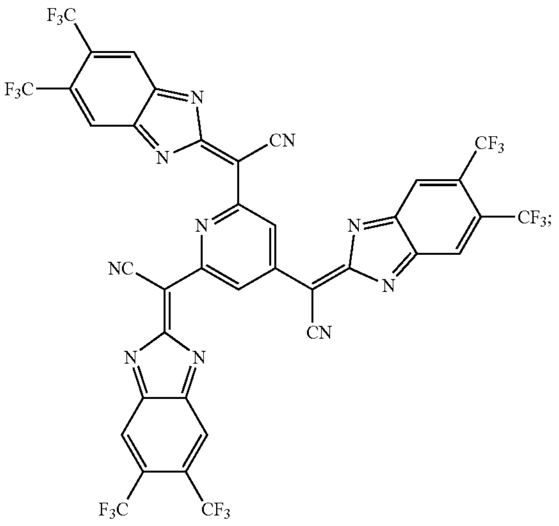
161
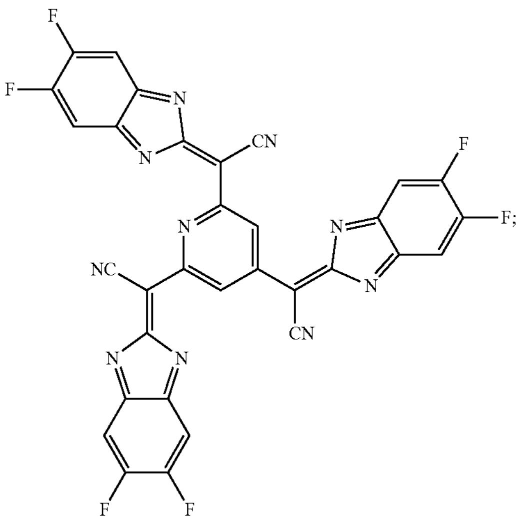
162
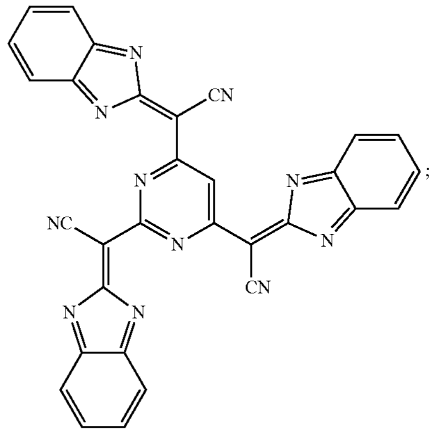
-continued
163
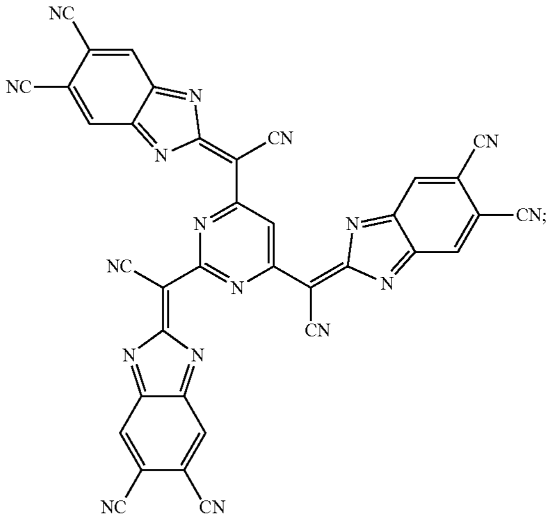
164
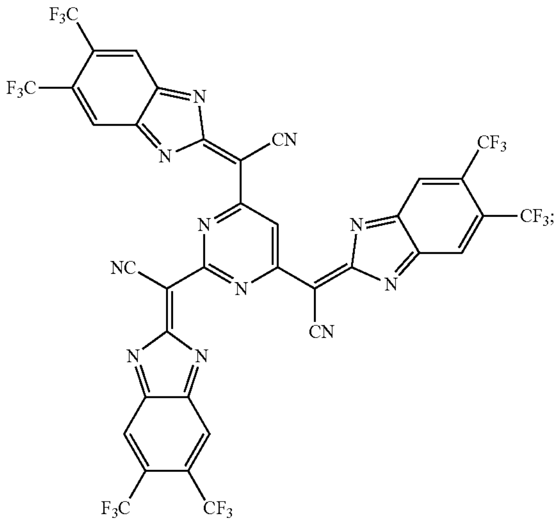
165
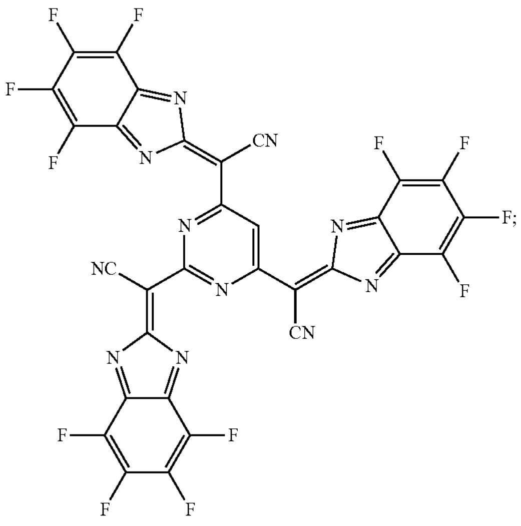

-continued
166
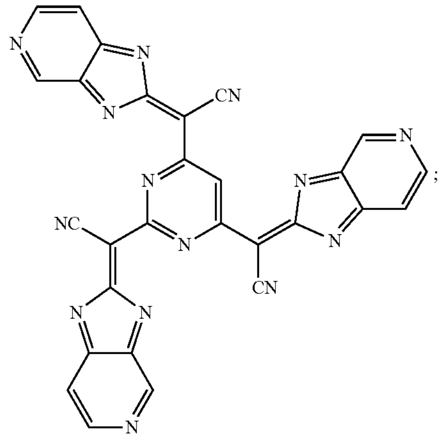
167
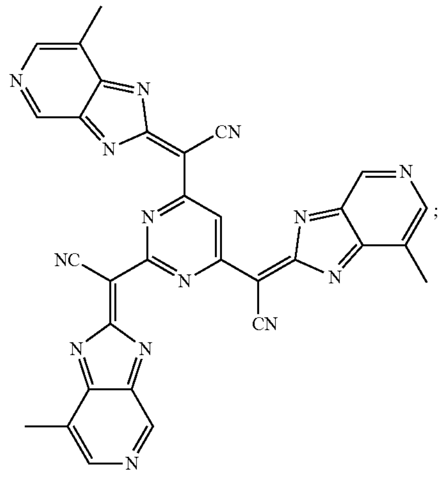
168
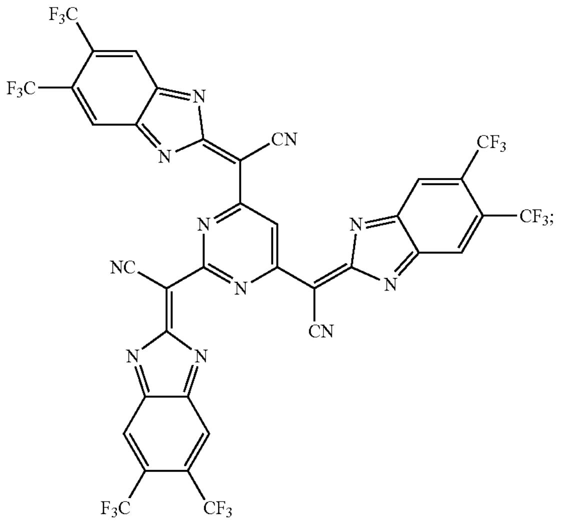
-continued
169
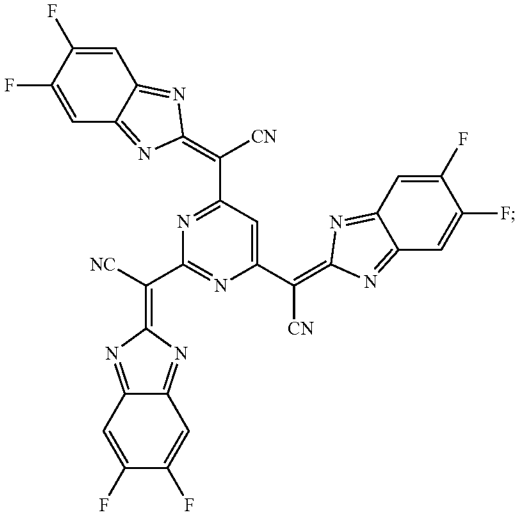
170
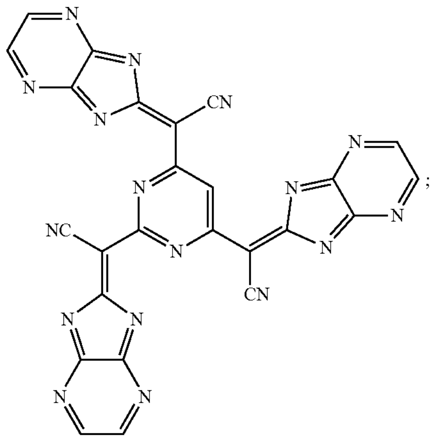
171
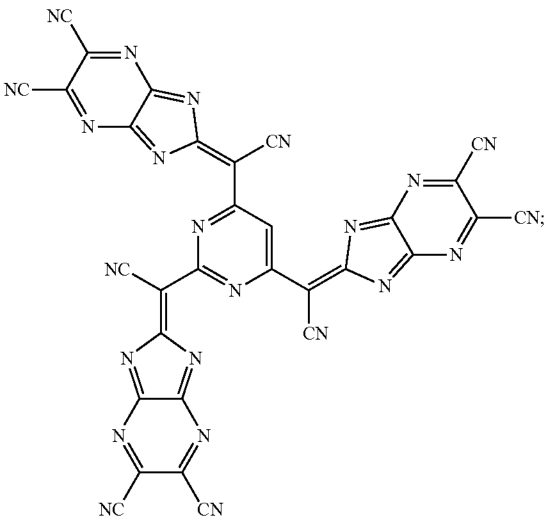

-continued
172
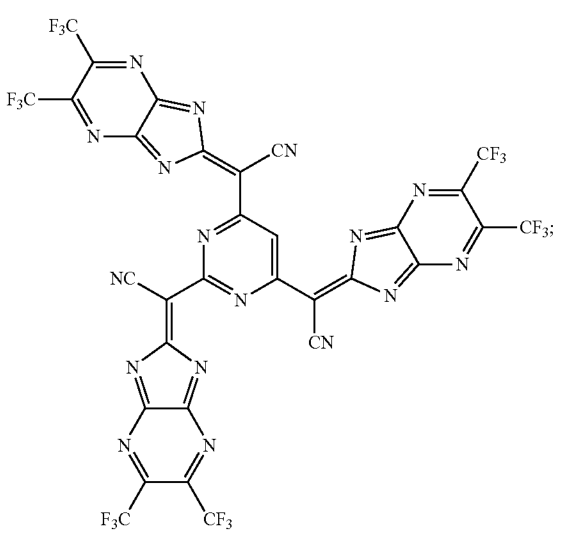
173
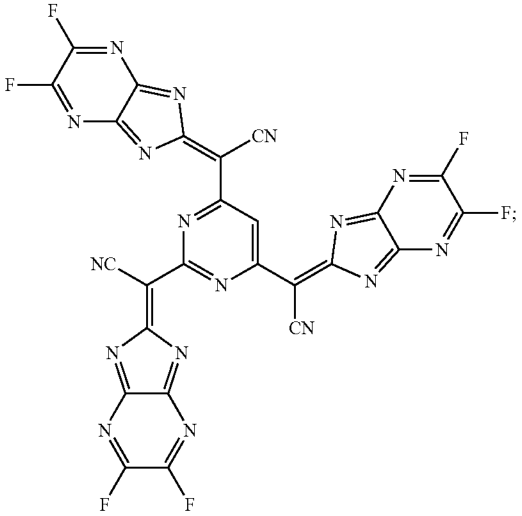
174
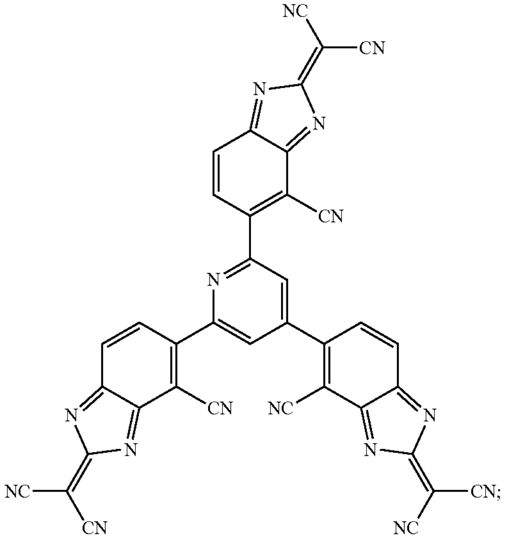
-continued
175
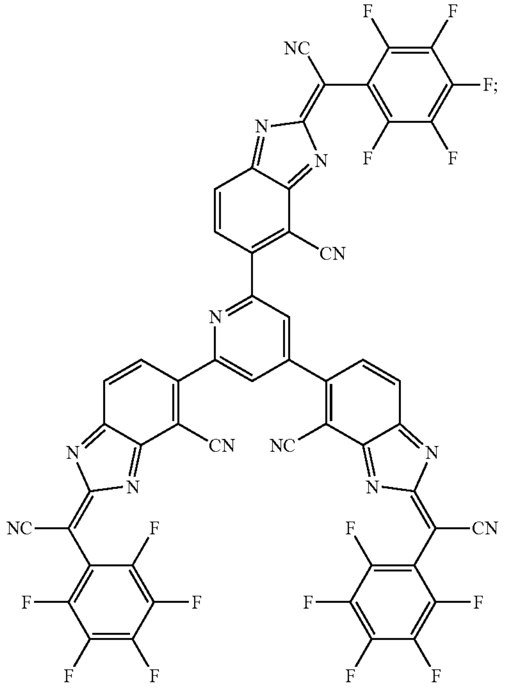
176
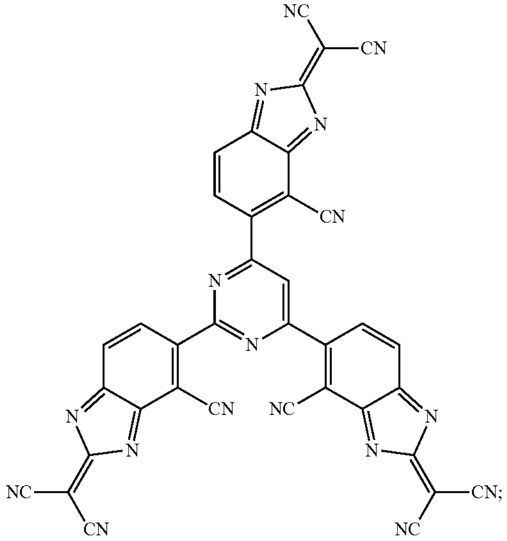
177
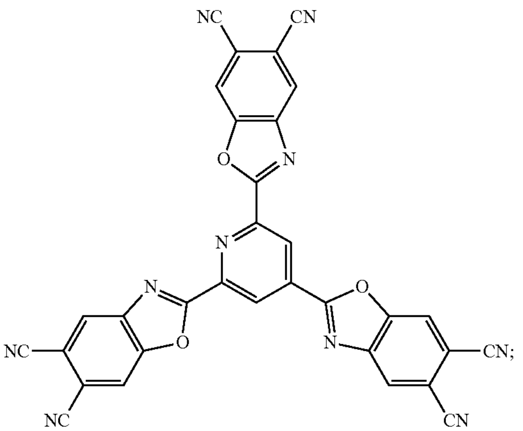
or -continued
178
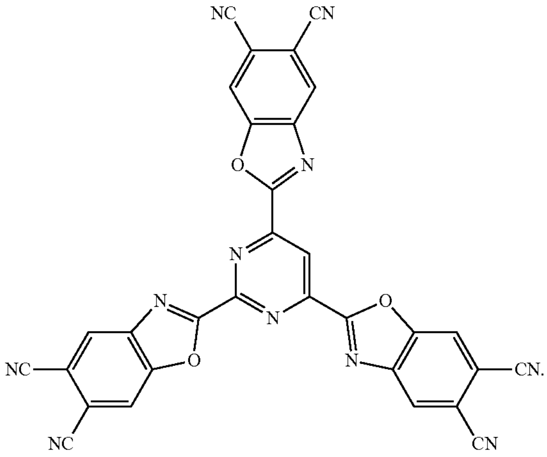
CN.
* * * * *

UNITED STATES PATENT AND TRADEMARK OFFICE

CERTIFICATE OF CORRECTION

PATENT NO. : 11,889,754 B2
APPLICATION NO. : 16/985079
DATED : January 30, 2024
INVENTOR(S) : Ji-Cheol Shin et al.

It is certified that error appears in the above-identified patent and that said Letters Patent is hereby corrected as shown below:

On the Title Page

Item (73) Assignees, second Assignee's name:
"P & HTECH, Yongin-si (KR)"
Should read:
--P&HTECH, Yongin-si (KR)--.

In the Claims

Column 166, Claim 3, Line 41:
"compound of to claim 1,"
Should read:
--compound of claim 1,--.

Signed and Sealed this
Twenty-third Day of September, 2025

John A. Squires
*Director of the United States Patent and Trademark Office*

Column 349, Claim 24, Structure 20:
"
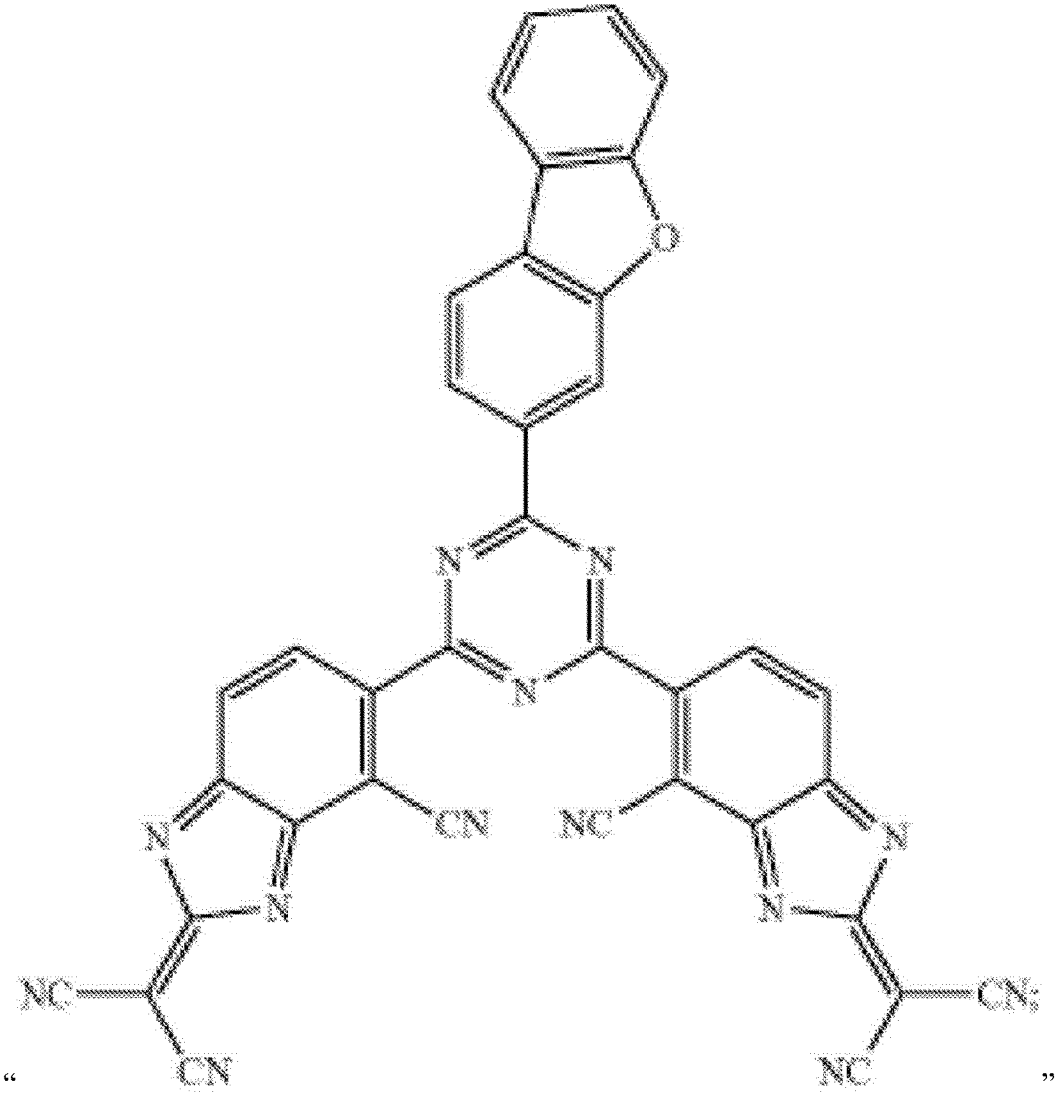
"
Should read:

20
--
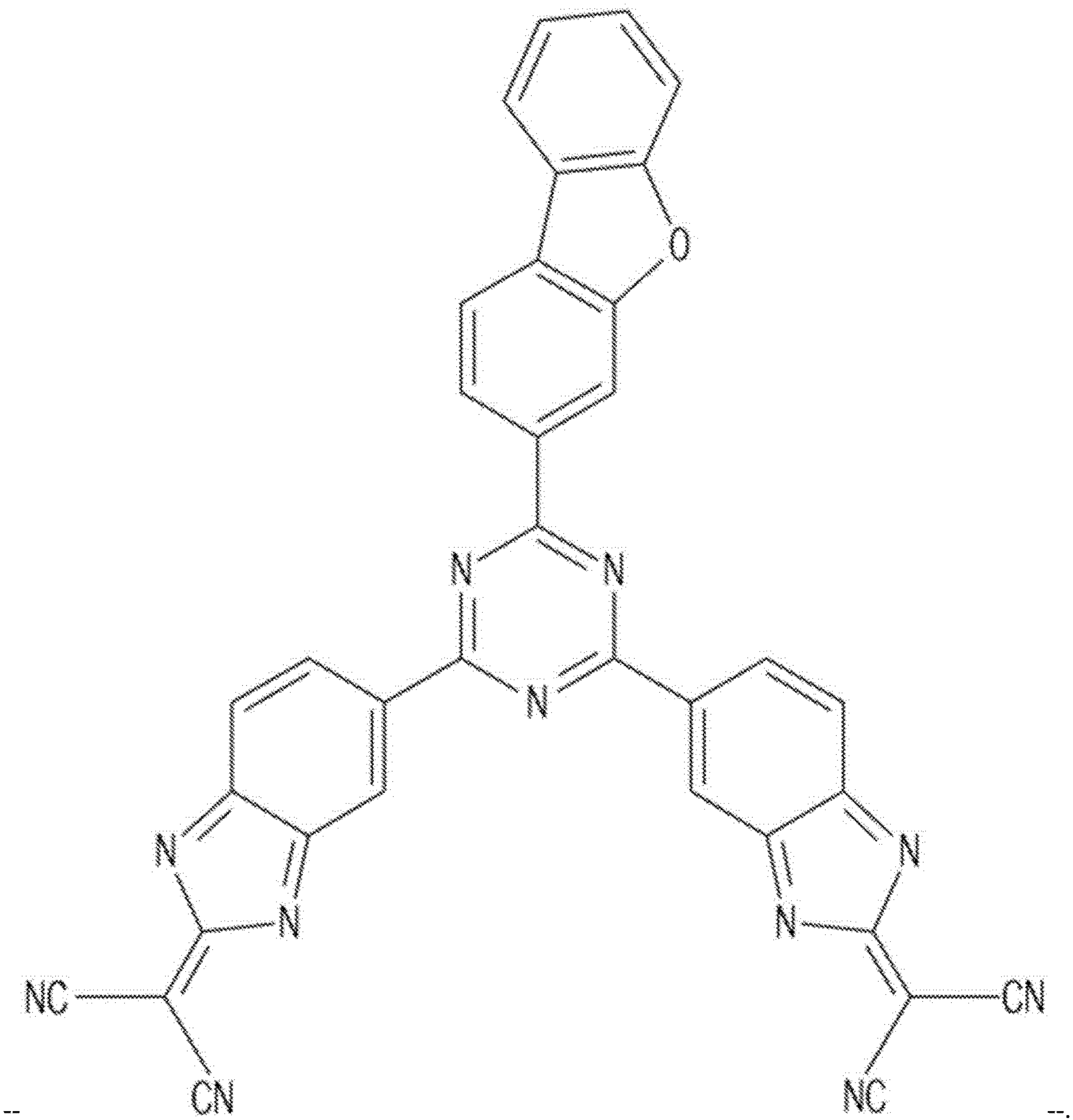
--.

Column 393, Claim 24, Structure 158:
158
"
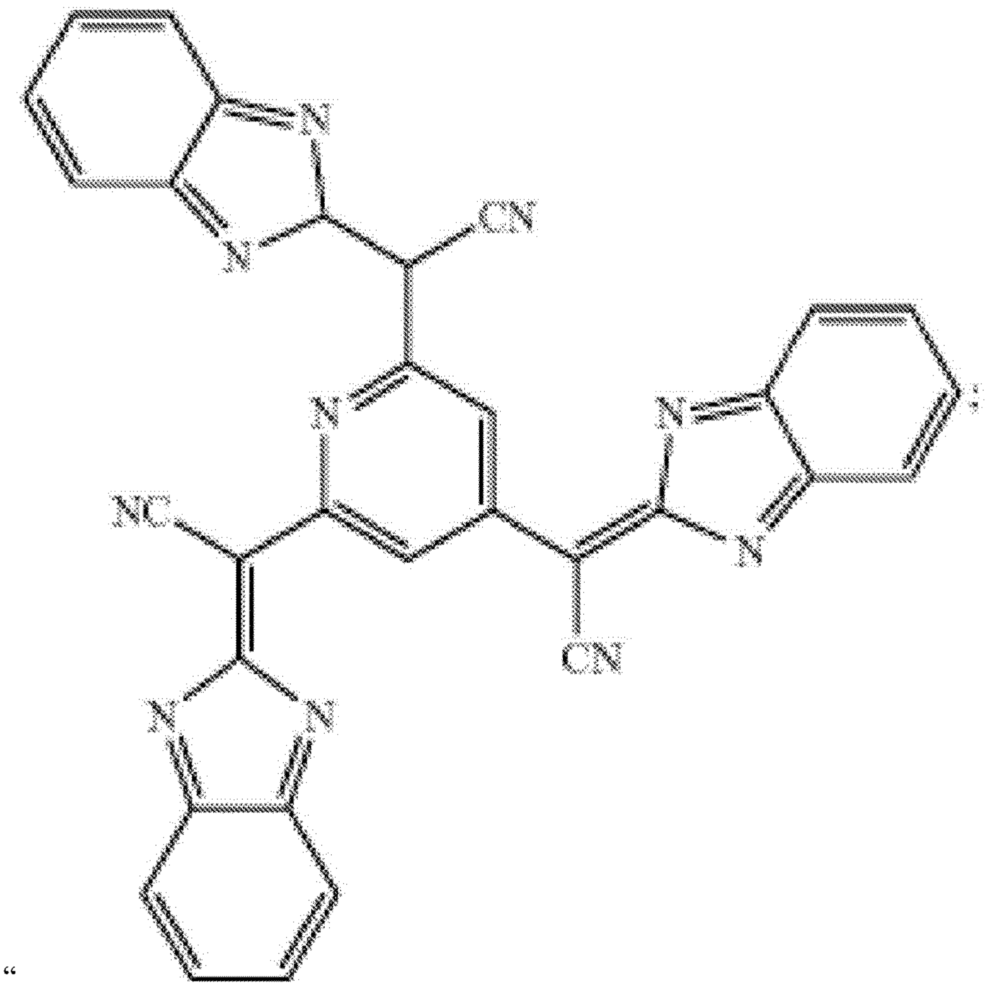
"
Should read:

158
-- 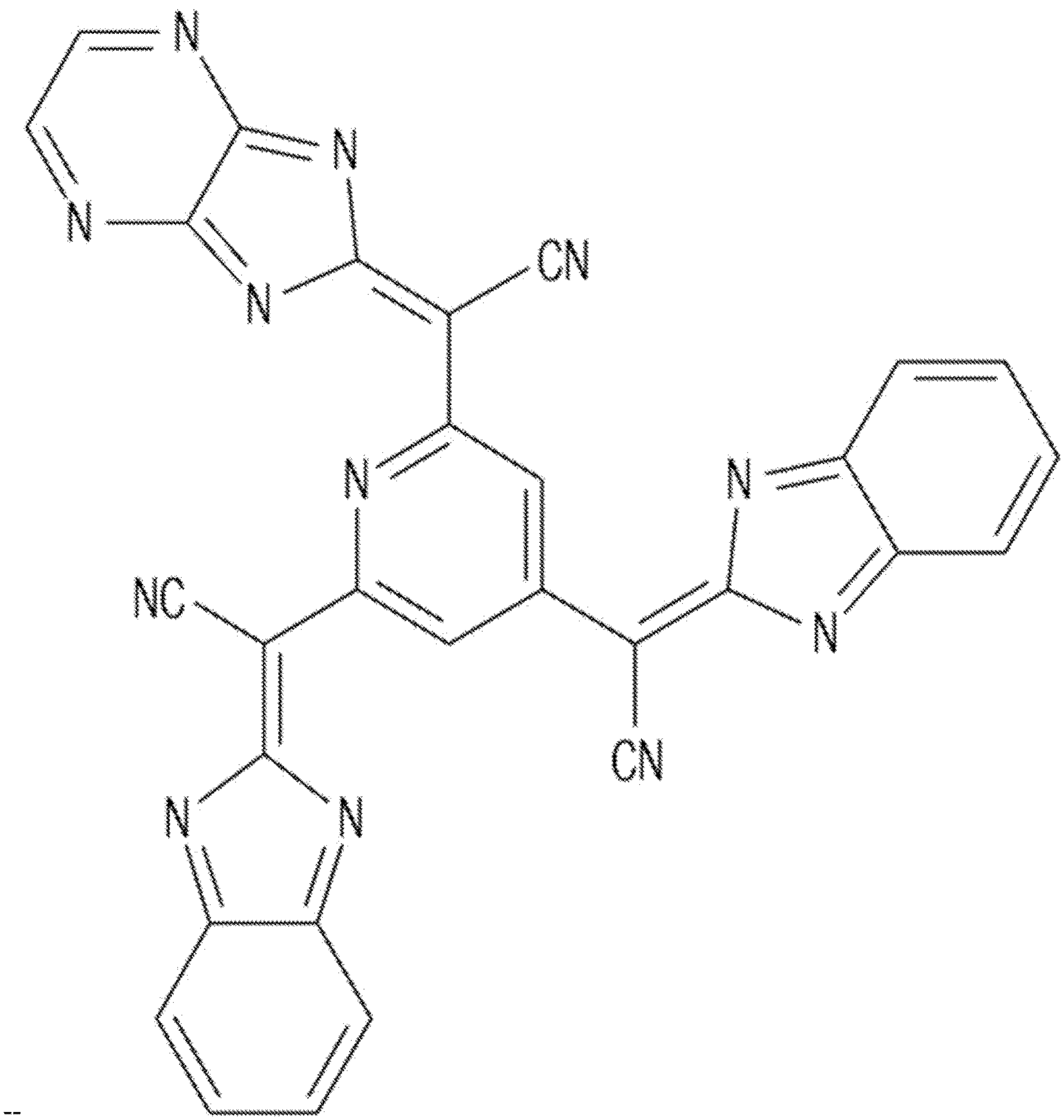 --.

Column 396, Claim 24, Structure 166:
166
"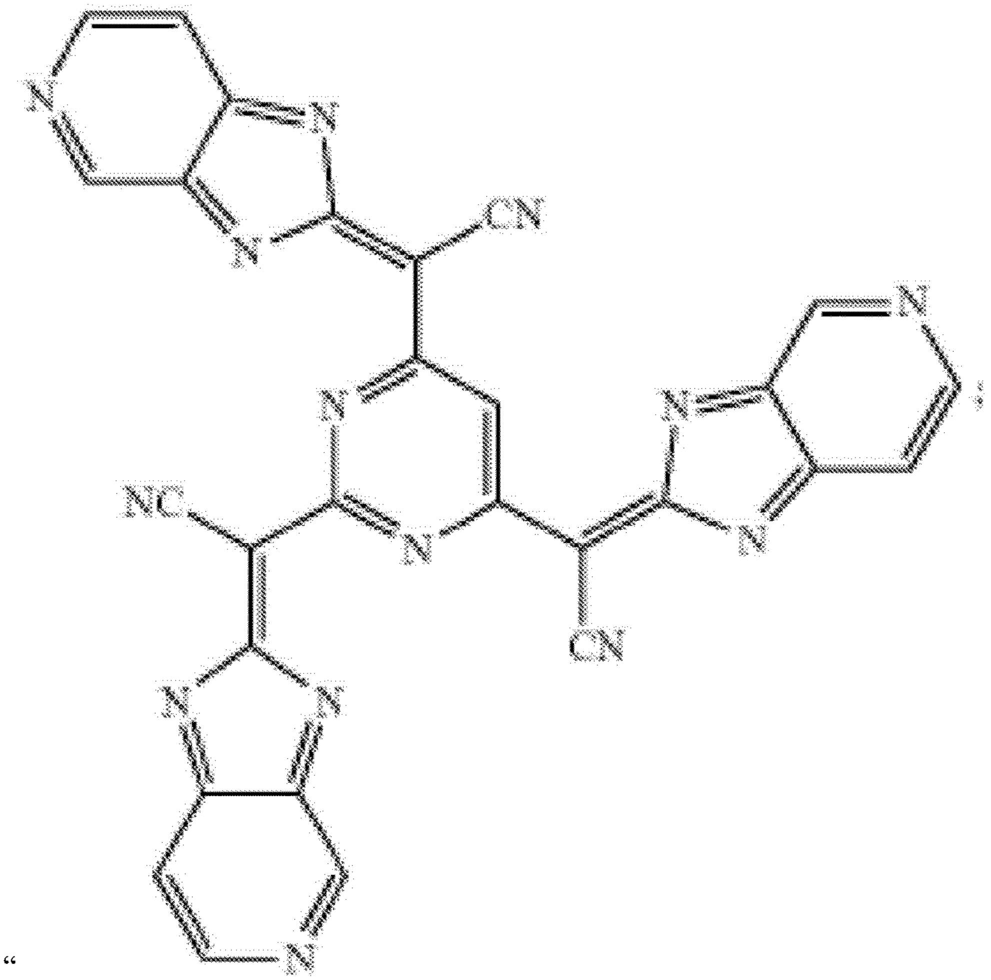"
Should read:

166
-- 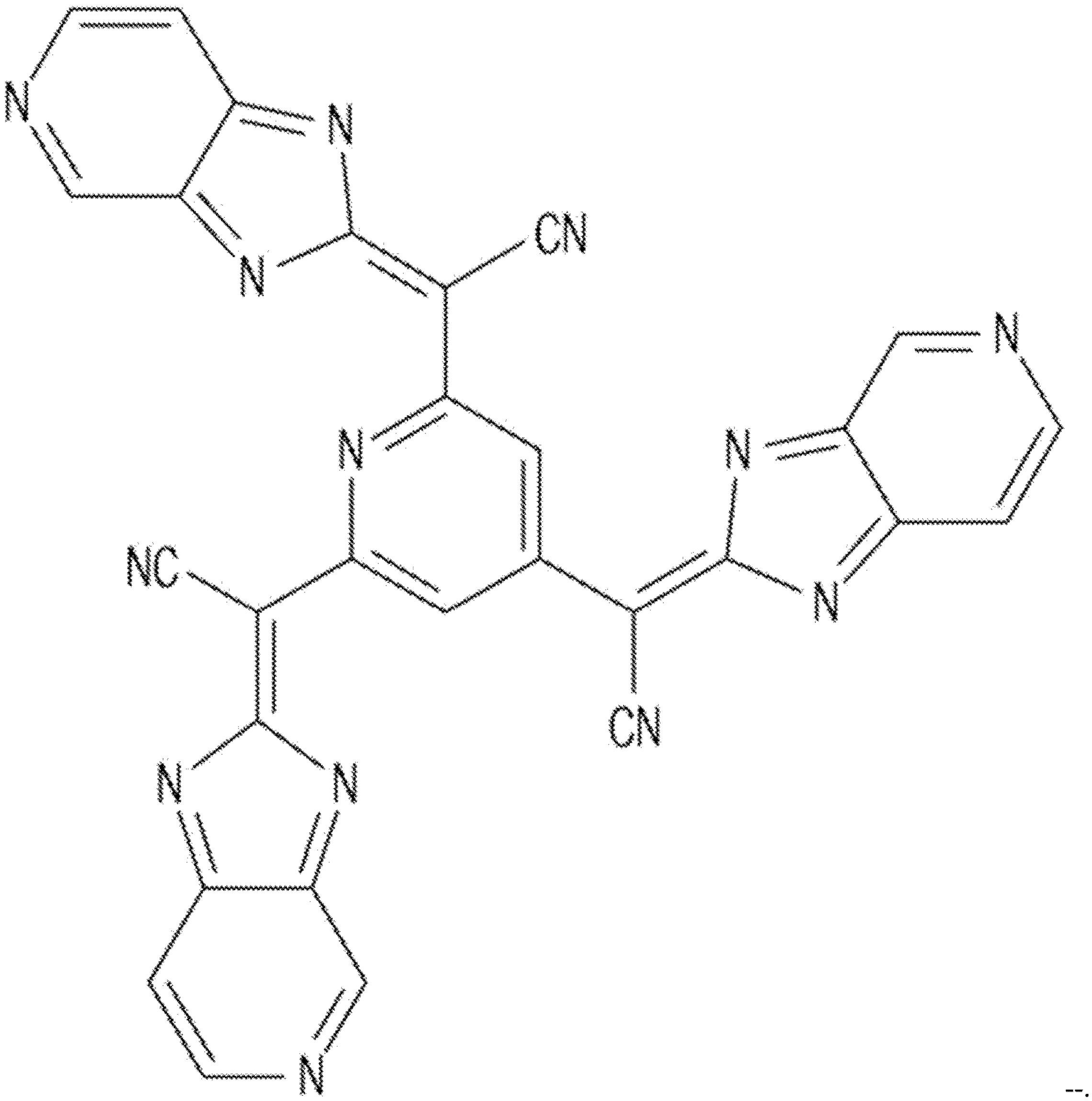 --.

Column 396, Claim 24, Structure 167:
167
“
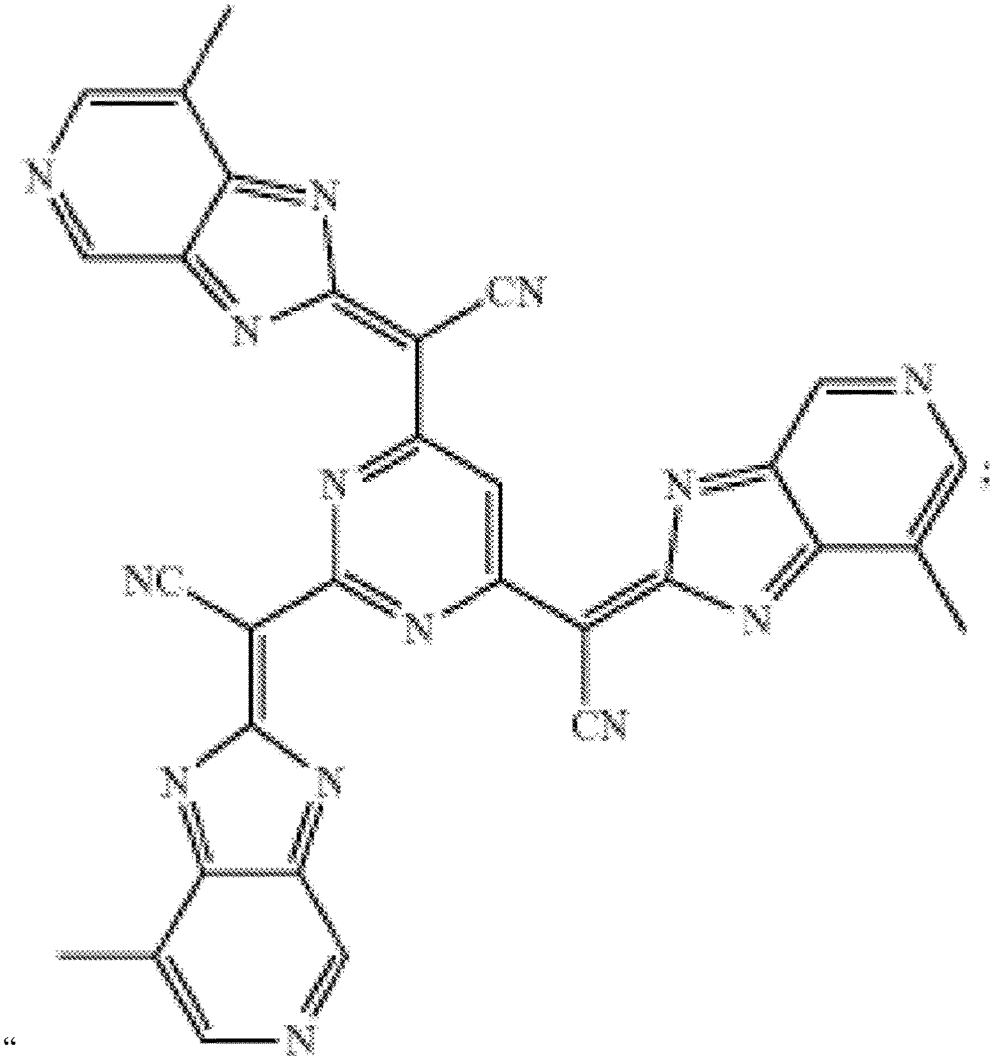
”
Should read:

167
-- 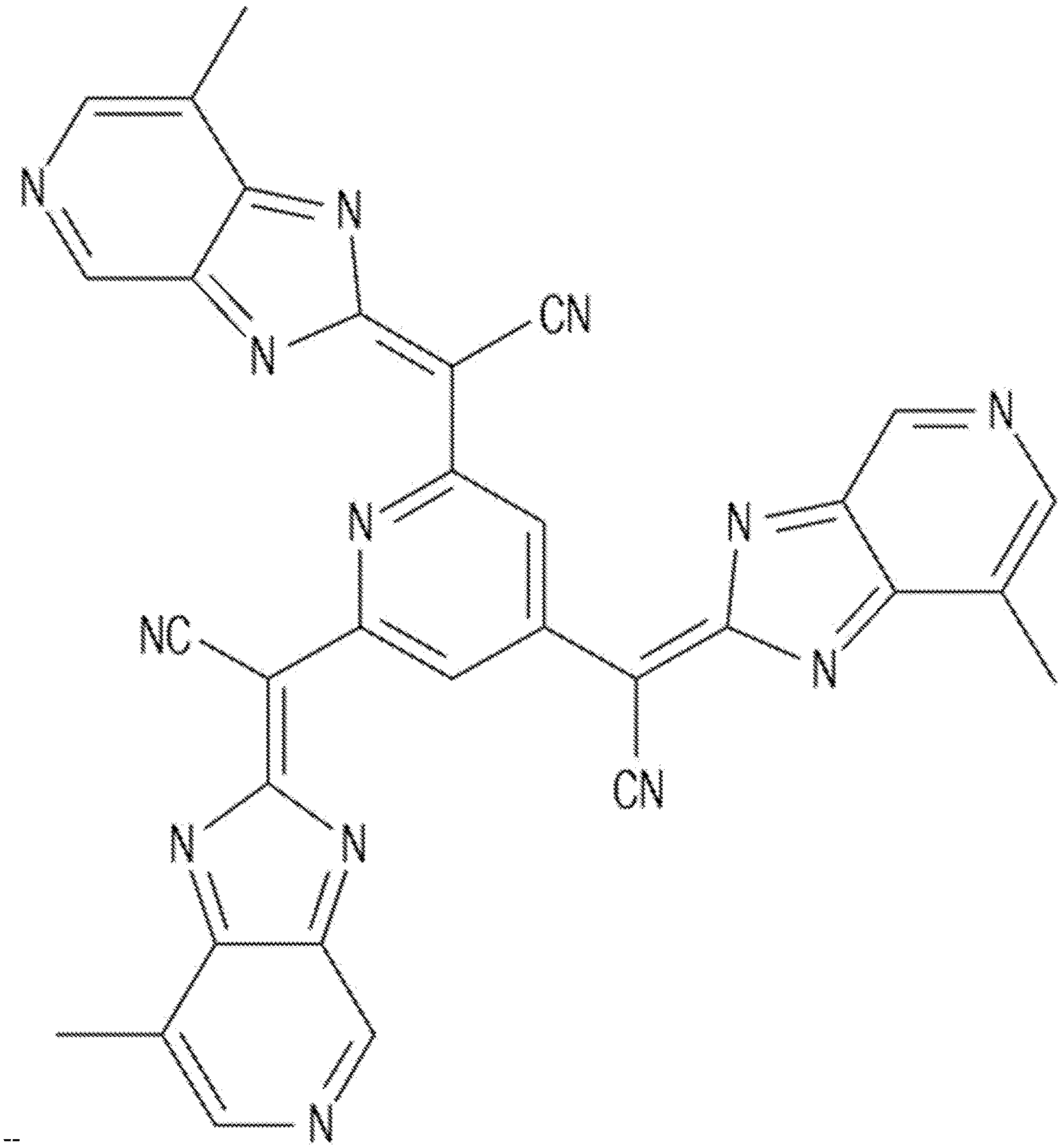 --.

Column 396, Claim 24, Structure 168:
168
“ 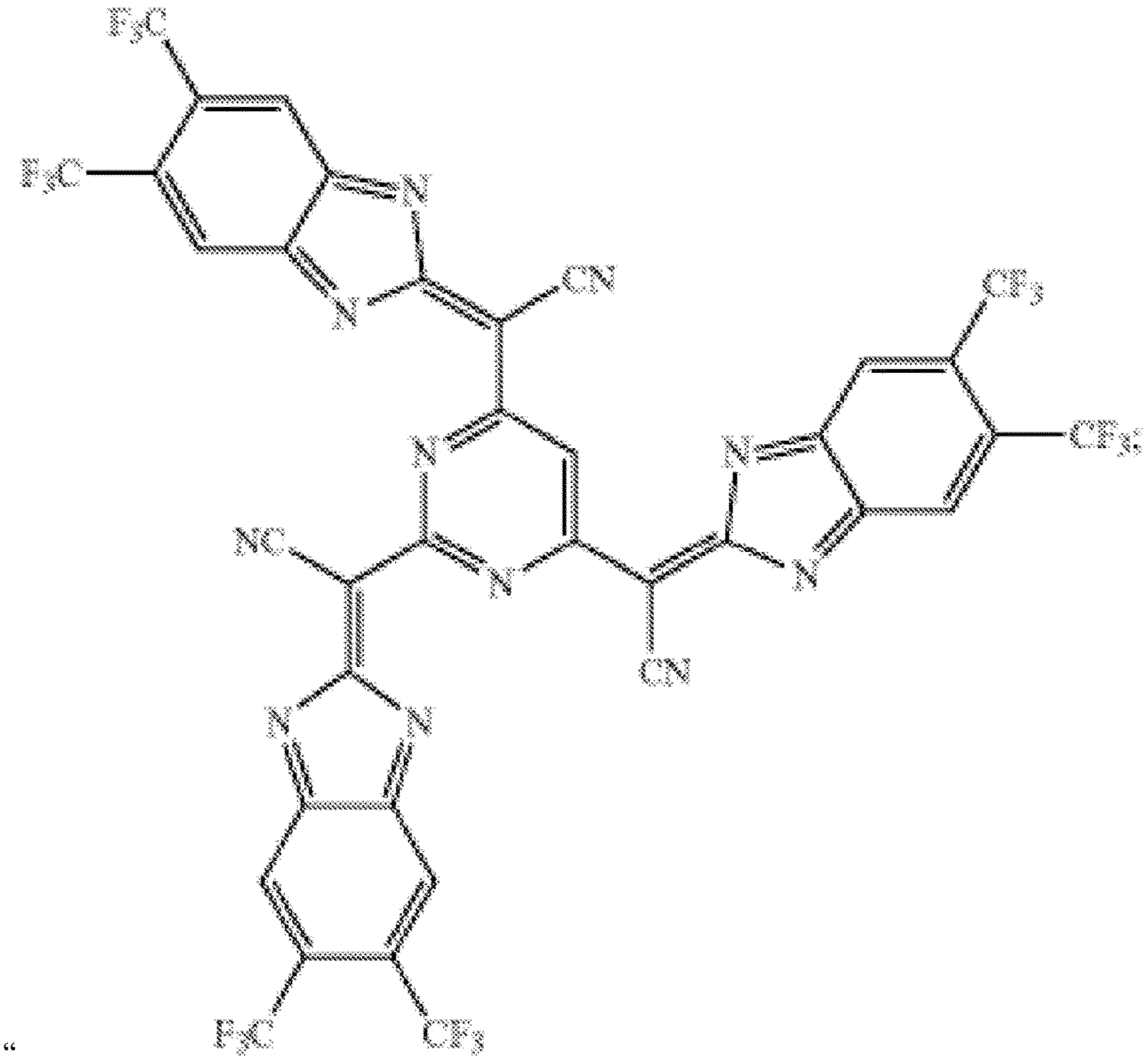 ”
Should read:

168
-- 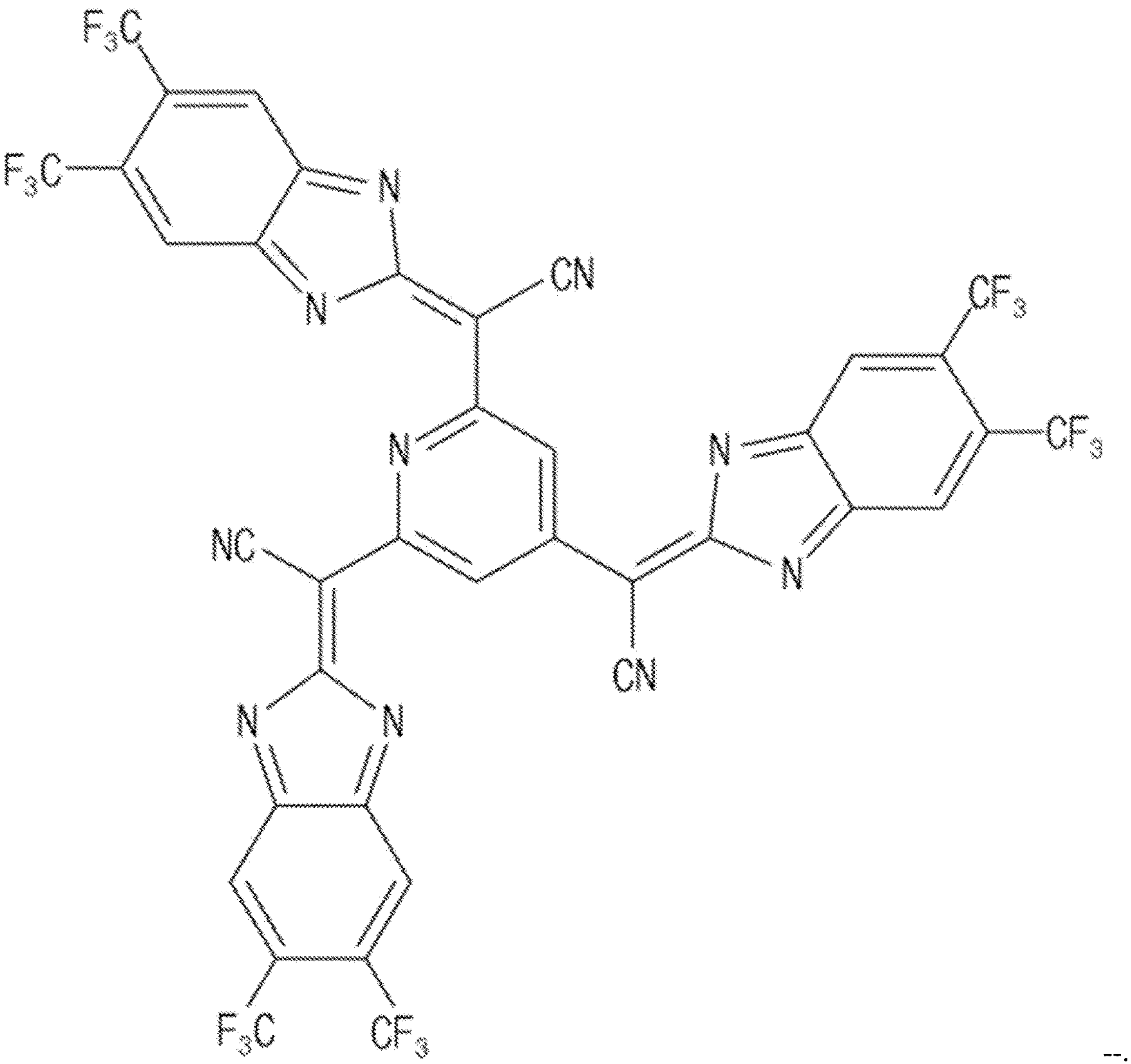 --.

Column 397, Claim 24, Structure 169:
169
"
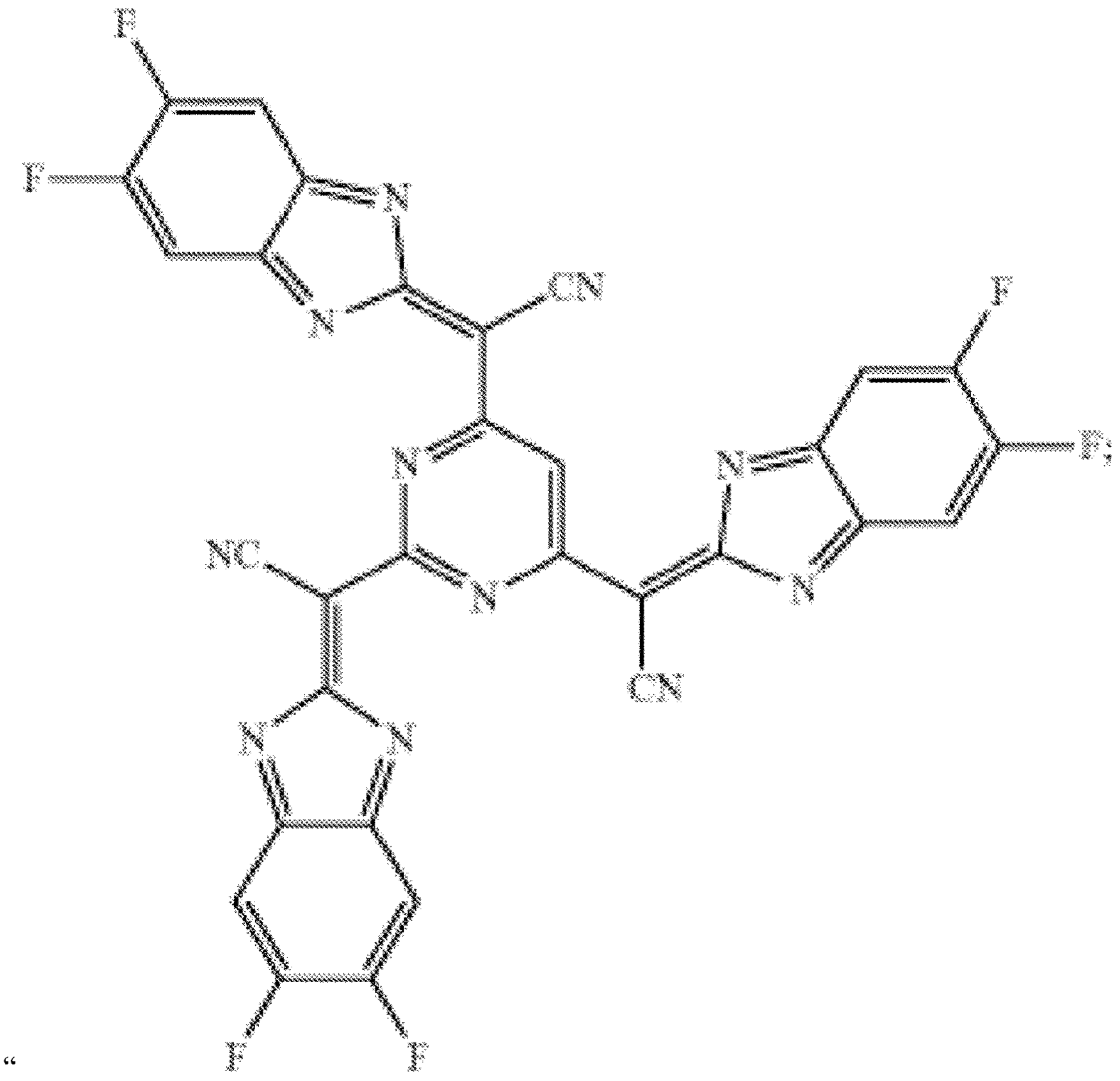
"
Should read:

169
--
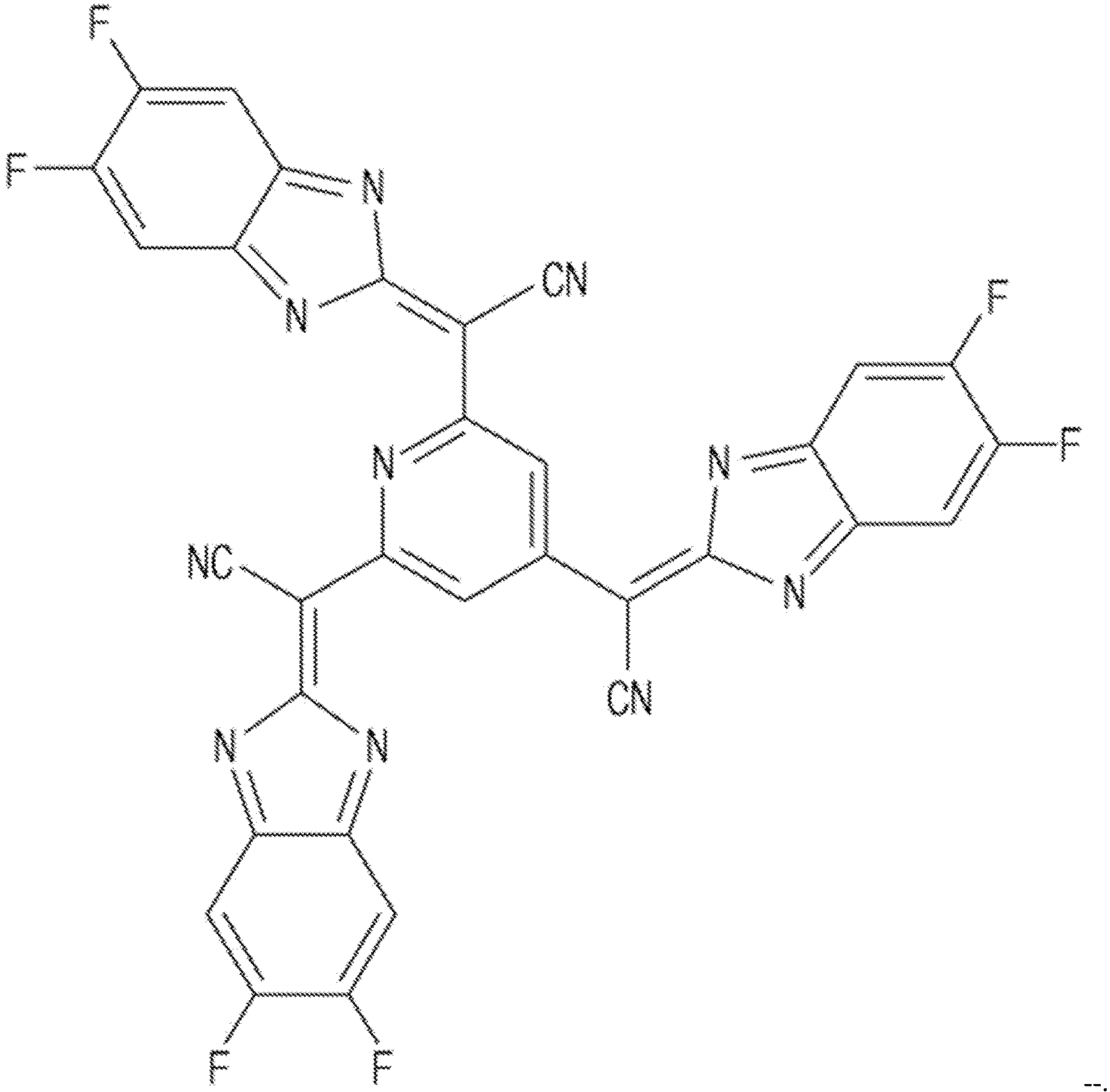
--.

Column 407, Claim 25, Structure 20:
"
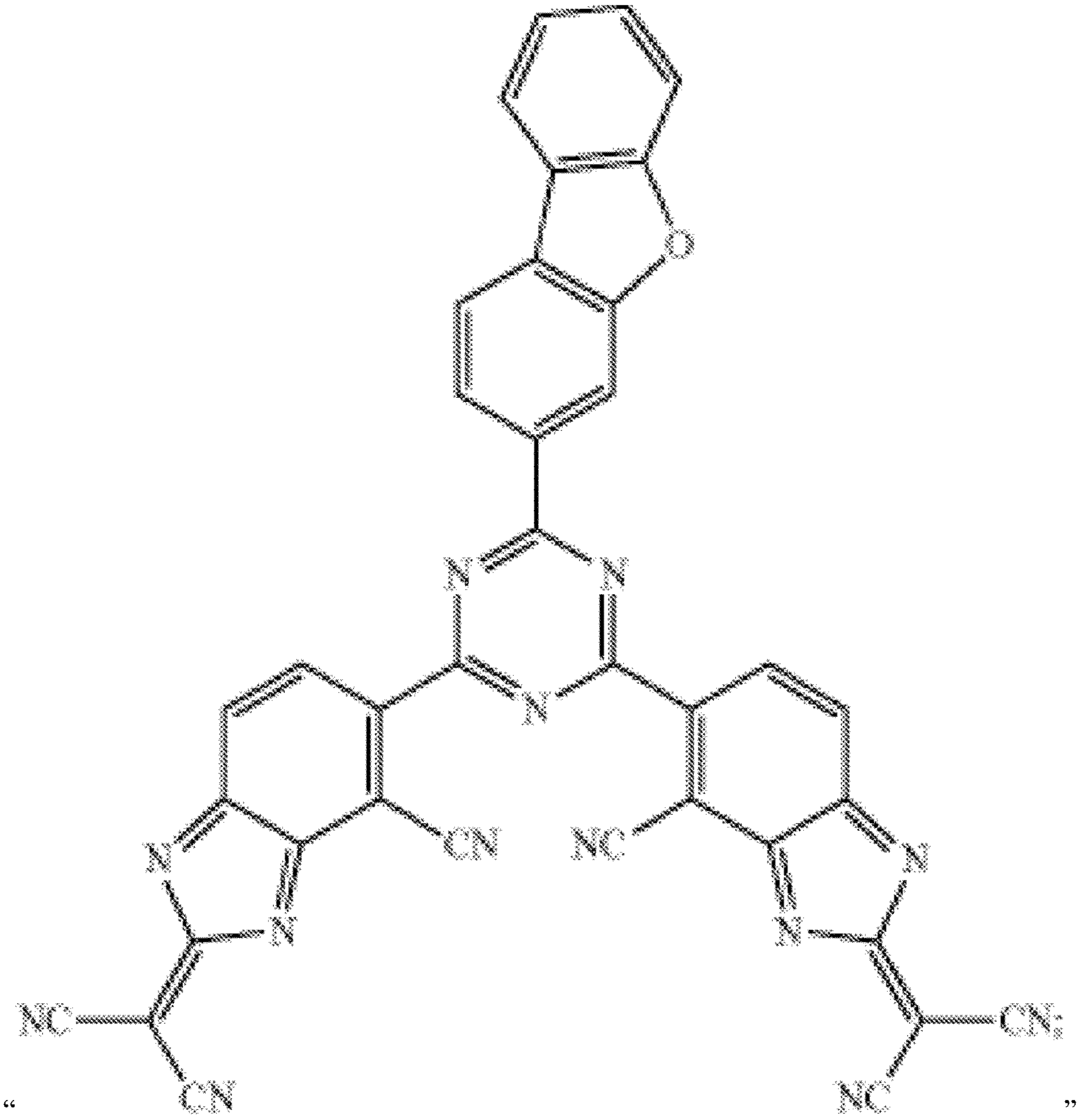
"
Should read:

20
-- 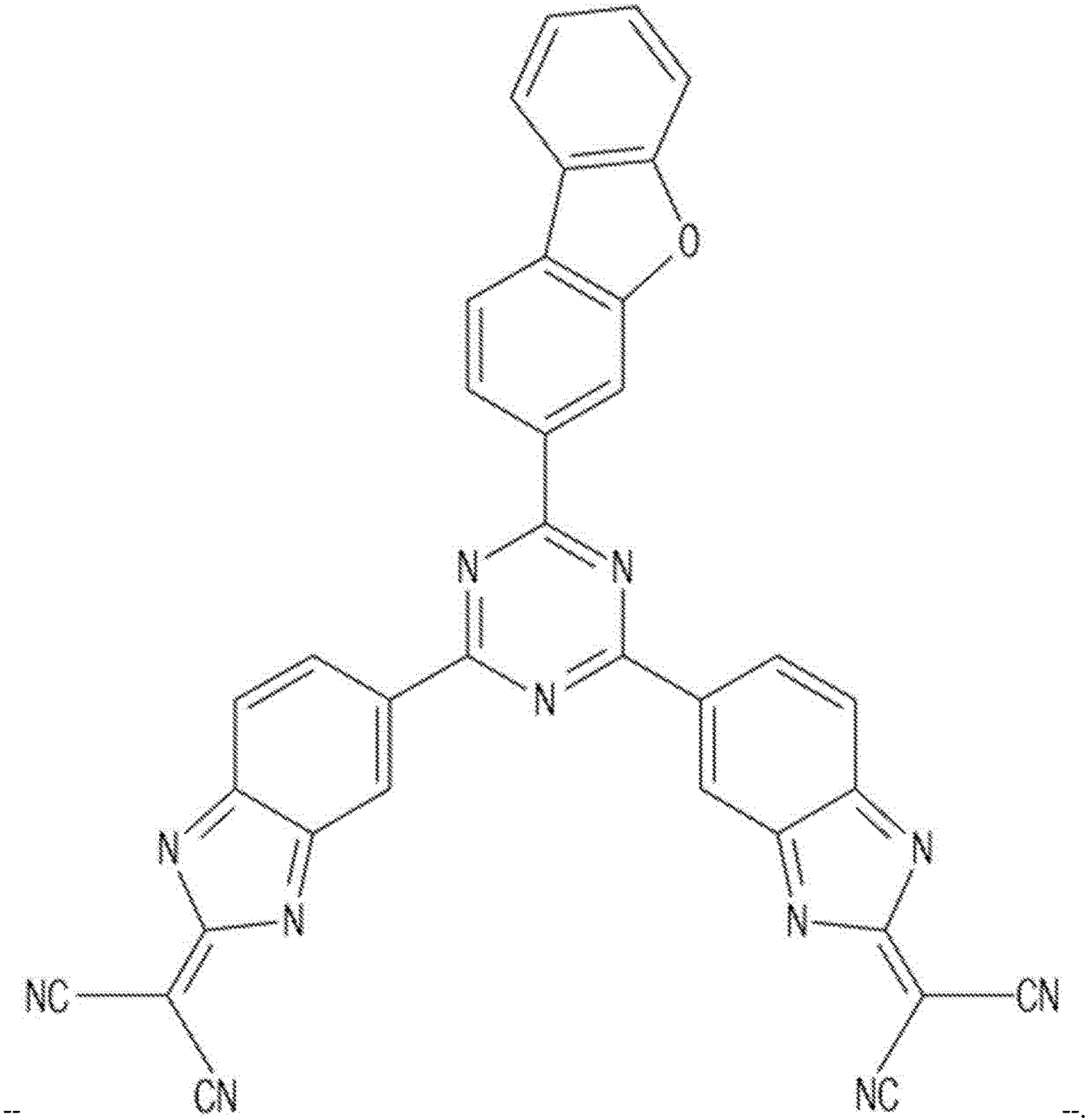 --.

Column 407, Claim 25, Structure 21:
"
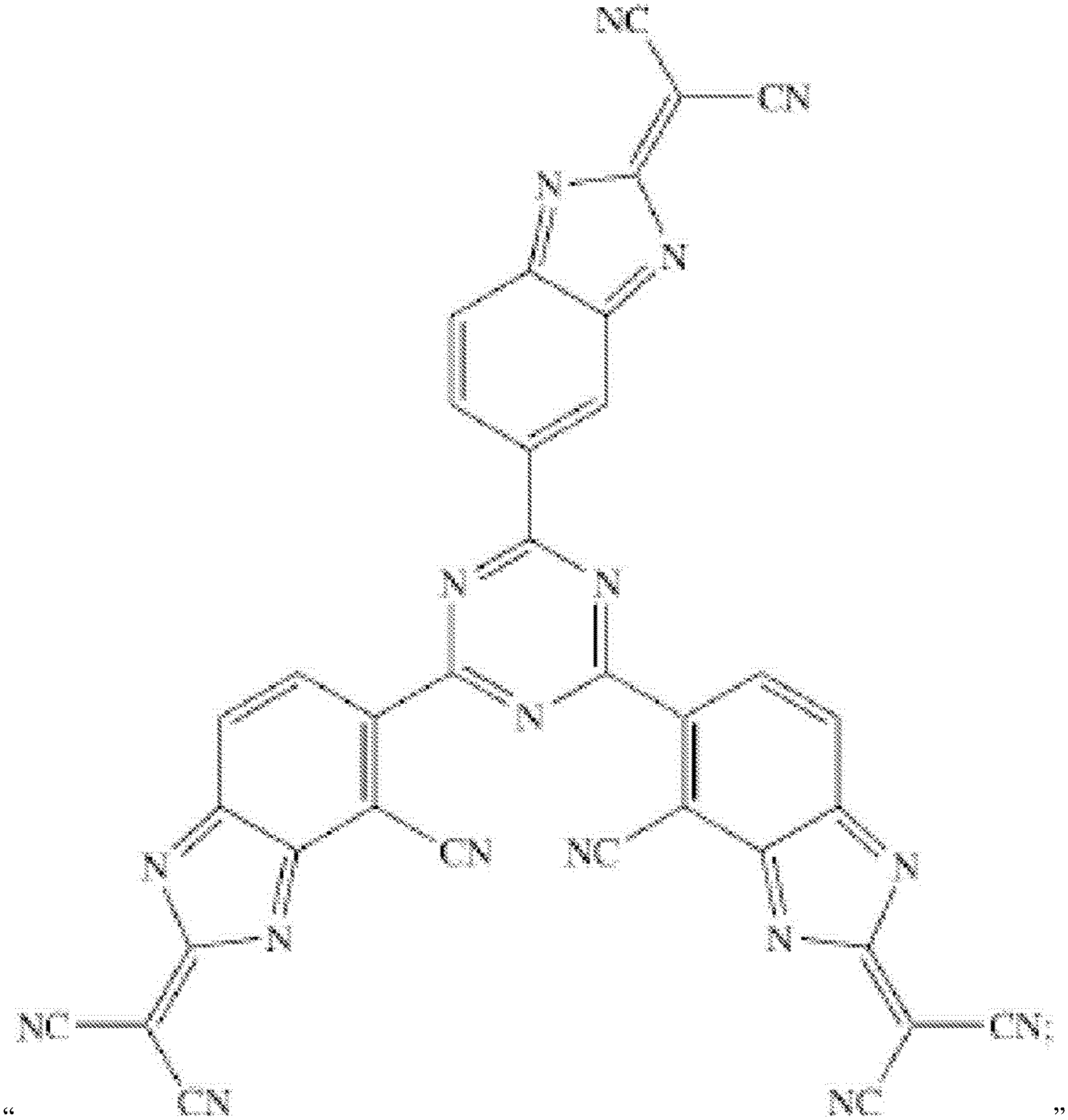
"
Should read:

21
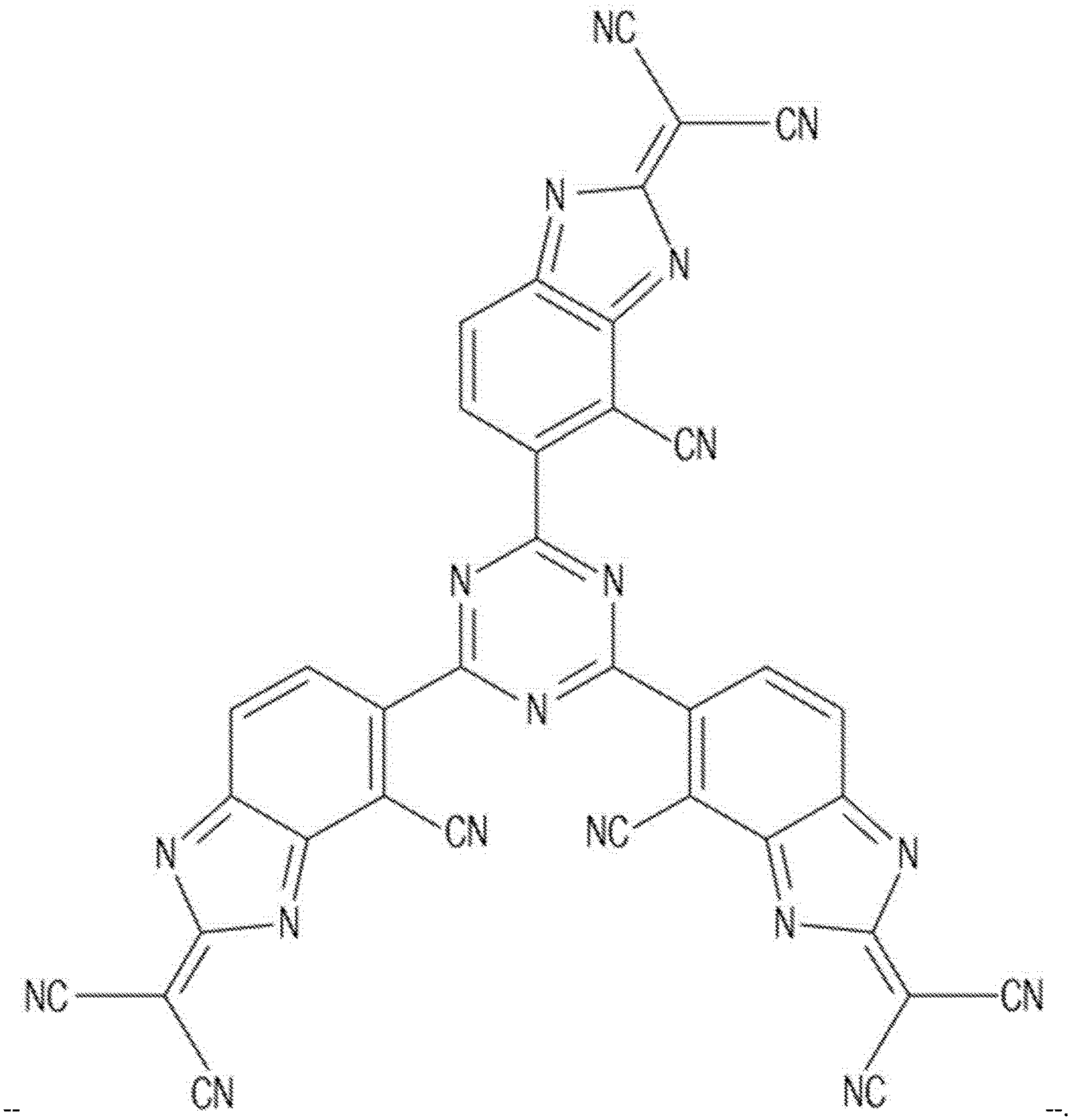
-- --.

Column 419, Claim 25, Structure 64:
64
"
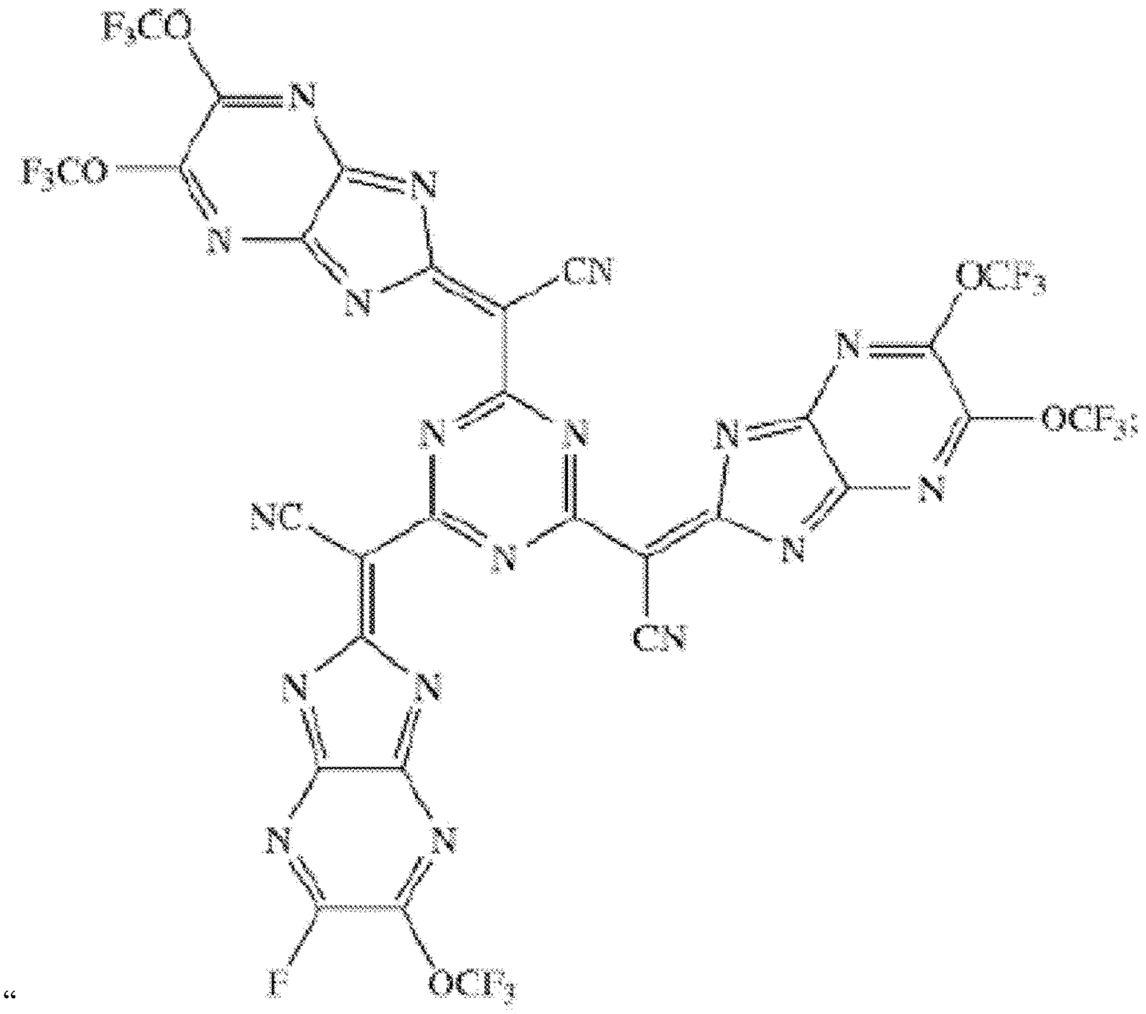
"
Should read:

64
-- 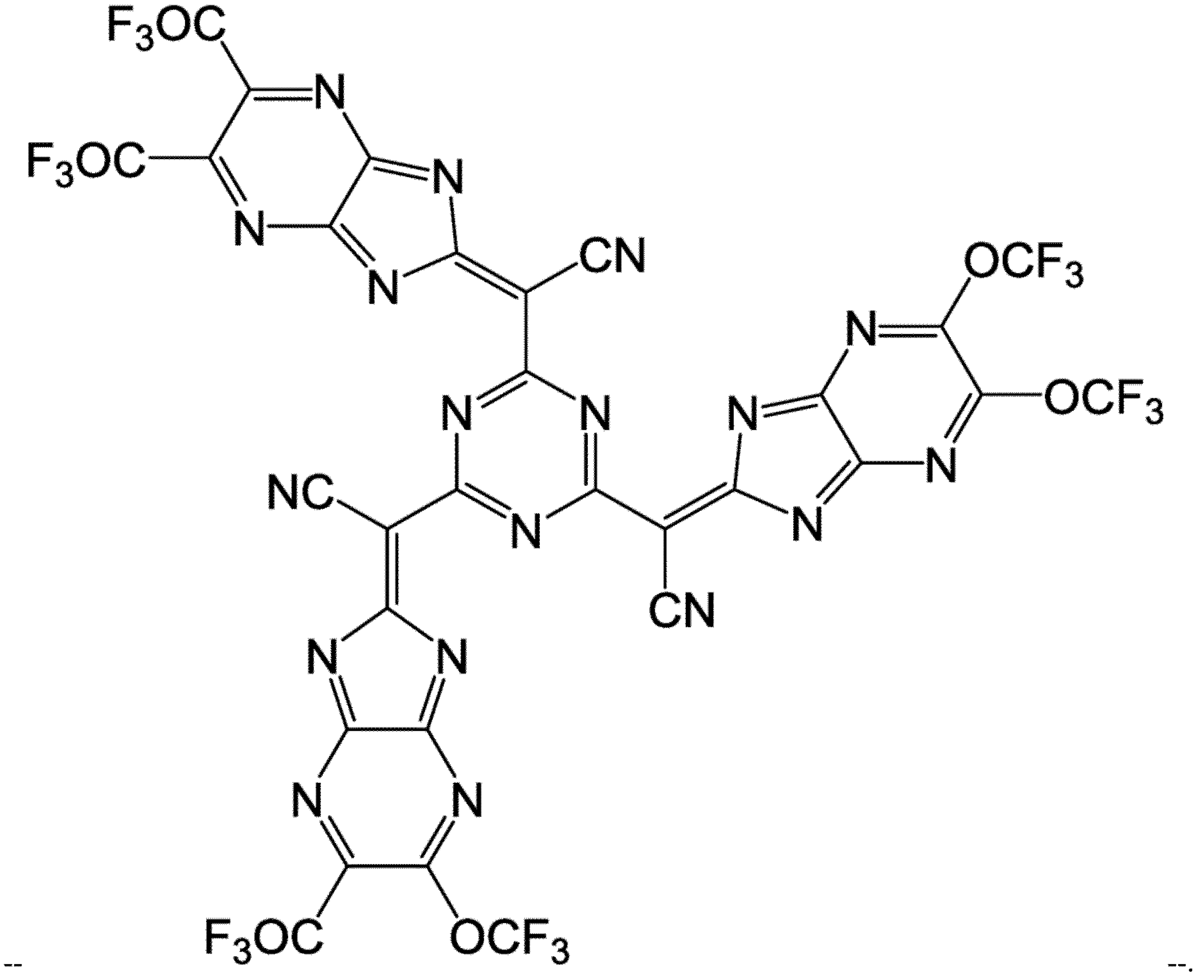 --.

Column 420, Claim 25, Structure 65:
65
"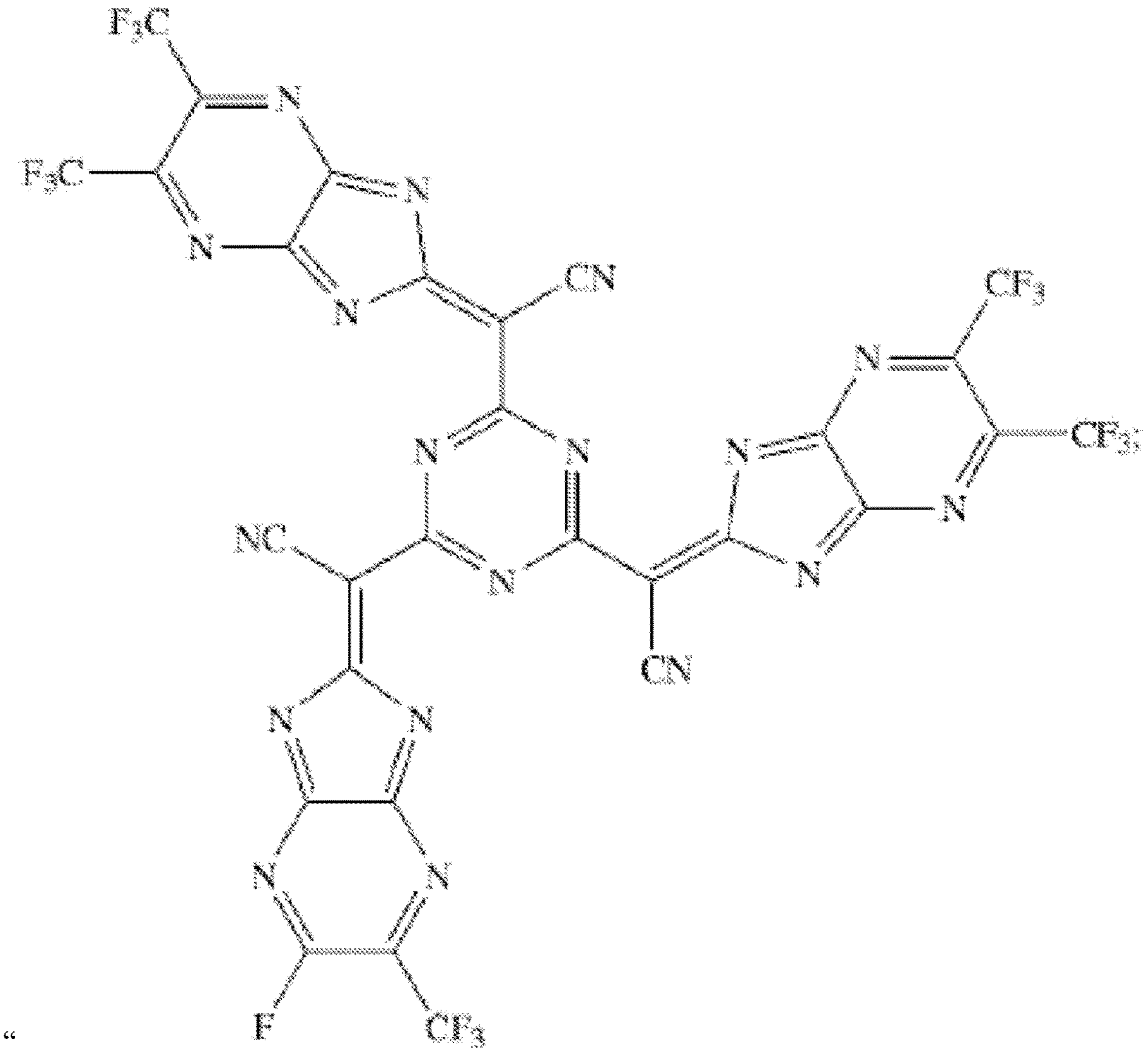"
Should read:

65
-- 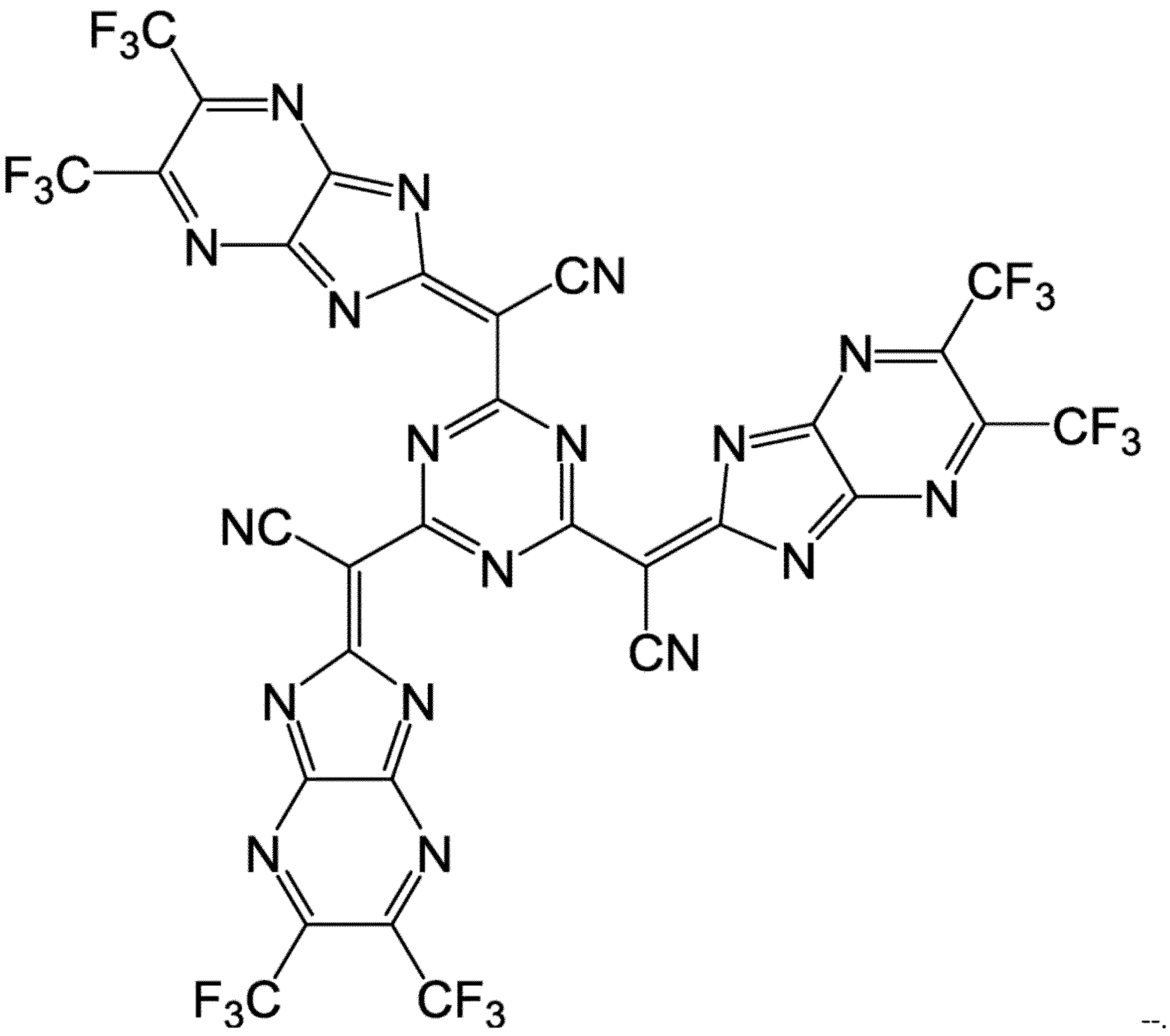 --.

Column 446, Claim 25, Structure 146:
145
“ 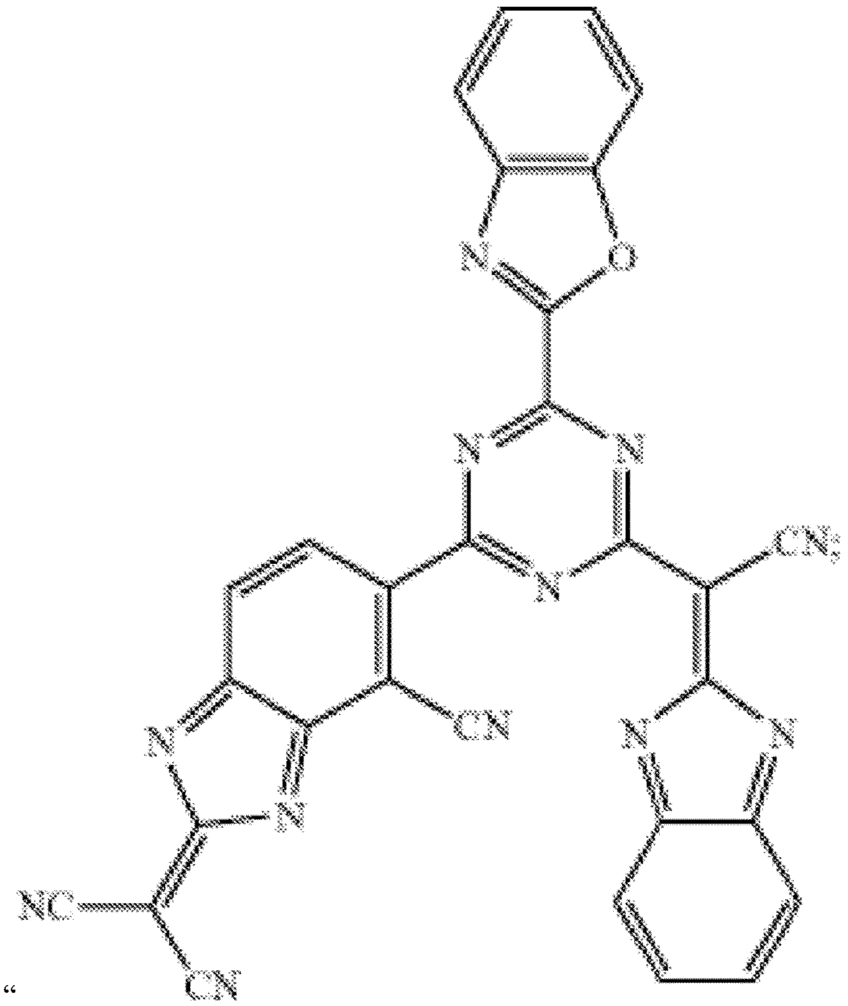 ”
Should read:

146
-- 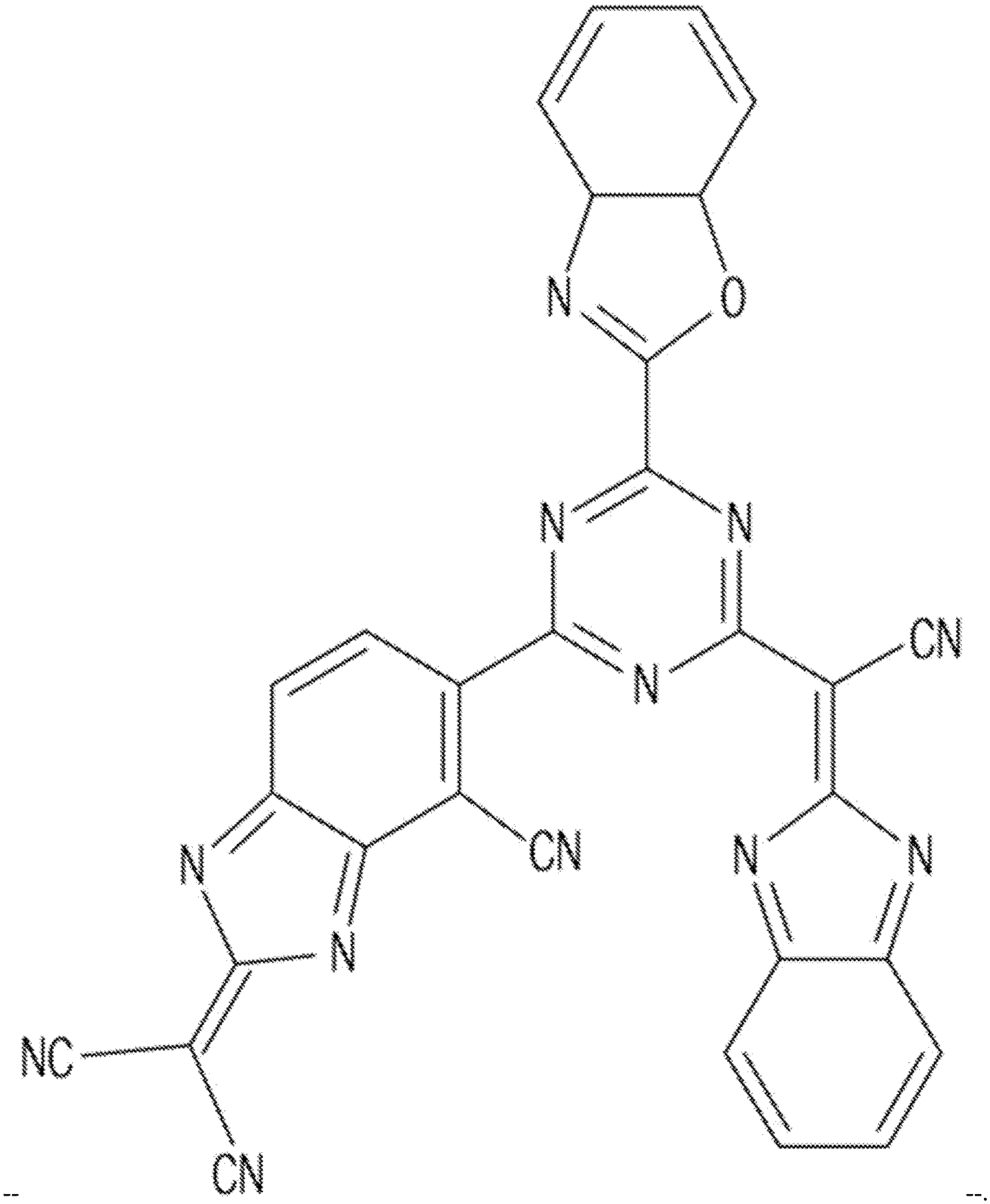 --.

Column 450, Claim 25, Structure 158:
158
"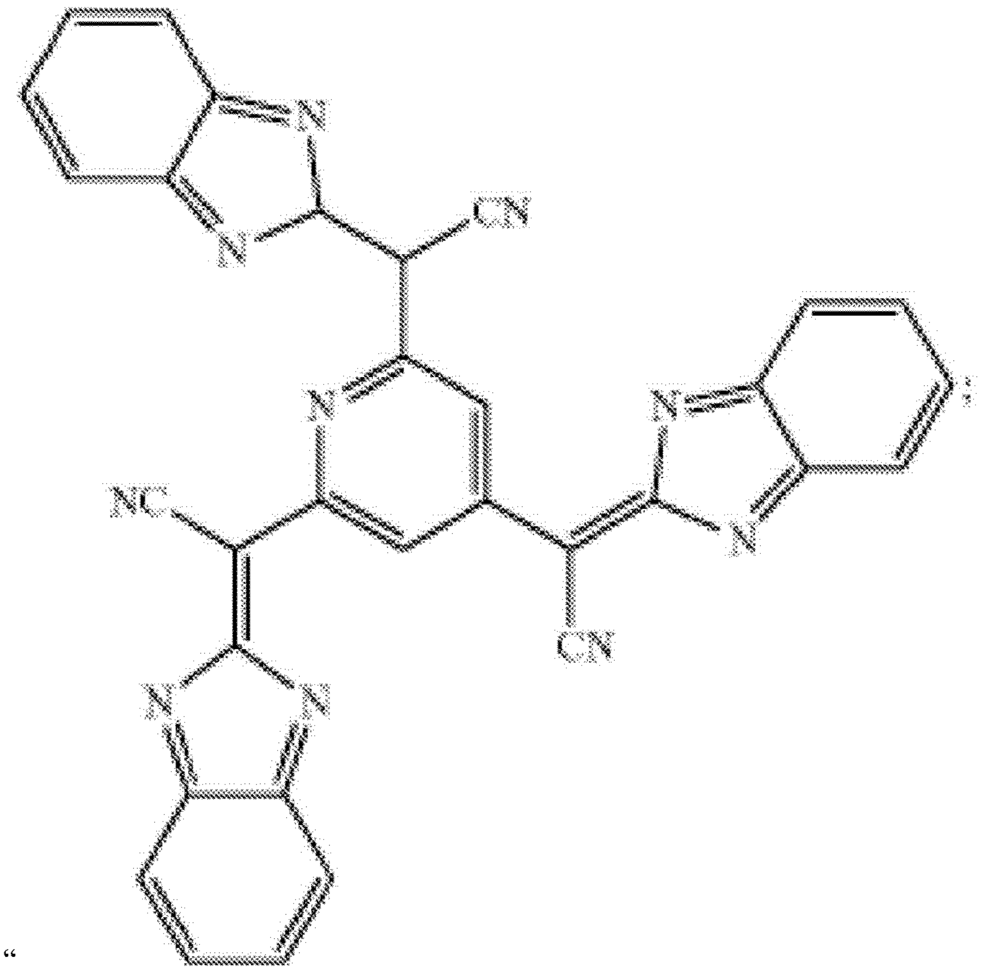"
Should read:

158
-- 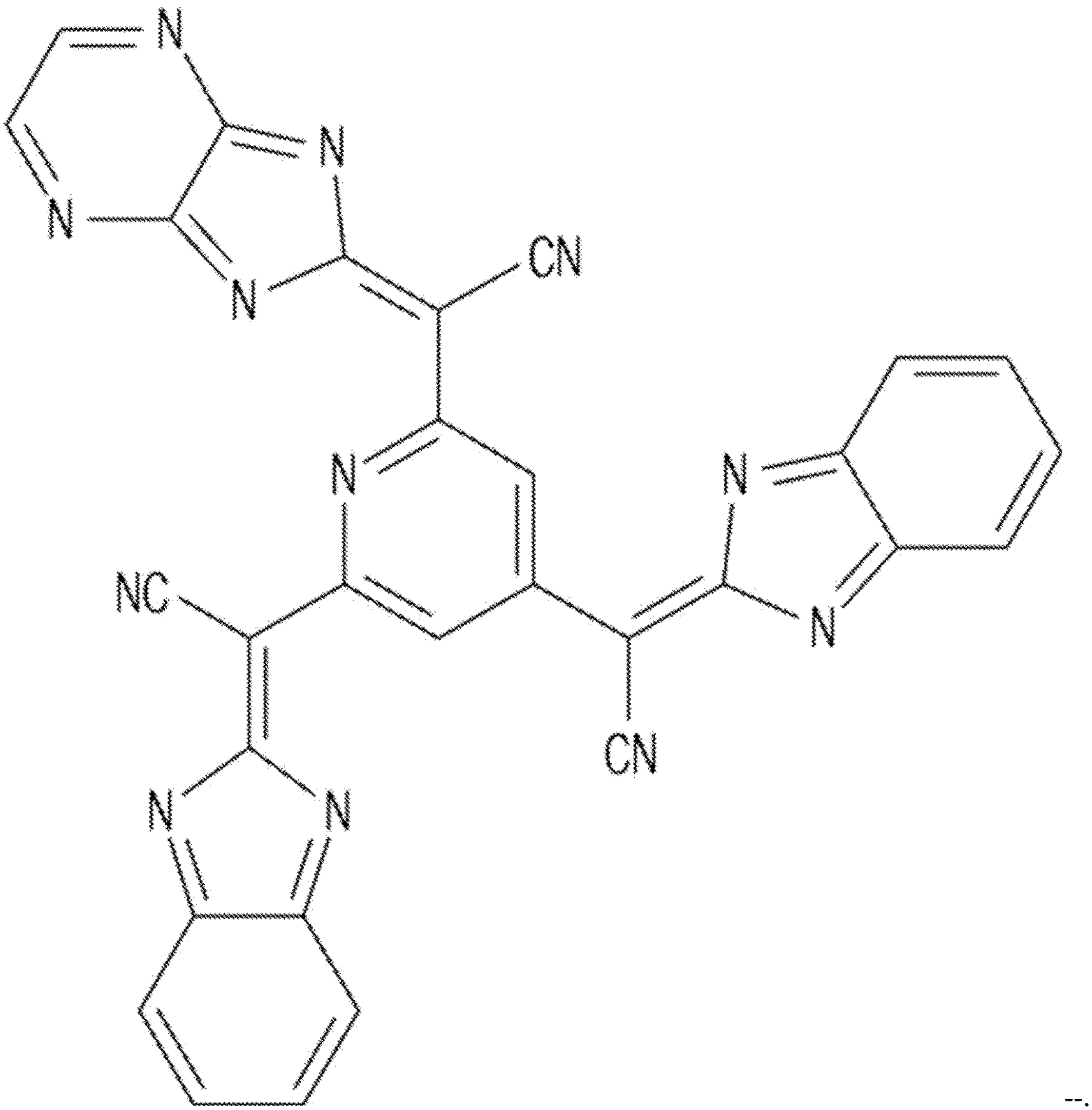 --.

Column 453, Claim 25, Structure 168:
"
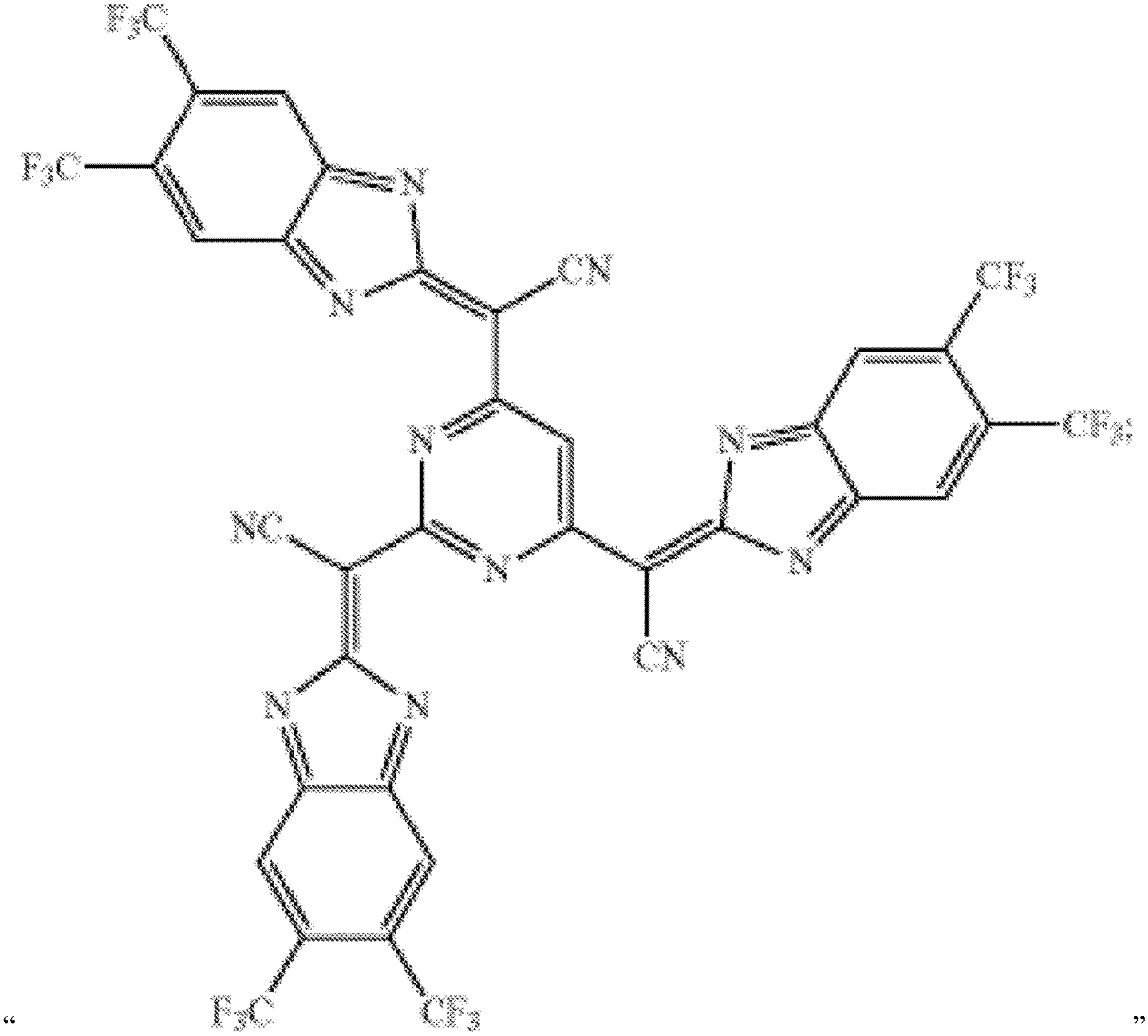
"
Should read:

168
-- 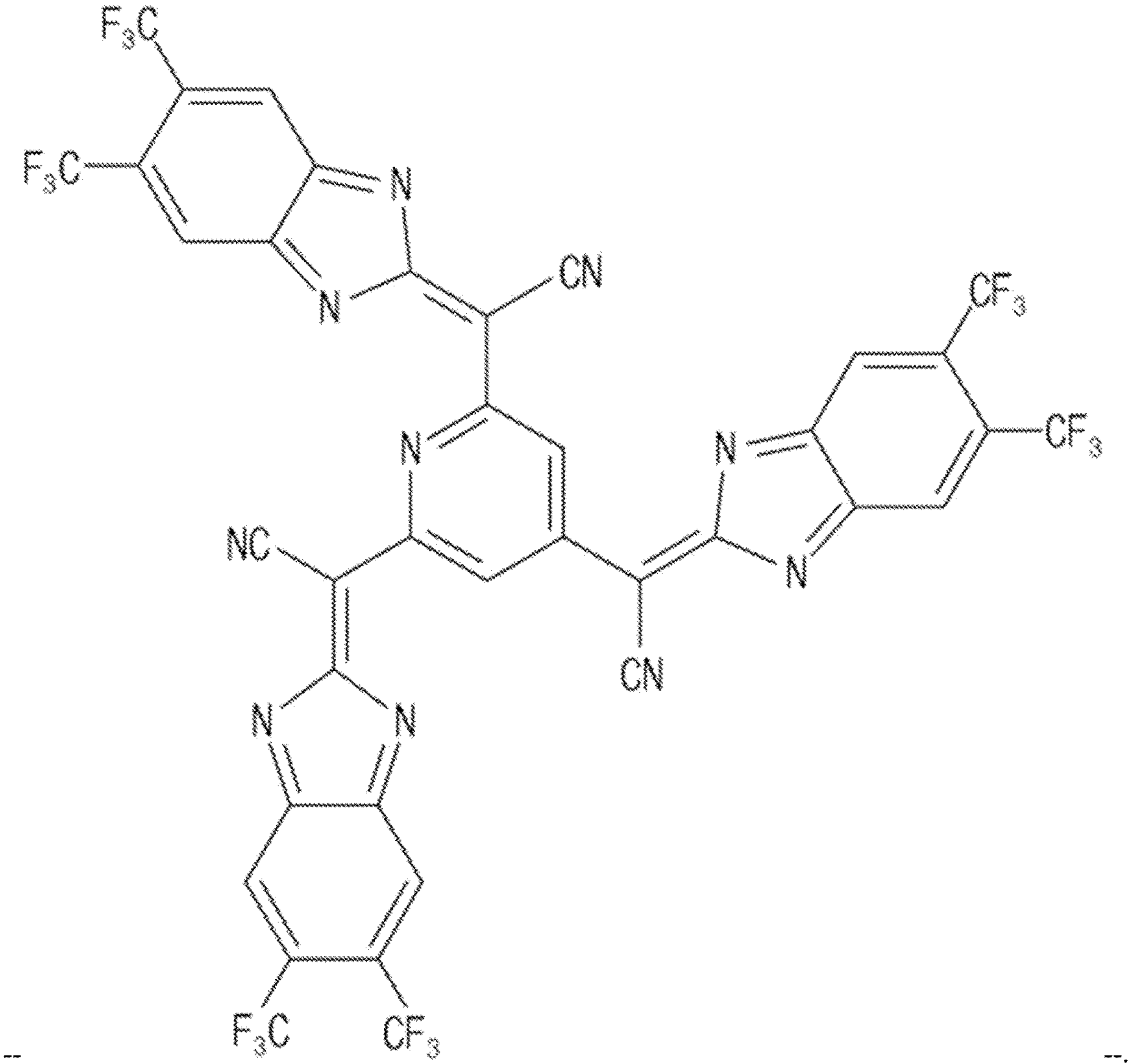 --.